US012583861B2

(12) United States Patent
Zhang et al.

(10) Patent No.: US 12,583,861 B2
(45) Date of Patent: Mar. 24, 2026

(54) DERIVATIVES OF IMIDAZO[4,5-D]PYRIDAZINE, THEIR PREPARATION AND THEIR THERAPEUTIC APPLICATION

(71) Applicant: SANOFI, Paris (FR)

(72) Inventors: Jidong Zhang, Paris (FR); Yannick Benedetti, Paris (FR); Esther Arranz, Paris (FR); Andreas Karlsson, Paris (FR); Marie-Priscille Brun, Paris (FR); François Bretin, Paris (FR)

(73) Assignee: SANOFI, Paris (FR)

( * ) Notice: Subject to any disclaimer, the term of this patent is extended or adjusted under 35 U.S.C. 154(b) by 346 days.

(21) Appl. No.: 18/273,360

(22) PCT Filed: Feb. 2, 2022

(86) PCT No.: PCT/EP2022/052387
§ 371 (c)(1),
(2) Date: Jul. 20, 2023

(87) PCT Pub. No.: WO2022/167438
PCT Pub. Date: Aug. 11, 2022

(65) Prior Publication Data

US 2024/0158401 A1 May 16, 2024

(30) Foreign Application Priority Data

Feb. 3, 2021 (EP) .................................... 21305143

(51) Int. Cl.
*C07D 487/04* (2006.01)

(52) U.S. Cl.
CPC .................................. *C07D 487/04* (2013.01)

(58) Field of Classification Search
None
See application file for complete search history.

(56) References Cited

U.S. PATENT DOCUMENTS

| | | | | |
|---|---|---|---|---|
| 7,232,823 B2 * | 6/2007 | Carpino | .................... | A61P 3/10 514/210.18 |
| 2004/0092740 A1 | 5/2004 | Dumas et al. | | |
| 2016/0166681 A1 | 6/2016 | David et al. | | |

FOREIGN PATENT DOCUMENTS

| | | | | |
|---|---|---|---|---|
| CN | 102060778 A | 5/2011 | | |
| CN | 102245609 A | 11/2011 | | |
| CN | 105213400 A | 1/2016 | | |
| RU | 1187438 A1 | 10/1997 | | |
| WO | 91019715 A1 | 12/1991 | | |
| WO | 2010042699 A1 | 4/2010 | | |
| WO | WO-2025031923 A1 * | 2/2025 | ......... | A61K 47/6849 |

OTHER PUBLICATIONS

Suzuki et al., Acylation of heteroaromatic amines. Perbenzoylation of diaminopyridazines, Journal of Heterocyclic Chemistry 15, 8 (1978) p. 1451-1453 (Year: 1978).*

Extended European Search Report for European Application No. 21305143.6 issued May 3, 2021, 10 pages.

Gettins, Marc (PCT Authorized Officer), International Search Report and Written Opinion of the International Searching Authority for International Application No. PCT/EP2022/052387 dated Mar. 28, 2022, 9 pages.

Hevener et al., Author Manuscript of "Structural Studies of Pterin-Based Inhibitors of Dihydropteroate Synthase," Journal of Medicinal Chemistry, vol. 53, No. 1, Jan. 14, 2010, pp. 166-177 (26 pages total).

Hussein et al., "Toll-like receptor agonists: a patent review (2011-2013)," Expert Opinion on Therapeutic Patents, vol. 24, No. 4, 2014 (Published online Jan. 24, 2014), pp. 453-470 (19 pages total).

Kieffer et al., "Small molecule agonists of toll-like receptors 7 and 8: a patent review 2014-2020," Expert Opinion on Therapeutic Patents, vol. 30, No. 11, 2020 (Published online Oct. 14, 2020), pp. 825-845 (22 pages total).

NCBI—National Center for Biotechnology Information, GenBank Accession No. AAK62676 (Version AAK62676.1), Toll-like receptor 7 [*Mus musculus*], Jul. 15, 2002, 3 pages.

NCBI—National Center for Biotechnology Information, GenBank Accession No. AAK62677 (Version AAK62677.1), Toll-like receptor 8 [*Mus musculus*], Jul. 15, 2002, 3 pages.

NCBI—National Center for Biotechnology Information, GenBank Accession No. AAZ95441 (Version AAZ95441.1), TLR8 [Homo sapiens], Nov. 25, 2009, 3 pages.

NCBI—National Center for Biotechnology Information, GenBank Accession No. AA299026 (Version AA299026.1), TLR7 [*Homo sapiens*], Nov. 25, 2009, 3 pages.

(Continued)

*Primary Examiner* — Jeffrey S Lundgren
*Assistant Examiner* — Anthony Joseph Seitz
(74) *Attorney, Agent, or Firm* — MH2 Technology Law Group, LLP

(57) ABSTRACT

The present invention relates to a compound of formula (I) wherein $R_1$ represents H, $(C_1-C_6)$alkyl-; hydroxy-$(C_1-C_6)$alkyl-; $NH_2$—$(C_1-C_6)$alkyl-; NH—$(C_1-C_6)$alkyl-$(C_1-C_6)$alkyl-; $N((C_1-C_6)alkyl)_2$-$(C_1-C_6)$alkyl-; $(C_2-C_6)$alkenyl-; $(C_2-C_6)$alkynyl-; phenyl$(C_1-C_6)$alkyl-; $(C_3-C_{10})$cycloalkyl$(C_1-C_6)$alkyl-; $(C_3-C_{10})$membered heterocycloalkyl$(C_1-C_6)$alkyl-; $(C_5-C_{10})$membered heteroaryl$(C_1-C_6)$alkyl-; $(C_3-C_{10})$membered heterocycloalkyl-NH—$(C_1-C_{16})$alkyl-; and $(C_3-C_{10})$membered heterocycloalkyl-N(C(O)—$(C_1-C_6)$alkyl)-$(C_1-C_{16})$alkyl-; $R_2$ represents a halogen atom, a $(C_1-C_6)$alkyl- group or other well defined groups; and $R_3$ represents a deuterium atom; H, $(C_1-C_6)$alkyl-; $(C_2-C_6)$alkenyl-; $(C_2-C_6)$alkynyl-; $(C_1-C_6)$alkylthio-; —$OR_6$; —$NR_7R_8$; $(C_3-C_{10})$membered heterocycloalkyl-; $(C_5-C_{10})$membered heteroaryl-; —$(C_6-C_{10})$membered aryl; and $(C_3-C_{10})$cycloalkyl-. The present invention further relates to intermediates of these compounds, processes for their preparation, a medicament and a pharmaceutical composition comprising them, and their therapeutic uses, in particular as TLR7 and/or TLR8 agonists, as well as their use in a vaccine.

18 Claims, No Drawings

(56) References Cited

OTHER PUBLICATIONS

Suzuki et al., "Acylation of Heteroaromatic Amines (I). Perbenzoylation of Diaminopyridazines," Journal of Heterocyclic Chemistry, vol. 15, Dec. 1978, pp. 1451-1453.
Švajger et al., "New antagonists of toll-like receptor 7 discovered through 3D ligand-based virtual screening," 1 Medicinal Chemistry Research, vol. 24, 2015 (Published online Jul. 15, 2014), pp. 362-371.

* cited by examiner

DERIVATIVES OF IMIDAZO[4,5-D]PYRIDAZINE, THEIR PREPARATION AND THEIR THERAPEUTIC APPLICATION

RELATED APPLICATIONS

The instant application is a 35 U.S.C. § 371 filing of International Patent Application No. PCT/EP2022/052387, filed Feb. 2, 2022, which claims priority to European Patent Application No. 21305143.6, filed Feb. 3, 2021, the entire contents of which are incorporated herein by reference for all purposes.

The present disclosure relates to novel imidazo[4,5-d] pyridazine compounds, processes for their preparation, novel intermediates, as well as their therapeutic uses thereof, for instance as Toll-like receptor 7 agonists and/or Toll-like receptor 8 agonists.

BACKGROUND OF THE INVENTION

The innate immune system contains several families of germline-encoded pattern recognition receptors (PRRs), including Toll-like receptors (TLRs). These receptors recognize microbial components termed pathogen-associated molecular patterns (PAMPs) which are highly conserved molecular structures on a wide range of pathogens such as viruses, fungi, bacteria, and parasites.

It is well known that TLRs are promising targets for the development of new and effective therapeutic agents. More particularly, TLR7 and TLR8 are both located within endolysosomes and play an important role in the immune response during viral infection by their ability to recognize single stranded RNA PAMPs, as well as synthetic small molecules. Their stimulation leads to intracellular signaling and downstream activation of genes coding, among others for co-stimulatory molecules, pro-inflammatory cytokines and type I interferons.

Various small molecules agonists of TLR7 (commonly named TLR7 agonists) and/or agonists of TLR8 (commonly named TLR8 agonists) have already been described, for example Imiquimod (R-837), Resiquimod (R-848), and Gardiquimod.

For example, Resiquimod can act simultaneously as TLR7 agonist and TLR8 agonist. Some other synthetic small molecules like Imiquimod activates preferentially TLR7.

The activation of TLR such as TLR7 and/or TLR8, by an agonist can induce secretion of type I interferons such as IFNα and IFNβ, Tumor necrosis factor (TNFα) and interleukins such as IL6, IL12, which are important actors in the initiation of innate and adaptative immunity. The secretion of these cytokines, associated with the expression of co-stimulatory molecules, are known to induce the maturation of dendritic cells, monocytes and macrophages, facilitating the presentation of antigen and the stimulation of the adaptive immune response.

TLR7 agonists and/or TLR8 agonists have already been reported as adjuvants for vaccines and for the treatment of infections and diseases, for example to treat cancer of the skin and bladder, of renal cell carcinoma, autoimmune diseases, inflammatory diseases, allergic diseases.

However, there is still a need to provide novel compounds which are useful as TLR7 agonists and/or TLR8 agonists.

The objective of the present disclosure is thus to provide novel compounds which act as agonists of TLR7 and/or TLR8 agonists.

SUMMARY OF THE DISCLOSURE

The present disclosure relates to a compound of formula (I) or a pharmaceutically acceptable salt thereof:

(I)

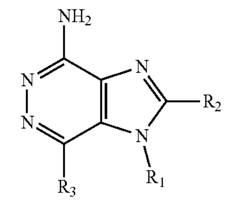

wherein:

$R_1$ represents:

a hydrogen atom, or a group selected from:

a)

a $(C_1$-$C_6)$alkyl- group;

a hydroxy-$(C_1$-$C_6)$alkyl- group;

a $NH_2$—$(C_1$-$C_6)$alkyl- group;

a NH—$(C_1$-$C_6)$alkyl-$(C_1$-$C_6)$alkyl- group, a $N((C_1$-$C_6)alkyl)_2$-$(C_1$-$C_6)$alkyl- group;

a $(C_2$-$C_6)$alkenyl- group;

a $(C_2$-$C_6)$alkynyl- group;

b)

a phenyl$(C_1$-$C_6)$alkyl- group being unsubstituted or substituted by at least one substituent selected from:

b1) a $(C_1$-$C_6)$alkoxy- group;

b2) a hydroxyl group;

b3) a —C(O)—H group; and b4) a $(C_1$-$C_6)$alkyl- group being unsubstituted or substituted by at least one substituent selected from:

b4.1) a hydroxyl group; and b4.2) a —$NR_4R_5$ group wherein $R_4$ and $R_5$, being independently from each other selected from:

b4.2.1) a hydrogen atom;

b4.2.2) a $(C_1$-$C_{16})$alkyl- group;

b4.2.3) a $CH_3$—[O—$(CH_2)_2]_n$— group with n being an integer from 1 to 30, a $(C_1$-$C_6)$alkoxy$(C_1$-$C_6)$alkyl- group, or a $(C_1$-$C_6)$alkoxy$(C_1$-$C_6)$alkoxy$(C_1$-$C_6)$alkyl- group;

b4.2.4) a $(C_1$-$C_6)$alkyl-$S(O_2)$— group;

b4.2.5) a $(C_1$-$C_6)$alkyl-NH—C(O)— group;

b4.2.6) a $(C_1$-$C_{16})$alkyl-C(O)— group;

b4.2.7) a $(C_1$-$C_{16})$alkyl-O—C(O)— group;

b4.2.8) a $CH_3$—[O—$(CH_2)_2]_n$—C(O)— group with n being an integer from 1 to 30;

b4.2.9) a $(C_3$-$C_{10})$cycloalkyl- group being unsubstituted or substituted by at least one substituent selected from:

a hydroxyl group; and a $(C_1$-$C_6)$alkyl- group; or b4.2.10) a $(C_3$-$C_{10})$membered heterocycloalkyl- group comprising from one to four heteroatoms selected from oxygen, nitrogen, sulfur, —S(O)— and —$SO_2$—;

b4.2.11) a phenyl-C(O)— group;

b4.2.12) a $(C_1$-$C_6)$alkoxy-phenyl-$(C_1$-$C_6)$alkyl-O—C(O)— group;

b4.2.13) a $(C_1$-$C_{16})$alkyl-C(O)—NH-phenyl-$(C_1$-$C_6)$alkyl-O—C(O)— group;

b4.2.14) a $(C_1-C_{16})$alkyl-O—C(O)—$(C_1-C_6)$alkyl- group;

or $R_4$ and $R_5$ form together with the nitrogen atom to which they are attached a $(C_3-C_{10})$membered heterocycloalkyl- group comprising one to four heteroatoms selected from oxygen, nitrogen and sulfur, said $(C_3-C_{10})$membered heterocycloalkyl- group being unsubstituted or substituted by at least one substituent selected from a $(C_1-C_6)$alkyl- group, and a $CH_3—[O—(CH_2)_2]_n—$ group with n being an integer from 1 to 30;

c) a $(C_3-C_{10})$cycloalkyl$(C_1-C_6)$alkyl- group being unsubstituted or substituted by at least one substituent selected from $—NH_2$ and a $NH_2—(C_1-C_6)$alkyl- group;

d) a $(C_3-C_{10})$membered heterocycloalkyl$(C_1-C_6)$alkyl- group comprising one to four heteroatoms selected from oxygen, nitrogen, and sulfur, said heterocycloalkyl group being unsubstituted or substituted by at least one substituent selected from a $(C_1-C_6)$alkyl- group and a $CH_3—[O—(CH_2)_2]_n—$ group with n being an integer from 1 to 30; and e) a $(C_5-C_{10})$membered heteroaryl$(C_1-C_6)$alkyl- group comprising one to four heteroatoms selected from oxygen, nitrogen, and sulfur, said heteroaryl being unsubstituted or substituted by at least one substituent selected from:

a $(C_1-C_6)$alkyl- group;

a $NH_2—(C_1-C_6)$alkyl- group and a cyano group;

f) a $(C_3-C_{10})$membered heterocycloalkyl-NH—$(C_1-C_{16})$alkyl- group, said heterocycloalkyl group comprising one to four heteroatoms selected from oxygen, nitrogen, S(O), $SO_2$ and sulfur;

g) a $(C_3-C_{10})$membered heterocycloalkyl-N(C(O)—$(C_1-C_6)$alkyl)-$(C_1-C_{16})$alkyl- group, said heterocycloalkyl group comprising one to four heteroatoms selected from oxygen, nitrogen, S(O), $SO_2$ and sulfur;

$R_2$ represents a halogen atom, or a group selected from:

a $(C_1-C_6)$alkyl- group;

a $(C_2-C_6)$alkenyl- group;

a $(C_2-C_6)$alkynyl- group;

a $(C_1-C_6)$alkylthio- group;

a $(C_1-C_6)$alkylthio$(C_1-C_6)$alkyl- group;

a $(C_1-C_6)$alkyl-S(O)— group;

a $(C_1-C_6)$alkyl-$S(O_2)$— group;

a $(C_1-C_6)$alkyl-S(O)—$(C_1-C_6)$alkyl- group;

a $(C_1-C_6)$alkyl-$S(O_2)$—$(C_1-C_6)$alkyl- group;

a $(C_1-C_6)$alkoxy- group;

a $(C_1-C_6)$alkoxy$(C_1-C_6)$alkyl- group;

a $(C_1-C_6)$haloalkoxy$(C_1-C_6)$alkyl- group;

a $(C_3-C_5)$cycloalkyl-O—$(C_1-C_6)$alkyl- group;

a $(C_1-C_6)$alkyl-NH—$(C_1-C_6)$alkyl- group;

a $((C_1-C_6)alkyl)_2$-N—$(C_1-C_6)$alkyl- group;

a $(C_1-C_6)$alkyl-NH— group; and a $((C_1-C_6)alkyl)_2$N— group;

$R_3$ represents:

a deuterium atom;

a hydrogen atom or a group selected from:

a)

a $(C_1-C_6)$alkyl- group;

a $(C_2-C_6)$alkenyl- group;

a $(C_2-C_6)$alkynyl- group; and a $(C_1-C_6)$alkylthio- group;

b)

a $—OR_6$ group wherein $R_6$ is selected from:

a hydrogen atom;

a $(C_1-C_6)$alkyl- group;

a $CH_3—[O—(CH_2)_2]_n—$ group with n being an integer from 1 to 30;

a $(C_2-C_6)$alkenyl- group;

a $(C_2-C_6)$alkynyl- group;

a $(C_3-C_{10})$cycloalkyl- group;

a phenyl group;

a phenyl$(C_1-C_6)$alkyl- group; and a $(C_3-C_{10})$membered heterocycloalkyl- group comprising one to four heteroatoms selected from oxygen, nitrogen, sulfur, —S(═O)— and $—S(═O)_2—$;

c)

a $—NR_7R_8$ group wherein $R_7$ and $R_8$ being, independently from each other, selected from:

a hydrogen atom;

a $CH_3—[O—(CH_2)_2]_n—$ with n being an integer from 1 to 30;

a $(C_1-C_6)$alkyl- group unsubstituted or substituted by a $(C_5-C_{10})$membered heteroaryl group comprising one to four heteroatoms selected from oxygen, nitrogen and sulfur; or a phenyl group being unsubstituted or substituted by at least one substituent selected from:

a cyano group and a $NR_9R_{10}—(C_1-C_6)$alkyl- group wherein:

$R_9$ and $R_{10}$ being, independently from each other, selected from:

a hydrogen atom;

a $(C_1-C_6)$alkyl- group;

a $CH_3—[O—(CH_2)_2]_n—$ with n being an integer from 1 to 30, or $R_9$ and $R_{10}$ together form with the nitrogen atom to which they are attached a $(C_3-C_{10})$membered heterocycloalkyl- group comprising one to four heteroatoms selected from oxygen, nitrogen, and sulfur, said $(C_3-C_{10})$membered heterocycloalkyl group being unsubstituted or substituted by at least one substituent selected from a $(C_1-C_6)$alkyl- group, and a $CH_3—[O—(CH_2)_2]_n—$ group with n being an integer from 1 to 30;

or $R_7$ and $R_8$ form together with the nitrogen atom to which they are attached a $(C_3-C_{10})$membered heterocycloalkyl- group comprising one to four heteroatoms selected from oxygen, nitrogen, and sulfur, said heterocycloalkyl group being unsubstituted or substituted by at least one substituent selected from:

a phenyl group and a hydroxy$(C_1-C_6)$alkyl-phenyl- group;

d)

a $(C_3-C_{10})$membered heterocycloalkyl- group comprising one to four heteroatoms selected from oxygen, nitrogen and sulfur;

e)

a $(C_5-C_{10})$membered heteroaryl- group comprising one to four heteroatoms selected from oxygen, nitrogen, and sulfur, said $(C_5-C_{10})$membered heteroaryl- group being unsubstituted or substituted by at least one $(C_1-C_6)$alkyl- group;

f)

a $—(C_6-C_{10})$membered aryl group; and g)

a $(C_3-C_{10})$cycloalkyl- group.

The disclosure further relates to processes for the preparation of the compounds of formula (I) in accordance with the present disclosure.

Thus, according to one specific embodiment, the disclosure relates to a first process for the preparation of the compounds of formula (I) or a pharmaceutically acceptable salt thereof in accordance with the present disclosure, as illustrated by scheme 1 below (also named SynMethod 1 in the present disclosure) and as detailed below.

According to another specific embodiment, the disclosure relates to a second process for the preparation of the compounds of formula (I) or a pharmaceutically acceptable salt thereof in accordance with the present disclosure, as illustrated by scheme 2 below (also named SynMethod 2, SynMethod 2a and SynMethod 2b in the present disclosure) and as detailed below.

According to another specific embodiment, the disclosure relates to a third process for the preparation of the compounds of formula (I) or a pharmaceutically acceptable salt thereof in accordance with the present disclosure, as illustrated by scheme 3 below (also named SynMethod 3 in the present disclosure) and as detailed below.

According to another specific embodiment, the disclosure relates to a fourth process for the preparation of the compounds of formula (I) or a pharmaceutically acceptable salt thereof in accordance with the present disclosure, as illustrated by scheme 4 below (also named SynMethod 4, SynMethod 4a and SynMethod 4b in the present disclosure) and as detailed below.

The disclosure also relates to intermediate compounds or a pharmaceutically acceptable salt thereof of formulae:

(VIIa)

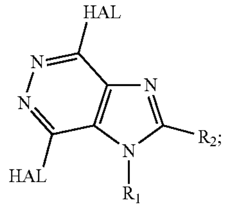

(VIII)

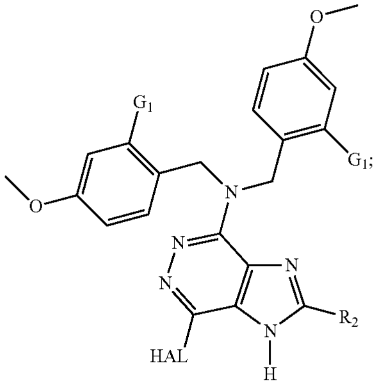

(VIIIa)

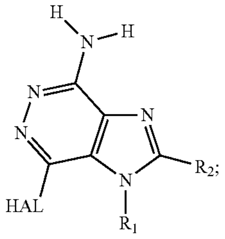

-continued (IX)

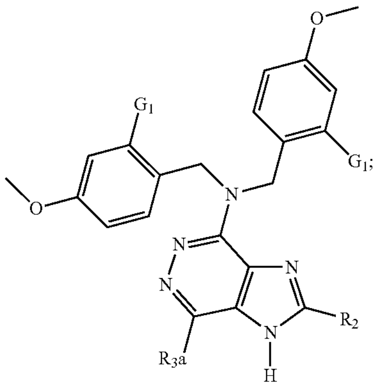

(X)

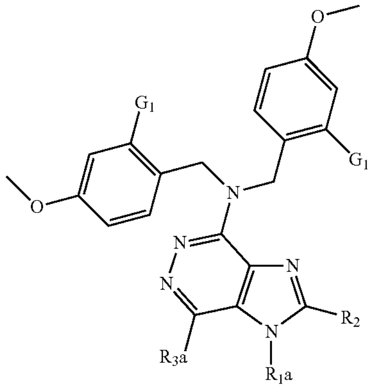

and (Ia)

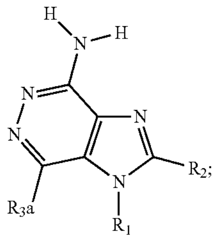

wherein $R_1$, $R_{1a}$, $R_2$, $R_{3a}$, HAL and $G_1$ are as defined in the present disclosure.

The present disclosure further concerns specific intermediate compounds or a pharmaceutically acceptable salt thereof selected from:

(H)

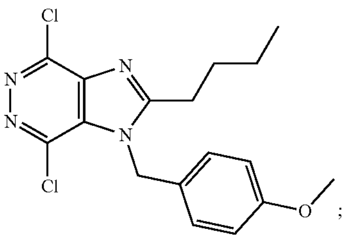

;

-continued (IA)

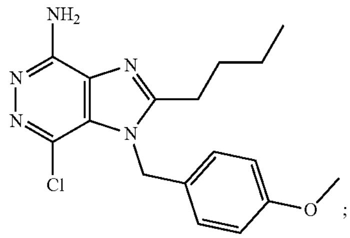

;

(J)

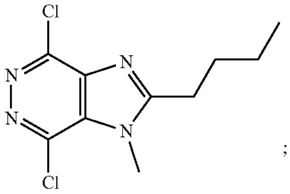

;

(K)

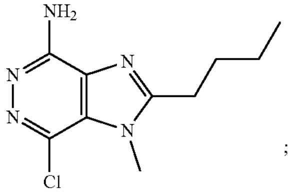

;

(L)

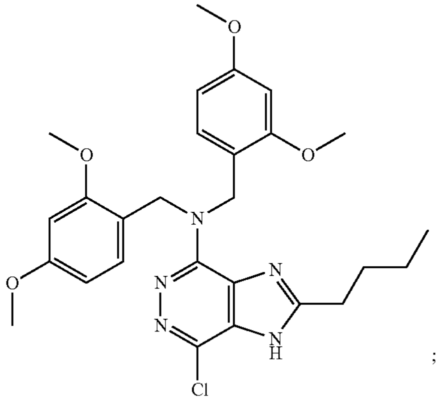

;

(M)

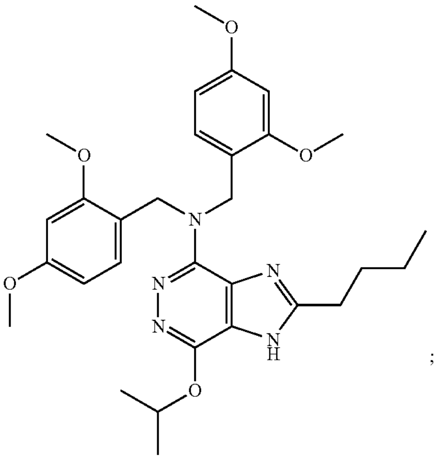

;

-continued (N)

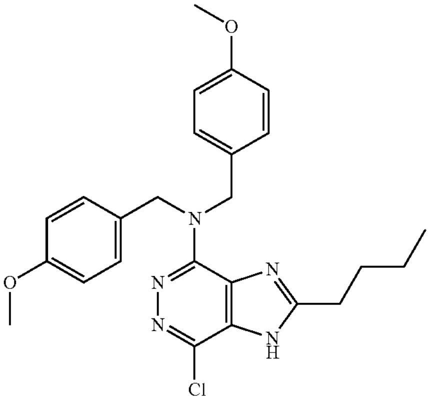

and (R)

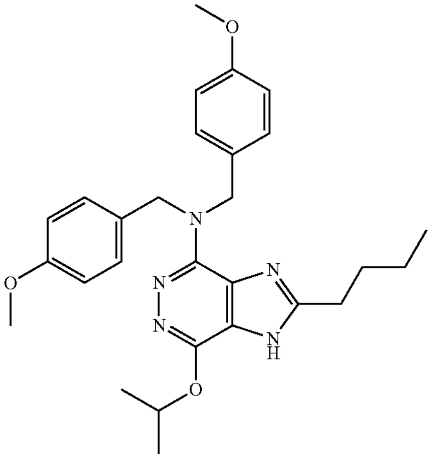

in which:

compounds (H) and (J) or a pharmaceutically acceptable salt thereof belong to formula (VIIa) as defined in the present disclosure;

compounds (Ia) and (K) or a pharmaceutically acceptable salt thereof belong to formula (VIIIa) as defined in the present disclosure;

compounds (L) and (N) or a pharmaceutically acceptable salt thereof belong to formula (VIII) as defined in the present disclosure and compounds (M) and (R) or a pharmaceutically acceptable salt thereof belong to formula (IX) as defined in the present disclosure.

The compounds of formula (I) may comprise one or more asymmetric carbon atoms. They may thus exist in the form of enantiomers, preferably pure enantiomers, or diastereoisomers and mixture thereof.

The compounds of formula (I) may be present as well under tautomer forms. Indeed, it is to be understood that the present disclosure encompasses all isomers of formulae (I), (Ia), (VIIa), (VIII), (VIIIa), (IX) and (X) and their pharmaceutically acceptable derivatives, including all geometric, tautomeric and optical forms, and mixtures thereof (e.g. racemic or non-racemic mixtures). It is to be understood that in the present disclosure isomers can be restricted to geometric, optical and tautomeric isomers.

The compounds of formulae (I), (Ia), (VIIa), (VIII), (VIIIa), (IX) and (X), may exist in the form of bases, acids, zwitterion or of addition salts with acids or bases, in particular pharmaceutically acceptable salts. Such addition salts, bases, acids and zwitterion form part of the disclosure. Hence, the disclosure relates, inter alia, to the compounds of formulae (I), (Ia), (VIIa), (VIII), (VIIIa), (IX) and (X), or to pharmaceutically acceptable salts thereof.

These salts may be prepared with pharmaceutically acceptable acids or bases, although the salts of other acids or bases useful, for example, for purifying or isolating the compounds of formulae (I), (Ia), (VIIa), (VIII), (VIIIa), (IX) and (X), also form part of the disclosure.

Among suitable salts which form part of the disclosure, the following may be cited: hydrochloride and trifluoroacetate.

Another subject-matter of the instant disclosure is a compound of formula (I) in accordance with the disclosure selected from the above and below lists, or a pharmaceutically acceptable salt thereof, for use as a medicine.

Another subject-matter of the instant disclosure is a compound of formula (I) in accordance with the disclosure selected from the above and below lists, or a pharmaceutically acceptable salt thereof, for use in therapy, especially as a TLR7 agonist and/or as a TLR8 agonist.

Another subject-matter of the instant disclosure is a compound of formula (I) in accordance with the disclosure selected from the above and below lists, or a pharmaceutically acceptable salt thereof, for use in the prevention and/or treatment of a disease or a disorder associated with TLR7 and/or TLR8 activity such a cell-proliferative disease, a cancer, a chronic myelogenous, a hairy cell leukemia, a dermatological disease such as a skin lesion or a skin cancer (for example an external genital and perianal warts/condyloma acuminate, a genital herpes, an actinic keratosis, a basal cell carcinoma, a cutaneous T-cell lymphoma), an autoimmune disease, an inflammatory disease, a respiratory disease, a sepsis, an allergy (for example an allergic rhinitis or an respiratory allergy), an asthma, a graft rejection, a graft-versus-host disease, an immunodeficiency.

Another subject-matter of the instant disclosure is a compound of formula (I) in accordance with the disclosure selected from the above and below lists, or a pharmaceutically acceptable salt thereof, for use in the prevention and/or treatment of a cancer.

Another subject-matter of the instant disclosure is a compound of formula (I) in accordance with the disclosure selected from the above and below lists, or a pharmaceutically acceptable salt thereof, for use in a vaccine. For example, a compound of formula (I) in accordance with the disclosure can be used as a vaccine adjuvant or the vaccine can be a self-adjuvanting vaccine.

Another subject-matter of the instant disclosure is a method of treating a disease or a disorder associated with TLR7 and/or TLR7/8 activity such as a cell-proliferative disease, a cancer, a chronic myelogenous, a hairy cell leukemia, a dermatological disease such as a skin lesion or a skin cancer (for example an external genital and perianal warts/condyloma acuminate, a genital herpes, an actinic keratosis, a basal cell carcinoma, a cutaneous T-cell lymphoma), an autoimmune disease, an inflammatory disease, a respiratory disease, a sepsis, an allergy (for example an allergic rhinitis or an respiratory allergy), an asthma, a graft rejection, a graft-versus-host disease, an immunodeficiency, which comprises administering to a subject in need thereof, for instance a human, a therapeutically effective amount of a compound of formula (I) in accordance with the disclosure selected from the above and below lists, or a pharmaceutically acceptable salt thereof.

The present disclosure also relates, in another aspect, to a method of preventing and/or treating a disease or a disorder associated with TLR7 and/or TLR7/8 activity such as a cell-proliferative disease, a cancer, a chronic myelogenous, a hairy cell leukemia, a dermatological disease such as a skin lesion or a skin cancer (for example an external genital and perianal warts/condyloma acuminate, a genital herpes, an actinic keratosis, a basal cell carcinoma, a cutaneous T-cell lymphoma), an autoimmune disease, an inflammatory disease, a respiratory disease, a sepsis, an allergy (for example an allergic rhinitis or an respiratory allergy), an asthma, a graft rejection, a graft-versus-host disease, an immunodeficiency, in a patient in need thereof, for instance a human, which comprises immunizing said patient with a vaccine comprising a compound of formula (I) in accordance with the disclosure selected from the above and below lists, or a pharmaceutically acceptable salt thereof.

The present disclosure also relates, in another aspect, to an adjuvant for vaccines.

The present disclosure further relates to the use of a compound of formula (I) in accordance with the disclosure selected from the above and below lists, or a pharmaceutically acceptable salt thereof, for the manufacture of a vaccine and/or of a medicament for preventing and/or treating a disease or a disorder associated with TLR7 and/or TLR7/8 activity such as a cell-proliferative disease, a cancer, a chronic myelogenous, a hairy cell leukemia, a dermatological disease such as a skin lesion or a skin cancer (for example an external genital and perianal warts/condyloma acuminate, a genital herpes, an actinic keratosis, a basal cell carcinoma, a cutaneous T-cell lymphoma), an autoimmune disease, an inflammatory disease, a respiratory disease, a sepsis, an allergy (for example an allergic rhinitis or an respiratory allergy), an asthma, a graft rejection, a graft-versus-host disease, an immunodeficiency.

Another subject-matter of the instant disclosure is a medicament comprising as active principle an effective dose of a compound of formula (I) in accordance with the disclosure selected from the above and below lists, or a pharmaceutically acceptable salt thereof.

Another subject-matter of the instant disclosure is a pharmaceutical composition comprising as active principle an effective dose of a compound of formula (I) in accordance with the disclosure selected from the above and below lists, or a pharmaceutically acceptable salt thereof, and at least one pharmaceutically acceptable excipient.

Definitions

In the context of the present disclosure, the terms below have the following definitions unless otherwise mentioned throughout the instant specification:

- a "halogen atom": a fluorine, a chlorine, a bromine or an iodine atom, and for example a fluorine and a chlorine atom;
- a "hydroxyl group": a "—OH" group;
- an "oxo group": a "═O" group;
- a "cyano group": a "—CN" group;
- a "($C_x$-$C_y$)alkyl" group: a linear or branched saturated hydrocarbon-based aliphatic group comprising from x to y carbon atoms, for example from 1 to 6 carbon atoms, or from 1 to 16 carbon atoms. By way of examples, mention may be made of, but not limited to: methyl, ethyl, propyl, n-propyl, isopropyl, butyl, isobutyl, sec-butyl, tert-butyl, pentyl, isopentyl, hexyl, isohexyl, octyl, nonyl, decyl groups, and the like;
- a "($C_x$-$C_y$)alkenyl" group: a linear or branched hydrocarbon-based aliphatic group comprising at least one unsaturation (double bond) and comprising, from x to y carbon atoms (x being an integer of at least 2), for example from 2 to 6 carbon atoms. By way of examples, mention may be made of, but not limited to: ethenyl, propenyl, butenyl, pentenyl, hexenyl groups, and the like;

a "($C_x$-$C_y$)alkynyl" group: a linear or branched hydrocarbon-based aliphatic group comprising at least one triple bond and comprising from x to y carbon atoms (x being an integer of at least 2) for example from 2 to 6 carbon atoms. By way of examples, mention may be made of, but not limited to: ethynyl, propynyl, butynyl, pentynyl, hexynyl groups, and the like;

a "($C_x$-$C_y$)alkoxy" group: an —O-alkyl group where the alkyl group is as previously defined. For example, a ($C_1$-$C_6$)alkoxy group. By way of examples, mention may be made of, (but not limited to: methoxy, ethoxy, propoxy, isopropoxy, linear, secondary or tertiary butoxy, isobutoxy, pentoxy, hexyloxy, heptyloxy, octyloxy, nonyloxy, decyloxy groups, and the like;

a "($C_x$-$C_y$)haloalkoxy" group: an —O-alkyl group where the alkyl group is as previously defined and is further substituted by at least one halogen atom as previously defined. For example, a ($C_1$-$C_6$)haloalkoxy group. By way of examples, mention may be made of but not limited to: chloromethoxy, fluoromethoxy, dichloromethoxy, 2-fluoropropoxy groups, and the like;

a "($C_x$-$C_y$)alkythio" group: an —S-alkyl group where the alkyl group is as previously defined. For example, a ($C_1$-$C_6$)alkylthio group. By way of examples, mention may be made of but not limited to: methylthio, ethylthio, propylthio, isopropylthio, linear, secondary or tertiary butylthio, isobutylthio, pentylthio, hexylthio, heptylthio, octylthio, nonylthio, decylthio groups, and the like;

a "($C_3$-$C_{10}$)cycloalkyl" group or a "($C_3$-$C_5$)cycloalkyl"" group: a cyclic alkyl group comprising, unless otherwise mentioned, from 3 to 10 carbon atoms (noted "($C_3$-$C_{10}$)cycloalkyl group") or from 3 to 5 carbon atoms (noted "($C_3$-$C_5$)cycloalkyl group"), saturated or partially unsaturated and unsubstituted or substituted. By way of examples, mention may be made of, but not limited to: cyclopropyl, cyclobutyl, cyclopentyl, cyclobutenyl, cyclopentenyl, cyclohexenyl, cyclohexyl, cycloheptyl, cyclooctyl, cyclononyl, cyclodecyl groups and the like;

a "($C_3$-$C_{10}$)heterocycloalkyl" group: a monocyclic alkyl group comprising, unless otherwise mentioned, from 3 to 10 carbon atoms (noted "a ($C_3$-$C_{10}$) membered heterocycloalkyl group") and comprising 1 to 4 heteroatoms selected from oxygen, nitrogen, sulfur, —S(O)—, and —$SO_2$— (in other terms, one heteroatom replaces one carbon atom). Such heterocycloalkyl group may be saturated or partially saturated and unsubstituted or substituted. By way of examples of heterocycloalkyl groups, mention may be made of, but not limited to: piperazine, morpholino, pyrrolidine, tetrahydropyrane, thietane dioxide, piperidine, thiolane, thiolane oxide, thiolane dioxide, dihydrofurane, tetrahydrofurane, azetidine, oxetane, thietane, 2H-pyrrole, 1H-, 2H- or 3H-pyrroline, tetrahydrothiophene, oxadiazole and for example 1,3,4-oxadiazole or 1,3,5-oxadioazole, thiadiazole and for example 1,3,4-thiadiazole, isoxazoline, 2- or 3-pyrazoline, pyrroline, pyrazolidine, imidazoline, imidazolidine, thiazolidine, isooxazoline, isoxazolidine, dioxalane, oxathiazole, oxathiadiazole, dioxazole groups and the like;

a "($C_5$-$C_{10}$)heteroaryl" group means: a cyclic aromatic group comprising from 5 to 10 carbon atoms and comprising from 1 and 4 heteroatoms selected from nitrogen, oxygen and sulfur (noted "a ($C_5$-$C_{10}$) membered heteroaryl group") (in other terms, one heteroatom replaces one carbon atom). Such heteroaryl group may be unsubstituted or substituted. By way of examples of 5 to 10-membered heteroaryl groups, mention may be made of, but not limited to: pyridine, furan, pyrrole, thiophene, pyrazole, oxazole, isoxazole, triazole, tetrazole, oxadiazole, furazan, thiazole, isothiazole, thiadiazole, imidazole, pyrimidine, pyridazine, triazine groups and the like;

a "($C_6$-$C_{10}$)aryl" group: a cyclic aromatic group comprising from 6 to 10 carbon atoms (noted "a ($C_6$-$C_{10}$) membered aryl group"). Such aryl group may be unsubstituted or substituted. By way of examples of 6 to 10-membered aryl groups, mention may be made of, but not limited to: phenyl, naphthyl groups, and the like;

a "deuterium atom" (D or $^2$H) is a stable, non-radioactive isotope of hydrogen and has an atomic weight of 2.0144;

a "hydroxyl protecting group" means: Ethers, Silyl Ethers, Esters, carbonates, carbamates etc, such as Acetyl (Ac), Benzoyl (Bz), Benzyl (Bn), β-methoxyethoxymethyl ether (MEM), dimethoxytrityl, [bis-(4-methoxyphenyl)phenylmethyl] (DMT), methoxymethyl ether (MOM), methoxytrityl [(4-methoxyphenyl) diphenylmethyl] (MMT), p-methoxybenzyl ether (PMB), p-methoxyphenyl ether (PMP), methylthiomethyl ether, pivaloyl (Piv), tetrahydropyranyl (THP), tetrahydrofuran (THF), trityl (triphenylmethyl, Tr), silyl ether (for instance trimethylsilyl (TMS), tert-butyldimethylsilyl (TBDMS), tri-iso-propylsilyloxymethyl (TOM), and triisopropylsilyl (TIPS) ethers), methyl ethers, ethoxyethyl ethers (EE), for instance acetyl (Ac), benzyl (Bn), β-methoxyethoxymethyl ether (MEM), dimethoxytrityl, [bis-(4-methoxyphenyl) phenylmethyl] (DMT), p-methoxybenzyl ether (PMB), tetrahydropyranyl (THP), trityl (triphenylmethyl, Tr), trimethylsilyl (TMS), and tert-butyldimethylsilyl (TBDMS). (see the manual Greene's protective groups in organic synthesis», P. G. M. WUTS and T. W. GREENE, fourth edition, 1807 Wiley 207, Wiley Interscience);

an "amino protecting group" means: carbamates, amides, alkyls, enamines, imides, imines, etc, such as carbobenzyloxy (Cbz) group, p-methoxybenzyl carbonyl (Moz or MeOZ) group, tert-butyloxycarbonyl (BOC) group, 9-fluorenylmethyloxycarbonyl (Fmoc) group, acetyl (Ac) group, benzoyl (Bz) group, benzyl (Bn) group, carbamate group, p-methoxyphenyl (PMP) group, tosyl (Ts) group, p-methoxybenzyl (PMB), 3,4-dimethoxybenzyl (DMPM), Troc (trichloroethyl chloroformate) group, other sulfonamides, for instance carbobenzyloxy (Cbz) group, tert-butyloxycarbonyl (BOC) group, 9-fluorenylmethyloxycarbonyl (Fmoc) group, acetyl (Ac) group, benzoyl (Bz) group, p-methoxybenzyl (PMB), 3,4-dimethoxybenzyl (DMPM), Troc (trichloroethyl chloroformate) group. (see the manual Greene's protective groups in organic synthesis», P. G. M. WUTS and T. W. GREENE, fourth edition, 1807 Wiley 207, Wiley Interscience;

a "carboxylic acid protecting group" means: Esters, silyl esters, amides, hydrazides, etc such as methyl esters, benzyl esters, tert-Butyl esters, esters of 2,6-disubstituted phenols (e.g. 2,6-dimethylphenol, 2,6-diisopropylphenol, 2,6-di-tert-butylphenol), silyl esters, orthoesters, oxazoline, for instance, methyl esters and benzyl esters. (see the manual Greene's protective groups in organic synthesis», P. G. M. WUTS and T. W. GREENE, fourth edition, 1807 Wiley 207, Wiley Interscience);

an "aldehyde protecting group" or a ketone protecting group (also named carbonyl protecting groups) means: acetals and ketals, dithio acetals and ketals, substituted hydrazones, oximes, etc, such as acetals and ketals, acylals and dithianes. (see the manual Greene's protective groups in organic synthesis», P. G. M. WUTS and T. W. GREENE, fourth edition, 1807 Wiley 207, Wiley Interscience);

A "zwitterion" means: a globally neutral molecule with a positive and a negative electrical charge and having an acid group and a basic group;

"room temperature" (also named rt) in the present disclosure means a temperature ranging from 18° C. to 30° C., for example from 18° C. to 25° C.;

"TLR": the terms "Toll-like receptor" and "TLR" refer to any member of a family of highly-conserved mammalian proteins which recognize pathogen-associated molecular patterns and act as key signaling elements in innate immunity. TLR polypeptides share a characteristic structure that includes an extracellular domain that has leucine-rich repeats, a transmembrane domain, and an intracellular domain that is involved in TLR signaling;

"TLR7": the terms "Toll-like receptor 7" and "TLR7" refer to nucleic acids or polypeptides sharing at least 70%; at least 80%, at least 90%, at least 95%, at least 96%, at least 97%), at least 98%, at least 99%, or more sequence identity to a publicly-available TLR7 sequence, e.g., GenBank accession number AAZ99026 for human TLR7 polypeptide, or GenBank accession number AAK62676 for murine TLR7 polypeptide;

"TLR8": the terms "Toll-like receptor 8" and "TLR8" refer to nucleic acids or polypeptides sharing at least 70%; at least 80%, at least 90%, at least 95%, at least 96%, at least 97%), at least 98%, at least 99%, or more sequence identity to a publicly-available TLR7 sequence, e.g., GenBank accession number AAZ95441 for human TLR8 polypeptide, or GenBank accession number AAK62677 for murine TLR8 polypeptide;

"TLR agonist": it is a substance that binds, directly or indirectly, to a TLR (e.g., TLR7 and/or TLR8) to induce TLR signaling. Any detectable difference in TLR signaling can indicate that an agonist stimulates or activates a TLR. Signaling differences can be manifested, for example, as changes in the expression of target genes, in the phosphorylation of signal transduction components, in the intracellular localization of downstream elements such as NF-kB, in the association of certain components (such as IRAK) with other proteins or intracellular structures, or in the biochemical activity of components such as kinases (such as MAPK);

"Immune response": An "immunological response" or "immune response" to an antigen or composition, as used herein, refers to the development in a subject of a humoral and/or cellular immune response to the antigen or composition;

Immune responses include innate and adaptive immune responses. Innate immune responses are fast-acting responses that provide a first line of defense for the immune system. In contrast, adaptive immunity uses selection and clonal expansion of immune cells having somatically rearranged receptor genes (e.g., T- and B-cell receptors) that recognize antigens from a given pathogen or disorder (e.g., a tumor), thereby providing specificity and immunological memory. Innate immune responses, among their many effects, lead to a rapid burst of inflammatory cytokines and activation of antigen-presenting cells (APCs) such as macrophages and dendritic cells. To distinguish pathogens from self-components, the innate immune system uses a variety of relatively invariable receptors that detect signatures from pathogens, known as pathogen-associated molecular patterns, or PAMPs. The mechanism behind this potentiation of the immune responses has been reported to involve pattern-recognition receptors (PRRs), which are differentially expressed on a variety of immune cells, including neutrophils, monocytes, macrophages, dendritic cells, natural killer cells, B cells and some nonimmune cells such as epithelial and endothelial cells. Engagement of PRRs leads to the activation of some of these cells and their secretion of cytokines and chemokines, as well as maturation and migration of other cells. In tandem, this creates an inflammatory environment that leads to the establishment of the adaptive immune response. PRRs include nonphagocytic receptors, such as Toll-like receptors (TLRs) and nucleotide-binding oligomerization domain (NOD) proteins, and receptors that induce phagocytosis, such as scavenger receptors, mannose receptors and β-glucan receptors. Dendritic cells are recognized as some of the most important cell types for initiating the priming of naive $CD4^+$ helper T ($T_H$) cells and for inducing $CD8^+$ T cell differentiation into killer cells. TLR signaling has been reported to play an important role in determining the quality of these helper T cell responses, for instance, with the nature of the TLR signal determining the specific type of TH response that is observed (e.g., $T_H1$ versus $T_H2$ response). A combination of antibody (humoral) and cellular immunity are produced as part of a $T_H1$-type response, whereas a $T_H2$-type response is predominantly an antibody response.

A "humoral immune response" refers to an immune response mediated by antibody molecules, while a "cellular immune response" refers to an immune response mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from $CD4^+$ and $CD8^+$ T-cells.

An "immune response" associated with TLR7 and/or TLR8 is an immune response which involves activation of TLR7 and/or TLR8 receptors. Activation of TLR7 and/or TLR8 receptors may be determined in vitro using methods such as those described in the Examples.

"Induce": "Induce" and variations thereof refer to any measurable increase in cellular activity. For example, induction of an immune response may include, for example, an increase in the production of a cytokine, activation, proliferation, or maturation of a population of immune cells, and/or other indicator of increased immune function."

DETAILED DESCRIPTION OF THE PRESENT DISCLOSURE

The disclosure relates to a compound of formula (I) or a pharmaceutically acceptable salt thereof:

(I)

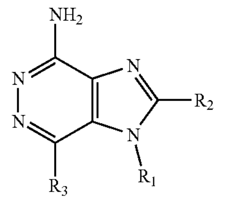

wherein:

$R_1$ represents:

a hydrogen atom, or a group selected from:

a)

a $(C_1$-$C_6)$alkyl- group;

a hydroxy-$(C_1$-$C_6)$alkyl- group;

a $NH_2$—$(C_1$-$C_6)$alkyl- group;

a NH—$(C_1$-$C_6)$alkyl-$(C_1$-$C_6)$alkyl- group, a $N((C_1$-$C_6)alkyl)_2$-$(C_1$-$C_6)$alkyl- group;

a $(C_2$-$C_6)$alkenyl- group;

a $(C_2$-$C_6)$alkynyl- group;

b)

a phenyl$(C_1$-$C_6)$alkyl- group being unsubstituted or substituted by at least one substituent selected from:

b1) a $(C_1$-$C_6)$alkoxy- group;

b2) a hydroxyl group;

b3) a —C(O)—H group; and b4) a $(C_1$-$C_6)$alkyl- group being unsubstituted or substituted by at least one substituent selected from:

b4.1) a hydroxyl group; and b4.2) a —$NR_4R_5$ group wherein $R_4$ and $R_5$, being independently from each other selected from:

b4.2.1) a hydrogen atom;

b4.2.2) a $(C_1$-$C_{16})$alkyl- group;

b4.2.3) a $CH_3$—[O—$(CH_2)_2]_n$— group with n being an integer from 1 to 30, a $(C_1$-$C_6)$alkoxy $(C_1$-$C_6)$alkyl- group, or a $(C_1$-$C_6)$alkoxy$(C_1$-$C_6)$alkoxy$(C_1$-$C_6)$alkyl- group;

b4.2.4) a $(C_1$-$C_6)$alkyl-$S(O_2)$— group;

b4.2.5) a $(C_1$-$C_6)$alkyl-NH—C(O)— group;

b4.2.6) a $(C_1$-$C_{16})$alkyl-C(O)— group;

b4.2.7) a $(C_1$-$C_{16})$alkyl-O—C(O)— group;

b4.2.8) a $CH_3$—[O—$(CH_2)_2]_n$—C(O)— group with n being an integer from 1 to 30;

b4.2.9) a $(C_3$-$C_{10})$cycloalkyl- group being unsubstituted or substituted by at least one substituent selected from:

a hydroxyl group; and a $(C_1$-$C_6)$alkyl- group; or b4.2.10) a $(C_3$-$C_{10})$membered heterocycloalkyl- group comprising from one to four heteroatoms selected from oxygen, nitrogen, sulfur, —S(O)— and —$SO_2$—;

b4.2.11) a phenyl-C(O)— group;

b4.2.12) a $(C_1$-$C_6)$alkoxy-phenyl-$(C_1$-$C_6)$alkyl-O—C(O)— group;

b4.2.13) a $(C_1$-$C_{16})$alkyl-C(O)—NH-phenyl-$(C_1$-$C_6)$alkyl-O—C(O)— group;

b4.2.14) a $(C_1$-$C_{16})$alkyl-O—C(O)—$(C_1$-$C_6)$alkyl- group;

or $R_4$ and $R_5$ form together with the nitrogen atom to which they are attached a $(C_3$-$C_{10})$membered heterocycloalkyl- group comprising one to four heteroatoms selected from oxygen, nitrogen and sulfur, said $(C_3$-$C_{10})$membered heterocycloalkyl- group being unsubstituted or substituted by at least one substituent selected from a $(C_1$-$C_6)$alkyl- group, and a $CH_3$—[O—$(CH_2)_2]_n$— group with n being an integer from 1 to 30;

c) a $(C_3$-$C_{10})$cycloalkyl$(C_1$-$C_6)$alkyl- group being unsubstituted or substituted by at least one substituent selected from —$NH_2$ and a $NH_2$—$(C_1$-$C_6)$alkyl- group;

d) a $(C_3$-$C_{10})$membered heterocycloalkyl$(C_1$-$C_6)$alkyl- group comprising one to four heteroatoms selected from oxygen, nitrogen, and sulfur, said heterocycloalkyl group being unsubstituted or substituted by at least one substituent selected from a $(C_1$-$C_6)$alkyl- group and a $CH_3$—[O—$(CH_2)_2]_n$— group with n being an integer from 1 to 30; and e) a $(C_5$-$C_{10})$membered heteroaryl$(C_1$-$C_6)$alkyl- group comprising one to four heteroatoms selected from oxygen, nitrogen, and sulfur, said heteroaryl being unsubstituted or substituted by at least one substituent selected from:

a $(C_1$-$C_6)$alkyl- group;

a $NH_2$—$(C_1$-$C_6)$alkyl- group and a cyano group;

f) a $(C_3$-$C_{10})$membered heterocycloalkyl-NH—$(C_1$-$C_{16})$alkyl- group, said heterocycloalkyl group comprising one to four heteroatoms selected from oxygen, nitrogen, S(O), $SO_2$ and sulfur;

g) a $(C_3$-$C_{10})$membered heterocycloalkyl-N(C(O)—$(C_1$-$C_6)$alkyl)-$(C_1$-$C_{16})$alkyl- group, said heterocycloalkyl group comprising one to four heteroatoms selected from oxygen, nitrogen, S(O), $SO_2$ and sulfur;

$R_2$ represents a halogen atom, or a group selected from:

a $(C_1$-$C_6)$alkyl- group;

a $(C_2$-$C_6)$alkenyl- group;

a $(C_2$-$C_6)$alkynyl- group;

a $(C_1$-$C_6)$alkylthio- group;

a $(C_1$-$C_6)$alkylthio$(C_1$-$C_6)$alkyl- group;

a $(C_1$-$C_6)$alkyl-S(O)— group;

a $(C_1$-$C_6)$alkyl-$S(O_2)$— group;

a $(C_1$-$C_6)$alkyl-S(O)—$(C_1$-$C_6)$alkyl- group;

a $(C_1$-$C_6)$alkyl-$S(O_2)$—$(C_1$-$C_6)$alkyl- group;

a $(C_1$-$C_6)$alkoxy- group;

a $(C_1$-$C_6)$alkoxy$(C_1$-$C_6)$alkyl- group;

a $(C_1$-$C_6)$haloalkoxy$(C_1$-$C_6)$alkyl- group;

a $(C_3$-$C_5)$cycloalkyl-O—$(C_1$-$C_6)$alkyl- group;

a $(C_1$-$C_6)$alkyl-NH—$(C_1$-$C_6)$alkyl- group;

a $((C_1$-$C_6)alkyl)_2$-N—$(C_1$-$C_6)$alkyl- group;

a $(C_1$-$C_6)$alkyl-NH— group; and a $((C_1$-$C_6)alkyl)_2$N— group;

$R_3$ represents:

a deuterium atom;

a hydrogen atom or a group selected from:

a)

a $(C_1-C_6)$alkyl- group;

a $(C_2-C_6)$alkenyl- group;

a $(C_2-C_6)$alkynyl- group; and a $(C_1-C_6)$alkylthio- group;

b)

a —$OR_6$ group wherein $R_6$ is selected from:

a hydrogen atom;

a $(C_1-C_6)$alkyl- group;

a $CH_3$—[O—$(CH_2)_2]_n$— group with n being an integer from 1 to 30;

a $(C_2-C_6)$alkenyl- group;

a $(C_2-C_6)$alkynyl- group;

a $(C_3-C_{10})$cycloalkyl- group;

a phenyl group;

a phenyl$(C_1-C_6)$alkyl- group; and a $(C_3-C_{10})$membered heterocycloalkyl- group comprising one to four heteroatoms selected from oxygen, nitrogen, sulfur, —S(═O)— and —$S(═O)_2$—;

c)

a —$NR_7R_8$ group wherein $R_7$ and $R_8$ being, independently from each other, selected from:

a hydrogen atom;

a $CH_3$—[O—$(CH_2)_2]_n$— with n being an integer from 1 to 30;

a $(C_1-C_6)$alkyl- group unsubstituted or substituted by a $(C_5-C_{10})$membered heteroaryl group comprising one to four heteroatoms selected from oxygen, nitrogen and sulfur; or a phenyl group being unsubstituted or substituted by at least one substituent selected from:

a cyano group and a $NR_9R_{10}$—$(C_1-C_6)$alkyl- group wherein:

$R_9$ and $R_{10}$ being, independently from each other, selected from:

a hydrogen atom;

a $(C_1-C_6)$alkyl- group;

a $CH_3$—[O—$(CH_2)_2]_n$— with n being an integer from 1 to 30, or $R_9$ and $R_{10}$ together form with the nitrogen atom to which they are attached a $(C_3-C_{10})$membered heterocycloalkyl- group comprising one to four heteroatoms selected from oxygen, nitrogen, and sulfur, said $(C_3-C_{10})$membered heterocycloalkyl group being unsubstituted or substituted by at least one substituent selected from a $(C_1-C_6)$alkyl- group, and a $CH_3$—[O—$(CH_2)_2]_n$— group with n being an integer from 1 to 30;

or $R_7$ and $R_8$ form together with the nitrogen atom to which they are attached a $(C_3-C_{10})$membered heterocycloalkyl- group comprising one to four heteroatoms selected from oxygen, nitrogen, and sulfur, said heterocycloalkyl group being unsubstituted or substituted by at least one substituent selected from:

a phenyl group and a hydroxy$(C_1-C_6)$alkyl-phenyl- group;

d)

a $(C_3-C_{10})$membered heterocycloalkyl- group comprising one to four heteroatoms selected from oxygen, nitrogen and sulfur;

e)

a $(C_5-C_{10})$membered heteroaryl- group comprising one to four heteroatoms selected from oxygen, nitrogen, and sulfur, said $(C_5-C_{10})$membered heteroaryl- group being unsubstituted or substituted by at least one $(C_1-C_6)$alkyl- group;

f)

a —$(C_6-C_{10})$membered aryl group; and g)

a $(C_3-C_{10})$cycloalkyl- group.

Among the compounds of formula (I) or a pharmaceutically acceptable salt thereof that are subject matter of the disclosure, a group of compounds is composed of the compounds for which $R_1$ represents a hydrogen atom or a group selected from:

a)

a $(C_1-C_6)$alkyl- group;

a hydroxy-$(C_1-C_6)$alkyl- group or a $NH_2$—$(C_1-C_6)$alkyl- group;

b)

a phenyl$(C_1-C_6)$alkyl- group being unsubstituted or substituted by one substituent, selected from:

b1) a $(C_1-C_6)$-alkoxy- group;

b3) a —C(O)—H group and b4) a $(C_1-C_6)$alkyl- group substituted by at least one substituent selected from:

b4.1) a hydroxyl group;

b4.2) a —$NR_4R_5$ group wherein $R_4$ and $R_5$, being independently from each other, selected from:

b4.2.1) a hydrogen atom;

b4.2.2) a $(C_1-C_{16})$alkyl- group;

b4.2.3) a $CH_3$—[O—$(CH_2)_2]_n$— group with n being an integer from 1 to 30, a $(C_1C_6)$alkoxy $(C_1-C_6)$alkyl- group, or a $(C_1-C_6)$alkoxy$(C_1-C_6)$alkoxy$(C_1-C_6)$alkyl- group;

b4.2.4) a $(C_1-C_6)$alkyl-$S(O_2)$— group;

b4.2.5) a $(C_1-C_6)$alkyl-NH—C(O)— group;

b4.2.6) a $(C_1-C_{16})$alkyl-C(O)— group;

b4.2.7) a $(C_1-C_{16})$alkyl-O—C(O)— group;

b4.2.8) a $CH_3$—[O—$(CH_2)_2]_n$—C(O)— group with n being an integer from 1 to 30;

b4.2.9) a $(C_3-C_{10})$cycloalkyl- group being unsubstituted or substituted by at least one a $(C_1-C_6)$ alkyl group or a hydroxyl group;

b4.2.10) a $(C_3-C_{10})$membered heterocycloalkyl-group comprising from one to four heteroatoms selected from oxygen, nitrogen and —$SO_2$—;

b4.2.11) a phenyl-C(O)— group;

b4.2.12) a $(C_1-C_6)$alkoxy-phenyl-$(C_1-C_6)$alkyl-O—C(O)— group;

b4.2.13) a $(C_1-C_{16})$alkyl-C(O)—NH-phenyl-$(C_1-C_6)$alkyl-O—C(O)— group;

b4.2.14) a $(C_1-C_{16})$alkyl-O—C(O)—$(C_1-C_6)$alkyl- group;

or $R_4$ and $R_5$ form together with the nitrogen atom to which they are attached a $(C_3C_{10})$membered heterocycloalkyl- group comprising one to two heteroatoms selected from oxygen and nitrogen;

c) a $(C_3-C_{10})$cycloalkyl$(C_1-C_6)$alkyl- group being unsubstituted or substituted by one substituent selected from —$NH_2$, and a $NH_2$—$(C_1-C_6)$alkyl- group;

d) a $(C_3-C_{10})$membered heterocycloalkyl$(C_1-C_6)$alkyl-group, unsubstituted comprising one to two nitrogen heteroatoms;

e) a $(C_5-C_{10})$membered heteroaryl$(C_1-C_6)$alkyl- group comprising one nitrogen heteroatom, said heteroaryl being unsubstituted or substituted by at least one substituent selected from:

a $NH_2$—$(C_1-C_6)$alkyl- group and a cyano group;

f) a $(C_3-C_{10})$membered heterocycloalkyl-NH—$(C_1-C_{16})$alkyl- group, said heterocycloalkyl group comprising one heteroatom selected from oxygen, nitrogen, S(O), $SO_2$ and sulfur;

g) a $(C_3-C_{10})$membered heterocycloalkyl-N(C(O)—$(C_1-C_6)$alkyl)-$(C_1-C_{16})$alkyl- group, said heterocycloalkyl group comprising one heteroatom selected from oxygen, nitrogen, S(O), $SO_2$ and sulfur.

Among the compounds of formula (I) or a pharmaceutically acceptable salt thereof that are subject matter of the disclosure, a group of compounds is composed of the compounds for which $R_1$ represents:

a hydrogen atom or a group selected from:

a)

a methyl group;

a $C(OH)(CH_3)_2$—$CH_2$— group, a $C(CH_3)(CH_2OH)_2$—$CH_2$— group, a $CH(CH_2OH)_2$—$CH_2$— group;

a $NH_2$—$(CH_2)_4$— group, a $NH_2$—$(CH_2)_6$— group or a $NH_2$—$(CH_2)_6$— group;

b) a phenylmethyl group (that is to say a benzyl group), the phenyl group being unsubstituted or substituted by at least one substituent selected from:

b1) a methoxy group, such as a methoxy group in para position of the phenyl group;

b3) a —C(O)—H group, such as —C(O)—H in para position of the phenyl group;

b4) a methyl group substituted by at least one substituent selected from:

b4.1) a hydroxyl group;

b4.2) a $—NR_4R_5$ group wherein $R_4$ and $R_5$ being, independently from each other, selected from:

b4.2.1) a hydrogen atom;

b4.2.2) a methyl group, an isopropyl group, a pentyl group, a hexyl group, a nonyl group, a decyl group;

b4.2.3) a $CH_3$—O—$(CH_2)_2$— group, a $CH_3$—O—$((CH_2)_2$—$O)_{11}$—$(CH_2)_2$— group, a $CH_3$—O—$((CH_2)_2$—$O)_7$—$(CH_2)_2$— group, a $CH_3$—O—$((CH_2)_2$—$O)_2$—$(CH_2)_2$— group, a $CH_3$—O—$((CH_2)_2$—$O)_3$—$(CH_2)_2$— group, a $CH_3$—O—$((CH_2)_2$—$O)_2$—$(CH_2)_2$— group or a $CH_3$—O—$(CH_2)_2$—O—$(CH_2)_2$— group;

b4.2.4) a $CH_3$—$S(O_2)$— group;

b4.2.5) a $CH_3$—$CH_2$—NH—C(O)— group;

b4.2.6) a $CH_3$—C(O)— group, a $CH_3$—$CH_2$—C(O)— group, a $CH_3$—$(CH_2)_5$—C(O)— group, a $CH_3$—$(CH_2)_9$—C(O)— group or a $CH_3$—$(CH_2)_3$—C(O)— group;

b4.2.7) a $CH_3$—$CH_2$—O—C(O)— group;

b4.2.8) a $CH_3$—[O—$(CH_2)_2]_2$—C(O)— group or a $CH_3$—O—$(CH_2)_2$—C(O)— group;

b4.2.9) a cyclopropyl group or a cyclobutyl group, said cyclopropyl or cyclobutyl group being unsubstituted or substituted by at least one substituent selected from a hydroxyl group or a methyl group;

b4.2.10) a tetrahydropyranyl group or a thietane dioxide group;

b4.2.11) a phenyl-C(O)— group;

b4.2.12) a $CH_3$—O-phenyl-$CH_2$—O—C(O)— group;

b4.2.13) a $CH_3$—C(O)—NH-phenyl-$CH_2$—O—C(O)— group;

b4.2.14) a $C(CH_3)_3$—O—C(O)—$CH_2$— group or a $C(CH_3)_3$—O—C(O)—$(CH_2)_2$— group;

or $R_4$ and $R_5$ form together with the nitrogen atom to which they are attached a piperazinyl group, a morpholino group or a pyrrolidinyl group;

c) a cyclohexyl-$CH_2$— group being unsubstituted or substituted by at least one substituent selected from a —$NH_2$ group and a $NH_2$—$CH_2$— group;

d) a piperazinyl-$(CH_2)_2$— group, a piperidinyl-$CH_2$— group or a piperidinyl-$(CH_2)_2$— group; and e) pyridyl-$CH_2$— group being unsubstituted or substituted by at least one substituent selected from a $NH_2$—$CH_2$— group and a cyano group;

f) a tetrahydropyranyl-NH—$(CH_2)_4$— group, a tetrahydropyranyl-NH—$(CH_2)_6$— group, a dioxothietanyl-NH—$(CH_2)_4$— group, or a dioxothietanyl-NH—$(CH_2)_6$— group;

g) a tetrahydropyranyl-N(C(O)—$CH_3$)—$(CH_2)_4$— group, a tetrahydropyranyl-N(C(O)—$CH_3$)—$(CH_2)_6$— group, a dioxothietanyl-N(C(O)—$CH_3$)—$(CH_2)_4$— group, or a dioxothietanyl-N(C(O)—$CH_3$)—$(CH_2)_6$— group.

Among the compounds of formula (I) or a pharmaceutically acceptable salt thereof that are subject matter of the disclosure, a group of compounds is composed of the compounds for which $R_2$ represents a group selected from:

a $(C_1-C_6)$alkyl- group;

a $(C_1-C_6)$alkylthio- group;

a $(C_1-C_6)$alkyl-S(O)— group;

a $(C_1-C_6)$alkyl-NH—$(C_1-C_6)$alkyl- group;

a $(C_1-C_6)$alkyl-NH— group; and a $(C_1-C_6)$alkoxy$(C_1-C_6)$alkyl- group.

Among the compounds of formula (I) or a pharmaceutically acceptable salt thereof that are subject matter of the disclosure, a group of compounds is composed of the compounds for which $R_2$ represents a group selected from:

a methyl group, an ethyl group, a n-propyl group, a n-butyl group;

a $CH_3$—$(CH_2)_2$—S— group;

a $CH_3$—$(CH_2)_2$—S(O)— group;

a $CH_3$—S—$(CH_2)_2$— group;

a $CH_3$—$CH_2$—O—$CH_2$— group;

a $CH_3$—O—$(CH_2)_2$— group;

a $CH_3$—$CH_2$—NH—$CH_2$— group; and a $CH_3$—$(CH_2)_2$—NH— group.

Among the compounds of formula (I) or a pharmaceutically acceptable salt thereof that are subject matter of the disclosure, a group of compounds is composed of the compounds for which $R_2$ represents a $(C_1-C_6)$alkyl group, for instance a butyl group, such as an n-butyl group, a methyl group, or a propyl group such as a n-propyl group.

Among the compounds of formula (I) or a pharmaceutically acceptable salt thereof that are subject matter of the disclosure, a group of compounds is composed of the compounds for which $R_3$ represents:

a hydrogen atom or a group selected from:

a) a $(C_1-C_6)$alkyl- group;

a $(C_2-C_6)$alkenyl- group;

a $(C_1-C_6)$alkylthio- group;

b)

a $—OR_6$ group wherein $R_6$ is selected from:

a hydrogen atom;

a $(C_1-C_6)$alkyl- group;

a $CH_3$—[O—$(CH_2)_2]_n$— group with n being an integer from 1 to 30;
a ($C_2$-$C_6$)alkenyl group;
a ($C_3$-$C_{10}$)cycloalkyl group;
a phenyl group;
a phenyl($C_1$-$C_6$ alkyl)- group; and
a ($C_3$-$C_{10}$)membered heterocycloalkyl- group comprising one heteroatom selected from oxygen, sulfur, —S(O)— and —$SO_2$—;

c)
a —$NR_7R_8$ group wherein $R_7$ and $R_8$, being independently from each other, selected from:
a hydrogen atom;
a $CH_3$—[O—$(CH_2)_2]_n$— with n being an integer from 1 to 30;
a ($C_1$-$C_6$)alkyl- group unsubstituted or substituted by:
a ($C_5$-$C_{10}$)membered heteroaryl- group comprising one oxygen atom; or
a phenyl group being unsubstituted or substituted by at least one substituent selected from:
a cyano group and
a $NR_9R_{10}$—($C_1$-$C_6$)alkyl- group wherein $R_9$ and $R_{10}$ being, independently from each other, selected from:
a hydrogen atom;
a —($C_1$-$C_6$)alkyl group or
a $CH_3$—[O—$(CH_2)_2]_n$— with n being an integer from 1 to 30;
or $R_9$ and $R_{10}$ together form with the nitrogen atom to which they are attached a ($C_3$-$C_{10}$)membered heterocycloalkyl- group comprising one to two heteroatoms selected from oxygen, and nitrogen,
said ($C_3$-$C_{10}$)membered heterocycloalkyl- group being substituted by at least one ($C_1$-$C_6$)alkyl- group, for instance one to three ($C_1$-$C_6$)alkyl- groups, such as one ($C_1$-$C_6$)alkyl- group;
or $R_7$ and $R_8$ form together with the nitrogen atom to which they are attached a ($C_3C_{10}$)membered heterocycloalkyl- group comprising one nitrogen heteroatom, said heterocycloalkyl group being unsubstituted or substituted by at least one substituent, for instance one to three substituents, such as one substituent selected from:
a phenyl group and
a hydroxy($C_1$-$C_6$)alkyl-phenyl- group;

d)
a ($C_3$-$C_{10}$)membered heterocycloalkyl- group comprising one heteroatom selected from oxygen and nitrogen;

e)
a ($C_5$-$C_{10}$)membered heteroaryl- group comprising one to two heteroatoms selected from oxygen, nitrogen, and sulfur,
said ($C_5$-$C_{10}$)membered heteroaryl- group being unsubstituted or substituted by at least one ($C_1$-$C_6$)alkyl-group, for instance one to three a ($C_1$-$C_6$)alkyl- groups, such as one ($C_1$-$C_6$)alkyl- group;

f)
a ($C_6$-$C_{10}$)membered aryl- group and g)
a ($C_3$-$C_{10}$)cycloalkyl- group.

Among the compounds of formula (I) or a pharmaceutically acceptable salt thereof that are subject matter of the disclosure, a group of compounds is composed of the compounds for which $R_3$ represents:

a hydrogen atom or
a group selected from:

a)
an isopropyl group, an isobutyl group, an isopentyl group;
a C—$(CH_3)$(=$CH_2$)— group, a $(CH_3)_2C$=CH— group, a $(CH_3)_2$CH—CH=CH— group;
an isopropylthio- group;

b)
a —$OR_6$ group wherein $R_6$ represents:
a hydrogen atom;
a methyl group, an ethyl group, an isopropyl group, a n-propyl group, a n-butyl group, a sec-butyl group;
a $CH_3$—O—$(CH_2)_2$— group;
a propenyl group;
a cyclopentyl group;
a phenyl group unsubstituted, a phenyl-$CH_2$— group;
a tetrahydropyranyl group, a thiolane group, a thiolane oxide group, a thiolane dioxide group or a tetrahydrofuranyl group;

c)
a —$NR_7R_8$ group wherein $R_7$ and $R_8$, being independently from each other, selected from:
a hydrogen atom;
a $CH_3$—O—$(CH_2)_2$— group;
a methyl group, an isopropyl group;
a furanyl-$(CH_2)_3$— group;
a phenyl-$(CH_2)$— group, said phenyl group being unsubstituted or substituted by at least one substituent, for instance one to five substituents, such as one substituent selected from:
a cyano group and
a $NR_9R_{10}$—$CH_2$— group wherein
$R_9$ and $R_{10}$, being independently from each other, selected from:
a hydrogen atom;
a methyl group or
a $CH_3$—O—$(CH_2)_2$— group;
or $R_9$ and $R_{10}$ together form with the nitrogen atom to which they are attached a morpholino group or a piperazinyl group, said morpholino group or piperazinyl group being unsubstituted or substituted by at least one methyl group,
or $R_7$ and $R_8$ form together with the nitrogen atom to which they are attached, a pyrrolidinyl group,
said pyrrolidinyl group being unsubstituted or substituted by at least one substituent, for instance one to three substituents, such as one substituent selected from:
a phenyl group or
a OH—$CH_2$-phenyl- group, for example a OH—$CH_2$— group is in para position of the phenyl group;

d)
a tetrahydrofuranyl group, a dihydropyrrolyl group or a dihydrofuranyl group;

e)
a thienyl group, a furanyl group, a pyrrolyl group, a pyrazolyl group,
said thienyl group, furanyl group, pyrrolyl group or pyrazolyl group being unsubstituted or substituted by at least one methyl group, for instance one to three methyl groups, such as one methyl group;

f)
a phenyl group;

g)

a cyclopentenyl group, a cyclopentyl group, a cyclohexenyl group and a cyclohexyl group.

All these sub-groups taken alone or in combination are part of the present disclosure.

According to a particular embodiment, the disclosure relates to a compound of formula (I) or a pharmaceutically acceptable salt thereof, provided that at least one of $R_1$, and $R_3$ is other than a hydrogen atom.

According to another particular embodiment, the disclosure relates to a compound of formula (I) or a pharmaceutically acceptable salt thereof, provided that $R_1$ and $R_3$ are simultaneously other than a hydrogen atom.

According to another embodiment, the disclosure relates to a compound of formula (I) or a pharmaceutically acceptable salt thereof:

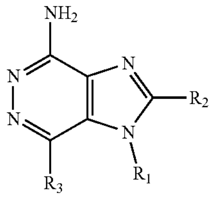

(I)

wherein:

$R_1$ represents a group selected from:

a)

a $(C_1-C_6)$alkyl group, for instance a methyl group;

a $NH_2$—$(C_1-C_6)$alkyl- group, for instance a $NH_2$—$(CH_2)_4$— group, a $NH_2$—$(CH_2)_5$— group, a $NH_2$—$(CH_2)_6$— group;

b) a phenyl$(C_1-C_6)$alkyl- group, for instance a benzyl group, the phenyl group being unsubstituted or substituted by at least one substituent, for instance one to five substituents, such as one substituent, selected from:

b1) a $(C_1-C_6)$alkoxy group, for instance a methoxy group, such as a methoxy group in para position of the phenyl group;

b3) —C(O)—H, such as —C(O)—H in para position of the phenyl group and b4) a $(C_1-C_6)$alkyl group, for instance a methyl group, such as a methyl group in para and/or meta position(s) of the phenyl group, said alkyl group being itself unsubstituted or substituted by at least one substituent, for instance one substituent, selected from:

b4.1) a hydroxyl group;

b4.2) a $—NR_4R_5$ group, $R_4$ and $R_5$ being independently from each other:

b4.2.1) a hydrogen atom;

b4.2.2) a $(C_1-C_{16})$alkyl- group, for instance an isopropyl group;

b4.2.3) a $CH_3$—[O—$(CH_2)_2]_n$— group with n being an integer from 1 to 30, for instance n being 6 or 8;

b4.2.5) a $(C_1-C_6)$alkyl-NH—C(O)— group, for instance a $CH_3$—$CH_2$—NH—C(O)— group;

b4.2.6) a $(C_1-C_{16})$alkyl-C(O)— group, for instance $CH_3$—C(O)—;

b4.2.7) a $(C_1-C_{16})$alkyl-O—C(O)— group, for instance a $CH_3$—$CH_2$—O—C(O)— group;

b4.2.8) a $CH_3$—[O—$(CH_2)_2]_n$—C(O)— group with n being an integer from 1 to 30, for instance n being 1;

b4.2.9) a $(C_3-C_{10})$cycloalkyl- group, for instance a cyclobutyl group, said cycloalkyl group being unsubstituted or substituted by at least one substituent, for instance one to five substituents, such as one $(C_1-C_6)$alkyl group, for instance a methyl group;

b4.2.10) a $(C_3-C_{10})$ membered heterocycloalkyl- group comprising from one heteroatom which is $—SO_2—$, for instance a thietane dioxide group;

b4.2.12) a $(C_1-C_6)$alkoxy-phenyl-$(C_1-C_6)$alkyl-O—C(O)— group, for instance a $CH_3$—O-para-phenyl-$CH_2$—O—C(O)— group;

or $R_4$ and $R_5$ form together with the nitrogen atom to which they are attached a $(C_3-C_{10})$membered heterocycloalkyl- group comprising one to four heteroatoms selected from oxygen, nitrogen and sulfur, said $(C_3-C_{10})$membered heterocycloalkyl- group being unsubstituted or substituted by at least one substituent selected from a $(C_1-C_6)$alkyl- group, and a $CH_3$—[O—$(CH_2)_2]_n$— group with n being an integer from 1 to 30, for instance $R_4$ and $R_5$ form together with the nitrogen atom to which they are attached a piperazinyl;

c) a $(C_3-C_{10})$cycloalkyl$(C_1-C_6)$alkyl- group, for instance a cyclohexyl-$CH_2$— group, said cycloalkyl being unsubstituted or substituted by at least one substituent, for instance one to five substituents, such as one substituent selected from $NH_2$, and a $NH_2$—$(C_1-C_6)$alkyl- group, for instance a $NH_2$—$CH_2$— group;

d) a $(C_3-C_{10})$membered heterocycloalkyl$(C_1-C_6)$alkyl- group, for instance a piperazinyl-$(CH_2)_2$— group or a piperidinyl-$(CH_2)_2$— group, said heterocycloalkyl group comprising 1 to 2 nitrogen heteroatoms, for instance a piperazinyl group or a piperidinyl group;

e) a $(C_5-C_{10})$membered heteroaryl$(C_1-C_6)$alkyl- group, for instance a pyridyl-$CH_2$— group, said heteroaryl comprising one nitrogen heteroatom, for instance a pyridyl group, said heteroaryl being unsubstituted or substituted by at least one substituent, for instance one to three substituents, such as one substituent, which is a cyano group;

f) a $(C_3-C_{10})$membered heterocycloalkyl-NH—$(C_1-C_{16})$alkyl- group, said heterocycloalkyl group comprising one to four heteroatoms, for instance one heteroatom, selected from oxygen, nitrogen, S(O), $SO_2$ and sulfur, for instance a dioxothietanyl-NH—$(CH_2)_4$— group and g) a $(C_3-C_{10})$membered heterocycloalkyl- N(C(O)—$(C_1-C_6)$alkyl)-$(C_1-C_{16})$alkyl- group, said heterocycloalkyl group comprising one to four heteroatoms, for instance one heteroatom, selected from oxygen, nitrogen, S(O), $SO_2$ and sulfur, for instance a tetrahydropyranyl-N(C(O)—$(CH_3)$)—$(CH_2)_4$— group, a tetrahydropyranyl-N(C(O)—$(CH_3)$)—$(CH_2)_6$— group, a dioxothietanyl-N(C(O)—$(CH_3)$)—$(CH_2)_4$— group or a dioxothietanyl-N(C(O)—$(CH_3)$)—$(CH_2)_6$— group;

$R_2$ represents a group selected from:

a $(C_1-C_6)$alkyl group, for instance a n-butyl group or a n-propyl group;

a $(C_1-C_6)$alkoxy$(C_1-C_6)$alkyl- group, for instance $CH_3CH_2$—O—$CH_2$— group and a $(C_1-C_6)$alkyl-S(O)— group, for instance a $CH_3CH_2CH_2$—S(O)— group;

$R_3$ represents a group selected from:

a) a ($C_1$-$C_6$)alkyl- group, for instance an isopropyl group, an isobutyl group, or an isopentyl group;

a ($C_2$-$C_6$)alkenyl- group, for instance a propenyl group such as $C(CH_3)({=}CH_2)$—, a butenyl group such as $(CH_3)_2C{=}CH$—, or a pentenyl group such as $(CH_3)_2CH—CH{=}CH$—;

a ($C_1$-$C_6$)alkylthio- group, for instance an isopropylthio- group;

b) a —$OR_6$ group, $R_6$ being:

a ($C_1$-$C_6$)alkyl- group, for instance a methyl group, an isopropyl group, a n-propyl group, a n-butyl group, or a sec-butyl group;

a $CH_3—[O—(CH_2)_2]_n$— group with n being an integer from 1 to 30, for instance $CH_3—O—(CH_2)_2$—;

a ($C_2$-$C_6$)alkenyl- group, for instance a propenyl group such as $—CH_2—CH{=}CH_2$;

a ($C_3$-$C_{10}$)cycloalkyl group, for instance a cyclopentyl group;

a phenyl group;

a phenyl($C_1$-$C_6$)alkyl)- group, for instance a benzyl group; or a ($C_3$-$C_{10}$)membered heterocycloalkyl- group comprising one heteroatom selected from oxygen, sulfur, —S(O)— and —$SO_2$—, for instance a tetrahydropyranyl group, a thiolane dioxide group, a thiolane group, a thiolane oxide group, and a tetrahydrofuranyl group;

c) a —$NR_7R_8$ group, $R_7$ and $R_8$ being independently from each other selected from:

a hydrogen atom;

a $CH_3—[O—(CH_2)_2]_n$— group with n being an integer from 1 to 30, for instance $CH_3—O—(CH_2)_2$—;

a ($C_1$-$C_6$)alkyl group, for instance a methyl group, or an isopropyl group, said ($C_1$-$C_6$)alkyl group being unsubstituted or substituted by a phenyl group (to form for instance a benzyl group), said phenyl group being unsubstituted or substituted by at least one $NH_2$—($C_1$-$C_6$)alkyl-, for instance one to five $NH_2$—($C_1$-$C_6$)alkyl-, such as one $NH_2$—($C_1$-$C_6$)alkyl-, such as $NH_2—CH_2$—:

or $R_7$ and $R_8$ form together with the nitrogen atom to which they are attached a ($C_3$-$C_{10}$) membered heterocycloalkyl- group comprising one nitrogen heteroatom, for instance a pyrrolidinyl group;

d) a ($C_3$-$C_{10}$)membered heterocycloalkyl- group comprising one oxygen heteroatom, for instance a tetrahydrofuranyl group or a dihydrofuranyl group;

e) a ($C_5$-$C_{10}$)membered heteroaryl- group comprising one to two heteroatoms selected from oxygen, nitrogen, and sulfur, for instance a thienyl group, a furanyl group, or a pyrrolyl group, said ($C_5$-$C_{10}$)membered heteroaryl- group being unsubstituted or substituted by at least one ($C_1$-$C_6$)alkyl- group, for instance one to three ($C_1$-$C_6$) alkyl- groups, such as one ($C_1$-$C_6$)alkyl- group, for instance a methyl group and g) a ($C_3$-$C_{10}$)cycloalkyl group, for instance a cyclopentenyl group, a cyclopentyl group, a cyclohexenyl group or a cyclohexyl group.

According to another embodiment, the disclosure relates to a compound of formula (I) or a pharmaceutically acceptable salt thereof:

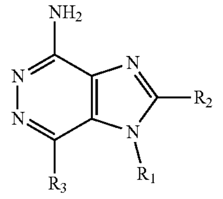

(I)

wherein:

$R_1$ represents a hydrogen atom or a group selected from:

a)

a ($C_1$-$C_6$)alkyl- group, for instance a methyl group;

a hydroxy-($C_1$-$C_6$)alkyl- group, for instance a $C(OH)(CH_3)_2—CH_2$— group a $C(CH_3)(CH_2OH)_2—CH_2$— group or a $CH(CH_2OH)_2—CH_2$— group;

b)

a phenyl($C_1$-$C_6$)alkyl- group, for instance a benzyl group, the phenyl group being unsubstituted or substituted by at least one ($C_1$-$C_6$)alkyl- group, for instance one to five ($C_1$-$C_6$)alkyl- groups, such as one ($C_1$-$C_6$)alkyl- group, for instance a methyl group, such as a methyl group in para and/or meta position(s) of the phenyl group, said alkyl group which can substitute said phenyl group being itself unsubstituted or substituted by at least one —$NR_4R_5$ group, for instance one —$NR_4R_5$ group, $R_4$ and $R_5$ being independently from each other:

b4.2.1) a hydrogen atom;

b4.2.2) a ($C_1$-$C_{16}$)alkyl- group, for instance a methyl group, a hexyl group or a decyl group;

b4.2.3) a $CH_3—[O—(CH_2)_2]_n$— group with n being an integer from 1 to 30, for instance n being 1, 2, 3, 4, or 12;

b4.2.4) a ($C_1$-$C_6$)alkyl-$S(O_2)$— group, for instance a $CH_3—S(O_2)$— group;

b4.2.6) a ($C_1$-$C_{16}$)alkyl-C(O)— group for instance a $CH_3—CH_2C(O)$— group;

b4.2.9) a ($C_3$-$C_{10}$)cycloalkyl- group, for instance a cyclopropyl group or a cyclobutyl group, said cycloalkyl group being unsubstituted or substituted by at least one ($C_1$-$C_6$)alkyl- group, for instance one to five ($C_1$-$C_6$)alkyl- groups, such as one ($C_1$-$C_6$)alkyl- group, for instance one methyl group or by at least one hydroxyl group;

b4.2.10) a ($C_3$-$C_{10}$)membered heterocycloalkyl- group comprising from one to four heteroatoms selected from oxygen, nitrogen, sulfur, —S(O)— and —$SO_2$, for instance a thietane dioxide group;

b4.2.11) a phenyl-C(O)— group;

b4.2.13) a ($C_1$-$C_{16}$)alkyl-C(O)—NH-phenyl-($C_1$-$C_6$)alkyl-O—C(O)— group, for instance a $CH_3$—C(O)—NH-phenyl-$CH_2$—O—C(O)— group;

b4.2.14) a ($C_1$-$C_{16}$)alkyl-O—C(O)—($C_1$-$C_6$)alkyl- group for instance a $C(CH_3)_3—O—C(O)—CH_2$— group or a $C(CH_3)_3—O—C(O)—(CH_2)_2$— group;

or $R_4$ and $R_5$ form together with the nitrogen atom to which they are attached a ($C_3$-$C_{10}$)membered heterocycloalkyl- group comprising one to four heteroatoms selected from oxygen, nitrogen and sulfur, for instance one to two heteroatoms selected from nitrogen and oxygen, said ($C_3$-$C_{10}$)membered heterocycloalkyl- group being unsubstituted or substituted by at least one substituent selected from a ($C_1$-$C_6$)alkyl- group, and a $CH_3$—[O—$(CH_2)_2]_n$— group with n being an integer from 1 to 30, for instance $R_4$ and $R_5$ form together with the nitrogen atom to which they are attached a pyrrolidinyl group or a morpholino group;

c)

a ($C_3$-$C_{10}$)cycloalkyl($C_1$-$C_6$)alkyl- group, for instance a cyclohexyl-$CH_2$— group, said cycloalkyl being unsubstituted or substituted by at least one $NH_2$ group, for instance one to five $NH_2$ groups, such as one $NH_2$ group;

e)

a ($C_5$-$C_{10}$) membered heteroaryl($C_1$-$C_6$)alkyl- group, for instance a pyridyl-$CH_2$— group, said heteroaryl comprising one nitrogen heteroatom, for instance a pyridyl group, said heteroaryl being unsubstituted or substituted by at least one $NH_2$—($C_1$-$C_6$)alkyl-group, for instance $NH_2$—$CH_2$—, for instance one to three $NH_2$—($C_1$-$C_6$)alkyl- group, for instance one to three $NH_2$—$CH_2$—, such as one $NH_2$—($C_1$-$C_6$)alkyl- group, for instance one $NH_2$—$CH_2$— and f)

a ($C_3$-$C_{10}$)membered heterocycloalkyl-NH—($C_1$-$C_{16}$) alkyl- group, said heterocycloalkyl group comprising one to four heteroatoms, for instance one heteroatom, selected from oxygen, nitrogen, S(O), $SO_2$ and sulfur, for instance a tetrahydropyranyl-NH—$(CH_2)_4$— group, a tetrahydropyranyl-NH—$(CH_2)_6$— group, or a dioxothietanyl-NH—$(CH_2)_6$— group;

$R_2$ represents a group selected from:

a ($C_1$-$C_6$)alkyl- group, for instance a methyl group, a n-butyl group;

a ($C_1$-$C_6$)alkylthio- group, for instance a $CH_3CH_2CH_2S$— group;

a ($C_1$-$C_6$)alkyl-NH—($C_1$-$C_6$)alkyl- group, for instance a $CH_3CH_2$—NH—$CH_2$— group;

a ($C_1$-$C_6$)alkyl-NH— group for instance a $CH_3CH_2CH_2$—NH— group;

$R_3$ represents a group selected from:

a)

a ($C_1$-$C_6$)alkyl- group, for instance a isopentyl group;

a ($C_2$-$C_6$)alkenyl- group, for instance a $(CH_3)_2$—CH—CH═CH— group;

a ($C_1$-$C_6$)alkylthio- group, for instance an isopropylthio- group b)

a —$OR_6$ group, $R_6$ being a ($C_1$-$C_6$)alkyl- group, for instance an isopropyl group and c)

a —$NR_7R_8$ group, $R_7$ and $R_8$ being independently from each other selected from a hydrogen atom; a ($C_1$-$C_6$)alkyl- group, for instance a methyl group, or an isopropyl group; a ($C_1$-$C_6$)alkyl- group substituted by a phenyl group, for instance a benzyl group, said phenyl group being unsubstituted or substituted by at least one $NR_9R_{10}$—($C_1$-$C_6$)alkyl- group, for instance one to five $NR_9R_{10}$—($C_1$-$C_6$)alkyl- groups, such as one $NR_9R_{10}$—($C_1$-$C_6$) alkyl- group, for instance $NR_9R_{10}$—$CH_2$— group, $R_9$ and $R_{10}$ being independently from each other a ($C_1$-$C_6$)alkyl- group, for instance a methyl group, or a $CH_3$—[O—$(CH_2)_2]_n$— group with n being an integer from 1 to 30, for instance a $CH_3$—O—$(CH_2)_2$— group, or $R_9$ and $R_{10}$ together form with the nitrogen atom to which they are attached a ($C_3$-$C_{10}$) membered heterocycloalkyl group comprising one to two heteroatoms selected from oxygen and nitrogen, for instance a morpholino group or $R_7$ and $R_8$ form together with the nitrogen atom to which they are attached a ($C_3$-$C_{10}$) membered heterocycloalkyl- group comprising one nitrogen heteroatom, for instance a pyrrolidinyl group, said heterocycloalkyl group being unsubstituted or substituted by at least one substituent, for instance one to three substituents, such as one substituent selected from a phenyl group, and a hydroxy($C_1$-$C_6$)alkyl-phenyl-group, for instance a OH—$CH_2$-phenyl group such as a para OH—$CH_2$-phenyl group;

d)

a ($C_3$-$C_{10}$)membered heterocycloalkyl- group comprising one to four heteroatoms selected from oxygen, nitrogen and sulfur for instance a dihydropyrrolyl group or a pyrrolidinyl group or e)

a ($C_5$-$C_{10}$)membered heteroaryl- group comprising one to four heteroatoms selected from oxygen, nitrogen, and sulfur, said ($C_5$-$C_{10}$)membered heteroaryl-group being unsubstituted or substituted by at least one a ($C_1$-$C_6$)alkyl- group, for instance a pyrrolyl group.

According to another embodiment, the disclosure relates to a compound of formula (I) or a pharmaceutically acceptable salt:

(I)

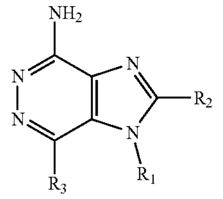

wherein:

$R_1$ represents a group selected from:

a)

a ($C_1$-$C_6$)alkyl- group, for instance a methyl group;

a hydroxy-($C_1$-$C_6$)alkyl- group, for instance a C(OH)$(CH_3)_2$—$CH_2$— group, $CH(CH_2OH)_2$—$CH_2$— group or a $C(CH_2OH)_2(CH_3)$—$CH_2$— group;

b)

a phenyl($C_1$-$C_6$)alkyl- group, for instance a benzyl group, the phenyl group being unsubstituted or substituted by at least one ($C_1$-$C_6$)alkyl- group, for instance one to five ($C_1$-$C_6$)alkyl- groups, such as one ($C_1$-$C_6$)alkyl group, for instance a methyl group, such as a methyl group in para and/or meta position(s) of the phenyl group, said alkyl group being itself unsubstituted or substituted by at least one substituent, for instance one substituent, selected from:

b4.1) a hydroxyl group;

b4.2) a —$NR_4R_5$ group, $R_4$ and $R_5$ being independently from each other:

b4.2.1) a hydrogen atom;

b4.2.6) a ($C_1$-$C_{16}$)alkyl-C(O)— group, for instance a $CH_3$—C(O)— group;

b4.2.9) a ($C_3$-$C_{10}$)cycloalkyl group, for instance a cyclopropyl group or a cyclobutyl group, said cycloalkyl group being unsubstituted or substituted by at least one ($C_1$-$C_6$)alkyl- group, for instance one to five $(C_1-C_6)$alkyl- groups, such as one $(C_1-C_6)$alkyl- group, for instance a methyl group;

or $R_4$ and $R_5$ form together with the nitrogen atom to which they are attached a $(C_3-C_{10})$membered heterocycloalkyl- group comprising one to four heteroatoms selected from oxygen, nitrogen and sulfur, for instance a nitrogen atom;

c)

a $(C_3-C_{10})$cycloalkyl$(C_1-C_6)$alkyl- group, for instance a cyclohexyl-$CH_2$— group, said cycloalkyl being unsubstituted or substituted by at least one substituent, for instance one to five substituents, such as one substituent selected from $NH_2$, and a $NH_2$—$(C_1-C_6)$alkyl- group, for instance a $NH_2$—$CH_2$— group; and e)

a $(C_5-C_{10})$ membered heteroaryl$(C_1-C_6)$alkyl- group, for instance a pyridyl-$CH_2$— group, said heteroaryl comprising one nitrogen heteroatom, for instance a pyridyl group, said heteroaryl being unsubstituted or substituted by at least one $NH_2$—$(C_1-C_6)$alkyl- group, for instance one to three $NH_2$—$(C_1-C_6)$alkyl- groups, such as one $NH_2$—$(C_1-C_6)$alkyl- group, for instance a $NH_2$—$CH_2$— group;

$R_2$ represents a group selected from:

a $(C_1-C_6)$alkyl- group, for instance a n-butyl group;

a $(C_1-C_6)$alkoxy$(C_1-C_6)$alkyl- group, for instance a $CH_3CH_2$—O—$CH_2$— group;

a $(C_1-C_6)$alkylthio- group, for instance a $CH_3CH_2CH_2$—S— group;

a $(C_1-C_6)$alkyl-NH—$(C_1-C_6)$alkyl- group, for instance a $CH_3CH_2$—NH—$CH_2$— group;

a $(C_1-C_6)$alkyl-NH— group, for instance a $CH_3CH_2CH_2$—NH— group;

$R_3$ represents a group selected from:

b)

a —$OR_6$ group, $R_6$ being a $(C_1-C_6)$alkyl- group, for instance an isopropyl group and c)

a —$NR_7R_8$ group, $R_7$ and $R_8$ being independently from each other selected from a $(C_1-C_6)$alkyl- group, for instance a methyl group; and a $(C_1-C_6)$alkyl- group substituted by a phenyl group, for instance a benzyl group, said phenyl group being unsubstituted or substituted by at least one $NR_9R_{10}$—$(C_1-C_6)$alkyl- group, for instance one to five $NR_9R_{10}$—$(C_1-C_6)$alkyl- groups, such as one $NR_9R_{10}$—$(C_1-C_6)$alkyl- group, for instance a $NR_9R_{10}$—$CH_2$— group, $R_9$ and $R_{10}$ being independently from each other a $(C_1-C_6)$alkyl group, for instance a methyl group or a $CH_3$—[O—$(CH_2)_2]_n$— with n being an integer from 1 to 30, for instance a —$(CH_2)_2$—$OCH_3$ group or d)

a $(C_3-C_{10})$membered heterocycloalkyl- group comprising one to four heteroatoms selected from oxygen, nitrogen and sulfur for instance a dihydropyrrolyl group.

According to another embodiment, the disclosure relates to a compound of formula (I) or a pharmaceutically acceptable salt:

(I)

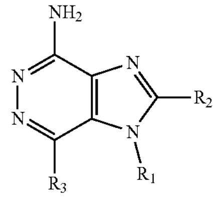

wherein:

$R_1$ represents:

a hydrogen atom, or a group selected from:

a)

a $(C_1-C_6)$alkyl- group for instance a methyl group;

b)

a phenyl$(C_1-C_6)$alkyl- group, for instance a phenylmethyl- group (that is to say a benzyl group) being unsubstituted or substituted by at least one substituent selected from:

b1) a $(C_1-C_6)$alkoxy- group, for instance a methoxy group; and b4) a $(C_1-C_6)$alkyl- group, for instance a methyl group, being unsubstituted or substituted by at least one:

b4.2) —$NR_4R_5$ group wherein $R_4$ and $R_5$, being independently from each other selected from:

b4.2.1) a hydrogen atom; and b4.2.3) a $CH_3$—[O—$(CH_2)_2]_n$— group with n being an integer from 1 to 30, for instance n is 12; and c) a $(C_3-C_{10})$cycloalkyl$(C_1-C_6)$alkyl- group, for instance a cyclohexylmethyl- group, being unsubstituted or substituted by at least one —$NH_2$ group;

$R_2$ represents a group selected from:

a $(C_1-C_6)$alkyl- group for instance a methyl group or a n-butyl group;

a $(C_1-C_6)$alkyl-NH—$(C_1-C_6)$alkyl- group, for instance a $CH_3CH_2$—NH—$CH_2$— group; and a $(C_1-C_6)$alkyl-NH— group, for instance a $CH_3CH_2CH_2$—NH— group;

$R_3$ represents:

a hydrogen atom or a group selected from:

b)

a —$OR_6$ group wherein $R_6$ is selected from:

a hydrogen atom; and a $(C_1-C_6)$alkyl- group, for instance an isopropyl group;

c)

a —$NR_7R_8$ group wherein $R_7$ and $R_8$ being, independently from each other, selected from:

a hydrogen atom;

a $(C_1-C_6)$alkyl- group, for instance a methyl group or an isopropyl group, unsubstituted or substituted by a phenyl group being unsubstituted or substituted by at least one:

a $NR_9R_{10}$—$(C_1-C_6)$alkyl- group wherein:

$R_9$ and $R_{10}$ together form with the nitrogen atom to which they are attached a $(C_3-C_{10})$membered heterocycloalkyl- group comprising one to four heteroatoms selected from oxygen, nitrogen, and sulfur, for instance a piperazinyl group, said $(C_3-C_{10})$membered heterocycloalkyl group being unsubstituted or substituted by at least one substituent selected from a $(C_1-C_6)$alkyl- group, for instance a methyl group;

d)

a $(C_3-C_{10})$membered heterocycloalkyl- group comprising one to four heteroatoms selected from oxygen, nitrogen and sulfur, for instance a dihydropyrrolyl group or a pyrrolidinyl group; and e)

a $(C_5-C_{10})$membered heteroaryl- group comprising one to four heteroatoms selected from oxygen, nitrogen, and sulfur, for instance a pyrazolyl group or a pyrrolyl group, said $(C_5-C_{10})$membered heteroaryl- group being unsubstituted or substituted by at least one $(C_1-C_6)$alkyl- group, for instance a methyl group.

In the present disclosure, the ∿∿∿ symbol on the bond denotes a covalent attachment site.

When $R_1$ represents a $(C_1-C_6)$alkyl- group, examples of suitable $R_1$ groups that may be mentioned include a methyl group, an ethyl group, a propyl group, a butyl group, a pentyl group or an hexyl group, for instance a methyl group, an ethyl group, a propyl group or a butyl group, such as a methyl group.

When $R_1$ represents a hydroxy-$(C_1-C_6)$alkyl- group, examples of suitable $R_1$ groups that may be mentioned include a hydroxymethyl group, a dihydroxyethyl group, a hydroxypropyl group, a hydroxybutyl group, a dihydroxybutyl group, a trihydoxybutyl group, a hydroxypentyl group, a dihydroxypentyl group, a hydroxyhexyl group, for instance a hydroxybutyl group such as $C(OH)(CH_3)_2—CH_2—$, a dihydroxybutyl group such as $CH(CH_2OH)_2—CH_2—$, or a dihydroxypentyl group such as $C(CH_3)(CH_2OH)_2—CH_2—$. In other terms, at least one hydroxyl group replaces a hydrogen atom belonging to the alkyl moiety.

When $R_1$ represents a $NH_2—(C_1-C_6)$alkyl- group, examples of suitable $R_1$ groups that may be mentioned include a $NH_2$-methyl- group, a $NH_2$-ethyl- group, a $NH_2$-propyl- group, a $NH_2$-butyl- group, a $NH_2$-pentyl- group or a $NH_2$-hexyl- group, for instance a $NH_2$-butyl- group such as $NH_2—(CH_2)_4—$, a $NH_2$-pentyl- group such as $NH_2—(CH_2)_5—$, or a $NH_2$-hexyl- group such as $NH_2—(CH_2)_6—$.

When $R_1$ represents a $NH—(C_1-C_6)$alkyl)-$(C_1-C_6)$alkyl- group, examples of suitable $R_1$ groups that may be mentioned include a $NH(CH_3)—CH_2—$ group, a $NH(C_2H_5)—CH_2—$ group, a $NH(CH_3)—(CH_2)_3—$ group or a $NH(C_3H_7)—(CH_2)_6—$ group.

When $R_1$ represents a $N((C_1-C_6)alkyl)_2$-$(C_1-C_6)$alkyl- group, examples of suitable $R_1$ groups that may be mentioned include a $N(CH_3)_2—CH_2—$ group, a $N(CH_3)(C_2H_5)—CH_2—$ group, a $N(C_3H_7)(CH_3)—(CH_2)_3—$ group or a $NH(C_4H_9)—(CH_2)_6—$ group.

When $R_1$ represents a $(C_2-C_6)$alkenyl- group, examples of suitable $R_1$ groups that may be mentioned include an ethenyl (or vinyl) group, a propenyl group, a butenyl group, a pentenyl group, or a hexenyl group, for instance a vinyl group or a propenyl group.

When $R_1$ represents a $(C_2-C_6)$alkynyl- group, examples of suitable $R_1$ groups that may be mentioned include an ethynyl group, a propynyl group, a butynyl group, a pentynyl group, or a hexynyl group, for instance an ethynyl group or a propynyl group.

When $R_1$ represents a phenyl$(C_1-C_6)$alkyl- group, examples of suitable $R_1$ groups that may be mentioned include a benzyl group, a phenylpropyl group, a phenylbutyl group, a phenylpentyl group, or a phenylhexyl group, for instance a benzyl group.

When $R_1$ represents a phenyl$(C_1-C_6)$alkyl- group, that the phenyl group is substituted by a $(C_1-C_6)$alkyl group, for instance a methyl group, such as a methyl group in para and/or meta position(s) of the phenyl group, and that said $(C_1-C_6)$alkyl group is itself substituted by a $—NR_4R_5$ group, examples of suitable $(C_3-C_{10})$membered heterocycloalkyl groups for $R_4$ and $R_5$ groups that may be mentioned include: piperazine, morpholino, pyrrolidine, tetrahydropyrane, thietane dioxide, piperidine, thiolane, thiolane oxide, thiolane dioxide, dihydrofurane, tetrahydrofurane, azetidine, oxetane, thietane, 2H-pyrrole, 1H-, 2H- or 3H-pyrroline, tetrahydrothiophene, oxadiazole, 1,3,4-oxadiazole, 1,3,5-oxadioazole, thiadiazole, 1,3,4-thiadiazole, isoxazoline, 2- or 3-pyrazoline, pyrroline, pyrazolidine, imidazoline, imidazolidine, thiazolidine, isooxazoline, isoxazolidine, dioxalane, oxathiazole, oxathiadiazole, and dioxazole groups, for instance tetrahydropyrane or thietane dioxide such as

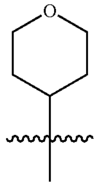

and

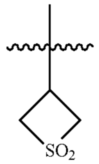

When $R_1$ represents a phenyl$(C_1-C_6)$alkyl- group, that the phenyl group is substituted by a $(C_1-C_6)$alkyl group, for instance a methyl group, such as a methyl group in para and/or meta position(s) of the phenyl group, and that said $(C_1-C_6)$alkyl group is itself substituted by a $—NR_4R_5$ group, examples of suitable unsubstituted or substituted $(C_3-C_{10})$cycloalkyl groups for $R_4$ and $R_5$ groups that may be mentioned include a cyclopropyl group, a cyclobutyl group, a cyclopentyl group, a cyclohexyl group, a cyclopropenyl group, a cyclobutenyl group, a cyclopentenyl group, or a cyclohexenyl group, for instance a cyclopropyl group or a cyclobutyl group, such as

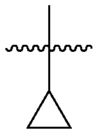

,

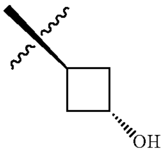

and

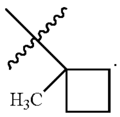

.

When $R_1$ represents a phenyl$(C_1-C_6)$alkyl- group, that the phenyl group is substituted by a $(C_1-C_6)$alkyl group, for instance a methyl group, such as a methyl group in para and/or meta position(s) of the phenyl group, and that said $(C_1-C_6)$alkyl group is itself substituted by a $—NR_4R_5$ group wherein $R_4$ and $R_5$ form together with the nitrogen atom to which they are attached a $(C_3-C_{10})$membered heterocycloalkyl- group, examples of suitable $—NR_4R_5$ group that may be mentioned include an unsubstituted or substituted $(C_3-C_{10})$membered heterocycloalkyl- group, for instance an unsubstituted or substituted piperazinyl group, an unsubstituted or substituted morpholino group or an unsubstituted or substituted pyrrolidinyl group, such as

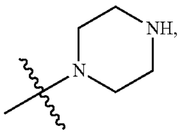
,
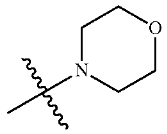
and
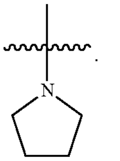
.

When $R_1$ represents an unsubstituted or substituted ($C_5$-$C_{10}$) membered heteroaryl($C_1$-$C_6$)alkyl- group, examples of suitable $R_1$ groups that may be mentioned include a pyridyl-$CH_2$— group, a pyridyl-$(CH_2)_2$— group, a pyridyl-$(CH_2)_3$— group, a pyridyl-$(CH_2)_4$— group, a pyridyl-$(CH_2)_5$— group, a pyridyl-$(CH_2)_6$— group, a pyridyl-$(C(CH_3)_2)$- group, for instance a pyridyl-$CH_2$— group in which the pyridyl group is unsubstituted or substituted and is for example as follows:

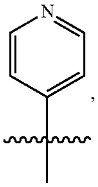
,
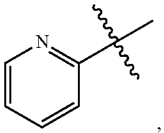
,
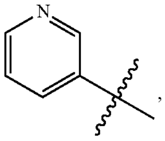
,
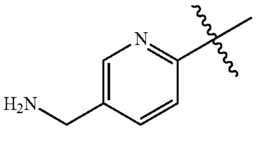
and
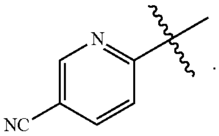
.

When $R_1$ represents a ($C_3$-$C_{10}$) membered heterocycloalkyl($C_1$-$C_6$)alkyl- group, examples of suitable $R_1$ groups that may be mentioned include a piperazinyl($C_1$-$C_6$)alkyl- group, a piperidinyl($C_1$-$C_6$)alkyl- group, a morpholino($C_1$-$C_6$)alkyl- group, a tetrahydofuran ($C_1$-$C_6$)alkyl- group, or a tetrahydropyran($C_1$-$C_6$)alkyl- group, for instance a piperazinyl-$(CH_2)_2$— group, a piperazinyl-$CH_2$— group, a piperazinyl-$(CH_2)_3$— group, a piperazinyl-$(CH_2)_4$— group, a piperidinyl-$(CH_2)$— group or a piperidinyl-$(CH_2)_2$— group, such as

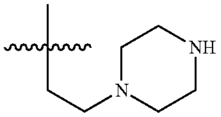
and
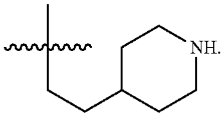
.

When $R_1$ represents an unsubstituted or substituted ($C_3$-$C_{10}$)cycloalkyl($C_1$-$C_6$)alkyl- group, examples of suitable $R_1$ groups that may be mentioned include a cyclopropyl($C_1$-$C_6$)alkyl- group, a cyclopropenyl($C_1$-$C_6$)alkyl- group, a cyclobutyl($C_1$-$C_6$)alkyl- group, a cyclobutenyl($C_1$-$C_6$)alkyl- group, a cyclopentyl($C_1$-$C_6$)alkyl- group, a cyclopentenyl ($C_1$-$C_6$)alkyl- group, a cyclohexyl($C_1$-$C_6$)alkyl- group, a cyclooctyl($C_1$-$C_6$)alkyl- group, a cyclononyl($C_1$-$C_6$)alkyl- group, or a cyclodecyl($C_1$-$C_6$)alkyl- group, for instance a cyclohexyl-$CH_2$— group in which the cyclohexyl group is unsubstituted or substituted, such as:

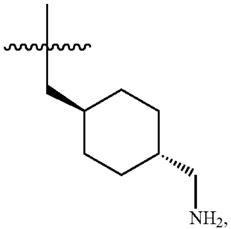
,
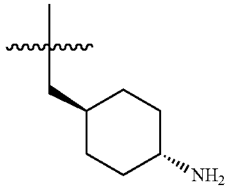
,
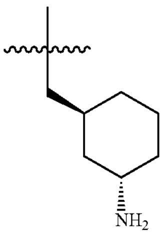
and
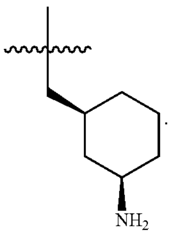
.

When $R_1$ represents a ($C_3$-$C_{10}$) membered heterocycloalkyl-NH—($C_1$-$C_{16}$)alkyl- group, examples of suitable $R_1$ groups that may be mentioned include a dioxothietanyl-NH—($C_1$-$C_{16}$ alkyl- group, a piperazinyl-NH—($C_1$-$C_{16}$) alkyl- group, a piperidinyl-NH—($C_1$-$C_{16}$)alkyl- group, a morpholino-NH—($C_1$-$C_{16}$)alkyl- group, a tetrahydofuranyl-NH—($C_1$-$C_{16}$)alkyl- group, or a tetrahydropyranyl-NH—($C_1$-$C_{16}$)alkyl- group, for instance a tetrahydropyranyl-NH—$(CH_2)_4$— group, a tetrahydropyranyl-NH—$(CH_2)_6$— group, a dioxothietanyl-NH—$(CH_2)_4$— group, a dioxothietanyl-NH—$(CH_2)_6$— group such as

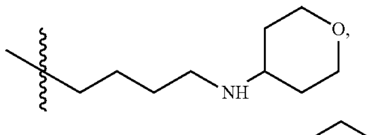
,
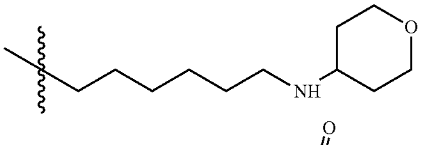
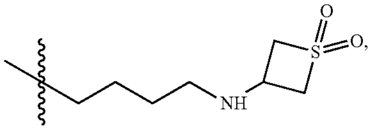
, and
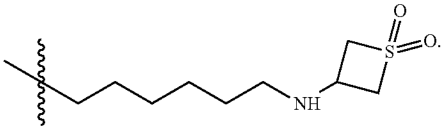
.

When $R_1$ represents a ($C_3$-$C_{10}$) membered heterocycloalkyl-N(C(O)—($C_1$-$C_6$)alkyl)-($C_1$-$C_{16}$)alkyl- group, examples of suitable $R_1$ groups that may be mentioned include a dioxothietanyl-N(C(O)—($C_1$-$C_6$)alkyl)-($C_1$-$C_{16}$) alkyl- group, a piperazinyl-N(C(O)—($C_1$-$C_6$)alkyl)-($C_1$-$C_{16}$)alkyl- group, a piperidinyl-N(C(O)—($C_1$-$C_6$)alkyl)-($C_1$-$C_{16}$)alkyl- group, a morpholino-N(C(O)—($C_1$-$C_6$) alkyl)-($C_1$-$C_{16}$)alkyl- group, a tetrahydofuranyl-N(C(O)—($C_1$-$C_6$)alkyl)-($C_1$-$C_{16}$)alkyl- group, or a tetrahydropyranyl-N(C(O)—($C_1$-$C_6$)alkyl)-($C_1$-$C_{16}$)alkyl- group, for instance a tetrahydropyranyl-N(C(O)$CH_3$)—$(CH_2)_4$— group, a tetrahydropyranyl-N(C(O)$CH_3$)—$(CH_2)_6$— group, a dioxothietanyl-N(C(O)$CH_3$)—$(CH_2)_4$— group, a dioxothietanyl-N (C(O)$CH_3$)—$(CH_2)_6$— group such as

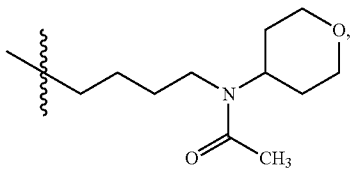

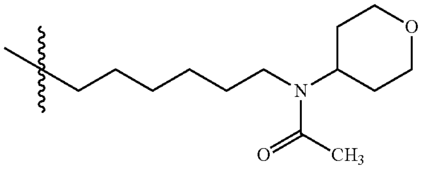

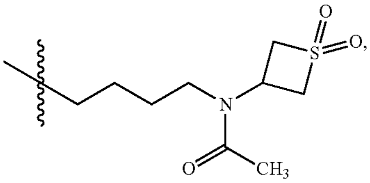

and

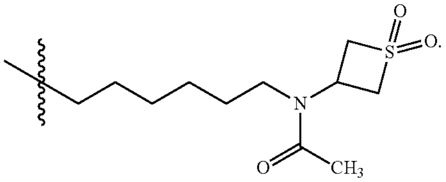

When $R_2$ represents a ($C_1$-$C_6$)alkyl- group, examples of suitable $R_2$ groups that may be mentioned include: a methyl group, an ethyl group, a propyl group, a butyl group, a pentyl group or a hexyl group, for instance a methyl group, an ethyl group, a propyl group such as a n-propyl group, a butyl group such as a n-butyl group.

When $R_2$ represents a ($C_2$-$C_6$)alkenyl- group, examples of suitable $R_2$ groups that may be mentioned include an ethenyl (or vinyl) group, a propenyl group, a butenyl group, a pentenyl group, or a hexenyl group, for instance a vinyl group or a propenyl group.

When $R_2$ represents a ($C_2$-$C_6$)alkynyl- group, examples of suitable $R_2$ groups that may be mentioned include an ethynyl group, a propynyl group, a butynyl group, a pentynyl group, or a hexynyl group, for instance an ethynyl group or a propynyl group.

When $R_2$ represents a ($C_1$-$C_6$)alkylthio- group, examples of suitable $R_2$ groups that may be mentioned include a methylthio group, an ethylthio group, a propylthio group, a butylthio group, a pentylthio group or a hexylthio group, for instance a propylthio group such as $CH_3$—$(CH_2)_2$—S—.

When $R_2$ represents a ($C_1$-$C_6$)alkylthio($C_1$-$C_6$)alkyl- group, examples of suitable $R_2$ groups that may be mentioned include a methythiomethyl group, a methylthioethyl group, an ethylthiopropyl group, a butylthioethyl group, a pentylthiohexyl group, for instance $CH_3$—S—$(CH_2)_2$—.

When $R_2$ represents a ($C_1$-$C_6$)alkyl-S(O)— group, examples of suitable $R_2$ groups that may be mentioned include a methyl-S(O)— group, an ethyl-S(O)— group, a propyl-S(O)— group, a butyl-S(O)— group, a pentyl-S (O)— group, a hexyl-S(O)— group, for instance a methyl-S(O)— group, an ethyl-S(O)— group or a propyl-S(O)— group.

When $R_2$ represents a ($C_1$-$C_6$)alkyl-$SO_2$— group, examples of suitable $R_2$ groups that may be mentioned include a methyl-$SO_2$— group, an ethyl-$SO_2$— group, a propyl-$SO_2$— group, a butyl-$SO_2$— group, a pentyl-$SO_2$— group, a hexyl-$SO_2$— group, for instance a methyl-$SO_2$— group or an ethyl-$SO_2$— group.

When $R_2$ represents a ($C_1$-$C_6$)alkyl-S(O)—($C_1$-$C_6$)alkyl- group, examples of suitable $R_2$ groups that may be mentioned include a methyl-S(O)-methyl group, an ethyl-S(O)-propyl group, or a pentyl-S(O)-hexyl group When $R_2$ represents a ($C_1$-$C_6$)alkyl-$SO_2$—($C_1$-$C_6$)alkyl- group, examples of suitable $R_2$ groups that may be mentioned include a methyl-$SO_2$-methyl- group, an ethyl-$SO_2$-propyl- group, a hexyl-$SO_2$-butyl- group.

When $R_2$ represents a ($C_1$-$C_6$)alkoxy- group, examples of suitable $R_2$ groups that may be mentioned include a methoxy group, an ethoxy group, a propoxy group such as a n-propoxy group or an isopropoxy group, a butoxy group such as a n-butoxy group, a sec-butoxy group, a tertio-butoxy or an isobutoxy group, a pentyloxy group such as a n-pentyloxy group, an isopentyloxy group or a tertio-pentyloxy group, or a hexyloxy group such as a n-hexyloxy group, an isohexyloxy group or a tertio-hexyloxy group.

When $R_2$ represents a ($C_1$-$C_6$)alkoxy($C_1$-$C_6$)alkyl- group, examples of suitable $R_2$ groups that may be mentioned include a methoxymethyl group, a methoxyethyl group, an ethoxypropyl group, a butoxyethyl group, such as $CH_3$—$CH_2$—O—$CH_2$— or $CH_3$—O—$(CH_2)_2$—.

When $R_2$ represents a ($C_1$-$C_6$)haloalkoxy($C_1$-$C_6$)alkyl- group, examples of suitable $R_2$ groups that may be mentioned include a trifluoromethoxymethyl group, or a difluoromethoxyethyl group, When $R_2$ represents a ($C_3$-$C_5$)cycloalkyl-O—($C_1$-$C_6$)alkyl- group, examples of suitable $R_2$ groups that may be mentioned include a cyclopropyl-O-methyl group, a cyclopropyl-O-ethyl group, cyclopropyl-O-hexyl group, a cyclopropenyl-O-ethyl group, a cyclobutyl-O-methyl group, a cyclobutyl-O-propyl group, a cyclobutenyl-O-butyl group, a cyclopentyl-O-methyl group, a cyclopentyl-O-ethyl group or a cyclopentenyl-O-ethyl group, such as a cyclobutyl-O-methyl group or a cyclopentyl-O-ethyl group.

When $R_2$ represents a ($C_1$-$C_6$)alkyl-NH— group, examples of suitable $R_2$ groups that may be mentioned include a methyl-NH— group, an ethyl-NH— group, a propyl-NH— group, a butyl-NH— group, a pentyl-NH— group or a hexyl- NH— group such as $CH_3NH$—, $CH_3CH_2NH$—, or $CH_3CH_2CH_2NH$—.

When $R_2$ represents a (($C_1$-$C_6$)alkyl)$_2$-N— group, examples of suitable $R_2$ groups that may be mentioned include a $(CH_3)_2$—N— group, a $(C_2H_5)_2$—N— group, a $(CH_3)(C_2H_5)$N— group or a $(C_3H_7)_2$—N— group.

When $R_2$ represents a ($C_1$-$C_6$)alkyl-NH—($C_1$-$C_6$)alkyl- group, examples of suitable $R_2$ groups that may be mentioned include a $CH_3$—NH—$CH_2$— group, a $CH_3$—$CH_2$—NH—$CH_2$— group a $CH_3$—NH—$C_2H_5$— group, or a $C_3H_7$—NH—$CH_2$— group.

When $R_2$ represents a (($C_1$-$C_6$)alkyl)$_2$-N—($C_1$-$C_6$)alkyl- group, examples of suitable $R_2$ groups that may be mentioned include a $(CH_3)_2$—N—$CH_2$— group, a $(CH_3)(C_2H_5)$N—$CH_2$— group or a $(CH_3)(C_2H_5)$N—$C_3H_7$— group.

When $R_3$ represents a ($C_1$-$C_6$)alkyl- group, examples of suitable $R_3$ groups that may be mentioned include: a methyl group, an ethyl group, a propyl group, a butyl group, a pentyl group or a hexyl group, for instance a propyl group, a butyl group, and a pentyl group such as an isopropyl group, an isobutyl group, or an isopentyl group.

When $R_3$ represents a ($C_2$-$C_6$)alkenyl- group, examples of suitable $R_3$ groups that may be mentioned include: an ethenyl (or vinyl) group, a propenyl group, a butenyl group, a pentenyl group, or a hexenyl group, for instance a propenyl group such as $C(CH_3)({=}CH_2)$—, a butenyl group such as $(CH_3)_2C{=}CH$—, or a pentenyl group such as $(CH_3)_2CH$—$CH{=}CH$—.

When $R_3$ represents a $(C_2-C_6)$alkynyl- group, examples of suitable $R_3$ groups that may be mentioned include: an ethynyl group, a propynyl group, a butynyl group, a pentynyl group, or a hexynyl group, for instance an ethynyl group or a propynyl group.

When $R_3$ represents a $(C_1-C_6)$alkylthio- group, examples of suitable $R_3$ groups that may be mentioned include: a methylthio- group, an ethylthio- group, a propylthio- group, a butylthio- group, a pentylthio- group or a hexylthio group, for instance a propylthio- group such as an isopropylthio- group.

When $R_3$ represents a —$OR_6$ group and that $R_6$ is a $(C_1-C_6)$alkyl- group, examples of suitable $R_6$ groups that may be mentioned include: a methyl group, an ethyl group, a propyl group, a butyl group, a pentyl group or a hexyl group, for instance a methyl group, an ethyl group, a propyl group or a butyl group, such as a methyl group, an ethyl group, an isopropyl group, a n-propyl group, a n-butyl group, or a sec-butyl group.

When $R_3$ represents a —$OR_6$ group and that $R_6$ is a $CH_3$—[O—$(CH_2)_2]_n$— group with n being an integer from 1 to 30, examples of suitable $R_6$ groups that may be mentioned include: $CH_3$—O—$(CH_2)_2$—, $CH_3$—[O—$(CH_2)_2]_2$—, $CH_3$—[O—$(CH_2)_2]_3$—, $CH_3$—[O—$(CH_2)_2]_4$—, $CH_3$—[O—$(CH_2)_2]_5$—, $CH_3$—[O—$(CH_2)_2]_6$—, $CH_3$—[O—$(CH_2)_2]_7$—, $CH_3$—[O—$(CH_2)_2]_8$—, $CH_3$—[O—$(CH_2)_2]_9$, $CH_3$—[O—$(CH_2)_2]_{10}$—, $CH_3$—[O—$(CH_2)_2]_{11}$—, $CH_3$—[O—$(CH_2)_2]_{12}$—, $CH_3$—[O—$(CH_2)_2]_{13}$—, $CH_3$—[O—$(CH_2)_2]_{14}$—, $CH_3$—[O—$(CH_2)_2]_{15}$—, $CH_3$—[O—$(CH_{12})_2]_{16}$—, $CH_3$—[O—$(CH_{12})_2]_{17}$—, $CH_3$—[O—$(CH_{12})_2]_{18}$—, $CH_3$—[O—$(CH_2)_2]_{19}$—, $CH_3$—[O—$(CH_2)_2]_{20}$—, $CH_3$—[O—$(CH_2)_2]_{21}$—, $CH_3$—[O—$(CH_2)_2]_{22}$—, $CH_3$—[O—$(CH_2)_2]_{23}$—, $CH_3$—[O—$(CH_2)_2]_{24}$—, $CH_3$—[O—$(CH_2)_2]_{25}$—, $CH_3$—[O—$(CH_2)_2]_{26}$—, $CH_3$—[O—$(CH_2)_2]_{27}$—, $CH_3$—[O—$(CH_2)_2]_{28}$—, $CH_3$—[O—$(CH_2)_2]_{29}$—, $CH_3$—[O—$(CH_2)_2]_{30}$—, such as $CH_3$—[O—$(CH_2)_2]_{24}$— and $CH_3$—O—$(CH_2)_2$—.

When $R_3$ represents a —$OR_6$ group and that $R_6$ is a $(C_2-C_6)$alkenyl- group, examples of suitable $R_6$ groups that may be mentioned include an ethenyl group, a propenyl group, a butenyl group, a pentenyl group, or a hexenyl group, for instance a propenyl group such as $CH{=}CH$—$CH_2$—.

When $R_3$ represents a —$OR_6$ group and that $R_6$ is a $(C_2-C_6)$alkynyl- group, examples of suitable $R_6$ groups that may be mentioned include: an ethynyl group, a propynyl group, a butynyl group, a pentynyl group, or a hexynyl group, for instance an ethynyl group or a propynyl group.

When $R_3$ represents a —$OR_6$ group and that $R_6$ is a $(C_3-C_{10})$cycloalkyl- group, examples of suitable $R_6$ groups that may be mentioned include a cyclopropyl group, a cyclobutyl group, a cyclopentyl group, a cyclohexyl group, a cyclopropenyl group, a cyclobutenyl group, a cyclopentenyl group, or a cyclohexenyl group, for instance a cyclopentyl group.

When $R_3$ represents a —$OR_6$ group and that $R_6$ is a phenyl($(C_1-C_6)$alkyl)- group, examples of suitable $R_6$ groups that may be mentioned include a benzyl group (that is to say a phenylmethyl group), a phenylpropyl group, a phenylbutyl group, a phenylpentyl group, or a phenylhexyl group, for instance a benzyl group.

When $R_3$ represents a —$OR_6$ group and that $R_6$ is a $(C_3-C_{10})$ membered heterocycloalkyl group, examples of suitable $R_6$ groups that may be mentioned include piperazine, morpholino, pyrrolidine, tetrahydropyrane, thietane dioxide, piperidine, thiolane, thiolane oxide, thiolane dioxide, dihydrofurane, tetrahydrofurane, azetidine, oxetane, thietane, 2H-pyrrole, 1H-, 2H- or 3H-pyrroline, tetrahydrothiophene, oxadiazole, 1,3,4-oxadiazole, 1,3,5-oxadioazole, thiadiazole, 1,3,4-thiadiazole, isoxazoline, 2- or 3-pyrazoline, pyrroline, pyrazolidine, imidazoline, imidazolidine, thiazolidine, isooxazoline, isoxazolidine, dioxalane, oxathiazole, oxathiadiazole, and dioxazole groups, for instance piperazine, morpholino, pyrrolidine, tetrahydropyrane, thietane dioxide, piperidine, thiolane, thiolane oxide, thiolane dioxide, dihydrofurane, and tetrahydrofurane groups, such as tetrahydropyrane group, a thiolane dioxide group, a thiolane group, a thiolane oxide group, and a tetrahydrofuranyl group, for example

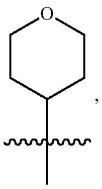,
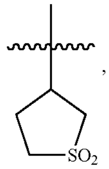,
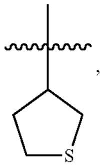,
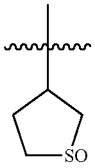,
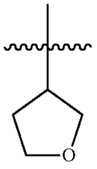
and
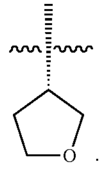.

When $R_3$ represents a —$NR_7R_8$ group and that $R_7$ and $R_8$ form together with the nitrogen to which they are attached an unsubstituted or substituted 3-10 membered heterocycloalkyl group, examples of suitable —$NR_7R_8$ groups that may be mentioned include an unsubstituted or substituted piperazine, morpholino, or pyrrolidine, for instance an unsubstituted or substituted pyrrolidinyl group, such as

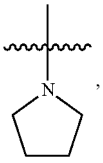,
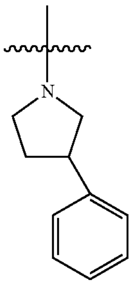
and
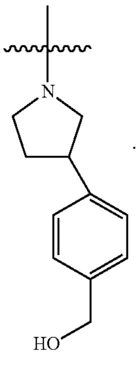.

When $R_3$ represents a —$NR_7R_8$ group and that $R_7$ and/or $R_8$ represents a 5-10 membered heteroaryl$(C_1-C_6)$alkyl- group, examples of suitable $R_7$ and/or $R_8$ groups that may be mentioned include pyridine$(C_1-C_6)$alkyl- group, furan$(C_1-C_6)$alkyl- group, pyrrole$(C_1-C_6)$alkyl- group, thiophene$(C_1-C_6)$alkyl- group, pyrazole$(C_1-C_6)$alkyl- group, oxazole$(C_1-C_6)$alkyl- group, isoxazole$(C_1-C_6)$alkyl- group, triazole$(C_1-C_6)$alkyl- group, tetrazole$(C_1-C_6)$alkyl- group, oxadiazole $(C_1-C_6)$alkyl- group, furazan$(C_1-C_6)$alkyl- group, thiazole $(C_1-C_6)$alkyl- group, isothiazole$(C_1-C_6)$alkyl- group, thiadiazole$(C_1-C_6)$alkyl- group, imidazole$(C_1-C_6)$alkyl-group, pyrimidine($C_1$-$C_6$)alkyl- group, pyridazine($C_1$-$C_6$)alkyl- group, and triazine($C_1$-$C_6$)alkyl- group, for instance a furanyl-$CH_2$— group, a furanyl-$(CH_2)_2$— group, a furanyl-$(CH_2)_3$— group, a furanyl-$(CH_2)_4$— group, a furanyl-$(CH_2)_5$— group, a furanyl-$(CH_2)_6$— group such as

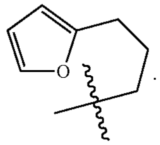 [SMILES: *CCCc1ccco1]

When $R_3$ represents a —$NR_7R_8$ group, that $R_7$ and/or $R_8$ represents a phenyl($C_1$-$C_6$)alkyl- group, for instance a benzyl group, and that said phenyl group is substituted by at least one substituent, such as one $NR_9R_{10}$—($C_1$-$C_6$)alkyl- group, examples of suitable $NR_9R_{10}$—($C_1$-$C_6$)alkyl- groups that may be mentioned include:

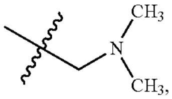
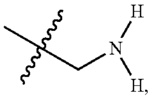
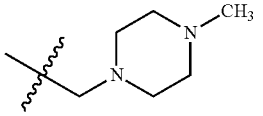
and
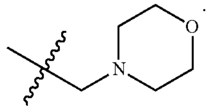

For $R_3$, when $R_9$ and $R_{10}$ together form with the nitrogen atom to which they are attached an unsubstituted or substituted ($C_3$-$C_{10}$) membered heterocycloalkyl- group, examples of suitable $NR_9R_{10}$ groups that may be mentioned include: piperazine, morpholino, pyrrolidine, tetrahydropyrane, thietane dioxide, piperidine, thiolane, thiolane oxide, thiolane dioxide, dihydrofurane, tetrahydrofurane, azetidine, oxetane, thietane, 2H-pyrrole, 1H-, 2H- or 3H-pyrroline, tetrahydrothiophene, oxadiazole, 1,3,4-oxadiazole, 1,3,5-oxadioazole, thiadiazole, 1,3,4-thiadiazole, isoxazoline, 2- or 3-pyrazoline, pyrroline, pyrazolidine, imidazoline, imidazolidine, thiazolidine, isooxazoline, isoxazolidine, dioxalane, oxathiazole, oxathiadiazole, and dioxazole groups, for instance a morpholino group or a piperazinyl group, such as

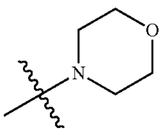
and
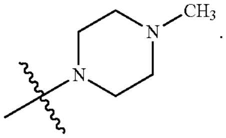
.

When $R_3$ represents a ($C_3$-$C_{10}$) membered heterocycloalkyl- group, examples of suitable 3-10 membered heterocycloalkyl groups that may be mentioned include piperazine, morpholino, pyrrolidine, tetrahydropyrane, dihydropyrrole, thietane dioxide, piperidine, thiolane, thiolane oxide, thiolane dioxide, dihydrofurane, tetrahydrofurane, azetidine, oxetane, thietane, 2H-pyrrole, 1H-, 2H- or 3H-pyrroline, tetrahydrothiophene, oxadiazole, 1,3,4-oxadiazole, 1,3,5-oxadioazole, thiadiazole, 1,3,4-thiadiazole, isoxazoline, 2- or 3-pyrazoline, pyrroline, pyrazolidine, imidazoline, imidazolidine, thiazolidine, isooxazoline, isoxazolidine, dioxalane, oxathiazole, oxathiadiazole, and dioxazole groups, for instance a tetrahydrofuranyl group, a dihydropyrrolyl group or a dihydrofuranyl group, such as

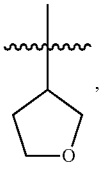
,
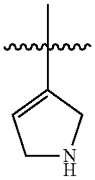
and
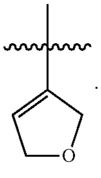
.

When $R_3$ represents a ($C_3$-$C_{10}$)cycloalkyl- group, examples of suitable ($C_3$-$C_{10}$)cycloalkyl groups that may be mentioned include a cyclopropyl group, a cyclobutyl group, a cyclopentyl group, a cyclohexyl group, a cyclopropenyl group, a cyclobutenyl group, a cyclopentenyl group, or a cyclohexenyl group, for instance a cyclopentenyl group, a cyclopentyl group, a cyclohexenyl group or a cyclohexyl group, such as

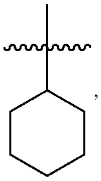
,
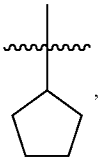
,
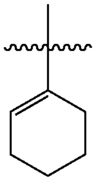
and
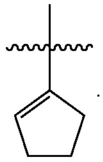
.

When $R_3$ represents an unsubstituted or substituted ($C_5$-$C_{10}$) membered heteroaryl- group, examples of suitable groups that may be mentioned include pyridine, furan, pyrrole, thiophene, pyrazole, oxazole, isoxazole, triazole, tetrazole, oxadiazole, furazan, thiazole, isothiazole, thiadiazole, imidazole, pyrimidine, pyridazine, and triazine groups, for instance a thienyl group, a furanyl group, a pyrrolyl group or a pyrazolyl group, such as

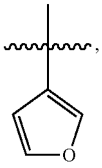
,
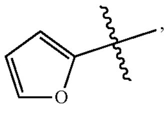
,
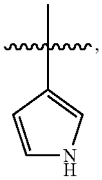
,
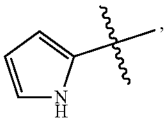
,
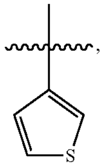
,
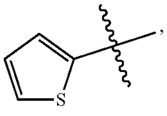
,
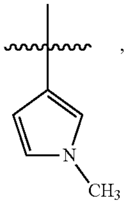
,
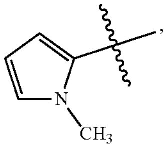
,
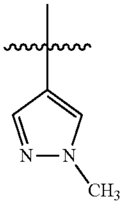
and
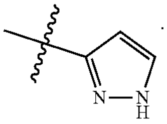
.

When $R_3$ represents a ($C_6$-$C_{10}$)aryl- group, examples of suitable ($C_6$-$C_{10}$)aryl- groups that may be mentioned include naphthyl group and phenyl group.

According to another embodiment, $R_3$ represents:

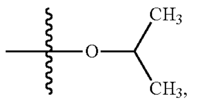

or

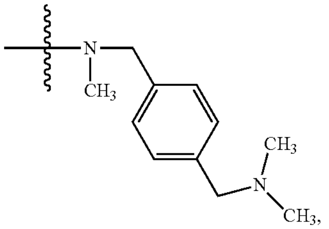

such as

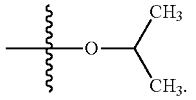

In the meaning of the present disclosure, examples of suitable $CH_3$—[O—$(CH_2)_2]_n$— groups with n being an integer from 1 to 30, that may be mentioned include: $CH_3$—O—$(CH_2)_2$—, $CH_3$—[O—$(CH_2)_2]_2$—, $CH_3$—[O—$(CH_2)_2]_3$—, $CH_3$—[O—$(CH_2)_2]_4$—, $CH_3$—[O—$(CH_2)_2]_5$—, $CH_3$—[O—$(CH_2)_2]_6$—, $CH_3$—[O—$(CH_2)_2]_7$—, $CH_3$—[O—$(CH_2)_2]_8$—, $CH_3$—[O—$(CH_2)_2]_9$, $CH_3$—[O—$(CH_2)_2]_{10}$—, $CH_3$—[O—$(CH_2)_2]_{11}$—, $CH_3$—[O—$(CH_2)_2]_{12}$—, $CH_3$—[O—$(CH_2)_2]_{13}$—, $CH_3$—[O—$(C_2)_2]_{14}$—, $CH_3$—[O—$(CH_2)_2]_{15}$—, $CH_3$—[O—$(C_2)_2]_{16}$—, $CH_3$—[O—$(CH_2)_2]_{17}$—, $CH_3$—[O—$(CH_2)_2]_{18}$—, $CH_3$—[O—$(CH_2)_2]_{19}$—, $CH_3$—[O—$(CH_2)_2]_{20}$—, $CH_3$—[O—$(CH_2)_2]_{21}$—, $CH_3$—[O—$(CH_2)_2]_{22}$—, $CH_3$—[O—$(CH_2)_2]_{23}$—, $CH_3$—[O—$(CH_2)_2]_{24}$—, $CH_3$—[O—$(CH_2)_2]_{25}$—, $CH_3$—[O—$(CH_2)_2]_{26}$—, $CH_3$—[O—$(CH_2)_2]_{27}$—, $CH_3$—[O—$(CH_2)_2]_{28}$—, $CH_3$—[O—$(CH_2)_2]_{29}$—, $CH_3$—[O—$(CH_2)_2]_{30}$—, such as $CH_3$—[O—$(CH_2)_2]_{24}$— and $CH_3$—O—$(CH_2)_2$.

Among the compounds of formula (I) that are subject matter of the present disclosure, mention may be made for instance of the following compounds:

(1) 2-butyl-7-isopropoxy-1-(4-methoxybenzyl)-1H-imidazo[4,5-d]pyridazin-4-amine;

(2) 2-butyl-N7-isopropyl-1-(4-methoxybenzyl)-1H-imidazo[4,5-d]pyridazin-4,7-diamine;

(3) 2-butyl-7-(isopropylthio)-1-(4-methoxybenzyl)-1H-imidazo[4,5-d]pyridazin-4-amine;

(4) 2-butyl-1-(4-methoxybenzyl)-7-(2-methoxyethoxy)-1H-imidazo[4,5-d]pyridazin-4-amine;

(5) 2-butyl-1-(4-methoxybenzyl)-7-propoxy-1H-imidazo[4,5-d]pyridazin-4-amine;

(6) 7-(allyloxy)-2-butyl-1-(4-methoxybenzyl)-1H-imidazo[4,5-d]pyridazin-4-amine;

(7) 7-(sec-butoxy)-2-butyl-1-(4-methoxybenzyl)-1H-imidazo[4,5-d]pyridazin-4-amine;

(8) 7-butoxy-2-butyl-1-(4-methoxybenzyl)-1H-imidazo[4,5-d]pyridazin-4-amine;

(9) 2-butyl-7-(cyclopentyloxy)-1-(4-methoxybenzyl)-1H-imidazo[4,5-d]pyridazin-4-amine;

(10) 2-butyl-1-(4-methoxybenzyl)-7-(pyrrolidin-1-yl)-1H-imidazo[4,5-d]pyridazin-4-amine;

(11) 2-butyl-1-(4-methoxybenzyl)-7-(1-methyl-1H-pyrrol-3-yl)-1H-imidazo[4,5d]pyridazin-4-amine;

(12) (E)-2-butyl-1-(4-methoxybenzyl)-7-(3-methylbut-1-en-1-yl)-1H-imidazo[4,5-d]pyridazin-4-amine;

(13) 2-butyl-7-isopentyl-1-(4-methoxybenzyl)-1H-imidazo[4,5-d]pyridazin-4-amine;

(14) 2-butyl-1-(4-methoxybenzyl)-7-(1H-pyrrol-3-yl)-1H-imidazo[4,5-d]pyridazin-4-amine;

(15) 2-butyl-7-(cyclopent-1-en-1-yl)-1-(4-methoxybenzyl)-1H-imidazo[4,5-d]pyridazin-4-amine hydrochloride;

(16) 2-butyl-7-cyclopentyl-1-(4-methoxybenzyl)-1H-imidazo[4,5-d]pyridazin-4-amine;

(17) 2-butyl-1-(4-methoxybenzyl)-7-(prop-1-en-2-yl)-1H-imidazo[4,5-d]pyridazin-4-amine;

(18) 2-butyl-7-isopropyl-1-(4-methoxybenzyl)-1H-imidazo[4,5-d]pyridazin-4-amine;

(19) 4-(aminomethyl)cyclohexyl)methyl)-2-butyl-7-isopropoxy-1H-imidazo[4,5-d]pyridazin-4-amine dihydrochloride;

(20) 4-(aminomethyl)cyclohexyl)methyl)-2-butyl-7-isopropoxy-1H-imidazo[4,5-d]pyridazin-4-amine 2,2,2-trifluoroacetate;

(21) 1-(4-(aminomethyl)benzyl)-2-butyl-7-isopropoxy-1H-imidazo[4,5-d]pyridazin-4-amine;

(22) 1-(4-(aminomethyl)benzyl)-2-butyl-7-isopropoxy-1H-imidazo[4,5-d]pyridazin-4-amine 2,2,2-trifluoroacetate;

(23) 1-(((1S,3R)-3-aminocyclohexyl)methyl)-2-butyl-7-isopropoxy-1H-imidazo[4,5-d]pyridazin-4-amine (and enantiomer);

(24) 1-(4-amino-2-butyl-7-isopropoxy-1H-imidazo[4,5-d]pyridazin-1-yl)-2-methylpropan-2-ol;

(25) Trans 1-(4-aminocyclohexyl)methyl)-2-butyl-7-isopropoxy-1H-imidazo[4,5-d]pyridazin-4-amine;

(26) 1-((5-(aminomethyl)pyridin-2-yl)methyl)-2-butyl-7-isopropoxy-1H-imidazo[4,5-d]pyridazin-4-amine;

(27) 6-((4-amino-2-butyl-7-isopropoxy-1H-imidazo[4,5-d]pyridazin-1-yl)methyl)nicotinonitrile;

(28) N-(4-((4-amino-2-butyl-7-isopropoxy-1H-imidazo[4,5d]pyridazin-1-yl)methyl)benzyl)acetamide;

(29) N-(4-((4-amino-2-butyl-7-isopropoxy-1H-imidazo[4,5-d]pyridazin-1-yl)methyl)benzyl)undecanamide;

(30) N-(4-((4-amino-2-butyl-7-isopropoxy-1H-imidazo[4,5-d]pyridazin-1-yl)methyl)benzyl)pentanamide;

(31) N-(4-((4-amino-2-butyl-7-isopropoxy-1H-imidazo[4,5-d]pyridazin-1-yl)methyl)benzyl)-3-(2-methoxyethoxy)propanamide;

(32) 1-(((1S,3S)-3-aminocyclohexyl)methyl)-2-butyl-7-isopropoxy-1H-imidazo[4,5-]pyridazin-4-amine (and enantiomer);

(33) 1-(3-(aminomethyl)benzyl)-2-butyl-7-isopropoxy-1H-imidazo[4,5-d]pyridazin-4-amine 2,2,2-trifluoroacetate;

(34) 4-((4-amino-2-butyl-7-isopropoxy-1H-imidazo[4,5-d]pyridazin-1-yl)methyl)benzaldehyde;

(35) (4-((4-amino-2-butyl-7-isopropoxy-1H-imidazo[4,5-d]pyridazin-1-yl)methyl)phenyl)methanol;

(36) 2-butyl-1-(4-((cyclopropylamino)methyl)benzyl)-7-isopropoxy-1H-imidazo[4,5-d]pyridazin-4-amine;

(37) 3-((4-((4-amino-2-butyl-7-isopropoxy-1H-imidazo[4,5-d]pyridazin-yl)methyl)benzyl)amino)thietane 1,1-dioxide;

(38) N-(4-((4-amino-2-butyl-7-isopropoxy-1H-imidazo[4,5-d]pyridazin-1-yl)methyl)benzyl)-N-(1,1-dioxidothietan-3-yl)acetamide;

(39) 2-butyl-7-isopropoxy-1-(4-(((1-methylcyclobutyl)amino)methyl)benzyl)-1H-imidazo[4,5-d]pyridazin-4-amine;

(40) 2-butyl-7-isopropoxy-1-(4-(piperazin-1-ylmethyl)benzyl)-1H-imidazo[4,5-d]pyridazin-4-amine;

(41) 2-butyl-N7,N7,1-trimethyl-1H-imidazo[4,5-d]pyridazin-4,7-diamine;

(42) 2-butyl-1-methyl-7-(pyrrolidin-1-yl)-1H-imidazo[4,5-d]pyridazin-4-amine;
(43) 2-butyl-N7-(4-((dimethylamino)methyl)benzyl)-N7,1-dimethyl-1H-imidazo[4,5-d]pyridazin-4,7-diamine;
(44) 2-butyl-N7,1-dimethyl-N7-(4-(morpholinomethyl)benzyl)-1H-imidazo[4,5-d]pyridazine-4,7-diamine;
(45) 4-(((4-amino-2-butyl-1-methyl-1H-imidazo[4,5-d]pyridazin-7-yl)(methyl)amino)methyl)benzonitrile;
(46) N7-(4-(aminomethyl)benzyl)-2-butyl-N7,1-dimethyl-1H-imidazo[4,5-d]pyridazine-4,7-diamine;
(47) 2-butyl-N7-(4-(((2-methoxyethyl)(methyl)amino)methyl)benzyl)-N7,1-dimethyl-1H-imidazo[4,5-d]pyridazine-4,7-diamine;
(48) 2-butyl-7-ethoxy-1-(4-methoxybenzyl)-1H-imidazo[4,5-d]pyridazin-4-amine;
(49) 2-butyl-1-(4-methoxybenzyl)-N7-(2-methoxyethyl)-1H-imidazo[4,5-d]pyridazine-4,7-diamine;
(50) 2-butyl-7-methoxy-1-(4-methoxybenzyl)-1H-imidazo[4,5-d]pyridazin-4-amine;
(51) 2-butyl-7-cyclohexyl-1-(4-methoxybenzyl)-1H-imidazo[4,5-d]pyridazin-4-amine;
(52) 7-(benzyloxy)-2-butyl-1-(4-methoxybenzyl)-1H-imidazo[4,5-d]pyridazin-4-amine;
(53) 2-butyl-1-(4-methoxybenzyl)-N7-methyl-1H-imidazo[4,5-d]pyridazine-4,7-diamine;
(54) (S)-2-butyl-1-(4-methoxybenzyl)-7-((tetrahydrofuran-3-yl)oxy)-1H-imidazo[4,5-d]pyridazin-4-amine;
(55) 2-butyl-7-(furan-2-yl)-1-(4-methoxybenzyl)-1H-imidazo[4,5-d]pyridazine-4-amine;
(56) 2-butyl-1-(4-methoxybenzyl)-7-((tetrahydrofuran-3-yl)oxy)-1H-imidazo[4,5-d]pyridazin-4-amine;
(57) 2-butyl-1-(4-methoxybenzyl)-7-((tetrahydro-2H-pyran-4-yl)oxy)-1H-imidazo[4,5-d]pyridazin-4-amine;
(58) 2-butyl-1-(4-methoxybenzyl)-7-((tetrahydrothiophen-3-yl)oxy)-1H-imidazo[4,5-d]pyridazin-4-amine;
(59) 2-butyl-1-(4-methoxybenzyl)-7-(tetrahydrofuran-3-yl)-1H-imidazo[4,5-d]pyridazin-4-amine;
(60) 2-butyl-1-(4-methoxybenzyl)-7-(2-methylprop-1-en-1-yl)-1H-imidazo[4,5-d]pyridazin-4-amine;
(61) 2-butyl-7-isobutyl-1-(4-methoxybenzyl)-1H-imidazo[4,5-d]pyridazin-4-amine;
(62) 2-butyl-1-(4-methoxybenzyl)-7-(thiophen-3-yl)-1H-imidazo[4,5-d]pyridazin-4-amine;
(63) 2-butyl-1-(4-methoxybenzyl)-7-(thiophen-2-yl)-1H-imidazo[4,5-d]pyridazin-4-amine;
(64) 2-butyl-1-(4-methoxybenzyl)-7-(1H-pyrrol-2-yl)-1H-imidazo[4,5-d]pyridazin-4-amine hydrochloride;
(65) 3-((4-amino-2-butyl-1-(4-methoxybenzyl)-1H-imidazo[4,5-d]pyridazin-7-yl)oxy)tetrahydrothiophene 1-oxide isomer A;
(66) 2-butyl-7-(cyclohex-1-en-1-yl)-1-(4-methoxybenzyl)-1H-imidazo[4,5-d]pyridazin-4-amine;
(67) 2-butyl-7-(furan-3-yl)-1-(4-methoxybenzyl)-1H-imidazo[4,5-d]pyridazin-4-amine;
(68) 3-((4-amino-2-butyl-1-(4-methoxybenzyl)-1H-imidazo[4,5-d]pyridazin-7-yl)oxy)tetrahydrothiophene 1,1-dioxide;
(69) 3-((4-amino-2-butyl-1-(4-methoxybenzyl)-1H-imidazo[4,5-d]pyridazin-7-yl)oxy)tetrahydrothiophene 1-oxide isomer B;
(70) 2-butyl-1-(4-methoxybenzyl)-7-(1-methyl-1H-pyrrol-2-yl)-1H-imidazo[4,5-d]pyridazin-4-amine hydrochloride;
(71) 2-butyl-1-(4-methoxybenzyl)-N7,N7-dimethyl-1H-imidazo[4,5-d]pyridazine-4,7-diamine;
(72) 2-butyl-1-(4-methoxybenzyl)-7-phenoxy-1H-imidazo[4,5-d]pyridazin-4-amine;
(73) 2-butyl-7-(2,5-dihydrofuran-3-yl)-1-(4-methoxybenzyl)-1H-imidazo[4,5-d]pyridazin-4-amine;
(74) 2-butyl-7-isopropoxy-1-(pyridin-3-ylmethyl)-1H-imidazo[4,5-d]pyridazin-4-amine;
(75) 2-butyl-7-isopropoxy-1-(pyridin-2-ylmethyl)-1H-imidazo[4,5-d]pyridazin-4-amine;
(76) 2-butyl-7-isopropoxy-1-(pyridin-4-ylmethyl)-1H-imidazo[4,5-d]pyridazin-4-amine 2,2,2-trifluoroacetate;
(77) 1-(5-aminopentyl)-2-butyl-7-isopropoxy-1H-imidazo[4,5-d]pyridazin-4-amine;
(78) 2-butyl-7-isopropoxy-1-(2-(piperidin-4-yl)ethyl)-1H-imidazo[4,5-d]pyridazin-4-amine;
(79) 2-butyl-7-isopropoxy-1-(2-(piperazin-1-yl)ethyl)-1H-imidazo[4,5-d]pyridazin-4-amine;
(80) 1-benzyl-2-butyl-7-isopropoxy-1H-imidazo[4,5-d]pyridazin-4-amine hydrochloride;
(81) 2-butyl-1-(cyclohexylmethyl)-7-isopropoxy-1H-imidazo[4,5-d]pyridazin-4-amine hydrochloride;
(82) 2-butyl-7-isopropoxy-1-(4-(((tetrahydro-2H-pyran-4-yl)amino)methyl)benzyl)-1H-imidazo[4,5-d]pyridazin-4-amine hydrochloride;
(83) 2-butyl-7-isopropoxy-1-(4-((isopropylamino)methyl)benzyl)-1H-imidazo[4,5-d]pyridazin-4-amine dihydrochloride;
(84) N-(4-((4-amino-2-butyl-7-isopropoxy-1H-imidazo[4,5-d]pyridazin-1-yl)methyl)benzyl)heptanamide;
(85) (4-(1-(4-amino-2-butyl-1-methyl-1H-imidazo[4,5-d]pyridazin-7-yl)pyrrolidin-3-yl)phenyl)methanol hydrochloride;
(86) 2-butyl-7-isopropoxy-1-methyl-1H-imidazo[4,5-d]pyridazin-4-amine;
(87) N7-(4-(aminomethyl)benzyl)-2-butyl-1-methyl-1H-imidazo[4,5-d]pyridazine-4,7-diamine;
(88) 2-butyl-N7-isopropyl-1-methyl-1H-imidazo[4,5-d]pyridazine-4,7-diamine;
(89) 2-butyl-1-methyl-7-(3-phenylpyrrolidin-1-yl)-1H-imidazo[4,5-d]pyridazin-4-amine;
(90) N7-benzyl-2-butyl-N7,1-dimethyl-1H-imidazo[4,5-d]pyridazine-4,7-diamine;
(91) 2-butyl-1-methyl-N7-(4-((4-methylpiperazin-1-yl)methyl)benzyl)-1H-imidazo[4,5-d]pyridazine-4,7-diamine;
(92) 2-butyl-1-(4-methoxybenzyl)-7-phenyl-1H-imidazo[4,5-d]pyridazin-4-amine;
(93) 4-amino-2-butyl-1-(4-methoxybenzyl)-1H-imidazo[4,5-d]pyridazin-7-ol;
(94) 2-butyl-N7-(3-(furan-2-yl)propyl)-1-(4-methoxybenzyl)-1H-imidazo[4,5-d]pyridazine-4,7-diamine;
(95) 2-butyl-1-(4-methoxybenzyl)-1H-imidazo[4,5-d]pyridazin-4-amine;
(96) 2-butyl-1-(4-methoxybenzyl)-7-(1H-pyrazol-3-yl)-1H-imidazo[4,5-d]pyridazin-4-amine;
(97) 2-butyl-1-(4-methoxybenzyl)-7-(1-methyl-1H-pyrazol-4-yl)-1H-imidazo[4,5-d]pyridazin-4-amine;
(98) 2-butyl-N7-isopropyl-1H-imidazo[4,5-d]pyridazine-4,7-diamine;
(99) 2-butyl-7-(isopropylthio)-1H-imidazo[4,5-d]pyridazin-4-amine;
(100) (1R,3R)-3-((4-((4-amino-2-butyl-7-isopropoxy-1H-imidazo[4,5-d]pyridazin-1-yl)methyl)benzyl)amino)cyclobutan-1-ol dihydrochloride salt;
(101) 2-butyl-7-isopropoxy-1-(4-(pyrrolidin-1-ylmethyl)benzyl)-1H-imidazo[4,5-d]pyridazin-4-amine;
(102) 2-butyl-7-isopropoxy-1-(4-(morpholinomethyl)benzyl)-1H-imidazo[4,5-d]pyridazin-4-amine;
(103) N-(4-((4-amino-2-butyl-7-isopropoxy-1H-imidazo[4,5-d]pyridazin-1-yl)methyl)benzyl)propionamide;

(104) 2-butyl-7-isopropoxy-1-(4-(((2-methoxyethyl)amino)methyl)benzyl)-1H-imidazo[4,5-d]pyridazin-4-amine;

(105) 2-butyl-4-isopropoxy-3-[[4-[[2-[2-[2-[2-[2-(2-methoxyethoxy)ethoxy]ethoxy]ethoxy]ethoxy]ethyl-amino]methyl]phenyl]methyl]imidazo[4,5-d]pyridazin-7-amine;

(106) N-(4-((4-amino-2-butyl-7-isopropoxy-1H-imidazo[4,5-d]pyridazin-1-yl)methyl)benzyl)benzamide;

(107) N-(4-((4-amino-2-butyl-7-isopropoxy-1H-imidazo[4,5-d]pyridazin-1-yl)methyl)benzyl)-3-methoxypropanamide;

(108) 2-butyl-7-isopropoxy-1-(4-(((2-(2-methoxyethoxy)ethyl)amino)methyl)benzyl)-1H-imidazo[4,5-d]pyridazin-4-amine;

(109) 2-butyl-1-(4-((hexylamino)methyl)benzyl)-7-isopropoxy-1H-imidazo[4,5-d]pyridazin-4-amine;

(110) 2-butyl-1-(4-((decylamino)methyl)benzyl)-7-isopropoxy-1H-imidazo[4,5-d]pyridazin-4-amine;

(111) ethyl (4-((4-amino-2-butyl-7-isopropoxy-1H-imidazo[4,5-d]pyridazin-1-yl)methyl)benzyl)carbamate;

(112) 4-methoxybenzyl (4-((4-amino-2-butyl-7-isopropoxy-1H-imidazo[4,5-d]pyridazin-1-yl)methyl)benzyl)carbamate;

(113) 1-(4-((4-amino-2-butyl-7-isopropoxy-1H-imidazo[4,5-d]pyridazin-1-yl)methyl)benzyl)-3-ethylurea;

(114) 4-acetamidobenzyl (4-((4-amino-2-butyl-7-isopropoxy-1H-imidazo[4,5-d]pyridazin-1-yl)methyl)benzyl)carbamate;

(115) N-(4-((4-amino-2-butyl-7-isopropoxy-1H-imidazo[4,5-d]pyridazin-1-yl)methyl)benzyl)methanesulfonamide;

(116) 2-butyl-1-(4-((dimethylamino)methyl)benzyl)-7-isopropoxy-1H-imidazo[4,5-d]pyridazin-4-amine;

(117) tert-butyl (4-((4-amino-2-butyl-7-isopropoxy-1H-imidazo[4,5-d]pyridazin-1-yl)methyl)benzyl)glycinate;

(118) 2-butyl-7-isopropoxy-1-(4-((methylamino)methyl)benzyl)-1H-imidazo[4,5-d]pyridazin-4-amine;

(119) tert-butyl 3-((4-((4-amino-2-butyl-7-isopropoxy-1H-imidazo[4,5-d]pyridazin-1-yl)methyl)benzyl)amino)propanoate;

(120) 1-(4-(5,8,11-trioxa-2-azadodecyl)benzyl)-2-butyl-7-isopropoxy-1H-imidazo[4,5-d]pyridazin-4-amine;

(121) 2-butyl-4-isopropoxy-3-[[4-[[2-[2-[2-(2-methoxyethoxy)ethoxy]ethoxy]ethylamino]methyl]phenyl]methyl]imidazo[4,5-d]pyridazin-7-amine;

(122) 2-butyl-4-isopropoxy-3-[[4-[[2-[2-[2-[2-[2-[2-[2-(2-methoxyethoxy)ethoxy]ethoxy]ethoxy]ethoxy]ethoxy]ethoxy]ethylamino]methyl]phenyl]methyl]imidazo[4,5-d]pyridazin-7-amine di2,2,2-trifluoroacetate;

(123) 2-butyl-4-isopropoxy-3-[[4-[[2-[2-[2-[2-[2-[2-[2-[2-[2-[2-[2-(2-methoxyethoxy)ethoxy]ethoxy]ethoxy]ethoxy]ethoxy]ethoxy]ethoxy]ethoxy]ethoxy]ethoxy]ethylamino]methyl]phenyl]methyl]imidazo[4,5-d]pyridazin-7-amine di2,2,2-trifluoroacetate;

(124) 2-butyl-7-isopropoxy-1-(3-((methylamino)methyl)benzyl)-1H-imidazo[4,5-d]pyridazin-4-amine;

(125) 2-butyl-1-(3-((dimethylamino)methyl)benzyl)-7-isopropoxy-1H-imidazo[4,5-d]pyridazin-4-amine;

(126) 2-butyl-1-(3-((cyclobutylamino)methyl)benzyl)-7-isopropoxy-1H-imidazo[4,5-d]pyridazin-4-amine dihydrochloride salt;

(127) 2-butyl-1-(3-((cyclopropylamino)methyl)benzyl)-7-isopropoxy-1H-imidazo[4,5-d]pyridazin-4-amine dihydrochloride salt;

(128) 2-butyl-7-isopropoxy-1-(3-((isopropylamino)methyl)benzyl)-1H-imidazo[4,5-d]pyridazin-4-amine dihydrochloride salt;

(129) 3-((3-((4-amino-2-butyl-7-isopropoxy-1H-imidazo[4,5-d]pyridazin-1-yl)methyl)benzyl)amino)thietane 1,1-dioxide;

(130) 2-butyl-7-isopropoxy-1-(3-(((1-methylcyclobutyl)amino)methyl)benzyl)-1H-imidazo[4,5-d]pyridazin-4-amine dihydrochloride salt;

(131) 2-butyl-7-isopropoxy-1-(3-(piperazin-1-ylmethyl)benzyl)-1H-imidazo[4,5-d]pyridazin-4-amine;

(132) (E)-1-(4-(aminomethyl)benzyl)-2-butyl-7-(3-methylbut-1-en-1-yl)-1H-imidazo[4,5-d]pyridazin-4-amine;

(133) 1-(4-(aminomethyl)benzyl)-2-butyl-7-isopentyl-1H-imidazo[4,5-d]pyridazin-4-amine;

(134) 1-(4-(aminomethyl)benzyl)-2-butyl-7-(pyrrolidin-1-yl)-1H-imidazo[4,5-d]pyridazin-4-amine;

(135) 1-(4-(aminomethyl)benzyl)-2-butyl-7-(1H-pyrrol-3-yl)-1H-imidazo[4,5-d]pyridazin-4-amine 2,2,2-trifluoroacetate;

(137) 1-(((1R,4R)-4-(aminomethyl)cyclohexyl)methyl)-2-butyl-7-((E)-3-methylbut-1-en-1-yl)-1H-imidazo[4,5-d]pyridazin-4-amine (138) 1-(((1R,4R)-4-(aminomethyl)cyclohexyl)methyl)-2-butyl-7-isopentyl-1H-imidazo[4,5-d]pyridazin-4-amine;

(139) 1-(((1R,4R)-4-aminocyclohexyl)methyl)-2-butyl-7-((E)-3-methylbut-1-en-1-yl)-1H-imidazo[4,5-d]pyridazin-4-amine;

(140) 1-(((1R,4R)-4-aminocyclohexyl)methyl)-2-butyl-7-isopentyl-1H-imidazo[4,5-d]pyridazin-4-amine;

(141) 1-(((1R,4R)-4-aminocyclohexyl)methyl)-2-butyl-7-(1H-pyrrol-3-yl)-1H-imidazo[4,5-d]pyridazin-4-amine;

(142) 1-(((1R,4R)-4-(aminomethyl)cyclohexyl)methyl)-2-butyl-7-(pyrrolidin-1-yl)-1H-imidazo[4,5-d]pyridazin-4-amine;

(143) 3-[(4-aminocyclohexyl)methyl]-2-butyl-4-pyrrolidin-1-yl-imidazo[4,5-d]pyridazin-7-amine;

(144) 1-[[4-(aminomethyl)phenyl]methyl]-2-butyl-7-(2,5-dihydro-1H-pyrrol-3-yl)imidazo[4,5-d]pyridazin-4-amine;

(145) 1-[[4-(aminomethyl)phenyl]methyl]-2-butyl-7-pyrrolidin-3-yl-imidazo[4,5-d]pyridazin-4-amine;

(146) 3-(6-aminohexyl)-2-butyl-4-isopropoxy-imidazo[4,5-d]pyridazin-7-amine dihydrochloride salt;

(147) 2-butyl-4-isopropoxy-3-[6-(tetrahydropyran-4-ylamino)hexyl]imidazo[4,5-d]pyridazin-7-amine dihydrochloride salt;

(148) N-[6-(7-amino-2-butyl-4-isopropoxy-imidazo[4,5-d]pyridazin-3-yl)hexyl]-N-tetrahydropyran-4-yl-acetamide;

(149) 3-(4-aminobutyl)-2-butyl-4-isopropoxy-imidazo[4,5-d]pyridazin-7-amine dihydrochloride salt;

(150) 2-butyl-4-isopropoxy-3-[4-(tetrahydropyran-4-ylamino)butyl]imidazo[4,5-d]pyridazin-7-amine hydrochloride salt;

(151) N-[4-(7-amino-2-butyl-4-isopropoxy-imidazo[4,5-d]pyridazin-3-yl)butyl]-N-tetrahydropyran-4-yl-acetamide;

(152) 2-butyl-3-[4-[(1,1-dioxothietan-3-yl)amino]butyl]-4-isopropoxy-imidazo[4,5-d]pyridazin-7-amine;

(153) N-[4-(7-amino-2-butyl-4-isopropoxy-imidazo[4,5-d]pyridazin-3-yl)butyl]-N-(1,1-dioxothietan-3-yl)acetamide;

(154) 2-butyl-3-[6-[(1,1-dioxothietan-3-yl)amino]hexyl]-4-isopropoxy-imidazo[4,5-d]pyridazin-7-amine;

(155) N-[6-(7-amino-2-butyl-4-isopropoxy-imidazo[4,5-d]pyridazin-3-yl)hexyl]-N-(1,1-dioxothietan-3-yl)acetamide hydrochloride salt;

(156) 2-[(7-amino-2-butyl-4-isopropoxy-imidazo[4,5-d]pyridazin-3-yl)methyl]-2-methyl-propane-1,3-diol hydrochloride salt;

(157) 2-[(7-amino-2-butyl-4-isopropoxy-imidazo[4,5-d]pyridazin-3-yl)methyl]propane-1,3-diol hydrochloride salt;
(158) 1-(4-(aminomethyl)benzyl)-7-isopropoxy-2-propyl-1H-imidazo[4,5-d]pyridazin-4-amine;
(159) 1-(4-(aminomethyl)benzyl)-2-(ethoxymethyl)-7-isopropoxy-1H-imidazo[4,5-d]pyridazin-4-amine;
(160) 1-(4-(aminomethyl)benzyl)-7-isopropoxy-2-methyl-1H-imidazo[4,5-d]pyridazin-4-amine;
(161) 3-[[4-(aminomethyl)phenyl]methyl]-4-isopropoxy-2-propylsulfanyl-imidazo[4,5-d]pyridazin-7-amine;
(162) 3-[[4-(aminomethyl)phenyl]methyl]-4-isopropoxy-2-propylsulfinyl-imidazo[4,5-d]pyridazin-7-amine;
(163) 3-[[4-(aminomethyl)phenyl]methyl]-4-isopropoxy-N2-propyl-imidazo[4,5-d]pyridazine-2,7-diamine;
(164) 3-[[4-(aminomethyl)phenyl]methyl]-2-(ethylaminomethyl)-4-isopropoxy-imidazo[4,5-d]pyridazin-7-amine;
(165) 2-butyl-7-isopropoxy-1-(piperidin- 4-ylmethyl)-1H-imidazo[4,5-d]pyridazin-4-amine; or
a pharmaceutically acceptable salt thereof.

Among the preceding listed compounds, the following compounds which are of interest may for example be cited:
(1) 2-butyl-7-isopropoxy-1-(4-methoxybenzyl)-1H-imidazo[4,5-d]pyridazin-4-amine;
(2) 2-butyl-N7-isopropyl-1-(4-methoxybenzyl)-1H-imidazo[4,5-d]pyridazin-4,7-diamine;
(3) 2-butyl-7-(isopropylthio)-1-(4-methoxybenzyl)-1H-imidazo[4,5-d]pyridazin-4-amine;
(4) 2-butyl-1-(4-methoxybenzyl)-7-(2-methoxyethoxy)-1H-imidazo[4,5-d]pyridazin-4-amine;
(5) 2-butyl-1-(4-methoxybenzyl)-7-propoxy-1H-imidazo[4,5-d]pyridazin-4-amine;
(6) 7-(allyloxy)-2-butyl-1-(4-methoxybenzyl)-1H-imidazo[4,5-d]pyridazin-4-amine;
(7) 7-(sec-butoxy)-2-butyl-1-(4-methoxybenzyl)-1H-imidazo[4,5-d]pyridazin-4-amine;
(8) 7-butoxy-2-butyl-1-(4-methoxybenzyl)-1H-imidazo[4,5-d]pyridazin-4-amine;
(9) 2-butyl-7-(cyclopentyloxy)-1-(4-methoxybenzyl)-1H-imidazo[4,5-d]pyridazin-4-amine;
(10) 2-butyl-1-(4-methoxybenzyl)-7-(pyrrolidin-1-yl)-1H-imidazo[4,5-d]pyridazin-4-amine;
(11) 2-butyl-1-(4-methoxybenzyl)-7-(1-methyl-1H-pyrrol-3-yl)-1H-imidazo[4,5d]pyridazin-4-amine;
(12) (E)-2-butyl-1-(4-methoxybenzyl)-7-(3-methylbut-1-en-1-yl)-1H-imidazo[4,5-d]pyridazin-4-amine;
(13) 2-butyl-7-isopentyl-1-(4-methoxybenzyl)-1H-imidazo[4,5-d]pyridazin-4-amine;
(14) 2-butyl-1-(4-methoxybenzyl)-7-(1H-pyrrol-3-yl)-1H-imidazo[4,5-d]pyridazin-4-amine;
(15) 2-butyl-7-(cyclopent-1-en-1-yl)-1-(4-methoxybenzyl)-1H-imidazo[4,5-d]pyridazin-4-amine hydrochloride;
(16) 2-butyl-7-cyclopentyl-1-(4-methoxybenzyl)-1H-imidazo[4,5-d]pyridazin-4-amine;
(17) 2-butyl-1-(4-methoxybenzyl)-7-(prop-1-en-2-yl)-1H-imidazo[4,5-d]pyridazin-4-amine;
(18) 2-butyl-7-isopropyl-1-(4-methoxybenzyl)-1H-imidazo[4,5-d]pyridazin-4-amine;
(19) 4-(aminomethyl)cyclohexyl)methyl)-2-butyl-7-isopropoxy-1H-imidazo[4,5-d]pyridazin-4-amine dihydrochloride; (20) 4-(aminomethyl)cyclohexyl)methyl)-2-butyl-7-isopropoxy-1H-imidazo[4,5-d]pyridazin-4-amine 2,2,2-trifluoroacetate;
(25) Trans 1-(4-aminocyclohexyl)methyl)-2-butyl-7-isopropoxy-1H-imidazo[4,5-d]pyridazin-4-amine;
(26) 1-((5-(aminomethyl)pyridin-2-yl)methyl)-2-butyl-7-isopropoxy-1H-imidazo[4,5-d]pyridazin-4-amine;
(27) 6-((4-amino-2-butyl-7-isopropoxy-1H-imidazo[4,5-d]pyridazin-1-yl)methyl)nicotinonitrile;
(28) N-(4-((4-amino-2-butyl-7-isopropoxy-1H-imidazo[4,5d]pyridazin-1-yl)methyl)benzyl)acetamide;
(29) N-(4-((4-amino-2-butyl-7-isopropoxy-1H-imidazo[4,5-d]pyridazin-1-yl)methyl)benzyl)undecanamide;
(30) N-(4-((4-amino-2-butyl-7-isopropoxy-1H-imidazo[4,5-d]pyridazin-1-yl)methyl)benzyl)pentanamide;
(31) N-(4-((4-amino-2-butyl-7-isopropoxy-1H-imidazo[4,5-d]pyridazin-1-yl)methyl)benzyl)-3-(2-methoxyethoxy)propanamide;
(34) 4-((4-amino-2-butyl-7-isopropoxy-1H-imidazo[4,5-d]pyridazin-1-yl)methyl)benzaldehyde;
(35) (4-((4-amino-2-butyl-7-isopropoxy-1H-imidazo[4,5-d]pyridazin-1-yl)methyl)phenyl)methanol;
(37) 3-((4-((4-amino-2-butyl-7-isopropoxy-1H-imidazo[4,5-d]pyridazin-yl)methyl)benzyl)amino)thietane 1,1-dioxide;
(48) 2-butyl-7-ethoxy-1-(4-methoxybenzyl)-1H-imidazo[4,5-d]pyridazin-4-amine;
(49) 2-butyl-1-(4-methoxybenzyl)-N7-(2-methoxyethyl)-1H-imidazo[4,5-d]pyridazine-4,7-diamine;
(50) 2-butyl-7-methoxy-1-(4-methoxybenzyl)-1H-imidazo[4,5-d]pyridazin-4-amine;
(51) 2-butyl-7-cyclohexyl-1-(4-methoxybenzyl)-1H-imidazo[4,5-d]pyridazin-4-amine;
(52) 7-(benzyloxy)-2-butyl-1-(4-methoxybenzyl)-1H-imidazo[4,5-d]pyridazin-4-amine;
(53) 2-butyl-1-(4-methoxybenzyl)-N7-methyl-1H-imidazo[4,5-d]pyridazine-4,7-diamine;
(54) (S)-2-butyl-1-(4-methoxybenzyl)-7-((tetrahydrofuran-3-yl)oxy)-1H-imidazo[4,5-d]pyridazin-4-amine;
(55) 2-butyl-7-(furan-2-yl)-1-(4-methoxybenzyl)-1H-imidazo[4,5-d]pyridazine-4-amine;
(56) 2-butyl-1-(4-methoxybenzyl)-7-((tetrahydrofuran-3-yl)oxy)-1H-imidazo[4,5-d]pyridazin-4-amine;
(57) 2-butyl-1-(4-methoxybenzyl)-7-((tetrahydro-2H-pyran-4-yl)oxy)-1H-imidazo[4,5-d]pyridazin-4-amine;
(58) 2-butyl-1-(4-methoxybenzyl)-7-((tetrahydrothiophen-3-yl)oxy)-1H-imidazo[4,5-d]pyridazin-4-amine;
(59) 2-butyl-1-(4-methoxybenzyl)-7-(tetrahydrofuran-3-yl)-1H-imidazo[4,5-d]pyridazin-4-amine;
(60) 2-butyl-1-(4-methoxybenzyl)-7-(2-methylprop-1-en-1-yl)-1H-imidazo[4,5-d]pyridazin-4-amine;
(61) 2-butyl-7-isobutyl-1-(4-methoxybenzyl)-1H-imidazo[4,5-d]pyridazin-4-amine;
(62) 2-butyl-1-(4-methoxybenzyl)-7-(thiophen-3-yl)-1H-imidazo[4,5-d]pyridazin-4-amine;
(63) 2-butyl-1-(4-methoxybenzyl)-7-(thiophen-2-yl)-1H-imidazo[4,5-d]pyridazin-4-amine;
(64) 2-butyl-1-(4-methoxybenzyl)-7-(1H-pyrrol-2-yl)-1H-imidazo[4,5-d]pyridazin-4-amine hydrochloride;
(65) 3-((4-amino-2-butyl-1-(4-methoxybenzyl)-1H-imidazo[4,5-d]pyridazin-7-yl)oxy)tetrahydrothiophene 1-oxide isomer A;
(66) 2-butyl-7-(cyclohex-1-en-1-yl)-1-(4-methoxybenzyl)-1H-imidazo[4,5-d]pyridazin-4-amine;
(67) 2-butyl-7-(furan-3-yl)-1-(4-methoxybenzyl)-1H-imidazo[4,5-d]pyridazin-4-amine;
(68) 3-((4-amino-2-butyl-1-(4-methoxybenzyl)-1H-imidazo[4,5-d]pyridazin-7-yl)oxy)tetrahydrothiophene 1,1-dioxide;
(69) 3-((4-amino-2-butyl-1-(4-methoxybenzyl)-1H-imidazo[4,5-d]pyridazin-7-yl)oxy)tetrahydrothiophene 1-oxide isomer B;
(70) 2-butyl-1-(4-methoxybenzyl)-7-(1-methyl-1H-pyrrol-2-yl)-1H-imidazo[4,5-d]pyridazin-4-amine hydrochloride;
(71) 2-butyl-1-(4-methoxybenzyl)-N7,N7-dimethyl-1H-imidazo[4,5-d]pyridazine-4,7-diamine;
(72) 2-butyl-1-(4-methoxybenzyl)-7-phenoxy-1H-imidazo[4,5-d]pyridazin-4-amine;

(73) 2-butyl-7-(2,5-dihydrofuran-3-yl)-1-(4-methoxybenzyl)-1H-imidazo[4,5-d]pyridazin-4-amine;
(75) 2-butyl-7-isopropoxy-1-(pyridin-2-ylmethyl)-1H-imidazo[4,5-d]pyridazin-4-amine;
(76) 2-butyl-7-isopropoxy-1-(pyridin-4-ylmethyl)-1H-imidazo[4,5-d]pyridazin-4-amine 2,2,2-trifluoroacetate;
(77) 1-(5-aminopentyl)-2-butyl-7-isopropoxy-1H-imidazo[4,5-d]pyridazin-4-amine;
(78) 2-butyl-7-isopropoxy-1-(2-(piperidin-4-yl)ethyl)-1H-imidazo[4,5-d]pyridazin-4-amine;
(79) 2-butyl-7-isopropoxy-1-(2-(piperazin-1-yl)ethyl)-1H-imidazo[4,5-d]pyridazin-4-amine;
(80) 1-benzyl-2-butyl-7-isopropoxy-1H-imidazo[4,5-d]pyridazin-4-amine hydrochloride;
(81) 2-butyl-1-(cyclohexylmethyl)-7-isopropoxy-1H-imidazo[4,5-d]pyridazin-4-amine hydrochloride;
(87) N7-(4-(aminomethyl)benzyl)-2-butyl-1-methyl-1H-imidazo[4,5-d]pyridazine-4,7-diamine;
(92) 2-butyl-1-(4-methoxybenzyl)-7-phenyl-1H-imidazo[4,5-d]pyridazin-4-amine;
(94) 2-butyl-N7-(3-(furan-2-yl)propyl)-1-(4-methoxybenzyl)-1H-imidazo[4,5-d]pyridazine-4,7-diamine;
(97) 2-butyl-1-(4-methoxybenzyl)-7-(1-methyl-1H-pyrazol-4-yl)-1H-imidazo[4,5-d]pyridazin-4-amine;
(105) 2-butyl-4-isopropoxy-3-[[4-[[2-[2-[2-[2-[2-(2-methoxyethoxy)ethoxy]ethoxy]ethoxy]ethoxy]ethylamino]methyl]phenyl]methyl]imidazo[4,5-d]pyridazin-7-amine;
(107) N-(4-((4-amino-2-butyl-7-isopropoxy-1H-imidazo[4,5-d]pyridazin-1-yl)methyl)benzyl)-3-methoxypropanamide;
(111) ethyl (4-((4-amino-2-butyl-7-isopropoxy-1H-imidazo[4,5-d]pyridazin-1-yl)methyl)benzyl)carbamate;
(112) 4-methoxybenzyl (4-((4-amino-2-butyl-7-isopropoxy-1H-imidazo[4,5-d]pyridazin-1-yl)methyl)benzyl)carbamate;
(113) 1-(4-((4-amino-2-butyl-7-isopropoxy-1H-imidazo[4,5-d]pyridazin-1-yl)methyl)benzyl)-3-ethylurea;
(122) 2-butyl-4-isopropoxy-3-[[4-[[2-[2-[2-[2-[2-[2-[2-(2-methoxyethoxy)ethoxy]ethoxy]ethoxy]ethoxy]ethoxy]ethoxy]ethylamino]methyl]phenyl]methyl]imidazo[4,5-d]pyridazin-7-amine di2,2,2-trifluoroacetate;
(128) 2-butyl-7-isopropoxy-1-(3-((isopropylamino)methyl)benzyl)-1H-imidazo[4,5-d]pyridazin-4-amine dihydrochloride salt;
(131) 2-butyl-7-isopropoxy-1-(3-(piperazin-1-ylmethyl)benzyl)-1H-imidazo[4,5-d]pyridazin-4-amine;
(134) 1-(4-(aminomethyl)benzyl)-2-butyl-7-(pyrrolidin-1-yl)-1H-imidazo[4,5-d]pyridazin-4-amine;
(137) 1-(((1R,4R)-4-(aminomethyl)cyclohexyl)methyl)-2-butyl-7-((E)-3-methylbut-1-en-1-yl)-1H-imidazo[4,5-d]pyridazin-4-amine;
(138) 1-(((1R,4R)-4-(aminomethyl)cyclohexyl)methyl)-2-butyl-7-isopentyl-1H-imidazo[4,5-d]pyridazin-4-amine;
(139) 1-(((1R,4R)-4-aminocyclohexyl)methyl)-2-butyl-7-((E)-3-methylbut-1-en-1-yl)-1H-imidazo[4,5-d]pyridazin-4-amine;
(140) 1-(((1R,4R)-4-aminocyclohexyl)methyl)-2-butyl-7-isopentyl-1H-imidazo[4,5-d]pyridazin-4-amine;
(142) 1-(((1R,4R)-4-(aminomethyl)cyclohexyl)methyl)-2-butyl-7-(pyrrolidin-1-yl)-1H-imidazo[4,5-d]pyridazin-4-amine;
(143) 3-[(4-aminocyclohexyl)methyl]-2-butyl-4-pyrrolidin-1-yl-imidazo[4,5-d]pyridazin-7-amine;
(146) 3-(6-aminohexyl)-2-butyl-4-isopropoxy-imidazo[4,5-d]pyridazin-7-amine dihydrochloride salt;
(148) N-[6-(7-amino-2-butyl-4-isopropoxy-imidazo[4,5-d]pyridazin-3-yl)hexyl]-N-tetrahydropyran-4-yl-acetamide;
(149) 3-(4-aminobutyl)-2-butyl-4-isopropoxy-imidazo[4,5-d]pyridazin-7-amine dihydrochloride salt;
(151) N-[4-(7-amino-2-butyl-4-isopropoxy-imidazo[4,5-d]pyridazin-3-yl)butyl]-N-tetrahydropyran-4-yl-acetamide;
(152) 2-butyl-3-[4-[(1,1-dioxothietan-3-yl)amino]butyl]-4-isopropoxy-imidazo[4,5-d]pyridazin-7-amine;
(153) N-[4-(7-amino-2-butyl-4-isopropoxy-imidazo[4,5-d]pyridazin-3-yl)butyl]-N-(1,1-dioxothietan-3-yl)acetamide;
(155) N-[6-(7-amino-2-butyl-4-isopropoxy-imidazo[4,5-d]pyridazin-3-yl)hexyl]-N-(1,1-dioxothietan-3-yl)acetamide hydrochloride salt;
(158) 1-(4-(aminomethyl)benzyl)-7-isopropoxy-2-propyl-1H-imidazo[4,5-d]pyridazin-4-amine;
(159) 1-(4-(aminomethyl)benzyl)-2-(ethoxymethyl)-7-isopropoxy-1H-imidazo[4,5-d]pyridazin-4-amine;
(162) 3-[[4-(aminomethyl)phenyl]methyl]-4-isopropoxy-2-propylsulfinyl-imidazo[4,5-d]pyridazin-7-amine;
(165) 2-butyl-7-isopropoxy-1-(piperidin-4-ylmethyl)-1H-imidazo[4,5-d]pyridazin-4-amine; or
a pharmaceutically acceptable salt thereof.

Among the preceding listed compounds, the following compounds which are of interest may for example be cited:
(21) 1-(4-(aminomethyl)benzyl)-2-butyl-7-isopropoxy-1H-imidazo[4,5-d]pyridazin-4-amine;
(22) 1-(4-(aminomethyl)benzyl)-2-butyl-7-isopropoxy-1H-imidazo[4,5-d]pyridazin-4-amine 2,2,2-trifluoroacetate;
(23) 1-(((1S,3R)-3-aminocyclohexyl)methyl)-2-butyl-7-isopropoxy-1H-imidazo[4,5-d]pyridazin-4-amine (and enantiomer);
(24) 1-(4-amino-2-butyl-7-isopropoxy-1H-imidazo[4,5-d]pyridazin-1-yl)-2-methylpropan-2-ol;
(32) 1-(((1S,3S)-3-aminocyclohexyl)methyl)-2-butyl-7-isopropoxy-1H-imidazo[4,5-]pyridazin-4-amine (and enantiomer);
(33) 1-(3-(aminomethyl)benzyl)-2-butyl-7-isopropoxy-1H-imidazo[4,5-d]pyridazin-4-amine 2,2,2-trifluoroacetate;
(36) 2-butyl-1-(4-((cyclopropylamino)methyl)benzyl)-7-isopropoxy-1H-imidazo[4,5-d]pyridazin-4-amine;
(38) N-(4-((4-amino-2-butyl-7-isopropoxy-1H-imidazo[4,5-d]pyridazin-1-yl)methyl)benzyl)-N-(1,1-dioxidothietan-3-yl)acetamide;
(39) 2-butyl-7-isopropoxy-1-(4-(((1-methylcyclobutyl)amino)methyl)benzyl)-1H-imidazo[4,5-d]pyridazin-4-amine;
(40) 2-butyl-7-isopropoxy-1-(4-(piperazin-1-ylmethyl)benzyl)-1H-imidazo[4,5-d]pyridazin-4-amine;
(41) 2-butyl-N7,N7,1-trimethyl-1H-imidazo[4,5-d]pyridazin-4,7-diamine;
(42) 2-butyl-1-methyl-7-(pyrrolidin-1-yl)-1H-imidazo[4,5-d]pyridazin-4-amine;
(43) 2-butyl-N7-(4-((dimethylamino)methyl)benzyl)-N7,1-dimethyl-1H-imidazo[4,5-d]pyridazin-4,7-diamine;
(44) 2-butyl-N7,1-dimethyl-N7-(4-(morpholinomethyl)benzyl)-1H-imidazo[4,5-d]pyridazine-4,7-diamine;
(45) 4-(((4-amino-2-butyl-1-methyl-1H-imidazo[4,5-d]pyridazin-7-yl)(methyl)amino)methyl)benzonitrile;
(46) N7-(4-(aminomethyl)benzyl)-2-butyl-N7,1-dimethyl-1H-imidazo[4,5-d]pyridazine-4,7-diamine;
(47) 2-butyl-N7-(4-(((2-methoxyethyl)(methyl)amino)methyl)benzyl)-N7,1-dimethyl-1H-imidazo[4,5-d]pyridazine-4,7-diamine;
(74) 2-butyl-7-isopropoxy-1-(pyridin-3-ylmethyl)-1H-imidazo[4,5-d]pyridazin-4-amine;
(82) 2-butyl-7-isopropoxy-1-(4-(((tetrahydro-2H-pyran-4-yl)amino)methyl)benzyl)-1H-imidazo[4,5-d]pyridazin-4-amine hydrochloride salt;
(83) 2-butyl-7-isopropoxy-1-(4-((isopropylamino)methyl)benzyl)-1H-imidazo[4,5-d]pyridazin-4-amine dihydrochloride salt;
(84) N-(4-((4-amino-2-butyl-7-isopropoxy-1H-imidazo[4,5-d]pyridazin-1-yl)methyl)benzyl)heptanamide;

(85) (4-(1-(4-amino-2-butyl-1-methyl-1H-imidazo[4,5-d]pyridazin-7-yl)pyrrolidin-3-yl)phenyl)methanol hydrochloride salt;

(86) 2-butyl-7-isopropoxy-1-methyl-1H-imidazo[4,5-d]pyridazin-4-amine;

(88) 2-butyl-N7-isopropyl-1-methyl-1H-imidazo[4,5-d]pyridazine-4,7-diamine;

(89) 2-butyl-1-methyl-7-(3-phenylpyrrolidin-1-yl)-1H-imidazo[4,5-d]pyridazin-4-amine;

(90) N7-benzyl-2-butyl-N7,1-dimethyl-1H-imidazo[4,5-d]pyridazine-4,7-diamine;

(91) 2-butyl-1-methyl-N7-(4-((4-methylpiperazin-1-yl)methyl)benzyl)-1H-imidazo[4,5-d]pyridazine-4,7-diamine;

(95) 2-butyl-1-(4-methoxybenzyl)-1H-imidazo[4,5-d]pyridazin-4-amine;

(98) 2-butyl-N7-isopropyl-1H-imidazo[4,5-d]pyridazine-4,7-diamine; and

(99) 2-butyl-7-(isopropylthio)-1H-imidazo[4,5-d]pyridazin-4-amine;

(100) (1R,3R)-3-((4-((4-amino-2-butyl-7-isopropoxy-1H-imidazo[4,5-d]pyridazin-1-yl)methyl)benzyl)amino)cyclobutan-1-ol dihydrochloride salt;

(101) 2-butyl-7-isopropoxy-1-(4-(pyrrolidin-1-ylmethyl)benzyl)-1H-imidazo[4,5-d]pyridazin-4-amine;

(102) 2-butyl-7-isopropoxy-1-(4-(morpholinomethyl)benzyl)-1H-imidazo[4,5-d]pyridazin-4-amine;

(103) N-(4-((4-amino-2-butyl-7-isopropoxy-1H-imidazo[4,5-d]pyridazin-1-yl)methyl)benzyl)propionamide;

(104) 2-butyl-7-isopropoxy-1-(4-(((2-methoxyethyl)amino)methyl)benzyl)-1H-imidazo[4,5-d]pyridazin-4-amine;

(106) N-(4-((4-amino-2-butyl-7-isopropoxy-1H-imidazo[4,5-d]pyridazin-1-yl)methyl)benzyl)benzamide;

(108) 2-butyl-7-isopropoxy-1-(4-(((2-(2-methoxyethoxy)ethyl)amino)methyl)benzyl)-1H-imidazo[4,5-d]pyridazin-4-amine;

(109) 2-butyl-1-(4-((hexylamino)methyl)benzyl)-7-isopropoxy-1H-imidazo[4,5-d]pyridazin-4-amine;

(110) 2-butyl-1-(4-((decylamino)methyl)benzyl)-7-isopropoxy-1H-imidazo[4,5-d]pyridazin-4-amine;

(114) 4-acetamidobenzyl (4-((4-amino-2-butyl-7-isopropoxy-1H-imidazo[4,5-d]pyridazin-1-yl)methyl)benzyl)carbamate;

(115) N-(4-((4-amino-2-butyl-7-isopropoxy-1H-imidazo[4,5-d]pyridazin-1-yl)methyl)benzyl)methanesulfonamide;

(116) 2-butyl-1-(4-((dimethylamino)methyl)benzyl)-7-isopropoxy-1H-imidazo[4,5-d]pyridazin-4-amine;

(117) tert-butyl (4-((4-amino-2-butyl-7-isopropoxy-1H-imidazo[4,5-d]pyridazin-1-yl)methyl)benzyl)glycinate;

(118) 2-butyl-7-isopropoxy-1-(4-((methylamino)methyl)benzyl)-1H-imidazo[4,5-d]pyridazin-4-amine;

(119) tert-butyl 3-((4-((4-amino-2-butyl-7-isopropoxy-1H-imidazo[4,5-d]pyridazin-1-yl)methyl)benzyl)amino)propanoate;

(120) 1-(4-(5,8,11-trioxa-2-azadodecyl)benzyl)-2-butyl-7-isopropoxy-1H-imidazo[4,5-d]pyridazin-4-amine;

(121) 2-butyl-4-isopropoxy-3-[[4-[[2-[2-[2-(2-methoxyethoxy)ethoxy]ethoxy]ethylamino]methyl]phenyl]methyl]imidazo[4,5-d]pyridazin-7-amine;

(123) 2-butyl-4-isopropoxy-3-[[4-[[2-[2-[2-[2-[2-[2-[2-[2-[2-[2-[2-(2-methoxyethoxy)ethoxy]ethoxy]ethoxy]ethoxy]ethoxy]ethoxy]ethoxy]ethoxy]ethoxy]ethoxy]ethylamino]methyl]phenyl]methyl]imidazo[4,5-d]pyridazin-7-amine di2,2,2-trifluoroacetate;

(124) 2-butyl-7-isopropoxy-1-(3-((methylamino)methyl)benzyl)-1H-imidazo[4,5-d]pyridazin-4-amine;

(125) 2-butyl- 1-(3-((dimethylamino)methyl)benzyl)-7-isopropoxy-1H-imidazo[4,5-d]pyridazin-4-amine;

(126) 2-butyl-1-(3-((cyclobutylamino)methyl)benzyl)-7-isopropoxy-1H-imidazo[4,5-d]pyridazin-4-amine dihydrochloride salt;

(127) 2-butyl-1-(3-((cyclopropylamino)methyl)benzyl)-7-isopropoxy-1H-imidazo[4,5-d]pyridazin-4-amine dihydrochloride salt;

(129) 3-((3-((4-amino-2-butyl-7-isopropoxy-1H-imidazo[4,5-d]pyridazin-1-yl)methyl)benzyl)amino)thietane 1,1-dioxide;

(130) 2-butyl-7-isopropoxy-1-(3-(((1-methylcyclobutyl)amino)methyl)benzyl)-1H-imidazo[4,5-d]pyridazin-4-amine dihydrochloride salt;

(132) (E)-1-(4-(aminomethyl)benzyl)-2-butyl-7-(3-methylbut-1-en-1-yl)-1H-imidazo[4,5-d]pyridazin-4-amine;

(133) 1-(4-(aminomethyl)benzyl)-2-butyl-7-isopentyl-1H-imidazo[4,5-d]pyridazin-4-amine;

(135) 1-(4-(aminomethyl)benzyl)-2-butyl-7-(1H-pyrrol-3-yl)-1H-imidazo[4,5-d]pyridazin-4-amine 2,2,2-trifluoroacetate;

(141) 1-(((1R,4R)-4-aminocyclohexyl)methyl)-2-butyl-7-(1H-pyrrol-3-yl)-1H-imidazo[4,5-d]pyridazin-4-amine;

(144) 1-[[4-(aminomethyl)phenyl]methyl]-2-butyl-7-(2,5-dihydro-1H-pyrrol-3-yl)imidazo[4,5-d]pyridazin-4-amine;

(145) 1-[[4-(aminomethyl)phenyl]methyl]-2-butyl-7-pyrrolidin-3-yl-imidazo[4,5-d]pyridazin-4-amine;

(147) 2-butyl-4-isopropoxy-3-[6-(tetrahydropyran-4-ylamino)hexyl]imidazo[4,5-d]pyridazin-7-amine dihydrochloride salt;

(150) 2-butyl-4-isopropoxy-3-[4-(tetrahydropyran-4-ylamino)butyl]imidazo[4,5-d]pyridazin-7-amine hydrochloride salt;

(154) 2-butyl-3-[6-[(1,1-dioxothietan-3-yl)amino]hexyl]-4-isopropoxy-imidazo[4,5-d]pyridazin-7-amine;

(156) 2-[(7-amino-2-butyl-4-isopropoxy-imidazo[4,5-d]pyridazin-3-yl)methyl]-2-methyl-propane-1,3-diol hydrochloride salt;

(157) 2-[(7-amino-2-butyl-4-isopropoxy-imidazo[4,5-d]pyridazin-3-yl)methyl]propane-1,3-diol hydrochloride salt;

(160) 1-(4-(aminomethyl)benzyl)-7-isopropoxy-2-methyl-1H-imidazo[4,5-d]pyridazin-4-amine;

(161) 3-[[4-(aminomethyl)phenyl]methyl]-4-isopropoxy-2-propyl sulfanyl-imidazo[4,5-d]pyridazin-7-amine;

(163) 3-[[4-(aminomethyl)phenyl]methyl]-4-isopropoxy-N2-propyl-imidazo[4,5-d]pyridazine-2,7-diamine;

(164) 3-[[4-(aminomethyl)phenyl]methyl]-2-(ethylaminomethyl)-4-isopropoxy-imidazo[4,5-d]pyridazin-7-amine or a pharmaceutically acceptable salt thereof.

Among the preceding listed compounds, the following compounds which are of interest may for example be cited:

(19) 4-(aminomethyl)cyclohexyl)methyl)-2-butyl-7-isopropoxy-1H-imidazo[4,5-d]pyridazin-4-amine dihydrochloride salt;

(20) 4-(aminomethyl)cyclohexyl)methyl)-2-butyl-7-isopropoxy-1H-imidazo[4,5-d]pyridazin-4-amine 2,2,2-trifluoroacetate;

(21) 1-(4-(aminomethyl)benzyl)-2-butyl-7-isopropoxy-1H-imidazo[4,5-d]pyridazin-4-amine;

(22) 1-(4-(aminomethyl)benzyl)-2-butyl-7-isopropoxy-1H-imidazo[4,5-d]pyridazin-4-amine 2,2,2-trifluoroacetate;

(23) 1-(((1S,3R)-3-aminocyclohexyl)methyl)-2-butyl-7-isopropoxy-1H-imidazo[4,5-d]pyridazin-4-amine (and enantiomer);

(24) 1-(4-amino-2-butyl-7-isopropoxy-1H-imidazo[4,5-d]pyridazin-1-yl)-2-methylpropan-2-ol;
(25) Trans 1-(4-aminocyclohexyl)methyl)-2-butyl-7-isopropoxy-1H-imidazo[4,5-d]pyridazin-4-amine;
(26) 1-((5-(aminomethyl)pyridin-2-yl)methyl)-2-butyl-7-isopropoxy-1H-imidazo[4,5-d]pyridazin-4-amine;
(28) N-(4-((4-amino-2-butyl-7-isopropoxy-1H-imidazo[4,5d]pyridazin-1-yl)methyl)benzyl)acetamide;
(33) 1-(3-(aminomethyl)benzyl)-2-butyl-7-isopropoxy-1H-imidazo[4,5-d]pyridazin-4-amine 2,2,2-trifluoroacetate;
(35) (4-((4-amino-2-butyl-7-isopropoxy-1H-imidazo[4,5-d]pyridazin-1-yl)methyl)phenyl)methanol;
(36) 2-butyl-1-(4-((cyclopropylamino)methyl)benzyl)-7-isopropoxy-1H-imidazo[4,5-d]pyridazin-4-amine;
(39) 2-butyl-7-isopropoxy-1-(4-(((1-methylcyclobutyl)amino)methyl)benzyl)-1H-imidazo[4,5-d]pyridazin-4-amine;
(40) 2-butyl-7-isopropoxy-1-(4-(piperazin-1-ylmethyl)benzyl)-1H-imidazo[4,5-d]pyridazin-4-amine;
(43) 2-butyl-N7-(4-((dimethylamino)methyl)benzyl)-N7,1-dimethyl-1H-imidazo[4,5-d]pyridazine-4,7-diamine;
(47) 2-butyl-N7-(4-(((2-methoxyethyl)(methyl)amino)methyl)benzyl)-N7,1-dimethyl-1H-imidazo[4,5-d]pyridazine-4,7-diamine;
(144) 1-[[4-(aminomethyl)phenyl]methyl]-2-butyl-7-(2,5-dihydro-1H-pyrrol-3-yl)imidazo[4,5-d]pyridazin-4-amine;
(156) 2-[(7-amino-2-butyl-4-isopropoxy-imidazo[4,5-d]pyridazin-3-yl)methyl]-2-methyl-propane-1,3-diol hydrochloride salt;
(157) 2-[(7-amino-2-butyl-4-isopropoxy-imidazo[4,5-d]pyridazin-3-yl)methyl]propane-1,3-diol hydrochloride salt;
(159) 1-(4-(aminomethyl)benzyl)-2-(ethoxymethyl)-7-isopropoxy-1H-imidazo[4,5-d]pyridazin-4-amine;
(161) 3-[[4-(aminomethyl)phenyl]methyl]-4-isopropoxy-2-propylsulfanyl-imidazo[4,5-d]pyridazin-7-amine;
(163) 3-[[4-(aminomethyl)phenyl]methyl]-4-isopropoxy-N2-propyl-imidazo[4,5-d]pyridazine-2,7-diamine;
(164) 3-[[4-(aminomethyl)phenyl]methyl]-2-(ethylaminomethyl)-4-isopropoxy-imidazo[4,5-d]pyridazin-7-amine or a pharmaceutically acceptable salt thereof.

Among the preceding listed compounds, the following compounds which are of interest may for example be cited:

(91) 2-butyl-1-methyl-N7-(4-((4-methylpiperazin-1-yl)methyl)benzyl)-1H-imidazo[4,5-d]pyridazine-4,7-diamine;
(93) 4-amino-2-butyl-1-(4-methoxybenzyl)-1H-imidazo[4,5-d]pyridazin-7-ol;
(95) 2-butyl-1-(4-methoxybenzyl)-1H-imidazo[4,5-d]pyridazin-4-amine;
(96) 2-butyl-1-(4-methoxybenzyl)-7-(1H-pyrazol-3-yl)-1H-imidazo[4,5-d]pyridazin-4-amine;
(97) 2-butyl-1-(4-methoxybenzyl)-7-(1-methyl-1H-pyrazol-4-yl)-1H-imidazo[4,5-d]pyridazin-4-amine;
(98) 2-butyl-N7-isopropyl-1H-imidazo[4,5-d]pyridazine-4,7-diamine;
(123) 2-butyl-4-isopropoxy-3-[[4-[[2-[2-[2-[2-[2-[2-[2-[2-[2-[2-[2-(2-methoxyethoxy)ethoxy]ethoxy]ethoxy]ethoxy]ethoxy]ethoxy]ethoxy]ethoxy]ethoxy]ethoxy]ethylamino]methyl]phenyl]methyl]imidazo[4,5-d]pyridazin-7-amine di2,2,2-trifluoroacetate;
(141) 1-(((1R,4R)-4-aminocyclohexyl)methyl)-2-butyl-7-(1H-pyrrol-3-yl)-1H-imidazo[4,5-d]pyridazin-4-amine;
(144) 1-[[4-(aminomethyl)phenyl]methyl]-2-butyl-7-(2,5-dihydro-1H-pyrrol-3-yl)imidazo[4,5-d]pyridazin-4-amine;
(145) 1-[[4-(aminomethyl)phenyl]methyl]-2-butyl-7-pyrrolidin-3-yl-imidazo[4,5-d]pyridazin-4-amine; (160) 1-(4-(aminomethyl)benzyl)-7-isopropoxy-2-methyl-1H-imidazo[4,5-d]pyridazin-4-amine;
(163) 3-[[4-(aminomethyl)phenyl]methyl]-4-isopropoxy-N2-propyl-imidazo[4,5-d]pyridazine-2,7-diamine;
(164) 3-[[4-(aminomethyl)phenyl]methyl]-2-(ethylaminomethyl)-4-isopropoxy-imidazo[4,5-d]pyridazin-7-amine or a pharmaceutically acceptable salt thereof.

In accordance with the present disclosure, the compounds of the formula (I) can be prepared for example by the following processes, corresponding to schemes 1 (SynMethod 1), 2 (including SynMethods 2, 2a, and 2b), 3 (SynMethod 3) and 4 (SynMethod 4).

These processes form also part of the present disclosure and are detailed below.

The compounds of the formula (I) and other related compounds having different substituents are synthesized using techniques and materials described below or otherwise known by the skilled person in the art. In addition, solvents, temperatures and other reaction conditions presented below may vary as deemed appropriate to the skilled person in the art.

General below methods for the preparation of compounds of the disclosure are optionally modified by the use of appropriate reagents and conditions for the introduction of the various moieties found in the formula (I) as described below.

SCHEME 1: Preparation of compounds of the formula (I) - General process (SynMethod 1)

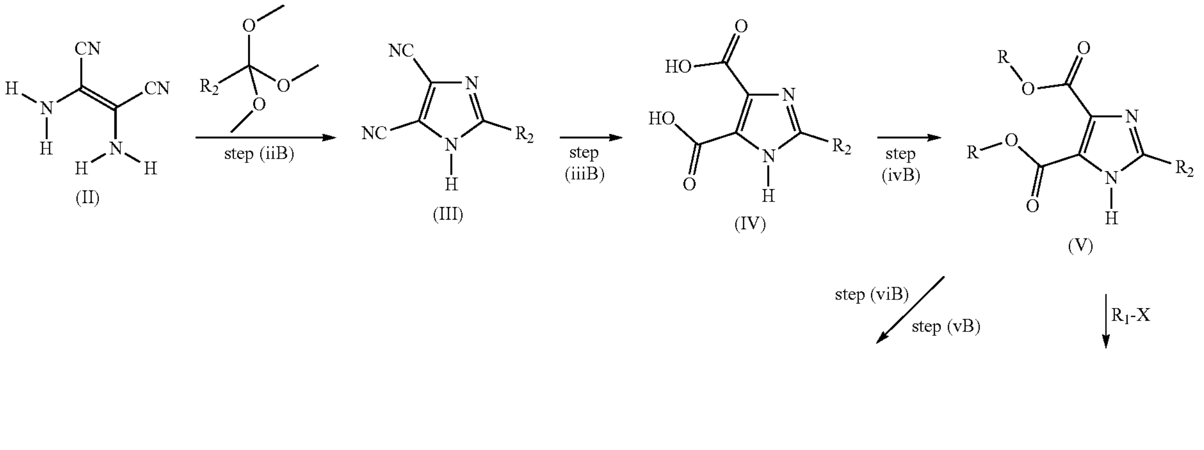

(II) (III) (IV) (V)

-continued

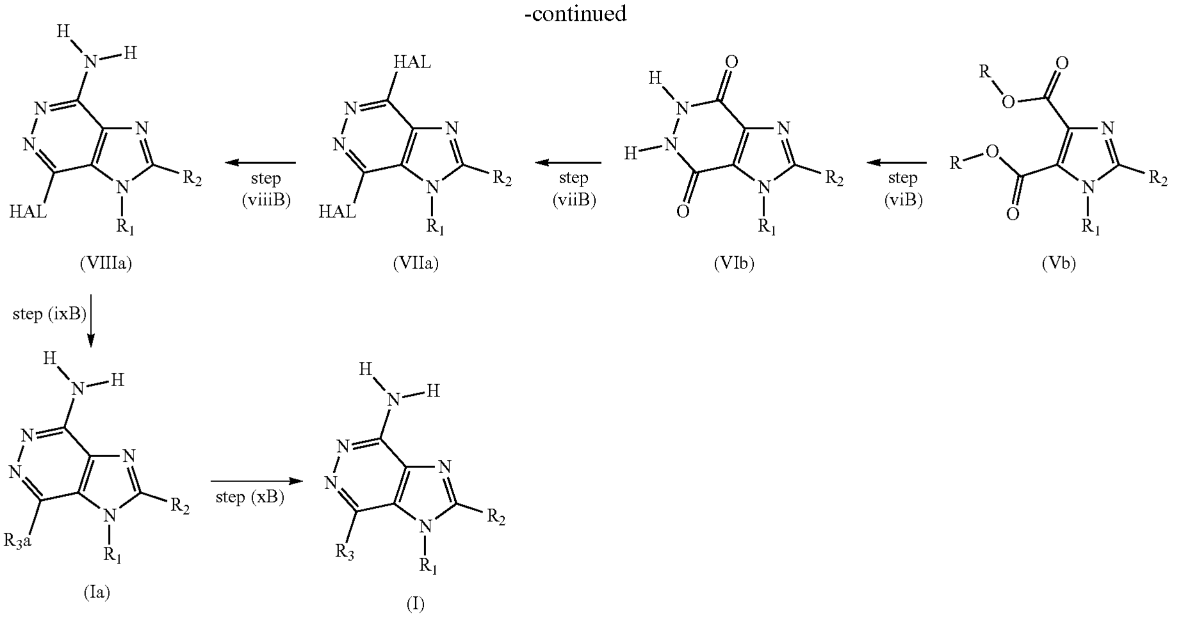

According to SCHEME 1, a process in accordance with the present disclosure comprises at least the following steps:

(iB) providing a compound of formula (II), (II)

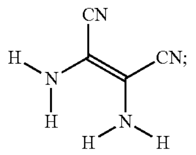

(iiB) cyclization of the compound of formula (II) provided in step (iB) by reaction with $R_2$—$C(OCH_3)_3$ or $R_2$—COCl wherein $R_2$ is as defined in the present disclosure in order to obtain a compound of formula (III), (III)

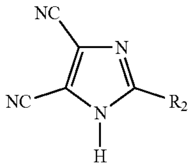

wherein $R_2$ is as defined in in the present disclosure;

(iiiB) hydrolysis of nitrile groups of the compound of formula (III) obtained from step (iiB) in order to obtain a compound of formula (IV), (IV)

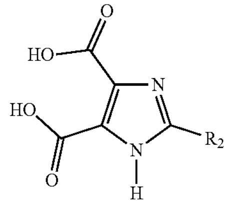

wherein $R_2$ is as defined in the present disclosure;

(ivB) esterification of carboxylic acid functions of the compound of formula (IV) obtained from step (iiiB) in order to obtain a compound of formula (V), (V)

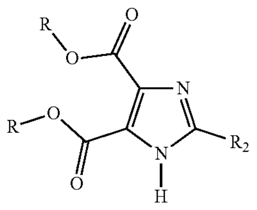

wherein R is a $(C_1$-$C_4)$alkyl- group, for instance a methyl group, an ethyl group, a propyl group or a butyl group, such as a methyl group and $R_2$ is as defined in the present disclosure;

(vB) optionally reacting the compound of formula (V) obtained from step (ivB) with $R_1$—X wherein $R_1$ is as defined in the present disclosure, and X represents a halogen atom, for instance chlorine, iodine or bromine atom in order to obtain a compound of formula (Vb), (Vb)

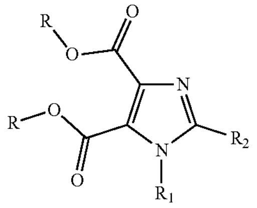

wherein R is a ($C_1$-$C_4$)alkyl group, for instance a methyl group, an ethyl group, a propyl group or a butyl group, such as a methyl group and $R_1$ and $R_2$ are as defined in the present disclosure;

(viB) cyclization of the compound of formula (Vb) obtained from step (vB) or the compound of formula (V) (in which $R_1$ is a hydrogen atom) obtained from step (ivB) in order to obtain a compound of formula (VIb), (VIb)

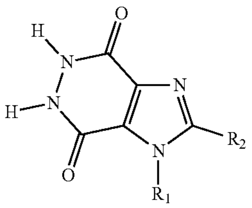

wherein $R_1$ and $R_2$ are as defined in the present disclosure;

(viiB) dihalogenation of the compound of formula (VIb) obtained from step (viB) in order to obtain a compound of formula (VIIa), (VIIa)

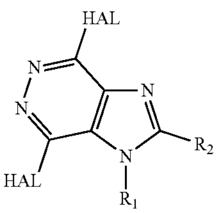

wherein $R_1$ and $R_2$ are as defined in the present disclosure and HAL is a halogen atom for instance a chlorine atom, a fluorine atom, an iodine atom or a bromine atom, for example the two HAL are the same and are chlorine atoms;

(viiiB) nucleophilic aromatic substitution of the compound of formula (VIIa) obtained from step (viiB) in order to obtain a compound of formula (VIIIa), (VIIIa)

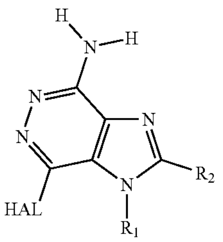

wherein $R_1$ and $R_2$ are as defined in the present disclosure and HAL is a halogen atom for instance a chlorine atom, a fluorine atom, an iodine atom or a bromine atom, for example a chlorine atom;

(ixB) substitution and/or coupling of the compound of formula (VIIIa) obtained from step (viiiB) in order to obtain a compound of formula (Ia), (Ia)

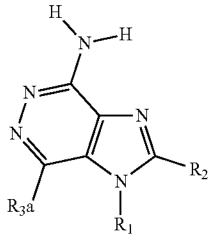

wherein $R_1$ and $R_2$ are as defined in the present disclosure, and $R_{3a}$ represents $R_3$ as defined in the present disclosure comprising or not a hydroxyl protecting group, an amino protecting group, a carboxylic acid protecting group, an aldehyde protecting group or a ketone protecting group;

(xB) when $R_{3a}$ is other than $R_3$ as defined in the present disclosure, then reacting the compound of formula (Ia) obtained from step (ixB) with any suitable reagents and in any suitable conditions in order to obtain a compound of formula (I) as defined in the present disclosure.

Said route allows to prepare, for example the following compounds of formula (I) in accordance with the present disclosure: 1, 2, 3, 4, 5, 6, 7, 8, 9, 10, 11, 12, 13, 14, 15, 16, 17, 18, 48, 49, 50, 51, 52, 53, 54, 55, 56, 57, 58, 59, 60, 61, 62, 63, 64, 65, 66, 67, 68, 69, 70, 71, 72, 73, 86, 92, 93, 94, 95, 96, 97, 98 and 99.

SCHEME 2: Preparation of compounds of the formula (I) - General process (SynMethods 2, 2a and 2b)
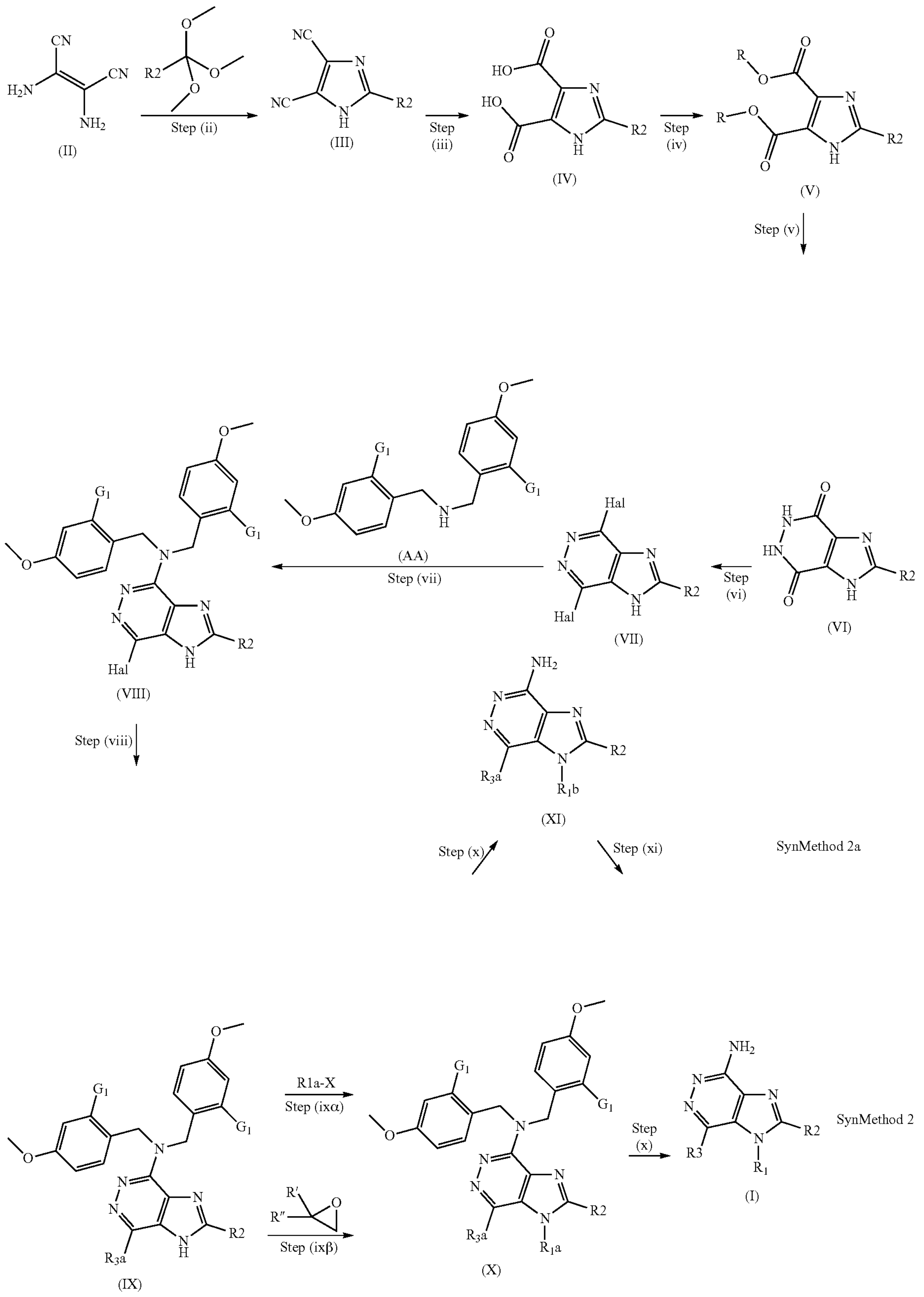
(II) (III) (IV) (V) (VI) (VII) (VIII) (XI) (IX) (X) (I)

-continued

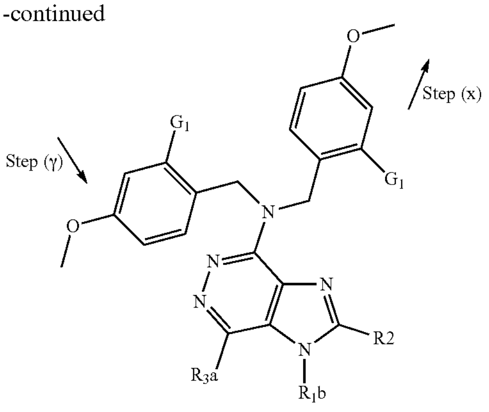

(XII)

SynMethod 2b

According to SCHEME 2, a process in accordance with the present disclosure comprises at least the following steps:

(i) providing a compound of formula (II), (II)

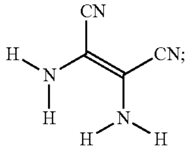

(ii) cyclization of the compound of formula (II) provided in step (i) by reaction with $R_2$—$C(OCH_3)_3$ or $R_2$—COCl wherein $R_2$ is as defined in the present disclosure or is a hydrogen atom in order to obtain a compound of formula (III), (III)

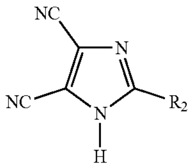

wherein $R_2$ is as defined in the present disclosure or is a hydrogen atom;

(iii) hydrolysis of nitrile groups of the compound of formula (III) obtained from step (ii) in order to obtain a compound of formula (IV), (IV)

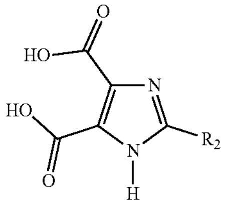

wherein $R_2$ is as defined in the present disclosure or is a hydrogen atom;

(iv) esterification of carboxylic acid functions of the compound of formula (IV) obtained from step (iii) in order to obtain a compound of formula (V), (V)

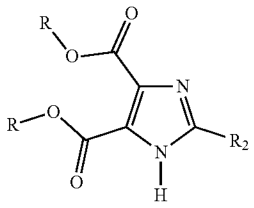

wherein R is a ($C_1$-$C_4$) alkyl group, for instance a methyl group, an ethyl group, a propyl group or a butyl group, such as a methyl group and $R_2$ is as defined in the present disclosure or is a hydrogen atom;

(v) cyclization of the compound of formula (V) obtained from step (iv) in order to obtain a compound of formula (VI), (VI)

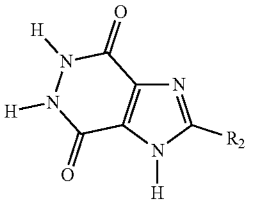

wherein $R_2$ is as defined in the present disclosure or is a hydrogen atom;

(vi) dihalogenation of the compound of formula (VI) obtained from step (v) in order to obtain a compound of formula (VII), (VII)

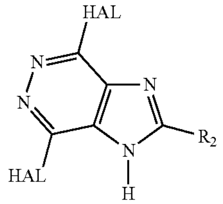

wherein $R_2$ is as defined in the present disclosure or is a hydrogen atom and HAL is a halogen atom, for instance a chlorine atom, a fluorine atom, an iodine atom or a bromine atom, for example the two HAL are the same and are chlorine atoms;

(vii) nucleophilic aromatic substitution of the compound of formula (VII) obtained from step (vi) with a compound of formula (AA)

(AA)

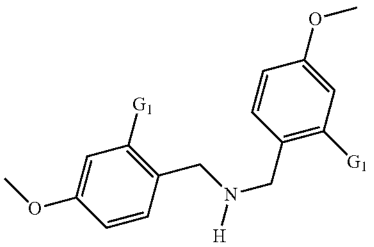

wherein the two $G_1$ represent independently a hydrogen atom or a methoxy group, for example the two $G_1$ are a methoxy group, in order to obtain a compound of formula (VIII), (VIII)

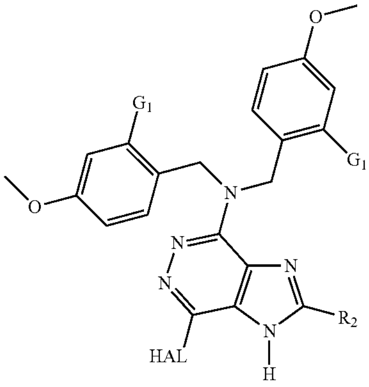

wherein $R_2$ is as defined in the present disclosure or is a hydrogen atom, HAL is a halogen atom for instance a chlorine atom, a fluorine atom, an iodine atom or a bromine atom, for example a chlorine atom, and the two $G_1$ represent independently a hydrogen atom or a methoxy group, for example the two $G_1$ are a methoxy group;

(viii) substitution and/or coupling reaction of the compound of formula (VIII) obtained from step (vii) in order to obtain a compound of formula (IX), (IX)

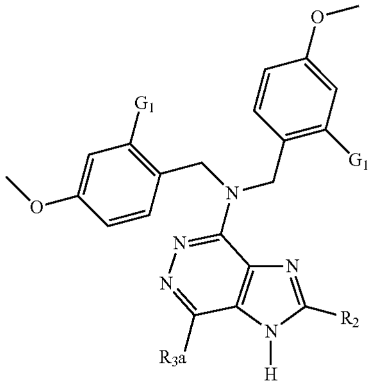

wherein $R_2$ is as defined in the present disclosure or is a hydrogen atom, $R_{3a}$ represents $R_3$ as defined in the present disclosure comprising or not a hydroxyl protecting group, an amino protecting group, a carboxylic acid protecting group, an aldehyde protecting group or a ketone protecting group and the two $G_1$ represent independently a hydrogen atom or a methoxy group, for example the two $G_1$ are a methoxy group;

then either (ixAlpha, also named ixα) reacting the compound of formula (IX) obtained from step (viii) with $R_{1a}$—X wherein $R_{1a}$ is $R_1$ as defined in the present disclosure comprising or not a hydroxyl protecting group, an amino protecting group, a carboxylic acid protecting group, an aldehyde protecting group or a ketone protecting group, and X represents a halogen atom, a tosylate or a mesylate in order to obtain a compound of formula (X), (X)

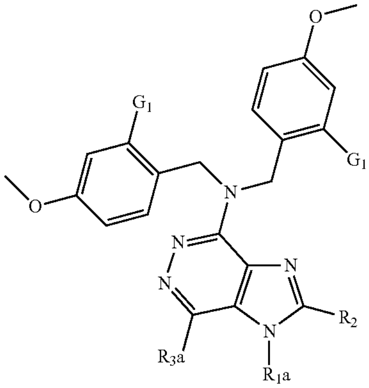

wherein $R_2$ is as defined in the present disclosure or is a hydrogen atom, $R_{3a}$ represents $R_3$ as defined in the present disclosure comprising or not a hydroxyl protecting group, an amino protecting group, a carboxylic acid protecting group, an aldehyde protecting group or a ketone protecting group, the two $G_1$ represent independently a hydrogen atom or a methoxy group, for example the two $G_1$ are a methoxy group, and $R_{1a}$ is as defined above in this step (ixAlpha);

or (ixBeta, also named ixβ) reacting the compound of formula (IX) obtained from step (viii) with an epoxide of formula

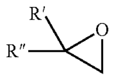

in which R' and R" are independently a hydrogen atom or a ($C_1$-$C_6$)alkyl group, such as a methyl group in order to obtain a compound of formula (X), (X)

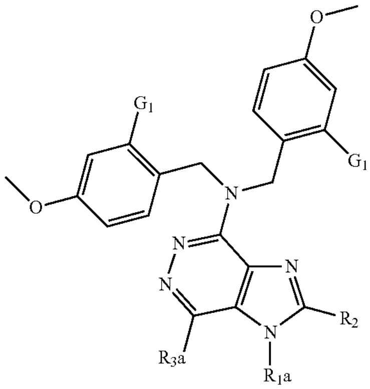

wherein $R_2$ is as defined in the present disclosure or is a hydrogen atom, $R_{3a}$ represents $R_3$ as defined in the present disclosure comprising or not a hydroxyl protecting group, an amino protecting group, a carboxylic acid protecting group, an aldehyde protecting group or a ketone protecting group, the two $G_1$ represent independently a hydrogen atom or a methoxy group, for example the two $G_1$ are a methoxy group, and $R_{1a}$ is as defined above in the step (ixAlpha);

and either (x) deprotecting the compound of formula (X) obtained from step (ixAlpha) or (ixBeta) in order to obtain a compound of formula (I) as defined in the present disclosure; and when $R_2$ is a hydrogen atom in compound of formula (X), before deprotection, the hydrogen was transformed to $R_2$ as defined in formula (I) through chemistry modification, such as metalation, followed for example either by reaction with alkyldisulfide, or dimethylformamide, or N-Bromosuccinimide, which was further submitted to other chemistry reaction, if necessary, such as oxidation, or reduction amination or nucleophilic substitution, to give requisite $R_2$;

or (x) deprotecting the compound of formula (X) obtained from step (ixAlpha) or (ixBeta) in order to obtain a compound of formula (XI)

(XI)

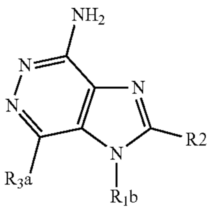

wherein $R_{3a}$ represents $R_3$ as defined in the present disclosure comprising or not a hydroxyl protecting group, an amino protecting group, a carboxylic acid protecting group, an aldehyde protecting group or a ketone protecting group, $R_2$ is as defined in the present disclosure and $R_{1b}$ is $R_{1a}$ as defined in the present disclosure or $R_{1a}$ with a function such as an amino group, an alcohol, and an aldehyde; and then (xi) reducing, reductive aminating, nucleophilic substituting, and/or oxidating the compound of formula (XI) obtained from this step (x) in order to obtain a compound of formula (I) as defined in the present disclosure;

or (Gamma, also named γ) reducing, reductive aminating, nucleophilic substituting, and/or oxidating the compound of formula (X) obtained from step (ixAlpha) or (ixBeta) in order to obtain a compound of formula (XII)

(XII)

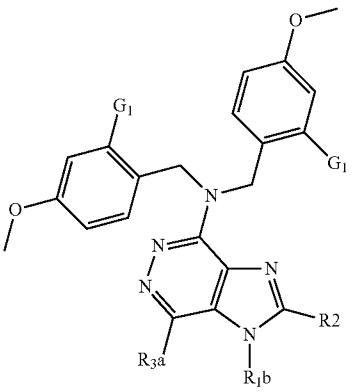

wherein $R_{3a}$ represents $R_3$ as defined in the present disclosure comprising or not a hydroxyl protecting group, an amino protecting group, a carboxylic acid protecting group, an aldehyde protecting group or a ketone protecting group, $R_2$ is as defined in the present disclosure, the two $G_1$ represent independently a hydrogen atom or a methoxy group, for example the two $G_1$ are a methoxy group, and Rib is a derivative of $R_{1a}$ as defined in the present disclosure through reductive amination, reduction, substitution, and/or oxydation; and then (x) deprotecting the compound of formula (XII) obtained from step (Gamma) in order to obtain a compound of formula (I) as defined in the present disclosure.

As shown in scheme 2, three options are available from compounds of formula (X).

The first option is called in the present disclosure SynMethod 2. It comprises only step (x) from a compound of formula (X) as defined in the present disclosure to obtain a compound of formula (I) as defined in the present disclosure.

The second option is called in the present disclosure SynMethod 2a. It comprises step (x) from a compound of formula (X) as defined in the present disclosure to obtain a compound of formula (XI) as defined in the present disclosure and then step (xi) from a compound of formula (XI) as defined in the present disclosure to obtain a compound of formula (I) as defined in the present disclosure.

The third option is called in the present disclosure SynMethod 2b. It comprises step (Gamma) (also named step y) from a compound of formula (X) as defined in the present disclosure to obtain a compound of formula (XII) as defined in the present disclosure and then step (x) from a compound of formula (XII) as defined in the present disclosure to obtain a compound of formula (I) as defined in the present disclosure.

Said route SynMethod 2 allows to prepare for example the following compounds of formula (I) in accordance with the present disclosure: 19, 20, 21, 22, 23, 24, 25, 27, 32, 33, 34, 74, 75, 76, 77, 78, 79, 80, 81, 82, 83 and 165.

Said route SynMethod 2a allows to prepare for example the following compounds of formula (I) in accordance with the present disclosure: 38, 39, 40, 84, 103, 104, 106, 107, 108, 109, 110, 111, 112, 113, 114, 115, 116, 117, 119, 148, 151, 153 and 155.

Said route SynMethod 2b allows to prepare for example the following compounds of formula (I) in accordance with the present disclosure: 26, 28, 29, 30, 31, 35, 36, 37, 100 to 102, 105, 120 to 131, 146, 147, 149, 150, 152, 154, and 156 to 160

SCHEME 3: Preparation of compounds of the formula (I) - General process (SynMethod 3)

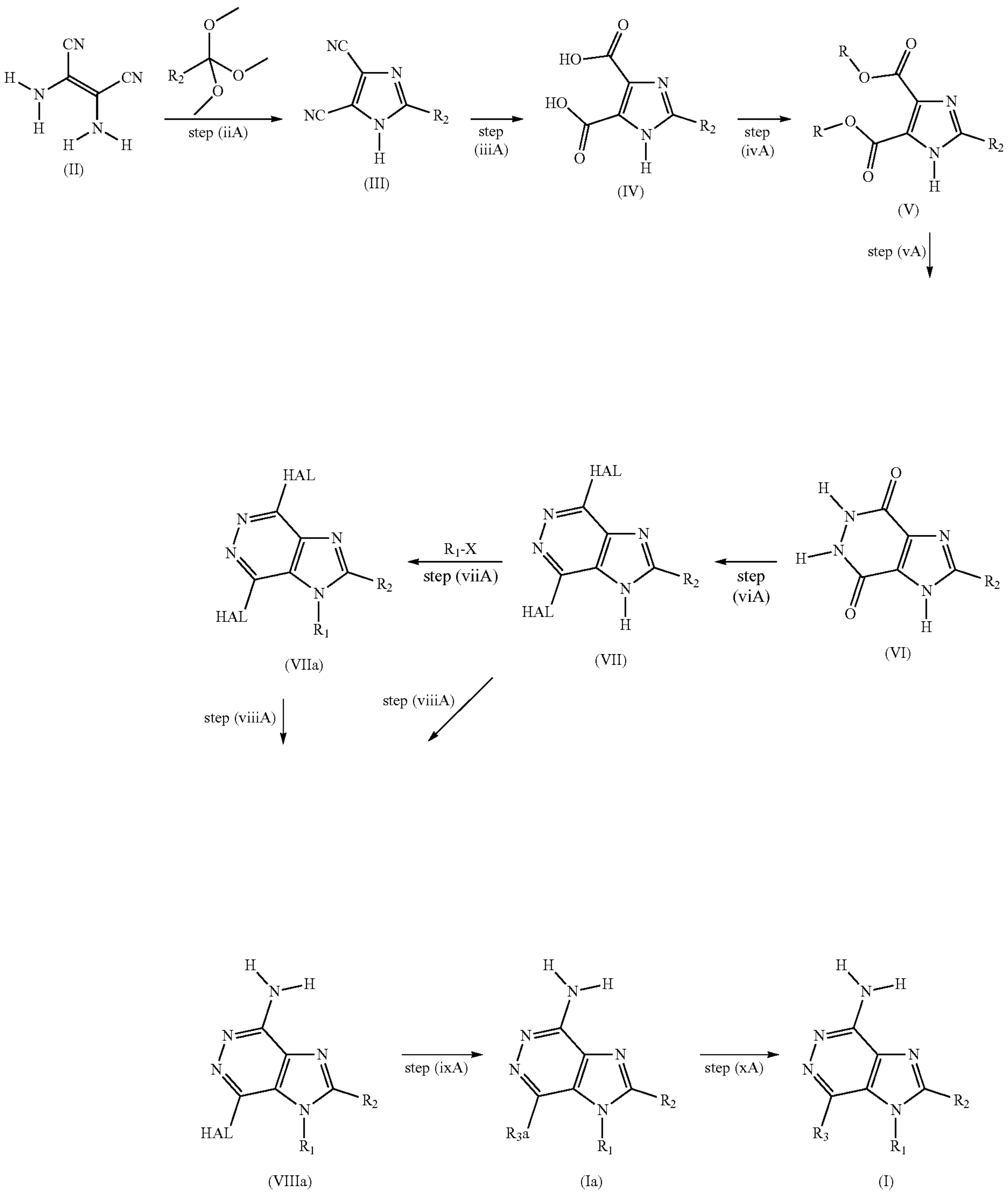

(II) (III) (IV) (V) (VI) (VII) (VIIa) (VIIIa) (Ia) (I)

According to SCHEME 3, a process in accordance with the present disclosure comprises at least the following steps:

(iA) providing a compound of formula (II)

(II)

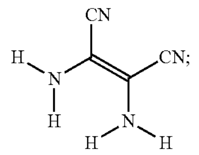

(iiA) cyclization of the compound of formula (II) provided in step (iA) by reaction with $R_2$—$C(OCH_3)_3$ or $R_2$—COCl wherein $R_2$ is as defined in the present disclosure in order to obtain a compound of formula (III), (III)

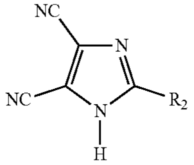

wherein $R_2$ is as defined in the present disclosure;

(iiiA) hydrolysis of nitrile groups of the compound of formula (III) obtained from step (iiA) in order to obtain a compound of formula (IV), (IV)

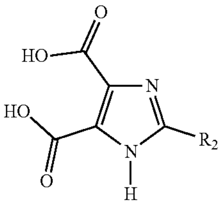

wherein $R_2$ is as defined in the present disclosure;

(ivA) esterification of carboxylic acid functions of the compound of formula (IV) obtained from step (iiiA) in order to obtain a compound of formula (V)

(V)

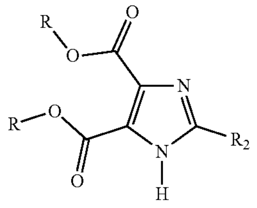

wherein R is a ($C_1$-$C_4$) alkyl group, for instance a methyl group, an ethyl group, a propyl group or a butyl group, such as a methyl group and $R_2$ is as defined in the present disclosure;

(vA) cyclization of the compound of formula (V) obtained from step (ivA) in order to obtain a compound of formula (VI), (VI)

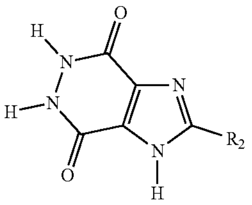

wherein $R_2$ is as defined in the present disclosure;

(viA) dihalogenation of the compound of formula (VI) obtained from step (vA) in order to obtain a compound of formula (VII);

(VII)

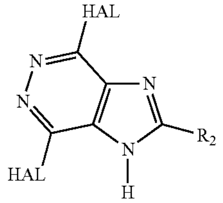

wherein $R_2$ is as defined in the present disclosure, and HAL is a halogen atom for instance a chlorine atom, a fluorine atom, an iodine atom or a bromine atom, for example the two HAL are the same and are chlorine atoms;

(viiA) optionally reacting the compound of formula (VII) obtained from step (viA) with $R_1$—X wherein $R_1$ is as defined in the present disclosure, and X represents a halogen atom for instance a chlorine atom, an iodine atom or a bromine atom in order to obtain a compound of formula (VIIa);

(VIIa)

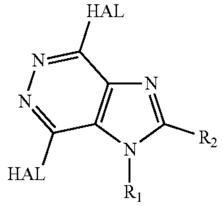

wherein $R_1$ and $R_2$ are as defined in the present disclosure, and HAL is a halogen atom for instance a chlorine atom, a fluorine atom, an iodine atom or a bromine atom, for example the two HAL are the same and are chlorine atoms;

(viiiA) nucleophilic aromatic substitution of the compound of formula (VIIa) obtained from step (viiA) or of the compound of formula (VII) (in which $R_1$ is a hydrogen atom) obtained from step (viA) in order to obtain a compound of formula (VIIIa), (VIIIa)

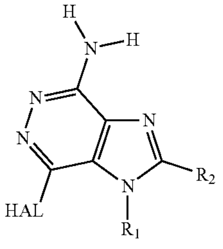

wherein $R_1$ and $R_2$ are as defined in the present disclosure, and HAL is a halogen atom for instance a chlorine atom, a fluorine atom, an iodine atom or a bromine atom, for example a chlorine atom;

(ixA) substitution and/or coupling of the compound of formula (VIIIa) obtained from step (viiiA) in order to obtain a compound of formula (Ia), (Ia)

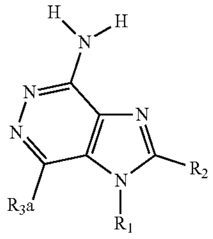

wherein $R_{3a}$ represents $R_3$ as defined in the present disclosure comprising or not a hydroxyl protecting group, an amino protecting group, a carboxylic acid protecting group, an aldehyde protecting group or a ketone protecting group, and $R_1$ and $R_2$ are as defined in the present disclosure;

(xA) when $R_{3a}$ is other than $R_3$ as defined in the present disclosure, then reacting the compound of formula (Ia) obtained from step (ixA) with any suitable reagents and in any suitable conditions in order to obtain a compound of formula (I) as defined in the present disclosure.

Said route SynMethod 3 allows to prepare for example the following compounds of formula (I) in accordance with the present disclosure: 41, 42, 43, 44, 45, 46, 47, 85, 87, 88, 89, 90 and 91.

SCHEME 4: Preparation of compounds of the formula (I) - General process (SynMethod 4)

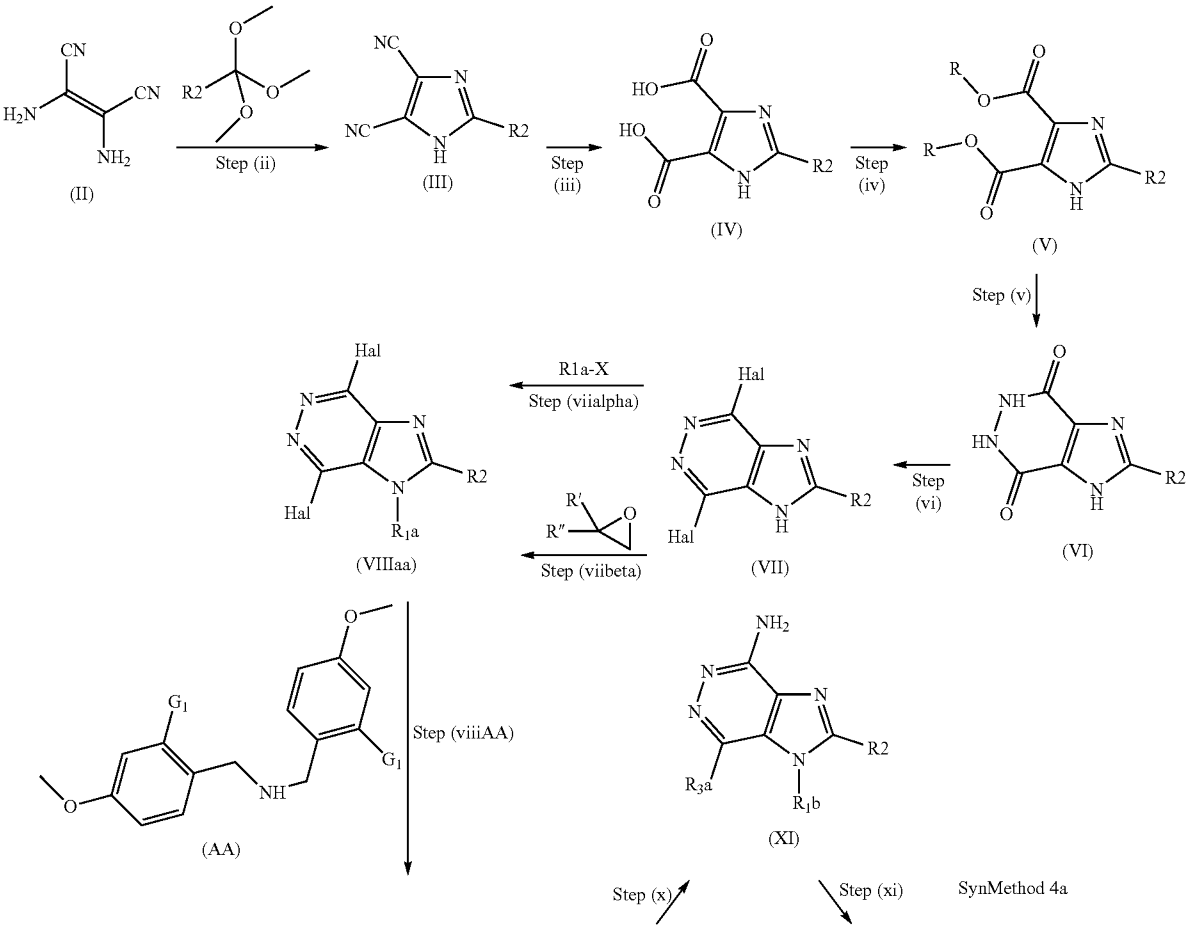

-continued

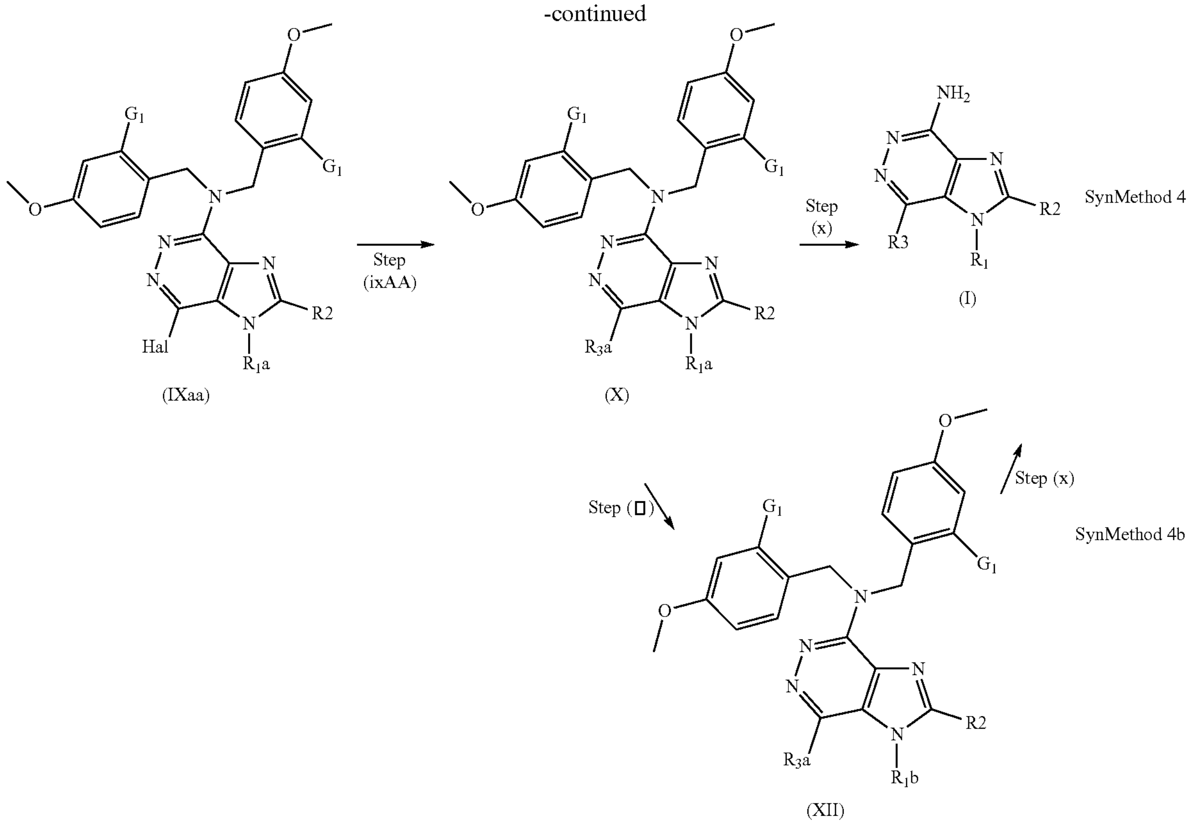

(IXaa) (X) (I) (XII)

According to SCHEME 4, a process in accordance with the present disclosure comprises at least the following steps:

(i) providing a compound of formula (II), (II)

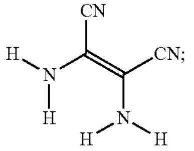

(ii) cyclization of the compound of formula (II) provided in step (i) by reaction with $R_2$—$C(OCH_3)_3$ or $R_2$—COCl wherein $R_2$ is as defined in the present disclosure in order to obtain a compound of formula (III), (III)

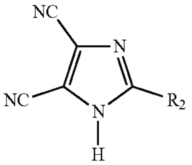

wherein $R_2$ is as defined in the present disclosure;

(iii) hydrolysis of nitrile groups of the compound of formula (III) obtained from step (ii) in order to obtain a compound of formula (IV), (IV)

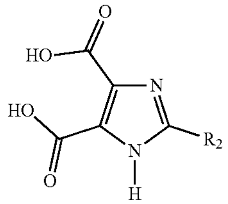

wherein $R_2$ is as defined in the present disclosure;

(iv) esterification of carboxylic acid functions of the compound of formula (IV) obtained from step (iii) in order to obtain a compound of formula (V), (V)

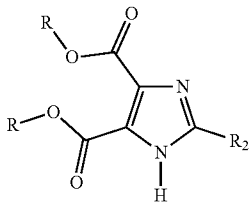

wherein R is a ($C_1$-$C_4$) alkyl group, for instance a methyl group, an ethyl group, a propyl group or a butyl group, such as a methyl group and $R_2$ is as defined in the present disclosure;

(v) cyclization of the compound of formula (V) obtained from step (iv) in order to obtain a compound of formula (VI), (VI)

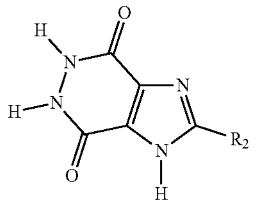

wherein $R_2$ is as defined in the present disclosure;

(vi) dihalogenation of the compound of formula (VI) obtained from step (v) in order to obtain a compound of formula (VII), (VII)

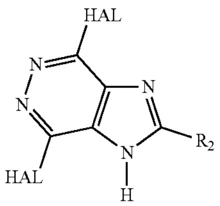

wherein $R_2$ is as defined in the present disclosure and HAL is a halogen atom, for instance a chlorine atom, a fluorine atom, an iodine atom or a bromine atom, for example the two HAL are the same and are chlorine atoms;

then either (viialpha, also named viiα) reacting the compound of formula (VII) obtained from step (vi) with $R_{1a}$—X wherein $R_{1a}$ is $R_1$ as defined in the present disclosure comprising or not a hydroxyl protecting group, an amino protecting group, a carboxylic acid protecting group, an aldehyde protecting group or a ketone protecting group, and X represents a halogen atom, a tosylate or a mesylate in order to obtain a compound of formula (VIIIaa), (VIIIaa)

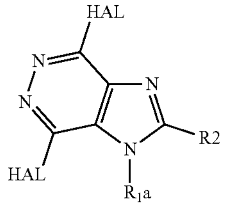

wherein $R_2$ is as defined in the present disclosure, HAL is a halogen atom, for instance a chlorine atom, a fluorine atom, an iodine atom or a bromine atom, for example the two HAL are the same and are chlorine atoms, and $R_{1a}$ is as defined above in this step (viialpha);

or (viiBeta, also named viiβ) reacting the compound of formula (VII) obtained from step (vi) with an epoxide of formula

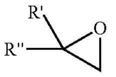

in which R' and R" are independently a hydrogen atom or a ($C_1$-$C_6$)alkyl group, such as a methyl group in order to obtain a compound of formula (VIIIaa), (VIIIaa)

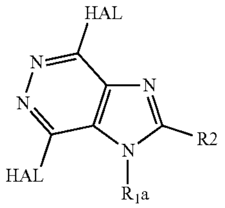

wherein $R_2$ is as defined in the present disclosure, HAL is a halogen atom, for instance a chlorine atom, a fluorine atom, an iodine atom or a bromine atom, for example the two HAL are the same and are chlorine atoms, and $R_{1a}$ is as defined above in the step (viialpha);

(viiiAA) nucleophilic aromatic substitution of the compound of formula (VIIIaa) obtained from step (viialpha) or step (viibeta) with a compound of formula (AA)

(AA)

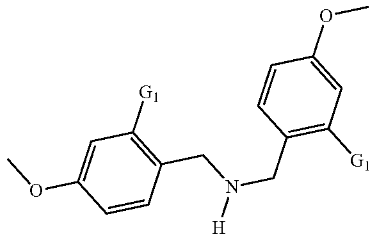

wherein the two $G_1$ represent independently a hydrogen atom or a methoxy group, for example the two $G_1$ are a methoxy group, in order to obtain a compound of formula (IXaa), (IXaa)

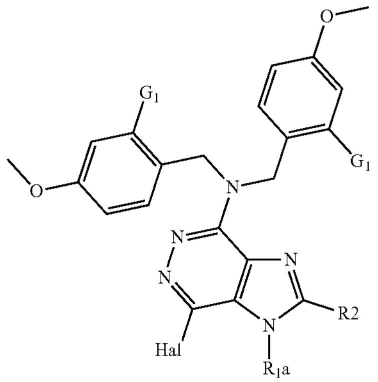

wherein $R_2$ is as defined in the present disclosure, HAL is a halogen atom for instance a chlorine atom, a fluorine atom, a iodine atom or a bromine atom, for example a chlorine atom, $R_{1a}$ is as defined above in the step (viialpha), and the two $G_1$ represent independently a hydrogen atom or a methoxy group, for example the two $G_1$ are a methoxy group;

(ixAA) substitution and/or coupling reaction of the compound of formula (IXaa) obtained from step (viiiAA) in order to obtain a compound of formula (X), (X)

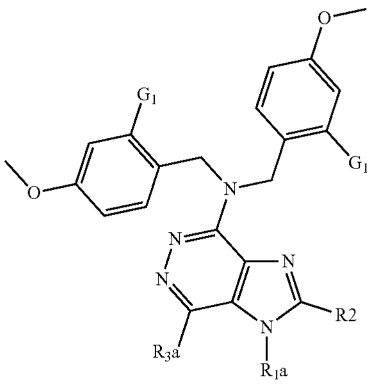

wherein $R_2$ is as defined in the present disclosure, $R_{1a}$ is as defined above in the step (viialpha), $R_{3a}$ represents $R_3$ as defined in the present disclosure comprising or not a hydroxyl protecting group, an amino protecting group, a carboxylic acid protecting group, an aldehyde protecting group or a ketone protecting group and the two $G_1$ represent independently a hydrogen atom or a methoxy group, for example the two $G_1$ are a methoxy group;

and either (x) deprotecting the compound of formula (X) obtained from step (ixAA) in order to obtain a compound of formula (I) as defined in the present disclosure;

or (x) deprotecting the compound of formula (X) obtained from step (ixAA) in order to obtain a compound of formula (XI)

(XI)

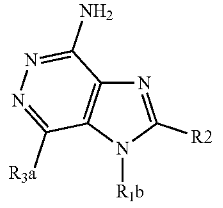

wherein $R_{3a}$ represents $R_3$ as defined in the present disclosure comprising or not a hydroxyl protecting group, an amino protecting group, a carboxylic acid protecting group, an aldehyde protecting group or a ketone protecting group, $R_2$ is as defined in the present disclosure and $R_{1b}$ is $R_1$a or $R_1$a with a function such as an amino group, an alcohol, and an aldehyde; and then (xi) reducing, reductive aminating, nucleophilic substituting, and/or oxidating the compound of formula (XI) obtained from this step (x) in order to obtain a compound of formula (I) as defined in the present disclosure;

or (Gamma, also named γ) reducing, reductive aminating, nucleophilic substituting, and/or oxidating the compound of formula (X) obtained from step (ixAA) in order to obtain a compound of formula (XII)

(XII)

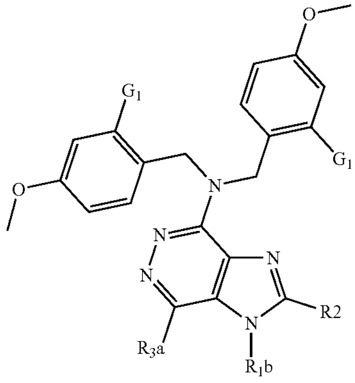

wherein $R_{3a}$ represents $R_3$ as defined in the present disclosure comprising or not a hydroxyl protecting group, an amino protecting group, a carboxylic acid protecting group, an aldehyde protecting group or a ketone protecting group, $R_2$ is as defined in the present disclosure, the two $G_1$ represent independently a hydrogen atom or a methoxy group, for example the two $G_1$ are a methoxy group, and Rib is a derivative of $R_{1a}$ through reductive amination, reduction, substitution, and/or oxidation; and then (x) deprotecting the compound of formula (XII) obtained from step (Gamma) in order to obtain a compound of formula (I) as defined in the present disclosure.

As shown in scheme 4, three options are available from compounds of formula (X).

The first option is called in the present disclosure SynMethod 4. It comprises only step (x) from a compound of formula (X) as defined in the present disclosure to obtain a compound of formula (I) as defined in the present disclosure.

The second option is called in the present disclosure SynMethod 4a. It comprises step (x) from a compound of formula (X) as defined in the present disclosure to obtain a compound of formula (XI) as defined in the present disclosure and then step (xi) from a compound of formula (XI) as defined in the present disclosure to obtain a compound of formula (I) as defined in the present disclosure.

The third option is called in the present disclosure SynMethod 4b. It comprises step (Gamma) (also named step y) from a compound of formula (X) as defined in the present disclosure to obtain a compound of formula (XII) as defined in the present disclosure and then step (x) from a compound of formula (XII) as defined in the present disclosure to obtain a compound of formula (I) as defined in the present disclosure.

Said route SynMethod 4 allows to prepare for example the following compounds of formula (I) in accordance with the present disclosure: 132 to 135, 137 to 145.

Concerning Steps (i), (iA) and (iB) (not Shown in the Schemes 1, 2, 3 and 4):

The compound of formula (II) is a commercially available compound, for example from Fisher or Merck-Sigma company or can be prepared by any method well known by the skilled person.

Concerning Steps (ii), (iiA) and (iiB) (Respectively Schemes 2 (or 4), 3 and 1):

The cyclization steps (ii), (iiA) and (iiB) of a compound (II) as defined in the present disclosure allow to obtain a compound of formula (III) as defined in the present disclosure.

For instance, the cyclization steps (ii), (iiA) and (iiB) of the compound (II) can be carried out by using as a reagent $R_2$—$C(OCH_3)_3$ wherein $R_2$ is as defined in the present disclosure (steps (ii), (iiA) and (iiB)) or is a hydrogen atom (step (ii)) and further in the presence of a solvent such as xylene, acetonitrile, dioxane, toluene or mixtures thereof, for example a mixture of xylene and acetonitrile, under heat that is to say at a temperature ranging from 25° C. to 200° C., for example from 85° C. to 150° C.

The cyclization steps (ii), (iiA) and (iiB) of the compound (II) can also be carried out by using as a reagent $R_2$—COCl wherein $R_2$ is as defined in the present disclosure (steps (ii), (iiA) and (iiB)) or is a hydrogen atom (step (ii)) in ethyl acetate (EtOAc) at room temperature and then treatment with sodium hydride (NaH) in dimethylformamide (DMF), followed by heating at reflux.

Concerning Steps (iii), (iiiA) and (iiiB) (Respectively Schemes 2 (or 4), 3 and 1):

The hydrolysis steps (iii), (iiiA) and (iiiB) of nitrile groups present on a compound of formula (III) as defined in the present disclosure allow to obtain a compound of formula (IV) as defined in the present disclosure.

For instance, the hydrolysis steps (iii), (iiiA) and (iiiB) of nitrile groups of the compound of formula (III) can be carried out in the presence of an acid such as sulfuric acid, hydrochloric acid or mixtures thereof, in the presence of water (water reflux) or in the presence of water and other organic solvent, such as dioxane, for example in the presence of sulfuric acid in water, under heat that is to say at a temperature ranging from 25° C. to 150° C. for example at 100° C.

The hydrolysis steps (iii), (iiiA) and (iiiB) of nitrile groups of the compound of formula (III) can also be carried out in refluxing sodium hydroxide followed by acidification with hydrochloric acid.

Concerning Steps (iv), (ivA) and (ivB) (Respectively Schemes 2 (or 4), 3 and 1):

The esterification steps (iv), (ivA) and (ivB) of carboxylic acid functions present on the compound of formula (IV) as defined in the present disclosure allow to obtain a compound of formula (V) as defined in the present disclosure.

For instance, the esterification steps (iv), (ivA) and (ivB) of carboxylic acid functions present on the compound of formula (IV) can be carried out in the presence of a chlorinating agent such as thionyl chloride ($SOCl_2$), phosphorus trichloride ($PCl_3$), phosphorus pentachloride ($PCl_5$), oxalyl chloride or mixtures thereof, for example $SOCl_2$, and in the presence of a primary alcohol R—OH in which R is a $C_1$-$C_4$ alkyl group (for instance a methyl group, an ethyl group, a propyl group or a butyl group, such as a methyl group), such as methanol, ethanol, propanol, or butanol, for example methanol, for instance in $SOCl_2$ and methanol, at a temperature ranging from 25° C. to 100° C., for example at 60° C.

The esterification steps (iv), (ivA) and (ivB) of carboxylic acid functions present on the compound of formula (IV) can also be carried out in the presence of $H_2SO_4$, $H_2O$, MeOH (methanol) at 100° C.

Concerning Step (vB) (Scheme 1):

The step (vB) from a compound of formula (V) as defined in the present disclosure allows to obtain a compound of formula (Vb) as defined in the present disclosure. The step (vB) is an optional step which can be carried out if a compound of formula (Vb) in which $R_1$ is as defined in the present disclosure (that is to say $R_1$ not only a hydrogen atom), is needed.

In other terms, a compound of formula (V) (corresponding to $R_1$ is a hydrogen atom):

can be directly submitted to step (viB) in order to provide a compound of formula (VIb) in which $R_1$ and $R_2$ are as defined in the present disclosure, or can be submitted to step (vB) in order to provide a compound of formula (Vb) in which $R_1$ and $R_2$ are as defined in the present disclosure and then the thus obtained compound of formula (Vb) is submitted to step (viB) in order to provide a compound of formula (VIb) in which $R_1$ and $R_2$ are as defined in the present disclosure.

Depending on the wished compound, the skilled person will choose the more appropriate step to be conducted.

For instance, the step (vB) can be carried out in the presence of $R_1$—X wherein $R_1$ and X are as defined in the present disclosure, and further in the presence of a base such as potassium carbonate, cesium carbonate, or sodium hydride, for example in potassium carbonate, in a solvent such as dimethylformamide, acetone, acetonitrile, 1,4-dioxane, tetrahydrofuran (THF), or mixtures thereof, for example in dimethylformamide, such as in the presence of potassium carbonate and dimethylformamide from 0° C. to 150° C., for example from 25° C. to 130° C.

Concerning Steps (v), (vA) and (viB) (Respectively Schemes 2 (or 4), 3 and 1):

The cyclization steps (v), (vA) and (viB) from respectively a compound of formula (V), (V) or (Vb) as defined in the present disclosure allow respectively to obtain a compound of formula (VI), (VI) and (VIb) as defined in the present disclosure.

For instance, the cyclization steps (v), (vA) and (viB) can be carried out in the presence of a reagent such as hydrazine hydrate, in the presence of a solvent such as methanol, ethanol or mixtures thereof, for example methanol, such as in the presence of hydrazine, water and methanol, under heat that is to say at a temperature ranging from 25° C. to 150° C., for example from 60° C. to 85° C.

Concerning Steps (vi), (viA) and (viiB) (Respectively Schemes 2 (or 4), 3 and 1):

The dihalogenation steps (vi), (viA) and (viiB) from respectively a compound of formula (VI), (VI) or (VIb) as defined in the present disclosure allow respectively to obtain a compound of formula (VII), (VII) and (VIIa) as defined in the present disclosure.

For instance, the dihalogenation steps (vi), (viA) and (viiB) can be carried out in the presence of a reagent such as phosphorus oxychloride ($POCl_3$), phosphorus pentachloride ($PCl_5$), or mixtures thereof, for example $POCl_3$, in the presence of a solvent such as N,N-dimethylaniline, such as in the presence of phosphorus oxychloride and N,N-dimethylaniline, under heat that is to say at a temperature ranging from 80° C. to 160° C., for example from 100° C. to 110° C.

The dihalogenation steps (vi), (viA) and (viiB) can also be carried out in the presence of a mixture of phosphorus oxychloride and phosphorus pentachloride at reflux temperature.

Concerning Step (vii) (Scheme 2):

The step (vii) from a compound of formula (VII) as defined in the present disclosure allows to obtain a compound of formula (VIII) as defined in the present disclosure.

The step (vii) is a nucleophilic aromatic substitution which for instance can be carried out in the presence of a solvent such as butanol, isoamyl alcohol, isopropanol or mixtures thereof, for example butanol, in the presence of a base such as N,N-diisopropylethylamine (DIEA), triethylamine (TEA), 1,8-Diazabicyclo[5.4.0]undec-7-ene DBU, for example N,N-diisopropylethylamine, such as in the presence of N,N-diisopropylethylamine and butanol, under heat that is to say at a temperature ranging from 80° C. to 200° C., for example from 120° C. to 130° C., or also in the presence of N-methyl-pyrrolidone, at 130° C. or in the presence of TEA, dimethylacetamide from room temperature to 50° C., and in the presence of a compound of formula (AA), (AA)

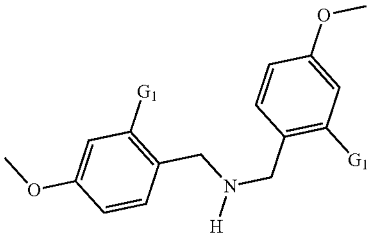

wherein $G_1$ represents a hydrogen atom or a methoxy group. Advantageously, to increase the speed of the reaction, the two $G_1$ radicals in formula (AA) are each a methoxy group.

Concerning Step (viiA) (Scheme 3):

The step (viiA) from a compound of formula (VII) as defined in the present disclosure allows to obtain a compound of formula (VIIa) as defined in the present disclosure.

The step (viiA) is an optional step which can be carried out if a compound of formula (VIIa) in which $R_1$ is as defined in the present disclosure (that is to say $R_1$ not only a hydrogen atom), is needed.

In other terms, a compound of formula (VII) (corresponding to $R_1$ is a hydrogen atom):

- can be directly submitted to step (ViiiA) in order to provide a compound of formula (VIIIa) in which $R_1$, $R_2$ and HAL are as defined in the present disclosure, or
- can be submitted to step (viiA) in order to provide a compound of formula (VIIa) in which $R_1$, $R_2$ and HAL are as defined in the present disclosure and then the thus obtained compound of formula (VIIa) is submitted to step (viiiA) in order to provide a compound of formula (VIIIa) in which $R_1$, $R_2$ and HAL are as defined in the present disclosure.

Depending on the wished compound, the skilled person will choose the more appropriate step to be conducted.

The step (viiA) can be carried out in the presence of $R_1$—X wherein $R_1$ and X are as defined in the present disclosure, such as in the presence of methyl iodide (MeI), in acetone and $K_2CO_3$, at room temperature (25° C.), or in the presence of $R_1$—X as defined in the present disclosure, in $Cs_2CO_3$, 1,4-Dioxane, from room temperature (25° C.) to 120° C.

Concerning Step (viialpha, Also Named viiα) and Step (viibeta, Also Named viiβ) (Scheme 4):

The step (viialpha) or the step (viibeta) from a compound of formula (VII) as defined in the present disclosure allow to obtain a compound of formula (VIIIaa) as defined in the present disclosure.

The step (viialpha) can be carried out in the presence of $R_{1a}$—X wherein $R_{1a}$ is $R_1$ as defined in the present disclosure, comprising or not a hydroxyl protecting group, an amino protecting group, a carboxylic acid protecting group, an aldehyde protecting group or a ketone protecting group, and X represents a halogen atom, a tosylate or a mesylate The step (viibeta) can be carried out in the presence of an epoxide of formula

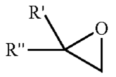

in which R' and R" are independently a hydrogen atom or a $(C_1\text{-}C_6)$alkyl group, such as a methyl group.

Concerning Step (viiiAA) (Scheme 4):

The step (viiiAA) from a compound of formula (VIIIaa) as defined in the present disclosure allows to obtain a compound of formula (IXaa) as defined in the present disclosure.

The step (viiiAA) is a nucleophilic aromatic substitution which for instance can be carried out in the presence of a solvent such as butanol, isoamyl alcohol, isopropanol or mixtures thereof, for example butanol, in the presence of a base such as N,N-diisopropylethylamine (DIEA), triethylamine (TEA), 1,8-Diazabicyclo[5.4.0]undec-7-ene DBU, for example N,N-diisopropylethylamine, such as in the presence of N,N-diisopropylethylamine and butanol, under heat that is to say at a temperature ranging from 80° C. to 200° C., for example from 120° C. to 130° C., or also in the presence of N-methyl-pyrrolidone, at 130° C. or in the presence of TEA, dimethylacetamide from room temperature to 50° C., and in the presence of a compound of formula (AA), (AA)

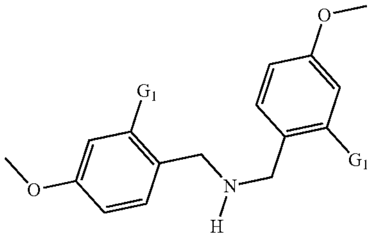

wherein $G_1$ represents a hydrogen atom or a methoxy group. Advantageously, to increase the speed of the reaction, the two $G_1$ radicals in formula (AA) are each a methoxy group.

Concerning Steps (viiiA) and (viiiB) (Respectively Schemes 3 and 1):

In scheme 1, the step (viiiB) is applied to a compound of formula (VIIa) as defined in the present disclosure to obtain a compound of formula (VIIIa) as defined in the present disclosure.

In scheme 3, depending on the wished compound, the step (viiiA) can be applied either to a compound of formula (VIIa) in which HAL, $R_1$ and $R_2$ are as defined in the present disclosure, obtained from step (viiA) as defined in the present disclosure or to a compound of formula (VII) in which HAL and $R_2$ are as defined in the present disclosure, obtained from step (viA) as defined in the present disclosure in order to obtain a compound of formula (VIIIa) as defined in the present disclosure.

For instance, the nucleophilic aromatic substitution steps (viiiA) and (ViiiB) can be carried out in the presence of a base such as ammonia ($NH_3$), for example in the presence of water, alcohol, dioxane, or mixtures thereof, such as in the presence of ammonia and water, under heat that is to say at a temperature ranging from 25° C. to 200° C., for example at 150° C.

Concerning Step (viii) (Scheme 2):

The step (viii) from a compound of formula (VIII) as defined in the present disclosure allows to obtain a compound of formula (IX) as defined in the present disclosure.

For instance, the step (viii) can be carried out in the presence of a reagent such as alcoholates, for example sodium propan-2-olate (iPrONa), for example sodium propan-2-olate, in a solvent such as isopropanol, for example in sodium propan-2olate/isopropanol, under heat that is to say at a temperature ranging from 50° C. to 200° C., for example from 150° C. to 170° C.

Concerning Step (ixAA) (Scheme 4):

The step (ixAA) from a compound of formula (IXaa) as defined in the present disclosure allows to obtain a compound of formula (X) as defined in the present disclosure.

For instance, the step (ixAA) can be carried out in the presence of a reagent such as alcoholates, for example sodium propan-2-olate (iPrONa), for example sodium propan-2-olate, in a solvent such as isopropanol, for example in sodium propan-2olate/isopropanol, under heat that is to say at a temperature ranging from 50° C. to 200° C., for example from 150° C. to 170° C.

Concerning Steps (ixA) and (ixB) (Respectively Schemes 3 and 1):

The substitution and/or coupling steps (ixA) and (ixB) from a compound of formula (VIIIa) as defined in the present disclosure allow to obtain a compound of formula (Ia) as defined in the present disclosure.

The substitution and/or coupling steps (ixA) and (ixB) can be any appropriate chemical reaction which involves the dehalogenating of the molecule for instance as an alkylation, a nucleophilic aromatic substitution, and/or a coupling such as Suzuki coupling, for example a reaction with the presence of $R_{3a}$—Y wherein $R_{3a}$ represents $R_3$ as defined in the formula (I) according to the present disclosure or is a hydroxyl protecting group, an amino protecting group, a carboxylic acid protecting group, a aldehyde and ketone protecting group, and Y represents, hydroxyl, amine, boronic acid.

Concerning Steps (xA) and (xB): (Respectively Schemes 3 and 1):

The steps (xA) and (xB) from a compound of formula (Ia) as defined in the present disclosure allow to obtain a compound of formula (I) as defined in the present disclosure. It is to be understood that if in compound of formula (Ia) obtained from respectively step (ixA) and steps (ixB), $R_{3a}$ is $R_3$ then it is not necessary to perform respectively step (xA) or step (xB).

Thus, the compounds of formula (Ia) in which $R_{3a}$ is other than $R_3$ as defined in the present disclosure, can be reacted with any suitable reagents and in any suitable conditions in order to obtain a compound of formula (I) as defined in the present disclosure. For example, these steps can be selected from reduction steps, deprotection steps, hydrolysis steps, oxidation steps, and combinations thereof, being understood that these steps can be carried out only once or several times, if needed. All these steps are well known by the skilled person.

Concerning Step (ixAlpha, Also Named ixα) and Step (ixBeta, Also Named ixβ) (Scheme 2):

The step (ixAlpha) or the step (ixBeta) from a compound of formula (IX) as defined in the present disclosure allow to obtain a compound of formula (X) as defined in the present disclosure.

The step (ixAlpha) can be carried out in the presence of $R_{1a}$—X wherein $R_{1a}$ is $R_1$ as defined in the present disclosure, comprising or not a hydroxyl protecting group, an amino protecting group, a carboxylic acid protecting group, an aldehyde protecting group or a ketone protecting group, and X represents a halogen atom, a tosylate or a mesylate The step (ixBeta) can be carried out in the presence of an epoxide of formula

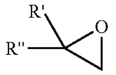

in which R' and R" are independently a hydrogen atom or a $(C_1-C_6)$alkyl group, such as a methyl group.

Concerning Step (Gamma, Also Named γ) (Scheme 2, SynMethod 2b or Scheme 4, SynMethod 4b):

The step (Gamma) from a compound of formula (X) as defined in the present disclosure allow to obtain a compound of formula (XII) as defined in the present disclosure.

The step (Gamma) can be a reduction, a reductive amination, a nucleophilic substitution, and/or an oxidation.

Concerning Step (x) (Scheme 2 or Scheme 4):

The deprotection step (x) can be carried out in order to deprotect the amino group linked to the pyridazine part of the imidazopyridazine ring and optionally, if applicable, the protected group corresponding to $R_{1a}$ and/or $R_{3a}$.

In other terms, the step (x) can be conducted either from a compound of formula (X) as defined in the present disclosure or from a compound of formula (XII) as defined in the present disclosure to obtain a compound of formula (I) as defined in the present disclosure, or can be conducted from a compound of formula (X) as defined in the present disclosure to obtain a compound of formula (XI) as defined in the present disclosure.

For instance, the step (x) can be carried out in the presence of an acid such as trifluoroacetic acid (TFA), hydrochloric acid, or mixtures thereof, for example TFA, in the presence of a solvent such as dichloromethane (DCM), dioxane, tetradydrofuran (THF), or mixtures thereof, for example DCM, for example in TFA and DCM.

Concerning Step (xi) (Scheme 2, SynMethod 2a or Scheme 4, SynMethod 4a):

The step (xi) from a compound of formula (XI) as defined in the present disclosure allow to obtain a compound of formula (I) as defined in the present disclosure.

The step (xi) can be a reduction, a reductive amination, a nucleophilic substitution, and/or an oxidation.

The specific compounds of formula (I) as defined in the present disclosure are indicated in Table 1 (number, chemical name and formula) and are further detailed hereafter. In Table 2, $^1H$ NMR, Retention time and liquid chromatography/mass spectra are also indicated.

The $^1H$ NMR of Table 2 is $^1H$ NMR Spectra (400 MHz, δ in ppm, DMSO-d6) as defined in the Experimental part.

The liquid chromatography/mass spectra (LC/MS) of Table 2 were obtained according to one of the seven methods described in the Experimental part.

The Retention time (RT) of Table 2 is defined in minutes.

TABLE 1

| Compound Number | Formula | Name |
|---|---|---|
| 1 | 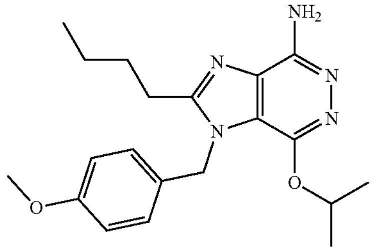 [SMILES: CCCCc1nc2c(N)nnc(OC(C)C)c2n1Cc1ccc(OC)cc1] | 2-butyl-7-isopropoxy-1-(4-methoxybenzyl)-1H-imidazo[4,5-d]pyridazin-4-amine |
| 2 | 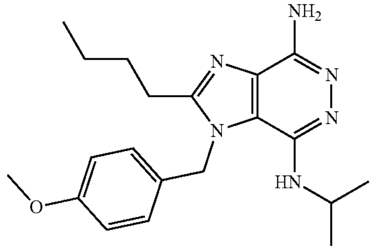 [SMILES: CCCCc1nc2c(N)nnc(NC(C)C)c2n1Cc1ccc(OC)cc1] | 2-butyl-N7-isopropyl-1-(4-methoxybenzyl)-1H-imidazo[4,5-d]pyridazine-4,7-diamine |
| 3 | 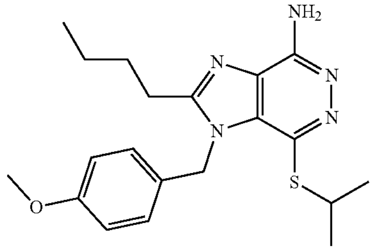 | 2-butyl-7-(isopropylthio)-1-(4-methoxybenzyl)-1H-imidazo[4,5-d]pyridazin-4-amine |
| 4 | 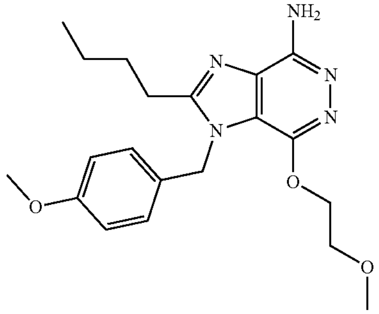 | 2-butyl-1-(4-methoxybenzyl)-7-(2-methoxyethoxy)-1H-imidazo[4,5-d]pyridazin-4-amine |
| 5 | 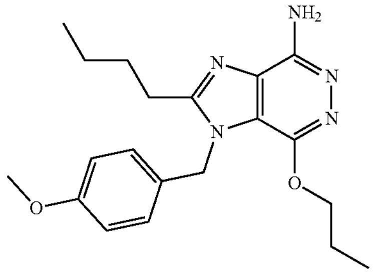 [SMILES: CCCCc1nc2c(N)nnc(OCCC)c2n1Cc1ccc(OC)cc1] | 2-butyl-1-(4-methoxybenzyl)-7-propoxy-1H-imidazo[4,5-d]pyridazin-4-amine |

TABLE 1-continued
| Compound Number | Formula | Name |
|---|---|---|
| 6 | 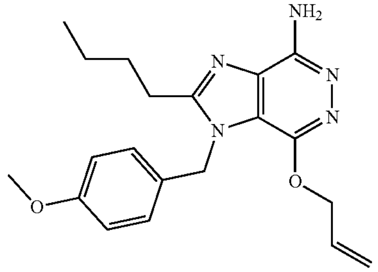 [SMILES: C=CCOc1nnc(N)c2nc(CCCC)n(Cc3ccc(OC)cc3)c12] | 7-(allyloxy)-2-butyl-1-(4-methoxybenzyl)-1H-imidazo[4,5-d]pyridazin-4-amine |
| 7 | 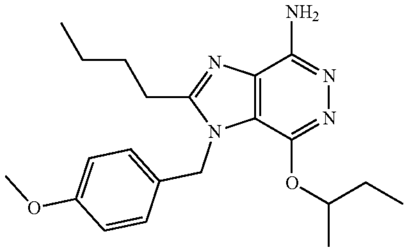 [SMILES: CCCCc1nc2c(N)nnc(OC(C)CC)c2n1Cc1ccc(OC)cc1] | 7-(sec-butoxy)-2-butyl-1-(4-methoxybenzyl)-1H-imidazo[4,5-d]pyridazin-4-amine |
| 8 | 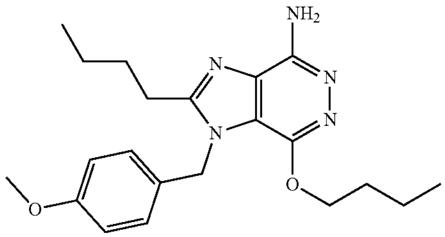 [SMILES: CCCCOc1nnc(N)c2nc(CCCC)n(Cc3ccc(OC)cc3)c12] | 7-butoxy-2-butyl-1-(4-methoxybenzyl)-1H-imidazo[4,5-d]pyridazin-4-amine |
| 9 | 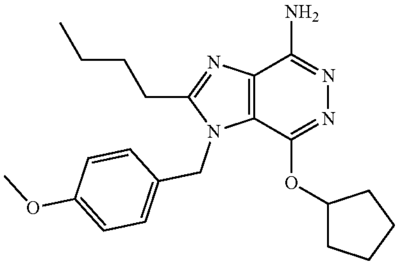 [SMILES: CCCCc1nc2c(N)nnc(OC3CCCC3)c2n1Cc1ccc(OC)cc1] | 2-butyl-7-(cyclopentyloxy)-1-(4-methoxybenzyl)-1H-imidazo[4,5-d]pyridazin-4-amine |
| 10 | 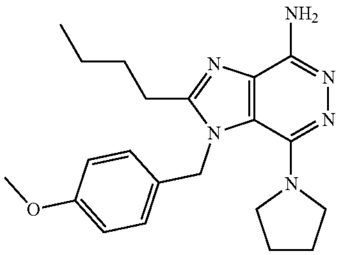 [SMILES: CCCCc1nc2c(N)nnc(N3CCCC3)c2n1Cc1ccc(OC)cc1] | 2-butyl-1-(4-methoxybenzyl)-7-(pyrrolidin-1-yl)-1H-imidazo[4,5-d]pyridazin-4-amine |

TABLE 1-continued

| Compound Number | Formula | Name |
|---|---|---|
| 11 | 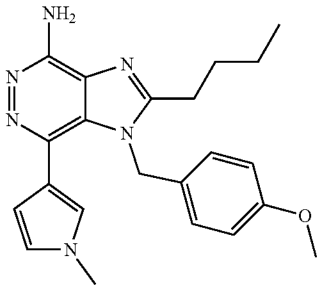 [SMILES: CCCCc1nc2c(N)nnc(-c3ccn(C)c3)c2n1Cc1ccc(OC)cc1] | 2-butyl-1-(4-methoxybenzyl)-7-(1-methyl-1H-pyrrol-3-yl)-1H-imidazo[4,5d]pyridazin-4-amine |
| 12 | 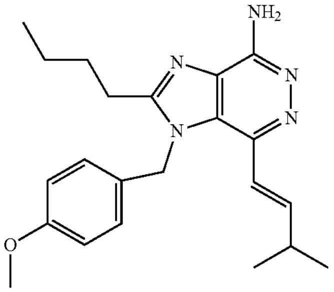 [SMILES: CCCCc1nc2c(N)nnc(/C=C/C(C)C)c2n1Cc1ccc(OC)cc1] | (E)-2-butyl-1-(4-methoxybenzyl)-7-(3-methylbut-1-en-1-yl)-1H-imidazo[4,5-d]pyridazin-4-amine |
| 13 | 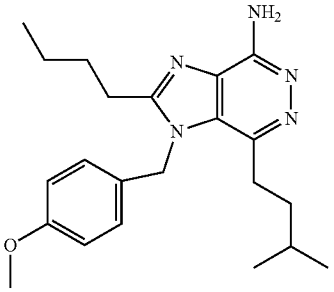 [SMILES: CCCCc1nc2c(N)nnc(CCC(C)C)c2n1Cc1ccc(OC)cc1] | 2-butyl-7-isopentyl-1-(4-methoxybenzyl)-1H-imidazo[4,5-d]pyridazin-4-amine |
| 14 | 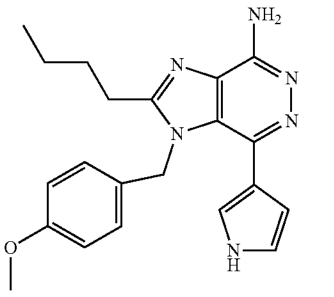 [SMILES: CCCCc1nc2c(N)nnc(-c3cc[nH]c3)c2n1Cc1ccc(OC)cc1] | 2-butyl-1-(4-methoxybenzyl)-7-(1H-pyrrol-3-yl)-1H-imidazo[4,5-d]pyridazin-4-amine |
| 15 | 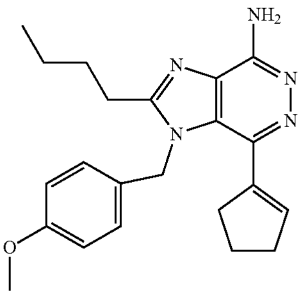 HCl | 2-butyl-7-(cyclopent-1-en-1-yl)-1-(4-methoxybenzyl)-1H-imidazo[4,5-d]pyridazin-4-amine hydrochloride salt |

TABLE 1-continued

| Compound Number | Formula | Name |
|---|---|---|
| 16 | 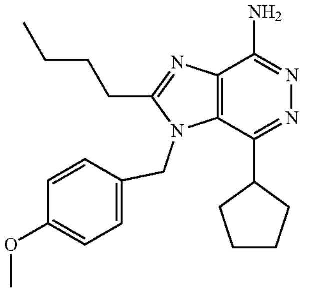 [SMILES: CCCCc1nc2c(N)nnc(C3CCCC3)c2n1Cc1ccc(OC)cc1] | 2-butyl-7-cyclopentyl-1-(4-methoxybenzyl)-1H-imidazo[4,5-d]pyridazin-4-amine |
| 17 | 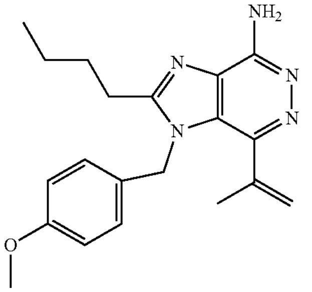 [SMILES: C=C(C)c1nnc(N)c2nc(CCCC)n(Cc3ccc(OC)cc3)c12] | 2-butyl-1-(4-methoxybenzyl)-7-(prop-1-en-2-yl)-1H-imidazo[4,5-d]pyridazin-4-amine |
| 18 | 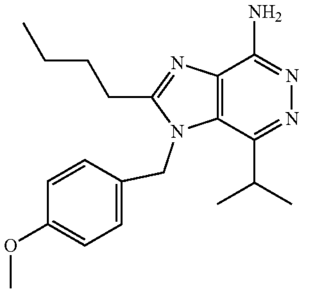 [SMILES: CCCCc1nc2c(N)nnc(C(C)C)c2n1Cc1ccc(OC)cc1] | 2-butyl-7-isopropyl-1-(4-methoxybenzyl)-1H-imidazo[4,5-d]pyridazin-4-amine |
| 19 | 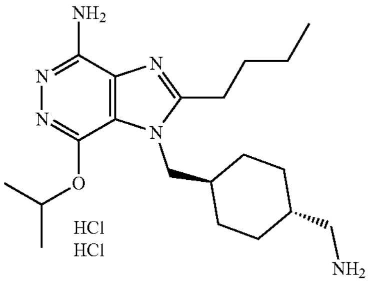 [SMILES: CCCCc1nc2c(N)nnc(OC(C)C)c2n1C[C@H]1CC[C@H](CN)CC1] | 4-(aminomethyl)cyclohexyl)methyl)-2-butyl-7-isopropoxy-1H-imidazo[4,5-d]pyridazin-4-amine dihydrochloride salt |
| 20 | 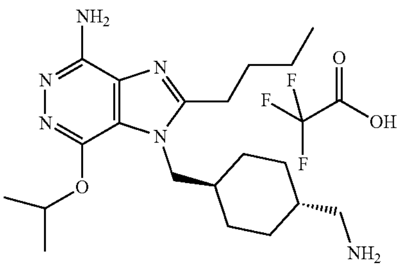 | 4-(aminomethyl)cyclohexyl)methyl)-2-butyl-7-isopropoxy-1H-imidazo[4,5-d]pyridazin-4-amine 2,2,2-trifluoroacetate |

TABLE 1-continued

| Compound Number | Formula | Name |
| --- | --- | --- |
| 21 | 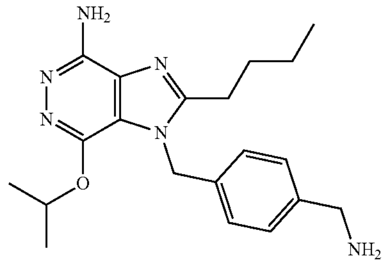 [SMILES: CCCCc1nc2c(N)nnc(OC(C)C)c2n1Cc1ccc(CN)cc1] | 1-(4-(aminomethyl)benzyl)-2-butyl-7-isopropoxy-1H-imidazo[4,5-d]pyridazin-4-amine |
| 22 | 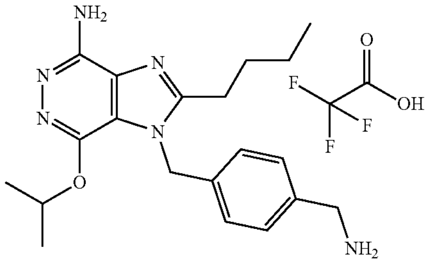 | 1-(4-(aminomethyl)benzyl)-2-butyl-7-isopropoxy-1H-imidazo[4,5-d]pyridazin-4-amine 2,2,2-trifluoroacetate |
| 23 | 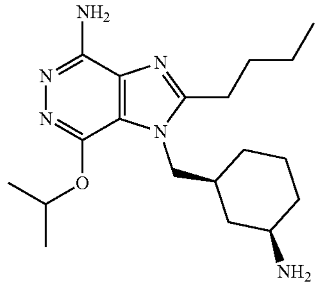 [SMILES: CCCCc1nc2c(N)nnc(OC(C)C)c2n1C[C@H]1CCC[C@@H](N)C1] | 1-(((1S,3R)-3-aminocyclohexyl)methyl)-2-butyl-7-isopropoxy-1H-imidazo[4,5-d]pyridazin-4-amine (and enantiomer) |
| 24 | 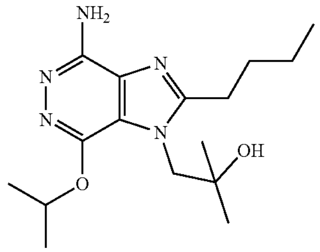 [SMILES: CCCCc1nc2c(N)nnc(OC(C)C)c2n1CC(C)(C)O] | 1-(4-amino-2-butyl-7-isopropoxy-1H-imidazo[4,5-d]pyridazin-1-yl)-2-methylpropan-2-ol |
| 25 | 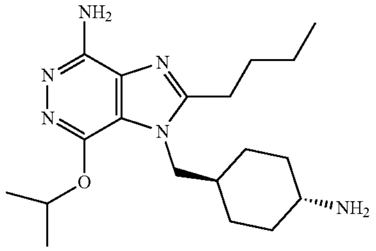 [SMILES: CCCCc1nc2c(N)nnc(OC(C)C)c2n1C[C@H]1CC[C@H](N)CC1] | Trans 1-(4-aminocyclohexyl)methyl)-2-butyl-7-isopropoxy-1H-imidazo[4,5-d]pyridazin-4-amine |

TABLE 1-continued

| Compound Number | Formula | Name |
|---|---|---|
| 26 | 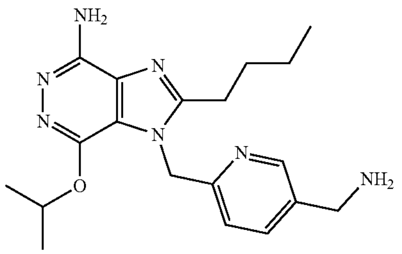 [SMILES: CCCCc1nc2c(N)nnc(OC(C)C)c2n1Cc1ccc(CN)cn1] | 1-((5-(aminomethyl)pyridin-2-yl)methyl)-2-butyl-7-isopropoxy-1H-imidazo[4,5-d]pyridazin-4-amine |
| 27 | 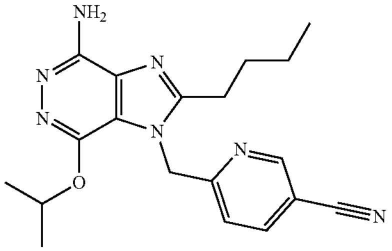 [SMILES: CCCCc1nc2c(N)nnc(OC(C)C)c2n1Cc1ccc(C#N)cn1] | 6-((4-amino-2-butyl-7-isopropoxy-1H-imidazo[4,5-d]pyridazin-1-yl)methyl)nicotinonitrile |
| 28 | 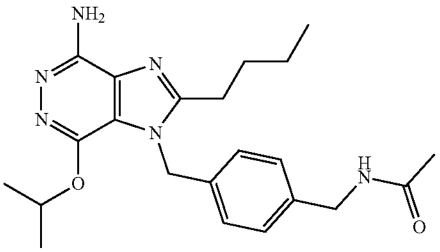 [SMILES: CCCCc1nc2c(N)nnc(OC(C)C)c2n1Cc1ccc(CNC(C)=O)cc1] | N-(4-((4-amino-2-butyl-7-isopropoxy-1H-imidazo[4,5d]pyridazin-1-yl)methyl) benzyl)acetamide |
| 29 | 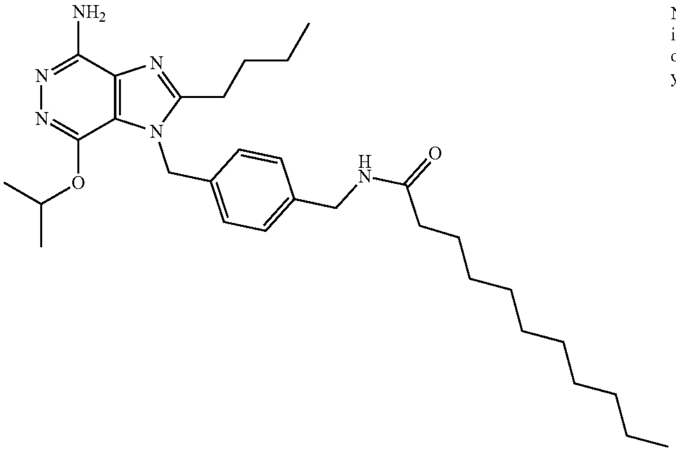 [SMILES: CCCCCCCCCCC(=O)NCc1ccc(Cn2c(CCCC)nc3c(N)nnc(OC(C)C)c32)cc1] | N-(4-((4-amino-2-butyl-7-isopropoxy-1H-imidazo[4,5-d]pyridazin-1-yl)methyl)benzyl)undecanamide |
| 30 | 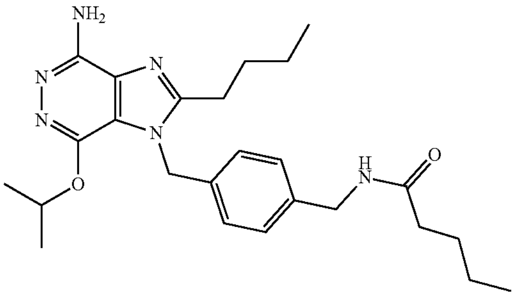 [SMILES: CCCCC(=O)NCc1ccc(Cn2c(CCCC)nc3c(N)nnc(OC(C)C)c32)cc1] | N-(4-((4-amino-2-butyl-7-isopropoxy-1H-imidazo[4,5-d]pyridazin-1-yl)meth-yl)benzyl)pentanamide |

TABLE 1-continued

| Compound Number | Formula | Name |
|---|---|---|
| 31 | 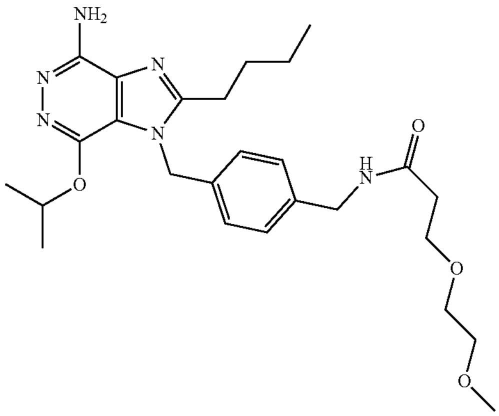 [SMILES: CCCCc1nc2c(N)nnc(OC(C)C)c2n1Cc1ccc(CNC(=O)CCOCCOC)cc1] | N-(4-((4-amino-2-butyl-7-isopropoxy-1H-imidazo[4,5-d]pyridazin-1-yl)methyl)benzyl)-3-(2-methoxyethoxy)propanamide |
| 32 | 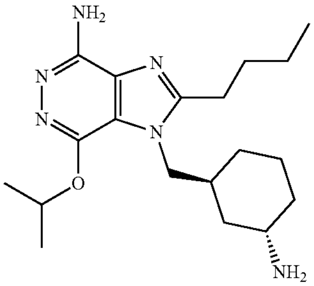 [SMILES: CCCCc1nc2c(N)nnc(OC(C)C)c2n1C[C@H]1CCC[C@H](N)C1] | 1-(((1S,3S)-3-aminocyclohexyl)methyl)-2-butyl-7-isopropoxy-1H-imidazo[4,5-]pyridazin-4-amine (and enantiomer) |
| 33 | 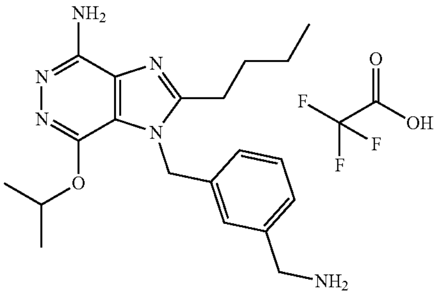 | 1-(3-(aminomethyl)benzyl)-2-butyl-7-isopropoxy-1H-imidazo[4,5-d]pyridazin-4-amine 2,2,2-trifluoroacetate |
| 34 | 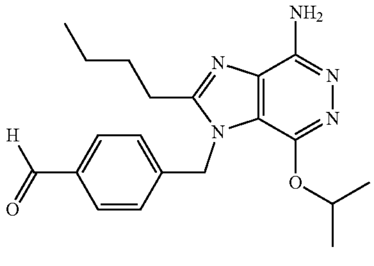 [SMILES: CCCCc1nc2c(N)nnc(OC(C)C)c2n1Cc1ccc(C=O)cc1] | 4-((4-amino-2-butyl-7-isopropoxy-1H-imidazo[4,5-d]pyridazin-1-yl)methyl)benzaldehyde |
| 35 | 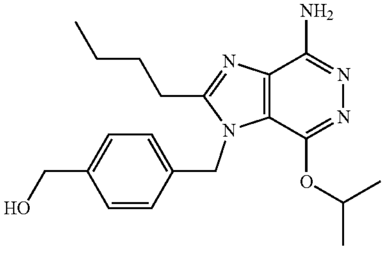 [SMILES: CCCCc1nc2c(N)nnc(OC(C)C)c2n1Cc1ccc(CO)cc1] | (4-((4-amino-2-butyl-7-isopropoxy-1H-imidazo[4,5-d]pyridazin-1-yl)methyl)phenyl)methanol |

TABLE 1-continued

| Compound Number | Formula | Name |
|---|---|---|
| 36 | 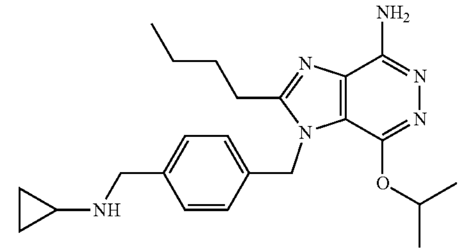 [SMILES: CCCCc1nc2c(N)nnc(OC(C)C)c2n1Cc1ccc(CNC2CC2)cc1] | 2-butyl-1-(4-((cyclopropylamino)methyl)benzyl)-7-isopropoxy-1H-imidazo[4,5-d]pyridazin-4-amine |
| 37 | 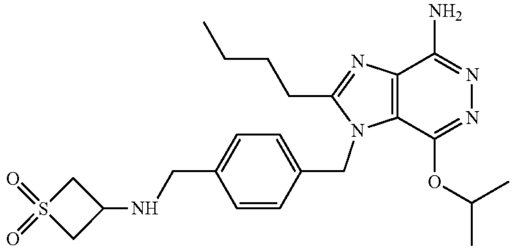 [SMILES: CCCCc1nc2c(N)nnc(OC(C)C)c2n1Cc1ccc(CNC2CS(=O)(=O)C2)cc1] | 3-((4-((4-amino-2-butyl-7-isopropoxy-1H-imidazo[4,5-d]pyridazin-yl)methyl)benzyl)amino)thietane 1,1-dioxide |
| 38 | 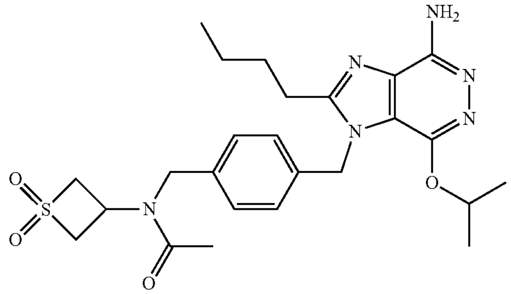 [SMILES: CCCCc1nc2c(N)nnc(OC(C)C)c2n1Cc1ccc(CN(C(C)=O)C2CS(=O)(=O)C2)cc1] | N-(4-((4-amino-2-butyl-7-isopropoxy-1H-imidazo[4,5-d]pyridazin-1-yl)methyl)benzyl)-N-(1,1-dioxidothietan-3-yl)acetamide. |
| 39 | 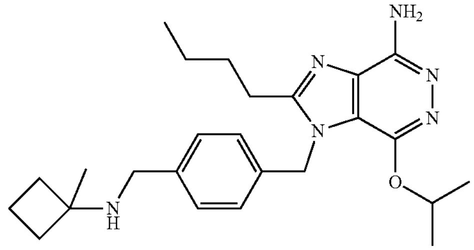 [SMILES: CCCCc1nc2c(N)nnc(OC(C)C)c2n1Cc1ccc(CNC2(C)CCC2)cc1] | 2-butyl-7-isopropoxy-1-(4-(((1-methylcyclobutyl)amino)methyl)benzyl)-1H-imidazo[4,5-d]pyridazin-4-amine |
| 40 | 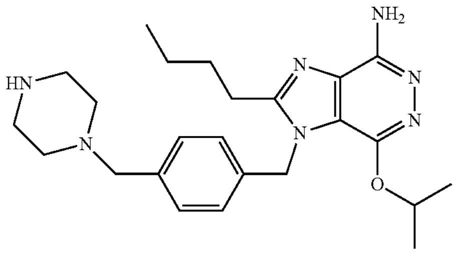 [SMILES: CCCCc1nc2c(N)nnc(OC(C)C)c2n1Cc1ccc(CN2CCNCC2)cc1] | 2-butyl-7-isopropoxy-1-(4-(piperazin-1-ylmethyl)benzyl)-1H-imidazo[4,5-d]pyridazin-4-amine |
| 41 | 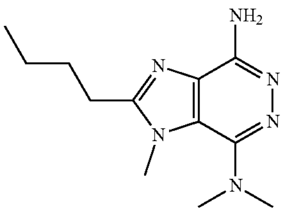 [SMILES: CCCCc1nc2c(N)nnc(N(C)C)c2n1C] | 2-butyl-N7,N7,1-trimethyl-1H-imidazo[4,5-d]pyridazine-4,7-diamine |

TABLE 1-continued
| Compound Number | Formula | Name |
|---|---|---|
| 42 | 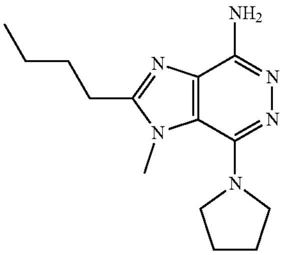 [SMILES: CCCCc1nc2c(N)nnc(N3CCCC3)c2n1C] | 2-butyl-1-methyl-7-(pyrrolidin-1-yl)-1H-imidazo[4,5-d]pyridazin-4-amine |
| 43 | 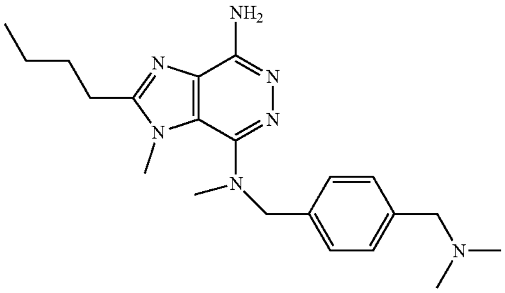 [SMILES: CCCCc1nc2c(N)nnc(N(C)Cc3ccc(CN(C)C)cc3)c2n1C] | 2-butyl-N7-(4-((dimethylamino)methyl)benzyl)-N7,1-dimethyl-1H-imidazo[4,5-d]pyridazine-4,7-diamine |
| 44 | 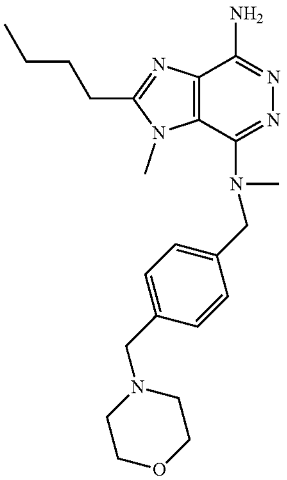 [SMILES: CCCCc1nc2c(N)nnc(N(C)Cc3ccc(CN4CCOCC4)cc3)c2n1C] | 2-butyl-N7,1-dimethyl-N7-(4-(morpholinomethyl)benzyl)-1H-imidazo[4,5-d]pyridazine-4,7-diamine |
| 45 | 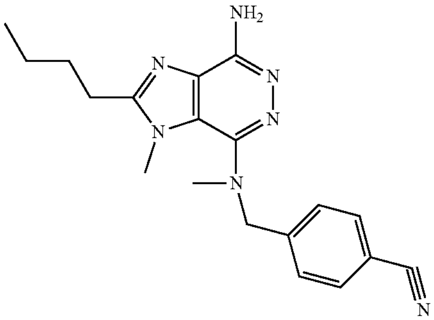 [SMILES: CCCCc1nc2c(N)nnc(N(C)Cc3ccc(C#N)cc3)c2n1C] | 4-(((4-amino-2-butyl-1-methyl-1H-imidazo[4,5-d]pyridazin-7-yl)(methyl)amino)methyl)benzonitrile |

TABLE 1-continued

| Compound Number | Formula | Name |
|---|---|---|
| 46 | 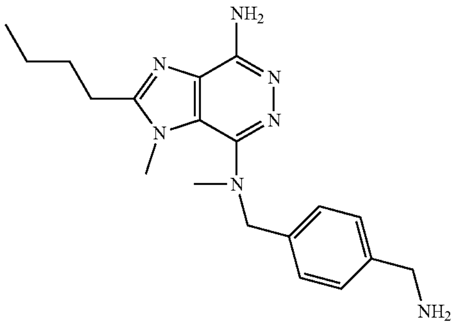 [SMILES: CCCCc1nc2c(N)nnc(N(C)Cc3ccc(CN)cc3)c2n1C] | N7-(4-(aminomethyl)benzyl)-2-butyl-N7,1-dimethyl-1H-imidazo[4,5-d]pyridazine-4,7-diamine |
| 47 | 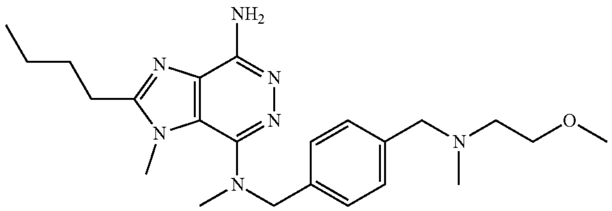 [SMILES: CCCCc1nc2c(N)nnc(N(C)Cc3ccc(CN(C)CCOC)cc3)c2n1C] | 2-butyl-N7-(4-(((2-methoxyethyl)(methyl)amino)methyl)benzyl)-N7,1-dimethyl-1H-imidazo[4,5-d]pyridazine-4,7-diamine |
| 48 | 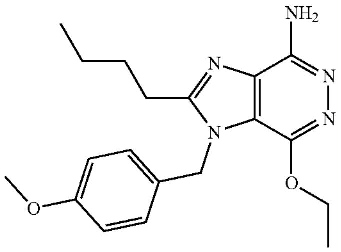 [SMILES: CCCCc1nc2c(N)nnc(OCC)c2n1Cc1ccc(OC)cc1] | 2-butyl-7-ethoxy-1-(4-methoxybenzyl)-1H-imidazo[4,5-d]pyridazin-4-amine |
| 49 | 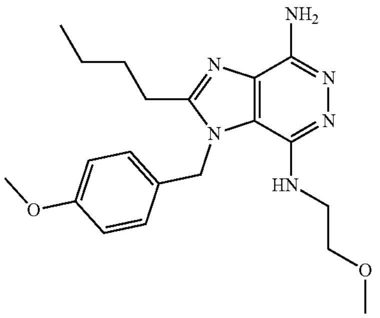 | 2-butyl-1-(4-methoxybenzyl)-N7-(2-methoxyethyl)-1H-imidazo[4,5-d]pyridazine-4,7-diamine |
| 50 | 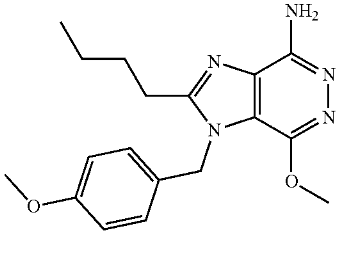 | 2-butyl-7-methoxy-1-(4-methoxybenzyl)-1H-imidazo[4,5-d]pyridazin-4-amine |

TABLE 1-continued

| Compound Number | Formula | Name |
| --- | --- | --- |
| 51 | 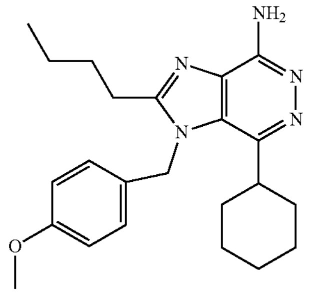 [SMILES: CCCCc1nc2c(N)nnc(C3CCCCC3)c2n1Cc1ccc(OC)cc1] | 2-butyl-7-cyclohexyl-1-(4-methoxybenzyl)-1H-imidazo[4,5-d]pyridazin-4-amine |
| 52 | 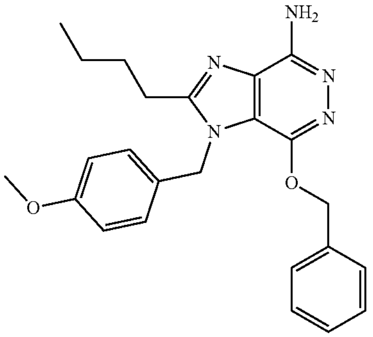 [SMILES: CCCCc1nc2c(N)nnc(OCc3ccccc3)c2n1Cc1ccc(OC)cc1] | 7-(benzyloxy)-2-butyl-1-(4-methoxybenzyl)-1H-imidazo[4,5-d]pyridazin-4-amine |
| 53 | 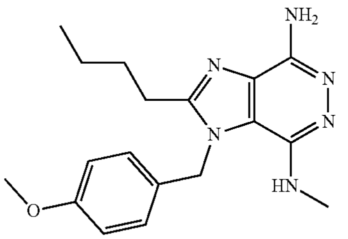 | 2-butyl-1-(4-methoxybenzyl)-N7-methyl-1H-imidazo[4,5-d]pyridazine-4,7-diamine |
| 54 | 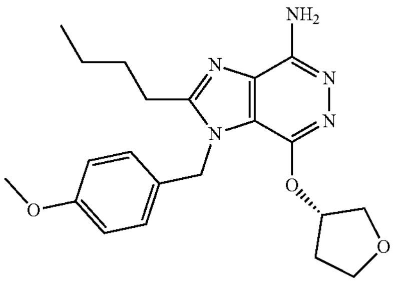 [SMILES: CCCCc1nc2c(N)nnc(O[C@H]3CCOC3)c2n1Cc1ccc(OC)cc1] | (S)-2-butyl-1-(4-methoxybenzyl)-7-((tetrahydrofuran-3-yl)oxy)-1H-imidazo[4,5-d]pyridazin-4-amine |
| 55 | 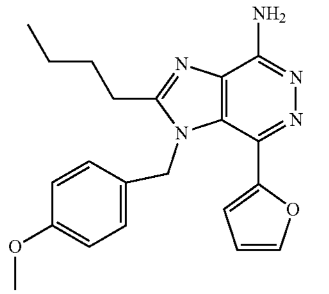 [SMILES: CCCCc1nc2c(N)nnc(-c3ccco3)c2n1Cc1ccc(OC)cc1] | 2-butyl-7-(furan-2-yl)-1-(4-methoxybenzyl)-1H-imidazo[4,5-d]pyridazin-4-amine |

TABLE 1-continued

| Compound Number | Formula | Name |
|---|---|---|
| 56 | 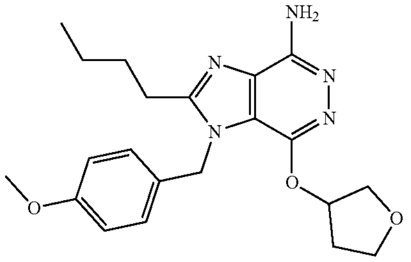 [SMILES: CCCCc1nc2c(N)nnc(OC3CCOC3)c2n1Cc1ccc(OC)cc1] | 2-butyl-1-(4-methoxybenzyl)-7-((tetrahydrofuran-3-yl)oxy)-1H-imidazo[4,5-d]pyridazin-4-amine |
| 57 | 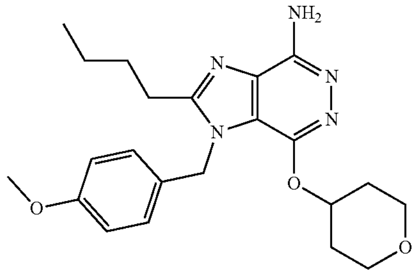 [SMILES: CCCCc1nc2c(N)nnc(OC3CCOCC3)c2n1Cc1ccc(OC)cc1] | 2-butyl-1-(4-methoxybenzyl)-7-((tetrahydro-2H-pyran-4-yl)oxy)-1H-imidazo[4,5-d]pyridazin-4-amine |
| 58 | 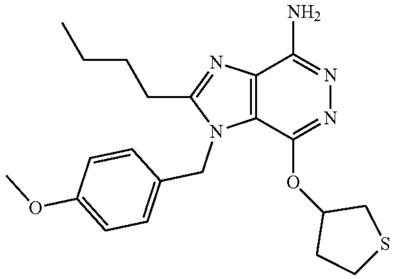 [SMILES: CCCCc1nc2c(N)nnc(OC3CCSC3)c2n1Cc1ccc(OC)cc1] | 2-butyl-1-(4-methoxybenzyl)-7-((tetrahydrothiophen-3-yl)oxy)-1H-imidazo[4,5-d]pyridazin-4-amine |
| 59 | 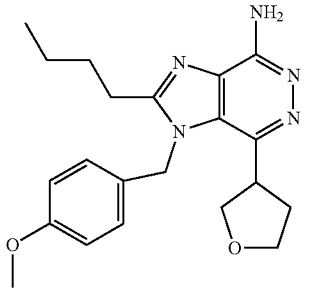 [SMILES: CCCCc1nc2c(N)nnc(C3CCOC3)c2n1Cc1ccc(OC)cc1] | 2-butyl-1-(4-methoxybenzyl)-7-(tetrahydrofuran-3-yl)-1H-imidazo[4,5-d]pyridazin-4-amine |
| 60 | 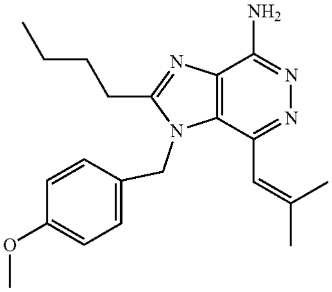 [SMILES: CCCCc1nc2c(N)nnc(C=C(C)C)c2n1Cc1ccc(OC)cc1] | 2-butyl-1-(4-methoxybenzyl)-7-(2-methylprop-1-en-1-yl)-1H-imidazo[4,5-d]pyridazin-4-amine |

TABLE 1-continued

| Compound Number | Formula | Name |
|---|---|---|
| 61 | 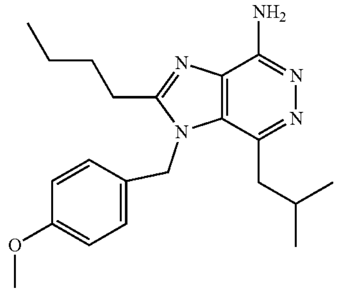 [SMILES: CCCCc1nc2c(N)nnc(CC(C)C)c2n1Cc1ccc(OC)cc1] | 2-butyl-7-isobutyl-1-(4-methoxybenzyl)-1H-imidazo[4,5-d]pyridazin-4-amine |
| 62 | 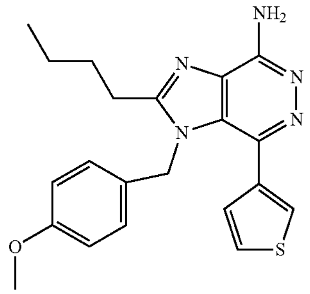 [SMILES: CCCCc1nc2c(N)nnc(-c3ccsc3)c2n1Cc1ccc(OC)cc1] | 2-butyl-1-(4-methoxybenzyl)-7-(thiophen-3-yl)-1H-imidazo[4,5-d]pyridazin-4-amine |
| 63 | 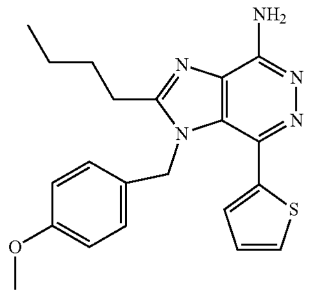 [SMILES: CCCCc1nc2c(N)nnc(-c3cccs3)c2n1Cc1ccc(OC)cc1] | 2-butyl-1-(4-methoxybenzyl)-7-(thiophen-2-yl)-1H-imidazo[4,5-d]pyridazin-4-amine |
| 64 | 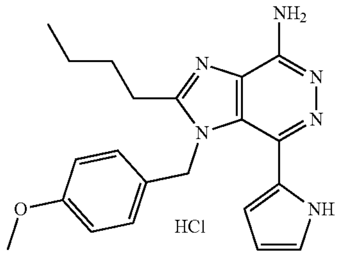 [SMILES: CCCCc1nc2c(N)nnc(-c3ccc[nH]3)c2n1Cc1ccc(OC)cc1 ; Cl] | 2-butyl-1-(4-methoxybenzyl)-7-(1H-pyrrol-2-yl)-1H-imidazo[4,5-d]pyridazin-4-amine hydrochloride salt |
| 65 | 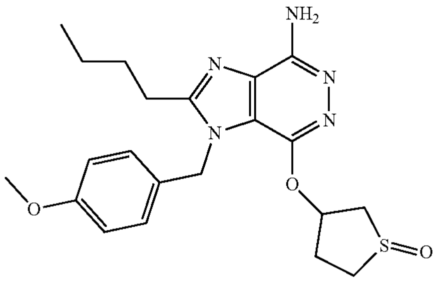 [SMILES: CCCCc1nc2c(N)nnc(OC3CCS(=O)C3)c2n1Cc1ccc(OC)cc1] | 3-((4-amino-2-butyl-1-(4-methoxybenzyl)-1H-imidazo[4,5-d]pyridazin-7-yl)oxy)tetrahydrothiophene 1-oxide, isomer A |

TABLE 1-continued

| Compound Number | Formula | Name |
| --- | --- | --- |
| 66 | 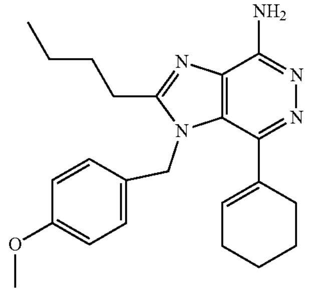 [SMILES: CCCCc1nc2c(N)nnc(C3=CCCCC3)c2n1Cc1ccc(OC)cc1] | 2-butyl-7-(cyclohex-1-en-1-yl)-1-(4-methoxybenzyl)-1H-imidazo[4,5-d]pyridazin-4-amine |
| 67 | 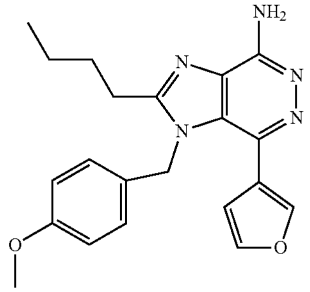 [SMILES: CCCCc1nc2c(N)nnc(-c3ccoc3)c2n1Cc1ccc(OC)cc1] | 2-butyl-7-(furan-3-yl)-1-(4-methoxybenzyl)-1H-imidazo[4,5-d]pyridazin-4-amine |
| 68 | 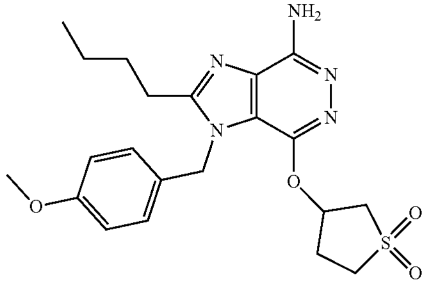 [SMILES: CCCCc1nc2c(N)nnc(OC3CCS(=O)(=O)C3)c2n1Cc1ccc(OC)cc1] | 3-((4-amino-2-butyl-1-(4-methoxybenzyl)-1H-imidazo[4,5-d]pyridazin-7-yl)oxy)tetrahydrothiophene 1,1-dioxide |
| 69 | 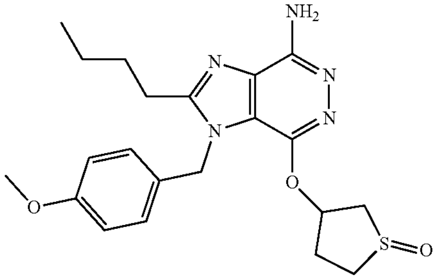 [SMILES: CCCCc1nc2c(N)nnc(OC3CCS(=O)C3)c2n1Cc1ccc(OC)cc1] | 3-((4-amino-2-butyl-1-(4-methoxybenzyl)-1H-imidazo[4,5-d]pyridazin-7-yl)oxy)tetrahydrothiophene 1-oxide, isomer B |
| 70 | 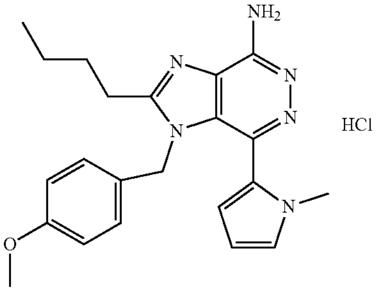 [SMILES: CCCCc1nc2c(N)nnc(-c3cccn3C)c2n1Cc1ccc(OC)cc1 ; Cl] | 2-butyl-1-(4-methoxybenzyl)-7-(1-methyl-1H-pyrrol-2-yl)-1H-imidazo[4,5-d]pyridazin-4-amine hydrochloride salt |

TABLE 1-continued

| Compound Number | Formula | Name |
| --- | --- | --- |
| 71 | 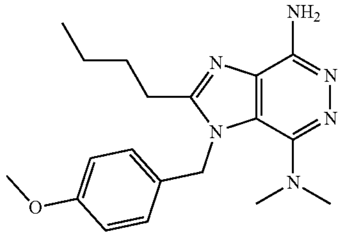 | 2-butyl-1-(4-methoxybenzyl)-N7,N7-dimethyl-1H-imidazo[4,5-d]pyridazine-4,7-diamine |
| 72 | 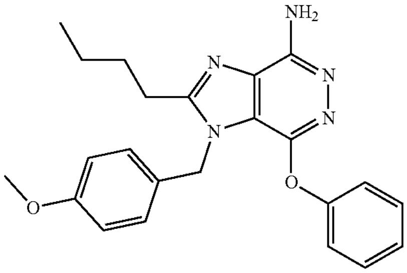 [SMILES: CCCCc1nc2c(N)nnc(Oc3ccccc3)c2n1Cc1ccc(OC)cc1] | 2-butyl-1-(4-methoxybenzyl)-7-phenoxy-1H-imidazo[4,5-d]pyridazin-4-amine |
| 73 | 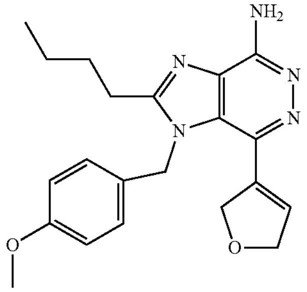 [SMILES: CCCCc1nc2c(N)nnc(C3=CCOC3)c2n1Cc1ccc(OC)cc1] | 2-butyl-7-(2,5-dihydrofuran-3-yl)-1-(4-methoxybenzyl)-1H-imidazo[4,5-d]pyridazin-4-amine |
| 74 | 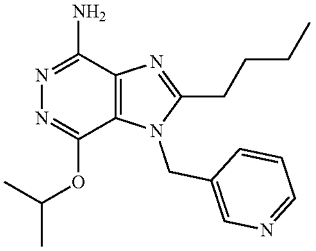 [SMILES: CCCCc1nc2c(N)nnc(OC(C)C)c2n1Cc1cccnc1] | 2-butyl-7-isopropoxy-1-(pyridin-3-ylmethyl)-1H-imidazo[4,5-d]pyridazin-4-amine |
| 75 | 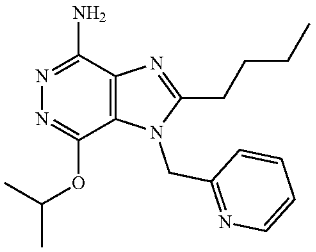 [SMILES: CCCCc1nc2c(N)nnc(OC(C)C)c2n1Cc1ccccn1] | 2-butyl-7-isopropoxy-1-(pyridin-2-ylmethyl)-1H-imidazo[4,5-d]pyridazin-4-amine |

TABLE 1-continued

| Compound Number | Formula | Name |
|---|---|---|
| 76 | 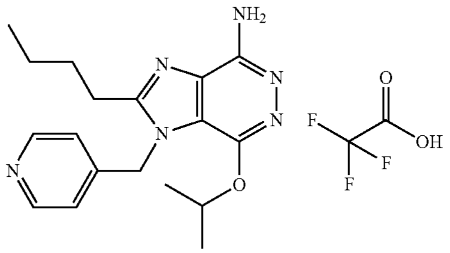 | 2-butyl-7-isopropoxy-1-(pyridin-4-ylmethyl)-1H-imidazo[4,5-d]pyridazin-4-amine 2,2,2-trifluoroacetate |
| 77 | 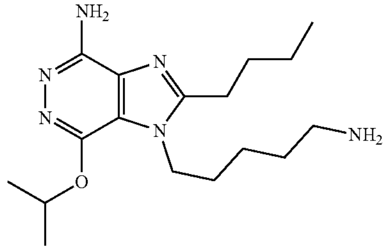 [SMILES: CCCCc1nc2c(N)nnc(OC(C)C)c2n1CCCCCN] | 1-(5-aminopentyl)-2-furyl-7-isopropoxy-1H-imidazo[4,5-d]pyridazin-4-amine |
| 78 | 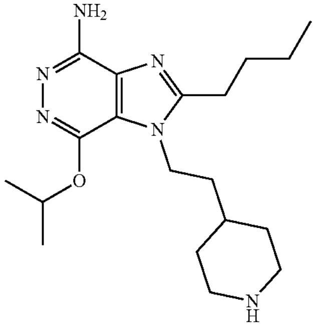 [SMILES: CCCCc1nc2c(N)nnc(OC(C)C)c2n1CCC1CCNCC1] | 2-butyl-7-isopropoxy-1-(2-(piperidin-4-yl)ethyl)-1H-imidazo[4,5-d]pyridazin-4-amine |
| 79 | 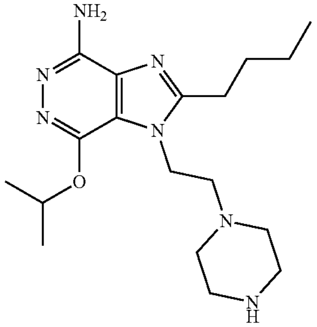 [SMILES: CCCCc1nc2c(N)nnc(OC(C)C)c2n1CCN1CCNCC1] | 2-butyl-7-isopropoxy-1-(2-(piperazin-1-yl)ethyl)-1H-imidazo[4,5-d]pyridazin-4-amine |
| 80 | 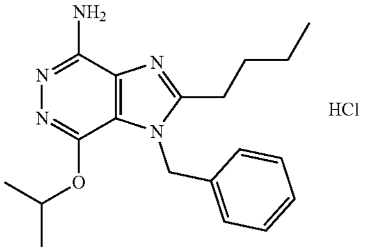 [SMILES: CCCCc1nc2c(N)nnc(OC(C)C)c2n1Cc1ccccc1 ; Cl] | 1-benzyl-2-butyl-7-isopropoxy-1H-imidazo[4,5-d]pyridazin-4-amine hydrochloride salt |

TABLE 1-continued

| Compound Number | Formula | Name |
|---|---|---|
| 81 | 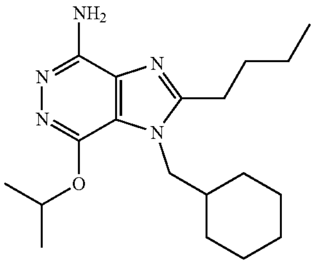 HCl | 2-butyl-1-(cyclohexylmethyl)-7-isopropoxy-1H-imidazo[4,5-d]pyridazin-4-amine hydrochloride salt |
| 82 | 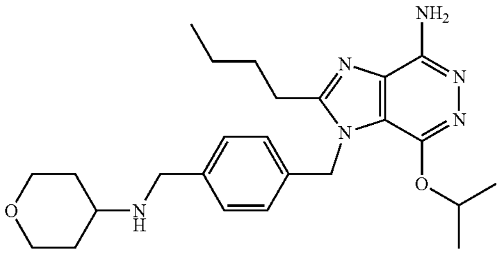 HCl | 2-butyl-7-isopropoxy-1-(4-(((tetrahydro-2H-pyran-4-yl)amino)methyl)benzyl)-1H-imidazo[4,5-d]pyridazin-4-amine hydrochloride salt |
| 83 | 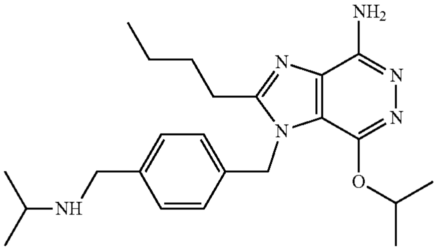 HCl HCl | 2-butyl-7-isopropoxy-1-(4-((isopropylamino)methyl)benzyl)-1H-imidazo[4,5-d]pyridazin-4-amine dihydrochloride salt |
| 84 | 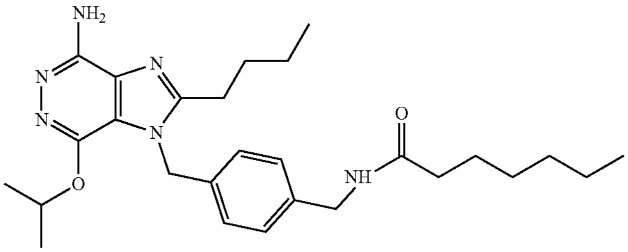 [SMILES: CCCCCCC(=O)NCc1ccc(Cn2c(CCCC)nc3c(N)nnc(OC(C)C)c32)cc1] | N-(4-((4-amino-2-butyl-7-isopropoxy-1H-imidazo[4,5-d]pyridazin-1-yl)methyl)benzyl)heptanamide |
| 85 | 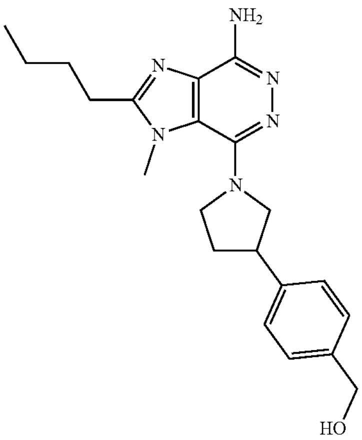 HCl | (4-(1-(4-amino-2-butyl-1-methyl-1H-imidazo[4,5-d]pyridazin-7-yl)pyrrolidin-3-yl)phenyl)methanol hydrochloride salt |

TABLE 1-continued
| Compound Number | Formula | Name |
|---|---|---|
| 86 | 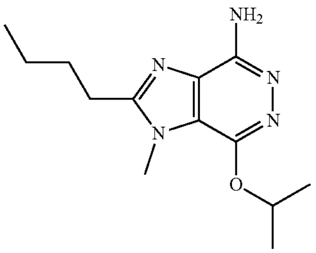 [SMILES: CCCCc1nc2c(N)nnc(OC(C)C)c2n1C] | 2-butyl-7-isopropoxy-1-methyl-1H-imidazo[4,5-d]pyridazin-4-amine |
| 87 | 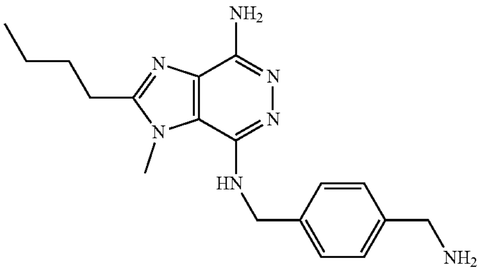 [SMILES: CCCCc1nc2c(N)nnc(NCc3ccc(CN)cc3)c2n1C] | N7-(4-(aminomethyl)benzyl)-2-butyl-1-methyl-1H-imidazo[4,5-d]pyridazine-4,7-diamine |
| 88 | 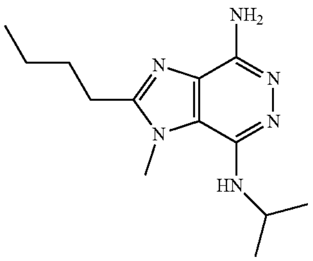 [SMILES: CCCCc1nc2c(N)nnc(NC(C)C)c2n1C] | 2-butyl-N7-isopropyl-1-methyl-1H-imidazo[4,5-d]pyridazine-4,7-diamine |
| 89 | 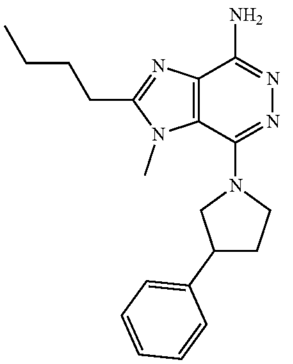 [SMILES: CCCCc1nc2c(N)nnc(N3CCC(c4ccccc4)C3)c2n1C] | 2-butyl-1-methyl-7-(3-phenylpyrrolidin-1-yl)-1H-imidazo[4,5-d]pyridazin-4-amine |
| 90 | 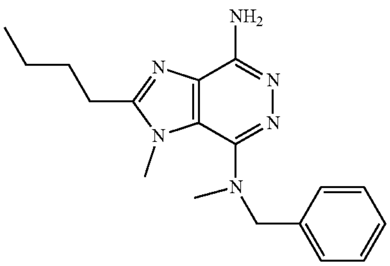 [SMILES: CCCCc1nc2c(N)nnc(N(C)Cc3ccccc3)c2n1C] | N7-benzyl-2-butyl-N7,1-dimethyl-1H-imidazo[4,5-d]pyridazine-4,7-diamine |

TABLE 1-continued
| Compound Number | Formula | Name |
|---|---|---|
| 91 | 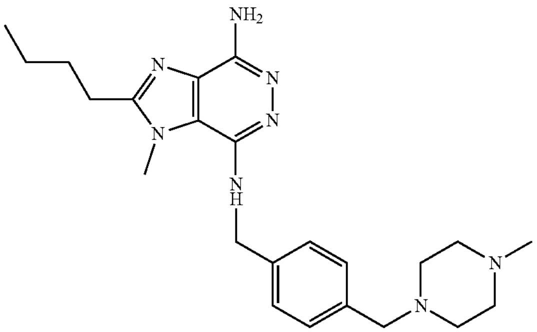 [SMILES: CCCCc1nc2c(N)nnc(NCc3ccc(CN4CCN(C)CC4)cc3)c2n1C] | 2-butyl-1-methyl-N7-(4-((4-methylpiperazin-1-yl)methyl)benzyl)-1H-imidazo[4,5-d]pyridazine-4,7-diamine |
| 92 | 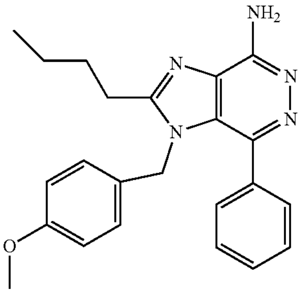 [SMILES: CCCCc1nc2c(N)nnc(-c3ccccc3)c2n1Cc1ccc(OC)cc1] | 2-butyl-1-(4-methoxybenzyl)-7-phenyl-1H-imidazo[4,5-d]pyridazin-4-amine |
| 93 | 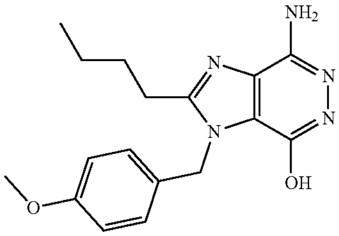 [SMILES: CCCCc1nc2c(N)nnc(O)c2n1Cc1ccc(OC)cc1] | 4-amino-2-butyl-1-(4-methoxybenzyl)-1H-imidazo[4,5-d]pyridazin-7-ol |
| 94 | 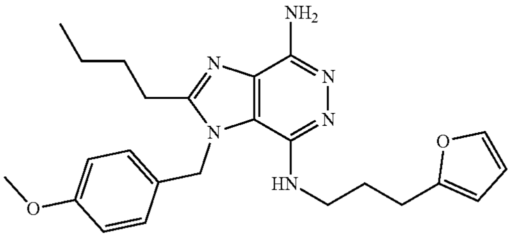 [SMILES: CCCCc1nc2c(N)nnc(NCCCc3ccco3)c2n1Cc1ccc(OC)cc1] | 2-butyl-N7-(3-(furan-2-yl)propyl)-1-(4-methoxybenzyl)-1H-imidazo[4,5-d]pyridazine-4,7-diamine |
| 95 | 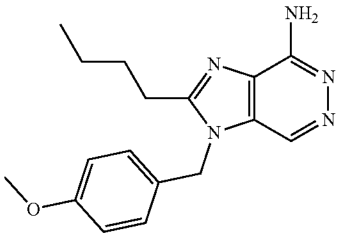 [SMILES: CCCCc1nc2c(N)nncc2n1Cc1ccc(OC)cc1] | 2-butyl-1-(4-methoxybenzyl)-1H-imidazo[4,5-d]pyridazin-4-amine |

TABLE 1-continued

| Compound Number | Formula | Name |
|---|---|---|
| 96 | 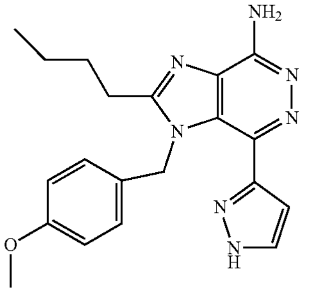 [SMILES: CCCCc1nc2c(N)nnc(-c3cc[nH]n3)c2n1Cc1ccc(OC)cc1] | 2-butyl-1-(4-methoxybenzyl)-7-(1H-pyrazol-3-yl)-1H-imidazo[4,5-d]pyridazin-4-amine |
| 97 | 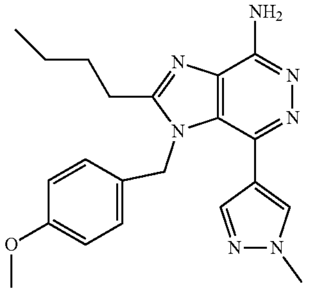 [SMILES: CCCCc1nc2c(N)nnc(-c3cnn(C)c3)c2n1Cc1ccc(OC)cc1] | 2-butyl-1-(4-methoxybenzyl)-7-(1-methyl-1H-pyrazol-4-yl)-1H-imidazo[4,5-d]pyridazin-4-amine |
| 98 | 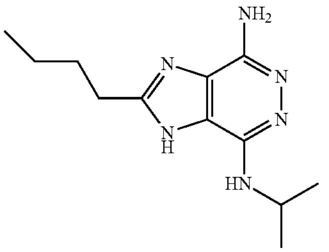 [SMILES: CCCCc1nc2c(N)nnc(NC(C)C)c2[nH]1] | 2-butyl-N7-isopropyl-1H-imidazo[4,5-d]pyridazine-4,7-diamine |
| 99 | 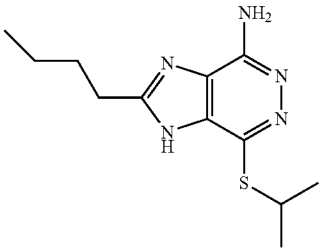 [SMILES: CCCCc1nc2c(N)nnc(SC(C)C)c2[nH]1] | 2-butyl-7-(isopropylthio)-1H-imidazo[4,5-d]pyridazin-4-amine |
| 100 | 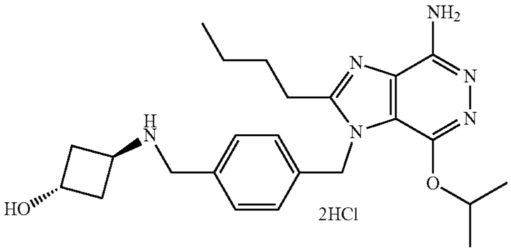 [SMILES: CCCCc1nc2c(N)nnc(OC(C)C)c2n1Cc1ccc(CN[C@H]2C[C@H](O)C2)cc1] | (1R,3R)-3-((4-((4-amino-2-butyl-7-isopropoxy-1H-imidazo[4,5-d]pyridazin-1-yl)methyl)benzyl)amino)cyclobutan-1-ol dihydrochloride salt (and enantiomer) |

TABLE 1-continued

| Compound Number | Formula | Name |
|---|---|---|
| 101 | 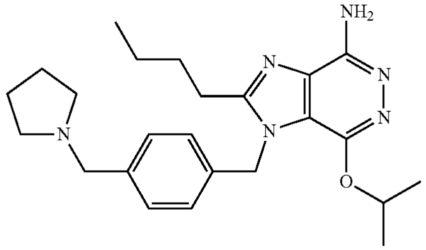 [SMILES: CCCCc1nc2c(N)nnc(OC(C)C)c2n1Cc1ccc(CN2CCCC2)cc1] | 2-butyl-7-isopropoxy-1-(4-(pyrrolidin-1-ylmethyl)benzyl)-1H-imidazo[4,5-d]pyridazin-4-amine |
| 102 | 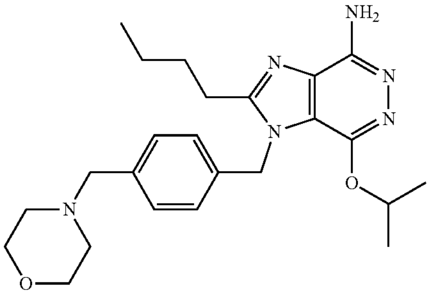 [SMILES: CCCCc1nc2c(N)nnc(OC(C)C)c2n1Cc1ccc(CN2CCOCC2)cc1] | 2-butyl-7-isopropoxy-1-(4-(morpholinomethyl)benzyl)-1H-imidazo[4,5-d]pyridazin-4-amine |
| 103 | 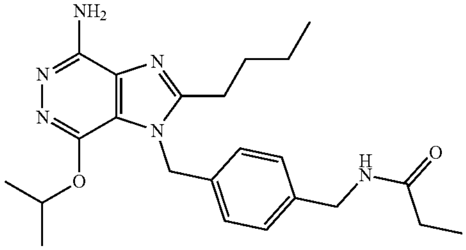 [SMILES: CCCCc1nc2c(N)nnc(OC(C)C)c2n1Cc1ccc(CNC(=O)CC)cc1] | N-(4-((4-amino-2-butyl-7-isopropoxy-1H-imidazo[4,5-d]pyridazin-1-yl)methyl)benzyl)propionamide |
| 104 | 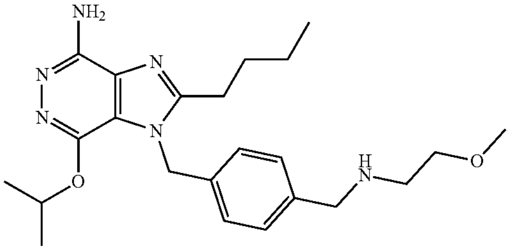 [SMILES: CCCCc1nc2c(N)nnc(OC(C)C)c2n1Cc1ccc(CNCCOC)cc1] | 2-butyl-7-isopropoxy-1-(4-(((2-methoxyethyl)amino)methyl)benzyl)-1H-imidazo[4,5-d]pyridazin-4-amine |
| 105 | 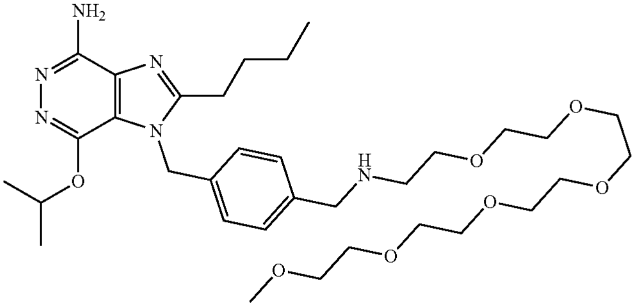 [SMILES: CCCCc1nc2c(N)nnc(OC(C)C)c2n1Cc1ccc(CNCCOCCOCCOCCOCCOCCOC)cc1] | 2-butyl-4-isopropoxy-3-[[4-[[2-[2-[2-[2-[2-(2-methoxyethoxy)ethoxy]ethoxy]ethoxy]ethoxy]ethylamino]methyl]phenyl]methyl]imidazo[4,5-d]pyridazin-7-amine |

TABLE 1-continued

| Compound Number | Formula | Name |
| --- | --- | --- |
| 106 | 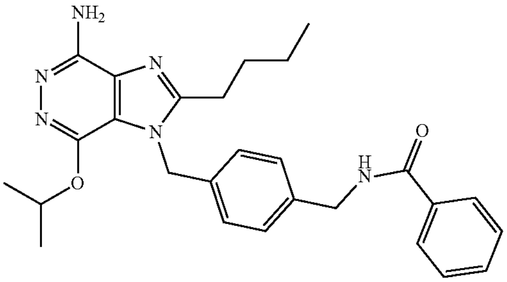 [SMILES: CCCCc1nc2c(N)nnc(OC(C)C)c2n1Cc1ccc(CNC(=O)c2ccccc2)cc1] | N-(4-((4-amino-2-butyl-7-isopropoxy-1H-imidazo[4,5-d]pyridazin-1-yl)methyl)benzyl)benzamide |
| 107 | 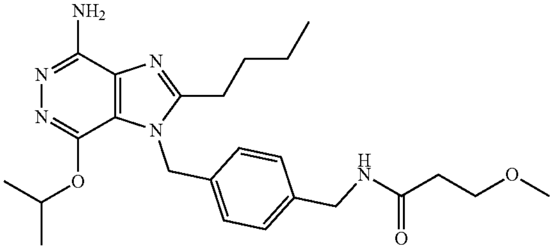 [SMILES: CCCCc1nc2c(N)nnc(OC(C)C)c2n1Cc1ccc(CNC(=O)CCOC)cc1] | N-(4-((4-amino-2-butyl-7-isopropoxy-1H-imidazo[4,5-d]pyridazin-1-yl)methyl)benzyl)-3-methoxypropanamide |
| 108 | 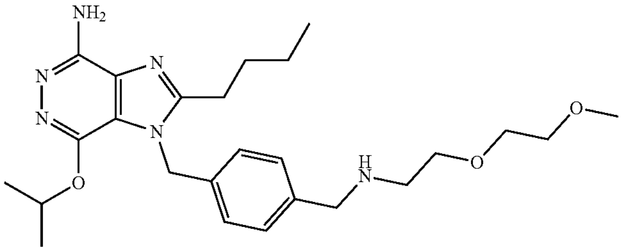 [SMILES: CCCCc1nc2c(N)nnc(OC(C)C)c2n1Cc1ccc(CNCCOCCOC)cc1] | 2-butyl-7-isopropoxy-1-(4-(((2-(2-methoxyethoxy)ethyl)amino)methyl)benzyl)-1H-imidazo[4,5-d]pyridazin-4-amine |
| 109 | 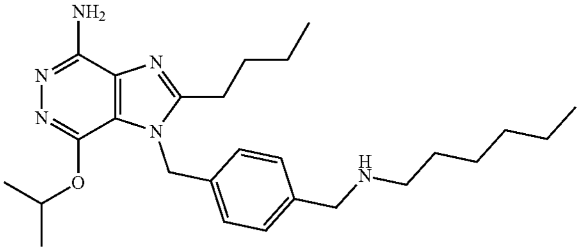 [SMILES: CCCCCCNCc1ccc(Cn2c(CCCC)nc3c(N)nnc(OC(C)C)c32)cc1] | 2-butyl-1-(4-((hexylamino)methyl)benzyl)-7-isopropoxy-1H-imidazo[4,5-d]pyridazin-4-amine |
| 110 | 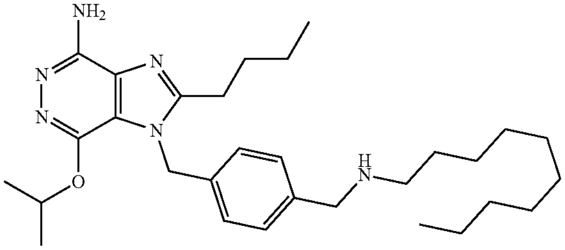 [SMILES: CCCCCCCCCCNCc1ccc(Cn2c(CCCC)nc3c(N)nnc(OC(C)C)c32)cc1] | 2-butyl-1-(4-((decylamino)methyl)benzyl)-7-isopropoxy-1H-imidazo[4,5-d]pyridazin-4-amine |

TABLE 1-continued

| Compound Number | Formula | Name |
|---|---|---|
| 111 | 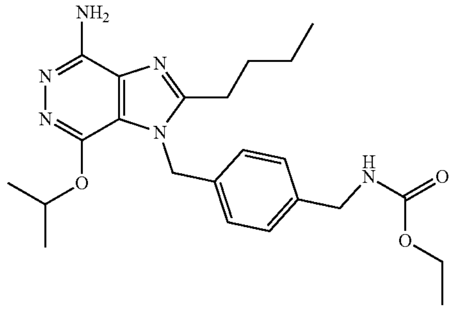 [SMILES: CCCCc1nc2c(N)nnc(OC(C)C)c2n1Cc1ccc(CNC(=O)OCC)cc1] | ethyl (4-((4-amino-2-butyl-7-isopropoxy-1H-imidazo[4,5-d]pyridazin-1-yl)methyl)benzyl)carbamate |
| 112 | 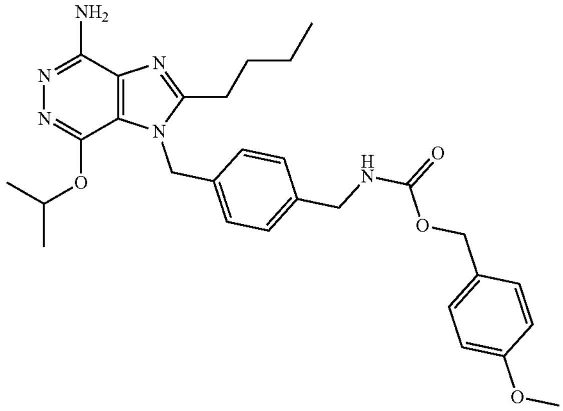 [SMILES: CCCCc1nc2c(N)nnc(OC(C)C)c2n1Cc1ccc(CNC(=O)OCc2ccc(OC)cc2)cc1] | 4-methoxybenzyl (4-((4-amino-2-butyl-7-isopropoxy-1H-imidazo[4,5-d]pyridazin-1-yl)methyl)benzyl)carbamate |
| 113 | 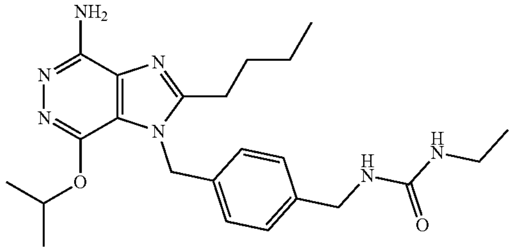 [SMILES: CCCCc1nc2c(N)nnc(OC(C)C)c2n1Cc1ccc(CNC(=O)NCC)cc1] | 1-(4-((4-amino-2-butyl-7-isopropoxy-1H-imidazo[4,5-d]pyridazin-1-yl)methyl)benzyl)-3-ethylurea |
| 114 | 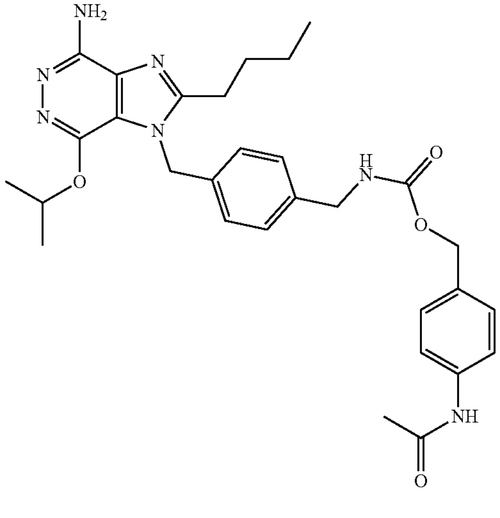 [SMILES: CCCCc1nc2c(N)nnc(OC(C)C)c2n1Cc1ccc(CNC(=O)OCc2ccc(NC(C)=O)cc2)cc1] | 4-acetamidobenzyl (4-((4-amino-2-butyl-7-isopropoxy-1H-imidazo[4,5-d]pyridazin-1-yl)methyl)benzyl)carbamate |

TABLE 1-continued

| Compound Number | Formula | Name |
|---|---|---|
| 115 | 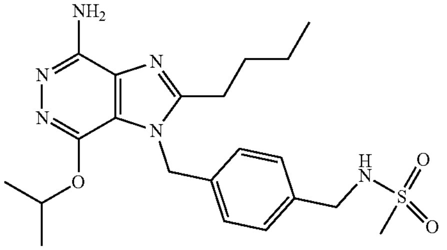 [SMILES: CCCCc1nc2c(N)nnc(OC(C)C)c2n1Cc1ccc(CNS(C)(=O)=O)cc1] | N-(4-((4-amino-2-butyl-7-isopropoxy-1H-imidazo[4,5-d]pyridazin-1-yl)methyl)benzyl)methanesulfon-amide |
| 116 | 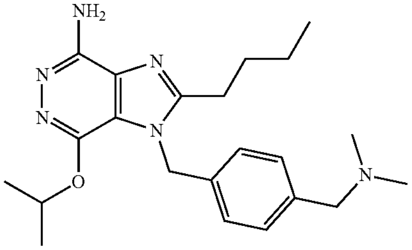 [SMILES: CCCCc1nc2c(N)nnc(OC(C)C)c2n1Cc1ccc(CN(C)C)cc1] | 2-butyl-1-(4-((dimethylamino)methyl)benzyl)-7-isopropoxy-1H-imidazo[4,5-d]pyridazin-4-amine |
| 117 | 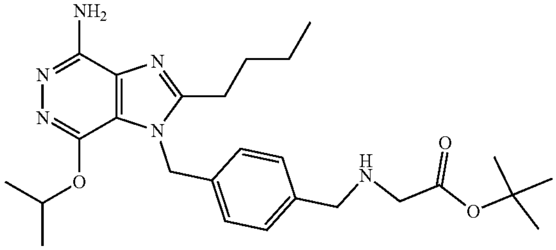 [SMILES: CCCCc1nc2c(N)nnc(OC(C)C)c2n1Cc1ccc(CNCC(=O)OC(C)(C)C)cc1] | tert-butyl (4-((4-amino-2-butyl-7-isopropoxy-1H-imidazo[4,5-d]pyridazin-1-yl)methyl)benzyl)glycinate |
| 118 | 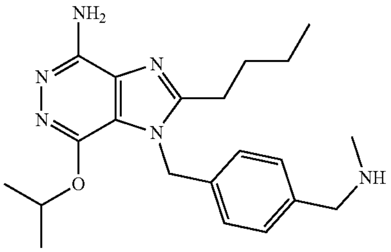 [SMILES: CCCCc1nc2c(N)nnc(OC(C)C)c2n1Cc1ccc(CNC)cc1] | 2-butyl-7-isopropoxy-1-(4-((methylamino)methyl)benzyl)-1H-imidazo[4,5-d]pyridazin-4-amine |
| 119 | 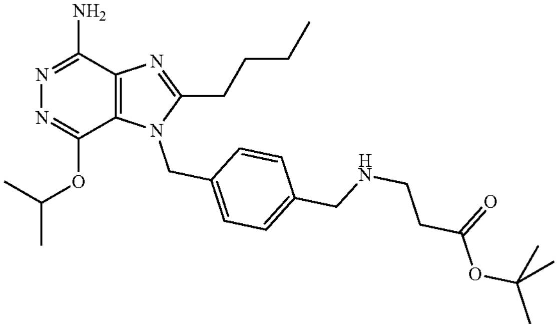 [SMILES: CCCCc1nc2c(N)nnc(OC(C)C)c2n1Cc1ccc(CNCCC(=O)OC(C)(C)C)cc1] | tert-butyl 3-((4-((4-amino-2-butyl-7-isopropoxy-1H-imidazo[4,5-d]pyridazin-1-yl)methyl)benzyl)amino)propano-ate |

TABLE 1-continued

| Compound Number | Formula | Name |
| --- | --- | --- |
| 120 | 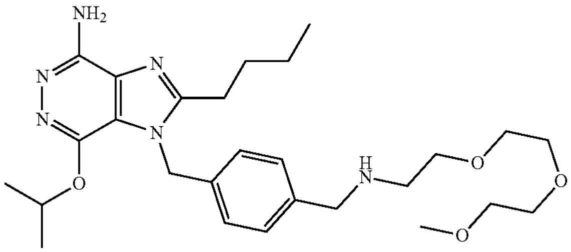 [SMILES: CCCCc1nc2c(N)nnc(OC(C)C)c2n1Cc1ccc(CNCCOCCOCCOC)cc1] | 1-(4-(5,8,11-trioxa-2-azadodecyl)benzyl)-2-butyl-7-isopropoxy-1H-imidazo[4,5-d]pyridazin-4-amine |
| 121 | 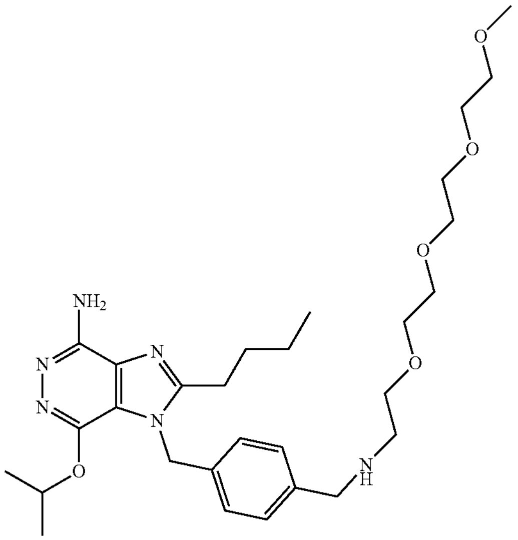 [SMILES: CCCCc1nc2c(N)nnc(OC(C)C)c2n1Cc1ccc(CNCCOCCOCCOCCOC)cc1] | 2-butyl-4-isopropoxy-3-[[4-[[2-[2-[2-(2-methoxyethoxy)ethoxy]ethoxy]ethylamino]methyl]phenyl]methyl]imidazo[4,5-d]pyridazin-7-amine |
| 122 | 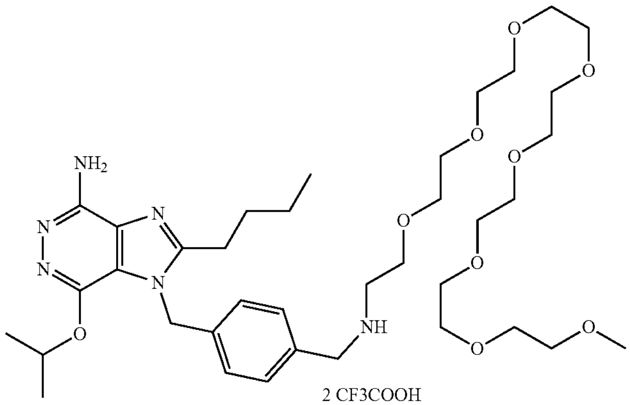 [SMILES: CCCCc1nc2c(N)nnc(OC(C)C)c2n1Cc1ccc(CNCCOCCOCCOCCOCCOCCOCCOCCOC)cc1] 2 CF3COOH | 2-butyl-4-isopropoxy-3-[[4-[[2-[2-[2-[2-[2-[2-(2-methoxyethoxy)ethoxy)ethoxy)ethoxy]ethoxy]ethoxy]ethoxy]ethylamino]methyl]phenyl]methyl]imidazo[4,5-d]pyridazin-7-amine, di2,2,2-trifluoroacetate |

TABLE 1-continued

| Compound Number | Formula | Name |
| --- | --- | --- |
| 123 | 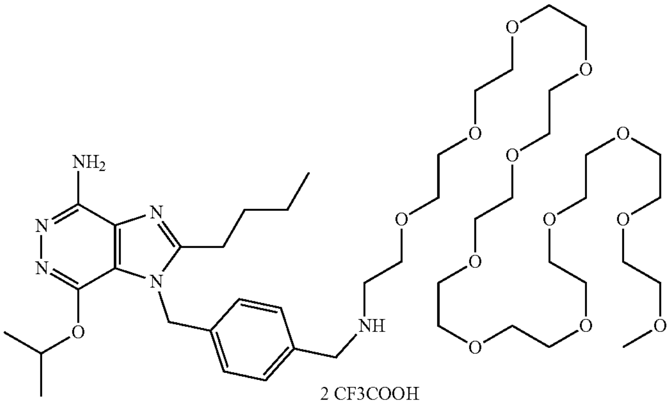 [SMILES: CCCCc1nc2c(N)nnc(OC(C)C)c2n1Cc1ccc(CNCCOCCOCCOCCOCCOCCOCCOCCOCCOCCOCCOCCOC)cc1] 2 CF3COOH | 2-butyl-4-isopropoxy-3-[[4-[[2-[2-[2-[2-[2-[2-[2-[2-[2-[2-[2-(2-methoxyethoxy)ethoxy]ethoxy]ethoxy]ethoxy]ethoxy]ethoxy]ethoxy]ethoxy]ethoxy]ethoxy]ethylamino]methyl]phenyl]methyl]imidazo[4,5-d]pyridazin-7-amine, di2,2,2-trifluoroacetate |
| 124 | 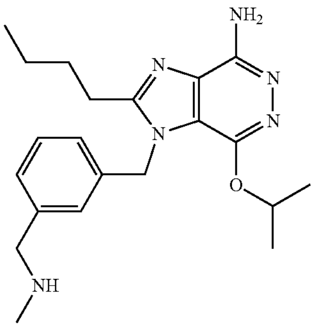 [SMILES: CCCCc1nc2c(N)nnc(OC(C)C)c2n1Cc1cccc(CNC)c1] | 2-butyl-7-isopropoxy-1-(3-((methylamino)methyl)benzyl)-1H-imidazo[4,5-d]pyridazin-4-amine |
| 125 | 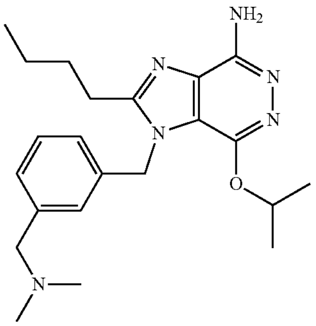 [SMILES: CCCCc1nc2c(N)nnc(OC(C)C)c2n1Cc1cccc(CN(C)C)c1] | 2-butyl-1-(3-((dimethylamino)methyl)benzyl)-7-isopropoxy-1H-imidazo[4,5-d]pyridazin-4-amine |
| 126 | 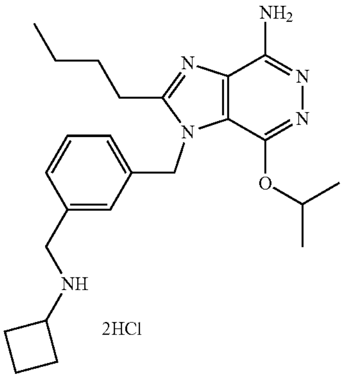 [SMILES: CCCCc1nc2c(N)nnc(OC(C)C)c2n1Cc1cccc(CNC2CCC2)c1] 2HCl | 2-butyl-1-(3-((cyclobutylamino)methyl)benzyl)-7-isopropoxy-1H-imidazo[4,5-d]pyridazin-4-amine dihydrochloride salt |

TABLE 1-continued

| Compound Number | Formula | Name |
|---|---|---|
| 127 | 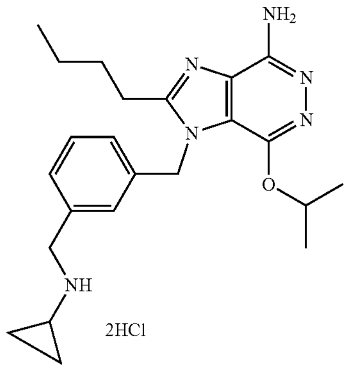 [SMILES: CCCCc1nc2c(N)nnc(OC(C)C)c2n1Cc1cccc(CNC2CC2)c1] | 2-butyl-1-(3-((cyclopropylamino)methyl)benzyl)-7-isopropoxy-1H-imidazo[4,5-d]pyridazin-4-amine dihydrochloride salt |
| 128 | 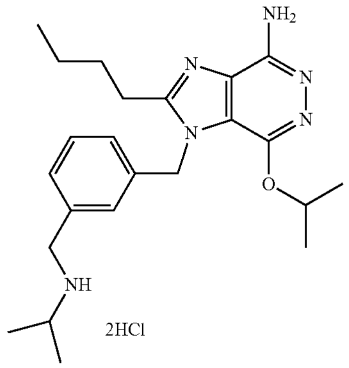 [SMILES: CCCCc1nc2c(N)nnc(OC(C)C)c2n1Cc1cccc(CNC(C)C)c1] | 2-butyl-7-isopropoxy-1-(3-((isopropylamino)methyl)benzyl)-1H-imidazo[4,5-d]pyridazin-4-amine dihydrochloride salt |
| 129 | 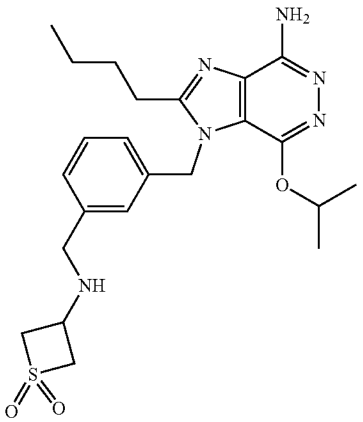 [SMILES: CCCCc1nc2c(N)nnc(OC(C)C)c2n1Cc1cccc(CNC2CS(=O)(=O)C2)c1] | 3-((3-((4-amino-2-butyl-7-isopropoxy-1H-imidazo[4,5-d]pyridazin-1-yl)methyl)benzyl)amino)thietane 1,1-dioxide |
| 130 | 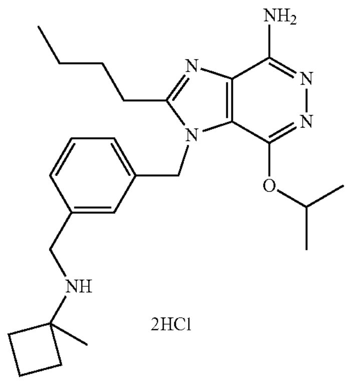 [SMILES: CCCCc1nc2c(N)nnc(OC(C)C)c2n1Cc1cccc(CNC2(C)CCC2)c1] | 2-butyl-7-isopropoxy-1-(3-(((1-methylcyclobutyl)amino)methyl)benzyl)-1H-imidazo[4,5-d]pyridazin-4-amine dihydrochloride salt |

TABLE 1-continued

| Compound Number | Formula | Name |
|---|---|---|
| 131 | 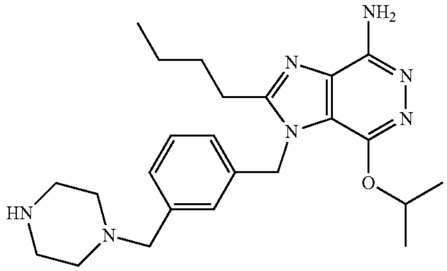 [SMILES: CCCCc1nc2c(N)nnc(OC(C)C)c2n1Cc1cccc(CN2CCNCC2)c1] | 2-butyl-7-isopropoxy-1-(3-(piperazin-1-ylmethyl)benzyl)-1H-imidazo[4,5-d]pyridazin-4-amine |
| 132 | 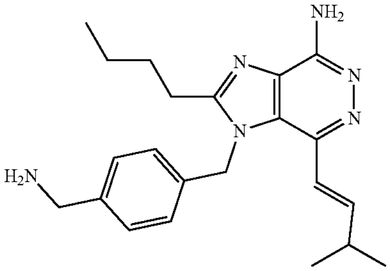 [SMILES: CCCCc1nc2c(N)nnc(/C=C/C(C)C)c2n1Cc1ccc(CN)cc1] | (E)-1-(4-(aminoethyl)benzyl)-2-butyl-7-(3-methylbut-1-en-1-yl)-1H-imidazo[4,5-d]pyridazin-4-amine |
| 133 | 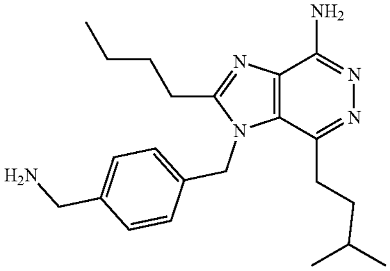 [SMILES: CCCCc1nc2c(N)nnc(CCC(C)C)c2n1Cc1ccc(CN)cc1] | 1-(4-(aminomethyl)benzyl)-2-butyl-7-isopentyl-1H-imidazo[4,5-d]pyridazin-4-amine |
| 134 | 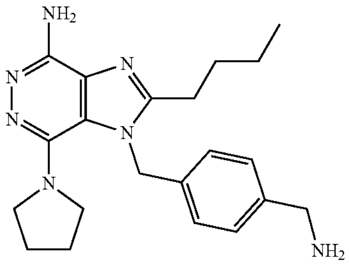 [SMILES: CCCCc1nc2c(N)nnc(N3CCCC3)c2n1Cc1ccc(CN)cc1] | 1-(4-(aminomethyl)benzyl)-2-butyl-7-(pyrrolidin-1-yl)-1H-imidazo[4,5-d]pyridazin-4-amine |
| 135 | 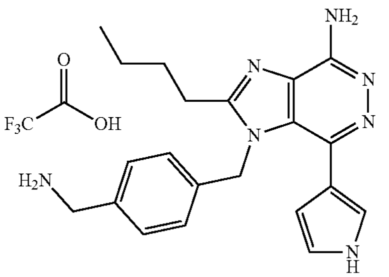 | 1-(4-(aminomethyl)benzyl)-2-butyl-7-(1H-pyrrol-3-yl)-1H-imidazo[4,5-d]pyridazin-4-amine 2,2,2-trifluoroacetate |

TABLE 1-continued

| Compound Number | Formula | Name |
|---|---|---|
| 137 | 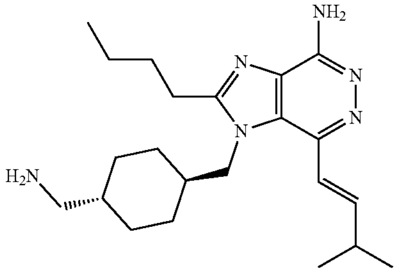 [SMILES: CCCCc1nc2c(N)nnc(/C=C/C(C)C)c2n1C[C@H]1CC[C@H](CN)CC1] | 1-(((1R,4R)-4-(aminomethyl)cyclohexyl)methyl)-2-butyl-7-((E)-3-methylbut-1-en-1-yl)-1H-imidazo[4,5-d]pyridazin-4-amine (and enantiomer) |
| 138 | 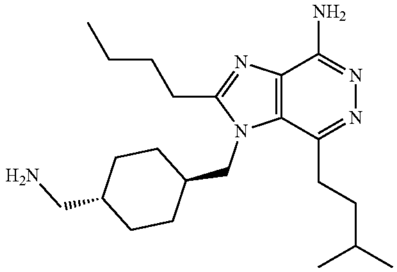 [SMILES: CCCCc1nc2c(N)nnc(CCC(C)C)c2n1C[C@H]1CC[C@H](CN)CC1] | 1-(((1R,4R)-4-(aminomethyl)cyclohexyl)methyl)-2-butyl-7-isopentyl-1H-imidazo[4,5-d]pyridazin-4-amine (and enantiomer) |
| 139 | 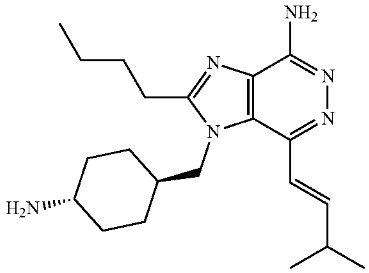 [SMILES: CCCCc1nc2c(N)nnc(/C=C/C(C)C)c2n1C[C@H]1CC[C@H](N)CC1] | 1-(((1R,4R)-4-aminocyclohexyl)methyl)-2-butyl-7-((E)-3-methylbut-1-en-1-yl)-1H-imidazo[4,5-d]pyridazin-4-amine (and enantiomer) |
| 140 | 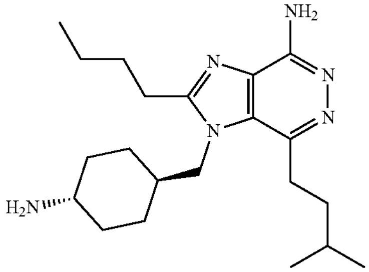 [SMILES: CCCCc1nc2c(N)nnc(CCC(C)C)c2n1C[C@H]1CC[C@H](N)CC1] | 1-(((1R,4R)-4-aminocyclohexyl)methyl)-2-butyl-7-isopentyl-1H-imidazo[4,5-d]pyridazin-4-amine (and enantiomer) |
| 141 | 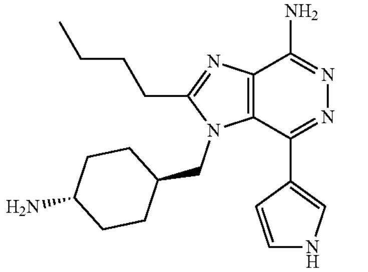 [SMILES: CCCCc1nc2c(N)nnc(-c3cc[nH]c3)c2n1C[C@H]1CC[C@H](N)CC1] | 1-(((1R,4R)-4-aminocyclohexyl)methyl)-2-butyl-7-(1H-pyrrol-3-yl)-1H-imidazo[4,5-d]pyridazin-4-amine (and enantiomer) |

TABLE 1-continued

| Compound Number | Formula | Name |
|---|---|---|
| 142 | 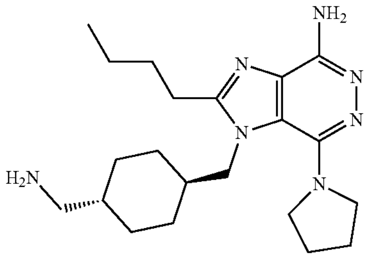 [SMILES: CCCCc1nc2c(N)nnc(N3CCCC3)c2n1C[C@H]1CC[C@H](CN)CC1] | 1-(((1R,4R)-4-(aminomethyl)cyclohexyl)methyl)-2-butyl-7-(pyrrolidin-1-yl)-1H-imidazo[4,5-d]pyridazin-4-amine (and enantiomer) |
| 143 | 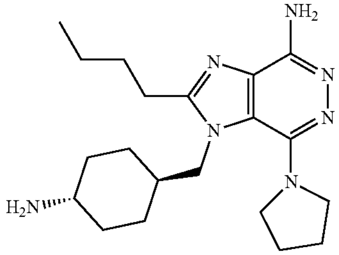 [SMILES: CCCCc1nc2c(N)nnc(N3CCCC3)c2n1C[C@H]1CC[C@H](N)CC1] | 3-[(4-aminocyclohexyl)methyl]-2-butyl-4-pyrrolidin-1-yl-imidazo[4,5-d]pyridazin-7-amine (and enantiomer) |
| 144 | 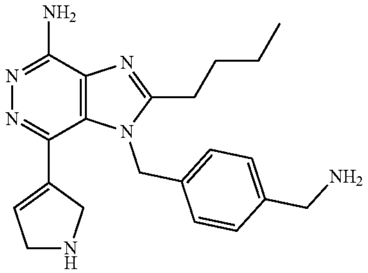 [SMILES: CCCCc1nc2c(N)nnc(C3=CCNC3)c2n1Cc1ccc(CN)cc1] | 1-[[4-(aminomethyl)phenyl]methyl]-2-butyl-7-(2,5-dihydro-1H-pyrrol-3-yl)imidazo[4,5-d]pyridazin-4-amine |
| 145 | 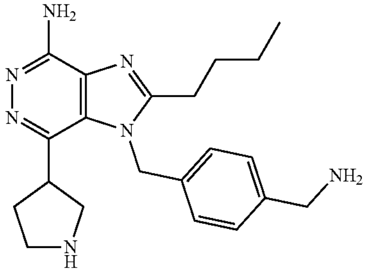 [SMILES: CCCCc1nc2c(N)nnc(C3CCNC3)c2n1Cc1ccc(CN)cc1] | 1-[[4-(aminomethyl)phenyl]methyl]-2-butyl-7-pyrrolidin-3-yl-imidazo[4,5-d]pyridazin-4-amine |
| 146 | 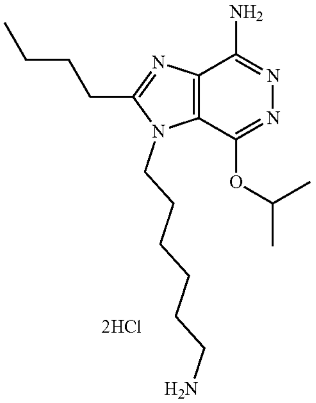 [SMILES: CCCCc1nc2c(N)nnc(OC(C)C)c2n1CCCCCCN] | 3-(6-aminohexyl)-2-butyl-4-isopropxoy-imidazo[4,5-d]pyridazin-7-amine dihydrochloride salt |

TABLE 1-continued
| Compound Number | Formula | Name |
|---|---|---|
| 147 | 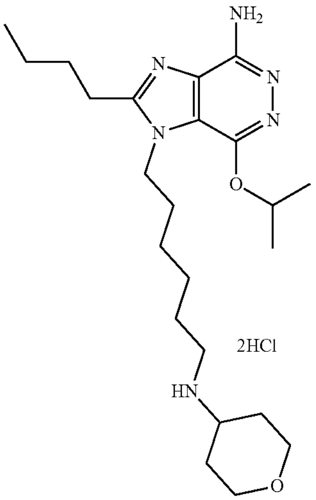 [SMILES: CCCCc1nc2c(N)nnc(OC(C)C)c2n1CCCCCCNC1CCOCC1] | 2-butyl-4-isopropoxy-3-[6-(tetrahydropyran-4-ylamino)hexyl]imidazo[4,5-d]pyridazin-7-amine dihydrochloride salt |
| 148 | 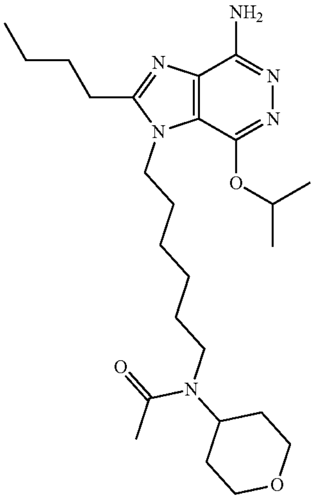 [SMILES: CCCCc1nc2c(N)nnc(OC(C)C)c2n1CCCCCCN(C(C)=O)C1CCOCC1] | N-[6-(7-amino-2-butyl-4-isopropoxy-imidazo[4,5-d]pyridazin-3-yl)hexyl]-N-tetrahydropyran-4-yl-acetamide |
| 149 | 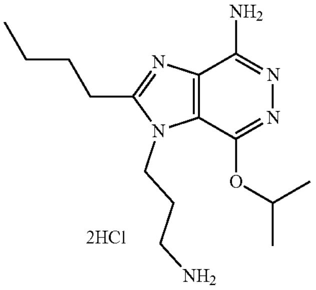 [SMILES: CCCCc1nc2c(N)nnc(OC(C)C)c2n1CCCN] | 3-(4-aminobutyl)-2-butyl-4-isopropoxy-imidazo[4,5-d]pyridazin-7-amine dihydrochloride salt |

TABLE 1-continued
| Compound Number | Formula | Name |
|---|---|---|
| 150 | 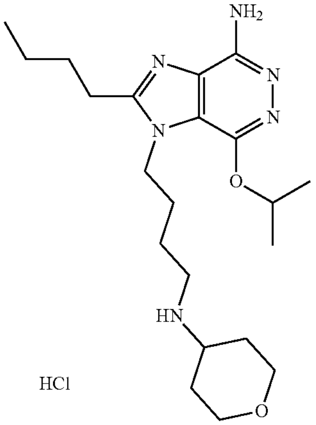 [SMILES: CCCCc1nc2c(N)nnc(OC(C)C)c2n1CCCCNC1CCOCC1 ; Cl] HCl | 2-butyl-4-isopropoxy-3-[4-(tetrahydropyran-4-ylamino)butyl]imidazo[4,5-d]pyridazin-7-amine hydrochloride salt |
| 151 | 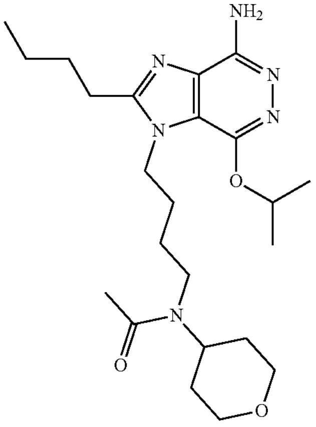 [SMILES: CCCCc1nc2c(N)nnc(OC(C)C)c2n1CCCCN(C(C)=O)C1CCOCC1] | N-[4-(7-amino-2-butyl-4-isopropoxy-imidazo[4,5-d]pyridazin-3-yl)butyl]-N-tetrahydropyran-4-yl-acetamide |
| 152 | 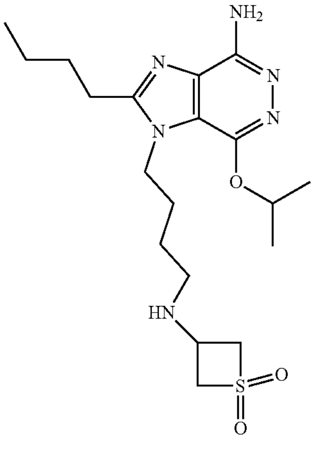 [SMILES: CCCCc1nc2c(N)nnc(OC(C)C)c2n1CCCCNC1CS(=O)(=O)C1] | 2-butyl-3-[4-[(1,1-dioxothietan-3-yl)amino)butyl]-4-isopropoxy-imidazo[4,5-d]pyridazin-7-amine |

TABLE 1-continued
| Compound Number | Formula | Name |
|---|---|---|
| 153 | 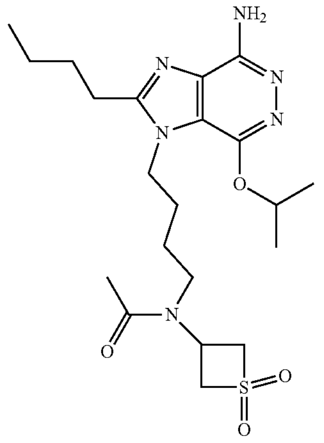 [SMILES: CCCCc1nc2c(N)nnc(OC(C)C)c2n1CCCCN(C(C)=O)C1CS(=O)(=O)C1] | N-[4-(7-amino-2-butyl-4-isopropoxy-imidazo[4,5-d]pyridazin-3-yl)butyl]-N-(1,1-dioxothietan-3-yl)acetamide |
| 154 | 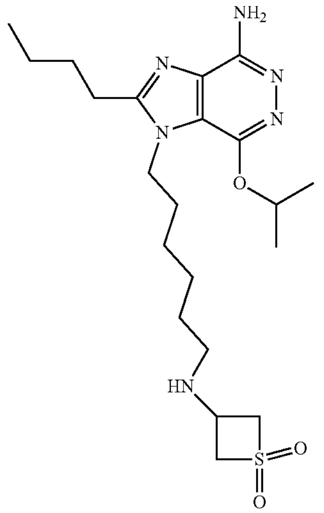 [SMILES: CCCCc1nc2c(N)nnc(OC(C)C)c2n1CCCCCCNC1CS(=O)(=O)C1] | 2-butyl-3-[6-[(1,1-dioxothietan-3-yl)amino]hexyl]-4-isopropoxy-imidazo[4,5-d]pyridazin-7-amine |
| 155 | 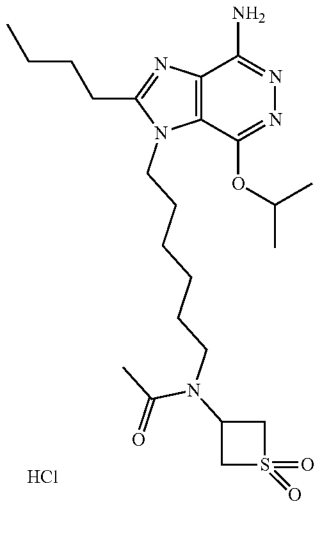 [SMILES: CCCCc1nc2c(N)nnc(OC(C)C)c2n1CCCCCCN(C(C)=O)C1CS(=O)(=O)C1 ; Cl] HCl | N-[6-(7-amino-2-butyl-4-isopropoxy-imidazo[4,5-d]pyridazin-3-yl)hexyl]-N-(1,1-dioxothietan-3-yl)acetamide hydrochloride salt |

TABLE 1-continued

| Compound Number | Formula | Name |
|---|---|---|
| 156 | 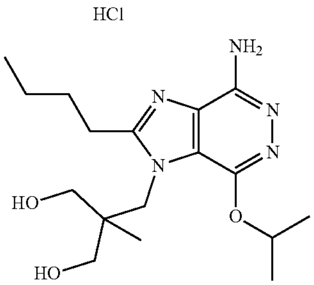 [SMILES: Cl ; CCCCc1nc2c(N)nnc(OC(C)C)c2n1CC(C)(CO)CO] | 2-[(7-amino-2-butyl-4-isopropoxy-imidazo[4,5-d]pyridazin-3-yl)methyl]-2-methyl-propane-1,3-diol hydrochloride salt |
| 157 | 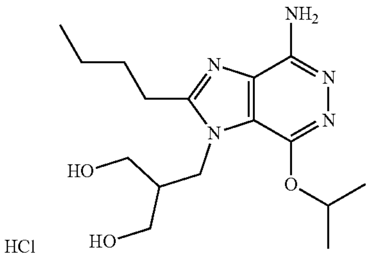 [SMILES: Cl ; CCCCc1nc2c(N)nnc(OC(C)C)c2n1CC(CO)CO] | 2-[(7-amino-2-butyl-4-isopropoxy-imidazo[4,5-d]pyridazin-3-yl)methyl]propane-1,3-diol hydrochloride salt |
| 158 | 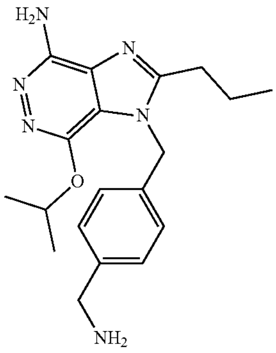 [SMILES: CCCc1nc2c(N)nnc(OC(C)C)c2n1Cc1ccc(CN)cc1] | 1-(4-(aminomethyl)benzyl)-7-isopropoxy-2-propyl-1H-imidazo[4,5-d]pyridazin-4-amine |
| 159 | 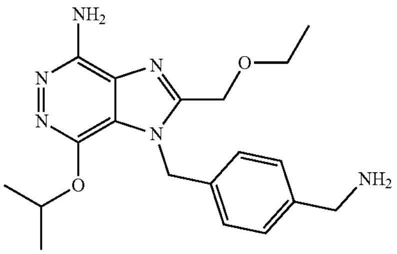 | 1-(4-(aminomethyl)benzyl)-2-(ethoxymethyl)-7-isopropoxy-1H-imidazo[4,5-d]pyridazin-4-amine |
| 160 | 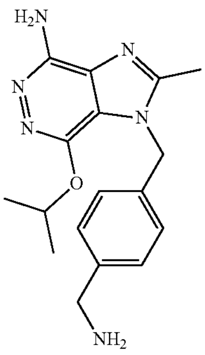 [SMILES: Cc1nc2c(N)nnc(OC(C)C)c2n1Cc1ccc(CN)cc1] | 1-(4-(aminomethyl)benzyl)-7-isopropoxy-2-methyl-1H-imidazo[4,5-d]pyridazin-4-amine |

TABLE 1-continued

| Compound Number | Formula | Name |
|---|---|---|
| 161 | 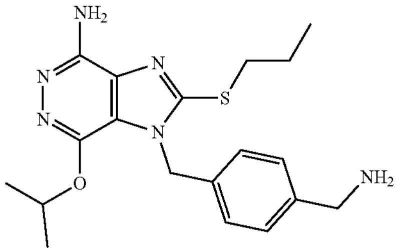 [SMILES: CCCSc1nc2c(N)nnc(OC(C)C)c2n1Cc1ccc(CN)cc1] | 3-[[4-(aminomethyl)phenyl]methyl]-4-isopropoxy-2-propylsulfanyl-imidazo[4,5-d]pyridazin-7-amine |
| 162 | 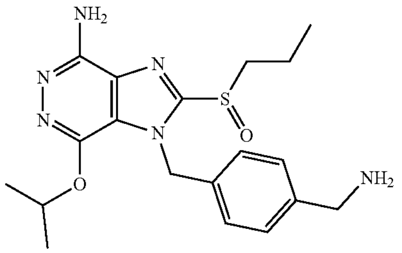 [SMILES: CCCS(=O)c1nc2c(N)nnc(OC(C)C)c2n1Cc1ccc(CN)cc1] | 3-[[4-(aminomethyl)phenyl]methyl]-4-isopropoxy-2-propylsulfinyl-imidazo[4,5-d]pyridazin-7-amine |
| 163 | 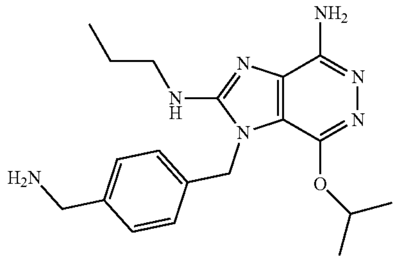 [SMILES: CCCNc1nc2c(N)nnc(OC(C)C)c2n1Cc1ccc(CN)cc1] | 3-[[4-(aminomethyl)phenyl]methyl]-4-isopropoxy-N2-propyl-imidazo[4,5-d]pyridazine-2,7-diamine |
| 164 | 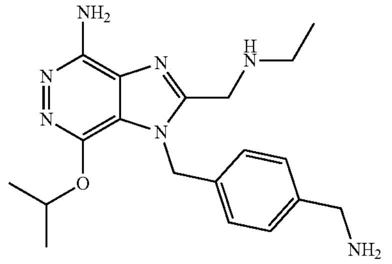 [SMILES: CCNCc1nc2c(N)nnc(OC(C)C)c2n1Cc1ccc(CN)cc1] | 3-[[4-(aminomethyl)phenyl]methyl]-2-(ethylaminomethyl)-4-isopropoxy-imidazo[4,5-d]pyridazin-7-amine |
| 165 | 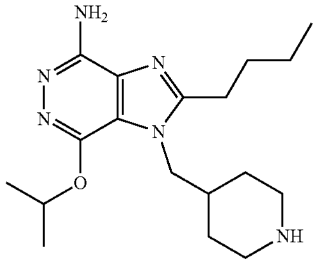 [SMILES: CCCCc1nc2c(N)nnc(OC(C)C)c2n1CC1CCNCC1] | 2-butyl-7-isopropoxy-1-(piperidin-4-ylmethyl)-1H-imidazo[4,5-d]pyridazin-4-amine |

TABLE 2

| Compound Number | RT | MS | $^1$H NMR |
|---|---|---|---|
| 1 | 1.2 | 370 | 0.85 (t, J = 7.4 Hz, 3 H); 1.25 (d, J = 6.2 Hz, 6 H); 1.33 (m, 2 H); 1.63 (m, 2 H); 2.81 (m, 2 H); 3.71 (s, 3 H); 5.36 (sept, J = 6.2 Hz, 1 H); 5.51 (s, 2 H); 5.91 (s, 2 H); 6.90 (d, J = 8.8 Hz, 2 H); 7.06 (d, J = 8.8 Hz, 2 H) |

TABLE 2-continued

| Compound Number | RT | MS | $^1$H NMR |
|---|---|---|---|
| 2 | 0.82 | 369 | 0.87 (t, J = 7.4 Hz, 3 H); 1.03 (d, J = 6.3 Hz, 6 H); 1.36 (m, 2 H); 1.67 (m, 2 H); 2.87 (m, 2 H); 3.71 (s, 3 H); 4.00 (m, 1 H); 4.79 (d, J = 6.5 Hz, 1 H); 5.59 (s, 2 H); 6.10 (s, 2 H); 6.90 (d, J = 8.9 Hz, 2 H); 7.00 (d, J = 8.9 Hz, 2 H) |
| 3 | 1.23 | 386 | 0.81 (t, J = 7.4 Hz, 3 H); 1.22 (d, J = 6.8 Hz, 6 H); 1.29 (m, 2 H); 1.60 (m, 2 H); 2.74 (m, 2 H); 3.71 (s, 3 H); 5.85 (sept, J = 6.8 Hz, 1 H); 5.74 (s, 2 H); 6.46 (s, 2 H); 6.90 (m, 4 H) |
| 4 | 1.13 | 386 | 0.85 (t, J = 7.4 Hz, 3 H); 1.33 (m, 2 H); 1.63 (m, 2 H); 2.82 (m, 2 H); 3.25 (s, 3 H); 3.65 (m, 2 H); 3.71 (s, 3 H); 4.50 (m, 2 H); 5.52 (s, 2 H); 5.98 (s, 2 H); 6.89 (d, J = 8.7 Hz, 2 H); 7.13 (d, J = 8.7 Hz, 2 H) |
| 5 | 1.2 | 370 | 0.84 (t, J = 7.4 Hz, 3 H); 0.89 (t, J = 7.4 Hz, 3 H); 1.32 (m, 2 H); 1.61 (m, 2 H); 1.70 (m, 2 H); 2.79 (m, 2 H); 3.71 (s, 3 H); 4.32 (t, J = 6.4 Hz, 2 H); 5.54 (s, 2 H); 5.97 (s, 2 H); 6.90 (d, J = 8.8 Hz, 2 H); 7.06 (d, J = 8.8 Hz, 2 H) |
| 6 | 1.17 | 368 | 0.84 (t, J = 7.4 Hz, 3 H); 1.32 (m, 2 H); 1.61 (m, 2 H); 2.80 (m, 2 H); 3.71 (s, 3 H); 4.93 (td, J = 1.6 et 5.21 Hz, 2 H); 5.19 (qd, J = 1.6 et 10.5 Hz, 1 H); 5.30 (qd, J = 1.6 et 17.3 Hz, 1 H); 5.54 (s, 2 H); 6.00 (s, 2 H); 6.06 (m, 1 H); 6.89 (d, J = 8.9 Hz, 2 H); 7.07 (d, J = 8.9 Hz, 2 H) |
| 7 | 1.28 | 384 | 0.81 (t, J = 7.4 Hz, 3 H); 0.85 (t, J = 7.4 Hz, 3 H); 1.22 (d, J = 6.2 Hz, 3 H); 1.33 (m, 2 H); 1.55 to 1.67 (m, 4 H); 2.79 (m, 2 H); 3.71 (s, 3 H); 5.23 (m, 1 H); 5.50 (d, J = 16.2 Hz, 1 H); 5.55 (d, J = 16.2 Hz, 1 H); 5.97 (s, 2 H); 6.78 (d, J = 8.9 Hz, 2 H); 7.03 (d, J = 8.9 Hz, 2 H) |
| 8 | 1.25 | 384 | 0.84 (t, J = 7.4 Hz, 3 H); 0.85 (t, J = 7.4 Hz, 3 H); 1.31 (m, 4 H); 1.63 (m, 4 H); 2.80 (m, 2 H); 3.71 (s, 3 H); 4.36 (t, J = 6.5 Hz, 2 H); 5.53 (s, 2 H); 5.96 (s, 2 H); 6.90 (d, J = 8.8 Hz, 2 H); 7.03 (d, J = 8.8 Hz, 2 H) |
| 9 | 0.96 | 396 | 0.83 (t, J = 7.40 Hz, 3 H) 1.32 (sxt, J = 7.60, 2 H) 1.45-1.76 (m, 8 H) 1.78-1.94 (m, 2 H) 2.78 (t, J = 7.60 Hz, 2 H) 3.70 (s, 3 H) 5.42-5.57 (m, 3 H) 5.92 (s, 2 H) 6.89 (d, J = 8.78 Hz, 2 H) 7.01 (d, J = 8.78 Hz, 2 H) |
| 10 | 1.26 | 381 | 0.83 (t, J = 7.5 Hz, 3 H); 1.31 (m, 2 H); 1.63 (m, 2 H); 1.82 (m, 4 H); 2.70 (m, 2 H); 3.15 (m, 4 H); 3.71 (s, 3 H); 5.62 (s, 2 H); 6.11 (s, 2 H); 6.88 (d, J = 8.9 Hz, 2 H); 6.96 (d, J = 8.9 Hz, 2 H) |
| 11 | 1.18 | 391 | 0.83 (t, J = 7.4 Hz, 3 H); 1.31 (m, 2 H); 1.63 (m, 2 H); 2.71 (m, 2 H); 3.60 (s, 3 H); 3.68 (m, 3 H); 5.32 (s, 2 H); 6.08 (dd, J = 1.9 et 2.5 Hz, 1 H); 6.28 (s, 2 H); 6.68 (d, J = 8.9 Hz, 2 H); 6.72 (m, 2 H); 6.81 (d, J = 8.3 Hz, 2 H) |
| 12 | 1.33 | 380 | 0.86 (t, J = 7.5 Hz, 3 H); 0.92 (d, J = 6.8 Hz, 6 H); 1.35 (m, 2 H); 1.,68 (m, 2 H); 2.,34 (m, 1H); 2.87 (m, 2 H); 3.,70 (s, 3 H); 5.,55 (s, 2 H); 6.,37 (s, 2 H); 6.,44 (dd, J = 5.,9 et 15.,5 Hz, 1 H); 6.,51(d, J = 15.,5 Hz, 1 H); 6.,86 (d, J = 9.1 Hz, 2 H); 6.,90 (d, J = 9.,1 Hz, 2 H) |
| 13 | 1.41 | 382 | 0.79 (d, J = 6.6 Hz, 6 H); 0.85 (t, J = 7.4 Hz, 3 H); 1.29 to 1.40 (m, 4 H); 1.48 (m, 1 H); 1.68 (m, 2 H); 2.74 to 2.84 (m, 4 H); 3.70 (s, 3 H); 5.52 (s, 2 H); 6.20 (s, 2 H); 6.79 (d, J = 8.7 Hz, 2 H); 6.91 (d, J = 8.7 Hz, 2 H) |
| 14 | 1.15 | 377 | 0.82 (t, J = 7.5 Hz, 3 H); 1.29 (m, 2 H); 1.61 (m, 2 H); 2.69 (m, 2 H); 3.68 (s, 3 H); 5.31 (s, 2 H); 6.16 (dt, J = 1.8 et 2.5 Hz, 1 H); 6.26 (s, 2H); 6.69 (d, J = 9.0 Hz, 2 H); 6.80 (m, 3 H); 6.85 (td, J = 1.8 et 2.5 Hz, 1 H); 11.00 (s, 1 H) |
| 15 | 1.27 | 378 | 0.86 (t, J = 7.5 Hz, 3 H); 1.36 (m, 2 H); 1.70 (m, 2 H); 1.80 (m, 2 H); 2.31 (m, 2 H); 2.47 (m, 2 H); 2.91 (m, 2 H); 3.71 (s, 3 H); 5.51 (s, 2 H); 6.00 (m, 1 H); 6.81 (d, J = 8.9 Hz, 2 H); 6.89 (d, J = 8.9 Hz, 2 H); 8.82 (m broad, 2 H); 14.60 (s broad, 1 H) |
| 16 | 2.36 | 380 | 0.85 (t, J = 7.5 Hz, 3 H); 1.35 (m, 2 H); 1.52 (m, 2 H); 1.61 to 1.83 (m, 8 H); 2.88 (m, 2 H); 3.45 (m, 1 H); 3.72 (s, 3 H); 5.66 (s, 2 H); 6.92 (s, 4 H); 8.15 (m, 2 H) |
| 17 | 1.22 | 352 | 0.86 (t, J = 7.,5 Hz, 3 H); 1.35 (m, 2 H); 1.69 (m, 2 H); 1.83 (s broad, 3 H); 2.82 (m, 2 H); 3.69 (s, 3 H); 4.94 (s broad, 1 H); 5.36 (s broad, 1 H); 5.48 (s, 2 H); 6.42 (s, 2 H); 6.72 (d, J = 8.9 Hz, 2 H); 6.86 (d, J = 8.9 Hz, 2 H) |
| 18 | 1.23 | 354 | 0.85 (t, J = 7.5 Hz, 3 H); 1.11 (d, J = 6.7 Hz, 6 H); 1.35 (m, 2 H); 1.68 (m, 2 H); 2.83 (m, 2 H); 3.26 (sept, J = 6.7 Hz, 1 H); 3.70 (s, 3 H); 5.53 (s, 2 H); 6.19 (s, 2 H); 6.82 (d, J = 9.0 Hz, 2 H); 6.91 (d, J = 9.0 Hz, 2 H) |
| 19 | 0.83 | 375 | 0.87 (q. J = 13 Hz. 2 H); 0.94 (t. J = 7 Hz. 3 H); 1.12 (q. J = 13 Hz. 2 H); 1.33 to 1.48 (m. 8 H); 1.51 to 1.63 (m. 3 H); 1.66 to 1.92 (m. 5 H); 2.63 (t. J = 6 Hz. 2 H); 2.93 (t. J = 8 Hz. 2 H); 4.21 (d. J = 7 Hz. 2 H); 5.24 (quin. J = 6 Hz. 1 H); 7.90 (s broad. 3 H); 8.57 (s broad. 2 H); 13.89 (s. 1 H) |
| 20 | 0.80 | 375 | 0.80 (m, 2 H); 0.93 (t, J = 7.5 Hz, 3 H); 1.10 (m, 2 H); 1.30 (m, 1 H); 1.36 (d, J = 6.2 Hz, 6 H); 1.41 (m, 2 H); 1.50 (m, 2 H); |

TABLE 2-continued

| Compound Number | RT | MS | $^1$H NMR |
|---|---|---|---|
| | | | 1.71 to 1.82 (m, 5 H); 2.46 (d, J = 6.9 Hz, 2 H); 2.83 (m, 2 H); 4.13 (d, J = 7.4 Hz, 2 H); 4.74 (m, 3 H); 5.39 (sept, J = 6.2 Hz, 1 H); 5.87 (s, 2 H) |
| 21 | 0.76 | 369 | 0.84 (t, J = 7 Hz. 3 H); 1.21 (s, 3 H); 1.23 (s, 3 H); 1.33 (m, 2 H); 1.63 (m, 2 H); 1.97 (m, 2 H); 2.79 (d, J = 15 Hz, 2 H); 3.66 (s, 2 H); 5.33 (spt, J = 6 Hz, 1 H); 5.54 (s, 2 H); 5.91 (s, 2 H); 7.01 (d, J = 8 Hz, 2 H); 7.28 (d, J = 8 Hz, 2 H) |
| 22 | 0.68 | 369 | 0.85 (t, J = 7.4 Hz, 3 H); 1.22 (d, J = 6.2 Hz, 6 H); 1.33 (m, 2 H); 1.66 (m, 2 H); 2.87 (m, 2 H); 4.02 (m, 2 H); 5.16 (m, 1 H); 5.67 (s, 2 H); 7.18 (d, J = 8.5 Hz, 2 H); 7.42 (d, J = 8.5 Hz, 2 H); 8.13 (s, 3 H); 8.47 (m, 2 H) |
| 23 | 0.85 | 361 | 0.75 to 1.00 (m, 2 H); 0.93 (t, J = 7.4 Hz, 3 H); 1.15 (m, 1 H); 1.33 to 1.54 (m, 9 H); 1.63 to 1.89 (m, 5 H); 2.07 (m broad, 2 H); 2.45 (m, 3 H); 2.83 (m, 2 H); 4.11 (m, 2 H); 5.38 (sept, J = 6.2 Hz, 1 H); 5.85 (s, 2 H) |
| 24 | 1.1 | 322 | 0.92 (t, J = 7.3 Hz, 3 H); 1.09 (s broad, 6 H); 1.36 (d, J = 6.2 Hz, 6 H); 1.39 (m, 2 H); 1.75 (m, 2 H); 3.01 (m, 2 H); 4.28 (s, 2 H); 4.78 (s, 1 H); 5.36 (sept, J = 6.2 Hz, 1 H); 6.24 (s, 2 H) |
| 25 | 0.78 | 36 | 0.92 (t, J = 7.3 Hz, 3 H); 0.94 (m, 2 H); 1.12 (m, 2 H); 1.34 to 1.48 (m, 5 H); 1.36 (d, J = 6.2 Hz, 6 H); 1.65 to 1.81 (m, 5 H); 2.82 (m, 2 H); 2.95 (m broad, 2 H); 4.10 (d, J = 7.5 Hz, 2 H); 5.39 (sept, J = 6.2 Hz, 1 H); 5.85 (s, 2 H) |
| 26 | 0.46 | 370 | 0.86 (t, J = 7.4 Hz, 3 H); 1.16 (d, J = 6.2 Hz, 6 H); 1.35 (m, 2 H); 1.68 (m, 2 H); 2.67 (m, 2 H); 2.87 (m, 2 H); 3.70 (s, 2 H); 5.25 (sept, J = 6.2 Hz, 1 H); 5.61 (s, 2 H); 5.89 (s, 2 H); 7.12 (d, J = 8.1 Hz, 1 H); 7.73 (dd, J = 2.3 et 8.1 Hz, 1 H); 8.38 (d, J = 2.3 Hz, 1 H) |
| 27 | 1.10 | 366 | 0.86 (t, J = 7 Hz, 3 H); 1.05 (d, J = 6 Hz, 6 H); 1.35 (dq, J = 7 et 15 Hz, 2 H); 1.68 (dt, J = 8 et 15 Hz, 2 H); 2.87 (t, J = 8 Hz. 2 H); 5.19 (spt, J = 6 Hz, 1 H); 5.75 (s, 2 H); 5.92 (s, 2 H); 7.45 (dd, J = 1 et 8 Hz, 1 H); 8.33 (dd, J = 2 et 8 Hz, 1 H); 8.90 (dd, J = 1 et 2 Hz, 1 H) |
| 28 | 1.09 | 411 | 0.84 (t, J = 7.5 Hz, 3 H); 1.21 (d, J = 6.2 Hz, 6 H); 1.32 (m, 2 H); 1.63 (m, 2 H); 1.83 (s, 3 H); 2.79 (m, 2 H); 4.19 (d, J = 6.0 Hz, 2 H); 5.32 (sept, J = 6.2 Hz, 1 H); 5.55 (s, 2 H); 5.91 (s, 2 H); 7.03 (d, J = 8.4 Hz, 2 H); 7.20 (d, J = 8.4 Hz, 2 H); 8.29 (t, J = 6.0 Hz, 1 H) |
| 29 | 1.59 | 537 | 0.84 (t, J = 7.4 Hz, 3 H); 0.85 (t, J = 6.9 Hz, 3 H); 1.21 (d, J = 6.2 Hz, 6 H); 1.22 (s braod, 14 H); 1.32 (m, 2 H); 1.48 (m, 2 H); 1.62 (m, 2 H); 2.08 (t, J = 7.4 Hz, 2 H); 2.79 (m, 2 H); 4.20 (d, J = 6.1 Hz, 2 H); 5.32 (sept, J = 6.2 Hz, 1 H); 5.54 (s, 2 H); 5.91 (s, 2 H); 7.02 (d, J = 8.4 Hz, 2 H); 7.19 (d, J = 8.4 Hz, 2 H); 8.24 (t, J = 6.1 Hz, 1 H) |
| 30 | 1.23 | 453 | 0.83 (t, J = 7.4 Hz, 6 H); 1.21 (d, J = 6.2 Hz, 6 H); 1.23 (m, 2 H); 1.32 (m, 2 H); 1.47 (m, 2 H); 1.62 (m, 2 H); 2.09 (t, J = 7.5 Hz, 2 H); 2.79 (m, 2 H); 4.20 (d, J = 6.0 Hz, 2 H); 5.31 (sept, J = 6.2 Hz, 1 H); 5.55 (s, 2 H); 5.96 (s, 2 H); 7.02 (d, J = 8.3 Hz, 2 H); 7.19 (d, J = 8.3 Hz, 2 H); 8.25 (t, J = 6.0 Hz, 1 H) |
| 31 | 1.11 | 499 | 0.85 (t, J = 7.4 Hz, 3 H); 1.21 (d, J = 6.2 Hz, 6 H); 1.32 (m, 2 H); 1.63 (m, 2 H); 2.34 (t, J = 6.5 Hz, 2 H); 2.78 (t, J = 7.6 Hz, 2 H); 3.16 (s, 3 H); 3.37 (m, 2 H); 3.46 (m, 2 H); 3.60 (t, J = 6.5 Hz, 2 H); 4.23 (d, J = 6.1 Hz, 2 H); 5.32 (sept, J = 6.2 Hz, 1 H); 5.55 (s, 2 H); 5.91 (s, 2 H); 7.02 (d, J = 8.3 Hz, 2 H); 7.20 (d, J = 8.3 Hz, 2 H); 8.31 (t, J = 6.1 Hz, 1 H) |
| 32 | 0.90 | 361 | 0.93 (t, J = 7.4 Hz, 3 H); 1.07 (m, 1 H); 1.26 to 1.62 (m, 15 H); 1.78 (m, 2 H); 1.90 (m broad, 2 H); 2.22 (m, 1 H); 2.82 (m, 2 H); 3.09 (m, 1 H); 4.11 (m, 2 H); 5.38 (sept, J = 6.2 Hz, 1 H); 5.84 (s, 2 H) |
| 33 | 0.81 | 369 | 0.86 (t, J = 7.4 Hz, 3 H); 1.22 (d, J = 6.2 Hz, 6 H); 1.34 (m, 2 H); 1.67 (m, 2 H); 2.80 (m, 2 H); 3.94 (s, 2 H); 5.32 (sept, J = 6.2 Hz, 1 H); 5.59 (s, 2 H); 5.98 (s, 2 H); 7.11 (t, J = 2.0 Hz, 1 H); 7.14 (td, J = 2.0 et 7.8 Hz, 1 H); 7.36 (td, J = 2.0 et 7.8 Hz, 1 H); 7.41 (t, J = 7.8 Hz, 1 H); 7.86 (m, 3 H) |
| 34 | 1.21 | 368 | 0.84 (t, J = 7.5 Hz, 3 H); 1.12 (d, J = 6.2 Hz, 6 H); 1.33 (m, 2 H); 1.64 (m, 2 H); 2.83 (m, 2 H); 5.26 (m, 1 H); 5.69 (s, 2 H); 5.97 (s, 2 H); 7.23 (d, J = 8.2 Hz, 2 H); 7.89 (d, J = 8.2 Hz, 2 H); 9.98 (s, 1 H) |
| 35 | 0.73 | 370 | 0.84 (t, J = 7.28 Hz, 3 H) 1.21 (d, J = 6.27 Hz, 6 H) 1.32 (sxt, J = 7.65 Hz, 2 H) 1.63 (quin, J = 7.59 Hz, 2 H) 2.79 (t, J = 7.81 Hz, 2 H) 4.45 (s, 2 H) 5.13 (br s, 1 H) 5.32 (spt, J = 6.15 Hz, 1 H) 5.56 (s, 2 H) 5.92 (s, 2 H) 7.02 (d, J = 8.28 Hz, 2 H) 7.27 (d, J = 8.28 Hz, 2 H) |
| 36 | 0.83 | 409 | 0.17 to 0.32 (m, 4 H); 0.83 (t, J = 7.3 Hz, 3 H); 1.20 (d, J = 6.2 Hz, 6 H); 1.31 (m, 2 H); 1.61 (m, 2 H); 1.97 (m, 1 H); 2.60 (m, 1 H); 2.80 (m, 2 H); 3.66 (s, 2 H); 5.32 (sept, J = 6.2 Hz, 1 H); 5.55 (s, 2 H); 5.92 (m, 2 H); 7.00 (d, J = 8.3 Hz, 2 H); 7.27 (d, J = 8.3 Hz, 2 H) |

TABLE 2-continued

| Compound Number | RT | MS | $^1$H NMR |
|---|---|---|---|
| 37 | 0.99 | 473 | 0.84 (t, J = 7.4 Hz, 3 H); 1.20 (d, J = 6.2 Hz, 6 H); 1.32 (m, 2 H); 1.62 (m, 2 H); 2;80 (m, 2 H); 2.91 (m, 1 H); 3.44 (m, 1 H); 3.59 (s, 2 H); 3.84 to 3.91 (m, 2 H); 4.17 to 4.25 (m, 2 H); 5.32 (sept, J = 6.2 Hz, 1 H); 5.56 (s, 2 H); 5.94 (s, 2 H); 7.02 (d, J = 8.2 Hz, 2 H); 7.28 (d, J = 8.2 Hz, 2 H) |
| 38 | 1.08 | 515 | 0.82 (t, J = 7 Hz, 3 H); 1.17 (d, J = 6 Hz, 6 H); 1.30 (dq, J = 7 & 15 Hz, 2 H); 1.59 (quin, J = 8 Hz, 2 H); 1.96 (s, 2 H); 2.19 (s broad, 1 H); 2.81 (t, J = 8 Hz, 2 H); 4.06 to 4.79 (m, 6 H); 5.05 (m, 1 H); 5.30 (quin, J = 6 Hz, 1 H); 5.57 (s broad, 2 H); 5.92 (s, 2 H); 6.94 to 7.26 (m, 4 H) |
| 39 | 0.9 | 437 | 0.85 (t, J = 7.4 Hz, 3 H); 1.19 (s, 3 H); 1.22 (d, J = 6.2 Hz, 6 H); 1.33 (m, 2 H); 1.58 to 1.73 (m, 6 H); 1.93 (m, 2 H); 2.09 (m broad, 1 H); 2.80 (m, 2 H); 3.58 (s, 2 H); 5.33 (sept, J = 6.2 Hz, 1 H); 5.56 (s, 2 H); 5.92 (s, 2 H); 7.01 (d, J = 8.3 Hz, 2 H); 7.31 (d, J = 8.3 Hz, 2 H) |
| 40 | 0.80 | 438 | 0.81 (t, J = 7 Hz, 3 H); 1.17 (d, J = 6 Hz, 6 H); 1.29 (dq, J = 7 & 15 Hz, 2 H); 1.59 (quin, J = 8 Hz, 2 H); 2.22 (s broad, 4 H); 2.63 (t, J = 5 Hz, 4 H); 2.81 (t, J = 7 Hz, 2 H); 3.36 (s, 2 H); 5.30 (spt, J = 6 Hz, 1 H); 5.55 (s, 2 H); 5.94 (s, 2 H); 7.00 (d, J = 8 Hz, 2 H); 7.24 (d, J = 8 Hz, 2 H) |
| 41 | 0.88 | 249 | 0.94 (t, J = 7.4 Hz, 3 H); 1.43 (m, 2 H); 1.77 (m, 2 H); 2.77 (s, 6 H); 2.86 (m, 2 H); 3.95 (s, 3 H); 6.06 (s, 2 H) |
| 42 | 1.85 | 275 | 0.94 (t, J = 7.4 Hz, 3 H); 1.43 (m, 2 H); 1.77 (m, 2 H); 1.89 (m, 4 H); 2.88 (m, 2 H); 3.30 (m, 4 H); 3.96 (s, 3 H); 6.88 (s, 2 H) |
| 43 | 0.84 | 382 | 0.94 (t, J = 7.4 Hz, 3 H); 1.42 (m, 2 H); 1.76 (m, 2 H); 2.12 (s, 6 H); 2.67 (s, 3 H); 2.86 (m, 2 H); 3.34 (s, 2 H); 4.01 (s, 3 H); 4.31 (s, 2 H); 6.05 (s, 2 H); 7.22 (d, J = 8.2 Hz, 2 H); 7.29 (d, J = 8.2 Hz, 2 H). |
| 44 | 0.73 | 424 | 0.94 (t, J = 7.3 Hz, 3 H); 1.42 (m, 2 H); 1.76 (m, 2 H); 2.32 (m, 4 H); 2.66 (s, 3 H); 2.86 (m, 2 H); 3.41 (s, 2 H); 3.56 (m, 4 H); 4.00 (s, 3 H); 4.30 (s, 2 H); 6.02 (s, 2 H); 7.23 (d, J = 8.3 Hz, 2 H); 7.29 (d, J = 8.3 Hz, 2 H) |
| 45 | 1.12 | 350 | 0.94 (t, J = 7.4 Hz, 3 H); 1.42 (m, 2 H); 1.76 (m, 2 H); 2.71 (s, 3 H); 2.86 (m, 2 H); 4.00 (s, 3 H); 4.45 (s, 2 H); 6.03 (s, 2 H); 7.55 (d, J = 8.5 Hz, 2 H); 7.76 (d, J = 8.5 Hz, 2 H) |
| 46 | 0.73 | 354 | 0.94 (t, J = 7.5 Hz, 3 H); 1.42 (m, 2 H); 1.76 (m, 2 H); 2.09 (m, 2 H); 2.66 (s, 3 H); 2.85 (m, 2 H); 3.66 (s, 2 H); 4.00 (s, 3 H); 4.29 (s, 2 H); 6.00 (s, 2 H); 7.14 to 7.30 (m, 4 H) |
| 47 | 0.72 | 426 | 0.94 (t, J = 7.4 Hz, 3 H); 1.41 (m, 2 H); 1.75 (m, 2 H); 2.12 (s, 3 H); 2.50 (m hidden, 2 H); 2.66 (s, 3 H); 2.85 (m, 2 H); 3.21 (s, 3 H); 3.43 (t, J = 6.0 Hz, 2 H); 3.45 (s, 2 H); 4.00 (s, 3 H); 4.30 (s, 2 H); 6.01 (s, 2 H); 7.21 (d, J = 8.2 Hz, 2 H); 7.28 (d, J = 8.2 Hz, 2 H) |
| 48 | 1.15 | 356 | 0.85 (t, J = 7.4 Hz, 3 H); 1.29 (t, J = 7.0 Hz, 3 H); 1.33 (m, 2 H); 1.62 (m, 2 H); 2.81 (m, 2 H); 3.71 (s, 3 H); 4.41 (q, J = 7.0 Hz, 2 H); 5.52 (s, 2 H); 6.00 (s, 2 H); 6.90 (d, J = 8.9 Hz, 2 H); 7.08 (d, J = 8.9 Hz, 2 H) |
| 49 | 1.09 | 385 | 0.86 (t, J = 7.4 Hz, 3 H); 1.34 (m, 2 H); 1.65 (m, 2 H); 2.84 (m, 2 H); 3.19 (s, 3 H); 3.43 (s, 4 H); 3.71 (s, 3 H); 5.33 (m, 1 H); 5.55 (s, 2 H); 5.99 (s broad, 2 H); 6.90 (d, J = 8.8 Hz, 2 H); 7.00 (d, J = 8.8 Hz, 2 H) |
| 50 | 1.09 | 342 | 0.84 (t, J = 7.5 Hz, 3 H); 1.32 (m, 2 H); 1.61 (m, 2 H); 2.78 (m, 2 H); 3.71 (s, 3 H); 3.98 (s, 3 H); 5.51 (s, 2 H); 5.97 (s, 2 H); 6.90 (d, J = 8.9 Hz, 2 H); 7.06 (d, J = 8.9 Hz, 2 H) |
| 51 | 1.40 | 394 | 0.87 (t, J = 7.4 Hz, 3 H); 1.05 to 1.21 (m, 3 H); 1.37 (m, 2 H); 1.42 to 1.76 (m, 9 H); 2.80 to 2.89 (m, 3H); 3.70 (s, 3 H); 5.51 (s, 2 H); 6.17 (s, 2 H); 6.83 (d, J = 8.9 Hz, 2 H); 6.91 (d, J = 8.9 Hz, 2 H) |
| 52 | 1.29 | 418 | 0.85 (t, J = 7.4 Hz, 3 H); 1.32 (m, 2 H); 1.63 (m, 2 H); 2.81 (m, 2 H); 3.71 (s, 3 H); 5.46 (s, 2 H); 5.52 (s, 2 H); 6.01 (s, 2 H); 6.86 (d, J = 8.8 Hz, 2 H); 6.98 (d, J = 8.8 Hz, 2 H); 7.31 (m, 5 H) |
| 53 | 1.07 | 341 | 0.84 (t, J = 7.5 Hz, 3 H); 1.32 (m, 2 H); 1.62 (m, 2 H); 2.78 (m, 2 H); 2.80 (d, J = 4.5 Hz, 3 H); 3.70 (s, 3 H); 5.59 (s, 2 H); 5.64 (m, 1 H); 5.86 (m broad, 2 H); 6.88 (d, J = 8.9 Hz, 2 H); 6.97 (d, J = 8.9 Hz, 2 H) |
| 54 | 1.17 | 398 | 0.84 (t, J = 7.5 Hz, 3 H); 1.32 (m, 2 H); 1.61 (m, 2 H); 1.97 (m, 1 H); 2.16 (m, 1 H); 2.81 (m, 2 H); 3.64 to 3.78 (m, 6 H); 3.92 (dd, J = 4.7 & 10.4 Hz, 1 H); 5.50 (s, 2 H); 5.64 (m, 1 H); 6.02 (s, 2 H); 6.87 (d, J = 8.9 Hz, 2 H); 7.06 (d, J = 8.9 Hz, 2 H) |
| 55 | 1.29 | 378 | 0.85 (t, J = 7.4 Hz, 3 H); 1.34 (m, 2 H); 1.67 (m, 2 H); 2.84 (m, 2 H); 3.67 (s, 3 H); 5.31 (s, 2 H); 6.58 (dd, J = 1.9 & 3.4 Hz, 1 H); 6.65 (m, 1 H); 6.67 (d, J = 8.8 Hz, 2 H); 6.72 (s, 2 H); 6.77 (d, J = 8.8 Hz, 2 H); 7.75 (d, J = 1.9 Hz, 1 H) |
| 56 | 1.15 | 398 | 0.84 (t, J = 7.5 Hz, 3 H); 1.32 (m, 2 H); 1.62 (m, 2 H); 1.91 (m, 1 H); 2.16 (m, 1 H); 2.81 (m, 2 H); 2.64 to 2.78 (m, 6 H); 3.92 (dd, J = 4.7 & 10.3 Hz, 1 H); 5.50 (s, 2 H); 5.64 (m, 1 H); 5.99 (s broad, 2 H); 6.89 (d, J = 8.9 Hz, 2 H); 7.06 (d, J = 8.9 Hz, 2 H) |

TABLE 2-continued

| Compound Number | RT | MS | $^1$H NMR |
|---|---|---|---|
| 57 | 1.17 | 412 | 0.84 (t, J = 7.5 Hz, 3 H); 1.32 (m, 2 H); 1.54 to 1.67 (m, 4 H); 1.97 (m, 2 H); 2.80 (m, 2 H); 3.47 (m, 2 H); 3.68 (m, 2 H); 3.71 (s, 3 H); 5.33 (m, 1 H); 5.55 (s, 2 H); 5.92 (s, 2 H); 6.89 (d, J = 8.8 Hz, 2 H); 7.03 (d, J = 8.8 Hz, 2 H) |
| 58 | 1.25 | 414 | 0.84 (t, J = 7.4 Hz, 3 H); 1.33 (m, 2 H); 1.62 (m, 2 H); 1.97 (m, 1 H); 2.28 (m, 1 H); 2.71 to 2.89 (m, 4 H); 2.96 (ddd, J = 1.7-2.3 & 12.1 Hz, 1 H); 3.17 (dd, J = 4.7 & 12.1 Hz, 1 H); 3.71 (s, 3 H); 5.50 (s, 2 H); 5.87 (m, 1 H); 5.98 (s broad, 2 H); 6.88 (d, J = 8.8 Hz, 2 H); 7.07 (d, J = 8.8 Hz, 2 H) |
| 59 | 1.33 | 382 | 0;86 (t, J = 7; 4 Hz, 3 H); 1.35 (m, 2 H); 1.68 (m, 2 H); 1.85 (m, 1 H); 2.17 (m, 1 H); 2.85 (m, 2 H); 3.66 to 3.74 (m, 7 H); 3.82 (dt, J = 5.9 to 8.0 Hz, 1 H); 5.54 (d, J = 18.0 Hz, 1 H); 5.60 (d, J = 18.0 Hz, 1 H); 6.30 (s, 2 H); 6.83 (d, J = 9.0 Hz, 2 H); 6.91 (d, J = 9.0 Hz, 2 H) |
| 60 | 1.21 | 366 | 0.85 (t, J = 7.4 Hz, 3 H); 1.34 (m, 2 H); 1.56 (d, J = 1.2 Hz, 3 H); 1.66 (m, 2 H); 1.77 (d, J = 1.2 Hz, 3 H); 2.82 (m, 2 H); 3.70 (s, 3 H); 5.46 (s, 2 H); 6.24 (m, 1 H); 6.33 (s, 2 H); 6.82 (d, J = 8.8 Hz, 2 H); 6.89 (d, J = 8.8 Hz, 2 H) |
| 61 | 1.33 | 368 | 0.80 (d, J = 6.6 Hz, 6 H); 0.85 (t, J = 7.5 Hz, 3 H); 1.35 (m, 2 H); 1.67 (m, 2 H); 1.95 (m, 1 H); 2.64 (d, J = 7.3 Hz, 2 H); 2.81 (m, 2 H); 3.70 (s, 3 H); 5.49 (s, 2 H); 6.21 (s, 2 H); 6.80 (d, J = 8.9 Hz, 2 H); 6.90 (d, J = 8.9 Hz, 2 H) |
| 62 | 1.23 | 394 | 0.84 (t, J = 7.4 Hz, 3 H); 1.33 (m, 2 H); 1.66 (m, 2 H); 2.78 (m, 2 H); 3.68 (s, 3 H); 5.15 (s, 2 H); 6.51 (s, 2 H); 6.54 (d, J = 8.9 Hz, 2 H); 6.75 (d, J = 8.9 Hz, 2 H); 7.13 (dd, J = 1.,4 et 3.0 Hz, 1 H); 7.54 (dd, J = 1.4 & 4.9 Hz, 1 H); 7.57 (dd, J = 3.0 & 4.9 Hz, 1 H) |
| 63 | 1.26 | 394 | 0.85 (t, J = 7.4 Hz, 3 H); 1.34 (m, 2 H); 1.67 (m, 2 H); 2.79 (m, 2 H); 3.67 (s, 3 H); 5.25 (s, 2 H); 6.57 (d, J = 8.8 Hz, 2 H); 6.66 (s, 2 H); 6.76 (d, J = 8.8 Hz, 2 H); 7.09 (dd, J = 3.5 et 5.2 Hz, 1 H); 7.15 (dd, J = 1.3 et 3.5 Hz, 1 H); 7.62 (dd, J = 1.3 & 5.2 Hz, 1 H) |
| 64 | 1.23 | 377 | 0.84 (t, J = 7.5 Hz, 3 H); 1.33 (m, 2 H); 1.65 (m, 2 H); 2.76 (m, 2 H); 3.68 (s, 3 H); 5.34 (s, 2 H); 6.09 (td, J = 2.4 et 3.1 Hz, 1 H); 6.18 (m, 1 H); 6.60 (m broad, 2 H); 6.69 (d, J = 8.5 Hz, 2 H); 6.79 (d, J = 8.9 Hz, 2 H); 6.86 (m, 1 H); 11.36 (m, 1 H) |
| 65 | 1.04 | 430 | 0.83 (t, J = 7.4 Hz, 3 H); 1.32 (m, 2 H); 1.61 (m, 2 H); 2.31 to 2.38 (m, 1 H); 2.53 to 2.63 (m, 2 H); 2.81 (m, 3 H); 2.99 to 3.07 (m, 1 H); 3.38 to 3.45 (m, 1 H); 3.71 (s, 3 H); 5.44 (s, 2 H); 6.00 (s, 2 H); 6.03 (m, 1 H); 6.89 (d, J = 8.9 Hz, 2 H); 6.94 (d, J = 8.9 Hz, 2 H) |
| 66 | 1.32 | 392 | 0.85 (t, J = 7.4 Hz, 3 H); 1.35 (m, 2 H); 1.53 (m, 4 H); 1.68 (m, 2 H); 2.01 (m, 4 H); 2.81 (m, 2 H); 3.69 (s, 3 H); 5.44 (s, 2 H); 5.55 (m, 1 H); 6.34 (s, 2 H); 6.69 (d, J = 8.9 Hz, 2 H); 6.86 (d, J = 8.9 Hz, 2 H) |
| 67 | 1.20 | 378 | 0.84 (t, J = 7.4 Hz, 3 H); 1.32 (m, 2 H); 1.65 (m, 2 H); 2.77 (m, 2 H); 3.68 (s, 3 H); 5.27 (s, 2 H); 6.52 (s, 2 H); 6.58 (dd, J = 0.9 & 1.8 Hz, 1 H); 6.64 (d, J = 8.9 Hz, 2 H); 6.80 (d, J = 8.9 Hz, 2 H); 7.71 (t, J = 1.8 Hz, 1 H); 7.74 (dd, J = 0.9 & 1.8 Hz, 1 H) |
| 68 | 2.59 | 446 | 0.85 (t, J = 7.5 Hz, 3 H); 1.33 (m, 2 H); 1.62 (m, 2 H); 2.38 to 2.47 (m, 1 H); 2.52 to 2.59 (m, 1H); 2.83 (m, 2 H); 3.01 to 3.13 (m, 1 H); 3.18 to 3.27 (m, 2 H); 3.53 to 3.58 (m, 1 H); 3.71 (s, 3 H); 5.53 (s, 2 H); 5.88 (m, 1 H); 6.19 (s broad, 2 H); 6.89 (d, J = 8.8 Hz, 2 H); 7.05 (d, J = 8.8 Hz, 2 H) |
| 69 | 1.03 | 430 | 0.85 (t, J = 7.4 Hz, 3 H); 1.33 (m, 2 H); 1.62 (m, 2 H); 2.28 to 2.38 (m, 1 H); 2.52 to 2.61 (m, 1 H); 2.76 to 2.85 (m, 3 H); 2.88 to 2.95 (m, 1 H); 3.14 to 3.22 (m partially hidden, 2 H); 3.71 (s, 3 H); 5.55 (s, 2 H); 5.89 (m, 1 H); 5.99 (s, 2 H); 6.88 (d, J = 8.8 Hz, 2 H); 7.09 (d, J = 8.8 Hz, 2 H) |
| 70 | 1.27 | 391 | 0.85 (t, J = 7.4 Hz, 3 H); 1.35 (m, 2 H); 1.69 (m, 2 H); 2.89 (m, 2 H); 3.17 (s, 3 H); 3.69 (s, 3 H); 5.24 (s, 2 H); 6.15 (dd, J = 2.5 & 3.6 Hz, 1 H); 6.38 (dd, J = 2.5 & 3.6 Hz, 1 H); 6.57 (d, J = 8.7 Hz, 2 H); 6.78 (d, J = 8.7 Hz, 2 H); 6.91 (t, J = 2.5 Hz, 1 H); 8.90 (m broad, 2 H); 14.80 (m broad, 1 H) |
| 71 | 1.12 | 355 | 0.83 (t, J = 7.4 Hz, 3 H); 1.31 (m, 2 H); 1.61 (m, 2 H); 2.69 (m, 2 H); 2.71 (s, 6 H); 3.69 (s, 3 H); 5.63 (s, 2 H); 6.09 (s, 2 H); 6.87 (d, J = 8.9 Hz, 2 H); 6.95 (d, J = 8.9 Hz, 2 H) |
| 72 | 1.25 | 404 | 0.86 (t, J = 7.4 Hz, 3 H); 1.34 (m, 2 H); 1.65 (m, 2 H); 2.85 (m, 2 H); 3.70 (s, 3 H); 5.52 (s, 2 H); 6.26 (s, 2 H); 6.87 (d, J = 8.8 Hz, 2 H); 7.02 to 7.07 (m, 4 H); 7.15 (tt, J = 1.2 & 7.4 Hz, 1 H); 7.35 (m, 2 H) |
| 73 | 1.11 | 380 | .87 (t, J = 7 Hz, 3 H), 1.37 (sxt, J = 7 Hz, 2 H), 1.70 (quin, J = 8 Hz, 2 H), 2.86 (t, J = 8 Hz, 2 H), 3.69 (s, 3 H), 4.54 (m, 2 H), 4.71 (br t, J = 4 Hz, 2 H), 5.47 (s, 2 H), 6.00 (s, 1 H), 6.57 (s, 2 H), 6.73 (d, J = 9 Hz, 2 H), 6.86 (d, J = 9 Hz, 2 H) |

TABLE 2-continued

| Compound Number | RT | MS | $^1$H NMR |
|---|---|---|---|
| 74 | 1.02 | 341 | 0.85 (t, J = 7.4 Hz, 3 H); 1.16 (d, J = 6.2 Hz, 6 H); 1.33 (m, 2 H); 1.65 (m, 2 H); 2.87 (m, 2 H); 5.29 (sept, J = 6.2 Hz, 1 H); 5.62 (s, 2 H); 5.99 (s, 2 H); 7.33 to 7.40 (m, 2 H); 8.41 (s broad, 1 H); 8.49 (dd, J = 2.0 & 4.5 Hz, 1 H) |
| 75 | 1.12 | 341 | 0.85 (t, J = 7.5 Hz, 3 H); 1.10 (d, J = 6.2 Hz, 6 H); 1.34 (m, 2 H); 1.67 (m, 2 H); 2.88 (m, 2 H); 5.22 (sept, J = 6.2 Hz, 1 H); 5.65 (s, 2 H); 6.02 (s, 2 H); 7.17 (td, J = 1.0 & 7.7 Hz, 1 H); 7.29 (ddd, J = 1.0-4.9 & 7.7 Hz, 1 H); 7.79 (dt, J = 1.8 & 7.7 Hz, 1 H); 8.44 (ddd, J = 1.0-1.8 & 4.9 Hz, 1 H) |
| 76 | 0.89 | 341 | 0.85 (t, J = 7.5 Hz, 3 H); 1.12 (d, J = 6.2 Hz, 6 H); 1.35 (m, 2 H); 1.67 (m, 2 H); 2.92 (m, 2 H); 5.07 (sept, J = 6.2 Hz, 1 H); 5.72 (s, 2 H); 7.13 (d broad, J = 4.5 Hz, 2 H); 8.56 (d broad, J = 4.5 Hz, 2 H); 8.73 (s broad, 2 H); 13.95 (s broad, 1 H) |
| 77 | 0.86 | 335 | 0.93 (t, J = 7.4 Hz, 3 H); 1.29 to 1.46 (m, 12 H); 1.65 to 1.80 (m, 4 H); 2.57 (t, J = 6.9 Hz, 2 H); 2.85 (m, 2 H); 3.47 (m broad, 2 H); 4.23 (m, 2 H); 5.39 (sept, J = 6.2 Hz, 1 H); 5.85 (s, 2 H) |
| 78 | 0.82 | 361 | 0.93 (t, J = 7.4 Hz, 3 H); 1.13 (m, 2 H); 1.37 (d, J = 6.2 Hz, 6 H); 1.41 (m, 2 H); 1.48 (m, 1 H); 1.57 to 1.69 (m, 4 H); 1.76 (m, 2 H); 2.50 (m partially hidden, 2 H); 2.84 (m, 2 H); 2.96 (m, 2 H); 3.58 (m broad, 2 H); 4.27 (m, 2 H); 5.42 (sept, J = 6.2 Hz, 1 H); 5.85 (s broad, 2 H) |
| 79 | 0.72 | 362 | 0.94 (t, J = 7 Hz, 3 H), 1.36 (d, J = 6 Hz, 6 H), 1.42 (sxt, J = 8 Hz, 2 H), 1.78 (quin, J = 8 Hz, 2 H), 2.39 (m, 4 H), 2.61 (t, J = 7 Hz, 2 H), 2.70 (m, 4 H), 2.87 (t, J = 8 Hz, 2 H), 4.33 (t, J = 7 Hz, 2 H), 5.40 (quin, J = 6 Hz, 1 H), 5.87 (s, 2 H) |
| 80 | 2.30 | 340 | 0.83 (t, J = 7 Hz, 3 H), 1.20 (d, J = 6 Hz, 6 H), 1.33 (sxt, J = 8 Hz, 2 H), 1.63 (quin, J = 8 Hz, 2 H), 2.90 (t, J = 8 Hz, 2 H), 5.16 (spt, J = 6 Hz, 1 H), 5.66 (s, 2 H), 7.11 (d, J = 7 Hz, 2 H), 7.28-7.39 (m, 3 H), 8.30 (br s, 2 H), 13.82 (br s, 1 H) |
| 81 | 2.56 | 346 | 0.93 (t, J = 7 Hz, 3 H), 1.00-1.21 (m, 5 H), 1.32-1.54 (m, 11 H), 1.57-1.85 (m, 5 H), 2.88 (t, J = 8 Hz, 2 H), 4.14 (d, J = 7 Hz, 2 H), 5.31 (spt, J = 6 Hz, 1 H), 7.27 (br s, 2 H), 13.63 (s, 1 H) |
| 82 | 1.44 | 453 | 0.85 (t, J = 7 Hz, 3 H), 1.22 (d, J = 6 Hz, 6 H), 1.34 (m, 2 H), 1.66 (m, 4 H), 2.00 (br d, J = 10 Hz, 2 H), 2.88 (t, J = 8 Hz, 2 H), 3.12-3.30 (m, 3 H), 3.91 (dd, J = 11, 4 Hz, 2 H), 4.14 (t, 6 Hz, 2 H), 5.14 (quin, J = 6 Hz, 1 H), 5.69 (s, 2 H), 7.19 (d, J = 8 Hz, 2 H), 7.58 (d, J = 8 Hz, 2 H), 8.64 (br s, 2 H), 9.38 (br s, 2 H), 13.91 (br, s, 1 H) |
| 83 | 1.46 | 411 | 0.84 (t, J = 7 Hz, 3 H), 1.17-1.36 (m, 14 H), 1.65 (m, 2 H), 2.87 (t, J = 7 Hz, 2 H), 3.15 (m, 1 H), 4.09 (br s, 2 H), 5.18 (dt, J = 12, 6 Hz, 1 H), 5.67 (s, 2 H), 7.10 (br s, 1 H), 7.18 (d, J = 8 Hz, 2 H), 7.59 (d, J = 8 Hz, 2 H), 8.01 (br s, 1 H), 9.26 (br s, 2 H), 14.07 (br s, 1 H) |
| 84 | 2.43 | 481 | 0.83 (m, 6 H), 1.21 (d, J = 6 Hz, 12 H), 1.32 (sxt, J = 6 Hz, 2 H), 1.48 (t, J = 7 Hz, 2 H), 1.62 (quin, J = 8 Hz, 2 H), 2.09 (t, J = 7 Hz, 2 H), 2.79 (t, J = 8 Hz, 2 H), 4.20 (d, J = 6 Hz, 2 H), 5.32 (spt, J = 6 Hz, 1 H), 5.55 (s, 2 H), 5.94 (s, 2 H), 7.02 (d, J = 8 Hz, 2 H), 7.19 (d, J = 8 Hz, 2 H), 8.27 (t, J = 6 Hz, 1 H) |
| 85 | 1.97 | 381 | 0.94 (t, J = 7.4 Hz, 3 H); 1.44 (m, 2 H); 1.78 (m, 2 H); 2.02 (m, 1 H); 2.38 (m, 1 H); 2.93 (m, 2 H); 3.39 to 3.56 (m, 3 H); 3.70 (m, 1 H); 3.77 (m, 1 H); 3.99 (s, 3 H); 4.47 (d, J = 5.6 Hz, 2 H); 5.14 (t, J = 5.6 Hz, 1 H); 7.27 (d, J = 8.5 Hz, 2 H); 7.31 (d, J = 8.5 Hz, 2 H); 8.30 (s broad, 2 H); 13.83 (s broad, 1 H) |
| 86 | 0.65 | 264 | 0.94 (t, J = 7.3 Hz, 3 H); 1.35 to 1.49 (m, 8 H); 1.76 (m, 2 H); 2.93 (m, 2H); 3.95 (s, 3 H); 5.22 (sept, J = 6.2 Hz, 1 H); 8.50 (s, 2 H); 13.73 (s broad, 1 H) |
| 87 | 0.46 | 340 | 0.94 (t, J = 7.40 Hz, 3 H); 1.41 (sxt, J = 7.44, 2 H); 1.73 (quin, J = 7.53 Hz, 2 H); 2.87 (t, J = 7.87 Hz, 2 H); 3.87 (s, 2 H); 3.99 (s, 3 H); 4.54 (s, 2 H); 6.32 (br s, 2 H); 7.33 (d, J = 8.22 Hz, 2 H); 7.41 (d, J = 8.22 Hz, 2 H) |
| 88 | 0.92 | 263 | 0.93 (t, J = 7.4 Hz, 3 H); 1.22 (d, J = 6.4 Hz, 6 H); 1.40 (m, 2 H); 1.71 (m, 2 H); 2.86 (t, J = 7.6 Hz, 2 H); 3.93 (s, 3 H); 4.08 (m, 1 H); 5.27 (d, J = 6.4 Hz, 1 H); 5.98 (s broad, 2 H) |
| 89 | 1.26 | 351 | .94 (t, J = 7.5 Hz, 3 H); 1.43 (m, 2 H); 1.76 (m, 2 H); 2.01 (m, 1 H); 2.42 (m, 1 H); 2.86 (m, 2 H); 3.34 (dd, J = 8.6 et 10.0 Hz, 1 H); 3.45 to 3.62 (m, 3 H); 3.73 (dd, J = 7.6 et 10.0 Hz, 1 H); 3.96 (s, 3 H); 6.03 (s broad, 2 H); 7.22 (tt, J = 1.9 et 7.2 Hz, 1 H); 7.31 to 7.39 (m, 4 H) |
| 90 | 1.22 | 325 | 0.94 (t, J = 7.4 Hz, 3 H); 1.42 (m, 2 H); 1.76 (m, 2 H); 2.76 (s, 3 H); 2.86 (m, 2 H); 4.01 (s, 3 H); 4.33 (s, 2 H); 6.01 (s, 2 H); 7.20 to 7.36 (m, 5 H) |
| 91 | 0.49 | 423 | 0.93 (t, J = 7 Hz, 3 H), 1.41 (sxt, J = 7 Hz, 2 H), 1.73 (quin, J = 8 Hz, 2 H), 2.14 (s, 3 H), 2.26-2.35 (m, 4 H), 2.51-2.53 (m, 4 H), 2.88 (t, J = 8 Hz, 2 H), 3.41 (m, 2 H), 3.99 (s, 3 H), 4.53 (s, 2 H), 6.34 (br s, 1 H), 6.42 (br s, 1 H), 7.21 (d, J = 1 Hz, 2 H), 7.36 (d, J = 1 Hz, 2 H), 8.20 (s, 2 H) |

TABLE 2-continued

| Compound Number | RT | MS | $^1$H NMR |
|---|---|---|---|
| 92 | 1.26 | 388 | 0.85 (t, J = 7 Hz, 3 H), 1.34 (sxt, J = 7 Hz, 2 H), 1.68 (quin, J = 8 Hz, 2 H), 2.78 (t, J = 8 Hz, 2 H), 3.66 (s, 3 H), 5.08 (s, 2 H), 6.43 (d, J = 1 Hz, 2 H), 6.52 (s, 2 H), 6.72 (d, J = 1 Hz, 2 H), 7.31-7.45 (m, 5 H) |
| 93 | 1.29 | 328 | 0.82 (t, J = 7 Hz, 3 H), 1.29 (sxt, J = 7 Hz, 2 H), 1.55 (quin, J = 8 Hz, 2 H), 2.72 (t, J = 8 Hz, 2 H), 3.71 (s, 3 H), 5.66 (d, J = 4 Hz, 4 H), 6.90 (d, J = 1 Hz, 2 H), 7.17 (d, J = 1 Hz, 2 H), 11.47 (s, 1 H) |
| 94 | 1.24 | 435 | 0.86 (t, J = 7 Hz, 3 H), 1.35 (sxt, J = 7 Hz, 2 H), 1.65 (quin, J = 8 Hz, 2 H), 1.79 (quin, J = 7 Hz, 2 H), 2.45-2.48 (m, 2 H), 2.83 (t, J = 8 Hz, 2 H), 3.28-3.30 (m, 2 H), 3.68 (s, 3 H), 5.32 (t, J = 5 Hz, 1 H), 5.61 (s, 2 H), 5.63 (br s, 2 H), 6.02 (d, J = 3 Hz, 1 H), 6.33 (m, 1 H), 6.87 (d, J = 9 Hz, 2 H), 6.97 (d, J = 9 Hz, 2 H), 7.48 (s, 1 H) |
| 95 | 1.04 | 312 | 0.86 (t, J = 7 Hz, 3 H), 1.35 (dq, J = 15, 7 Hz, 2 H), 1.66 (quin, J = 8 Hz, 2 H), 2.87 (t, J = 8 Hz, 2 H), 3.72 (s, 3 H), 5.44 (s, 2 H), 6.42 (s, 2 H), 6.91 (d, J = 1 Hz, 2 H), 7.11 (d, J = 1 Hz, 2 H), 8.80 (s, 1 H) |
| 96 | 1.05 | 378 | 0.83 (t, J = 7 Hz, 3 H), 1.32 (sxt, J = 7 Hz, 2 H), 1.64 (quin, J = 8 Hz, 2 H), 2.74 (t, J = 8 Hz, 2 H), 3.68 (s, 3 H), 5.22 (s, 2 H), 6.43 (s, 2 H), 6.63 (d, J = 1 Hz, 2 H), 6.80 (d, J = 1 Hz, 2 H), 7.53 (br s, 1 H), 7.78 (br s, 1 H), 12.97 (br s, 1 H) |
| 97 | 1.08 | 392 | 0.84 (t, J = 7 Hz, 3 H), 1.33 (sxt, J = 7 Hz, 2 H), 1.66 (quin, J = 8 Hz, 2 H), 2.78 (t, J = 7 Hz, 2 H), 3.69 (s, 3 H), 3.82 (s, 3 H), 5.24 (s, 2 H), 6.44 (s, 2 H), 6.58 (d, J = 1 Hz, 2 H), 6.80 (d, J = 1 Hz, 2 H), 7.43 (s, 1 H), 7.63 (s, 1 H) |
| 98 | 0.90 | 249 | 0.90 (t, J = 7 Hz, 3 H), 1.20 (d, J = 6 Hz, 6 H), 1.33 (sxt, J = 7 Hz, 2 H), 1.71 (quin, J = 7 Hz, 2 H), 2.76 (t, J = 8 Hz, 2 H), 4.05 (dq, J = 13, 6 Hz, 1 H), 6.05 (s, 1 H), 6.59 (s, 2 H), 12.20 (br s, 1 H) |
| 99 | 0.93 | 266 | 0.91 (t, J = 7 Hz, 3 H), 1.18-1.48 (m, 8 H), 1.73 (quin, J = 7 Hz, 2 H), 2.84 (m, 2 H), 3.68-4.33 (m, 1 H), 5.91-6.51 (m, 2 H), 12.25-13.06 (m, 1 H) |
| 100 | 1.39 | 439 | 0.84 (t, J = 7 Hz, 3 H), 1.22 (d, J = 6 Hz, 6 H), 1.27-1.46 (m, 2 H), 1.65 (quin, J = 8 Hz, 2 H), 1.99-2.12 (m, 2 H), 2.39-2.45 (m, 2 H), 2.88 (t, J = 8 Hz, 2 H), 3.65 (m, 1 H), 4.02 (m, 2 H), 4.36 (m, 1 H), 5.14 (spt, J = 6 Hz, 1 H), 5.25 (m, 1 H), 5.69 (s, 2 H), 7.18 (d, J = 8 Hz, 2 H), 7.52 (d, J = 8 Hz, 2 H), 8.62 (br s, 2 H), 9.52 (m, 2 H), 13.93 (br s, 1 H) |
| 101 | 0.79 | 423 | 0.82 (t, J = 7 Hz, 3 H), 1.18 (d, J = 6 Hz, 6 H), 1.23-1.38 (m, 2 H), 1.56-1.70 (m, 6 H), 2.27-2.41 (m, 4 H), 2.82 (t, J = 8 Hz, 2 H), 3.51 (s, 2 H), 5.31 (spt, J = 6 Hz, 1 H), 5.56 (s, 2 H), 5.95 (s, 2 H), 7.00 (d, J = 8 Hz, 2 H), 7.26 (d, J = 8 Hz, 2 H) |
| 102 | 0.78 | 439 | 0.82 (t, J = 7 Hz, 3 H), 1.18 (d, J = 6 Hz, 6 H), 1.23-1.39 (m, 2 H), 1.53-1.66 (m, 2 H), 2.20-2.33 (m, 4 H), 2.70-2.94 (m, 2 H), 3.41 (s, 2 H), 3.47-3.60 (m, 4 H), 5.31 (m, 1 H), 5.56 (s, 2 H), 5.99 (s, 2 H), 7.02 (d, J = 8 Hz, 2 H), 7.26 (d, J = 8 Hz, 2 H) |
| 103 | 1.09 | 425 | 0.85 (t, J = 7 Hz, 3 H), 1.00 (t, J = 8 Hz, 3 H), 1.21 (d, J = 6 Hz, 6 H), 1.26-1.39 (m, 2 H), 1.59-1.68 (m, 2 H), 2.11 (q, J = 8 Hz, 2 H), 2.76-2.83 (m, 2 H), 4.21 (d, J = 6 Hz, 2 H), 5.32 (spt, J = 6 Hz, 1 H), 5.55 (s, 2 H), 5.95 (s, 2 H), 7.03 (m, J = 8 Hz, 2 H), 7.20 (m, J = 8 Hz, 2 H), 8.24 (t, J = 6 Hz, 1 H) |
| 104 | 0.80 | 427 | 1H NMR (400 MHz, DMSO-d6) δ ppm 0.83 (t, J = 7 Hz, 3 H), 1.20 (d, J = 6 Hz, 6 H), 1.24-1.41 (m, 2 H), 1.55-1.67 (m, 2 H), 2.59 (t, J = 6 Hz, 2 H), 2.75-2.86 (m, 2 H), 3.20 (s, 3 H), 3.33-3.41 (m partially hidden, 2 H), 3.67 (s, 2 H), 5.32 (spt, J = 6 Hz, 1 H), 5.55 (s, 2 H), 5.93 (s, 2 H), 7.01 (d, J = 8 Hz, 2 H), 7.27 (d, J = 8 Hz, 2 H) |
| 105 | 1.01 | 647 | 0.84 (t, J = 7 Hz, 3 H), 1.21 (d, J = 6 Hz, 6 H), 1.26-1.38 (m, 2 H), 1.63 (t, J = 8 Hz, 2 H), 2.59 (t, J = 6 Hz, 2 H), 2.70-2.90 (m, 2 H), 3.22-3.25 (m, 3 H), 3.39-3.55 (m, 22 H), 3.67 (s, 2 H), 5.78 (m, 1 H), 5.56 (s, 2 H), 5.90 (s, 2 H), 7.02 (d, J = 8 Hz, 2 H), 7.28 (d, J = 8 Hz, 2 H) |
| 106 | 2.71 | 473 | 0.83 (t, J = 7 Hz, 3 H), 1.20 (d, J = 6 Hz, 6 H), 1.24-1.38 (m, 2 H), 1.56-1.69 (m, 2 H), 2.70-2.88 (m, 2 H), 4.43 (d, J = 6 Hz, 2 H), 5.31 (spt, J = 6 Hz, 1 H), 5.55 (s, 2 H), 5.95 (s, 2 H), 7.04 (d, J = 8 Hz, 2 H), 7.28 (d, J = 8 Hz, 2 H), 7.43-7.48 (m, 2 H), 7.52 (m, 1 H), 7.83-7.88 (m, 2 H), 9.00 (t, J = 6 Hz, 1 H) |
| 107 | 1.08 | 455 | 0.84 (t, J = 7 Hz, 3 H), 1.21 (d, J = 6 Hz, 6 H), 1.27-1.37 (m, 2 H), 1.59-1.67 (m, 2 H), 2.33 (m, 2 H), 2.79 (m, 2 H), 3.19 (s, 3 H), 3.52 (t, J = 6 Hz, 2 H), 4.22 (d, J = 6 Hz, 2 H), 5.32 (spt, J = 6 Hz, 1 H), 5.55 (s, 2 H), 5.99 (br s, 2 H), 7.03 (d, J = 8 Hz, 2 H), 7.20 (d, J = 8 Hz, 2 H), 8.33 (t, J = 6 Hz, 1 H) |
| 108 | 0.83 | 471 | 0.83 (t, J = 7 Hz, 3 H), 1.20 (d, J = 6 Hz, 6 H), 1.25-1.38 (m, 2 H), 1.56-1.67 (m, 2 H), 2.61 (m, 2 H), 2.80 (m, 2 H), 3.21 (s, 3 H), 3.38-3.49 (m, 6 H), 3.70 (s, 2 H), 5.31 (spt, J = 6 Hz, 1 H), 5.56 (s, 2 H), 5.94 (s, 2 H), 7.02 (d, J = 8 Hz, 2 H), 7.29 (d, J = 8 Hz, 2 H) |

TABLE 2-continued

| Compound Number | RT | MS | $^1$H NMR |
|---|---|---|---|
| 109 | 0.97 | 453 | 0.83 (t, J = 7 Hz, 6 H), 1.11-1.44 (m, 16 H), 1.61 (m, 2 H), 2.41 (m, 2 H), 2.80 (m, 2 H), 3.65 (s, 2 H), 5.31 (spt, J = 6 Hz, 1 H), 5.55 (s, 2 H), 5.94 (s, 2 H), 7.01 (d, J = 8 Hz, 2 H), 7.28 (d, J = 8 Hz, 2 H) |
| 110 | 1.20 | 509 | 0.77-0.91 (m, 6 H), 1.16-1.39 (m, 24 H), 1.61 (quin, J = 8 Hz, 2 H), 2.40 (m, 2 H), 2.81 (t, J = 8 Hz, 2 H), 3.64 (s, 2 H), 5.32 (m, 1 H), 5.56 (s, 2 H), 5.92 (s, 2 H), 7.01 (m, J = 8 Hz, 2 H), 7.28 (m, J = 8 Hz, 2 H) |
| 111 | 1.21 | 441 | 0.84 (t, J = 7 Hz, 3 H), 1.14 (t, J = 7 Hz, 3 H), 1.20 (d, J = 6 Hz, 6 H), 1.26-1.37 (m, 2 H), 1.62 (m, 2 H), 2.79 (m, 2 H), 3.97 (q, J = 7 Hz, 2 H), 4.12 (d, J = 6 Hz, 2 H), 5.32 (spt, J = 6 Hz, 1 H), 5.55 (s, 2 H), 5.91 (s, 2 H), 7.02 (d, J = 8 Hz, 2 H), 7.20 (d, J = 8 Hz, 2 H), 7.59 (t, J = 6 Hz, 1 H) |
| 112 | 1.32 | 533 | 0.85 (t, J = 7 Hz, 3 H), 1.21 (d, J = 6 Hz, 6 H), 1.27-1.38 (m, 2 H), 1.63 (quin, J = 8 Hz, 2 H), 2.80 (t, J = 8 Hz, 2 H), 3.74 (s, 3 H), 4.15 (br d, J = 6 Hz, 2 H), 4.94 (s, 2 H), 5.32 (spt, J = 6 Hz, 1 H), 5.56 (s, 2 H), 5.96 (br s, 2 H), 6.90 (d, J = 8 Hz, 2 H), 7.03 (d, J = 8 Hz, 2 H), 7.21 (d, J = 8 Hz, 2 H), 7.28 (d, J = 8 Hz, 2 H), 7.71 (br t, J = 6 Hz, 1 H) |
| 113 | 1.07 | 440 | 0.84 (t, J = 7 Hz, 4 H), 0.97 (t, J = 7 Hz, 3 H), 1.21 (d, J = 6 Hz, 6 H), 1.32 (m, 2 H), 1.63 (quin, J = 8 Hz, 2 H), 2.79 (m, 2 H), 3.00 (m, 2 H), 4.15 (d, J = 6 Hz, 2 H), 5.32 (spt, J = 6 Hz, 1 H), 5.55 (s, 2 H), 5.84 (t, J = 6 Hz, 1 H), 5.94 (s, 2 H), 6.24 (t, J = 6 Hz, 1 H), 7.02 (d, J = 8 Hz, 2 H), 7.19 (d, J = 8 Hz, 2 H) |
| 114 | 1.19 | 560 | 0.84 (t, J = 7 Hz, 3 H), 1.20 (d, J = 6 Hz, 6 H), 1.27-1.37 (m, 2 H), 1.59-1.67 (m, 2 H), 2.03 (s, 3 H), 2.79 (m, 2 H), 4.14 (d, J = 6 Hz, 2 H), 4.93 (s, 2 H), 5.31 (spt, J = 6 Hz, 1 H), 5.55 (s, 2 H), 5.91 (s, 2 H), 7.02 (d, J = 8 Hz, 2 H), 7.21 (d, J = 8 Hz, 2 H), 7.25 (d, J = 8 Hz, 2 H), 7.54 (d, J = 9 Hz, 2 H), 7.73 (t, J = 6 Hz, 1 H), 9.94 (s, 1 H) |
| 115 | 1.07 | 447 | 0.85 (t, J = 7 Hz, 3 H), 1.21 (d, J = 6 Hz, 6 H), 1.28-1.38 (m, 2 H), 1.64 (quin, J = 8 Hz, 2 H), 2.73-2.87 (m, 5 H), 4.12 (d, J = 6 Hz, 2 H), 5.32 (spt, J = 6 Hz, 1 H), 5.58 (s, 2 H), 5.93 (s, 2 H), 7.06 (d, J = 8 Hz, 2 H), 7.31 (d, J = 8 Hz, 2 H), 7.52 (t, J = 6 Hz, 1 H) |
| 116 | 0.78 | 397 | 0.82 (t, J = 7 Hz, 3 H), 1.17 (d, J = 6 Hz, 6 H), 1.26-1.38 (m, 2 H), 1.51-1.69 (m, 2 H), 2.08 (s, 6 H), 2.73-2.90 (m, 2 H), 3.32 (s hidden, 2 H), 5.30 (spt, J = 6 Hz, 1 H), 5.56 (s, 2 H), 5.92 (s, 2 H), 7.00 (d, J = 8 Hz, 2 H), 7.24 (d, J = 8 Hz, 2 H) |
| 117 | 0.94 | 483 | 0.83 (t, J = 7 Hz, 3 H), 1.19 (d, J = 6 Hz, 6 H), 1.28-1.37 (m, 2 H), 1.38 (s, 9 H), 1.61 (quin, J = 8 Hz, 2 H), 2.77-2.84 (m, 2 H), 3.11 (s, 2 H), 3.65 (s, 2 H), 5.32 (spt, J = 6 Hz, 1 H), 5.55 (s, 2 H), 5.92 (s, 2 H), 7.01 (d, J = 8 Hz, 2 H), 7.26 (d, J = 8 Hz, 2 H) |
| 118 | 0.62 | 383 | 0.83 (t, J = 7 Hz, 3 H), 1.15-1.36 (m, 2 H), 1.20 (d, J = 6 Hz, 6 H), 1.61 (dt, J = 15, 8 Hz, 2 H), 2.20 (s, 3 H), 2.70-2.91 (m, 2 H), 3.58 (s, 2 H), 5.32 (quin, J = 6 Hz, 1 H), 5.55 (s, 2 H), 5.92 (s, 2 H), 7.01 (d, J = 8 Hz, 2 H), 7.26 (d, J = 8 Hz, 2 H) |
| 119 | 1.69 | 497 | 0.83 (t, J = 7 Hz, 3 H), 1.19 (d, J = 6 Hz, 6 H), 1.25-1.34 (m, 2 H), 1.36 (s, 9 H), 1.61 (quin, J = 8 Hz, 2 H), 2.28-2.30 (m, 2 H), 2.61-2.65 (m, 2 H), 2.76-2.84 (m, 2 H), 3.65 (s, 2 H), 5.32 (quin, J = 6 Hz, 1 H), 5.55 (s, 2 H), 5.93 (s, 2 H), 7.01 (d, J = 8 Hz, 2 H), 7.27 (d, J = 8 Hz, 2 H) |
| 120 | 0.87 | 515 | 0.83 (t, J = 7 Hz, 3 H), 1.20 (d, J = 6 Hz, 6 H), 1.25-1.39 (m, 2 H), 1.57-1.66 (m, 2 H), 2.61 (m, 2 H), 2.75-2.86 (m, 2 H), 3.20 (s, 3 H), 3.37-3.52 (m, 10 H), 3.68 (s, 2 H), 5.31 (m, 1 H), 5.55 (s, 2 H), 5.93 (s, 2 H), 7.01 (d, J = 8 Hz, 2 H), 7.28 (d, J = 8 Hz, 2 H) |
| 121 | 0.96 | 559 | 0.85 (br d, J = 7 Hz, 3 H), 1.19 (br d, J = 6 Hz, 6 H), 1.24-1.42 (m, 2 H), 1.64 (br s, 2 H), 2.70-2.92 (m, 4 H), 3.21 (s, 3 H), 3.36-3.65 (m, 14 H), 3.97 (br s, 2 H), 5.11-5.35 (m, 1 H), 5.59 (br s, 2 H), 6.11-6.37 (m, 2 H), 7.07 (d, J = 8 Hz, 2 H), 7.38 (d, J = 8 Hz, 2 H) |
| 122 | 0.76 | 735 | 0.84 (t, J = 7 Hz, 3 H), 1.21 (d, J = 6 Hz, 6 H), 1.28-1.38 (m, 2 H), 1.65 (t, J = 8 Hz, 2 H), 2.88 (t, J = 8 Hz, 2 H), 3.05 (br s, 2 H), 3.22-3.25 (m, 3 H), 3.41-3.58 (m, 28 H), 3.66 (t, J = 5 Hz, 2 H), 4.16 (br s, 2 H), 5.15 (quin, J = 6 Hz, 1 H), 5.68 (s, 2 H), 7.19 (m, J = 8 Hz, 2 H), 7.47 (m, J = 8 Hz, 2 H), 8.43-9.07 (m, 4 H) |
| 123 | 0.81 | 911 | 0.84 (t, J = 7 Hz, 3 H), 1.21 (d, J = 6 Hz, 6 H), 1.28-1.37 (m, 2 H), 1.65 (quin, J = 8 Hz, 2 H), 2.88 (t, J = 8 Hz, 2 H), 3.01-3.11 (m, 2 H), 3.20-3.28 (m, 3 H), 3.40-3.57 (m, 44 H), 3.61-3.71 (m, 2 H), 4.13-4.20 (m, 2 H), 5.14 (quin, J = 6 Hz, 1 H), 5.68 (s, 2 H), 7.19 (br d, J = 8 Hz, 2 H), 7.47 (br d, J = 8 Hz, 2 H), 8.46-9.14 (m, 4 H), 13.75 (br s, 1 H) |
| 124 | 0.77 | 383 | 0.83 (t, J = 7 Hz, 3 H), 1.20 (d, J = 6 Hz, 6 H), 1.26-1.36 (m, 2 H), 1.56-1.66 (m, 2 H), 2.18 (s, 3 H), 2.78-2.86 (m, 2 H), 3.39-3.39 (m, 1 H), 3.57 (s, 2 H), 5.32 (spt, J = 6 Hz, 1 H), 5.56 (s, 2 H), 5.95 (s, 2 H), 6.90 (d, J = 8 Hz, 1 H), 7.08 (s, 1 H), 7.20-7.30 (m, 2 H) |

TABLE 2-continued

| Compound Number | RT | MS | $^1$H NMR |
|---|---|---|---|
| 125 | 0.78 | 397 | 0.82 (t, J = 7 Hz, 3 H), 1.19 (d, J = 6 Hz, 6 H), 1.30 (dq, J = 15, 7 Hz, 2 H), 1.56-1.65 (m, 2 H), 2.07 (s, 6 H), 2.81 (t, J = 8 Hz, 2 H), 3.31 (s partially hidden, 2 H), 5.31 (spt, J = 6 Hz, 1 H), 5.58 (s, 2 H), 5.94 (s, 2 H), 6.94 (d, J = 8 Hz, 1 H), 7.04 (s, 1 H), 7.18 (d, J = 8 Hz, 1 H), 7.28 (t, J = 8 Hz, 1 H) |
| 126 | 0.84 | 423 | 0.86 (t, J = 7 Hz, 3 H), 1.22 (d, J = 6 Hz, 6 H), 1.30-1.40 (m, 2 H), 1.63-1.81 (m, 4 H), 1.98-2.06 (m, 2 H), 2.11-2.21 (m, 2 H), 2.90 (t, J = 8 Hz, 2 H), 3.47-3.54 (m partially hidden, 1 H), 3.96 (br t, J = 6 Hz, 2 H), 5.15 (spt, J = 6 Hz, 1 H), 5.68 (s, 2 H), 7.19-7.25 (m, 2 H), 7.44 (t, J = 8 Hz, 1 H), 7.50 (br d, J = 8 Hz, 1 H), 8.63 (br s, 2 H), 9.53-9.64 (m, 2 H), 13.96 (br s, 1 H) |
| 127 | 0.83 | 409 | 0.57-0.72 (m, 2 H), 0.79-0.92 (m, 5 H), 1.22 (d, J = 6 Hz, 6 H), 1.26-1.43 (m, 2 H), 1.58-1.77 (m, 2 H), 2.40-2.65 (m hidden, 1 H) 2.90 (t, J = 8 Hz, 2 H), 4.13 (m, 2 H), 5.14 (spt, J = 6 Hz, 1 H), 5.67 (s, 2 H), 7.22-7.27 (m, 2 H), 7.43 (t, J = 8 Hz, 1 H), 7.52 (br d, J = 8 Hz, 1 H), 8.63 (br s, 2 H), 9.52-9.68 (m, 2 H), 13.97 (s, 1 H) |
| 128 | 0.81 | 411 | 0.85 (t, J = 7 Hz, 3 H), 1.22 (m, 12 H), 1.28-1.41 (m, 2 H), 1.67 (quin, J = 8 Hz, 2 H), 2.90 (t, J = 8 Hz, 2 H), 3.10 (m, 1 H), 3.80-4.31 (m hidden, 2 H), 5.14 (spt, J = 6 Hz, 1 H), 5.67 (s, 2 H), 7.23 (d, J = 8 Hz, 1 H), 7.29 (s, 1 H), 7.44 (t, J = 8 Hz, 1 H), 7.57 (d, J = 8 Hz, 1 H), 8.64 (br s, 2 H), 9.28-9.42 (m, 2 H), 14.01 (s, 1 H) |
| 129 | 0.99 | 473 | 0.84 (t, J = 7 Hz, 3 H), 1.20 (d, J = 6 Hz, 6 H), 1.24-1.40 (m, 2 H), 1.63 (quin, J = 8 Hz, 2 H), 2.76-2.85 (m, 1 H), 2.91 (m, 1 H), 3.36-3.49 (m, 1 H), 3.58 (d, J = 7 Hz, 2 H), 3.83-3.92 (m, 2 H), 4.14-4.25 (m, 2 H), 5.32 (spt, J = 6 Hz, 1 H), 5.57 (s, 2 H), 5.93 (s, 2 H), 6.90 (d, J = 8 Hz, 1 H), 7.09 (s, 1 H), 7.22-7.31 (m, 2 H) |
| 130 | 0.88 | 437 | 0.86 (t, J = 7 Hz, 3 H), 1.24 (d, J = 6 Hz, 6 H), 1.35 (m, 2 H), 1.49 (s, 3 H), 1.68 (s, 2 H), 1.82 (br s, 4 H), 2.33-2.41 (m, 2 H), 2.89 (t, J = 8 Hz, 2 H), 3.93-4.02 (m, 2 H), 5.16 (m, 1 H), 5.67 (s, 2 H), 7.22 (br d, J = 7 Hz, 1 H), 7.29 (br s, 1 H), 7.45 (t, J = 8 Hz, 1 H), 7.52 (d, J = 7 Hz, 1 H), 8.61 (br s, 2 H), 9.20-9.39 (m, 2 H), 13.81 (s, 1 H) |
| 131 | 0.84 | 438 | 0.83 (t, J = 7 Hz, 3 H), 1.19 (d, J = 6 Hz, 6 H), 1.31 (m, 2 H), 1.62 (m, J = 8, 8 Hz, 2 H), 2.25-2.32 (m partially hidden, 4 H), 2.71-2.78 (m, 4 H), 2.82 (t, J = 8 Hz, 2 H), 3.39 (s, 2 H), 5.31 (m, 1 H), 5.58 (s, 2 H), 5.99 (br s, 2 H), 6.96 (br d, J = 8 Hz, 1 H), 7.04 (s, 1 H), 7.20 (br d, J = 8 Hz, 1 H), 7.29 (t, J = 8 Hz, 1 H), 8.30 (m, 2 H) |
| 132 | 0.77 | 379 | 0.86 (t, J = 7 Hz, 3 H), 0.92 (d, J = 7 Hz, 6 H), 1.30-1.41 (m, 2 H), 1.55-1.99 (m, 4 H), 2.30 (m, 1 H), 2.87 (t, J = 8 Hz, 2 H), 3.67 (s, 2 H), 5.60 (s, 2 H), 6.31-6.56 (m, 4 H), 6.87 (d, J = 8 Hz, 2 H), 7.29 (d, J = 8 Hz, 2 H) |
| 133 | 0.79 | 381 | 0.78 (d, J = 7 Hz, 6 H), 0.85 (t, J = 7 Hz, 3 H), 1.29-1.41 (m, 4 H), 1.47 (m, 1 H), 1.63-1.75 (m, 2 H), 1.76-2.10 (m, 2 H), 2.71-2.86 (m, 4 H), 3.67 (s, 2 H), 5.56 (s, 2 H), 6.21 (s, 2 H), 6.79 (d, J = 8 Hz, 2 H), 7.29 (d, J = 8 Hz, 2 H) |
| 134 | 0.73 | 380 | 0.82 (t, J = 7 Hz, 3 H), 1.30 (sxt, J = 7 Hz, 2 H), 1.64 (quin, J = 8 Hz, 2 H), 1.73-1.92 (m, 6 H), 2.68 (t, J = 8 Hz, 2 H), 3.13 (br t, J = 6 Hz, 4 H), 3.66 (s, 2 H), 5.66 (s, 2 H), 6.08 (s, 2 H), 6.92 (d, J = 8 Hz, 2 H), 7.26 (d, J = 8 Hz, 2 H) |
| 135 | 0.59 | 376 | 0.84 (t, J = 7 Hz, 3 H), 1.25-1.36 (m, 2 H), 1.66 (m, 2 H), 2.62-2.79 (m, 2 H), 3.68 (s, 1 H), 3.97 (s, 2 H), 5.43 (s, 2 H), 6.13-6.17 (m, 1 H), 6.75-6.88 (m, 3 H), 6.92 (br s, 2 H), 7.33 (d, J = 8 Hz, 2 H), 8.04-8.25 (m, 3 H), 11.08 (br s, 1 H) |
| 137 | 0.85 | 385 | 0.64-0.77 (m, 2 H), 0.94 (t, J = 7 Hz, 3 H), 1.04-1.23 (m, 8 H), 1.34-1.51 (m, 4 H), 1.56-1.91 (m, 6 H), 2.32 (d, J = 6 Hz, 2 H), 2.42-2.63 (m partially hidden, 1 H), 2.87 (t, J = 8 Hz, 2 H), 4.17 (br d, J = 7 Hz, 2 H), 6.31 (s, 2 H), 6.60 (dd, J = 15, 6 Hz, 1 H), 6.78 (dd, J = 15, 1 Hz, 1 H) |
| 138 | 0.89 | 387 | 0.70-0.82 (m, 2 H), 0.91-0.99 (m, 9 H), 1.04-1.23 (m, 3 H), 1.35-1.86 (m, 14 H), 2.33 (d, J = 6 Hz, 2 H), 2.88 (t, J = 8 Hz, 2 H), 2.93-3.04 (m, 2 H), 4.11 (d, J = 7 Hz, 2 H), 6.12 (s, 2 H) |
| 139 | 0.80 | 371 | 0.73-0.90 (m, 2 H), 0.94 (t, J = 7 Hz, 3 H), 1.10-1.22 (m, 2 H), 1.13 (d, J = 7 Hz, 6 H), 1.32-1.67 (m, 7 H), 1.68-1.84 (m, 4 H), 2.44 (m, 1 H), 2.57 (m, 1 H), 2.87 (t, J = 8 Hz, 2 H), 4.16 (d, J = 7 Hz, 2 H), 6.31 (s, 2 H), 6.60 (dd, J = 15, 7 Hz, 1 H), 6.78 (dd, J = 15, 1 Hz, 1 H) |
| 140 | 0.84 | 373 | 0.87-1.01 (m, 11 H), 1.04-1.25 (m, 2 H), 1.34-1.50 (m, 4 H), 1.55-1.82 (m, 8 H), 2.45 (s, 1 H), 2.87 (t, J = 8 Hz, 2 H), 2.93-3.04 (m, 2 H), 4.10 (d, J = 7 Hz, 2 H), 6.12 (s, 2 H) |
| 141 | 0.18 | 368 | 0.57-0.69 (m, 2 H), 0.70-0.83 (m, 2 H), 0.85-0.95 (m, 2 H), 0.93 (t, J = 7 Hz, 3 H), 1.12 (m, 1 H), 1.42 (dq, J = 15, 7 Hz, 2 H), 1.34-1.67 (m, 2 H), 1.55 (br d, J = 10 Hz, 2 H), 1.78 (dt, J = 15, 7 Hz, 2 H), 2.21-2.30 (m, 1 H), 2.79-2.91 (m, 2 H), 3.94 (d, J = 7 Hz, 2 H), 6.20 (s, 2 H), 6.22-6.28 (m, 1 H), 6.87 (q, J = 3 Hz, 1 H), 7.00 (q, J = 2 Hz, 1 H), 11.06 (s, 1 H) |

TABLE 2-continued

| Compound Number | RT | MS | $^1$H NMR |
|---|---|---|---|
| 142 | 0.83 | 386 | 0.64-0.77 (m, 2 H), 0.94 (t, J = 7 Hz, 3 H), 0.96-1.06 (m, 2 H), 1.06-1.18 (m, 1 H), 1.23-1.47 (m, 4 H), 1.57-1.83 (m, 5 H), 1.85-1.92 (m, 4 H), 2.31 (d, J = 7 Hz, 2 H), 2.85 (m, 2 H), 3.11-3.25 (m, 4 H), 4.13 (d, J = 7 Hz, 2 H), 6.02 (s, 2 H) |
| 143 | 0.88 | 372 | 0.81-0.90 (m, 2 H), 0.94 (t, J = 7 Hz, 3 H), 0.99-1.09 (m, 2 H), 1.24-1.34 (m, 2 H), 1.43 (s, 2 H), 1.50-1.74 (m, 3 H), 1.74-1.84 (m, 2 H), 1.86-1.92 (m, 4 H), 2.37-2.45 (m, 1 H), 2.85 (t, J = 7 Hz, 2 H), 3.14-3.24 (m, 4 H), 4.12 (d, J = 7 Hz, 2 H), 6.01 (s, 2 H) |
| 144 | 0.13 | 378 | 0.86 (t, J = 7 Hz, 3 H), 1.27-1.42 (m, 2 H), 1.70 (dt, J = 15, 8 Hz, 2 H), 2.81 (t, J = 8 Hz, 2 H), 3.67 (s, 4 H), 3.74 (br s, 2 H), 5.49 (s, 2 H), 5.80 (s, 1 H), 6.42 (br s, 2 H), 6.75 (br d, J = 8 Hz, 2 H), 7.26 (br d, J = 8 Hz, 2 H) |
| 145 | 0.12 | 380 | 0.85 (t, J = 7 Hz, 3 H), 1.34 (m, 2 H), 1.64-1.81 (m, 3 H), 1.97 (m, 1 H), 2.77-2.90 (m, 4 H), 2.93-3.09 (m, 2 H), 3.58 (m, 1 H), 3.69 (s, 2 H), 5.62 (s, 2 H), 6.23 (br s, 2 H), 6.85 (m, J = 8 Hz, 2 H), 7.30 (m, J = 8 Hz, 2 H) |
| 146 | 0.20- | 349 | 0.94 (t, J = 7 Hz, 3 H), 1.31-1.49 (m, 12 H), 1.56 (m, 2 H), 1.67-1.86 (m, 4 H), 2.74 (m, 2 H), 2.95 (t, J = 8 Hz, 2 H), 4.33 (m, 2 H), 5.24 (spt, J = 6 Hz, 1 H), 7.99 (br s, 3 H), 8.56 (br s, 2 H), 14.02 (s, 1 H) |
| 147 | 1.46- | 433 | 0.94 (t, J = 7 Hz, 3 H), 1.28-1.51 (m, 6 H), 1.42 (d, J = 6 Hz, 6 H), 1.57-1.70 (m, 4 H), 1.70-1.84 (m, 4 H), 1.94 (br d, J = 10 Hz, 2 H), 2.80-2.89 (m, 2 H), 2.95 (t, J = 8 Hz, 2 H), 3.18-3.22 (m, 1 H), 3.29 (br t, J = 11 Hz, 2 H), 3.90 (br dd, J = 11, 4 Hz, 2 H), 4.23-4.44 (m, 2 H), 5.24 (quin, J = 6 Hz, 1 H), 8.55 (br s, 2 H), 9.10 (br s, 2 H), 13.95 (br s, 1 H) |
| 148 | 0.98 | 475 | 0.93 (t, J = 7 Hz, 3 H), 1.19-1.85 (m, 16 H), 1.36 (d, J = 6 Hz, 6 H), 1.91-2.10 (m, 3 H), 2.85 (t, J = 8 Hz, 2 H), 3.02-3.19 (m, 2 H), 3.30-3.42 (m, 2 H), 3.75 (m, 1 H), 3.87 (br d, J = 12 Hz, 2 H), 4.19-4.30 (m, 2 H), 5.39 (dt, J = 12, 6 Hz, 1 H), 5.82 (s, 2 H) |
| 149 | 0.94 | 321 | 0.95 (t, J = 7 Hz, 3 H), 1.37-1.96 (m, 14 H), 2.74-2.84 (m, 2 H), 2.96 (t, J = 8 Hz, 2 H), 4.37 (t, J = 7 Hz, 2 H), 5.23 (quin, J = 6 Hz, 1 H), 7.94 (br s, 3 H), 8.57 (s, 2 H), 13.92 (s, 1 H) |
| 150 | 0.75 | 405 | 0.95 (t, J = 7 Hz, 3 H), 1.37-1.88 (m, 10 H), 1.44 (d, J = 6 Hz, 6 H), 1.94 (br d, J = 10 Hz, 2 H), 2.88-2.93 (m, 2 H), 2.97 (t, J = 8 Hz, 2 H), 3.18-3.23 (m, 1 H), 3.29 (br t, J = 11 Hz, 2 H), 3.91 (br dd, J = 12, 4 Hz, 2 H), 4.37 (br t, J = 7 Hz, 2 H), 5.23 (quin, J = 6 Hz, 1 H), 8.56 (s, 2 H), 9.12 (br s, 1 H), 13.91 (s, 1 H) |
| 151 | 0.87 | 447 | 0.93 (t, J = 7 Hz, 3 H), 1.31-1.60 (m, 12 H), 1.60-1.85 (m, 6 H), 1.90-2.11 (m, 3 H), 2.77-2.96 (m, 2 H), 3.04-3.23 (m, 2 H), 3.32-3.46 (m, 2 H), 3.69-3.97 (m, 3 H), 4.18-4.35 (m, 2 H), 5.35-5.44 (m, 1 H), 5.81 (br s, 2 H) |
| 152 | 0.78 | 425 | 0.93 (t, J = 7 Hz, 3 H), 1.37 (d, J = 6 Hz, 6 H), 1.36-1.46 (m, 4 H), 1.68-1.81 (m, 4 H), 2.40-2.45 (m, 2 H), 2.81-2.88 (m, 2 H), 3.43-3.55 (m, 1 H), 3.78-3.86 (m, 2 H), 4.20-4.29 (m, 4 H), 5.39 (quin, J = 6 Hz, 1 H), 5.82 (s, 2 H) |
| 153 | 1.01 | 467 | 0.94 (t, J = 7 Hz, 3 H), 1.29-1.49 (m, 8 H), 1.56 (m, 2 H), 1.65-1.81 (m, 4 H), 2.03 (br s, 3 H), 2.86 (t, J = 8 Hz, 2 H), 3.37 (m, 2 H), 4.11-4.75 (m, 7 H), 5.39 (spt, J = 6 Hz, 1 H), 5.81 (s, 2 H) |
| 154 | 0.84 | 453 | 0.94 (t, J = 7 Hz, 3 H), 1.27-1.50 (m, 12 H), 1.69-1.82 (m, 4 H), 2.18-2.43 (m, 4 H), 2.85 (t, J = 8 Hz, 2 H), 3.48 (m, 1 H), 3.83 (m, 2 H), 4.20-4.30 (m, 4 H), 5.40 (spt, J = 6 Hz, 1 H), 5.82 (s, 2 H) |
| 155 | 1.13 | 495 | 0.94 (t, J = 7 Hz, 3 H), 1.24-1.56 (m, 8 H), 1.41 (d, J = 6 Hz, 6 H), 1.72-1.84 (m, 4 H), 2.03 (s, 3 H), 2.94 (t, J = 8 Hz, 2 H), 3.29-3.35 (m, 2 H), 4.05-4.71 (m, 7 H), 5.24 (spt, J = 6 Hz, 1 H), 8.53 (br s, 2 H), 13.85 (br s, 1 H) |
| 156 | 0.95 | 352 | 0.66 (s, 3 H), 0.93 (t, J = 7 Hz, 3 H), 1.35-1.50 (m, 8 H), 1.78 (br s, 2 H), 2.97-3.10 (m, 2 H), 3.11-3.45 (m, 4 H), 4.18-4.64 (m, 2 H), 5.24 (quin, J = 6 Hz, 1 H), 8.49 (s, 2 H), 13.82 (br s, 1 H) |
| 157 | 0.90 | 338 | 0.94 (t, J = 7 Hz, 3 H), 1.34-1.49 (m, 8 H), 1.73-1.87 (m, 2 H), 2.06 (m, 1 H), 2.98 (br t, J = 8 Hz, 2 H), 3.35-3.50 (m, 4 H), 4.34 (d, J = 8 Hz, 2 H), 4.59 (br s, 2 H), 5.23 (m, 1 H), 8.47 (br s, 2 H), 13.80 (br s, 1 H) |
| 158 | 0.20 | 355 | 0.91 (t, J = 7 Hz, 3 H), 1.22 (d, J = 6 Hz, 6 H), 1.64-1.75 (m, 2 H), 1.76-2.07 (m, 2 H), 2.78 (t, J = 7 Hz, 2 H), 3.66 (s, 2 H), 5.33 (spt, J = 6 Hz, 1 H), 5.55 (s, 2 H), 5.88 (s, 2 H), 7.01 (d, J = 8 Hz, 2 H), 7.28 (d, J = 8 Hz, 2 H) |
| 159 | 0.47 | 371 | 1.04 (t, J = 7 Hz, 3 H), 1.20 (d, J = 6 Hz, 6 H), 1.75-2 (m, 2 H), 3.48 (q, J = 7 Hz, 2 H), 3.66 (s, 2 H), 4.68 (s, 2 H), 5.31 (spt, J = 6 Hz, 1 H), 5.58 (s, 2 H), 6.03 (s, 2 H), 7.04 (d, J = 8 Hz, 2 H), 7.26 (d, J = 8 Hz, 2 H) |

TABLE 2-continued

| Compound Number | RT | MS | $^1$H NMR |
|---|---|---|---|
| 160 | 0.33 | 327 | 1.25 (d, J = 6 Hz, 6 H), 2 (s, 2H), 2.5 (s, 3H), 3.67 (s, 2H), 5.35 (m, 1H), 5.52 (s, 2H), 5.92 (s, 2H), 7.07 (d, J = 8Hz, 2H), 7.29 (d, J = 8 Hz, 2H) |
| 161 | 0.90 | 387 | 0.96 (t, J = 7 Hz, 3 H), 1.25 (d, J = 6 Hz, 6 H), 1.72 (sxt, J = 7 Hz, 2 H), 2.06-2.30 (m, 2 H), 3.30-3.33 (m, 2 H), 3.67 (s, 2 H), 5.34 (quin, J = 6 Hz, 1 H), 5.43 (s, 2 H), 5.91 (s, 2 H), 7.11 (d, J = 1 Hz, 2 H), 7.29 (d, J = 1 Hz, 2 H) |
| 162 | 0.20 | 403 | 0.97 (t, J = 7 Hz, 3 H), 1.25 (dd, J = 6, 2 Hz, 6 H), 1.60-1.71 (m, 2 H), 1.77 (br s, 2 H), 3.15 (m, 1 H), 3.37 (m, 1 H), 3.68 (s, 2 H), 5.36 (dt, J = 12, 6 Hz, 1 H), 5.81 (s, 2 H), 6.29 (s, 2 H), 7.12 (br d, J = 1 Hz, 2 H), 7.30 (br d, J = 1 Hz, 2 H) |
| 163 | 0.74 | 370 | 0.87 (t, J = 7 Hz, 3 H), 1.21 (d, J = 6 Hz, 6 H), 1.60 (sxt, J = 7 Hz, 2 H), 3.31-3.81 (m, 6 H), 5.27 (dt, J = 12, 6 Hz, 1 H), 5.34 (s, 2 H), 5.39 (br s, 2 H), 7.00 (br t, J = 5 Hz, 1 H), 7.10 (d, J = 8 Hz, 2 H), 7.27 (d, J = 8 Hz, 2 H) |
| 164 | 0.12 | 370 | 0.96 (t, J = 7 Hz, 3 H), 1.22 (d, J = 6 Hz, 6 H), 1.76-2.25 (m, 3 H), 2.52-2.61 (m, 2 H), 3.66 (s, 2 H), 3.90 (s, 2 H), 5.32 (quin, J = 6 Hz, 1 H), 5.66 (s, 2 H), 5.95 (s, 2 H), 7.04 (d, J = 8 Hz, 2 H), 7.27 (d, J = 8 Hz, 2 H) |
| 165 | 0.69 | 347 | 0.93 (t, J = 7 Hz, 3 H), 1.13-1.27 (m, 2 H), 1.30-1.52 (m, 4 H), 1.37 (d, J = 6 Hz, 6 H), 1.71-1.91 (m, 3 H), 2.31-2.45 (m, 2 H), 2.77-2.89 (m, 2 H), 2.94 (br d, J = 12 Hz, 2 H), 4.13 (d, J = 7 Hz, 2 H), 5.39 (quin, J = 6 Hz, 1 H), 5.84 (s, 2 H) |

Among the intermediate compounds of formulae (VIIa), (VIII), (VIIIa) and (IX) or a pharmaceutically acceptable salt thereof, that are subject matter of the present disclosure, mention may be made for instance of the following compounds as shown in Table 3 below:

TABLE 3

| Compound | Formula | IUPAC name |
|---|---|---|
| H | 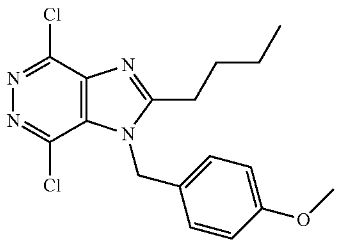 [SMILES: CCCCc1nc2c(Cl)nnc(Cl)c2n1Cc1ccc(OC)cc1] | 2-butyl-4,7-dichloro-3-[(4-methoxyphenyl)methyl]imidazo[4,5-d]pyridazine |
| IA | 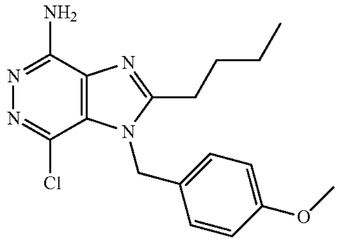 [SMILES: CCCCc1nc2c(N)nnc(Cl)c2n1Cc1ccc(OC)cc1] | 2-butyl-7-chloro-1-(4-methoxybenzyl)-1H-imidazo[4,5-d]pyridazin-4-amine |
| J | 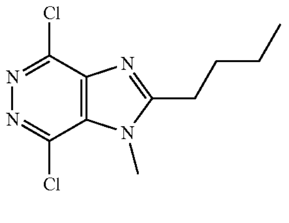 [SMILES: CCCCc1nc2c(Cl)nnc(Cl)c2n1C] | 2-butyl-4,7-dichloro-1-methyl-1H-imidazo[4,5-d]pyridazine |

TABLE 3-continued
| Compound | Formula | IUPAC name |
| --- | --- | --- |
| K | 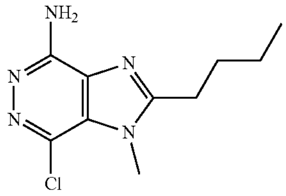 [SMILES: CCCCc1nc2c(N)nnc(Cl)c2n1C] | 2-butyl-7-chloro-1-methyl-1H-imidazo[4,5-d]pyridazin-4-amine |
| L | 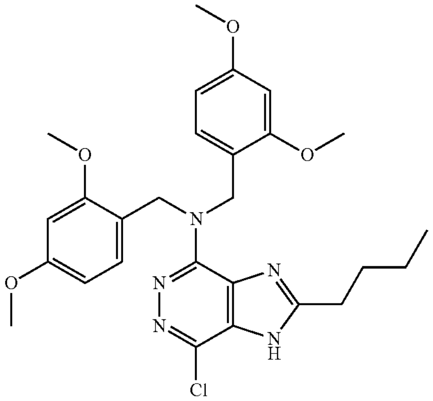 [SMILES: CCCCc1nc2c(N(Cc3ccc(OC)cc3OC)Cc3ccc(OC)cc3OC)nnc(Cl)c2[nH]1] | 2-butyl-7-chloro-N,N-bis(2,4-dimethoxyphenyl)-1H-imidazo[4,5-d]pyridazin-4-amine |
| M | 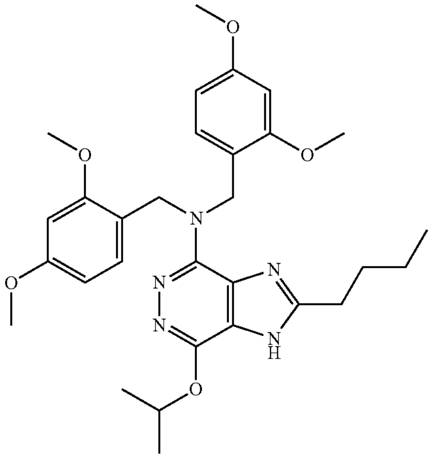 [SMILES: CCCCc1nc2c(N(Cc3ccc(OC)cc3OC)Cc3ccc(OC)cc3OC)nnc(OC(C)C)c2[nH]1] | 2-butyl-N,N-bis(2,4-dimethoxybenzyl)-7-isopropoxy-1H-imidazo[4,5-d]pyridazin-4-amine |
| N | 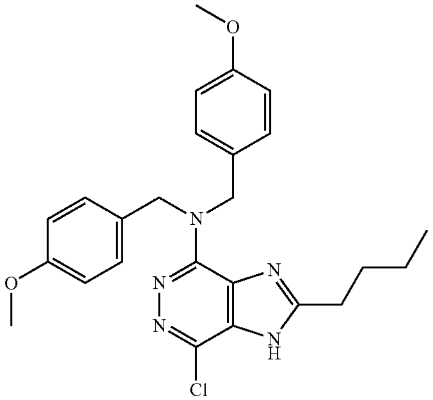 [SMILES: CCCCc1nc2c(N(Cc3ccc(OC)cc3)Cc3ccc(OC)cc3)nnc(Cl)c2[nH]1] | 2-butyl-7-chloro-N,N-bis(4-methoxybenzyl)-1H-imidazo[4,5-d]pyridazin-4-amine |

TABLE 3-continued

| Compound | Formula | IUPAC name |
|---|---|---|
| R | 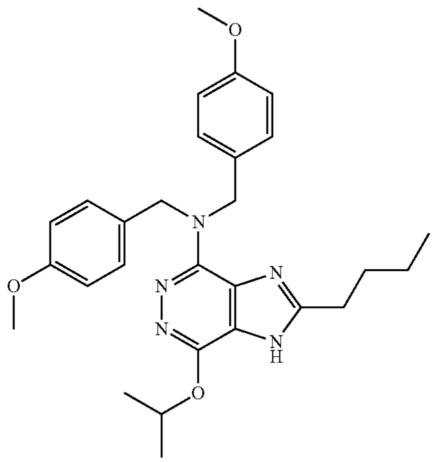 | 2-butyl-N,N-bis,4-methoxybenzyl)-7-isopropoxy-1H-imidazo[4,5-d]pyridazin-4-amine |

In Table 4 below, $^1$H NMR, Retention time and liquid chromatography/mass spectra are also indicated.

The $^1$H NMR of Table 4 is $^1$H NMR Spectra (400 MHz, δ in ppm, DMSO-d6) as defined in the Experimental part.

The liquid chromatography/mass spectra (LC/MS) of Table 4 were obtained according to one of the seven methods described in the Experimental part.

The Retention time (RT) of Table 4 is defined in minutes.

TABLE 4

| Compound | RT | MS | $^1$H NMR |
|---|---|---|---|
| H | 1.59 | 365 | 6.92-6.85 (m, 4H) 5.68 (s, 2H) 3.79 (s, 3H) 2.91-2.87 (t, 2H) 1.82-1.78 (m, 2H) 1.44-1.38 (m, 2H) 0.93-0.89 (t, 3H) |
| IA | 1.22 | 346 | 0.84 (t, J = 7.4 Hz, 3 H); 1.32 (m, 2 H); 1.64 (m, 2 H); 2.83 (m, 2H); 3.72 (s, 3 H); 5.65 (s, 2 H); 6.71 (s broad, 2 H); 6.91 (d, J = 8.9 Hz, 2 H); 6.96 (d, J = 8.9 Hz, 2 H) |
| J | 1.32 | 259 | 0.95 (t, J = 7.4 Hz, 3 H); 1.43 (m, 2 H); 1.79 (m, 2 H); 3.00 (m, 2 H); 4.04 (s, 3 H) |
| K | 0.84 | 240 | 0.93 (t, J = 7.4 Hz, 3 H); 1.41 (m, 2 H); 1.74 (m, 2 H); 2.90 (m, 2 H); 3.95 (s, 3 H); 6.63 (s broad, 2 H) |
| L | 1.59 | 526 | 0.85 (t, J = 7.4 Hz, 3 H); 1.28 (m, 2 H); 1.68 (m, 2 H); 2.82 (t, J = 7.6 Hz, 2 H); 3.72 (s, 12 H); 5.07 (s broad, 4 H); 6.39 (dd, J = 2.4 et 8.4 Hz, 2 H); 6.54 (d, J = 2.4 Hz, 2 H); 6.95 (d, J = 8.4 Hz, 2 H); 13.35 (s broad, 1 H) |
| M | 1.58 | 550 | 0.84 (t, J = 7.4 Hz, 3 H); 1.26 (m, 2 H); 1.37 (d, J = 6.2 Hz, 6 H); 1.66 (m, 2 H); 2.77 (t, J = 7.6 Hz, 2 H); 3.70 (s, 6 H); 3.71 (s, 6 H); 8.4 Hz, 5.00 (s broad, 4 H); 5.41 (sept, J = 6.2 Hz, 1 H); 6.38 (dd, J = 2.4 et 2 H); 6.52 (d, J = 2.4 Hz, 2 H); 6.94 (d, J = 8.4 Hz, 2 H); 13.01 (s broad, 1 H) |
| N | 1.78 | 466 | 0.86 (t, J = 7 Hz, 3 H), 1.31 (sxt, J = 7 Hz, 2 H), 1.72 (quin, J = 8 Hz, 2 H), 2.86 (t, J = 7 Hz, 2 H), 3.72 (s, 6 H), 5.08 (br s, 4 H), 6.86 (d, J = 9 Hz, 4 H), 7.19 (d, J = 9 Hz, 4 H), 13.45 (br s, 1 H) |
| R | 2.79 | 490 | 0.86 (t, J = 7 Hz, 3 H), 1.30 (sxt, J = 7 Hz, 2 H), 1.39 (d, J = 6 Hz, 6 H), 1.71 (quin, J = 7 Hz, 2 H), 2.82 (t, J = 7 Hz, 2 H), 3.71 (s, 6 H), 4.98 (s, 4 H), 5.44 (spt, J = 6 Hz, 1 H), 6.84 (d, J = 9 Hz, 4 H), 7.16 (d, J = 8 Hz, 4 H), 13.11 (s, 1 H) |

The examples which follow describe the preparation of some compounds in accordance with the disclosure. The numbers of the compounds exemplified below match those given in the Tables 1 and 3 above. All reactions are performed under inert atmosphere, unless otherwise stated.

In the following examples, when the source of the starting products is not specified, it should be understood that said products are known compounds.

EXAMPLES

In the Preparations and in the Examples, the following abbreviations are used:

ACN, MeCN or $CH_3CN$: acetonitrile
$CDCl_3$: deuterated chloroform
DCM: dichloromethane
DIPEA: diisopropylethylamine
DMF: N,N-dimethylformamide
DMSO: dimethylsulfoxide
EDCI: 1-ethyl-3-(3-dimethylaminopropyl)carbodiimide
$Et_2O$: diethyl ether
EtOAc: ethyl acetate
EtOH: ethanol
HBTU: (2-(1H-benzotriazol-1-yl)-1,1,3,3-tetramethyluronium hexafluorophosphate
HOB t: hydroxybenzotriazole
iPrOH: isopropanol mCPBA: meta-Chloroperoxybenzoic acid
MeOH: methanol
Me-THF: methyl tetrahydrofuran
$MgSO_4$: magnesium sulfate
MS: mass spectrometry
MTBE: methyl ter-butyl ether
NaCl: sodium chloride
NBS: N-bromosuccinimide
nBuLi: n-Butyllithium
rt: room temperature
RT: Retention Time
NMR: nuclear magnetic resonance
NMP: N-methyl-2-pyrrolidone
TEA: triethylamine
TFA: trifluoroacetic acid
THF: tetrahydrofuran
$Ti(iPrO)_4$: Titanium (IV) isopropoxide
TLC: thin-layer chromatography
TMS: tetramethyl silane
h or hr(s): hour(s)

Materials and Methods

The progress of the synthetic reactions is monitored by TLC. The plates are made of glass and are coated with Merck 60 F254 silica gel. After elution, the plates are observed under ultraviolet light at 254 nm.

The microwave reactions were performed using a Biotage Initiator 8 EXP microwave machine. The products were purified, when necessary, on a Biotage Isolera chromatograph or a Spot 2 chromatograph from Merck. The columns used are Merck 15-40 μm silica columns (2.5 g to 800 g).

Analyses

Mass Spectrometry (MS):

Method A:

The spectra were acquired on a Waters UPLC-SQD.
Ionization: electrospray in positive and/or negative mode (ES+/−)
Column: ACQUITY CORTECS C18+-1.6 μm-2.1×50 mm
Solvents: A: $H_2O$ (0.1% formic acid) B: $CH_3CN$ (0.1% formic acid)
Column temperature: 40° C.
Flow rate: 1 mL/min
Gradient (3 min): from 2 to 100% B in 2.0 min; 2.6 min: 100% B; 2.7 min: 2% B Method A has been used for compounds: 2, 9, 35, 65, 69, 86, 87 and 91.

Method B:

The spectra were acquired on a Waters UPLC-SQD.
Ionization: electrospray in positive and/or negative mode (ES+/−)
Column: ACQUITY CORTECS C18+-1.6 μm-2.1×50 mm
Solvents: A: $H_2O$ (0.1% TFA) B: $CH_3CN$ (0.1% TFA)
Column temperature: 40° C.
Flow rate: 1 mL/min
Gradient (10 min): 1 min 2% B, from 2 to 100% B in 6.5 min; 1.7 min: 100% B; from 100% B to 2% B in 0.1 min; 1.7 min: 2% B Method B has been used for compounds: 68.

Method N:

The spectra were acquired on a Waters UPLC-SQD2:
Ionization: electrospray in positive and/or negative mode (ES+/−).
Column ACQUITY CSH C18-1.7 μm-2.1×50 mm
Solvents: A: $H_2O$ (0.1% formic acid) B: $CH_3CN$ (0.1% formic acid)
Column temperature: 60° C.
Flow rate: 1 mL/min
Gradient (2.5 min): from 3 to 100% B in 2.1 min; 2.45 min: 100% B; 2.50 min: 3% of B Method N has been used for compounds: 1, 3, 4, 5, 6, 7, 8, 10, 11, 12, 13, 14, 15, 17, 18, 19, 20, 21, 22, 23, 24, 25, 26, 27, 28, 29, 30, 31, 32, 33, 34, 36, 37, 38, 39, 40, 41, 43, 44, 45, 46, 47, 48, 49, 50, 51, 52, 53, 54, 55, 56, 57, 58, 59, 60, 61, 62, 63, 64, 66, 67, 70, 71, 72, 73, 74, 75, 76, 77, 78, 79, 88, 89, 90, 92, 93, 94, 95, 96, 97, 101, 102, 103, 104, 105, 107 to 117, 120, 121, 124 to 135, 137 to 146, 149, 150, 152 to 161, 163 to 165; intermediates: (IA), (IB), (J), (K), (L), (M) and (N).

Method N1:

The spectra were acquired on a Waters UPLC-SQD2:
Ionization: electrospray in positive and/or negative mode (ES+/−).
Column ACQUITY CSH C18-1.7 μm-2.1×50 mm
Solvents: A: $H_2O$ (0.1% formic acid) B: $CH_3CN$ (0.1% formic acid)
Column temperature: 60° C.
Flow rate: 1 mL/min
Gradient (10 min): from 3 to 100% B in 8.6 min; 9.6 min: 100% B; 9.8 min: 3% B Method N1 has been used for compound: 106.

Method O:

The spectra were acquired on a WATERS QUATTRO PREMIER
Ionization: electrospray in positive and/or negative (ES+/−)
Column: ACQUITY MSS T3-1.8 μm-2.1×50 mm
Solvents: A: $H_2O$ (0.1% formic acid) B: $CH_3CN$ (0.1% formic acid)
Column temperature: 55° C.
Flow rate: 0.9 ml/min
Gradient (3.7 min): de 5 to 100% of B in 3 min; 3.1 min: 5% of B Method O has been used for compounds: 80, 81, 82, 83, 84, 100, 118, 119, 147 and intermediate (O).

Method P:

The spectra were acquired on a Waters XeVo-QTof
Ionization: electrospray in positive (ES+).
Column ACQUITY BEH C18-1.7 μm-2.1×100 mm
Solvents: A: $H_2O$ (0.1% formic acid) B: $CH_3CN$ (0.1% formic acid)
Column temperature: 45° C.
Flow rate: 0.6 mL/min
Gradient (5.3 min): 0.3 min 5% B; from 5 to 100% B in 3.7 min; 0.6 min: 100% B; 0.7 min: 5% B Method P has been used for compounds: 16, 42 and 85.

Method M:

The spectra were acquired on an Agilent 1200 & 6110B
Ionization: electrospray in positive (ES+).
Kinetex C18 50*2.1 mm, 5 μm
Solvents: A: $H_2O$+0.037% (v/v) TFA B: ACN+0.018% (v/v) TFA
Column temperature: 40° C.
Flow rate: 1 mL/min
Gradient (5 min): from 5 to 95% B in 3 min; 1 min: 95% B; 1.50 min: 5% B Method M has been used for intermediates: (A), (B) and (E) and for compounds: 122, 123, 148, 151 and 162.

Method Z:

The spectra were acquired on a Waters Acquity UPLC system with PDA detector

Ionization: electrospray in positive and/or negative mode (ES+/−)

Acquity BEH C18 column (50 mm×2.1 mm) 1.7 μm

Solvents: A: $H_2O$ (0.05% formic acid) B: $CH_3CN$ (0.05% formic acid)

Column temperature: 35° C.

Flow rate: 0.6 mL/min

Gradient (4 min): 0.4 min: 3% B; from 3 to 98% B in 1.6 min; 1.5 min: 98% B;

0.50 min: 3% B

Method Z has been used for intermediates: (F), (G) and (H).

$^1$H Nuclear Magnetic Resonance (NMR)

The $^1$H NMR spectra were recorded on a Brüker Avance and/or Varian G spectrometer (300 MHz, 400 MHz, 500 MHz or 600 MHz) in deuterated DMSO. The chemical shifts are expressed in units (ppm) using tetramethyl silane (TMS) as internal reference. For the interpretation of the spectra, the following abbreviations were used: s=singlet, d=doublet, t=triplet, q=quartet, quint=quintet, sext=sextet, dd=doubled doublet, ddd=doublet of doubled doublets, m=multiplet, ax.=axial, equat.=equatorial.

Preparation

All the following compounds were synthesized according to the protocols described below.

Preparation of Intermediate (E):

Preparation 1: Intermediate (A) 2-butyl-1H-imidazole-4,5-dicarbonitrile

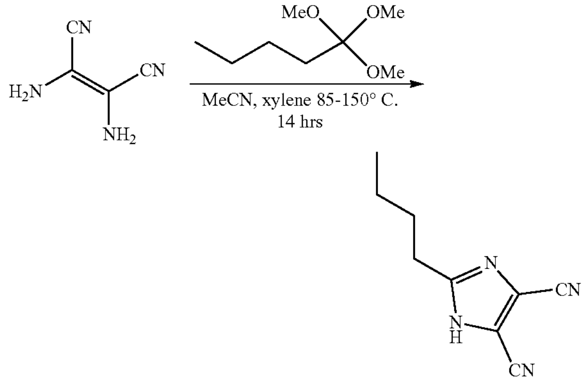

(A)

A suspension of (Z)-2,3-diaminobut-2-enenitrile (45.0 g, 416 mmol, 1.00 eq) and 1,1,1-trimethoxypentane (67.5 g, 416 mmol, 1.00 eq) in MeCN (90.0 mL) was stirred in an oil bath and it was kept at 85° C. for 6 hrs. At the end of this time, the reaction mixture was concentrated by evaporation under reduced pressure. The whole of this compound was dissolved in xylene (90.0 mL), and the resulting solution was stirred in an oil bath kept at 150° C. for 8 hrs. The mixture was concentrated to give a residue, which was filtered, and washed with methylbenzene. Then the filter cake was dried to give the expected product. The product was used in the next step without any purification. Intermediate (A) (63.0 g, 87% Yield)

$^1$H NMR (400 MHz, δ in ppm, $CDCl_3$): 2.82 (t, J=7.6 Hz, 15.2 Hz, 2H), 1.72-1.80 (m, 2H), 1.36-1.45 (m, 2H), 0.93-0.97 (m, 3H)

MS Method M: RT=1.019 min, m/z 175.1 $(M+H)^+$

Preparation 2: Intermediate (B) 2-butyl-1H-imidazole-4,5-dicarboxylic acid

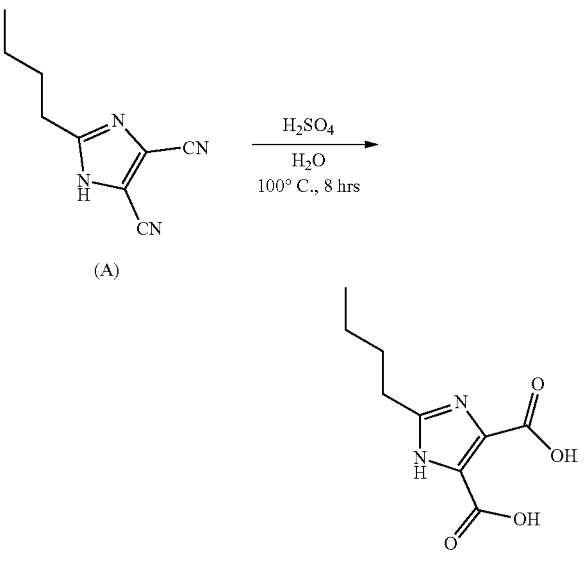

(B)

A solution of compound (A) (63.0 g, 362 mmol, 1.00 eq) in $H_2SO_4$ (284 mL) and $H_2O$ (126 mL) was stirred at 100° C. for 8 hrs. By TLC one major new spot with lower polarity was observed. The pH of the solution was adjusted to 9-10 using 10% sodium hydroxide solution. The mixture was filtered, and the filter cake was concentrated to give the expected product which was used into the next step without further purification. Intermediate (B) (76.5 g, 99.7% yield) was obtained as a black brown solid.

$^1$H NMR (400 MHz, δ in ppm, DMSO-$d_6$): 2.59 (t, J=7.6 Hz, 2H), 1.57-1.63 (m, 2H), 1.19-1.28 (m, 2H), 1.27-1.33 (m, 2H), 0.86 (t, J=7.2 Hz, 14.8 Hz, 2H).

MS Method M: RT=1.163 min, m/z 213.1 $(M+H)^+$.

Preparation 3: Intermediate (C) dimethyl 2-butyl-1H-imidazole-4,5-dicarboxylate

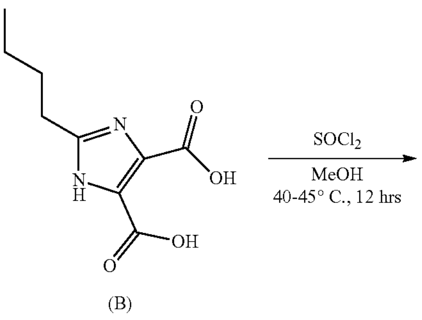

-continued

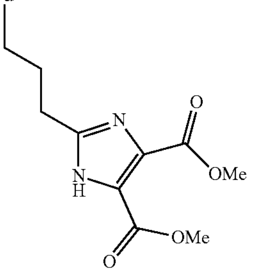

(C)

To a mixture of compound (B) (76.5 g, 361 mmol, 1.00 eq) in MeOH (230 mL) was added $SOCl_2$ (214 g, 1.80 mol, 131 mL, 5.00 eq) slowly and degassed and purged with $N_2$ for 3 times, and then the mixture was stirred at 40-45° C. for 12 hrs under $N_2$ atmosphere. The mixture was cooled and then poured slowly to chilled water (500 mL). It was neutralized by the addition of 10% sodium hydroxide solution. Then the mixture was extracted with EtOAc (3×500 mL). The combined organic layers were washed with brine (1.00 L), dried over $Na_2SO_4$, filtered and concentrated under reduced pressure to give a residue. The crude product was used into the next step without further purification. Intermediate (C) (81.0 g, 93.5% yield) was obtained as a black brown solid.

$^1H$ NMR (400 MHz, δ in ppm, DMSO-$d_6$): 3.87 (s, 6H), 2.77 (t, J=8.0 Hz, 2H), 1.68-1.76 (m, 2H), 1.30-1.40 (m, 2H), 0.90 (t, J=7.6 Hz, 3H).

Preparation 4: Intermediate (D) 2-butyl-5,6-dihydro-1H-imidazo[4,5-d]pyridazine-4,7-dione

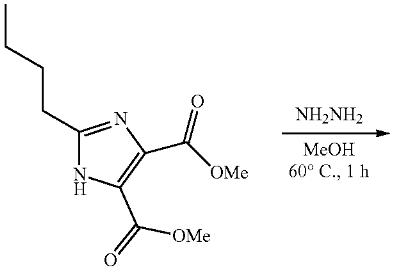

(C)

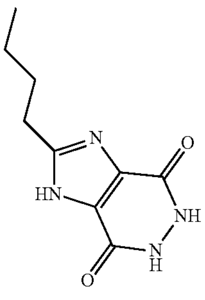

(D)

A mixture of compound (C) (81.0 g, 337 mmol, 1.00 eq), $NH_2NH_2 \cdot H_2O$ (51.7 g, 1.01 mol, 50.2 mL, 98.0% purity, 3.00 eq) in MeOH (243 mL) was degassed and purged with $N_2$ for 3 times, and then the mixture was stirred at 60° C. for 1 hour under $N_2$ atmosphere. The reaction mixture was filtered and washed with methanol. This material was suspended in water (1.00 L), heated to 85° C., and then rendered acidic by addition of conc. HCl (100 mL). After stirring for 12 hours at 85° C., the mixture was cooled and the white product filtered with suction and washed with water. The crude product was used into the next step without further purification. Intermediate (D) (49.5 g, 70.5% yield) was obtained as an off-white solid.

Preparation 5: Intermediate (E) 2-butyl-4,7-dichloro-1H-imidazo[4,5-d]pyridazine

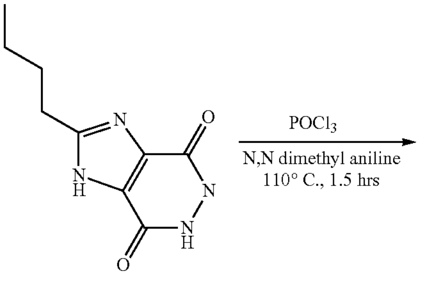

(D)

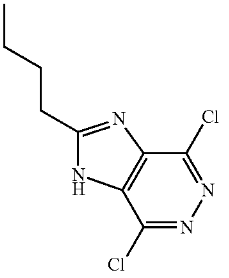

(E)

To a cooled solution of compound (D) (49.5 g, 238 mmol, 1.00 eq) in $POCl_3$ (248 mL) was added N,N-dimethyl aniline (50.0 mL) and the reaction mixture was stirred at 110° C. for 90 mins. The reaction mixture was concentrated under reduced pressure to give a residue. The residue was poured into cold water (2.00 L) and adjusted pH to 7 with solid sodium bicarbonate and extracted with EtOAc (2×1 L). The combined organic layers were washed with brine (500 mL), dried over $Na_2SO_4$, filtered and concentrated under reduced pressure to give a residue. The residue in MTBE (200 mL) was stirred for 2 hrs. The suspension was filtered, and the filter cake was collected. Intermediate (E) (54.5 g, 92.0% yield) was obtained as a yellow solid.

$^1H$ NMR (400 MHz, δ in ppm, $CDCl_3$): 3.18 (t, J=7.6 Hz, 2H), 1.90-1.97 (m, 2H), 1.40-1.49 (m, 1H), 0.92 (t, J=7.2 Hz, 3H).

MS Method M: RT=2.161 min, m/z 245.0 $(M+H)^+$.

Preparation of Intermediate (H):

Preparation 6: Intermediate (F) dimethyl 2-butyl-1-[(4-methoxyphenyl)methyl]imidazole-4,5-dicarboxylate

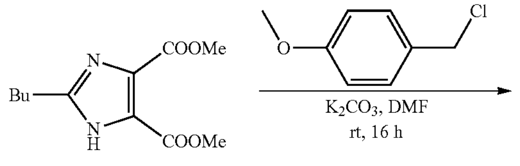

(C)

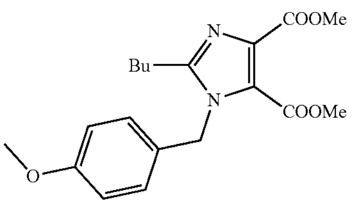

(F)

To a solution of intermediate (C) (300 g, 1.25 mol) in DMF (3.5 L), was added $K_2CO_3$ (260 g, 1.88 mol) and stirred at rt for 1 h, then was added 4-Methoxybenzyl chloride (244.6 g, 1.56 mol) and stirred at rt for 16 h. The reaction mixture was poured into water (5 L), extracted with EtOAc (2×3 L), the combined organic layer was dried over anhydrous sodium sulphate, filtered and concentrated under vacuum to afford intermediate (F) (450 g, crude) as a pale-yellow color oil which was taken to next step as such.

$^1$H NMR (400 MHz, δ in ppm, $CDCl_3$): 6.95 (d, J=8.8 Hz, 2H) 6.84 (d, J=8.6 Hz, 2H) 5.31 (s, 2H) 3.91 (s, 3H) 3.81 (s, 3H) 3.78 (s, 3H) 2.68-2.64 (t, 2H) 1.36-1.63 (m, 2H) 1.37-1.31 (m, 2H) 0.89-0.84 (t, 3H).

MS: Method Z, TR=1.97 min, m/z 361.1 $(M+H)^+$

Preparation 7: Intermediate (G) 2-butyl-3-[(4-methoxyphenyl)methyl]-5,6-dihydroimidazo[4,5-d]pyridazine-4,7-dione

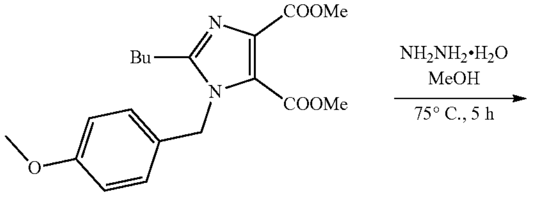

(F)

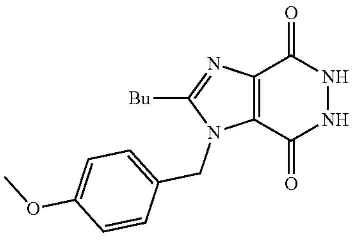

(G)

To a solution of intermediate (F) (450 g, 1.25 mol) in methanol (1.3 L) was added $NH_2NH_2 \cdot H_2O$ (175.2 g, 3.49.8 mol) and heated to 75° C. for 5 h. The reaction mixture was cooled to room temperature, diluted with $Et_2O$ (1 L) and the precipitated solid was filtered and dried to afford intermediate (G) (250 g, 61.7% yield) as off-white color solid.

$^1$H NMR (400 MHz, δ in ppm, DMSO-$d_6$): 7.17 (d, J=8.8 Hz, 2H) 6.89 (d, J=8.4 Hz, 2H) 6.87-6.64 (bs, 2H) 5.68 (s, 2H) 3.72 (s, 3H) 2.69-2.65 (t, 2H) 1.59-1.54 (m, 2H) 1.32-1.23 (m, 2H) 0.83-0.8 (t, 3H).

MS: Method Z, RT=1.59 min m/z 329.1 $(M+H)^+$.

Preparation 8: Intermediate (H) 2-butyl-4,7-dichloro-3-[(4-methoxyphenyl)methyl]imidazo[4,5-d]pyridazine

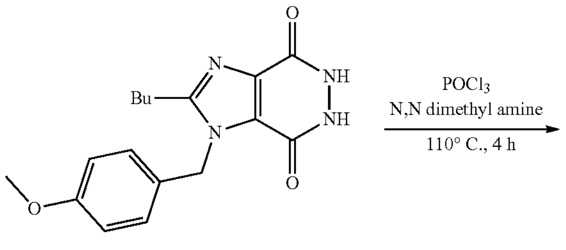

(G)

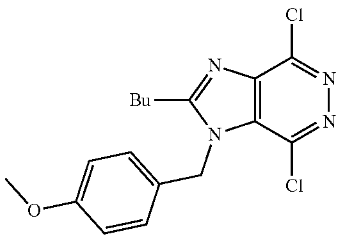

(H)

To a cooled solution of intermediate (G) (70 g, 213.4 mmol) in $POCl_3$ (620 mL, 8.8 Vol) was added N, N-dimethyl aniline (140 mL, 2 Vol) and the reaction mixture was stirred at 110° C. for 4 h. The reaction mixture was cooled to room temperature, poured into cold water (5 L) and adjusted pH to 7 with solid $Na_2CO_3$ and extracted with EtOAc (2×3 L). The combined organic layer was dried over anhydrous sodium sulphate, filtered and concentrated under vacuum. The crude product was triturated with $Et_2O$ (200 mL) for 2h, filtered and dried to afford intermediate (H) (38 g, 48.5% yield) as pale-yellow color solid.

$^1$H NMR (400 MHz, δ in ppm, $CDCl_3$): 6.92-6.85 (m, 4H) 5.68 (s, 2H) 3.79 (s, 3H) 2.91-2.87 (t, 2H) 1.82-1.78 (m, 2H) 1.44-1.38 (m, 2H) 0.93-0.89 (t, 3H) MS: Method Z, m/z 365.3 $(M+H)^+$

Preparation 9: Intermediate (IA) 2-butyl-7-chloro-1-(4-methoxybenzyl)-1H-imidazo[4,5-d]pyridazin-4-amine and

Intermediate (IB) 2-butyl-7-chloro-1-(4-methoxybenzyl)-1H-imidazo[4,5-d]pyridazin-4-amine hydrochloride

Intermediate (IA) 2-butyl-7-chloro-1-(4-methoxybenzyl)-1H- imidazo[4,5-d]pyridazin-4-amine

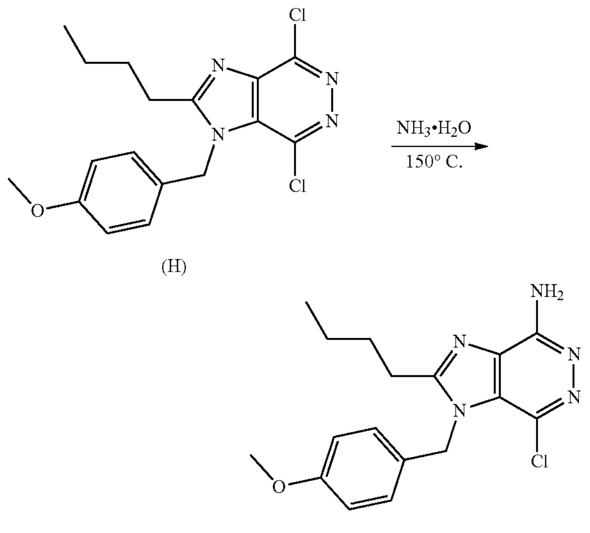

(H)

(IA)

A mixture of intermediate (H) (5 g, 13.7 mmol) and ammonia solution (10 mL, 35%) were introduced into a microwave vial. The suspension was heated at 150° C. during 6 hours under microwave. The resulting mixture was filtered and washed with water to give 5 g of crude product, which was purified by crystallization in EtOH to afford intermediate (IA) (2.15 g, 45% yield) as white solid. 1H NMR (400 MHz, δ in ppm, DMSO-$d_6$): 0.84 (t, J=7.4 Hz, 3H); 1.32 (m, 2H); 1.64 (m, 2H); 2.83 (m, 2H); 3.72 (s, 3H); 5.65 (s, 2H); 6.71 (s broad, 2H); 6.91 (d, J=8.9 Hz, 2H); 6.96 (d, J=8.9 Hz, 2H)

MS method N: RT (min): 1.22; $[M+H]^+$ 346; ES−$[MH-+HCO_2H]^-$: m/z 390

Intermediate (IB) 2-butyl-7-chloro-1-(4-methoxybenzyl)-1H-imidazo[4,5-d]pyridazin-4-amine hydrochloride

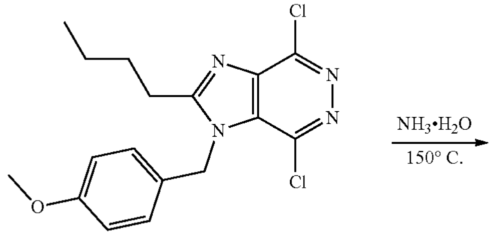

(H)

-continued

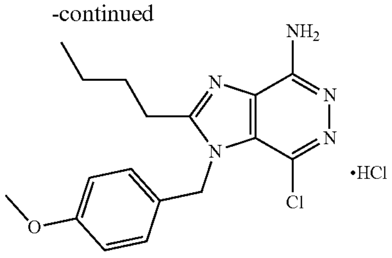

(IB)

A mixture of intermediate (H) (5 g, 13.7 mmol) and ammonia solution (25 mL, 35%) were introduced into an autoclave. The suspension was heated at 150° C. during 6h under internet pressure of 25 bars and then kept overnight without heating. The resulting precipitates were filtered and the filter cake was dissolved in HCl Dioxane (200 mL, 4N), which was concentrated under reduced pressure to 1/10$^{th}$ volume. The new precipitates were filtered, washed with EtOAc, and dried overnight at 30° C. under vacuum to intermediate (IB) (3.65 g, 54% yield), which was used directly to the following steps.

$^1$H NMR (400 MHz, δ in ppm, DMSO-$d_6$): 0.83 (t, J=7 Hz, 3H), 1.32 (sxt, J=7 Hz, 2H), 1.63 (quin, J=8 Hz, 2H), 2.90 (t, J=8 Hz, 2H), 3.73 (s, 3H), 5.75 (s, 2H), 6.92 (d, J=9 Hz, 2H), 7.07 (d, J=9 Hz, 2H), 8.97 (br s, 2H), 15.13 (br s, 1H)

MS method N: RT (min): 1.22; $[M+H]^+$ 346; ES−$[MH-+HCO_2H]^-$: m/z 390

Preparation 10: Intermediate (J) 2-butyl-4,7-dichloro-1-methyl-1H-imidazo[4,5-d]pyridazine

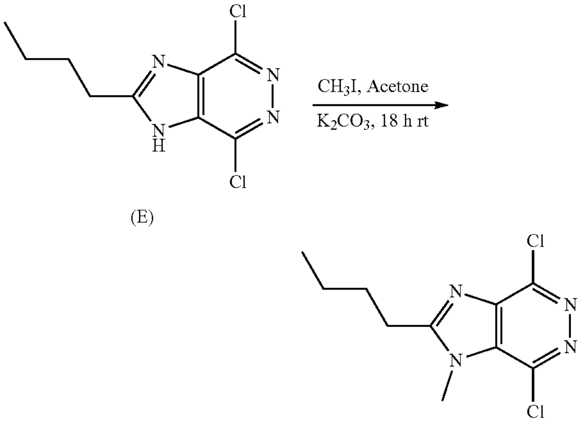

(E)

(J)

To a solution of intermediate (E) (4.9 g, 20 mmol) in acetone (200 mL) was added potassium carbonate (8.29 g, 60 mmol). The suspension was stirred 30 min at rt. Then it was added methyl iodide (1.9 mL, 30 mmol) and the mixture was stirred 18 hours at rt. The reaction mixture was filtered, washed with acetone (2×20 mL) and DCM (2×20 mL). The filtrate was concentrated under reduced pressure to give 6.75 g of a yellow solid. The solid was dissolved in EtOAc (250 mL) and washed with water (150 mL) and brine (150 mL). The organic layer was dried over anhydrous $MgSO_4$, filtered and concentrated under vacuum to give 5.1 g of yellow solid.

The product was purified by a silica gel column chromatography on a Merck cartridge (300 g 15-40 μm silica) using as eluent a mixture DCM/MeOH/$CH_3CN$ (96/2/2) to afford the expected product (J) (3.64 g, 70% yield) as a yellow solid.

$^1$H NMR (400 MHz, δ in ppm, DMSO-$d_6$): 0.95 (t, J=7.4 Hz, 3H); 1.43 (m, 2H); 1.79 (m, 2H); 3.00 (m, 2H); 4.04 (s, 3H)

MS method N: RT (min): 1.32; $[M+H]^+$ 259

Preparation 11: Intermediate (K) 2-butyl-7-chloro-1-methyl-1H-imidazo[4,5-d]pyridazin-4-amine

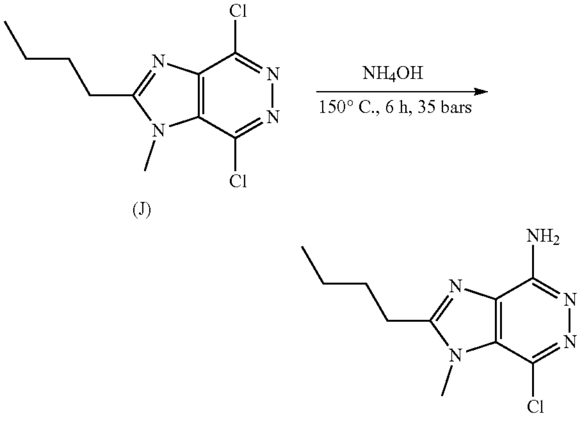

(J)

(K)

A mixture of intermediate (J) (3.64 g, 14 mmol) and ammonia solution (100 mL, 35%) were introduced into an autoclave and heated 6 hours at 150° C. under 35 bars. The solid was dissolved into 100 mL of MeOH and concentrated under vacuum to give 4.16 g of crude product. The product was poured into water (100 mL) and stirred 1 h at rt. The suspension was filtered, washed with water and dried to afford expected product (K) (1.44 g, 43% yield) as a beige solid.

$^1$H NMR (400 MHz, δ in ppm, DMSO-$d_6$): 0.93 (t, J=7.4 Hz, 3H); 1.41 (m, 2H); 1.74 (m, 2H); 2.90 (m, 2H); 3.95 (s, 3H); 6.63 (s broad, 2H)

MS method N: RT (min): 0.84; $[M+H]^+$ 240

Preparation 12: Intermediate (L) 2-butyl-7-chloro-N,N-bis(2,4-dimethoxybenzyl)-1H-imidazo[4,5-d]pyridazin-4-amine

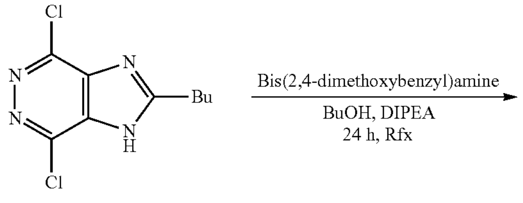

(E)

-continued

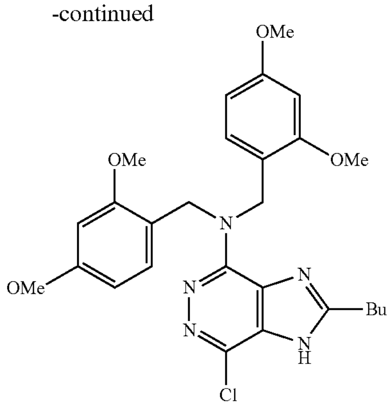

(L)

To a solution of intermediate (E) (15 g, 61.20 mmol) in n-butanol (150 mL) was added DIPEA (107 mL, 612.63 mmol) and bis(2,4-dimethoxybenzyl)amine (7 g, 22.1 mmol). The reaction mixture was refluxed during 1 hour. A further 5 g (15.8 mmol) of bis(2,4-dimethoxybenzyl)amine were added and the heating was continued for 1 hour. This operation was repeated twice again (2×5 g, 31.5 mmol). The resulting mixture was heated overnight. After cooling to room temperature, the reaction mixture was concentrated under reduced pressure to remove most of n-butanol. The residue was diluted with DCM (500 mL), then washed with $H_2O$ (250 mL), brine (200 mL), dried over anhydrous $MgSO_4$, filtered and the filtrate was concentrated under reduced pressure to give 38.8 g of crude product. The residue was purified by chromatography on a Merck cartridge (800 g of 15-40 μm silica) using as eluent DCM/Acetone 96/4 to 90/10 to give compound (L) (12 g, 37% yield) as a pale-yellow solid.

$^1$H NMR (400 MHz, δ in ppm, DMSO-$d_6$): 0.85 (t, J=7.4 Hz, 3H); 1.28 (m, 2H); 1.68 (m, 2H); 2.82 (t, J=7.6 Hz, 2H); 3.72 (s, 12H); 5.07 (s broad, 4H); 6.39 (dd, J=2.4 & 8.4 Hz, 2H); 6.54 (d, J=2.4 Hz, 2H); 6.95 (d, J=8.4 Hz, 2H); 13.35 (s broad, 1H)

MS method N: RT (min): 1.59; $[M+H]^+$ 526

Preparation 13: Intermediate (M) 2-butyl-N,N-bis(2,4-dimethoxybenzyl)-7-isopropoxy-1H-imidazo[4,5-d]pyridazin-4-amine

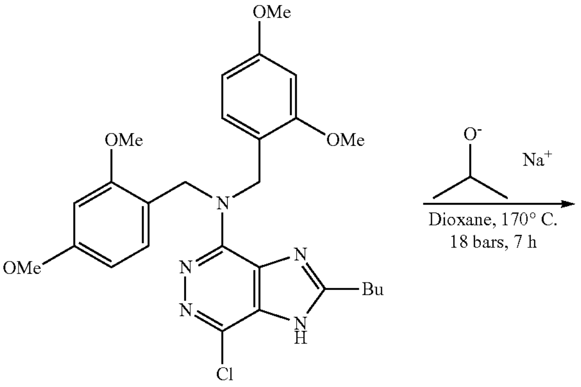

(L)

-continued

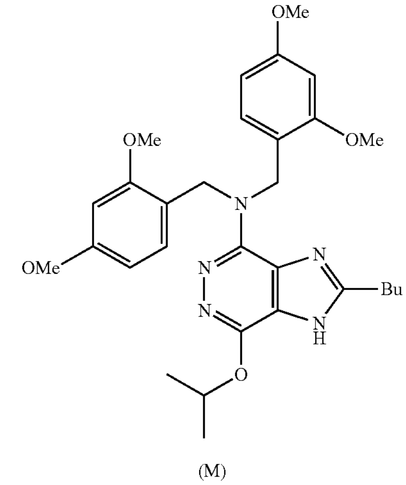

(M)

-continued

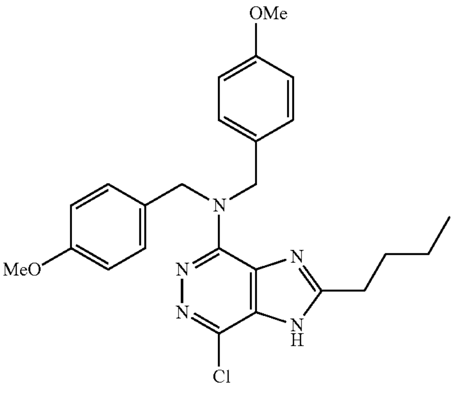

(N)

To a suspension of intermediate (L) (4 g, 7.60 mmol) in dioxane (30 mL) was added sodium isopropoxide (3.74 g, 45.62 mmol) and 2-propanol (30 mL, 1.05 mol). The mixture was heated at 170° C. under 18 bars for 7 hours. The reaction mixture was cooled and filtered, and the cake was washed with EtOAc (100 mL). The filtrate was concentrated under reduced pressure. The crude product was dissolved with EtOAc (150 mL) then washed with $H_2O$ (2×75 mL), brine (75 mL), dried over anhydrous $MgSO_4$, filtered and the filtrate was concentrated under reduced pressure to give 4.37 g of product. The residue was purified by chromatography on a Merck cartridge (200 g of 15-40 μm silica) with an EtOAc/Heptane (55/45) elution. Compound (M) (2.11 g, 50% yield) was obtained as a white solid.

$^1$H NMR (400 MHz, δ in ppm, DMSO-$d_6$): 0.84 (t, J=7.4 Hz, 3H); 1.26 (m, 2H); 1.37 (d, J=6.2 Hz, 6H); 1.66 (m, 2H); 2.77 (t, J=7.6 Hz, 2H); 3.70 (s, 6H); 3.71 (s, 6H); 5.00 (s broad, 4H); 5.41 (sept, J=6.2 Hz, 1H); 6.38 (dd, J=2.4 & 8.4 Hz, 2H); 6.52 (d, J=2.4 Hz, 2H); 6.94 (d, J=8.4 Hz, 2H); 13.01 (s broad, 1H)

MS method N: RT (min): 1.58; $[M+H]^+$ 550

Preparation 14: Intermediate (N) 2-butyl-7-chloro-N,N-bis(4-methoxybenzyl)-1H-imidazo[4,5-d]pyridazin-4-amine

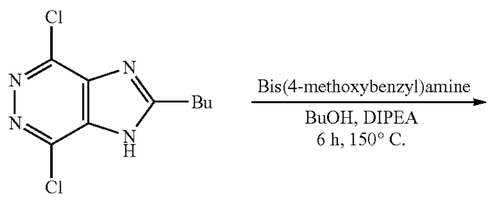

(E)

To a solution of intermediate (E) (1.6 g, 6.53 mmol) in n-butanol (8 mL), in a microwave vial, was added DIPEA (3.42 mL, 19.58 mmol) and bis(4-methoxybenzyl)amine (1.68 g, 6.53 mmol). The resulting mixture was stirred 5 mins at rt, and then heated at 150° C. during 6 h under microwave. After cooling to room temperature, the reaction mixture was filtered. And the filtrate was concentrated under vacuum to give 3.75 g of crude product, which was purified by chromatography on a Merck cartridge (150 g of 15-40 μm silica) using as eluent Heptane/EtOAc 90/10 to 20/80 to give compound (N) (1.25 g, 41% yield) as a pale-yellow solid.

$^1$H NMR (400 MHz, δ in ppm, DMSO-$d_6$): 0.86 (t, J=7 Hz, 3H), 1.31 (sxt, J=7 Hz, 2H), 1.72 (quin, J=8 Hz, 2H), 2.86 (t, J=7 Hz, 2H), 3.72 (s, 6H), 5.08 (br s, 4H), 6.86 (d, J=9 Hz, 4H), 7.19 (d, J=9 Hz, 4H), 13.45 (br s, 1H)

MS method N: RT (min): 1.78; $[M+H]^+$ 466

Preparation 15: Intermediate (R) 2-butyl-N,N-bis,4-methoxybenzyl)-7-isopropoxy-1H-imidazo[4,5-d]pyridazin-4-amine

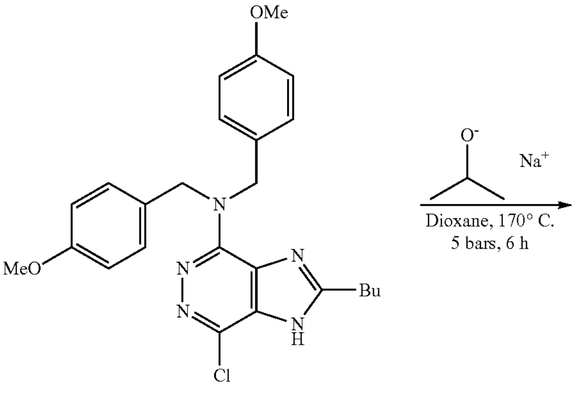

(N)

-continued

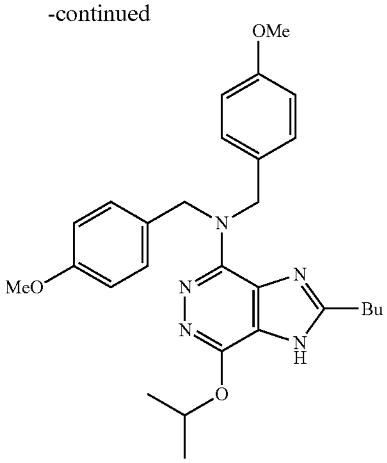

(R)

To a solution of isopropanol (11 mL), was added under stirring, sodium (418.6 mg, 18.03 mmol), the mixture was heated at 70° C. until the end of hydrogen bubbling. The hot sodium isopropoxide solution was added quickly into a microwave vial containing 2-butyl-7-chloro-N,N-bis(4-methoxybenzyl)-1H-imidazo[4,5-d]pyridazin-4-amine, intermediate (N) (1.2 g, 2.58 mmol) in dioxane (8 mL). The mixture was heated at 170° C. under 5 bars for 6 hours and kept overnight. The reaction mixture was filtered and washed with EtOAc to give 1.94 g of crude product. The crude product was dissolved with EtOAc (100 mL) under stirring to give a suspension, which was filtered and washed with EtOAc. The filtrate was concentrated under reduced pressure to give 1.63 g of crude material which was purified by chromatography on a Merck cartridge (150 g of 15-40 μm silica) with eluant EtOAc/Heptane 20/80 to 80/20. Compound (R) (0.76 g, 60% yield) was obtained as a white solid. $^1$H NMR (400 MHz, δ in ppm, DMSO-$d_6$): 0.86 (t, J=7 Hz, 3H), 1.30 (sxt, J=7 Hz, 2H), 1.39 (d, J=6 Hz, 6H), 1.71 (quin, J=7 Hz, 2H), 2.82 (t, J=7 Hz, 2H), 3.71 (s, 6H), 4.98 (s, 4H), 5.44 (spt, J=6 Hz, 1H), 6.84 (d, J=9 Hz, 4H), 7.16 (d, J=8 Hz, 4H), 13.11 (s, 1H)

MS method O: RT (min): 2.79; $[M+H]^+$ 490

EXAMPLES

Example (1): Preparation of Compound 1: 2-butyl-7-isopropoxy-1-(4-methoxybenzyl)-1H-imidazo[4,5-d]pyridazin-4-amine

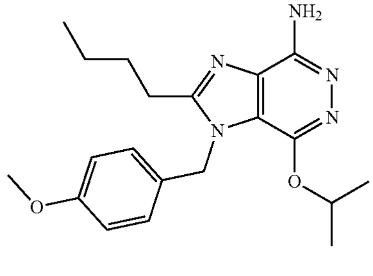 [SMILES: CCCCc1nc2c(N)nnc(OC(C)C)c2n1Cc1ccc(OC)cc1]

To a suspension of potassium hydroxide (250 mg, 3.79 mmol) in anhydrous $CH_3CN$ (2 mL) was added 2-propanol (500 μL, 6.50 mmol). The mixture was stirred 5 min at rt. Then, 2-butyl-7-chloro-1-(4-methoxybenzyl)-1H-imidazo[4,5-d]pyridazin-4-amine hydrochloride, intermediate (IB) (200 mg, 0.52 mmol), was added. The mixture was heated 2 hours at 150° C. under microwave. The mixture was cooled, filtered, then washed with 2-propanol and ethyl acetate. The filtrate was concentrated under reduced pressure to give 836 mg of crude product. The residue was dissolved in EtOAc (100 mL), washed with $H_2O$, brine, dried over anhydrous $MgSO_4$, filtered and the filtrate was concentrated under reduced pressure to give 242 mg of crude material which was purified by chromatography on a Merck cartridge (10 g of 15-40 μm silica) with a 99/1 to 95/5 EtOAc/EtOH elution. Example (1) (27 mg, 14% yield) was obtained as a white solid.

$^1$H NMR (400 MHz, δ in ppm, DMSO-$d_6$): 0.85 (t, J=7.4 Hz, 3H); 1.25 (d, J=6.2 Hz, 6H); 1.33 (m, 2H); 1.63 (m, 2H); 2.81 (m, 2H); 3.71 (s, 3H); 5.36 (sept, J=6.2 Hz, 1H); 5.51 (s, 2H); 5.91 (s, 2H); 6.90 (d, J=8.8 Hz, 2H); 7.06 (d, J=8.8 Hz, 2H)

MS method N: RT (min): 1.2; $[M+H]^+$ 370.

The following compounds may be made by analogy to Example 1: 48, 50, 52, 54, 56, 57, 58, 65, 68, 69, 72 and 86.

Example (2): Preparation of Compound 2: 2-butyl-N7-isopropyl-1-(4-methoxybenzyl)-1H-imidazo[4,5-d]pyridazine-4,7-diamine

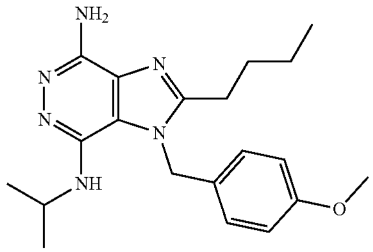 [SMILES: CCCCc1nc2c(N)nnc(NC(C)C)c2n1Cc1ccc(OC)cc1]

To a solution of 2-butyl-7-chloro-1-(4-methoxybenzyl)-1H-imidazo[4,5-d]pyridazin-4-amine, intermediate (IA), (200 mg, 0.58 mol) in 1,4-Dioxane (10 mL) was added isopropyl amine (1.8 mL, 20.85 mmol). The reaction mixture was heated 3 h at 230° C. under microwave. The mixture was concentrated under reduced pressure to give 208 mg of crude product, which was purified by chromatography on a Merck cartridge (10 g of 15-40 μm silica) with a DCM/MeOH/$NH_4OH$ elution 98/2/0.5 to 90/10/0.5. Example (2) (8 mg, 4% yield) was obtained as a white amorphous solid.

$^1$H NMR (400 MHz, δ in ppm, DMSO-$d_6$): 0.87 (t, J=7.4 Hz, 3H); 1.03 (d, J=6.3 Hz, 6H); 1.36 (m, 2H); 1.67 (m, 2H); 2.87 (m, 2H); 3.71 (s, 3H); 4.00 (m, 1H); 4.79 (d, J=6.5 Hz, 1H); 5.59 (s, 2H); 6.10 (s, 2H); 6.90 (d, J=8.9 Hz, 2H); 7.00 (d, J=8.9 Hz, 2H)

MS method A: RT (min): 0.82; $[M+H]^+$ 369.

The following compounds may be made by analogy to Example 2: 49, 53, 71, 94, 98.

Example (3): Preparation of Compound 3: 2-butyl-7-(isopropylthio)-1-(4-methoxybenzyl)-1H-imidazo[4,5-d]pyridazin-4-amine

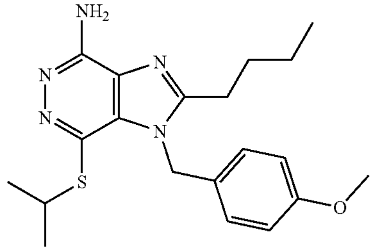 [SMILES: CCCCc1nc2c(N)nnc(SC(C)C)c2n1Cc1ccc(OC)cc1]

To a suspension of potassium hydroxide (150 mg, 2.27 mmol) in acetonitrile (2 mL), was added 2-propanethiol (400 μl, 4.18 mmol). The mixture was stirring 5 min at rt then, 2-butyl-7-chloro-1-(4-methoxybenzyl)-1H-imidazo[4,5-d]pyridazin-4-amine, intermediate (IA), (180 mg, 0.52 mmol) was added. The reaction mixture was heated 2 h at 150° C. under microwave. The mixture was filtered, washed with EtOAc. The filtrate was concentrated under reduced pressure to give 695 mg of crude product, which was purified by chromatography on a Merck cartridge (20 g of 15-40 μm silica) with a 80/20 to 50/50, DCM/DCM-MeOH (90/10) elution. Example (3) (26 mg, 13% yield) was obtained as a white solid.

$^1$H NMR (400 MHz, δ in ppm, DMSO-$d_6$): 0.81 (t, J=7.4 Hz, 3H); 1.22 (d, J=6.8 Hz, 6H); 1.29 (m, 2H); 1.60 (m, 2H); 2.74 (m, 2H); 3.71 (s, 3H); 5.85 (sept, J=6.8 Hz, 1H); 5.74 (s, 2H); 6.46 (s, 2H); 6.90 (m, 4H)

MS method N: RT (min): 1.23; $[M+H]^+$ 386

The following compounds may be made by analogy to Example 3: 99.

Example (4): Preparation of Compound 4: 2-butyl-1-(4-methoxybenzyl)-7-(2-methoxyethoxy)-1H-imidazo[4,5-d]pyridazin-4-amine

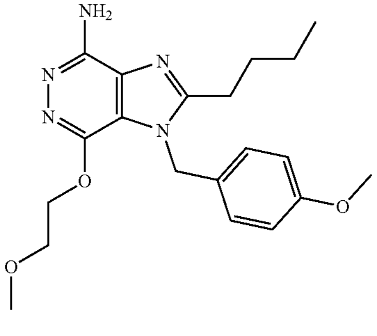 [SMILES: CCCCc1nc2c(N)nnc(OCCOC)c2n1Cc1ccc(OC)cc1]

To a suspension of potassium hydroxide (90 mg, 1.36 mmol), in anhydrous acetonitrile (4 mL) was added 2-methoxyethanol (460.71 μL, 5.78 mmol). The mixture was stirred 5 min at rt, then 2-butyl-7-chloro-1-(4-methoxybenzyl)-1H-imidazo[4,5-d]pyridazin-4-amine, intermediate (IA), (200 mg, 0.58 mmol), was added. The reaction mixture was heated 2 h at 170° C. under microwave. The mixture was filtered, washed with 2-propanol and EtOAc. The filtrate was concentrated under reduced pressure and the residue was purified by chromatography on a Merck cartridge (20 g of 15-40 μm silica) with a 100/0 to 0/100 DCM/DCM-MeOH (95-5) elution. Example (4) (46 mg, 21% yield) was obtained as a white solid.

$^1$H NMR (400 MHz, δ in ppm, DMSO-$d_6$): 0.85 (t, J=7.4 Hz, 3H); 1.33 (m, 2H); 1.63 (m, 2H); 2.82 (m, 2H); 3.25 (s, 3H); 3.65 (m, 2H); 3.71 (s, 3H); 4.50 (m, 2H); 5.52 (s, 2H); 5.98 (s, 2H); 6.89 (d, J=8.7 Hz, 2H); 7.13 (d, J=8.7 Hz, 2H)

MS method N: RT (min): 1.13; $[M+H]^+$ 386

Example (5): Preparation of Compound 5: 2-butyl-1-(4-methoxybenzyl)-7-propoxy-1H-imidazo[4,5-d]pyridazin-4-amine

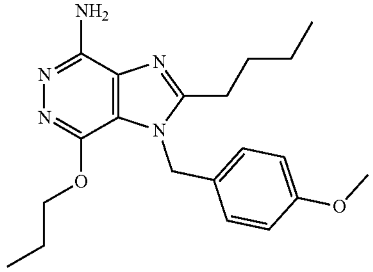 [SMILES: CCCCc1nc2c(N)nnc(OCCC)c2n1Cc1ccc(OC)cc1]

Sodium (43 mg, 1.87 mmol) was added to 1-propanol (3 mL, 39.73 mmol) and the mixture was stirred until the end of hydrogen bubbling. The sodium propoxide solution was added to a mixture of 2-butyl-7-chloro-1-(4-methoxybenzyl)-1H-imidazo[4,5-d]pyridazin-4-amine hydrochloride, intermediate (IB), (200 mg, 0.52 mmol) and triethylamine (150 μL, 1.07 mmol), in a microwave reactor, and the reaction mixture was heated 2 h at 150° C. under microwave. The mixture was filtered, and the filtrate was concentrated under reduced pressure. The residue was dissolved in EtOAc, washed with water and brine. The organic layer was dried over anhydrous $MgSO_4$, filtered and concentrated under reduced pressure to give 147 mg of crude product, which was purified by chromatography on a Merck cartridge (10 g of 15-40 μm silica) with a 90/10 to 80/20 DCM/DCM-MeOH-MeCN (80-10-10) elution. Example (5) (73 mg, 38% yield) was obtained as a white solid.

$^1$H NMR (400 MHz, δ in ppm, DMSO-$d_6$): 0.84 (t, J=7.4 Hz, 3H); 0.89 (t, J=7.4 Hz, 3H); 1.32 (m, 2H); 1.61 (m, 2H); 1.70 (m, 2H); 2.79 (m, 2H); 3.71 (s, 3H); 4.32 (t, J=6.4 Hz, 2H); 5.54 (s, 2H); 5.97 (s, 2H); 6.90 (d, J=8.8 Hz, 2H); 7.06 (d, J=8.8 Hz, 2H)

MS method N: RT (min): 1.2; $[M+H]^+$ 370

Example (6): Preparation of Compound 6: 7-(allyloxy)-2-butyl-1-(4-methoxybenzyl)-1H-imidazo[4,5-d]pyridazin-4-amine

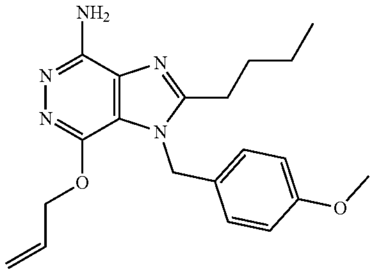 [SMILES: C=CCOc1nnc(N)c2nc(CCCC)n(Cc3ccc(OC)cc3)c12]

Sodium (43 mg, 1.87 mmol) was added to allyl alcohol (3 mL, 43.47 mmol) and the mixture was stirred at rt until the end of hydrogen bubbling. The sodium allyl oxide solution was added to 2-butyl-7-chloro-1-(4-methoxybenzyl)-1H-imidazo[4,5-d]pyridazin-4-amine, intermediate (IA), (200 mg, 0.58 mmol), in a microwave reactor, and the reaction mixture was heated 2 h at 150° C. under microwave. The mixture was filtered, and the filtrate was concentrated under reduced pressure. The residue was dissolved with EtOAc, washed with water and brine. The organic layer was dried over anhydrous $MgSO_4$, filtered and concentrated under reduced pressure to give 496 mg of crude product, which was purified by chromatography on a Merck cartridge (10 g of 15-40 μm silica) with a 80/20 to 0/100 DCM/DCM-MeOH (90-10) elution. Example (6) (43 mg, 20% yield) was obtained as a white solid.

$^1$H NMR (400 MHz, δ in ppm, DMSO-$d_6$): 0.84 (t, J=7.4 Hz, 3H); 1.32 (m, 2H); 1.61 (m, 2H); 2.80 (m, 2H); 3.71 (s, 3H); 4.93 (td, J=1.6 & 5.21 Hz, 2H); 5.19 (qd, J=1.6 & 10.5 Hz, 1H); 5.30 (qd, J=1.6 & 17.3 Hz, 1H); 5.54 (s, 2H); 6.00 (s, 2H); 6.06 (m, 1H); 6.89 (d, J=8.9 Hz, 2H); 7.07 (d, J=8.9 Hz, 2H) MS method N: RT (min): 1.17; $[M+H]^+$ 368

Example (7): Preparation of Compound 7: 7-(sec-butoxy)-2-butyl-1-(4-methoxybenzyl)-1H-imidazo[4,5-d]pyridazin-4-amine

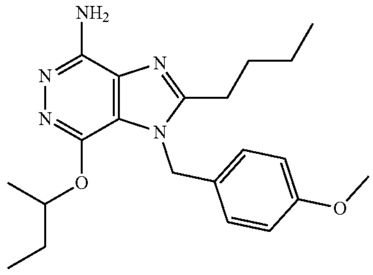 [SMILES: CCCCc1nc2c(N)nnc(OC(C)CC)c2n1Cc1ccc(OC)cc1]

Sodium (43 mg, 1.87 mmol) was added to 2-butanol (3 mL, 32.46 mmol) and the mixture was stirred at rt until the end of hydrogen bubbling. The sodium 2-butoxide solution was added to a mixture of 2-butyl-7-chloro-1-(4-methoxybenzyl)-1H-imidazo[4,5-d]pyridazin-4-amine hydrochloride, intermediate (IB) (200 mg, 0.52 mmol) and triethylamine (150 μL, 1.07 mmol) in a microwave reactor and the reaction mixture was heated 2h at 150° C. under microwave. The mixture was filtered, and the filtrate was concentrated under reduced pressure. The residue was dissolved with EtOAc, washed with water and brine. The organic layer was dried over anhydrous $MgSO_4$, filtered and concentrated under reduced pressure to give 165 mg of crude product, which was purified on a Gilson GX271 system, by using a CSH 50×250 mm, 5 μm column (Waters™) operating at 150 ml/min and at room temperature. The following A/B gradient was used: t=0 min: 18% of solution B, t=5 min: 18% of solution B, t=25 min: 38% of solution B, with A: water/formic acid 0.1% (v/v) and B: acetonitrile/formic acid 0.1% (v/v). Example (7) (82 mg, 41% yield) was obtained as a white amorphous solid.

$^1$H NMR (400 MHz, δ in ppm, DMSO-$d_6$): 0.81 (t, J=7.4 Hz, 3H); 0.85 (t, J=7.4 Hz, 3H); 1.22 (d, J=6.2 Hz, 3H); 1.33 (m, 2H); 1.55 to 1.67 (m, 4H); 2.79 (m, 2H); 3.71 (s, 3H); 5.23 (m, 1H); 5.50 (d, J=16.2 Hz, 1H); 5.55 (d, J=16.2 Hz, 1H); 5.97 (s, 2H); 6.78 (d, J=8.9 Hz, 2H); 7.03 (d, J=8.9 Hz, 2H)

MS method N: RT (min): 1.28; $[M+H]^+$ 384

Example (8): Preparation of Compound 8: 7-butoxy-2-butyl-1-(4-methoxybenzyl)-1H-imidazo[4,5-d]pyridazin-4-amine

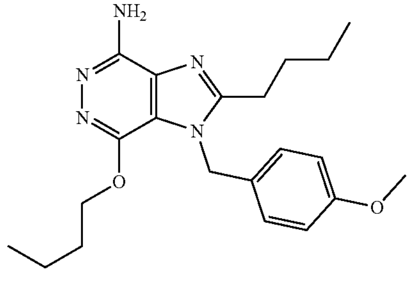 [SMILES: CCCCOc1nnc(N)c2nc(CCCC)n(Cc3ccc(OC)cc3)c12]

Sodium (86 mg, 3.74 mmol) was added to 1-Butanol (3 mL, 32.46 mmol) and the mixture was stirred at rt until the end of hydrogen bubbling. The sodium butoxide solution was added to a mixture of 2-butyl-7-chloro-1-(4-methoxybenzyl)-1H-imidazo[4,5-d]pyridazin-4-amine hydrochloride, intermediate (IB), (200 mg, 0.52 mmol) and Triethylamine (150 μL, 1.07 mmol) in a microwave reactor and the reaction mixture was heated 2 h at 150° C. under microwave. The mixture was concentrated under reduced pressure and the residue was dissolved with EtOAc, washed with water and brine. The organic layer was dried over anhydrous $MgSO_4$, filtered and concentrated under reduced pressure to give 156 mg of crude product, which was purified by chromatography on a Merck cartridge (10 g of 15-40 μm silica) with a 90/10 to 80/20 DCM/DCM80-MeOH10-MeCN10 elution. Example (8) (59 mg, 29% yield) was obtained as a white solid.

$^1$H NMR (400 MHz, δ in ppm, DMSO-$d_6$): 0.84 (t, J=7.4 Hz, 3H); 0.85 (t, J=7.4 Hz, 3H); 1.31 (m, 4H); 1.63 (m, 4H); 2.80 (m, 2H); 3.71 (s, 3H); 4.36 (t, J=6.5 Hz, 2H); 5.53 (s, 2H); 5.96 (s, 2H); 6.90 (d, J=8.8 Hz, 2H); 7.03 (d, J=8.8 Hz, 2H)

MS method N: RT (min): 1.25; $[M+H]^+$ 384; ES−: $[M-H+HCO_2H]^-$: m/z 428

Example (9): Preparation of Compound 9: 2-butyl-7-(cyclopentyloxy)-1-(4-methoxybenzyl)-1H-imidazo[4,5-d]pyridazin-4-amine

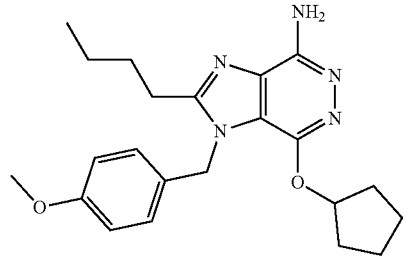 [SMILES: CCCCc1nc2c(N)nnc(OC3CCCC3)c2n1Cc1ccc(OC)cc1]

A mixture of cyclopentanol (1.5 mL, 16.34 mmol) and sodium (93.11 mg, 4.05 mmol) was stirred at 80° C. for 1 h. Then, a solution of 2-butyl-7-chloro-1-(4-methoxybenzyl)-1H-imidazo[4,5-d]pyridazin-4-amine, intermediate (IA), (0.2 g, 58 mmol) in 1,4-Dioxane (4 mL) was added and the mixture was heated at 170° C. under microwave for 6 h. The reaction mixture was concentrated under reduced pressure to afford 310 mg of crude product, which was purified by chromatography on a Merck cartridge (20 g of 15-40 μm silica) with DCM/MeOH (95/5) elution, to afford 63 mg (26.5%, yield) of Example (9) as a white solid.

$^1$H NMR (400 MHz, δ in ppm, DMSO-$d_6$): 0.83 (t, J=7.40 Hz, 3H) 1.32 (sxt, J=7.60, 2H) 1.45-1.76 (m, 8H) 1.78-1.94 (m, 2H) 2.78 (t, J=7.60 Hz, 2H) 3.70 (s, 3H) 5.42-5.57 (m, 3H) 5.92 (s, 2H) 6.89 (d, J=8.78 Hz, 2H) 7.01 (d, J=8.78 Hz, 2H)

MS method A: RT (min): 0.96; $[M+H]^+$ 396

Example (10): Preparation of Compound 10: 2-butyl-1-(4-methoxybenzyl)-7-(pyrrolidin-1-yl)-1H-imidazo[4,5-d]pyridazin-4-amine

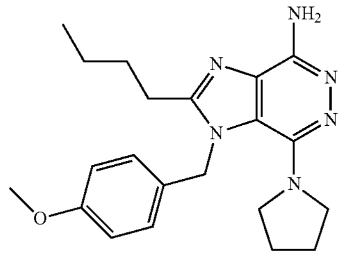 [SMILES: CCCCc1nc2c(N)nnc(N3CCCC3)c2n1Cc1ccc(OC)cc1]

A mixture of 2-butyl-7-chloro-1-(4-methoxybenzyl)-1H-imidazo[4,5-d]pyridazin-4-amine, intermediate (IA) (0.2 g, 0.58 mmol) in pyrrolidine (2 mL, 23.72 mmol) and water (1 mL) was stirred at 160° C. under microwave for 4 h. The reaction mixture was concentrated under reduced pressure to afford 347 mg of crude product, which was purified by chromatography on a Merck cartridge (20 g of 15-40 μm silica) with DCM/MeOH (90/10) elution, to afford 20 mg (9.1%, yield) of Example (10) as a white foam.

$^1$H NMR (400 MHz, δ in ppm, DMSO-$d_6$): 0.83 (t, J=7.5 Hz, 3H); 1.31 (m, 2H); 1.63 (m, 2H); 1.82 (m, 4H); 2.70 (m, 2H); 3.15 (m, 4H); 3.71 (s, 3H); 5.62 (s, 2H); 6.11 (s, 2H); 6.88 (d, J=8.9 Hz, 2H); 6.96 (d, J=8.9 Hz, 2H)

MS method N: RT (min): 1.26; $[M+H]^+$ 381

Example (11): Preparation of Compound 11: 2-butyl-1-(4-methoxybenzyl)-7-(1-methyl-1H-pyrrol-3-yl)-1H-imidazo[4,5d]pyridazin-4-amine

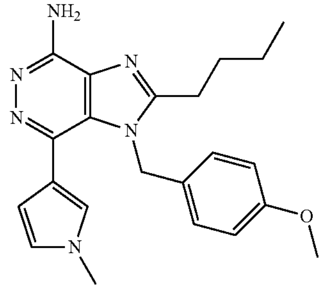 [SMILES: CCCCc1nc2c(N)nnc(-c3ccn(C)c3)c2n1Cc1ccc(OC)cc1]

In a microwave vial was added a solution of 2-butyl-7-chloro-1-(4-methoxybenzyl)-1H-imidazo[4,5-d]pyridazin-4-amine, intermediate (IA), (250 mg, 0.72 mmol) in 1,4-Dioxane (5 mL), followed by addition of Pd(dppf)$Cl_2$·DCM (88.55 mg, 0.11 mmol), 1-Methyl-3-(4,4,5,5-tetramethyl-1,3,2-dioxa borolan-2-yl)-1H pyrrole (224.55 mg, 1.08 mmol) and finally 2M aqueous solution of $Cs_2CO_3$ (1.45 mL, 2.89 mmol). The mixture was heated at 135° C. for 60 min under microwave. The solvent was evaporated under reduced pressure, and the residue was dissolved in DCM and washed with a saturated aqueous solution of $NaHCO_3$. The organic layer was separated, dried over $MgSO_4$, filtered and evaporated under reduced pressure. The crude material was purified by silica gel chromatography using as eluent a mixture $CHCl_3$/iPrOH (90/10) to give 18.3 mg (6.5%, yield) of Example (11) as a creamy solid.

$^1$H NMR (400 MHz, δ in ppm, DMSO-$d_6$): 0.83 (t, J=7.4 Hz, 3H); 1.31 (m, 2H); 1.63 (m, 2H); 2.71 (m, 2H); 3.60 (s, 3H); 3.68 (m, 3H); 5.32 (s, 2H); 6.08 (dd, J=1.9 & 2.5 Hz, 1H); 6.28 (s, 2H); 6.68 (d, J=8.9 Hz, 2H); 6.72 (m, 2H); 6.81 (d, J=8.3 Hz, 2H)

MS method N: RT (min): 1.18; $[M+H]^+$ 391

The following compounds may be made by analogy to Example 11: 55, 62, 63, 64, 67, 70, 92, 93, 95, 96 and 97.

Example (12 A): Preparation of Compound 12: (E)-2-butyl-1-(4-methoxybenzyl)-7-(3-methylbut-1-en-1-yl)-1H-imidazo[4,5-d]pyridazin-4-amine and Example (12 B): Preparation of Compound 13: 2-butyl-7-isopentyl-1-(4-methoxybenzyl)-1H-imidazo[4,5-d]pyridazin-4-amine Step 1: Example (12 A): Preparation of Compound 12: (E)-2-butyl-1-(4-methoxybenzyl)-7-(3-methyl-but-1-en-1-yl)-1H-imidazo[4,5-d]pyridazin-4-amine

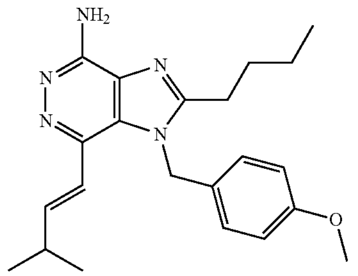 [SMILES: CCCCc1nc2c(N)nnc(/C=C/C(C)C)c2n1Cc1ccc(OC)cc1]

In a microwave vial was added 2-butyl-7-chloro-1-(4-methoxybenzyl)-1H-imidazo[4,5-d]pyridazin-4-amine, intermediate (IA), (500 mg, 1.45 mmol) in 1,4-Dioxane (10 mL), followed by addition of Pd(dppf)$Cl_2$·DCM (177.10 mg, 0.22 mmol), (E)-4,4,5,5-tetramethyl-2-(3-methylbut-1-en-1-yl)-1,3,2-dioxaborolane (567 mg, 2.89 mmol) and finally a 2M aqueous solution of $Cs_2CO_3$ (2.89 mL, 5.78 mmol). The mixture was heated at 120° C. for 1 h 30 min under microwave. The solvent was evaporated under reduced pressure and the residue was diluted with DCM, and washed with a saturated aqueous solution of $NaHCO_3$. The organic layer was separated, dried over $MgSO_4$, filtered and evaporated under reduced pressure. The crude material was purified by silica gel chromatography using as eluent a mixture DCM/$NH_3$ in MeOH (2N) (97/3) to give 70 mg (12.7%, yield) as a beige solid.

$^1$H NMR (400 MHz, δ in ppm, DMSO-$d_6$): 0.86 (t, J=7.5 Hz, 3H); 0.92 (d, J=6.8 Hz, 6H); 1.35 (m, 2H); 1.68 (m, 2H); 2.34 (m, 1H); 2.87 (m, 2H); 3.70 (s, 3H); 5.55 (s, 2H); 6.37

(s, 2H); 6.44 (dd, J=5.9 & 15.5 Hz, 1H); 6.51 (d, J=15.5 Hz, 1H); 6.86 (d, J=9.1 Hz, 2H); 6.90 (d, J=9.1 Hz, 2H)

MS method N: RT (min): 1.33; $[M+H]^+$ 380

Step 2: Example (12B) Preparation of Compound 13: 2-butyl-7-isopentyl-1-(4-methoxybenzyl)-1H-imidazo[4,5-d]pyridazin-4-amine

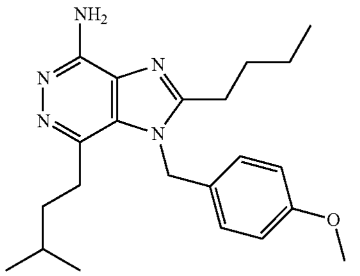 [SMILES: CCCCc1nc2c(N)nnc(CCC(C)C)c2n1Cc1ccc(OC)cc1]

To a solution of (E)-2-butyl-1-(4-methoxybenzyl)-7-(3-methylbut-1-en-1-yl)-1H-imidazo[4,5-d]pyridazin-4-amine Example (12A) (40 mg, 0.11 mmol) in MeOH (7 mL) was added Pd/C 10% (23 mg). The mixture was kept under Hydrogen atmosphere (4 bars) at 30° C. for 1 h 30 min. The mixture was filtered through a 0.2 μm filter membrane and the filtrate was evaporated under reduced pressure to give 28 mg (67%, yield) of Example (12B) as a cream solid.

$^1$H NMR (400 MHz, δ in ppm, DMSO-$d_6$): 0.79 (d, J=6.6 Hz, 6H); 0.85 (t, J=7.4 Hz, 3H); 1.29 to 1.40 (m, 4H); 1.48 (m, 1H); 1.68 (m, 2H); 2.74 to 2.84 (m, 4H); 3.70 (s, 3H); 5.52 (s, 2H); 6.20 (s, 2H); 6.79 (d, J=8.7 Hz, 2H); 6.91 (d, J=8.7 Hz, 2H) MS method N: RT (min): 1.41; $[M+H]^+$ 382

The following compounds may be made by analogy to Example 12:51, 59, 60, 61, 66 and 73.

Example (13): Preparation of Compound 14: 2-butyl-1-(4-methoxybenzyl)-7-(1H-pyrrol-3-yl)-1H-imidazo[4,5-d]pyridazin-4-amine

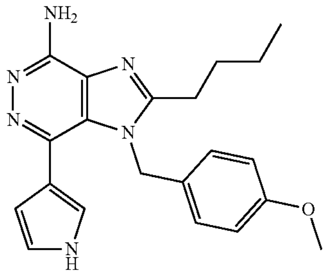 [SMILES: CCCCc1nc2c(N)nnc(-c3cc[nH]c3)c2n1Cc1ccc(OC)cc1]

In a microwave vial was added a solution of 2-butyl-7-chloro-1-(4-methoxybenzyl)-1H-imidazo[4,5-d]pyridazin-4-amine, intermediate (IA), (150 mg, 0.43 mmol) in 1,4-Dioxane (3 mL), followed by addition of Pd(dppf)$Cl_2$·DCM (53.13 mg, 0.065 mmol), 3-(4,4,5,5-tetramethyl-1,3,2-dioxaborolan-2-yl)-1H-pyrrole (167.47 mg 0.87 mmol) and finally 2M aqueous solution of $Cs_2CO_3$ (867.48 μL, 1.73 mmol). The mixture was heated at 110° C. for 60 min under microwave and at 130° C. for 45 min. Then the solvent was evaporated under reduced pressure, and the residue was dissolved in DCM and washed with a saturated aqueous solution of $NaHCO_3$. The organic layer was separated, dried over $MgSO_4$, filtered and evaporated under reduced pressure. The crude material was purified by silica gel chromatography using as eluent a mixture 97/3 DCM/$NH_3$ in MeOH (2N) to give 41.24 mg (25.5%, yield) of Example (13) as a white solid.

$^1$H NMR (400 MHz, δ in ppm, DMSO-$d_6$): 0.82 (t, J=7.5 Hz, 3H); 1.29 (m, 2H); 1.61 (m, 2H); 2.69 (m, 2H); 3.68 (s, 3H); 5.31 (s, 2H); 6.16 (dt, J=1.8 & 2.5 Hz, 1H); 6.26 (s, 2H); 6.69 (d, J=9.0 Hz, 2H); 6.80 (m, 3H); 6.85 (td, J=1.8 & 2.5 Hz, 1H); 11.00 (s, 1H)

MS method N: RT (min): 1.15; $[M+H]^+$ 377; ES−: $[M-H+HCO_2H]^-$: m/z 421

Example (14A): Preparation of Compound 15: 2-butyl-7-(cyclopent-1-en-1-yl)-1-(4-methoxybenzyl)-1H-imidazo[4,5-d]pyridazin-4-amine hydrochloride and Example (14B): Preparation of Compound 16: 2-butyl-7-cyclopentyl-1-(4-methoxybenzyl)-1H-imidazo[4,5-d]pyridazin-4-amine Step 1: Example (14A): Preparation of Compound 15: 2-butyl-7-(cyclopent-1-en-1-yl)-1-(4-methoxybenzyl)-1H-imidazo[4,5-d]pyridazin-4-amine hydrochloride

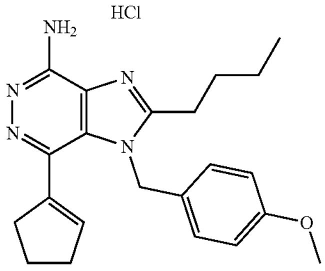 [SMILES: Cl ; CCCCc1nc2c(N)nnc(C3=CCCC3)c2n1Cc1ccc(OC)cc1]

In a microwave vial was added a solution of 2-butyl-7-chloro-1-(4-methoxybenzyl)-1H-imidazo[4,5-d]pyridazin-4-amine, intermediate (IA), (250 mg, 0.72 mmol) in a mixture of Me-THF/DMF (8/2, 4 mL), followed by addition of Pd(dppf)$Cl_2$·DCM (88.55 mg, 0.11 mmol), cyclopent-1-en-1-ylboronic acid (121.38 mg, 1.08 mmol) and finally 2M aqueous solution of $Cs_2CO_3$ (1.45 mL, 2.89 mmol). The mixture was heated at 100° C. for 2 h under microwave. It was then diluted with Me-THF and washed with $H_2O$ and with a saturated aqueous solution of NaCl. The organic layer was separated, dried over $MgSO_4$, filtered and evaporated under reduced pressure. The crude material was purified by silica gel chromatography using as eluent a mixture DCM/MeOH 98/2. The first fractions containing expected compound, was evaporated to dryness and then dissolved in $Et_2O$, and at 0° C. was added a solution 2M of HCl in $Et_2O$. The resulting solid was filtered and dried under vacuum to give 37 mg (12.4%, yield) of Example (14A). A second fraction containing expected compound was evaporated to dryness to give 70 mg of as free base and engaged in the next step as it.

$^1$H NMR (400 MHz, δ in ppm, DMSO-$d_6$): 0.86 (t, J=7.5 Hz, 3H); 1.36 (m, 2H); 1.70 (m, 2H); 1.80 (m, 2H); 2.31 (m, 2H); 2.47 (m, 2H); 2.91 (m, 2H); 3.71 (s, 3H); 5.51 (s, 2H); 6.00 (m, 1H); 6.81 (d, J=8.9 Hz, 2H); 6.89 (d, J=8.9 Hz, 2H); 8.82 (m broad, 2H); 14.60 (s broad, 1H)

MS method N: RT (min): 1.27; $[M+H]^+$ 378

Step 2: Example (14B): Preparation of Compound 16: 2-butyl-7-cyclopentyl-1-(4-methoxybenzyl)-1H-imidazo[4,5-d]pyridazin-4-amine

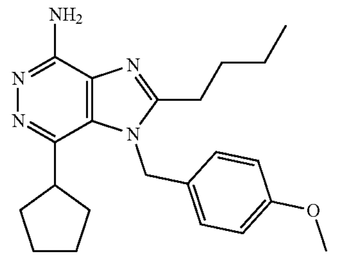 [SMILES: CCCCc1nc2c(N)nnc(C3CCCC3)c2n1Cc1ccc(OC)cc1]

To a solution of 2-butyl-7-(cyclopent-1-en-1-yl)-1-(4-methoxybenzyl)-1H-imidazo[4,5-d]pyridazin-4-amine (70 mg, 0.19 mmol), from Step 1, in MeOH (6 mL) was added platinum (IV) oxide hydrate (13 mg). The mixture was kept under Hydrogen atmosphere (2 bars) at 25° C. for 1 h 50 min. The mixture was filtered through a 0.2 μm filter membrane and the filtrate was evaporated under reduced pressure. The obtained crude material was purified by silica gel chromatography using as eluent a mixture DCM/MeOH (98/2) to give 46 mg (63.8%, yield) of Example (14B) as a white solid.

$^1H$ NMR (400 MHz, δ in ppm, DMSO-$d_6$): 0.85 (t, J=7.5 Hz, 3H); 1.35 (m, 2H); 1.52 (m, 2H); 1.61 to 1.83 (m, 8H); 2.88 (m, 2H); 3.45 (m, 1H); 3.72 (s, 3H); 5.66 (s, 2H); 6.92 (s, 4H); 8.15 (m, 2H)

MS method P: RT (min): 2.36; $[M+H]^+$ 380

Example (15A): Preparation of Compound 17: 2-butyl-1-(4-methoxybenzyl)-7-(prop-1-en-2-yl)-1H-imidazo[4,5-d]pyridazin-4-amine and Example (15B): Preparation of Compound 18: 2-butyl-7-isopropyl-1-(4-methoxybenzyl)-1H-imidazo[4,5-d]pyridazin-4-amine Step 1: Example (15A): Preparation of Compound 17: 2-butyl-1-(4-methoxybenzyl)-7-(prop-1-en-2-yl)-1H-imidazo[4,5-d]pyridazin-4-amine

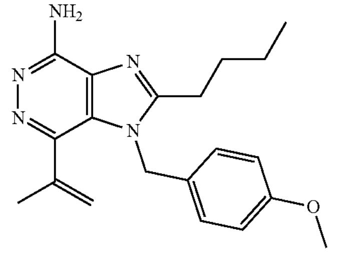 [SMILES: C=C(C)c1nnc(N)c2nc(CCCC)n(Cc3ccc(OC)cc3)c12]

To a suspension of 2-butyl-7-chloro-1-(4-methoxybenzyl)-1H-imidazo[4,5-d]pyridazin-4-amine, intermediate (IA), (200 mg, 0.58 mmol) in 1,4-Dioxane (6 mL) was added Pd(dppf)$Cl_2$·DCM (47.3 mg, 0.58 mmol), 4,4,5,5-Tetramethyl-2-(prop-1-en-2-yl)-1,3,2-dioxaborolane (228.85 μL, 1.16 mmol) and finally a 2M aqueous solution of $Cs_2CO_3$ (809.64 μl, 1.62 mmol). The mixture was heated at reflux for 6 h, then diluted with EtOAc and washed with $H_2O$. The organic layer was separated and washed with an aqueous saturated solution of NaCl solution. The organic layer was separated, dried over $MgSO_4$, filtered and evaporated under reduced pressure. The crude material was purified by silica gel chromatography using as eluent a mixture DCM/MeOH (97/3) to give 88 mg as a creamy foam. The obtained product was triturated with $Et_2O$, filtered and dried to give 71.2 mg (35%, yield) of Example (15A).

$^1H$ NMR (400 MHz, δ in ppm, DMSO-$d_6$): 0.86 (t, J=7.5 Hz, 3H); 1.35 (m, 2H); 1.69 (m, 2H); 1.83 (s broad, 3H); 2.82 (m, 2H); 3.69 (s, 3H); 4.94 (s broad, 1H); 5.36 (s broad, 1H); 5.48 (s, 2H); 6.42 (s, 2H); 6.72 (d, J=8.9 Hz, 2H); 6.86 (d, J=8.9 Hz, 2H)

MS method N: RT (min): 1.22; $[M+H]^+$ 352

Step 2: Example (15B) Preparation of Compound 18: 2-butyl-7-isopropyl-1-(4-methoxybenzyl)-1H-imidazo[4,5-d]pyridazin-4-amine

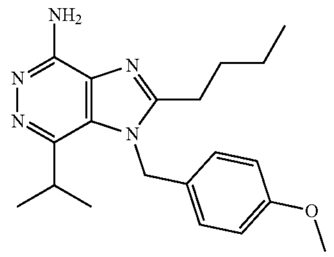 [SMILES: CCCCc1nc2c(N)nnc(C(C)C)c2n1Cc1ccc(OC)cc1]

To a solution of 2-butyl-1-(4-methoxybenzyl)-7-(prop-1-en-2-yl)-1H-imidazo[4,5-d]pyridazin-4-amine (55 mg, 0.16 mmol), Example (15A), in MeOH (6 mL) was added platinum (IV) oxide hydrate (7 mg). The mixture was kept under Hydrogen atmosphere (2 bars) at 25° C. for 2 h. Then platinum (IV) oxide hydrate (7 mg) was added and the mixture was kept under Hydrogen atmosphere (2 bars) at 25° C. for 4 h 30 min. The mixture was filtered through a 0.2 μm filter membrane and the filtrate was evaporated under reduced pressure to give 65 mg of crude product, which was purified by silica gel chromatography using as eluent a mixture $CHCl_3$/iPrOH (94/6) to give 25 mg (44.2%, yield) of Example (15B), as a white solid.

$^1H$ NMR (400 MHz, δ in ppm, DMSO-$d_6$): 0.85 (t, J=7.5 Hz, 3H); 1.11 (d, J=6.7 Hz, 6H); 1.35 (m, 2H); 1.68 (m, 2H); 2.83 (m, 2H); 3.26 (sept, J=6.7 Hz, 1H); 3.70 (s, 3H); 5.53 (s, 2H); 6.19 (s, 2H); 6.82 (d, J=9.0 Hz, 2H); 6.91 (d, J=9.0 Hz, 2H)

MS method N RT (min): 1.23; $[M+H]^+$ 354

The following compound may be made by analogy to Example 15: 159.

Example (16A): Preparation of Compound 19: 1-(((1r,4r)-4-(aminomethyl)cyclohexyl)methyl)-2-butyl-7-isopropoxy-1H-imidazo[4,5-d]pyridazin-4-amine dihydrochloride Step 1: tert-butyl (4-(4-(bis(2,4-dimethoxybenzyl) amino)-2-butyl-7-isopropoxy-1H-imidazo[4,5-d] pyridazin-1-yl)methyl)cyclohexyl)methyl)carbamate

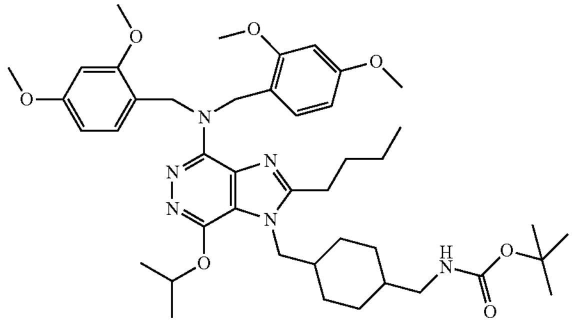 [SMILES: CCCCc1nc2c(N(Cc3ccc(OC)cc3OC)Cc3ccc(OC)cc3OC)nnc(OC(C)C)c2n1CC1CCC(CNC(=O)OC(C)(C)C)CC1]

To a suspension of 2-butyl-N,N-bis(2,4-dimethoxybenzyl)-7-isopropoxy-1H-imidazo[4,5-d]pyridazin-4-amine, intermediate (M) (1 g, 1.82 mmol) in Me-THF (20 mL) was added $Cs_2CO_3$ (1.78 g, 5.46 mmol). The mixture was stirred at rt 30 min. Then tert-butyl n-([(1r,4r)-4(bromomethyl) cyclohexyl]methyl)carbamate (879 mg, 2.73 mmol) in Me-THF (12 mL) was added. The mixture was stirred 5 min at rt then refluxing for 24 hours. After, the reaction mixture was diluted with EtOAc (150 mL), washed with water and brine, concentrated under reduced pressure to give 1.73 g of crude product, which was purified by chromatography on a Merck cartridge (70 g of 15-40 μm silica) with a 0/100 to 50/50 EtOAc/Heptane elution. Expected product (1.03 g, 73% yield) was obtained as a white solid.

$^1$H NMR (400 MHz, δ in ppm, DMSO-$d_6$): 0.75 (m. 2H); 0.83 (t. J=7 Hz. 3H); 1.08 (m. 2H); 1.24 to 1.40 (m. 18H); 1.48 (d. J=12 Hz. 2H); 1.58 to 1.81 (m. 5H); 2.73 (t. J=6 Hz. 2H); 2.77 (t. J=7 Hz. 2H); 3.66 to 3.76 (m. 12H); 4.10 (d. J=6 Hz. 2H); 5.00 (s broad. 4H); 5.37 (spt. J=6 Hz. 1H); 6.39 (dd. J=2 & 8 Hz. 2H); 6.52 (d. J=2 Hz. 2H); 6.78 (t. J=6 Hz. 1H); 6.96 (d, J=8 Hz, 2H)

MS method N: RT (min): 1.87; $[M+H]^+$ 775

Step 2: Example (16A): Preparation of Compound 19: 1-(((1r,4r)-4-(aminomethyl)cyclohexyl)methyl)-2-butyl-7-isopropoxy-1H-imidazo[4,5-d]pyridazin-4-amine dihydrochloride

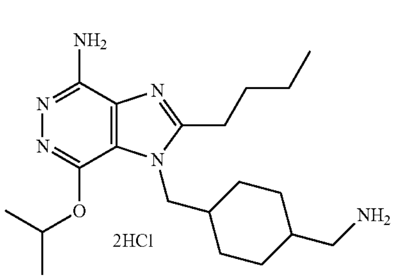 [SMILES: CCCCc1nc2c(N)nnc(OC(C)C)c2n1CC1CCC(CN)CC1]

To a solution of tert-butyl (4-((4-(bis(4-methoxybenzyl) amino)-2-butyl-7-isopropoxy-1H-imidazo[4,5-d]pyridazin-1-yl)methyl)cyclohexyl)methyl)carbamate of Step 1 (1.03 g, 1.33 mmol) in DCM (6 mL) was added 2,2,2-trifluoroacetic acid (6 mL, 77.9 mmol) and 1,3-dimethoxybenzene (522 μL, 3.99 mmol). The mixture was stirred 24 h at rt. The reaction was diluted with DCM (50 mL) and $H_2O$ (10 mL). The pH of the mixture was adjusted to pH 10-12 with 30% NaOH under stirring in an ice bath. The product was extracted with DCM (4×50 mL), the combined organic layers were washed with brine, dried over $MgSO_4$, filtered and concentrated under reduced pressure to give 3.1 g of crude product. The residue was purified by chromatography on a Macherey Nagel cartridge (40 g of 15-40 μm diol) with 100//0 to 50//50 DCM-DCM/MeOH/$H_2O$ (80/10/1) to give an oil. The oil was treated with $iPr_2O$ (10 mL), a white solid was filtered and washed with $iPr_2O$ (3×5 mL) dried in vacuo to give 617 mg of powder. 500 mg of this product was purified with C18 19×150 mm 5 μm column, eluted with ammonium bicarbonate 10 mM (pH10)/acetonitrile to afford 188 mg of material, which was dissolved in HCl in MeOH (1.25N) and the mixture was evaporated under reduced pressure. The residue was then dissolved in water, filtrated over a 0.22 μm membrane, the filtrate was freeze-dried to give 190 mg (39.5%, yield) Example 16A, under hydrochloric acid form (2HCl).

$^1$H NMR (400 MHz, δ in ppm, DMSO-$d_6$):0.87 (q. J=13 Hz. 2H); 0.94 (t. J=7 Hz. 3H); 1.12 (q. J=13 Hz. 2H); 1.33 to 1.48 (m. 8H); 1.51 to 1.63 (m, 3H); 1.66 to 1.92 (m, 5H); 2.63 (t, J=6 Hz, 2H); 2.93 (t, J=8 Hz, 2H); 4.21 (d, J=7 Hz, 2H); 5.24 (quin, J=6 Hz, 1H); 7.90 (s broad, 3H); 8.57 (s broad, 2H); 13.89 (s, 1H)

MS method N: RT (min): 0.83; $[M+H]^+$ 375

Example (16B): Preparation of Compound 20: Trans 4-(aminomethyl)cyclohexyl)methyl)-2-butyl-7-isopropoxy-1H-imidazo[4,5-d]pyridazin-4-amine 2,2,2-trifluoroacetate Step 1: tert-butyl (4-(4-(bis(4-methoxybenzyl) amino)-2-butyl-7-isopropoxy-1H-imidazo[4,5-d] pyridazin-1-yl)methyl)cyclohexyl)methyl)carbamate

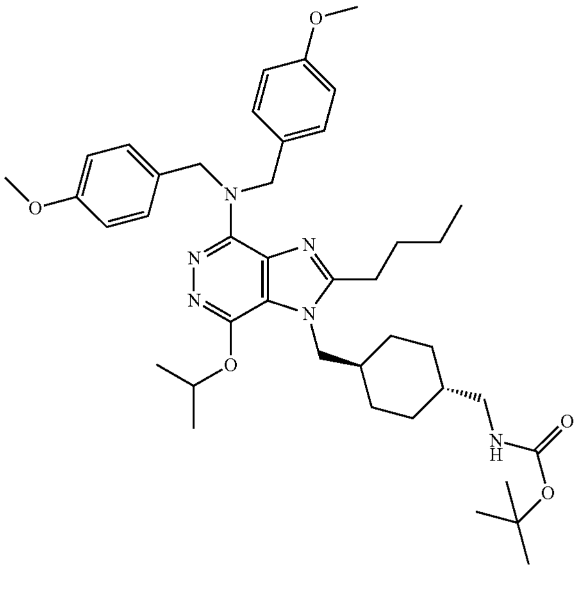 [SMILES: CCCCc1nc2c(N(Cc3ccc(OC)cc3)Cc3ccc(OC)cc3)nnc(OC(C)C)c2n1C[C@H]1CC[C@H](CNC(=O)OC(C)(C)C)CC1]

To a suspension of 2-butyl-7-isopropoxy-N,N-bis(4-methoxybenzyl)-1H-imidazo[4,5-d]pyridazin-4-amine, Intermediate (R) (414 mg, 0.85 mmol) in THF (23 mL) was added $Cs_2CO_3$ (827 mg, 2.54 mmol). The mixture was stirred 30 min at rt. Then, tert-butyl N-([(1r,4r)-4(bromomethyl)cyclohexyl]methyl)carbamate (545 mg, 1.69 mmol) and DMF (6 mL) was added. The mixture was stirred 5 min at rt then heated 1 h at 100° C. under microwave. The reaction mixture was filtered, the filtrate was diluted with EtOAc (200 mL), washed with water and brine, concentrated under reduced pressure to give 820 mg of crude product. The residue was purified by chromatography on a Merck cartridge (50 g of 15-40 μm silica) with a 10/90 to 80/20 EtOAc/Heptane elution. Expected product (233 mg, 39% yield) was obtained as a white solid.

$^1$H NMR (400 MHz, δ in ppm, DMSO-$d_6$): 0.78 (m, 2H); 0.86 (t, J=7.5 Hz, 3H); 1.08 (m, 2H); 1.23 to 1.41 (m, 3H); 1.36 (s, 9H); 1.37 (d, J=6.2 Hz, 6H); 1.49 (m, 2H); 1.63 to 1.82 (m, 5H); 2.73 (t, J=6.1 Hz, 2H); 2.83 (t, J=7.6 Hz, 2H); 3.71 (s, 6H); 4.14 (d, J=7.2 Hz, 2H); 4.97 (s, 4H); 5.41 (sept, J=6.2 Hz, 1H); 6.78 (t, J=6.1 Hz, 1H); 6.84 (d, J=8.8 Hz, 4H); 7.17 (d, J=8.8 Hz, 4H)

MS method N: RT (min): 1.82; $[M+H]^+$ 715; $ES^-[MH^- + HCO_2H]^-$: m/z 759

Step 2: Example (16B): Preparation of Compound 20: 4-(aminomethyl)cyclohexyl)methyl)-2-butyl-7-isopropoxy-1H-imidazo[4,5-d]pyridazin-4-amine 2,2,2-trifluoroacetate

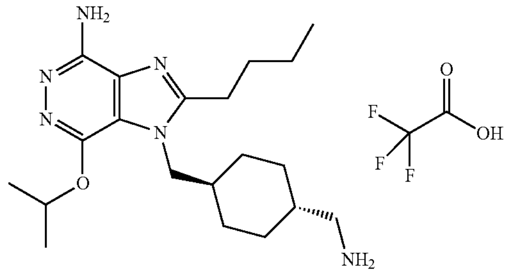 [SMILES: CCCCc1nc2c(N)nnc(OC(C)C)c2n1C[C@H]1CC[C@H](CN)CC1 ; O=C(O)C(F)(F)F]

To a solution of tert-butyl (4-((4-(bis(4-methoxybenzyl) amino)-2-butyl-7-isopropoxy-1H-imidazo[4,5-d]pyridazin-1-yl)methyl)cyclohexyl)methyl)carbamate of Step 1 (230 mg, 0.32 mmol) in DCM (4 mL) was added 2,2,2-trifluoroacetic acid (4 mL, 0.32 mmol). The mixture was stirred 6 days at rt. The reaction was diluted with EtOAc (120 mL) and extracted with $H_2O$ (100 mL). The aqueous phase was freeze-dried, to give 123 mg of crude product. The residue was poured into saturated solution of $NaHCO_3$, and extracted with EtOAc (3×50 mL), dried over anhydrous $MgSO_4$, filtered and the filtrate was concentrated under reduced pressure. Example (16B) (50 mg, 37%, yield) was obtained as a white solid.

$^1$H NMR (400 MHz, δ in ppm, DMSO-$d_6$): 0.80 (m, 2H); 0.93 (t, J=7.5 Hz, 3H); 1.10 (m, 2H); 1.30 (m, 1H); 1.36 (d, J=6.2 Hz, 6H); 1.41 (m, 2H); 1.50 (m, 2H); 1.71 to 1.82 (m, 5H); 2.46 (d, J=6.9 Hz, 2H); 2.83 (m, 2H); 4.13 (d, J=7.4 Hz, 2H); 4.74 (m, 3H); 5.39 (sept, J=6.2 Hz, 1H); 5.87 (s, 2H)

MS method N: RT (min): 0.80; $[M+H]^+$ 375; ES+[M+2H−iPr]2+: m/z 167

Example (17A): Preparation of Compound 21: 1-(4-(aminomethyl)benzyl)-2-butyl-7-isopropoxy-1H-imidazo[4,5-d]pyridazin-4-amine Step 1: tert-butyl (4-((4-(bis(2,4-dimethoxybenzyl) amino)-2-butyl-7-isopropoxy-1H-imidazo[4,5-d] pyridazin-1-yl)methyl)benzyl)carbamate

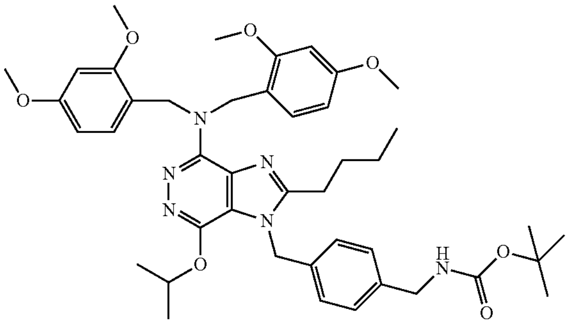 [SMILES: CCCCc1nc2c(N(Cc3ccc(OC)cc3OC)Cc3ccc(OC)cc3OC)nnc(OC(C)C)c2n1Cc1ccc(CNC(=O)OC(C)(C)C)cc1]

To a suspension of 2-butyl-N,N-bis(2,4-dimethoxybenzyl)-7-isopropoxy-1H-imidazo[4,5-d]pyridazin-4-amine, intermediate (M) (1 g, 1.82 mmol) in Me-THF (30 mL) was added $Cs_2CO_3$ (1.78 g, 5.46 mmol). The mixture was stirred 30 min at rt, tert-butyl 4-(bromomethyl)benzylcarbamate (819 mg, 2.73 mmol) was then added. The mixture was stirred at rt for 16 h. The reaction mixture was diluted with 150 mL of Me-THF and washed with water and brine, dried over anhydrous $MgSO_4$, filtered and the filtrate was concentrated under reduced pressure to give 1.73 g of crude product. The residue was purified by chromatography on a Merck cartridge (50 g of 15-40 μm silica) with 100/0 to 50/50 DCM-DCM/MeOH(90/10). Expected product (1.34 g, 96%, yield) was obtained as a white foam.

$^1$H NMR (400 MHz, δ in ppm, DMSO-$d_6$): 0.76 (t, J=7 Hz, 3H); 1.21 (m, 8H); 1.37 (s, 9H); 1.55 (quin, J=7 Hz, 2H); 2.74 (t, J=7 Hz, 2H); 3.71 (s, 12H); 4.07 (d, J=6 Hz, 2H); 5.01 (s, 4H); 5.31 (quin, J=6 Hz, 1H); 5.55 (s, 2H); 6.39 (dd, J=2 et & 8 Hz, 2H); 6.52 (d, J=2 Hz, 2H); 6.97 (d, J=8 Hz, 2H); 7.03 (d, J=8 Hz, 2H); 7.19 (d, J=8 Hz, 2H); 7.34 (t, J=6 Hz, 1H)

MS method N: RT (min): 1.87; $[M+H]^+$ 769

Step 2: Example (17A): Preparation of Compound 21: 1-(4-(aminomethyl)benzyl)-2-butyl-7-isopropoxy-1H-imidazo[4,5-d]pyridazin-4-amine

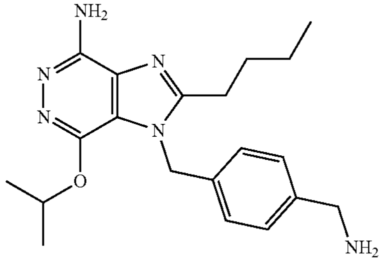 [SMILES: CCCCc1nc2c(N)nnc(OC(C)C)c2n1Cc1ccc(CN)cc1]

To a solution of tert-butyl (4-((4-(bis(2,4-dimethoxybenzyl)amino)-2-butyl-7-isopropoxy-1H-imidazo[4,5-d] pyridazin-1-yl)methyl)benzyl)carbamate of Step 1 (684 mg, 0.889 mmol) in DCM (10 mL) cooled in an ice bath was added 1,3-dimethoxybenzene (349 μL, 2.67 mmol) and 2,2,2-trifluoroacetic acid (10 mL, 129.8 mmol). After 15 minutes, the ice bath was removed and the mixture was stirred 16 hours at rt. The reaction mixture was diluted with DCM (100 mL) and $H_2O$ (50 mL), the aqueous phase was washed by DCM (2×50 mL). The pH of the aqueous layer was adjusted to pH 11 with 30% NaOH under stirring in an ice bath. The product was extracted with DCM (4×50 mL), the combined organic layer was dried over $MgSO_4$, filtered and concentrated under reduced pressure to give 306 mg of crude product, which was purified by chromatography on a Macherey Nagel cartridge (26 g of 15-40 μm diol) with 100/0 to 0/100 DCM-DCM/MeOH (90/10), to give 91 mg of purified compound, which was further purified with C18 19×150 mm 5 μm column, eluted with ammonium bicarbonate 10 mM (pH10)/acetonitrile to afford 64 mg (19.5%, yield) of Example (17A).

$^1$H NMR (400 MHz, δ in ppm, DMSO-$d_6$): 0.84 (t, J=7 Hz, 3H); 1.21 (s, 3H); 1.23 (s, 3H); 1.33 (m, 2H); 1.63 (m, 2H); 1.97 (m, 2H); 2.79 (d, J=15 Hz, 2H); 3.66 (s, 2H); 5.33 (spt, J=6 Hz, 1H); 5.54 (s, 2H); 5.91 (s, 2H); 7.01 (d, J=8 Hz, 2H); 7.28 (d, J=8 Hz, 2H)

MS method N: RT (min): 0.76; $[M+H]^+$ 369

The following compounds may be made by analogy to Example 17A: 158 and 160.

Example (17B): Preparation of Compound 22: 1-(4-(aminomethyl)benzyl)-2-butyl-7-isopropoxy-1H-imidazo[4,5-d]pyridazin-4-amine 2,2,2-trifluoroacetate Step 1: tert-butyl (4-((4-(bis(4-methoxybenzyl)amino)-2-butyl-7-isopropoxy-1H-imidazo[4,5-d]pyridazin-1-yl)methyl)benzyl)carbamate

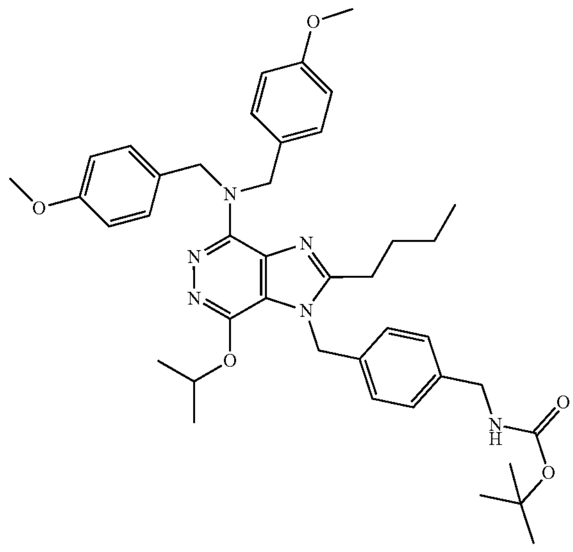 [SMILES: CCCCc1nc2c(N(Cc3ccc(OC)cc3)Cc3ccc(OC)cc3)nnc(OC(C)C)c2n1Cc1ccc(CNC(=O)OC(C)(C)C)cc1]

To a suspension of 2-butyl-7-isopropoxy-N,N-bis(4-methoxybenzyl)-1H-imidazo[4,5-d]pyridazin-4-amine, intermediate (R) (133 mg, 0.27 mmol) in THF (7 mL) was added $Cs_2CO_3$ (266 mg, 0.81 mmol). The mixture was stirred 15 min at rt, tert-butyl 4-(bromomethyl)benzylcarbamate (163 mg, 0.52 mmol) was then added. The mixture was stirred at rt for 20 h. The reaction mixture was filtered, and the filtrate was concentrated under reduced pressure to give 269 mg of crude product, which was purified by chromatography on a Merck cartridge (20 g of 15-40 μm silica) with a 10/90 to 60/40 EtOAc/Heptane elution. Expected product (83 mg, 43%, yield) was obtained as a white solid.

$^1$H NMR (400 MHz, δ in ppm, DMSO-$d_6$): 0.78 (t, J=7.4 Hz, 3H); 1.21 (d, J=6.2 Hz, 6H); 1.28 (m, 2H); 1.36 (s, 9H); 1.60 (m, 2H); 2.79 (t, J=7.6 Hz, 2H); 3.71 (s, 6H); 4.07 (d, J=6.2 Hz, 2H); 4.98 (s, 4H); 5.34 (sept, J=6.2 Hz, 1H); 5.59 (s, 2H); 6.85 (d, J=8.8 Hz, 4H); 7.04 (d, J=8.2 Hz, 2H); 7.18 (d, J=8.8 Hz, 4H); 7.20 (d, J=8.2 Hz, 2H); 7.35 (t, J=6.2 Hz, 1H)

MS method N: RT (min): 1.67; $[M+H]^+$ 709; $ES^+[2MH^++HCO_2H]^-$: m/z 1462; $ES-[MH-+HCO_2H]^-$: m/z 753

Step 2: Example (17B) Preparation of Compound 22: 1-(4-(aminomethyl)benzyl)-2-butyl-7-isopropoxy-1H-imidazo[4,5-d]pyridazin-4-amine 2,2,2-trifluoroacetate

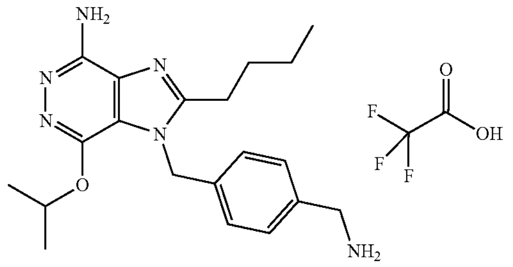 [SMILES: CCCCc1nc2c(N)nnc(OC(C)C)c2n1Cc1ccc(CN)cc1 ; O=C(O)C(F)(F)F]

To a solution of tert-butyl (4-((4-(bis(4-methoxybenzyl)amino)-2-butyl-7-isopropoxy-1H-imidazo[4,5-d]pyridazin-1-yl)methyl)benzyl)carbamate of Step 1 (70 mg, 0.099 mmol) in DCM (1.2 mL) was added 2,2,2-trifluoroacetic acid (1.2 mL, 15.51 mmol). The mixture was stirred 8 days at rt. The reaction was diluted with DCM (80 mL) and extracted with $H_2O$ (200 mL). The aqueous phase was washed by EtOAc (2×50 mL). The aqueous phase was freeze-dried overnight. Example (17B) (75 mg, 93%, yield) was obtained as a white lyophilizate.

$^1$H NMR (400 MHz, δ in ppm, DMSO-$d_6$): 0.85 (t, J=7.4 Hz, 3H); 1.22 (d, J=6.2 Hz, 6H); 1.33 (m, 2H); 1.66 (m, 2H); 2.87 (m, 2H); 4.02 (m, 2H); 5.16 (m, 1H); 5.67 (s, 2H); 7.18 (d, J=8.5 Hz, 2H); 7.42 (d, J=8.5 Hz, 2H); 8.13 (s, 3H); 8.47 (m, 2H)

MS method N: RT (min): 0.68; $[M+H]^+$ 369

Example (18): Preparation of Compound 23: 1-(((1S,3R)-3-aminocyclohexyl)methyl)-2-butyl-7-isopropoxy-1H-imidazo[4,5-d]pyridazin-4-amine (and Enantiomer)

Step 1: tert-butyl ((1R,3S)-3-((4-(bis(2,4-dimethoxybenzyl)amino)-2-butyl-7-isopropoxy-1H-imidazo[4,5-d]pyridazin-1-yl)methyl)cyclohexyl)carbamate (and Enantiomer)

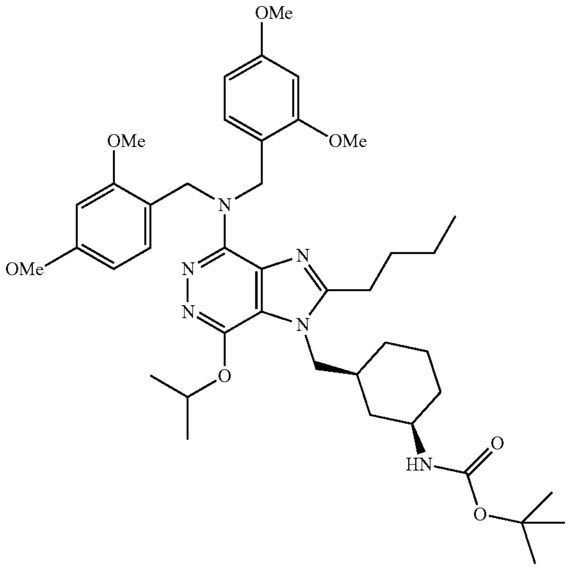 [SMILES: CCCCc1nc2c(N(Cc3ccc(OC)cc3OC)Cc3ccc(OC)cc3OC)nnc(OC(C)C)c2n1C[C@H]1CCC[C@@H](NC(=O)OC(C)(C)C)C1]

To a suspension of intermediate (M) (500 mg, 0.91 mmol) in Me-THF (15 mL) was added $Cs_2CO_3$ (449.05 mg, 1.36 mmol). The mixture was stirred at rt during 30 min. Tert-butyl [cis-3-(bromomethyl)cyclohexyl]carbamate (419.70 mg, 1.36 mmol) was then added, which was stirred at rt for 20h and then heated at 60° C. for 5 days. The mixture was diluted with Me-THF (250 mL) then washed with $H_2O$ (2×80 mL), brine (80 mL), dried over anhydrous $MgSO_4$, and filtered. The filtrate was concentrated under reduced pressure to give 940 mg of crude product, which was purified by chromatography on a Merck cartridge (50 g of 15-μm silica) with a 10/90 to 80/20 EtOAc/Heptane elution. Expected compound (490 mg, 71% yield) was obtained as a white solid.

$^1H$ NMR (400 MHz, δ in ppm, DMSO-$d_6$): 0.80 to 1.44 (m, 7H); 0.83 (t, J=7.5 Hz, 3H); 1.34 (s, 9H); 1.35 (d, J=6.2 Hz, 3H); 1.38 (d, J=6.2 Hz, 3H); 1.57 (m, 1H); 1.61 to 1.76 (m, 4H); 1.85 (m, 1H); 2.78 (t, J=7.4 Hz, 2H); 3.12 (m, 1H); 3.70 (s, 6H); 3.71 (s, 6H); 4.12 (m, 2H); 5.00 (s, 4H); 5.38 (sept, J=6.2 Hz, 1H); 6.38 (dd, J=2.4 & 8.4 Hz, 2H); 6.52 (d, J=2.4 Hz, 2H); 6.76 (d, J=7.9 Hz, 1H); 6.95 (d, J=8.4 Hz, 2H)

MS method N: RT (min): 1.83; $[M+H]^+$ 761

Step 2: Example (18) Preparation of Compound 23: 1-(((1S,3R)-3-aminocyclohexyl)methyl)-2-butyl-7-isopropoxy-1H-imidazo[4,5-d]pyridazin-4-amine (and Enantiomer)

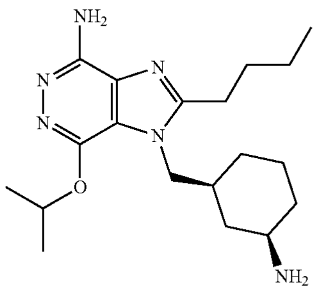 [SMILES: CCCCc1nc2c(N)nnc(OC(C)C)c2n1C[C@H]1CCC[C@@H](N)C1]

To a solution of tert-butyl ((1R,3S)-34(4-(bis(2,4-dimethoxybenzyl)amino)-2-butyl-7-isopropoxy-1H-imidazo[4,5-d]pyridazin-1-yl)methyl)cyclohexyl)carbamate (and enantiomer) of Step 1 (480 mg, 0.63 mmol) in DCM (2.5 mL) was added 2,2,2-trifluoroacetic acid (2.5 mL, 32.65 mmol). The mixture was stirred at room temperature for 24 hours. The reaction was poured into DCM (100 mL) and washed with $H_2O$ (2×80 mL). The aqueous phase was neutralized by addition of sodium hydroxide 5M, and was extracted by EtOAc (3×75 mL). The organic phase was washed with $H_2O$, brine, dried over anhydrous $MgSO_4$, filtered and the filtrate was concentrated under reduced pressure to give 115 mg (50.7% yield) of Example (18) as a white powder.

$^1H$ NMR (400 MHz, δ in ppm, DMSO-$d_6$): 0.75 to 1.00 (m, 2H); 0.93 (t, J=7.4 Hz, 3H); 1.15 (m, 1H); 1.33 to 1.54 (m, 9H); 1.63 to 1.89 (m, 5H); 2.07 (m broad, 2H); 2.45 (m, 3H); 2.83 (m, 2H); 4.11 (m, 2H); 5.38 (sept, J=6.2 Hz, 1H); 5.85 (s, 2H)

MS method N: RT (min): 0.85; $[M+H]^+$ 361; ES+$[M+2H]^{2+}$: m/z 181

Example (19): Preparation of Compound 24: 1-(4-amino-2-butyl-7-isopropoxy-1H-imidazo[4,5-d]pyridazin-1-yl)-2-methylpropan-2-ol Step 1: 1-(4-(bis(2,4-dimethoxybenzyl)amino)-2-butyl-7-isopropoxy-1H-imidazo[4,5-d]pyridazin-1-yl)-2-methylpropan-2-ol

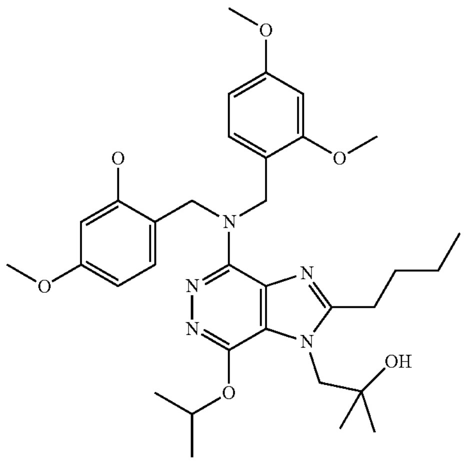

To a suspension of intermediate (M) (500 mg, 91 mmol) in Me-THF (15 mL), was added $Cs_2CO_3$ (900 mg, 2.73 mmol). The mixture was stirred 30 min at rt. Then, 2.2-dimethyloxirane (125 μL, 1.37 mmol) was added. The mixture was heated 20 h under microwave at 60° C., then concentrated under reduced pressure. The residue was diluted in MeCN (15 mL), 2.2-dimethyloxirane (250 μL, 2.74 mmol) was added, and the mixture was heated 48 h under microwave at 90° C. The reaction mixture was then diluted with Me-THF (250 mL), washed with water and brine, dried over $MgSO_4$, filtered and concentrated under reduced pressure to give 533 mg of crude product, which was purified by chromatography on a Merck cartridge (40 g of 15-40 μm silica) with a 10/90 to 60/40 EtOAc/Heptane elution. Expected product (236 mg, 42%, yield) was obtained as a white amorphous solid.

$^1$H NMR (400 MHz, δ in ppm, DMSO-$d_6$): 0.83 (t, J=7.4 Hz, 3H); 1.09 (s broad, 6H); 1.29 (m, 2H); 1.36 (d, J=6.2 Hz, 6H); 1.64 (m, 2H); 2.95 (t, J=7.6 Hz, 2H); 3.70 (s, 6H); 3.71 (s, 6H); 4.29 (s broad, 2H); 4.76 (s, 1H); 5.01 (s, 4H); 5.38 (sept, J=6.2 Hz, 1H); 6.39 (dd, J=2.4 & 8.4 Hz, 2H); 6.52 (d, J=2.4 Hz, 2H); 6.96 (d, J=8.4 Hz, 2H)

MS method N: RT (min): 1.59; $[M+H]^+$ 622; $ES^-[M-H+HCO_2H]^-$: m/z 666

Step 2: Example (19): Preparation of Compound 24: 1-(4-amino-2-butyl-7-isopropoxy-1H-imidazo[4,5-d]pyridazin-1-yl)-2-methylpropan-2-ol

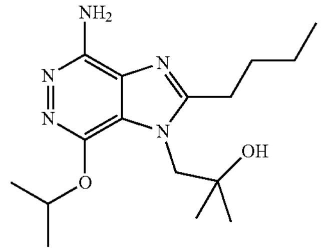 [SMILES: CCCCc1nc2c(N)nnc(OC(C)C)c2n1CC(C)(C)O]

To a solution of 1-(4-(bis(2,4-dimethoxybenzyl)amino)-2-butyl-7-isopropoxy-1H-imidazo[4,5-d]pyridazin-1-yl)-2-methylpropan-2-ol of Step 1 (230 mg, 0.37 mol) in DCM (2 mL) was added 2,2,2-trifluoroacetic acid (1.5 mL, 20.19 mmol). The mixture was stirred 5 h at rt. The reaction mixture was diluted with DCM (100 mL) and extracted with $H_2O$ (2×80 mL). The aqueous phase was neutralized with NaOH (5 M) up to pH 10, extracted with EtOAc (3×75 mL), the organic phase was washed with water and brine, dried over magnesium sulfate, filtered and concentrated under reduced pressure. Example (19), (37 mg, 31%, yield) was obtained as a white solid.

$^1$H NMR (400 MHz, δ in ppm, DMSO-$d_6$): 0.92 (t, J=7.3 Hz, 3H); 1.09 (s broad, 6H); 1.36 (d, J=6.2 Hz, 6H); 1.39 (m, 2H); 1.75 (m, 2H); 3.01 (m, 2H); 4.28 (s, 2H); 4.78 (s, 1H); 5.36 (sept, J=6.2 Hz, 1H); 6.24 (s, 2H)

MS method N: RT (min): 1.1; $[M+H]^+$ 322

The following compounds may be made by analogy to Example 19: 74, 75, 76, 80, 81.

Example (20): Preparation of Compound 25: Trans 1-(4-aminocyclohexyl)methyl)-2-butyl-7-isopropoxy-1H-imidazo[4,5-d]pyridazin-4-amine Step 1: tert-butyl 4-((4-(bis(2,4-dimethoxybenzyl)amino)-2-butyl-7-isopropoxy-1H-imidazo[4,5-d]pyridazin-1-yl)methyl)cyclohexyl)carbamate

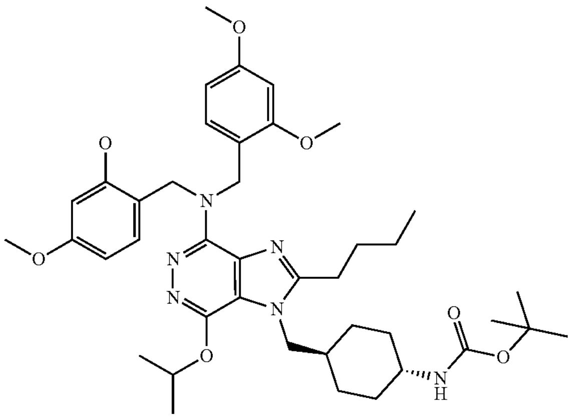 [SMILES: CCCCc1nc2c(N(Cc3ccc(OC)cc3O)Cc3ccc(OC)cc3OC)nnc(OC(C)C)c2n1C[C@H]1CC[C@H](NC(=O)OC(C)(C)C)CC1]

To a suspension of intermediate (M) (400 mg, 0.73 mmol) in Me-THF (15 mL), was added $Cs_2CO_3$ (720 mg, 2.19 mmol). The mixture was stirred 30 min at rt. Then, tert-butyl 4-(bromomethyl)cyclohexyl)carbamate (320 mg, 1.10 mmol) was added. The mixture was stirred at rt for 24 h, then heated at 90° C. under microwave 18h. After, the reaction mixture was diluted with Me-THF (Methyltetrahydrofuran) (250 mL), washed with water and brine, dried over $MgSO_4$, filtered and concentrated under reduced pressure to give 692 mg of crude product, which was purified by chromatography on a Merck cartridge (40 g of 15-40 μm silica) with a 10/90 to 100/00 EtOAc/Heptane elution. Expected product (357 mg, 64%, yield) was obtained as a white solid.

$^1$H NMR (400 MHz, δ in ppm, DMSO-$d_6$): 0.83 (t, J=7.5 Hz, 3H); 1.04 (m, 2H); 1.14 (m, 2H); 1.09 (m, 2H); 1.36 (s, 9H); 1.37 (d, J=6.2 Hz, 6H); 1.47 (m, 2H); 1.60 to 1.79 (m, 5H); 2.77 (t, J=7.4 Hz, 2H); 3.17 (m, 1H); 3.70 (s, 6H); 3.71 (s, 6H); 4.10 (d, J=7.2 Hz, 2H); 5.00 (s, 4H); 5.38 (sept, J=6.2 Hz, 1H); 6.39 (dd, J=2.5 & 8.4 Hz, 2H); 6.52 (d, J=2.5 Hz, 2H); 6.68 (d, J=7.9 Hz, 1H); 6.96 (d, J=8.4 Hz, 2H)

MS method N: RT (min): 1.79; $[M+H]^+$ 761

Step 2: Example (20): Preparation of Compound 25: Trans 1-(4-aminocyclohexyl)methyl)-2-butyl-7-isopropoxy-1H-imidazo[4,5-d]pyridazin-4-amine

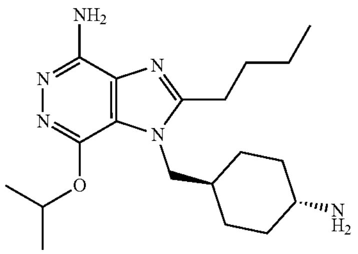 [SMILES: CCCCc1nc2c(N)nnc(OC(C)C)c2n1C[C@H]1CC[C@H](N)CC1]

To a solution of tert-butyl 4-((4-(bis(2,4-dimethoxybenzyl)amino)-2-butyl-7-isopropoxy-1H-imidazo[4,5-d]pyridazin-1-yl)methyl)cyclohexyl)carbamate of Step 1 (345 mg, 0.45 mmol) in DCM (2 mL) was added 2,2,2-trifluoroacetic acid (2 mL, 26.66 mmol). The mixture was stirred 24 hours at rt. The reaction mixture was diluted with DCM (100 mL) and extracted with $H_2O$ (2×80 mL). The aqueous phase was neutralized with NaOH (5M) up to pH 10, extracted with EtOAc (3×75 mL), the organic phase was washed with water and brine, dried over magnesium sulfate, filtered and concentrated under reduced pressure. Example (20) (142 mg, 87%, yield) was obtained as a white solid.

$^1$H NMR (400 MHz, δ in ppm, DMSO-$d_6$): 0.92 (t, J=7.3 Hz, 3H); 0.94 (m, 2H); 1.12 (m, 2H); 1.34 to 1.48 (m, 5H); 1.36 (d, J=6.2 Hz, 6H); 1.65 to 1.81 (m, 5H); 2.82 (m, 2H); 2.95 (m broad, 2H); 4.10 (d, J=7.5 Hz, 2H); 5.39 (sept, J=6.2 Hz, 1H); 5.85 (s, 2H)

MS method N: RT (min): 0.78; $[M+H]^+$ 361; ES+$[M+2H]^{2+}$: m/z 181)

The following compounds may be made by analogy to Example 20: 77, 78, 79, 146, 149, 165.

Example (21A): Preparation of Compound 26 1-((5-(aminomethyl)pyridin-2-yl)methyl)-2-butyl-7-isopropoxy-1H-imidazo[4,5-d]pyridazin-4-amine and Example (21B): Preparation of Compound 27: -((4-amino-2-butyl-7-isopropoxy-1H-imidazo[4,5-d]pyridazin-1-yl)methyl)nicotinonitrile Step 1: 6-((4-(bis(2,4-dimethoxybenzyl)amino)-2-butyl-7-isopropoxy-1H-imidazo[4,5-d]pyridazin-1-yl)methyl)nicotinonitrile

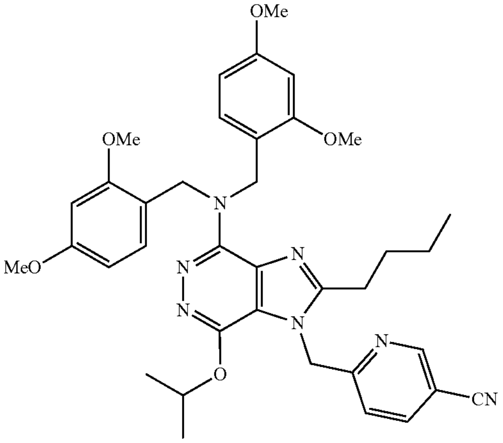 [SMILES: CCCCc1nc2c(N(Cc3ccc(OC)cc3OC)Cc3ccc(OC)cc3OC)nnc(OC(C)C)c2n1Cc1ccc(C#N)cn1]

To a suspension of intermediate (M) (500 mg, 0.91 mmol) in Me-THF (15 mL), was added $Cs_2CO_3$ (898 mg, 2.73 mmol). The mixture was stirred 30 min at rt, then 6-(bromomethyl)nicotinonitrile (285 mg, 1.37 mmol) was added. The mixture was stirred 1 h at rt. After, the reaction mixture was diluted with Me-THF, washed with water and brine, dried over $MgSO_4$, filtered and concentrated under reduced pressure to give 661 mg of crude product, which was purified by chromatography on a Merck cartridge (50 g of 15-40 μm silica) with a 10/90 to 80/20 EtOAc/Heptane elution. Expected product (467 mg, 77% yield) was obtained as a white solid.

$^1$H NMR (400 MHz, δ in ppm, DMSO-$d_6$): 0.80 (t, J=7.5 Hz, 3H); 1.06 (d, J=6.2 Hz, 6H); 1.28 (m, 2H); 1.61 (m, 2H); 2.81 (t, J=7.6 Hz, 2H); 3.71 (s, 6H); 3.72 (s, 6H); 5.02 (s, 4H); 5.18 (sept, J=6.2 Hz, 1H); 5.75 (s, 2H); 6.40 (dd, J=2.4 & 8.4 Hz, 2H); 6.53 (d, J=2.4 Hz, 2H); 6.98 (d, J=8.4 Hz, 2H); 7.49 (dd, J=0.9 & 8.3 Hz, 1H); 8.33 (dd, J=2.2 & 8.3 Hz, 1H); 8.90 (dd, J=0.9 & 2.2 Hz, 1H)

MS method O: RT (min): 2.96; $[M+H]^+$ 666

Step 2: 1-((5-(aminomethyl)pyridin-2-yl)methyl)-2-butyl-N,N-bis(2,4-dimethoxybenzyl)-7-isopropoxy-1H-imidazo[4,5-d]pyridazin-4-amine

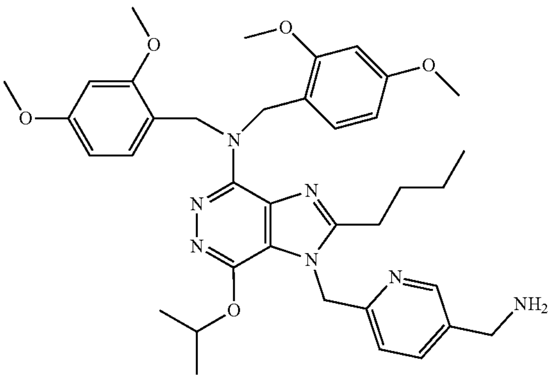 [SMILES: CCCCc1nc2c(N(Cc3ccc(OC)cc3OC)Cc3ccc(OC)cc3OC)nnc(OC(C)C)c2n1Cc1ccc(CN)cn1]

To a solution of 6-((4-(bis(2,4-dimethoxybenzyl)amino)-2-butyl-7-isopropoxy-1H-imidazo[4,5-d]pyridazin-1-yl)methyl)nicotinonitrile of Step 1 (460 mg, 0.69 mmol) in EtOH (10 mL) was added Pd/C10% (46 mg, 0.43 mmol). The mixture was hydrogenated under 17 bars at 25° C. for 6 h and filtered. The filtrate was concentrated under vacuum to give 413 mg of crude product, which was purified by chromatography on a Merck cartridge (20 g of 15-40 μm silica) with 99/1/0.1 to 93/7/0.1 DCM/MeOH/$NH_4OH$ elution. Expected product (178 mg, 38% yield) was obtained as a white solid.

$^1$H NMR (400 MHz, δ in ppm, DMSO-$d_6$): 0.79 (t, J=7.4 Hz, 3H); 1.17 (d, J=6.2 Hz, 6H); 1.27 (m, 2H); 1.61 (m, 2H); 1.95 (m broad, 2H); 2.83 (t, J=7.6 Hz, 2H); 3.67 (s, 2H); 3.71 (s, 6H); 3.72 (s, 6H); 5.01 (s, 4H); 5.24 (sept, J=6.2 Hz, 1H); 5.61 (s, 2H); 6.39 (dd, J=2.4 & 8.4 Hz, 2H); 6.52 (d, J=2.4 Hz, 2H); 6.97 (d, J=8.4 Hz, 2H); 7.16 (dd, J=0.8 & 8.1 Hz, 1H); 7.73 (dd, J=2.3 & 8.1 Hz, 1H); 8.37 (dd, J=0.8 & 2.3 Hz, 1H)

MS method N: RT (min): 1.32; $[M+H]^+$ 670; ES+$[M+2H]^{2+}$: m/z 335.7

Step 3 (I): Example (21A): Preparation of Compound 26: 1-((5-(aminomethyl)pyridin-2-yl)methyl)-2-butyl-7-isopropoxy-1H-imidazo[4,5-d]pyridazin-4-amine

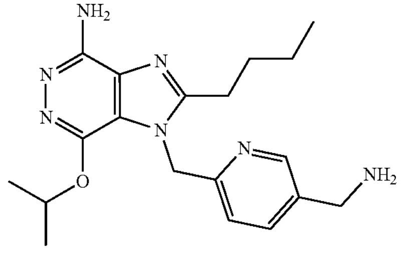 [SMILES: CCCCc1nc2c(N)nnc(OC(C)C)c2n1Cc1ccc(CN)cn1]

To a solution of 1-((5-(aminomethyl)pyridin-2-yl)methyl)-2-butyl-N,N-bis(2,4-dimethoxybenzyl)-7-isopropoxy-1H-imidazo[4,5-d]pyridazin-4-amine, of Step 2 (175 mg, 0.26 mmol) in DCM (1.2 mL) was added 2,2,2-trifluoroacetic acid (1.20 mL, 15.68 mmol). The mixture was stirred 24 h at rt. The reaction mixture was diluted with DCM (100 mL) and extracted with $H_2O$ (2×80 mL). The aqueous phase was adjusted to pH 10 with 5 N sodium hydroxide solution, extracted with EtOAc (3×75 mL), the organic phase was washed with water and brine, dried over magnesium sulfate, filtered and concentrated under reduced pressure. Example (21A) (79 mg, 82% yield) was obtained as a white solid.

$^1$H NMR (400 MHz, δ in ppm, DMSO-$d_6$): 0.86 (t, J=7.4 Hz, 3H); 1.16 (d, J=6.2 Hz, 6H); 1.35 (m, 2H); 1.68 (m, 2H); 2.67 (m, 2H); 2.87 (m, 2H); 3.70 (s, 2H); 5.25 (sept, J=6.2 Hz, 1H); 5.61 (s, 2H); 5.89 (s, 2H); 7.12 (d, J=8.1 Hz, 1H); 7.73 (dd, J=2.3 & 8.1 Hz, 1H); 8.38 (d, J=2.3 Hz, 1H)

MS method N: RT (min): 0.46; $[M+H]^+$ 370

Step 3 (II): Example (21-B): Preparation of Compound 27: 6-((4-amino-2-butyl-7-isopropoxy-1H-imidazo[4,5-d]pyridazin-1-yl)methyl)nicotinonitrile

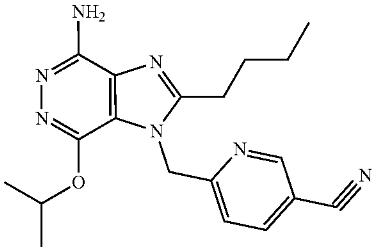 [SMILES: CCCCc1nc2c(N)nnc(OC(C)C)c2n1Cc1ccc(C#N)cn1]

To a solution of 6-((4-(bis(2,4-dimethoxybenzyl)amino)-2-butyl-7-isopropoxy-1H-imidazo[4,5-d]pyridazin-1-yl)methyl)nicotinonitrile, of Step 1 (225 mg, 0.34 mmol) in DCM (1.5 mL) was added 2,2,2-trifluoroacetic acid (1.50 mL, 19.59 mmol). The mixture was stirred 24 h at rt. The reaction mixture was diluted with DCM (100 mL) and extracted with $H_2O$ (2×80 mL). The aqueous phase was adjusted to pH 12 with 5 N sodium hydroxide solution, saturated with NaCl, extracted with EtOAc (3×75 mL), the organic phase was washed with water and brine, dried over magnesium sulfate, filtered and concentrated under reduced pressure. Example (21B), (110 mg, 89% yield) was obtained as a white solid.

$^1$H NMR (400 MHz, δ in ppm, DMSO-$d_6$): 0.86 (t, J=7 Hz, 3H); 1.05 (d, J=6 Hz, 6H); 1.35 (dq, J=7 & 15 Hz, 2H); 1.68 (dt, J=8 & 15 Hz, 2H); 2.87 (t, J=8 Hz, 2H); 5.19 (spt, J=6 Hz, 1H); 5.75 (s, 2H); 5.92 (s, 2H); 7.45 (dd, J=1 & 8 Hz, 1H); 8.33 (dd, J=2 & 8 Hz, 1H); 8.90 (dd, J=1 & 2 Hz, 1H)

MS method N: RT (min): 1.10; $[M+H]^+$ m:z 366

Example (22): Preparation of Compound 28: N-(4-((4-amino-2-butyl-7-isopropoxy-1H-imidazo[4,5c]pyridazin-1-yl)methyl)benzyl)acetamide

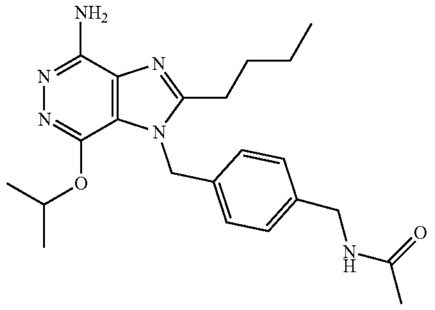 [SMILES: CCCCc1nc2c(N)nnc(OC(C)C)c2n1Cc1ccc(CNC(C)=O)cc1]

To a solution of 1-(4-(aminomethyl)benzyl)-2-butyl-7-isopropoxy-1H-imidazo[4,5-d]pyridazin-4-amine (Example (17A)) (200 mg, 0.54 mmol) in DMF (6 mL) was added DIPEA (95 μL, 0.54 mmol), and acetic anhydride (61 μL, 0.65 mmol). The solution was stirred at rt for 2 h and then was poured into a mixture water (30 mL) and ice (30 g) which was stirred at rt 30 min. Then solid $NaHCO_3$ was added until pH 8. The solution was extracted with EtOAc (3×40 mL). The organic layer was dried over anhydrous $MgSO_4$, filtered and concentrated under vacuum to give 139 mg of white solid, which was dissolved in MeOH (10 mL). Potassium carbonate (108 mg) was added and the suspension was stirred at room temperature for 18h. The reaction mixture was concentrated under vacuum, dissolved in DCM (10 mL) washed with water (5 mL), and brine (5 mL). The organic layer was dried over anhydrous $MgSO_4$, filtered and concentrated under vacuum to give the crude product, which was stirred 15 min at room temperature in diisopropyl ether (2 mL). The suspension was filtered. The solid was washed with diisopropyl ether (2×1 mL) and dried under vacuum. Example (22) (70 mg, 65% yield) was obtained as a white solid.

$^1H$ NMR (400 MHz, δ in ppm, DMSO-$d_6$): 0.84 (t, J=7.5 Hz, 3H); 1.21 (d, J=6.2 Hz, 6H); 1.32 (m, 2H); 1.63 (m, 2H); 1.83 (s, 3H); 2.79 (m, 2H); 4.19 (d, J=6.0 Hz, 2H); 5.32 (sept, J=6.2 Hz, 1H); 5.55 (s, 2H); 5.91 (s, 2H); 7.03 (d, J=8.4 Hz, 2H); 7.20 (d, J=8.4 Hz, 2H); 8.29 (t, J=6.0 Hz, 1H)

MS method N: RT (min): 1.09; $[M+H]^+$ 411

Example (23): Preparation of Compound 29: N-(4-((4-amino-2-butyl-7-isopropoxy-1H-imidazo[4,5-d]pyridazin-1-yl)methyl)benzyl)undecanamide

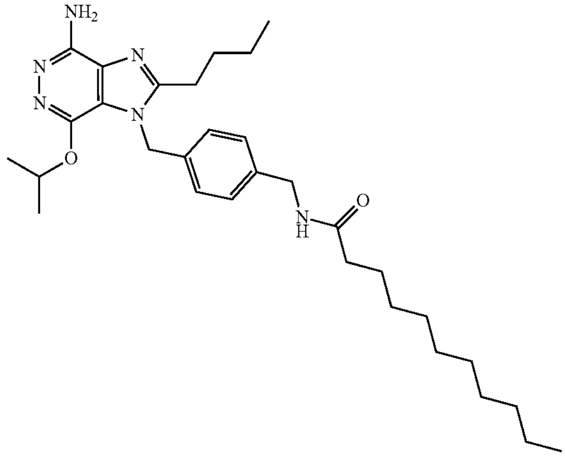 [SMILES: CCCCCCCCCCC(=O)NCc1ccc(Cn2c(CCCC)nc3c(N)nnc(OC(C)C)c32)cc1]

To a solution of 1-(4-(aminomethyl)benzyl)-2-butyl-7-isopropoxy-1H-imidazo[4,5-d]pyridazin-4-amine (Example (17A)) (127 mg, 0.35 mmol) in DMF (3 mL) was added Undecanoic acid (65 μL, 0.35 mmol), and TEA (345 μL, 0.35 mmol). The solution was stirred 5 min at rt. Then HBTU (167 mg, 0.43 mmol) was added. The mixture was stirred at rt for 2 hours. The reaction mixture was poured into a mixture water (30 mL) and ice (30 g) and was stirred at rt for 30 min, then extracted with EtOAc (3×30 mL). The organic layer was dried over anhydrous $MgSO_4$, filtered and concentrated under vacuum to give 200 mg of the crude product, which was purified by chromatography on a Merck cartridge (10 g of 15-40 μm silica) with DCM/MeOH (93/7) elution to obtain colorless gum. This gum was dissolved in MeOH (2.5 mL) and filtered through Amberlist A-26 OH column. The MeOH filtrate was concentrated under vacuum to give a gum (48 mg), which was stirred at room temperature for 15 min with diisopropyl ether. The supernatant solution was eliminated, and the gum was dried under vacuum. Example (23) was obtained (31 mg, 15% yield) as a colorless gum.

$^1H$ NMR (400 MHz, δ in ppm, DMSO-$d_6$): 0.84 (t, J=7.4 Hz, 3H); 0.85 (t, J=6.9 Hz, 3H); 1.21 (d, J=6.2 Hz, 6H); 1.22 (s broad, 14H); 1.32 (m, 2H); 1.48 (m, 2H); 1.62 (m, 2H); 2.08 (t, J=7.4 Hz, 2H); 2.79 (m, 2H); 4.20 (d, J=6.1 Hz, 2H); 5.32 (sept, J=6.2 Hz, 1H); 5.54 (s, 2H); 5.91 (s, 2H); 7.02 (d, J=8.4 Hz, 2H); 7.19 (d, J=8.4 Hz, 2H); 8.24 (t, J=6.1 Hz, 1H)

MS method N: RT (min): 1.59; $[M+H]^+$ 537; $ES^-$ $[M-H+HCO_2H]^-$: m/z 581

The following compounds may be made by analogy to Example 23: 84, 103, 106 and 107.

Example (24): Preparation of Compound 30: N-(4-((4-amino-2-butyl-7-isopropoxy-1H-imidazo[4,5-d]pyridazin-1-yl)methyl)benzyl)pentanamide

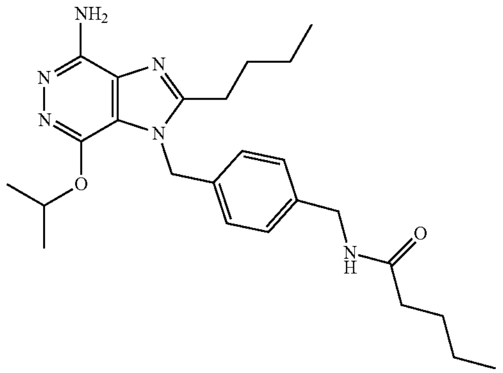 [SMILES: CCCCC(=O)NCc1ccc(Cn2c(CCCC)nc3c(N)nnc(OC(C)C)c32)cc1]

To a solution of 1-(4-(aminomethyl)benzyl)-2-butyl-7-isopropoxy-1H-imidazo[4,5-d]pyridazin-4-amine (Example (17A)) (200 mg, 0.42 mmol) in THF (5 mL) was added Valeric acid (51 µL, 0.46 mmol), EDCI (238 mg, 1.24 mmol), HOBt (95 mg, 1.5 eq), and dropwise DIPEA (290 µl, 4 eq). The solution was stirred at rt for 2h. The reaction mixture was diluted with EtOAc (50 mL), washed with water (25 mL), saturated aqueous sodium hydrogen carbonate (25 mL), and water (2×25 mL). The organic layer was dried over anhydrous $MgSO_4$, filtered and concentrated under vacuum to give 156 mg of crude product which was purified by chromatography on Merck cartridge (10 g of 15-40 µm silica) with DCM/MeOH/$CH_3CN$ (90/5/5) elution to give Example (24) (94 mg, 50% yield) as a white solid.

$^1$H NMR (400 MHz, δ in ppm, DMSO-$d_6$): 0.83 (t, J=7.4 Hz, 6H); 1.21 (d, J=6.2 Hz, 6H); 1.23 (m, 2H); 1.32 (m, 2H); 1.47 (m, 2H); 1.62 (m, 2H); 2.09 (t, J=7.5 Hz, 2H); 2.79 (m, 2H); 4.20 (d, J=6.0 Hz, 2H); 5.31 (sept, J=6.2 Hz, 1H); 5.55 (s, 2H); 5.96 (s, 2H); 7.02 (d, J=8.3 Hz, 2H); 7.19 (d, J=8.3 Hz, 2H); 8.25 (t, J=6.0 Hz, 1H)

MS method N: RT (min): 1.23; $[M+H]^+$ 453; $ES^-$ $[M-H+HCO_2H]^-$: m/z 497

Example (25): Preparation of Compound 31: N-(4-((4-amino-2-butyl-7-isopropoxy-1H-imidazo[4,5-d]pyridazin-1-yl)methyl)benzyl)-3-(2-methoxyethoxy)propanamide

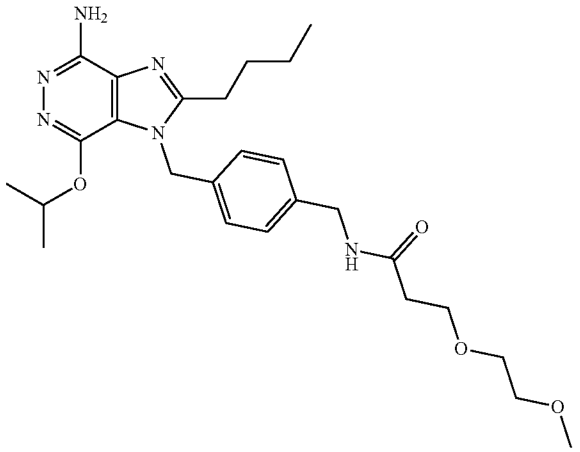 [SMILES: CCCCc1nc2c(N)nnc(OC(C)C)c2n1Cc1ccc(CNC(=O)CCOCCOC)cc1]

To a solution of 1-(4-(aminomethyl)benzyl)-2-butyl-7-isopropoxy-1H-imidazo[4,5-d]pyridazin-4-amine (Example (17A)) (200 mg, 0.42 mmol) in THF (5 mL) was added 3-(2-methoxyethoxy) propanoic acid (65 mg, 0.41 mmol), EDCI (238 mg, 1.24 mmol), HOBT (95 mg, 1.5 eq) and dropwise DIPEA (290 µl, 4 eq). The solution was stirred at rt for 2 hours. The reaction mixture was diluted with EtOAc (50 mL), washed with water (25 mL), saturated aqueous solution sodium hydrogen carbonate (25 mL), and water (2×25 mL). The organic layer was dried over anhydrous $MgSO_4$, filtered and concentrated under vacuum to give 182 mg of crude product which was purified by chromatography on a Merck cartridge (10 g of 15-40 µm silica) with DCM/Methanol/Acetonitrile (85/7.5/7.5) elution to give Example (25) (58.5 mg, 28% yield) as a colorless gum.

$^1$H NMR (400 MHz, δ in ppm, DMSO-$d_6$): 0.85 (t, J=7.4 Hz, 3H); 1.21 (d, J=6.2 Hz, 6H); 1.32 (m, 2H); 1.63 (m, 2H); 2.34 (t, J=6.5 Hz, 2H); 2.78 (t, J=7.6 Hz, 2H); 3.16 (s, 3H); 3.37 (m, 2H); 3.46 (m, 2H); 3.60 (t, J=6.5 Hz, 2H); 4.23 (d, J=6.1 Hz, 2H); 5.32 (sept, J=6.2 Hz, 1H); 5.55 (s, 2H); 5.91 (s, 2H); 7.02 (d, J=8.3 Hz, 2H); 7.20 (d, J=8.3 Hz, 2H); 8.31 (t, J=6.1 Hz, 1H)

MS method N: RT (min): 1.11; $[M+H]^+$ 499

Example (26): Preparation of Compound 32: 1-(((1S,3S)-3-aminocyclohexyl)methyl)-2-butyl-7-isopropoxy-1H-imidazo[4,5-]pyridazin-4-amine (and Enantiomer)

Step 1: tert-butyl N-[(1S,3S)-3-((4-(bis(2,4-dimethoxybenzyl)amino)-2-butyl-7-isopropoxy-1H-imidazo[4,5-d]pyridazin-1-yl)methyl)cyclohexyl)carbamate (and Enantiomer)

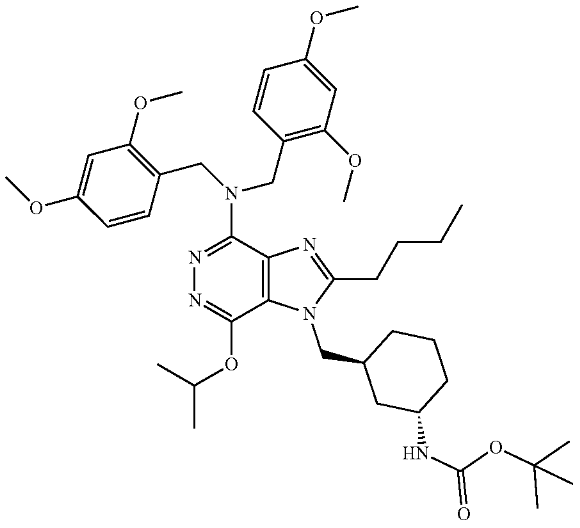 [SMILES: CCCCc1nc2c(N(Cc3ccc(OC)cc3OC)Cc3ccc(OC)cc3OC)nnc(OC(C)C)c2n1C[C@H]1CCC[C@H](NC(=O)OC(C)(C)C)C1]

To a suspension of intermediate (M) (500 mg, 0.91 mmol) in Me-THF (15 mL) was added $Cs_2CO_3$ (898 mg, 2.73 mmol). The mixture was stirred 30 min at rt. Then tert-butyl [trans-3-(bromomethyl)cyclohexyl]carbamate (410 mg, 1.36 mmol) was added. The mixture was stirred 4 days at rt, then heated under microwave at 90° C. for 9 hours. The reaction mixture was diluted with Me-THF (250 mL), washed with water and brine, dried over $MgSO_4$, filtered and concentrated under reduced pressure to give 1.23 g of crude product, which was purified by chromatography on a Merck cartridge (70 g of 15-40 μm silica) with a 50/50 to 100/0 EtOAc/Heptane elution. Expected product (434 mg, 63% yield) was obtained as a white solid.

$^1$H NMR (400 MHz, δ in ppm, DMSO-$d_6$): 0.84 (t, J=7.5 Hz, 3H); 1.08 (m, 1H); 1.20 to 1.55 (m, 9H); 1.32 (s, 9H); 1.36 (d, J=6.2 Hz, 3H); 1.38 (d, J=6.2 Hz, 3H); 1.66 (m, 2H); 2.11 (m, 1H); 2.78 (t, J=7.5 Hz, 2H); 3.68 (m partially hidden, 1H); 3.70 (s, 6H); 3.71 (s, 6H); 4.11 (d, J=7.2 Hz, 2H); 5.00 (s, 4H); 5.36 (sept, J=6.2 Hz, 1H); 6.38 (dd, J=2.4 & 8.4 Hz, 2H); 6.52 (d, J=2.4 Hz, 2H); 6.73 (d, J=7.2 Hz, 1H); 6.95 (d, J=8.4 Hz, 2H)

MS method N: RT (min): 1.82; $[M+H]^+$ 761

Step 2: Example (26): Preparation of Compound 32: 1-(((1S,3S)-3-aminocyclohexyl)methyl)-2-butyl-7-isopropoxy-1H-imidazo[4,5-]pyridazin-4-amine (and Enantiomer)

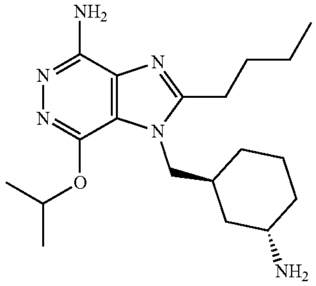 [SMILES: CCCCc1nc2c(N)nnc(OC(C)C)c2n1C[C@H]1CCC[C@H](N)C1]

To a solution of tert-butyl 3-((4-(bis(2,4-dimethoxybenzyl)amino)-2-butyl-7-isopropoxy-1H-imidazo[4,5-d]pyridazin-1-yl)methyl)cyclohexyl)carbamate (435 mg, 0.57 mmol) in DCM (2.5 mL) was added 2,2,2-trifluoroacetic acid (2.5 mL, 32.65 mmol). The mixture was stirred 24 hours at rt. The reaction mixture was diluted with DCM (100 mL) and extracted with $H_2O$ (2×80 mL). The aqueous phase was adjusted to pH 10 with 5 N sodium hydroxide solution, extracted with EtOAc (3×75 mL). the organic phase was washed with water and brine, dried over $MgSO_4$, filtered and evaporated under reduced pressure. Example (26) (136 mg, 66% yield) was obtained as a white solid.

$^1$H NMR (400 MHz, δ in ppm, DMSO-$d_6$): 0.93 (t, J=7.4 Hz, 3H); 1.07 (m, 1H); 1.26 to 1.62 (m, 15H); 1.78 (m, 2H); 1.90 (m broad, 2H); 2.22 (m, 1H); 2.82 (m, 2H); 3.09 (m, 1H); 4.11 (m, 2H); 5.38 (sept, J=6.2 Hz, 1H); 5.84 (s, 2H)

MS method N: RT (min): 0.90; $[M+H]^+$ 361; ES+$[M+2H]^{2+}$: m/z 181

Example (27): Preparation of Compound 33: 1-(3-(aminomethyl)benzyl)-2-butyl-7-isopropoxy-1H-imidazo[4,5-d]pyridazin-4-amine 2,2,2-trifluoroacetate

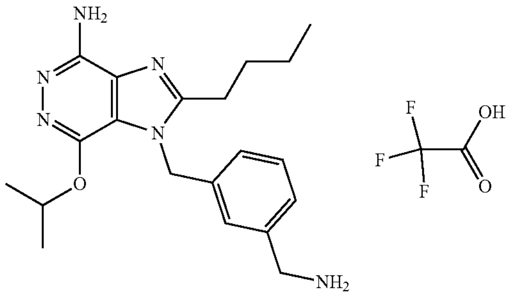 [SMILES: CCCCc1nc2c(N)nnc(OC(C)C)c2n1Cc1cccc(CN)c1 ; O=C(O)C(F)(F)F]

Step 1: tert-butyl (34(4-(bis(2,4-dimethoxybenzyl) amino)-2-butyl-7-isopropoxy-1H-imidazo[4,5-d] pyridazin-1-yl)methyl)benzyl)carbamate

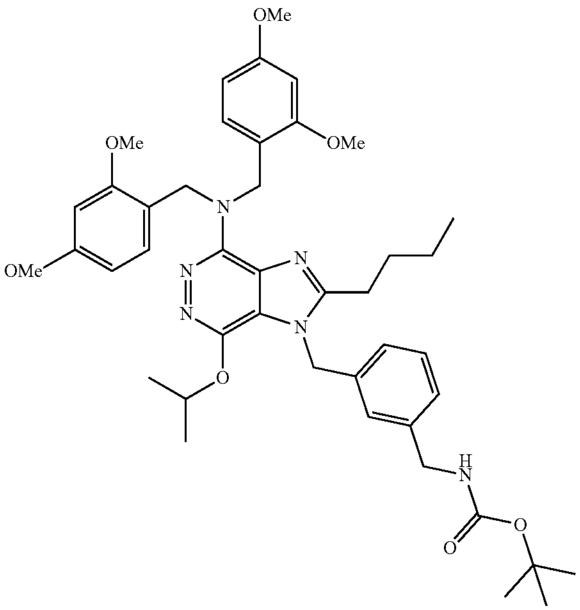 [SMILES: CCCCc1nc2c(N(Cc3ccc(OC)cc3OC)Cc3ccc(OC)cc3OC)nnc(OC(C)C)c2n1Cc1cccc(CNC(=O)OC(C)(C)C)c1]

To a suspension of intermediate (M) (200 mg, 0.36 mmol) in THF (11 mL) was added $Cs_2CO_3$ (356 mg, 1.09 mmol). The mixture was stirred 30 min at rt. Then, tert-butyl 3-bromomethyl)benzylcarbamate (230 mg, 0.73 mmol) was added. The mixture was stirred 20 hours at rt, then filtered, and the filtrate was concentrated under reduced pressure to give 526 mg of crude product. The residue was dissolved in EtOAc, washed with water and brine, concentrated under reduced pressure to give 428 mg of crude product, which was purified by chromatography on a Merck cartridge (30 g of 15-40 μm silica) with a 10/90 to 80/20 EtOAc/Heptane elution. Expected product (61 mg, 22% yield) was obtained as a white solid.

$^1H$ NMR (400 MHz, δ in ppm, DMSO-$d_6$): 0.77 (t, J=7.5 Hz, 3H); 1.22 (d, J=6.2 Hz, 6H); 1.24 (m, 2H); 1.34 (s, 9H); 1.56 (m, 2H); 2.75 (t, J=7.6 Hz, 2H); 3.71 (s, 12H); 4.06 (d, J=6.4 Hz, 2H); 5.01 (s, 4H); 5.32 (sept, J=6.2 Hz, 1H); 5.56 (s, 2H); 6.39 (dd, J=2.5 & 8.4 Hz, 2H); 6.52 (d, J=2.5 Hz, 2H); 6.94 (d broad, J=7.9 Hz, 1H); 6.98 (d, J=8.4 Hz, 2H); 7.03 (s broad, 1H); 7.14 (d broad, J=7.9 Hz, 1H); 7.28 (t, J=7.9 Hz, 1H); 7.32 (t, J=6.4 Hz, 1H)

MS method O: RT (min): 3.22; $[M+H]^+$ 769

Step 2: Example (27): Preparation of Compound 33: 1-(3-(aminomethyl)benzyl)-2-butyl-7-isopropoxy-1H-imidazo[4,5-d]pyridazin-4-amine 2,2,2-trifluoroacetate

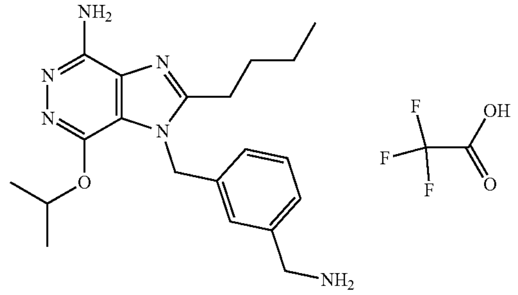 [SMILES: CCCCc1nc2c(N)nnc(OC(C)C)c2n1Cc1cccc(CN)c1 ; O=C(O)C(F)(F)F]

To a solution of tert-butyl (34(4-(bis(2,4-dimethoxybenzyl)amino)-2-butyl-7-isopropoxy-1H-imidazo[4,5-d] pyridazin-1-yl)methyl)benzyl)carbamate of Step 1 (60 mg, 0.08 mmol) in DCM (1 mL) was added 2,2,2-trifluoroacetic acid (1 mL, 13 mmol). The mixture was stirred 8 hours at rt. The reaction was diluted with DCM (100 mL) and extracted with $H_2O$ (2×50 mL). The aqueous phase was neutralized with a saturated solution of $K_2CO_3$ up to pH 8 and extracted by EtOAc (3×75 mL), the organic phase was dried over anhydrous $MgSO_4$, filtered and the filtrate was concentrated under reduced pressure. Example (27) (24 mg, 83% yield) was obtained as a white solid.

$^1H$ NMR (400 MHz, δ in ppm, DMSO-$d_6$): 0.86 (t, J=7.4 Hz, 3H); 1.22 (d, J=6.2 Hz, 6H); 1.34 (m, 2H); 1.67 (m, 2H); 2.80 (m, 2H); 3.94 (s, 2H); 5.32 (sept, J=6.2 Hz, 1H); 5.59 (s, 2H); 5.98 (s, 2H); 7.11 (t, J=2.0 Hz, 1H); 7.14 (td, J=2.0 et 7.8 Hz, 1H); 7.36 (td, J=2.0 et 7.8 Hz, 1H); 7.41 (t, J=7.8 Hz, 1H); 7.86 (m, 3H)

MS method N: RT (min): 0.81; $[M+H]^+$ 369

Example (28): Preparation of Compound 34: 4-((4-amino-2-butyl-7-isopropoxy-1H-imidazo[4,5-d] pyridazin-1-yl)methyl)benzaldehyde

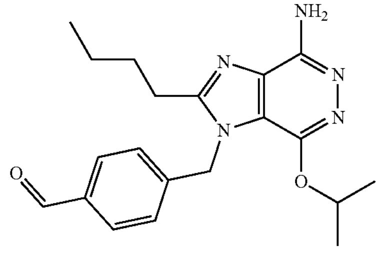 [SMILES: CCCCc1nc2c(N)nnc(OC(C)C)c2n1Cc1ccc(C=O)cc1]

Step 1: 4-((4-(bis(2,4-dimethoxybenzyl)amino)-2-butyl-7-isopropoxy-1H-imidazo[4,5-d]pyridazin-1-yl)methyl)benzaldehyde

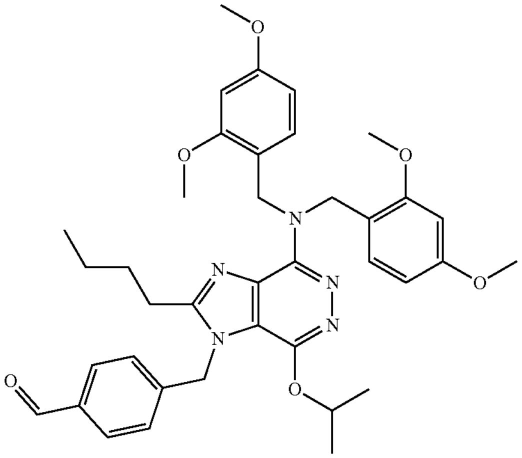 [SMILES: CCCCc1nc2c(N(Cc3ccc(OC)cc3OC)Cc3ccc(OC)cc3OC)nnc(OC(C)C)c2n1Cc1ccc(C=O)cc1]

To a suspension of intermediate (M) (2.2 g, 3.12 mmol) in Me-THF (21 mL) was added 4-(bromomethyl)benzaldehyde (847 mg, 4.26 mmol) and $Cs_2CO_3$ (1.32 g, 4.11 mmol)). The mixture was stirred at rt during 24 h. The mixture was poured into Me-THF (15 mL) then washed with $H_2O$ (15 mL), dried over anhydrous $MgSO_4$, filtered and the filtrate was concentrated under reduced pressure to give 3 g of crude product, which was purified by chromatography on a Merck cartridge (150 g of 15-40 μm silica) with EtOAc/Heptane (38/62) elution. Expected product (1.5 g, 71% yield) was obtained as a white solid.

$^1$H NMR (400 MHz, δ in ppm, DMSO-$d_6$): 0.76 (t, J=7.4 Hz, 3H); 1.13 (d, J=6.2 Hz, 6H); 1.24 (m, 2H); 1.56 (m, 2H); 2.77 (t, J=7.5 Hz, 2H); 3.71 (s, 12H); 5.02 (s, 4H); 5.26 (sept, J=6.2 Hz, 1H); 5.69 (s, 2H); 6.40 (dd, J=2.5 & 8.4 Hz, 2H); 6.53 (d, J=2.5 Hz, 2H); 6.99 (d, J=8.4 Hz, 2H); 7.25 (d, J=8.3 Hz, 2H); 7.89 (d, J=8.3 Hz, 2H); 9.97 (s, 1H)

MS method N: RT (min): 1.66; $[M+H]^+$ 668; $ES^-$ $[2M-H+HCO_2H]^-$: m/z 1379

Step 2: Example (28) Preparation of Compound 34: 4-((4-amino-2-butyl-7-isopropoxy-1H-imidazo[4,5-d]pyridazin-1-yl)methyl)benzaldehyde

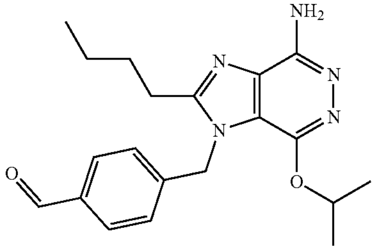 [SMILES: CCCCc1nc2c(N)nnc(OC(C)C)c2n1Cc1ccc(C=O)cc1]

To a solution of 4-((4-(bis(2,4-dimethoxybenzyl)amino)-2-butyl-7-isopropoxy-1H-imidazo[4,5-d]pyridazin-1-yl)methyl)benzaldehyde of Step 1 (110 mg, 0.17 mmol) in DCM (1.6 mL) was added 2,2,2-trifluoroacetic acid (1.6 mL, 21 mmol). The mixture was stirred at rt for 24 h. The reaction was poured into DCM (10 mL) and washed with sodium hydroxide 1M. The organic layer was dried over anhydrous $MgSO_4$, filtered and concentrated under vacuum to give 96 mg of crude product. The crude product was purified by chromatography on a Merck cartridge (5 g of 15-40 μm silica) with DCM/MeOH (96/4) elution. Example (28) (23 mg, 36.8% yield) was obtained as a solid.

$^1$H NMR (400 MHz, δ in ppm, DMSO-$d_6$): 0.84 (t, J=7.5 Hz, 3H); 1.12 (d, J=6.2 Hz, 6H); 1.33 (m, 2H); 1.64 (m, 2H); 2.83 (m, 2H); 5.26 (m, 1H); 5.69 (s, 2H); 5.97 (s, 2H); 7.23 (d, J=8.2 Hz, 2H); 7.89 (d, J=8.2 Hz, 2H); 9.98 (s, 1H)

MS method N: RT (min): 1.21; $[M+H]^+$ 368

Example (29): Preparation of Compound 35: (4-((4-amino-2-butyl-7-isopropoxy-1H-imidazo[4,5-d]pyridazin-1-yl)methyl)phenyl)methanol

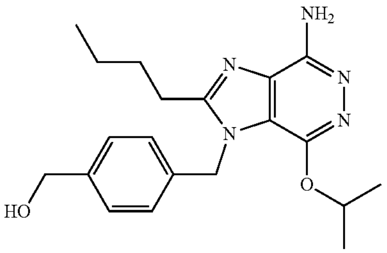 [SMILES: CCCCc1nc2c(N)nnc(OC(C)C)c2n1Cc1ccc(CO)cc1]

To a solution of compound 4-((4-(bis(2,4-dimethoxybenzyl)amino)-2-butyl-7-isopropoxy-1H-imidazo[4,5-d]pyridazin-1-yl)methyl)benzaldehyde of Step 1 in Example (28) (200 mg, 0.30 mmol) in DCM (3 mL) was added 2,2,2-trifluoroacetic acid (1.6 mL, 21 mmol) and triethylsilane (145 μL, 0.90 mmol). The mixture was stirred at room temperature for 24 hours. The reaction was poured into DCM and washed with sodium hydroxide 1M. The organic layer was dried over anhydrous $MgSO_4$, filtered and concentrated under vacuum to give 200 mg of crude product, which was purified by preparative HPLC at room temperature by using a 250×50 mm, 5 μm CSH column (WATERS™) and a water/acetonitrile gradient with 0.1% formic acid (t=0 min: 10% of acetonitrile; t=5 min: 10% and t=25 min: 30%). The compound was eluted at 18.8 min and lyophilized to afford 22 mg (19.8% yield) of Example (29) as a white foam.

$^1$H NMR (400 MHz, δ in ppm, DMSO-$d_6$): 0.84 (t, J=7.28 Hz, 3H) 1.21 (d, J=6.27 Hz, 6H) 1.32 (sxt, J=7.65 Hz, 2H) 1.63 (quin, J=7.59 Hz, 2H) 2.79 (t, J=7.81 Hz, 2H) 4.45 (s, 2H) 5.13 (br s, 1H) 5.32 (spt, J=6.15 Hz, 1H) 5.56 (s, 2H) 5.92 (s, 2H) 7.02 (d, J=8.28 Hz, 2H) 7.27 (d, J=8.28 Hz, 2H)

MS method A: RT (min): 0.73; $[M+H]^+$ 370

Example (30): Preparation of Compound 36: 2-butyl-1-(4-((cyclopropylamino)methyl)benzyl)-7-isopropoxy-1H-imidazo[4,5-c]pyridazin-4-amine

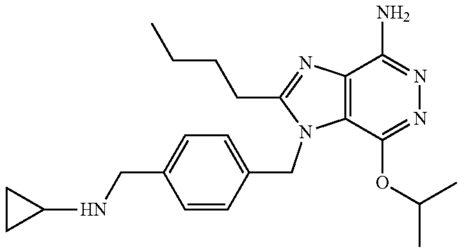 [SMILES: CCCCc1nc2c(N)nnc(OC(C)C)c2n1Cc1ccc(CNC2CC2)cc1]

Step 1: 2-butyl-1-(4-((cyclopropylamino)methyl) benzyl)-N,N-bis(2,4-dimethoxybenzyl)-7-iso-propoxy-1H-imidazo[4,5-d]pyridazin-4-amine

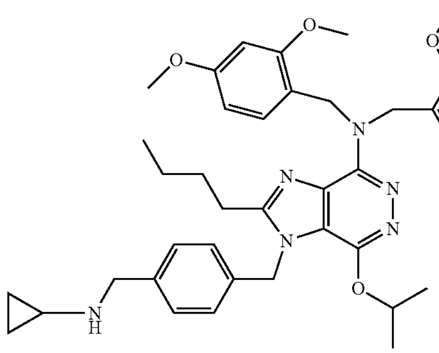

To a solution of 4-((4-(bis(2,4-dimethoxybenzyl)amino)-2-butyl-7-isopropoxy-1H-imidazo[4,5-d]pyridazin-1-yl) methyl)benzaldehyde of Step 1 in Example (28) (200 mg, 0.30 mmol) in MeOH (2 mL) was added cyclopropylamine (25.41 μL, 0.36 mmol) and acetic acid (34.29 μL, 0.60 mmol). The mixture was stirred at rt during 10 min and then sodium cyanoborohydride (29.72 mg, 0.45 mmol) was added. The mixture was stirred at rt during 3 h. The reaction was poured into $H_2O$ and adjusted pH to 8 by addition of ammonia solution (35%). Then the mixture was extracted by EtOAc. The organic layer was dried over anhydrous $MgSO_4$, filtered and concentrated under vacuum to give 0.25 g of oil. The product was purified by chromatography on a Merck cartridge (20 g of 15-40 μm silica) with [(EtOAc/EtOH 3/1) 40%-Heptane 60%] elution. Expected product (154 mg, 72.4% yield) was obtained as a solid.

$^1$H NMR (400 MHz, δ in ppm, DMSO-$d_6$): 0.19 (m, 2H); 0.29 (m, 2H); 0.76 (t, J=7.4 Hz, 3H); 1.21 (d, J=6.2 Hz, 6H); 1.24 (m, 2H); 1.54 (m, 2H); 1.97 (m, 1H); 2.56 (m, 1H); 2.75 (t, J=7.6 Hz, 2H); 3.65 (d, J=5.4 Hz, 2H); 3.71 (s, 12H); 5.01 (s, 4H); 5.31 (sept, J=6.2 Hz, 1H); 5.56 (s, 2H); 6.39 (dd, J=2.5 & 8.5 Hz, 2H); 6.52 (d, J=2.5 Hz, 2H); 6.97 (d, J=8.5 Hz, 2H); 7.02 (d, J=8.3 Hz, 2H); 7.27 (d, J=8.3 Hz, 2H)

MS method N: RT (min): 1.57; $[M+H]^+$ 709; $ES^+$ $[M+2H]^{2+}$: m/z 355

Step 2: Example (30) Preparation of Compound 36: 2-butyl-1-(4-((cyclopropylamino)methyl)benzyl)-7-isopropoxy-1H-imidazo[4,5-d]pyridazin-4-amine

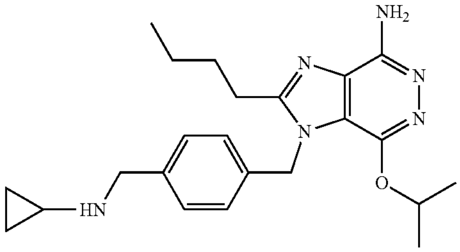 [SMILES: CCCCc1nc2c(N)nnc(OC(C)C)c2n1Cc1ccc(CNC2CC2)cc1]

To a solution of 2-butyl-1-(4-((cyclopropylamino)methyl) benzyl)-N,N-bis(2,4-dimethoxybenzyl)-7-isopropoxy-1H-imidazo[4,5-d]pyridazin-4-amine of Step 1 (140 mg, 0.20 mol) in DCM (2 mL) was added 2,2,2-trifluoroacetic acid (910 μL, 11.81 mmol). The mixture was stirred at rt for 24 h. The reaction was poured into DCM (10 mL) and washed with sodium hydroxide 1M. The organic layer was dried over anhydrous $MgSO_4$, filtered and concentrated under vacuum to give 90 mg of crude product. The crude product was purified by chromatography on a Merck cartridge (10 g of 15-40 μm silica) with DCM/MeOH/$NH_4OH$ (95/5/0.2) elution, to afford Example (30) (40 mg, 49% yield) as a solid.

$^1$H NMR (400 MHz, δ in ppm, DMSO-$d_6$): 0.17 to 0.32 (m, 4H); 0.83 (t, J=7.3 Hz, 3H); 1.20 (d, J=6.2 Hz, 6H); 1.31 (m, 2H); 1.61 (m, 2H); 1.97 (m, 1H); 2.60 (m, 1H); 2.80 (m, 2H); 3.66 (s, 2H); 5.32 (sept, J=6.2 Hz, 1H); 5.55 (s, 2H); 5.92 (m, 2H); 7.00 (d, J=8.3 Hz, 2H); 7.27 (d, J=8.3 Hz, 2H)

MS method N: RT (min): 0.83; $[M+H]^+$ 409; ES+ $[M+2H-iPr]^{2+}$: m/z 184

The following compounds may be made by analogy to Example 30: 82, 83, 100, 101, 102.

Example (31): Preparation of Compound 37: 3-((4-((4-amino-2-butyl-7-isopropoxy-1H-imidazo[4,5-d] pyridazin-yl)methyl)benzyl)amino)thietane 1,1-dioxide

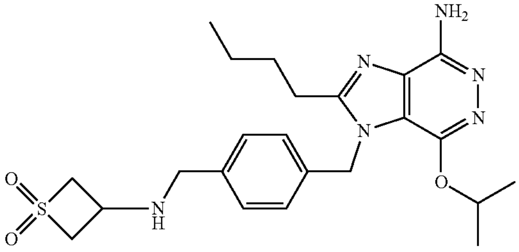 [SMILES: CCCCc1nc2c(N)nnc(OC(C)C)c2n1Cc1ccc(CNC2CS(=O)(=O)C2)cc1]

Step 1: 3-((4-((4-(bis(2,4-dimethoxybenzyl)amino)-2-butyl-7-isopropoxy-1H-imidazo[4,5-]pyridazin-yl) methyl)benzyl)amino)thietane 1,1-dioxide

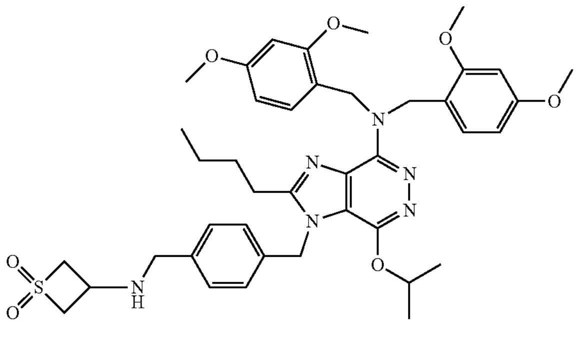 [SMILES: CCCCc1nc2c(N(Cc3ccc(OC)cc3OC)Cc3ccc(OC)cc3OC)nnc(OC(C)C)c2n1Cc1ccc(CNC2CS(=O)(=O)C2)cc1]

To a solution of 4-((4-(bis(2,4-dimethoxybenzyl)amino)-2-butyl-7-isopropoxy-1H-imidazo[4,5-d]pyridazin-1-yl) methyl)benzaldehyde of Step 1 in Example (28) (810 mg, 1.21 mmol) in MeOH (10 mL) was added 3-aminothietane 1,1-dioxide hydrochloride (301.85 mg, 1.82 mmol), triethylamine (338.13 µL, 2.43 mmol) and acetic acid (208.31 µL, 3.64 mmol). The mixture was stirred at rt during 10 min and then sodium cyanoborohydride (114.33 mg, 1.82 mmol) was added. The mixture was stirred at rt during 4 h. The reaction was poured into water and pH adjusted to 8 by addition of ammonia solution (35%). Then the mixture was extracted by EtOAc. The organic layer was dried over anhydrous $MgSO_4$, filtered and concentrated under vacuum to afford 1 g of crude product, which was used in the next step without further purification.

Step 2: Example (31) Preparation of Compound 37: 3-((4-((4-amino-2-butyl-7-isopropoxy-1H-imidazo [4,5-d]pyridazin-yl)methyl)benzyl)amino)thietane 1,1-dioxide

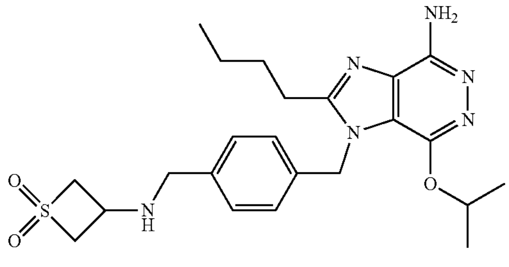 [SMILES: CCCCc1nc2c(N)nnc(OC(C)C)c2n1Cc1ccc(CNC2CS(=O)(=O)C2)cc1]

To a solution of 3-((4-((4-(bis(2,4-dimethoxybenzyl) amino)-2-butyl-7-isopropoxy-1H-imidazo[4,5-d]pyridazin-1-yl)methyl)benzyl)amino)thietane 1,1-dioxide of Step 1 (150 mg, 0.19 mmol) in DCM (5 mL) was added 2,2,2-trifluoroacetic acid (897.05 in, 11.64 mmol). The mixture was stirred at rt for 24 hours. The reaction was poured into DCM and washed with sodium hydroxide 1M. The organic layer was dried over anhydrous $MgSO_4$, filtered and concentrated under vacuum to give 99 mg of white foam. The crude product was purified by chromatography on a Merck cartridge (10 g of 15-40 µm silica) with DCM/MeOH/ $NH_4OH$ (95/5/0.2) elution, to afford Example (31) (61 mg, 66% yield) as a white solid.

$^1H$ NMR (400 MHz, δ in ppm, DMSO-$d_6$): 0.84 (t, J=7.4 Hz, 3H); 1.20 (d, J=6.2 Hz, 6H); 1.32 (m, 2H); 1.62 (m, 2H); 2.80 (m, 2H); 2.91 (m, 1H); 3.44 (m, 1H); 3.59 (s, 2H); 3.84 to 3.91 (m, 2H); 4.17 to 4.25 (m, 2H); 5.32 (sept, J=6.2 Hz, 1H); 5.56 (s, 2H); 5.94 (s, 2H); 7.02 (d, J=8.2 Hz, 2H); 7.28 (d, J=8.2 Hz, 2H)

MS method N: RT (min): 0.99; $[M+H]^+$ 473

Example (32): Preparation of Compound 38: N-(4-((4-amino-2-butyl-7-isopropoxy-1H-imidazo[4,5-d] pyridazin-1-yl)methyl)benzyl)-N-(1,1-dioxidothietan-3-yl)acetamide

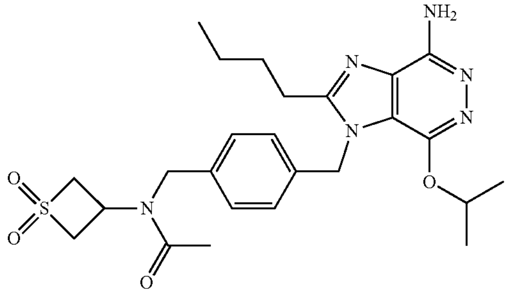 [SMILES: CCCCc1nc2c(N)nnc(OC(C)C)c2n1Cc1ccc(CN(C(C)=O)C2CS(=O)(=O)C2)cc1]

Step 1: N-(4-((4-(bis(2,4-dimethoxybenzyl)amino)-2-butyl-7-isopropoxy-1H-imidazo[4,5-d]pyridazin-1-yl)methyl)benzyl)-N-(1,1-dioxidothietan-3-yl) acetamide

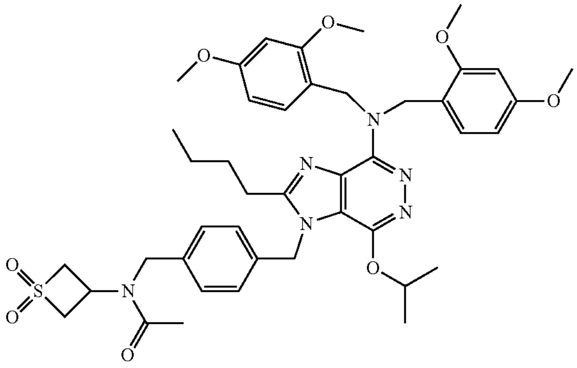 [SMILES: CCCCc1nc2c(N(Cc3ccc(OC)cc3OC)Cc3ccc(OC)cc3OC)nnc(OC(C)C)c2n1Cc1ccc(CN(C(C)=O)C2CS(=O)(=O)C2)cc1]

To a solution of 3-((4-((4-(bis(2,4-dimethoxybenzyl) amino)-2-butyl-7-isopropoxy-1H-imidazo[4,5-d]pyridazin-1-yl)methyl)benzyl)amino)thietane 1,1-dioxide of Step 1 in Example (31) (300 mg, 0.39 mmol) in Pyridine (3 mL), was added acetic anhydride (109.86 µL, 1.16 mmol). The mixture was stirred at rt for 48 h. At the end of this time, the reaction mixture was concentrated by evaporation under reduced pressure. The residue was poured into EtOAc and washed with water. The organic layer was dried over anhydrous $MgSO_4$, filtered and concentrated under vacuum to give 308 mg of white foam. The crude product was purified by chromatography on a Merck cartridge (20 g of 15-40 µm silica) with DCM/MeOH (95/5) elution, to afford 275 mg of expected product as a white foam. The compound was used into the next step without further purification.

Step 2: Example (32) Preparation of Compound 38: N-(4-((4-amino-2-butyl-7-isopropoxy-1H-imidazo[4,5-d]pyridazin-1-yl)methyl)benzyl)-N-(1,1-dioxidothietan-3-yl)acetamide

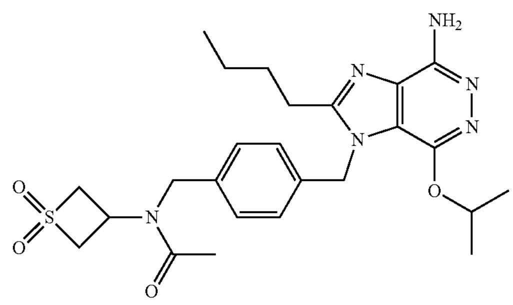 [SMILES: CCCCc1nc2c(N)nnc(OC(C)C)c2n1Cc1ccc(CN(C(C)=O)C2CS(=O)(=O)C2)cc1]

To a solution of N-(4-((4-(bis(2,4-dimethoxybenzyl)amino)-2-butyl-7-isopropoxy-1H-imidazo[4,5-d]pyridazin-1-yl)methyl)benzyl)-N-(1,1-dioxidothietan-3-yl)acetamide of Step 1 (270 mg, 0.33 mol) in DCM (7 mL) was added 2,2,2-trifluoroacetic acid (1 mL, 12.98 mmol). The mixture was stirred at rt for 24 h. The reaction was poured into DCM and washed with sodium hydroxide 1M. The organic layer was dried over anhydrous $MgSO_4$, filtered and concentrated under vacuum to give 220 mg of white foam. The crude product was purified by chromatography on a Merck cartridge (20 g of 15-40 μm silica) with $CH_2Cl_2$/MeOH/$NH_4OH$ (93/7/0.2) elution, to afford 110 mg (64.5%, yield) of Example (32) as a white foam.

$^1$H NMR (400 MHz, δ in ppm, DMSO-$d_6$): 0.82 (t, J=7 Hz, 3H); 1.17 (d, J=6 Hz, 6H); 1.30 (dq, J=7 & 15 Hz, 2H); 1.59 (quin, J=8 Hz, 2H); 1.96 (s, 2H); 2.19 (s broad, 1H); 2.81 (t, J=8 Hz, 2H); 4.06 to 4.79 (m, 6H); 5.05 (m, 1H); 5.30 (quin, J=6 Hz, 1H); 5.57 (s broad, 2H); 5.92 (s, 2H); 6.94 to 7.26 (m, 4H)

MS method N: RT (min): 1.08; $[M+H]^+$ m/z 515, ES− $[M-H+HCO_2H]^-$: m/z 559

Example (33): Preparation of Compound 39: 2-butyl-7-isopropoxy-1-(4-(((1-methylcyclobutyl)amino)methyl)benzyl)-1H-imidazo[4,5-d]pyridazin-4-amine

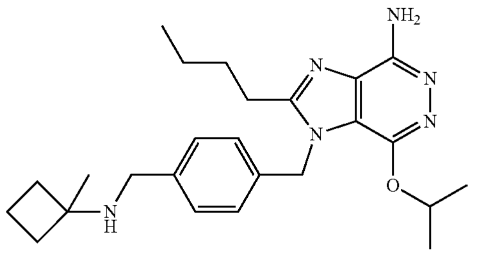 [SMILES: CCCCc1nc2c(N)nnc(OC(C)C)c2n1Cc1ccc(CNC2(C)CCC2)cc1]

Step 1: 2-butyl-N,N-bis(2,4-dimethoxybenzyl)-7-isopropoxy-1-(4-(((1-methylcyclobutyl) amino) methyl)benzyl)-1H-imidazo[4,5-d]pyridazin-4-amine

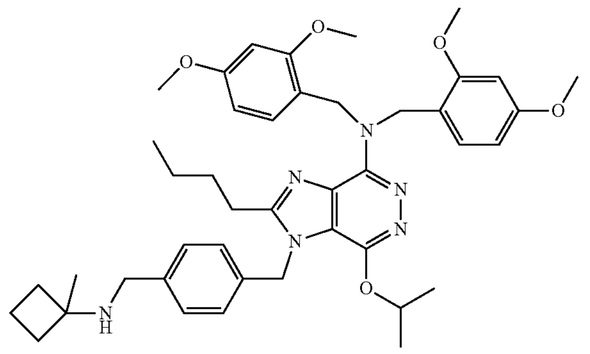 [SMILES: CCCCc1nc2c(N(Cc3ccc(OC)cc3OC)Cc3ccc(OC)cc3OC)nnc(OC(C)C)c2n1Cc1ccc(CNC2(C)CCC2)cc1]

To a solution of 4-((4-(bis(2,4-dimethoxybenzyl)amino)-2-butyl-7-isopropoxy-1H-imidazo[4,5-d]pyridazin-1-yl) methyl)benzaldehyde of Step 1 in Example (28) (300 mg, 0.45 mmol) in methanol (2 mL) was added 1-methylcyclobutanamine hydrochloride (86.26 mg, 0.67 mmol), triethylamine (125.23 μL, 0.90 mmol) and acetic acid (77.15 μL, 1.35 mmol). The mixture was stirring at rt during 10 min and then sodium cyanoborohydride (43.21 mg, 0.67 mmol) was added. The mixture was stirred at rt during 5 h. The reaction was poured into water and adjusted pH to 8 by addition of ammonia solution (35%). Then the mixture was extracted by EtOAc. The organic layer was dried over anhydrous $MgSO_4$, filtered and concentrated under vacuum to give 0.45 g of oil. The crude product was purified by chromatography on a Merck cartridge (30 g of 15-40 μm silica) with [(EtOAc/EtOH 3/1) 50%-Heptane 50%] elution, to afford expected product (146 mg, 44.1% yield) as a solid.

$^1$H NMR (400 MHz, δ in ppm, DMSO-$d_6$): 0.76 (t, J=7.5 Hz, 3H); 1.18 (s, 3H); 1.23 (d, J=6.2 Hz, 6H); 1.25 (m, 2H); 1.55 (m, 2H); 1.58 to 1.72 (m, 4H); 1.85 to 2.01 (m, 3H); 2.74 (t, J=7.6 Hz, 2H); 3.56 (d, J=6.4 Hz, 2H); 3.71 (s, 12H); 5.01 (s, 4H); 5.33 (sept, J=6.2 Hz, 1H); 5.55 (s, 2H); 6.39 (dd, J=2.4 & 8.4 Hz, 2H); 6.52 (d, J=2.4 Hz, 2H); 6.97 (d, J=8.4 Hz, 2H); 7.02 (d, J=8.3 Hz, 2H); 7.30 (d, J=8.3 Hz, 2H)

MS method N: RT (min): 1.32; $[M+H]^+$ 737; $ES^+$ $[M+2H]^{2+}$: m/z 369

Step 2: Example (33): Preparation of Compound 39: 2-butyl-7-isopropoxy-1-(4-(((1-methylcyclobutyl)amino)methyl)benzyl)-1H-imidazo[4,5-d]pyridazin-4-amine

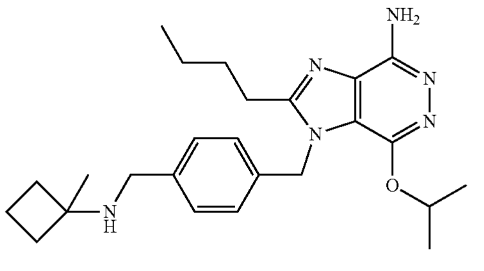 [SMILES: CCCCc1nc2c(N)nnc(OC(C)C)c2n1Cc1ccc(CNC2(C)CCC2)cc1]

To a solution de 2-butyl-N,N-bis(2,4-dimethoxybenzyl)-7-isopropoxy-1-(4-(((1-methyl cyclobutyl)amino)methyl) benzyl)-1H-imidazo[4,5-d]pyridazin-4-amine of Step 1 (140 mg, 0.19 mmol) in DCM (4 mL) was added 2,2,2-trifluoroacetic acid (878 µL, 11.40 mmol). The mixture was stirred at rt for 24 hours. The reaction was poured into DCM and washed with sodium hydroxide 1M. The organic layer was dried over anhydrous $MgSO_4$, filtered and concentrated under vacuum to give 83 mg of white solid. The crude product was purified by chromatography on a Merck cartridge (10 g of 15-40 µm silica) with $CH_2Cl_2$/MeOH/$NH_4OH$ (94/6/0.2) elution, to afford Example (33) (66 mg, 79.7% yield) as a white solid.

$^1$H NMR (400 MHz, δ in ppm, DMSO-$d_6$): 0.85 (t, J=7.4 Hz, 3H); 1.19 (s, 3H); 1.22 (d, J=6.2 Hz, 6H); 1.33 (m, 2H); 1.58 to 1.73 (m, 6H); 1.93 (m, 2H); 2.09 (m broad, 1H); 2.80 (m, 2H); 3.58 (s, 2H); 5.33 (sept, J=6.2 Hz, 1H); 5.56 (s, 2H); 5.92 (s, 2H); 7.01 (d, J=8.3 Hz, 2H); 7.31 (d, J=8.3 Hz, 2H)

MS method N: RT (min): 0.9; $[M+H]^+$ 437; $ES^+$ $[M+C_5H_8]^+$: m/z 369

The following compounds may be made by analogy to Example 33: 85, 87, 88, 89, 90, 91.

Example (34): Preparation of Compound 40: 2-butyl-7-isopropoxy-1-(4-(piperazin-1-ylmethyl) benzyl)-1H-imidazo[4,5-d]pyridazin-4-amine

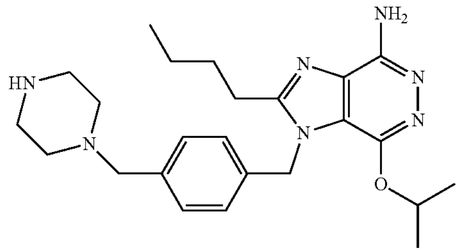 [SMILES: CCCCc1nc2c(N)nnc(OC(C)C)c2n1Cc1ccc(CN2CCNCC2)cc1]

Step 1: tert-butyl 4-(4-((4-(bis(2,4-dimethoxybenzyl)amino)-2-butyl-7-isopropoxy-1H-imidazo[4,5-d] pyridazin-1-yl)methyl)benzyl)piperazine-1-carboxylate

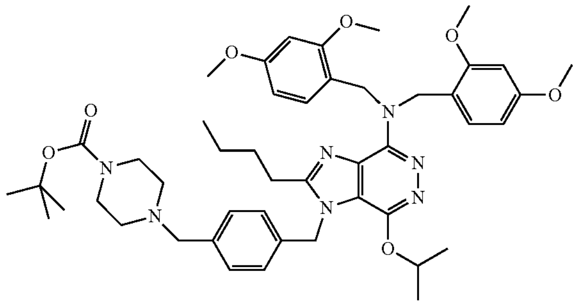 [SMILES: CCCCc1nc2c(N(Cc3ccc(OC)cc3OC)Cc3ccc(OC)cc3OC)nnc(OC(C)C)c2n1Cc1ccc(CN2CCN(C(=O)OC(C)(C)C)CC2)cc1]

To a solution of 4-((4-(bis(2,4-dimethoxybenzyl)amino)-2-butyl-7-isopropoxy-1H-imidazo[4,5-d]pyridazin-1-yl) methyl)benzaldehyde of Step 1 in Example (28) (200 mg, 0.30 mmol) in methanol (2.5 mL) was added 1-Boc-piperazine (85.38 mg, 0.45 mmol), acetic acid (34.29 µL, 0.60 mmol). The mixture was stirring at rt during 10 min and then sodium cyanoborohydride (28.23 mg, 0.45 mmol) was added. The stirring was continued at rt during 4.5 h. The reaction was poured into water and pH adjusted to 9 by addition of ammonia solution (35%). Then the mixture was extracted by EtOAc. The organic layer was dried over anhydrous $MgSO_4$, filtered and concentrated under vacuum to give 0.45 g of oil. The crude product (289 mg) as white gum was used directly in the next step.

Step 2: Example (34) Preparation of Compound 40: 2-butyl-7-isopropoxy-1-(4-(piperazin-1-ylmethyl) benzyl)-1H-imidazo[4,5-d]pyridazin-4-amine

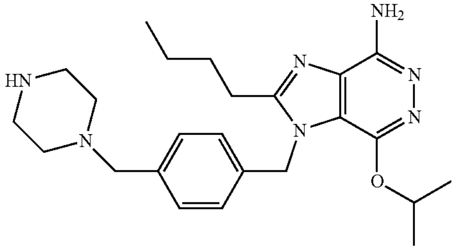 [SMILES: CCCCc1nc2c(N)nnc(OC(C)C)c2n1Cc1ccc(CN2CCNCC2)cc1]

To a solution of tert-butyl 4-(4-((4-(bis(2,4-dimethoxybenzyl)amino)-2-butyl-7-isopropoxy-1H-imidazo[4,5-d] pyridazin-1-yl)methyl)benzyl)piperazine-1-carboxylate of Step 1 (250 mg, 0.3 mmol) in DCM (6.3 mL) was added 2,2,2-trifluoroacetic acid (919.29 µL, 11.93 mmol). The mixture was stirred at rt for 24 hours. The reaction was poured into DCM and washed with sodium hydroxide 1M. The organic layer was dried over anhydrous $MgSO_4$, filtered and concentrated under vacuum to give 145 mg of crude product, which was purified by chromatography on a Merck cartridge (20 g of 15-40 µm silica) with $CH_2Cl_2$/MeOH/$NH_4OH$ (90/10/0.2) elution, to afford Example (34) (45 mg, 35% yield) as a white solid.

$^1$H NMR (400 MHz, δ in ppm, DMSO-$d_6$): 0.81 (t, J=7 Hz, 3H); 1.17 (d, J=6 Hz, 6H); 1.29 (dq, J=7 & 15 Hz, 2H); 1.59 (quin, J=8 Hz, 2H); 2.22 (s broad, 4H); 2.63 (t, J=5 Hz, 4H); 2.81 (t, J=7 Hz, 2H); 3.36 (s, 2H); 5.30 (spt, J=6 Hz, 1H); 5.55 (s, 2H); 5.94 (s, 2H); 7.00 (d, J=8 Hz, 2H); 7.24 (d, J=8 Hz, 2H) MS method N: RT (min): 0.80; $[M+H]^+$ 438

Example (35): Preparation of Compound 41: 2-butyl-N7,N7,1-trimethyl-1H-imidazo[4,5-d] pyridazine-4,7-diamine

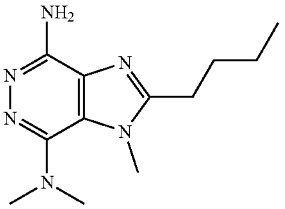 [SMILES: CCCCc1nc2c(N)nnc(N(C)C)c2n1C]

A mixture of Intermediate (K) (95 mg, 0.40 mmol) in DMF (1 mL) and Dimethylamine (7 mL, 40% in Water) were introduced into an autoclave and heated 6 hours at 160° C. The reaction mixture was poured into water (100 mL) and extracted with EtOAc (3×30 mL). The organic layer was collected and dried over anhydrous $MgSO_4$, filtered and concentrated under vacuum to give 40 mg of crude product which was purified by chromatography on a Merck cartridge (2.5 g, 15-40 μm silica) with a DCM/Methanol (93/7) elution to afford Example (34) (13 mg, 14% yield) as a white solid.

$^1$H NMR (400 MHz, δ in ppm, DMSO-$d_6$): 0.94 (t, J=7.4 Hz, 3H); 1.43 (m, 2H); 1.77 (m, 2H); 2.77 (s, 6H); 2.86 (m, 2H); 3.95 (s, 3H); 6.06 (s, 2H)

MS method N: RT (min): 0.88; $[M+H]^+$ 249

Example (36): Preparation of Compound 42: 2-butyl-1-methyl-7-(pyrrolidin-1-yl)-1H-imidazo[4,5-d]pyridazin-4-amine

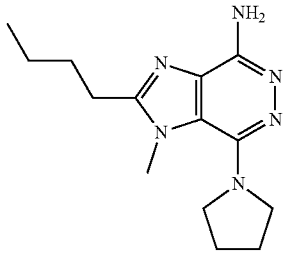 [SMILES: CCCCc1nc2c(N)nnc(N3CCCC3)c2n1C]

A mixture of Intermediate (K) (50 mg, 0.21 mmol), water (1 mL) and pyrrolidine (1 mL) were introduced into a microwave vial. The suspension was heated at 160° C. during 7 hours under microwave. The reaction mixture was concentrated under vacuum to give 100 mg of crude product, which was purified by chromatography on a Merck cartridge (10 g 15-40 μm silica) with a DCM/MeOH/MeCN (85/7.5/7.5) elution to afford Example (36) (32 mg, 55% yield) as a yellow amorphous solid.

$^1$H NMR (400 MHz, δ in ppm, DMSO-$d_6$): 0.94 (t, J=7.4 Hz, 3H); 1.43 (m, 2H); 1.77 (m, 2H); 1.89 (m, 4H); 2.88 (m, 2H); 3.30 (m, 4H); 3.96 (s, 3H); 6.88 (s, 2H)

MS method P: RT (min): 1.85; $[M+H]^+$ 275

Example (37): Preparation of Compound 43: 2-butyl-N7-(4-((dimethylamino)methyl)benzyl)-N7,1-dimethyl-1H-imidazo[4,5-d]pyridazine-4,7-diamine

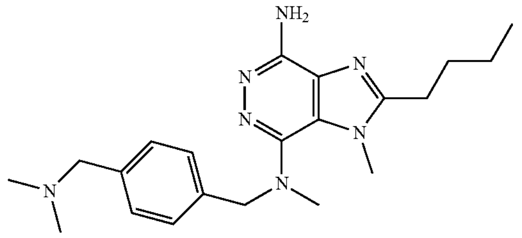 [SMILES: CCCCc1nc2c(N)nnc(N(C)Cc3ccc(CN(C)C)cc3)c2n1C]

A mixture of Intermediate (K) (200 mg, 0.83 mmol), dimethyl((4-[(methylamino)methyl]phenyl)methyl)amine (783 mg, 4.17 mmol), 1-Butanol (2 mL) and 3-chloropyridine hydrochloride (413 mg, 2.75 mmol) were introduced into microwave vial. The suspension was heated at 160° C. during 3 hours under microwave. The reaction mixture was concentrated under vacuum to give 1.2 g of crude product. This material was dissolved in EtOAc (25 mL) and washed with water (20 mL). The organic layer was dried over anhydrous $MgSO_4$, filtered and concentrated under vacuum to give 381 mg of crude compound, which was purified by chromatography on a Merck cartridge (20 g 15-40 μm silica) with a DCM/Methanol (8/2) elution, to afford Example (37) (83 mg, 26% yield) as a yellow solid.

$^1$H NMR (400 MHz, δ in ppm, DMSO-$d_6$): 0.94 (t, J=7.4 Hz, 3H); 1.42 (m, 2H); 1.76 (m, 2H); 2.12 (s, 6H); 2.67 (s, 3H); 2.86 (m, 2H); 3.34 (s, 2H); 4.01 (s, 3H); 4.31 (s, 2H); 6.05 (s, 2H); 7.22 (d, J=8.2 Hz, 2H); 7.29 (d, J=8.2 Hz, 2H).

MS method N: RT (min): 0.84; $[M+H]^+$ 382; ES+ $[M+2H]^{2+}$: m/z 191.5

Example (38): Preparation of Compound 44: 2-butyl-N7,1-dimethyl-N7-(4-(morpholinomethyl)benzyl)-1H-imidazo[4,5-d]pyridazine-4,7-diamine

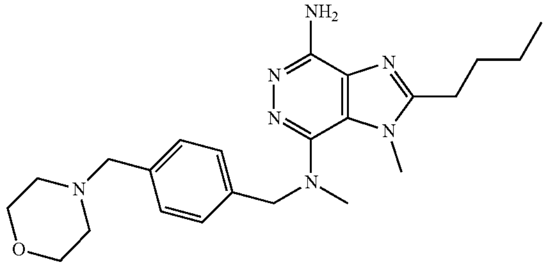 [SMILES: CCCCc1nc2c(N)nnc(N(C)Cc3ccc(CN4CCOCC4)cc3)c2n1C]

A mixture of Intermediate (K) (100 mg, 0.42 mmol), Methyl-(4-morpholin-4-ylmethyl-benzyl)-amine (484 mg, 2.09 mmol), 1-Butanol (2 mL), 3-chloropyridine hydrochloride (206.5 mg, 1.38 mmol) were introduced into a microwave vial. The suspension was heated at 160° C. during 6 hours in microwave. The reaction mixture was concentrated under vacuum to give 604 mg of crude product. This material was dissolved in EtOAc (50 mL) and washed with water (50 mL). The organic layer was dried over anhydrous $MgSO_4$, filtered and concentrated under vacuum to give 221 mg of yellow solid, which was purified by chromatography on a Merck cartridge (15 g 15-40 μm silica) with a DCM/MeOH (9/1) elution to afford 75 mg as beige solid, which was stirred for 1 hour with isopropyl ether (2 mL). After filtration and drying, Example (38) (55 mg, 35% yield) was obtained as a white solid.

$^1$H NMR (400 MHz, δ in ppm, DMSO-$d_6$): 0.94 (t, J=7.3 Hz, 3H); 1.42 (m, 2H); 1.76 (m, 2H); 2.32 (m, 4H); 2.66 (s, 3H); 2.86 (m, 2H); 3.41 (s, 2H); 3.56 (m, 4H); 4.00 (s, 3H); 4.30 (s, 2H); 6.02 (s, 2H); 7.23 (d, J=8.3 Hz, 2H); 7.29 (d, J=8.3 Hz, 2H)

MS method N: RT (min): 0.73; $[M+H]^+$ 424; ES+ $[M+2H]^{2+}$: m/z 212.5

Example (39A): Preparation of Compound 45: 4-(((4-amino-2-butyl-1-methyl-1H-imidazo[4,5-d]pyridazin-7-yl)(methyl)amino)methyl)benzonitrile and Example (39B): Preparation of Compound 46: N7-(4-(aminomethyl)benzyl)-2-butyl-N7,1-dimethyl-1H-imidazo[4,5-d]pyridazine-4,7-diamine Step 1: Example (39A): Preparation of Compound 45: 4-(((4-amino-2-butyl-1-methyl-1H-imidazo[4,5-d]pyridazin-7-yl)(methylamino)methyl)benzonitrile

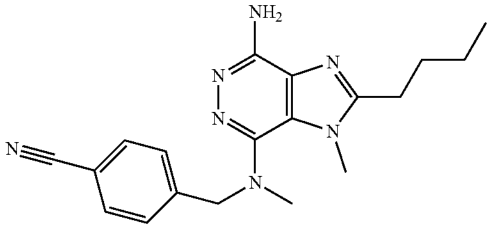 [SMILES: CCCCc1nc2c(N)nnc(N(C)Cc3ccc(C#N)cc3)c2n1C]

A mixture of Intermediate (K) (400 mg, 1.67 mmol), 4-(methylaminomethyl)benzonitrile (1.28 g, 8.34 mmol), 1-Butanol (10 mL), 3-chloropyridine hydrochloride (826 mg, 5.51 mmol) were introduced into a microwave vial. The suspension was heated at 160° C. during hours under microwave. The reaction mixture was concentrated under vacuum to give 1.9 g of crude product. This material was dissolved in EtOAc (100 mL) and washed with water (100 mL). The organic layer was dried over anhydrous $MgSO_4$, filtered and concentrated under vacuum to give 703 mg of yellow solid, which was purified by chromatography on a Merck cartridge (40 g 15-40 μm silica) with a DCM/Methanol/Acetonitrile (96/2/2) elution to afford Example (39A) (124 mg, 21% yield) as a white solid.

$^1$H NMR (400 MHz, δ in ppm, DMSO-$d_6$): 0.94 (t, J=7.4 Hz, 3H); 1.42 (m, 2H); 1.76 (m, 2H); 2.71 (s, 3H); 2.86 (m, 2H); 4.00 (s, 3H); 4.45 (s, 2H); 6.03 (s, 2H); 7.55 (d, J=8.5 Hz, 2H); 7.76 (d, J=8.5 Hz, 2H)

MS method N: RT (min): 1.12; $[M+H]^+$ 350

Step 2: Example (39B) Preparation of Compound 46: N7-(4-(aminomethyl)benzyl)-2-butyl-N7,1-dimethyl-1H-imidazo[4,5-d]pyridazine-4,7-diamine

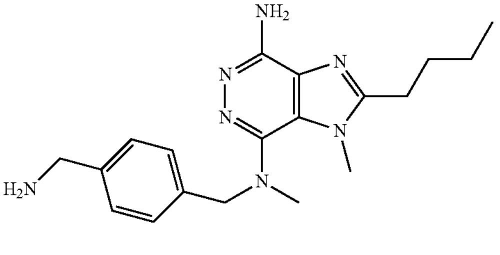 [SMILES: CCCCc1nc2c(N)nnc(N(C)Cc3ccc(CN)cc3)c2n1C]

To a solution of 4-(((4-amino-2-butyl-1-methyl-1H-imidazo[4,5-d]pyridazin 7yl)(methyl)amino)methyl)benzonitrile of Step 1 (104 mg, 0.30 mmol) in THF (4 mL) was added dropwise $BH_3$-THF 1M (893 μL, 0.89 mmol). The solution was heated under reflux 18 hours. Then Methanol-HCl 1M (3 mL) was added and the mixture was heated 24 hours under reflux. The reaction mixture was concentrated under reduced pressure to give 414 mg of white solid. The residue was dissolved in DCM (10 mL) and washed with water (10 mL). The organic layer was dried over anhydrous $MgSO_4$, filtered and concentrated under vacuum to give 114 mg of white solid, which was purified by chromatography on a Macherey Nagel Chromabond Sorbenz $NH_2$ cartridge (16.4 g) with DCM/Methanol (95/5) elution to obtain Example (39B) (13 mg, 12% yield) as a white solid.

$^1$H NMR (400 MHz, δ in ppm, DMSO-$d_6$): 0.94 (t, J=7.5 Hz, 3H); 1.42 (m, 2H); 1.76 (m, 2H); 2.09 (m, 2H); 2.66 (s, 3H); 2.85 (m, 2H); 3.66 (s, 2H); 4.00 (s, 3H); 4.29 (s, 2H); 6.00 (s, 2H); 7.14 to 7.30 (m, 4H)

MS method N: RT (min): 0.73; $[M+H]^+$ 354; $ES^+$ $[M+2H-NH_3]^{2+}$: m/z 169

Example (40): Preparation of Compound 47: 2-butyl-N7-(4-(((2-methoxyethyl)(methyl)amino)methyl)benzyl)-N7,1-dimethyl-1H-imidazo[4,5-d]pyridazine-4,7-diamine

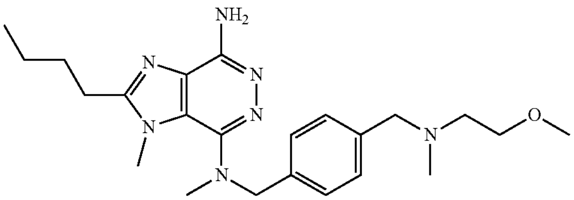 [SMILES: CCCCc1nc2c(N)nnc(N(C)Cc3ccc(CN(C)CCOC)cc3)c2n1C]

A mixture of Intermediate (K) (100 mg, 0.42 mmol), 2-methoxy-N-methyl-N-(4-((methylamino)methyl)benzyl)ethan-1-amine (464 mg, 2.09 mmol), 1-Butanol (2 mL), and 3-chloropyridine hydrochloride (206.5 mg, 1.38 mmol) were introduced into a microwave vial. The suspension was heated at 160° C. during 3 hours under microwave. The reaction mixture was concentrated under vacuum to give 731 mg of crude product. This material was dissolved in EtOAc (25 mL) and washed with water (20 mL). The organic layer was dried over anhydrous $MgSO_4$, filtered and concentrated under vacuum to give 244 mg of crude compound, which was purified by chromatography on a Merck cartridge (20 g 15-40 μm silica) with DCM/MeOH (9/1) elution to afford Example (40) (32 mg, 18% yield) as a white solid.

$^1$H NMR (400 MHz, δ in ppm, DMSO-$d_6$): 0.94 (t, J=7.4 Hz, 3H); 1.41 (m, 2H); 1.75 (m, 2H); 2.12 (s, 3H); 2.50 (m hidden, 2H); 2.66 (s, 3H); 2.85 (m, 2H); 3.21 (s, 3H); 3.43 (t, J=6.0 Hz, 2H); 3.45 (s, 2H); 4.00 (s, 3H); 4.30 (s, 2H); 6.01 (s, 2H); 7.21 (d, J=8.2 Hz, 2H); 7.28 (d, J=8.2 Hz, 2H)

MS method N: RT (min): 0.72; $[M+H]^+$ 426; $ES^+$ $[M+2H]^{2+}$: m/z 213.5

Example (41): Preparation of Compound 104: 2-butyl-7-isopropoxy-1-(4-(((2-methoxyethyl)amino)methyl)benzyl)-1H-imidazo[4,5-d]pyridazin-4-amine

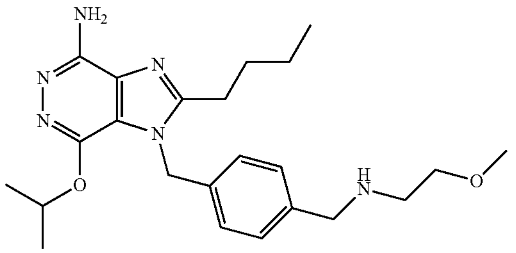 [SMILES: CCCCc1nc2c(N)nnc(OC(C)C)c2n1Cc1ccc(CNCCOC)cc1]

Under argon, to a solution of 1-(4-(aminomethyl)benzyl)-2-butyl-7-isopropoxy-1H-imidazo[4,5-d]pyridazin-4-amine (200 mg, 0.54 mmol (Example (17A)) in 3 mL of DMF was added $Cs_2CO_3$ (531 mg, 1.63 mmol) and the mixture was stirred for 30 mins. 2-Bromomethyl methyl ether (80.00 μl, 0.80 mmol) was then added and the mixture was stirred at rt for 24 h. The reaction mixture was poured into 50 ml of iced water. The aqueous solution was extracted with EtOAc (3×25 ml), the organic layers were combined and washed brine. The organic layer was dried over anhydrous $MgSO_4$, filtered and concentrated under vacuum to give 244 mg of crude compound, which was purified by chromatography on a Merck cartridge (20 g 15-40 μm silica) with DCM/DCM-MeOH(8-2)/$NH_3 \cdot H_2O$ (90/10/0.015 to 80/20 0.015) elution to afford Example (41) (72 mg, 31% yield) as a white solid.

$^1$H NMR (400 MHz, δ in ppm, DMSO-$d_6$): 0.83 (t, J=7 Hz, 3H), 1.20 (d, J=6 Hz, 6H), 1.24-1.41 (m, 2H), 1.55-1.67 (m, 2H), 2.59 (t, J=6 Hz, 2H), 2.75-2.86 (m, 2H), 3.20 (s, 3H), 3.33-3.41 (m partially hidden, 2H), 3.67 (s, 2H), 5.32 (spt, J=6 Hz, 1H), 5.55 (s, 2H), 5.93 (s, 2H), 7.01 (d, J=8 Hz, 2H), 7.27 (d, J=8 Hz, 2H)

MS method N: RT (min): 0.80; $[M+H]^+$ 427

The following compounds may be made by analogy to Example 41: 108, 109, 110, 116, 117, 119.

Example (42): Preparation of Compound 105: 2-butyl-4-isopropoxy-3-[[4-[[2-[2-[2-[2-[2-(2-methoxyethoxy)ethoxy]ethoxy]ethoxy]ethoxy]ethyl-amino]methyl]phenyl]methyl]imidazo[4,5-d]pyridazin-7-amine

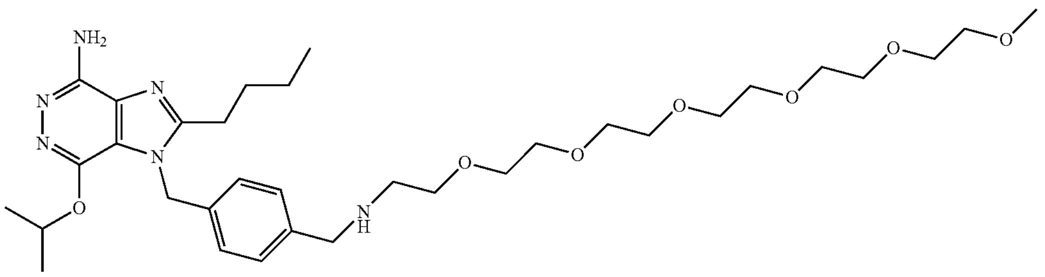 [SMILES: CCCCc1nc2c(N)nnc(OC(C)C)c2n1Cc1ccc(CNCCOCCOCCOCCOCCOCCOC)cc1]

Step 1: tert-butyl N-[[4-[[7-[bis[(2,4-dimethoxyphenyl)methyl]amino]-2-butyl-4-propan-2-yloxyimidazo[4,5-d]pyridazin-3-yl]methyl]phenyl]methyl]-N-[2-[2-[2-[2-[2-(2 methoxyethoxy)ethoxy]ethoxy]ethoxy]ethoxy]ethyl]carbamate

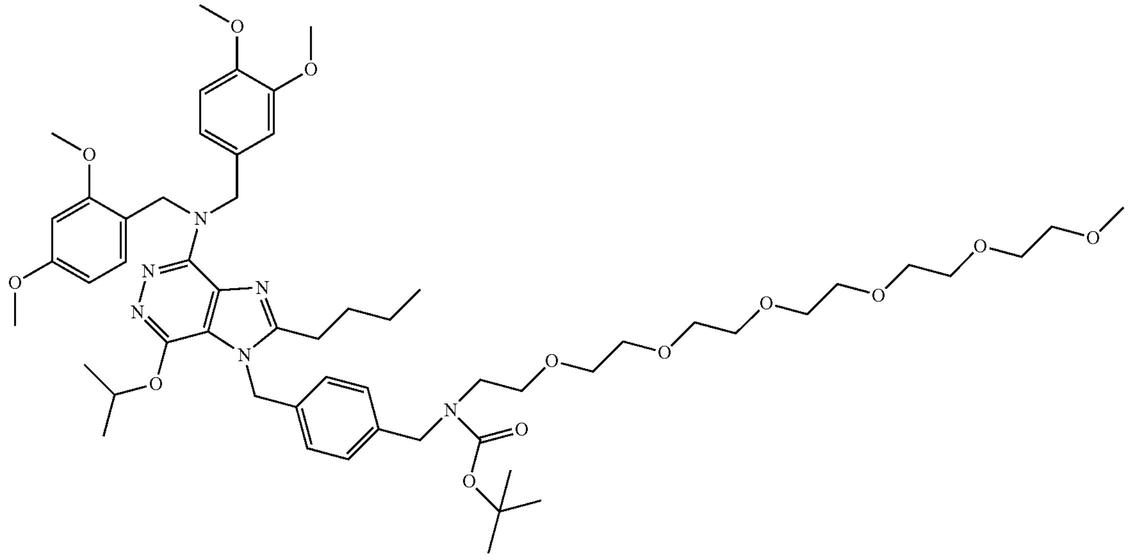 [SMILES: CCCCc1nc2c(N(Cc3ccc(OC)c(OC)c3)Cc3ccc(OC)cc3OC)nnc(OC(C)C)c2n1Cc1ccc(CN(CCOCCOCCOCCOCCOCCOC)C(=O)OC(C)(C)C)cc1]

Under argon, to a solution of tert-butyl (4-((4-(bis(2,4-dimethoxybenzyl)amino)-2-butyl-7-isopropoxy-1H-imidazo[4,5-d]pyridazin-1-yl)methyl)benzyl)carbamate of Step 1 in Example (17A) (200 mg, 0.26 mmol) in DMF (3 ml) was added sodium hydride (31 mg, 0.78 mmol) at rt and the mixture was stirred till the end of gas bubbling. M-PEG6-Bromide (123 μl, 0.39 mmol) was then added and the mixture was stirred at rt overnight. A second portion of sodium hydride (31 mg, 0.78 mmol) was added and the mixture was stirred again for 24 h. The reaction mixture was poured into 100 ml of iced water. The aqueous solution was extracted with DCM (100 ml) and MeTHF (100 ml), the organic layers were combined and concentrated under vacuum to give 65 mg of crude compound. The aqueous phase was concentrated under vacuum to give 404 mg of crude compound, which were treated with a mixture of EtOAc/EtOH, after filtration of insoluble residues, the filtrate was concentrated under vacuum and combined with the 65 mg of crude compound from organic phase. The crude materiel then was purified by chromatography on a Merck cartridge (10 g 15-40 μm silica) with EtOAc/EtOH 98/2 to 90/10 elution to afford expected compound (54 mg, 20% yield) as a white solid.

$^1$H NMR (400 MHz, δ in ppm, DMSO-d6): 0.75 (t, J=7.4 Hz, 3H) 1.12-1.47 (m, 17H) 1.55 (m, 2H) 2.77 (m, 2H) 3.21 (m, 3H) 3.38-3.55 (m, 24H) 3.71 (s, 12H) 4.38 (s, 2H) 5.01 (s, 4H) 5.31 (m, 1H) 5.57 (s, 2H) 6.39 (m, J=8.3 Hz, 2H) 6.53 (d, J=2.3 Hz, 2H) 6.97 (m, J=8.3 Hz, 2H) 7.05 (d, J=8.3 Hz, 2H) 7.19 (d, J=8.3 Hz, 2H)

MS method N: RT (min): 1.79; $[M+H]^+$ 1047

Step 2: Example (42): Preparation of Compound 105: 2-butyl-4-isopropoxy-3-[[4-[[2-[2-[2-[2-[2-(2-methoxyethoxy)ethoxy]ethoxy]ethoxy]ethoxy]ethylamino]methyl]phenyl]methyl]imidazo[4,5-d] pyridazin-7-amine

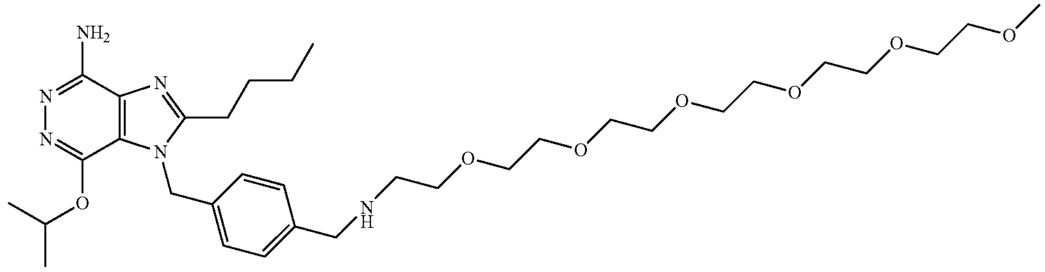 [SMILES: CCCCc1nc2c(N)nnc(OC(C)C)c2n1Cc1ccc(CNCCOCCOCCOCCOCCOCCOC)cc1]

Under argon, to a solution of tert-butyl N-[[4-[[7-[bis[(2,4-dimethoxyphenyl)methyl]amino]-2-butyl-4-isopropoxy-imidazo[4,5-d]pyridazin-3-yl]methyl]phenyl]methyl]-N-[2-[2-[2-[2-[2-(2-methoxyethoxy)ethoxy]ethoxy]ethoxy] ethoxy]ethyl]carbamate of Step 1 (50 mg, 0.048 mmol) in DCM (0.2 ml) was added TFA (203 μl. 2.63 mmol) at rt, resulting a purple solution, which was stirred for 48 h. The reaction mixture was then concentrated under vacuum and taken into MeOH (3 ml), the insoluble residues were then filtrated and washed with MeOH. The methanolic solution was concentrated and loaded over of 5 g SCX cartridge, which was eluted with 100 ml MeOH and 100 ml MeOH/ $NH_3$ (2M). The MeOH/$NH_3$ phase was concentrated under vacuum to give Example (42) (29.3 mg, 95% yield) as a white solid.

$^1$H NMR (400 MHz, δ in ppm, DMSO-$d_6$): 0.84 (t, J=7 Hz, 3H), 1.21 (d, J=6 Hz, 6H), 1.26-1.38 (m, 2H), 1.63 (t, J=8 Hz, 2H), 2.59 (t, J=6 Hz, 2H), 2.70-2.90 (m, 2H), 3.22-3.25 (m, 3H), 3.39-3.55 (m, 22H), 3.67 (s, 2H), 5.78 (m, 1H), 5.56 (s, 2H), 5.90 (s, 2H), 7.02 (d, J=8 Hz, 2H), 7.28 (d, J=8 Hz, 2H)

MS method N: RT (min): 1.01; $[M+H]^+$ 647

The following compounds may be made by analogy to Example 42: 118, 120, 121, 122, 123.

Example (43): Preparation of Compound 111: ethyl (4-((4-amino-2-butyl-7-isopropoxy-1H-imidazo[4,5-d]pyridazin-1-yl)methyl)benzyl)carbamate

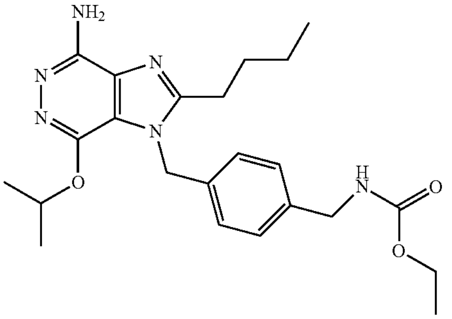 [SMILES: CCCCc1nc2c(N)nnc(OC(C)C)c2n1Cc1ccc(CNC(=O)OCC)cc1]

Under argon, to a solution of 1-(4-(aminomethyl)benzyl)-2-butyl-7-isopropoxy-1H-imidazo[4,5-d]pyridazin-4-amine (Example (17A)) (200 mg, 0.54 mmol) in anhydrous THF (5 ml) was added DIPEA (114 μl, 0.65 mmol) and followed by dropwise addition of Ethyl Chloroformate (64 μl, 0.65 mmol). The reaction mixture, a colourless solution containing a gummy white solid, was stirred for 1 h. 5 ml of HCl (1M) and 10 ml EtOAc were added to the reaction mixture and transferred to a separating funnel. After decantation, the aqueous phase was extracted with EtOAc (2×10 ml). The organic layers were combined, dried over anhydrous $MgSO_4$, filtered and concentrated under vacuum to give 154 mg of crude compound, which was purified by chromatography on a Merck cartridge (10 g 15-40 μm silica) with DCM/MeOH/$CH_3CN$ (90/5/5) elution to afford Example (43) (40 mg, 17% yield) as a white solid.

$^1$H NMR (400 MHz, δ in ppm, DMSO-$d_6$): 0.84 (t, J=7 Hz, 3H), 1.14 (t, J=7 Hz, 3H), 1.20 (d, J=6 Hz, 6H), 1.26-1.37 (m, 2H), 1.62 (m, 2H), 2.79 (m, 2H), 3.97 (q, J=7 Hz, 2H), 4.12 (d, J=6 Hz, 2H), 5.32 (spt, J=6 Hz, 1H), 5.55 (s, 2H), 5.91 (s, 2H), 7.02 (d, J=8 Hz, 2H), 7.20 (d, J=8 Hz, 2H), 7.59 (t, J=6 Hz, 1H)

MS method N: RT (min): 1.21; $[M+H]^+$ 441

The following compounds may be made by analogy to Example 43: 112, 114.

Example (44): Preparation of Compound 113: 1-(4-((4-amino-2-butyl-7-isopropoxy-1H-imidazo[4,5-d]pyridazin-1-yl)methyl)benzyl)-3-ethylurea

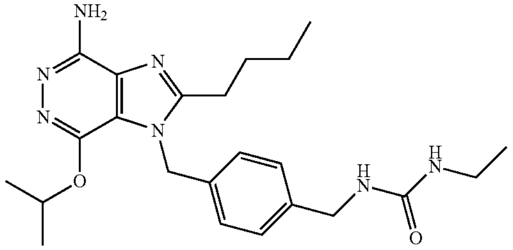 [SMILES: CCCCc1nc2c(N)nnc(OC(C)C)c2n1Cc1ccc(CNC(=O)NCC)cc1]

Under argon, to a solution of 1-(4-(aminomethyl)benzyl)-2-butyl-7-isopropoxy-1H-imidazo[4,5-d]pyridazin-4-amine (Example (17A)) (150 mg, 0.41 mmol) in anhydrous DCM (5 ml) was added Ethyl Isocyanate (39.50, 0.49 mmol). The reaction mixture, a colourless solution, was stirred for 4 h at rt. The reaction mixture was then concentrated under vacuum to give 188 mg of crude compound, which was purified by chromatography on a Merck cartridge (10 g 15-40 μm silica) with DCM/MeOH (93/7) elution to afford Example (44) (155 mg, 87% yield) as a white solid.

$^1$H NMR (400 MHz, δ in ppm, DMSO-$d_6$): 0.84 (t, J=7 Hz, 4H), 0.97 (t, J=7 Hz, 3H), 1.21 (d, J=6 Hz, 6H), 1.32 (m, 2H), 1.63 (quin, J=8 Hz, 2H), 2.79 (m, 2H), 3.00 (m, 2H), 4.15 (d, J=6 Hz, 2H), 5.32 (spt, J=6 Hz, 1H), 5.55 (s, 2H), 5.84 (t, J=6 Hz, 1H), 5.94 (s, 2H), 6.24 (t, J=6 Hz, 1H), 7.02 (d, J=8 Hz, 2H), 7.19 (d, J=8 Hz, 2H)

MS method N: RT (min): 1.07; $[M+H]^+$ 440

Example (45): Preparation of Compound 115: N-(4-((4-amino-2-butyl-7-isopropoxy-1H-imidazo[4,5-d]pyridazin-1-yl)methyl)benzyl)methanesulfonamide

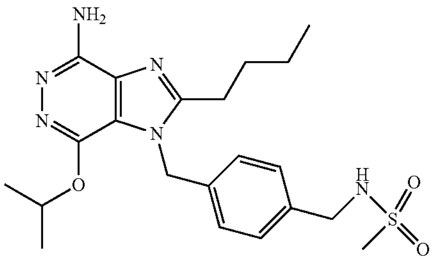 [SMILES: CCCCc1nc2c(N)nnc(OC(C)C)c2n1Cc1ccc(CNS(C)(=O)=O)cc1]

Under argon, to a solution of 1-(4-(aminomethyl)benzyl)-2-butyl-7-isopropoxy-1H-imidazo[4,5-d]pyridazin-4-amine (Example (17A)) (150 mg, 0.41 mmol) in anhydrous pyridine (10 ml) was added Methanesulfonyl Chloride (35 μl, 0.45 mmol). The reaction mixture, a limpid yellow solution, was stirred for 5 h at rt. The reaction mixture was then diluted in 50 ml EtOAc, charged into a separating funnel and washed brine (2×20 ml). The organic layer was dried over $MgSO_4$, filtered and concentrated under vacuum to give 121 mg of crude yellowish compound, which was purified by chromatography on a Merck cartridge (10 g 15-40 μm silica) with DCM/MeOH (93/7) elution to afford Example (45) (82 mg, 45% yield) as a white solid.

$^1$H NMR (400 MHz, δ in ppm, DMSO-$d_6$): 0.85 (t, J=7 Hz, 3H), 1.21 (d, J=6 Hz, 6H), 1.28-1.38 (m, 2H), 1.64 (quin, J=8 Hz, 2H), 2.73-2.87 (m, 5H), 4.12 (d, J=6 Hz, 2H), 5.32 (spt, J=6 Hz, 1H), 5.58 (s, 2H), 5.93 (s, 2H), 7.06 (d, J=8 Hz, 2H), 7.31 (d, J=8 Hz, 2H), 7.52 (t, J=6 Hz, 1H)

MS method N: RT (min): 1.07; $[M+H]^+$ 447

Example (46): Preparation of Compound 124: 2-butyl-7-isopropoxy-1-(3-((methylamino)methyl)benzyl)-1H-imidazo[4,5-d]pyridazin-4-amine

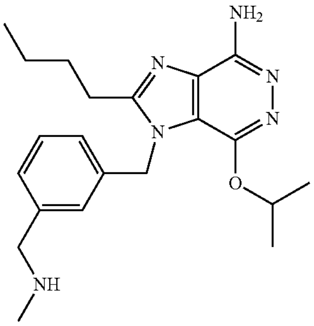 [SMILES: CCCCc1nc2c(N)nnc(OC(C)C)c2n1Cc1cccc(CNC)c1]

Step 1: 3-((4-(bis(2,4-dimethoxybenzyl)amino)-2-butyl-7-isopropoxy-1H-imidazo[4,5-d]pyridazin-1-yl)methyl)benzaldehyde

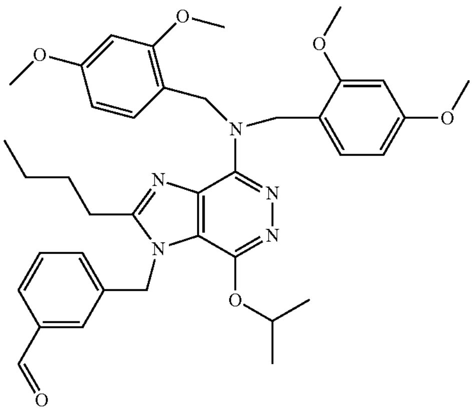 [SMILES: CCCCc1nc2c(N(Cc3ccc(OC)cc3OC)Cc3ccc(OC)cc3OC)nnc(OC(C)C)c2n1Cc1cccc(C=O)c1]

To a suspension of intermediate (M) (1.0 g, 1.82 mmol) in Me-THF (10 mL) was added 4-(bromomethyl)benzaldehyde (0.507 g, 2.73 mmol) and $Cs_2CO_3$ (0.889 g, 2.73 mmol). The mixture was stirred at rt overnight. Additional 4-(bromomethyl)benzaldehyde (0.110 g, 0.553 mmol) and $Cs_2CO_3$ (0.178 g, 0.546 mmol) were then added and the mixture was stirred for 2 h 30 mins at rt. The mixture was poured into Me-THF (15 mL), washed with $H_2O$ (15 mL), dried over anhydrous $MgSO_4$, and filtered. The filtrate was concentrated under reduced pressure to give 1.7 g of crude product, which was purified by chromatography on a Merck cartridge (150 g of 15-40 μm silica) with EtOAc/Heptane (30/70 to 50/50) elution. Expected product (0.73 g, 60% yield) was obtained as a white solid.

$^1H$ NMR (400 MHz, δ in ppm, DMSO-$d_6$): 0.76 (t, J=7.4 Hz, 3H), 1.13-1.32 (m, 2H), 1.16 (d, J=6.3 Hz, 5H), 1.52-1.61 (m, 2H), 2.81 (t, J=7.4 Hz, 2H), 3.71 (s, 12H), 5.02 (s, 4H), 5.25-5.34 (m, 1H), 5.68 (s, 2H), 6.40 (dd, J=8.4, 2.4 Hz, 2H), 6.53 (d, J=2.5 Hz, 2H), 6.98 (d, J=8.3 Hz, 2H), 7.43 (d, J=8.0 Hz, 1H), 7.58-7.65 (m, 2H), 7.85 (d, J=7.8 Hz, 1H), 9.98 (s, 1H)

MS method N: RT(min): 1.22; $[M+H]^+$ 668

Step 2: 2-butyl-N,N-bis(2,4-dimethoxybenzyl)-7-isopropoxy-1-(3-((methylamino)methyl)benzyl)-1H-imidazo[4,5-d]pyridazin-4-amine

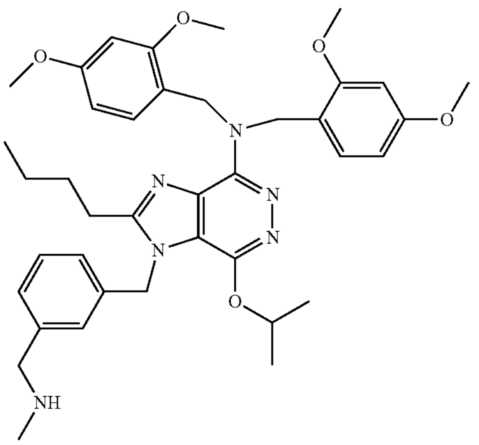 [SMILES: CCCCc1nc2c(N(Cc3ccc(OC)cc3OC)Cc3ccc(OC)cc3OC)nnc(OC(C)C)c2n1Cc1cccc(CNC)c1]

To a round bottomed flask containing 3-((4-(bis(2,4-dimethoxybenzyl)amino)-2-butyl-7-isopropoxy-1H-imidazo[4,5-d]pyridazin-1-yl)methyl)benzaldehyde of Step 1 (0.180 g, 0.270 mmol), was added a 2N solution of methylamine in ethanol (3.6 ml, 7.2 mmol), the mixture was stirred under argon at rt overnight. Sodium borohydride (0.015 g, 0.404 mmol) was then added. The resulting suspension was stirred for 1 h at rt and diluted in EtOAc and washed with water. The organic phase was dried over anhydrous $MgSO_4$, filtered and the filtrate was concentrated under reduced pressure to give 0.18 g of crude product, which was purified by chromatography on a Merck cartridge (20 g of 15-40 μm silica) with EtOAc/Heptane (30/70) to DCM/MeOH (90/10) elution. Expected product (0.17 g, 92% yield) was obtained as a colorless oil.

$^1H$ NMR (400 MHz, δ in ppm, DMSO-$d_6$): 0.76 (t, J=7.4 Hz, 3H) 1.14-1.30 (m, 2H) 1.21 (d, J=6 Hz, 6H) 1.55 (quin, J=7.44 Hz, 2H) 2.19 (s, 3H) 2.70-2.83 (m, 2H) 3.59 (s, 2H) 3.71 (s, 12H) 5.01 (s, 4H) 5.32 (spt, J=6.2 Hz, 1H) 5.57 (s, 2H) 6.39 (dd, J=8.4, 2.4 Hz, 2H) 6.53 (d, J=2.4 Hz, 2H) 6.92 (b d, J=7.5 Hz, 1H) 6.97 (d, J=8.4 Hz, 2H) 7.11 (b s, 1H) 7.18-7.32 (m, 2H)

MS method N: RT(min): 1.22; $[M+H]^+$ 683

The following compounds may be made by analogy to Example 46: 125, 126, 127, 128, 129, 130, 131.

Step 3: Example (46) Preparation of Compound 124: 2-butyl-7-isopropoxy-1-(3-((methylamino)methyl)benzyl)-1H-imidazo[4,5-d]pyridazin-4-amine

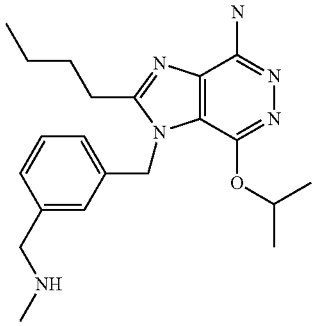 [SMILES: CCCCc1nc2c(N)nnc(OC(C)C)c2n1Cc1cccc(CNC)c1]

Under argon, to a solution of 2-butyl-N,N-bis(2,4-dimethoxybenzyl)-7-isopropoxy-1-(3-((methylamino)methyl)benzyl)-1H-imidazo[4,5-d]pyridazin-4-amine (0.17 g, 0.249 mmol) of Step 2, in DCM (5 ml) was added TFA (1.2 ml, 15.8 mmol) at rt and the resulting purple solution was stirred for 18 h. The reaction mixture was diluted in DCM, washed with a 1 N NaOH solution, the organic phase we dried over $MgSO_4$, filtered, and evaporated to dryness. The crude product was treated with 2N HCl, which gave a white powder. After a further treatment with SCX cartridge (2 g), it yielded Example (46) under free base (44 mg, 46% yield) as a white solid.

$^1H$ NMR (400 MHz, δ in ppm, DMSO-$d_6$): 0.82 (t, J=7 Hz, 3H), 1.19 (d, J=6 Hz, 6H), 1.30 (dq, J=15, 7 Hz, 2H), 1.56-1.65 (m, 2H), 2.07 (s, 6H), 2.81 (t, J=8 Hz, 2H), 3.31 (s partially hidden, 2H), 5.31 (spt, J=6 Hz, 1H), 5.58 (s, 2H), 5.94 (s, 2H), 6.94 (d, J=8 Hz, 1H), 7.04 (s, 1H), 7.18 (d, J=8 Hz, 1H), 7.28 (t, J=8 Hz, 1H)

MS method N: RT (min): 0.77; $[M+H]^+$ 383

Example (47): Preparation of Compound 132: (E)-1-(4-(aminomethyl)benzyl)-2-butyl-7-(3-methylbut-1-en-1-yl)-1H-imidazo[4,5-d]pyridazin-4-amine

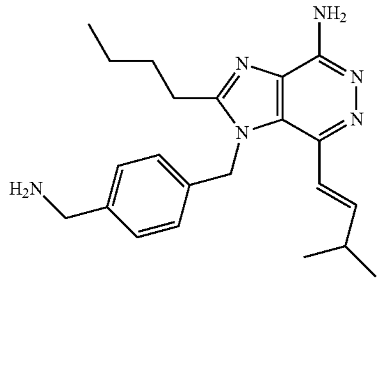 [SMILES: CCCCc1nc2c(N)nnc(/C=C/C(C)C)c2n1Cc1ccc(CN)cc1]

Step 1: tert-butyl (4-((2-butyl-4,7-dichloro-1H-imidazo[4,5-d]pyridazin-1-yl)methyl) benzyl)carbamate

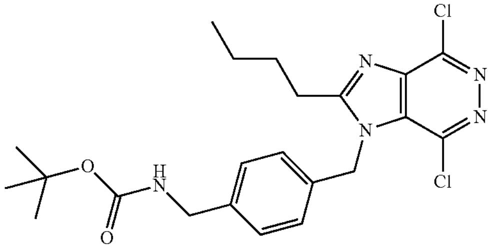 [SMILES: CCCCc1nc2c(Cl)nnc(Cl)c2n1Cc1ccc(CNC(=O)OC(C)(C)C)cc1]

To a solution of 2-butyl-dichloro-1H-imidazo[4,5-d] pyridazine (Intermediate (E)) (3.0 g, 12.25 mmol) in Acetonitrile (75 ml) was added tert-butyl (4-(bromomethyl) benzyl)carbamate (4.34 g, 14.45 mmol) and then $K_2CO_3$ (5.08 g, 36.74 mmol). The resulting mixture was stirred at rt for 48 hrs. Then it was added EtOAc (100 ml) and $H_2O$ (100 ml). The phase aqueous was separated and it was extracted again with EtOAc. The organic layers were combined and washed brine, the organic layer was separated, dried over $MgSO_4$, filtered and evaporated to give 6.09 g of crude material. The crude materiel was purified by a silica gel column using as eluent a mixture DCM/Acetone (97/3) to give 2.21 g of the expected product (38% Yield) as a white foam.

$^1$H NMR (400 MHz, δ in ppm, DMSO-d6): 0.84 (t, J=7.34 Hz, 3H) 1.20-1.44 (m, 11H) 1.68 (m, 2H) 2.85-2.97 (m, 2H) 4.09 (d, J=6.11 Hz, 2H) 5.80 (s, 2H) 7.03 (d, J=8.31 Hz, 2H) 7.19 (d, J=8.07 Hz, 2H) 7.39 (t, J=6.24 Hz, 1H)

MS method O: RT (min): 3.49; $[M+H]^+$ 464

Step 2: tert-butyl (4-((4-(bis(2,4-dimethoxybenzyl) amino)-2-butyl-7-chloro-1H-imidazo[4,5-d] pyridazin-1-yl)methyl)benzyl)carbamate

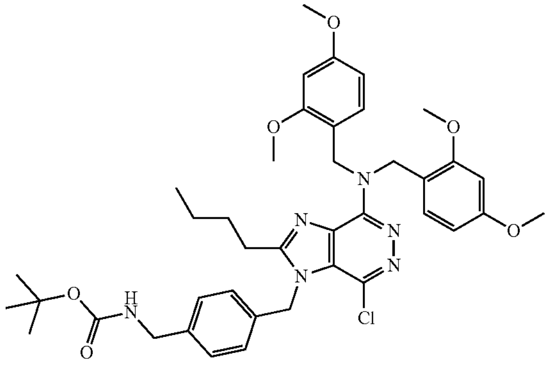 [SMILES: CCCCc1nc2c(N(Cc3ccc(OC)cc3OC)Cc3ccc(OC)cc3OC)nnc(Cl)c2n1Cc1ccc(CNC(=O)OC(C)(C)C)cc1]

In a round-bottom flask was added tert-butyl (44(2-butyl-4,7-dichloro-1H-imidazo[4,5-d]pyridazin-1-yl)methyl)benzyl)carbamate of Step 1 (2.18 g, 4.71 mmol), n-Butanol (30 ml) and DIPEA (8.23 ml), and bis(2,4-dimethoxybenzyl) amine (412.5 mg, 1.24 mmol)). The resulting mixture was heated at reflux for 1 hr. It was then added 412.5 mg of bis(2,4-dimethoxybenzyl)amine, and heated at reflux for 15 mins, this operation was repeated twice again (2×412.5 mg). The mixture was heated at reflux for 52 hrs. The solvent was then evaporated, the brown residue was diluted with Ethyl acetate and washed with brine. The organic layer was separated, dried over $MgSO_4$, filtered and evaporated. The crude material was purified by a silica gel column (Merck) using as solvent Heptane/Acetone (70/30) to give 1.42 g of expected product (40.4% Yield).

$^1$H NMR (400 MHz, δ in ppm, DMSO-d6): 0.74 (t, J=7.3 Hz, 3H) 1.22 (m, 2H) 1.37 (s, 9H) 1.45-1.66 (m, 2H) 2.75 (t, J=7.4 Hz, 2H) 3.72 (s, 12H) 4.08 (d, J=6.11 Hz, 2H) 5.10 (br s, 4H) 5.70 (s, 2H) 6.41 (dd, J=8.3, 2.4 Hz, 2H) 6.55 (d, J=2.4 Hz, 2H) 6.95 (d, J=8 Hz, 2H) 6.99 (d, J=8.3 Hz, 2H) 7.20 (d, J=8.31 Hz, 2H) 7.37 (t, J=6.24 Hz, 1H)

MS method O: RT (min): 3.80; $[M+H]^+$ 745

Step 3: tert-butyl (E)-(4-((4-(bis(2,4-dimethoxybenzyl)amino)-2-butyl-7-(3-methylbut-1-en-1-yl)-1H-imidazo[4,5-d]pyridazin-1-yl)methyl)benzyl)carbamate

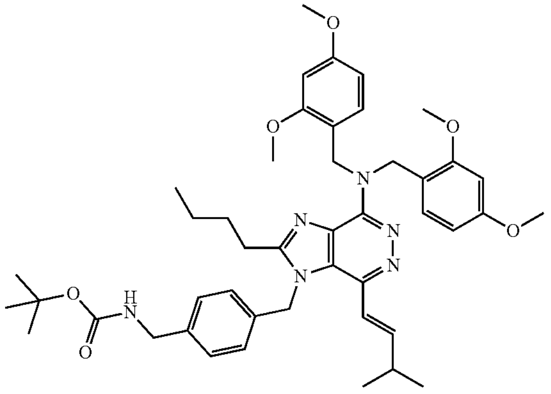 [SMILES: CCCCc1nc2c(N(Cc3ccc(OC)cc3OC)Cc3ccc(OC)cc3OC)nnc(/C=C/C(C)C)c2n1Cc1ccc(CNC(=O)OC(C)(C)C)cc1]

In a microwave vial was prepared a solution of tert-butyl (4-((4-(bis(2,4-dimethoxybenzyl)amino)-2-butyl-7-chloro-1H-imidazo[4,5-d]pyridazin-1-yl)methyl)benzyl) carbamate of Step 2 (150 mg, 0.201 mmol) in 1,4-dioxane (3 ml). Then it was added (E)-4,4,5,5-tetramethyl-2-(3-methylbut-1-en-1-yl)-1,3,2-dioxaborolane (78.93 mg, 0.402 mmol), Pd(PPh3)4 (36.72 mg, 0.030 mmol) and 2M solution of $Cs_2CO_3$ (0.402 ml, 0.805 mmol). The solution was purged with Argon for 5 minutes. Then it was heated in the microwave system at 130° C. during 1 h 30 min. The reaction mixture was diluted with EtOAc and washed with $H_2O$ and brine. The organic layer was separated, dried over $MgSO_4$, filtered and evaporated. The crude material was purified by a silica gel column (Merck) using as eluent a mixture Heptane/EtOAc (60/40) to give 67 mg of the expected product (42.7% yield).

$^1$H NMR (400 MHz, δ in ppm, DMSO-d6): 0.77 (t, J=7 Hz, 3H) 0.89 (d, J=7 Hz, 6H) 1.18-1.41 (m, 11H) 1.54-1.66 (m, 2H) 2.27 (m, 1H) 2.79 (t, J=7 Hz, 2H) 3.73 (d, J=8 Hz, 12H) 4.07 (d, J=6 Hz, 2H) 5.13 (br s, 4H) 5.59 (s, 2H) 6.40 (dd, J=8, 2 Hz, 2H) 6.45-6.53 (m, 2H) 6.55 (d, J=2 Hz, 2H) 6.89 (m, J=8 Hz, 2H) 6.99 (d, J=8 Hz, 2H) 7.20 (m, J=8 Hz, 2H) 7.37 (t, J=6 Hz, 1H)

MS method N: RT (min): 1.74; $[M+H]^+$ 779

Step 4: Example (47): Preparation of Compound 132: (E)-1-(4-(aminomethyl)benzyl)-2-butyl-7-(3-methylbut-1-en-1-yl)-1H-imidazo[4,5-d]pyridazin-4-amine

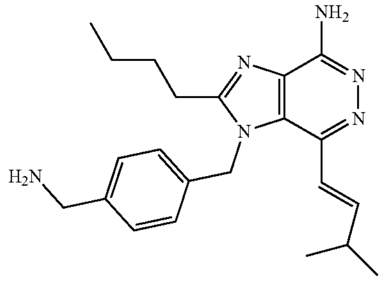 [SMILES: CCCCc1nc2c(N)nnc(/C=C/C(C)C)c2n1Cc1ccc(CN)cc1]

To a solution of tert-butyl (E)-(4-((4-(bis(2,4-dimethoxybenzyl)amino)-2-butyl-7-(3-methylbut-1-en-1-yl)-1H-imidazo[4,5-d]pyridazin-1-yl)methyl)benzyl)carbamate of Step 3 (108 mg, 0.138 mmol) in DCM (1 ml) was added dropwise TFA (486 μl, 6.48 mmol). The mixture was stirred at rt for 4 hrs. The reaction mixture was diluted with EtOAc, washed with a 1N solution of NaOH, and with brine. The organic layer was separated, dried over $MgSO_4$, filtered and evaporated to give 146 mg of a brown oil. The crude material was purified by a silica gel column (Merck) using as eluent a mixture DCM/$NH_3$-MeOH 2N (96/4) to give 35.9 mg of Example (47) as a white solid (68.4% yield).

$^1$H NMR (400 MHz, δ in ppm, DMSO-$d_6$): 0.86 (t, J=7 Hz, 3H), 0.92 (d, J=7 Hz, 6H), 1.30-1.41 (m, 2H), 1.55-1.99 (m, 4H), 2.30 (m, 1H), 2.87 (t, J=8 Hz, 2H), 3.67 (s, 2H), 5.60 (s, 2H), 6.31-6.56 (m, 4H), 6.87 (d, J=8 Hz, 2H), 7.29 (d, J=8 Hz, 2H)

MS method N: RT (min): 0.77; $[M+H]^+$ 379

The following compounds may be made by analogy to Example 47:135, 137, 139, 141.

Example (48): Preparation of Compound 133 (1-(4-(aminomethyl)benzyl)-2-butyl-7-isopentyl-1H-imidazo[4,5-d]pyridazin-4-amine

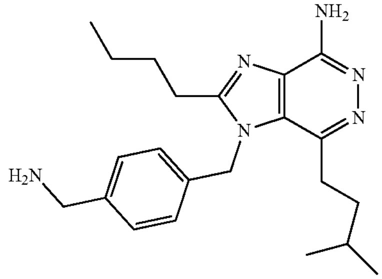 [SMILES: CCCCc1nc2c(N)nnc(CCC(C)C)c2n1Cc1ccc(CN)cc1]

Step 1: tert-butyl (4-((4-(bis(2,4-dimethoxybenzyl)amino)-2-butyl-7-isopentyl-1H-imidazo[4,5-d]pyridazin-1-yl)methyl)benzyl)carbamate

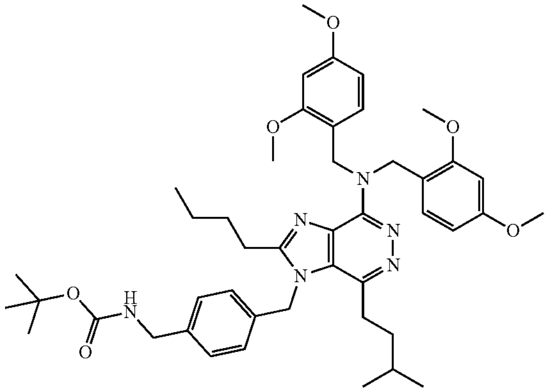 [SMILES: CCCCc1nc2c(N(Cc3ccc(OC)cc3OC)Cc3ccc(OC)cc3OC)nnc(CCC(C)C)c2n1Cc1ccc(CNC(=O)OC(C)(C)C)cc1]

In a hydrogenation cube was added a solution of tert-butyl (E)-(4-((4-(bis(2,4-dimethoxybenzyl)amino)-2-butyl-7-(3-methylbut-1-en-1-yl)-1H-imidazo[4,5-d]pyridazin-1-yl)methyl)benzyl)carbamate of Step 3 in Example (47) (195 mg, 0.250 mmol) in MeOH (15 ml) and Pd/C 10% (39.96 mg). The mixture was kept under hydrogen (1 bar) at 25° C. for 2 hr. Then reaction mixture was filtered over a celite pad, the filtrate was evaporated to give 185 mg of the expected product as white solid, which was used directly for next step without further purification.

$^1$H NMR (400 MHz, δ in ppm, DMSO-d6): 0.74-0.78 (m, 9H) 1.16-1.30 (m, 4H) 1.31-1.53 (m, 10H) 1.53-1.68 (m, 2H) 2.71-2.81 (m, 4H) 3.69-3.76 (m, 12H) 4.07 (d, J=6.1 Hz, 2H) 5.11 (br s, 4H) 5.57 (s, 2H) 6.41 (dd, J=8.4, 2.4 Hz, 2H) 6.55 (d, J=2.4 Hz, 2H) 6.83 (d, J=8.1 Hz, 2H) 7.00 (d, J=8.4 Hz, 2H) 7.21 (d, J=8.1 Hz, 2H) 7.37 (t, J=6.24 Hz, 1H)

MS method N: RT (min): 1.75; $[M+H]^+$ 781

Step 2: Example (48): Preparation of Compound 133: 1-(4-(aminomethyl)benzyl)-2-butyl-7-isopentyl-1H-imidazo[4,5-d]pyridazin-4-amine

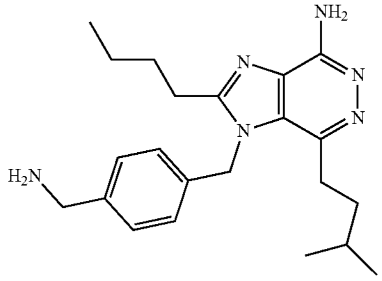 [SMILES: CCCCc1nc2c(N)nnc(CCC(C)C)c2n1Cc1ccc(CN)cc1]

To a solution of (tert-butyl (4-((4-(bis(2,4-dimethoxybenzyl)amino)-2-butyl-7-isopentyl-1H-imidazo[4,5-d]pyridazin-1-yl)methyl)benzyl)carbamate) of Step 1 (178.7 mg, 0.229 mmol) in DCM (2 ml) was added dropwise TFA (1.03 ml, 13.73 mmol). The mixture was stirred at room rt for 12 hrs. The reaction mixture was diluted with EtOAc, washed with a 1N solution of NaOH, and brine. The organic layer was separated, dried over $MgSO_4$, filtered and evaporated. The crude material was purified by a silica gel column (Merck, 20 g) using as eluent a mixture DCM/$NH_3$-MeOH 2N (96/4) to give 54.5 mg (62.6% yield) of Example (48) as a white solid.

$^1$H NMR (400 MHz, δ in ppm, DMSO-d6): 0.78 (d, J=7 Hz, 6H), 0.85 (t, J=7 Hz, 3H), 1.29-1.41 (m, 4H), 1.47 (m, 1H), 1.63-1.75 (m, 2H), 1.76-2.10 (m, 2H), 2.71-2.86 (m, 4H), 3.67 (s, 2H), 5.56 (s, 2H), 6.21 (s, 2H), 6.79 (d, J=8 Hz, 2H), 7.29 (d, J=8 Hz, 2H)

MS method N: RT (min): 0.79; $[M+H]^+$ 381

The following compounds may be made by analogy to Example 48: 138, 140.

Example (49): Preparation of Compound 134: 1-(4-(aminomethyl)benzyl)-2-butyl-7-(pyrrolidin-1-yl)-1H-imidazo[4,5-d]pyridazin-4-amine

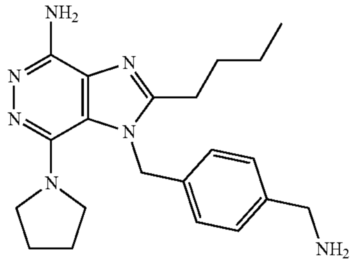 [SMILES: CCCCc1nc2c(N)nnc(N3CCCC3)c2n1Cc1ccc(CN)cc1]

Step 1: tert-butyl (4-((4-(bis(2,4-dimethoxybenzyl)amino)-2-butyl-7-(pyrrolidin-1-yl)-1H-imidazo[4,5-d]pyridazin-1-yl)methyl)benzyl)carbamate

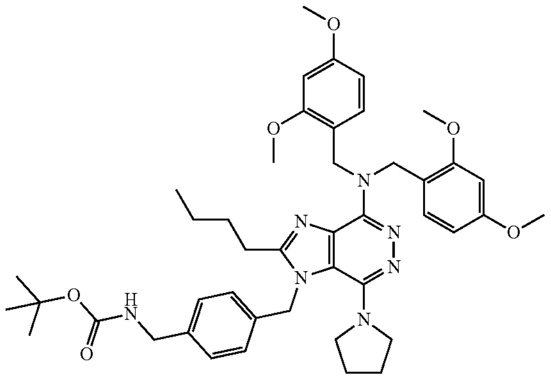 [SMILES: CCCCc1nc2c(N(Cc3ccc(OC)cc3OC)Cc3ccc(OC)cc3OC)nnc(N3CCCC3)c2n1Cc1ccc(CNC(=O)OC(C)(C)C)cc1]

To a 2-5 ml microwave tube equipped with magnetic stir was added tert-butyl (4-((4-(bis(2,4-dimethoxybenzyl)amino)-2-butyl-7-chloro-1H-imidazo[4,5-d]pyridazin-1-yl)methyl)benzyl) carbamate of Step 2 in Example 47 (150 mg, 0.201 mmol), 3-chloropyridine chlorhydride (99.6 mg, 664 μmol) and 2.2 ml of pyrrolidine. After 5 min of magnetic stirring and 2 min under ultrasound, one homogeneous solution was obtained. The microwave tube was then hermetically caped and heated at 160° C. for a total of 2 h 15 min. The reaction mixture was then diluted in EtOAc (50 ml) and washed with water (3×50 ml). The organic layer was dried over $MgSO_4$, filtered and evaporated to dryness to give 136 mg of crude product which was purified by a silica gel column (Merck Gotek 15-40 μm, 20 g) using as eluent a mixture $CHCl_3$/iPrOH—$NH_3$ (2N) (99/1 to 98/2) to give 34 mg (21.7% yield) of the expected product as an oil.

$^1$H NMR (400 MHz, δ in ppm, DMSO-$d_6$): 0.74 (t, J=7.4 Hz, 3H), 1.14-1.25 (m, 2H), 1.37 (s, 9H), 1.54 (quin, J=7.4 Hz, 2H), 1.79 (m, 4H), 2.62 (t, J=7.4 Hz, 2H), 3.12 (m, 4H), 3.72 (s, 12H), 4.07 (d, J=6.3 Hz, 2H), 5.06 (s, 4H), 5.69 (s, 2H), 6.41 (dd, J=8.3, 2.3 Hz, 2H), 6.54 (d, J=2.3 Hz, 2H), 6.95 (br d, J=8.3 Hz, 2H), 6.99 (d, J=8.3 Hz, 2H), 7.18 (d, J=8.3 Hz, 2H), 7.34 (t, J=6.3 Hz, 1H)

MS method N: RT (min): 1.72; $[M+H]^+$ 780

Step 2: Example (49): Preparation of Compound 134: 1-(4-(aminomethyl)benzyl)-2-butyl-7-(pyrrolidin-1-yl)-1H-imidazo[4,5-d]pyridazin-4-amine

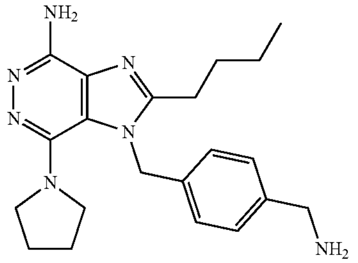 [SMILES: CCCCc1nc2c(N)nnc(N3CCCC3)c2n1Cc1ccc(CN)cc1]

To a solution of tert-butyl (4-((4-(bis(2,4-dimethoxybenzyl)amino)-2-butyl-7-(pyrrolidin-1-yl)-1H-imidazo[4,5-d]pyridazin-1-yl)methyl)benzyl)carbamate of Step 1 (120 mg, 154 μM) in DCM (1 ml) was added dropwise TFA (0.69 ml, 6.54 mmol)). The mixture (purple solution) was stirred at rt for 7 h then evaporated to dryness. The crude product was dissolved in MeOH with some purple precipitates which were filtered. The filtrate was loaded into a SCX cartridge (20 g, pre-washed with 10 ml of MeOH), the cartridge was then eluted with MeOH (60 ml) and followed by elution with MeOH—$NH_3$ (2N). The ammoniacal methanolic solution was evaporated to dryness to give 62.2 mg of white powder. The crude material was purified by a silica gel column (Merck, 10 g) using as eluent a mixture DCM/$NH_3$-MeOH 2N (96/4) to give 42 mg (60% yield) of Example (49) as a white solid.

$^1$H NMR (400 MHz, δ in ppm, DMSO-$d_6$): 0.82 (t, J=7 Hz, 3H), 1.30 (sxt, J=7 Hz, 2H), 1.64 (quin, J=8 Hz, 2H), 1.73-1.92 (m, 6H), 2.68 (t, J=8 Hz, 2H), 3.13 (br t, J=6 Hz, 4H), 3.66 (s, 2H), 5.66 (s, 2H), 6.08 (s, 2H), 6.92 (d, J=8 Hz, 2H), 7.26 (d, J=8 Hz, 2H)

MS method N: RT (min): 0.73; $[M+H]^+$ 380

The following compounds may be made by analogy to Example 49: 142, 143.

Example (50): Preparation of Compound 144: 1-[[4-(aminomethyl)phenyl]methyl]-2-butyl-7-(2,5-dihydro-1H-pyrrol-3-yl)imidazo[4,5-d]pyridazin-4-amine

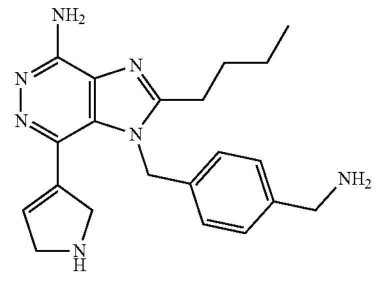 [SMILES: CCCCc1nc2c(N)nnc(C3=CCNC3)c2n1Cc1ccc(CN)cc1]

Step 1: tert-butyl 3-[4-[bis[(2,4-dimethoxyphenyl)methyl]amino]-1-[[4-[(tert-butoxycarbonylamino)methyl]phenyl]methyl]-2-butyl-imidazo[4,5-d]pyridazin-7-yl]-2,5-dihydropyrrole-1-carboxylate

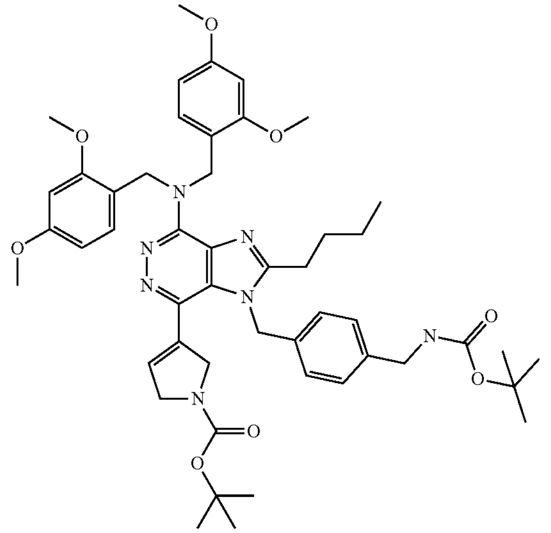 [SMILES: CCCCc1nc2c(N(Cc3ccc(OC)cc3OC)Cc3ccc(OC)cc3OC)nnc(C3=CCN(C(=O)OC(C)(C)C)C3)c2n1Cc1ccc(CNC(=O)OC(C)(C)C)cc1]

To a 10-20 ml microwave tube, equipped with magnetic stir was added tert-butyl (4-((4-(bis(2,4-dimethoxybenzyl)amino)-2-butyl-7-chloro-1H-imidazo[4,5-d]pyridazin-1-yl)methyl)benzyl) carbamate of Step 2 in Example (47) (472 mg, 0.507 mmol) in Dioxane (7.5 ml), was added 1'-bis(phosphino)ferrocene-palladium (II) dichloride complex (41.4 mg, 0.051 mmol), water (2.5 ml), Cesium carbonate (330.2 mg, 1.01 mmol) and tert-butyl 3-(4,4,5,5-tetramethyl-1,3,2-dioxaborolan-2-yl)-2,5-dihydro-1H-pyrrole-1-carboxylate (164.5 mg, 0.557 mmol). Under magnetic stirring, after 5 min argon bubbling, the microwave tube was hermetically capped and heated under microwave at 160° C. for 10 min. The reaction mixture was then diluted in EtOAc (50 ml) and washed with water (50 ml). The aqueous phase was re-extrated with EtOAc (2×50 ml). The combined organic layer was washed with brine (50 ml), dried over $MgSO_4$, filtered and evaporated to dryness to give 726 mg of crude product as black foam, which was purified by a silica gel column (Merck Gotek 15-40 μm, 80 g) using as eluent a mixture Heptane/EtOAc (60/40) to give 261 mg (58% yield) of the expected product.

$^1$H NMR (400 MHz, δ in ppm, DMSO-$d_6$): 0.79 (t, J=7.4 Hz, 3H) 1.27 (m, 2H) 1.31-1.53 (m, 18H) 1.63 (m, 2H) 2.80 (br t, J=7.4 Hz, 2H) 3.73 (m, 12H) 3.78-3.98 (m, 2H) 3.99-4.10 (m, 2H) 4.12-4.25 (m, 2H) 5.15 (br s, 4H) 5.48 (s, 2H) 5.72-5.86 (m, 1H) 6.41 (dd, J=8.4, 2.4 Hz, 2H) 6.55 (d, J=2.4 Hz, 2H) 6.73 (m, 2H) 7.00 (d, J=8.4 Hz, 2H) 7.10-7.30 (m, 3H)

MS method O: RT (min): 3.25; $[M+H]^+$ 878

Step 2: 1-[[4-(aminomethyl)phenyl]methyl]-2-butyl-7-(2,5-dihydro-1H-pyrrol-3-yl)-N-[(3,5-dimethoxyphenyl)methyl]imidazo[4,5-d]pyridazin-4-amine

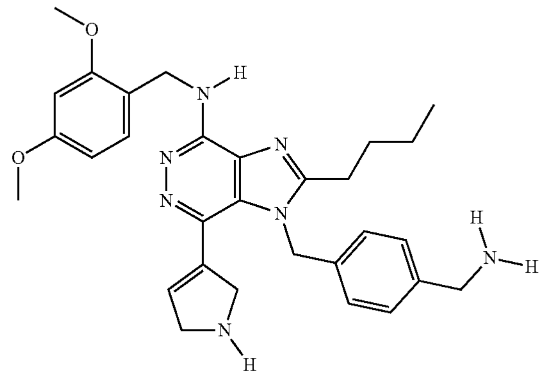 [SMILES: CCCCc1nc2c(NCc3ccc(OC)cc3OC)nnc(C3=CCNC3)c2n1Cc1ccc(CN)cc1]

To a solution of tert-butyl 3-[4-[bis[(2,4-dimethoxyphenyl)methyl]amino]-1-[[4-[(tert-butoxycarbonylamino)methyl]phenyl]methyl]-2-butyl-imidazo[4,5-d]pyridazin-7-yl]-2,5-dihydropyrrole-1-carboxylate of Step 1 (255 mg, 0.324 mmol) in DCM (5 ml) was added dropwise TFA (2.0 ml, 18.96 mmol). The mixture (purple solution) was stirred at rt for 2 h 15 min, and evaporated to dryness to give 250 mg of pink powder. The crude product was dissolved in MeOH with some purple precipitates which are filtered. The filtrate was loaded into a SCX cartridge (25 g, pre-washed with 10 ml of MeOH), the cartridge was eluted with MeOH (60 ml) and followed by elution with MeOH—$NH_3$ (2N). The ammoniacal methanolic solution was evaporated to dryness to give 193 mg of colourless foam. The crude material was purified by a silica gel column (20 g, Merck) using as eluent a mixture DCM/$NH_3$-MeOH 7N (88/12) to give 90 mg (57% Yield) of the expected product as a white foam.

$^1$H NMR (400 MHz, δ in ppm, DMSO-$d_6$): 0.86 (t, J=7.4 Hz, 3H) 1.26-1.45 (m, 2H) 1.71 (m, 2H) 2.82 (m, 2H) 3.62-3.77 (m, 9H) 3.83 (s, 3H) 4.66 (d, J=6 Hz, 2H) 5.50 (s, 2H) 5.80 (m, 1H) 6.42 (dd, J=8.4, 2.4 Hz, 1H) 6.56 (d, J=2.4 Hz, 1H) 6.77 (d, J=8.3 Hz, 2H) 6.90 (t, J=6.3 Hz, 1H) 7.12 (d, J=8.4 Hz, 1H) 7.27 (d, J=8.3 Hz, 2H)

MS method N: RT (min): 0.63; $[M+H]^+$ 528

Step 3: Example (50): Preparation of Compound 144: 1-[[4-(aminomethyl)phenyl]methyl]-2-butyl-7-(2,5-dihydro-1H-pyrrol-3-yl)imidazo[4,5-d]pyridazin-4-amine

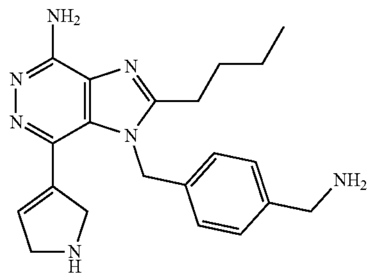 [SMILES: CCCCc1nc2c(N)nnc(C3=CCNC3)c2n1Cc1ccc(CN)cc1]

To a solution of 1-[[4-(aminomethyl)phenyl]methyl]-2-butyl-7-(2,5-dihydro-1H-pyrrol-3-yl)-N-[(3,5-dimethoxyphenyl)methyl]imidazo[4,5-d]pyridazin-4-amine of Step 2 (120 mg, 0.227 mmol) in DCM (0.5 ml) was added dropwise TFA (0.7 ml, 6.63 mmol). The mixture (purple solution) was stirred at rt for 24 h then evaporated to dryness. The crude product was dissolved in 10 ml MeOH, and the suspension was loaded into a SCX cartridge (10 g, pre-washed with 10 ml of MeOH), the cartridge was eluted with MeOH (30 ml) and followed by elution with MeOH—$NH_3$ (2N). The ammoniacal methanolic solution was evaporated to dryness to give 96.6 mg of colorless foam. The crude material was purified by a silica gel column (10 g, Merck) using as eluent a mixture DCM/$NH_3$-MeOH 7N (85/15) to give 26.4 mg (44% Yield) of Example (50) as a white foam.

$^1$H NMR (400 MHz, δ in ppm, DMSO-d6: 0.86 (t, J=7 Hz, 3H), 1.27-1.42 (m, 2H), 1.70 (dt, J=15, 8 Hz, 2H), 2.81 (t, J=8 Hz, 2H), 3.67 (s, 4H), 3.74 (br s, 2H), 5.49 (s, 2H), 5.80 (s, 1H), 6.42 (br s, 2H), 6.75 (br d, J=8 Hz, 2H), 7.26 (br d, J=8 Hz, 2H)

MS method N: RT (min): 0.13; $[M+H]^+$ 378

Example (51): Preparation of Compound 145: 1-[[4-(aminomethyl)phenyl]methyl]-2-butyl-7-pyrrolidin-3-yl-imidazo[4,5-d]pyridazin-4-amine

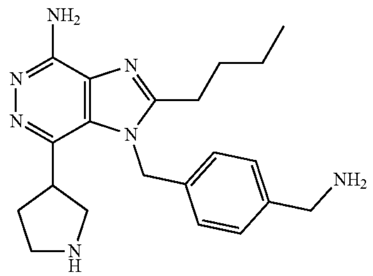 [SMILES: CCCCc1nc2c(N)nnc(C3CCNC3)c2n1Cc1ccc(CN)cc1]

Step 1: tert-butyl 3-[4-[bis[(2,4-dimethoxyphenyl)methyl]amino]-1-[[4-[(tert-butoxycarbonylamino)methyl]phenyl]methyl]-2-butyl-imidazo[4,5-d]pyridazin-7-yl]pyrrolidine-1-carboxylate

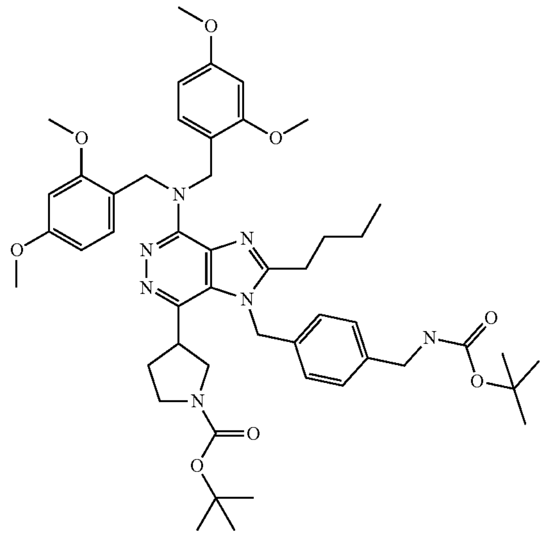 [SMILES: CCCCc1nc2c(N(Cc3ccc(OC)cc3OC)Cc3ccc(OC)cc3OC)nnc(C3CCN(C(=O)OC(C)(C)C)C3)c2n1Cc1ccc(CNC(=O)OC(C)(C)C)cc1]

To a hydrogenation tube was added a solution of tert-butyl 3-[4-[bis[(2,4-dimethoxyphenyl)methyl]amino]-1-[[4-[(tert-butoxycarbonylamino)methyl]phenyl]methyl]-2-butyl-imidazo[4,5-d]pyridazin-7-yl]-2,5-dihydropyrrole-1-carboxylate of Step 1 in Example (50) (203 mg, 0.231 mmol), in MeOH (6 ml) and Pd/C (21.84 mg, 0.21 mmol). The mixture was kept under Hydrogen (3 bar) at 25° C. for 26 h. Then reaction mixture was filtered over a GHpolypro filter (0.2 μm), and the filtrate was evaporated to give 205 mg of crude product, which was purified by a silica gel column (30 g, Merck) using as eluent a mixture Heptane/EtOAc (50/50) to give 142 mg (58.3% yield) of the expected compound.

$^1$H NMR (400 MHz, δ in ppm, DMSO-$d_6$):0.77 (t, J=7.4 Hz, 3H) 1.16-1.30 (m, 2H) 1.31-1.44 (m, 18H) 1.61 (m, 3H) 1.95 (m, 1H) 2.77 (t, J=7.1 Hz, 2H) 3.12 (m, 1H) 3.30-3.42 (m, 2H) 3.54 (m, 1H) 3.67-3.77 (m, 13H) 4.00-4.12 (m, 2H) 5.12 (br s, 4H) 5.61 (br s, 2H) 6.40 (dd, J=8.4, 2.4 Hz, 2H) 6.54 (d, J=2.4 Hz, 2H) 6.88 (d, J=8.4 Hz, 2H) 6.99 (d, J=8.3 Hz, 2H) 7.21 (d, J=8.3 Hz, 2H) 7.30 (m, 1H).

MS method N: RT (min): 1.77; $[M+H]^+$ 880

Step 2: Example (51): Preparation of Compound 145: 1-[[4-(aminomethyl)phenyl]methyl]-2-butyl-7-pyrrolidin-3-yl-imidazo[4,5-d]pyridazin-4-amine

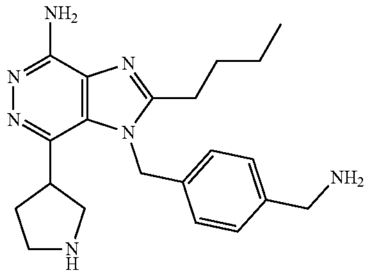

To a solution of tert-butyl 3-[4-[bis[(2,4-dimethoxyphenyl)methyl]amino]-1-[[4-[(tert-butoxycarbonylamino)methyl]phenyl]methyl]-2-butyl-imidazo[4,5-d]pyridazin-7-yl]pyrrolidine-1-carboxylate of Step 1 (212 mg, 0.241 mmol) in DCM (2.6 ml) was added dropwise TFA (2.0 ml, 18.94). The mixture (purple solution) was stirred at rt for 10 h then evaporated to dryness to give 120 mg of crude product as pink foam. The crude product was dissolved in 10 ml MeOH, and the suspension was loaded into a SCX cartridge (25 g, pre-washed with 10 ml of MeOH), the cartridge was eluted with MeOH (60 ml) and followed by elution with MeOH—$NH_3$ (2N) (40 ml). The ammoniacal methanolic solution was evaporated to dryness to give 112 mg of colourless powder. The crude material was purified by a silica gel column (10 g, Merck) using as eluent a mixture DCM/$NH_3$-MeOH 7N (85/15) to give 50 mg (54.7% Yield) of Example (51) as a white powder.

$^1$H NMR (400 MHz, δ in ppm, DMSO-d6: 0.85 (t, J=7 Hz, 3H), 1.34 (m, 2H), 1.64-1.81 (m, 3H), 1.97 (m, 1H), 2.77-2.90 (m, 4H), 2.93-3.09 (m, 2H), 3.58 (m, 1H), 3.69 (s, 2H), 5.62 (s, 2H), 6.23 (br s, 2H), 6.85 (m, J=8 Hz, 2H), 7.30 (m, J=8 Hz, 2H)

MS method N: RT (min): 0.12; $[M+H]^+$ 380

Example (52): Preparation of Compound 147: (2-butyl-4-isopropoxy-3-[6-(tetrahydropyran-4-ylamino)hexyl]imidazo[4,5-d]pyridazin-7-amine, dihydrochloride

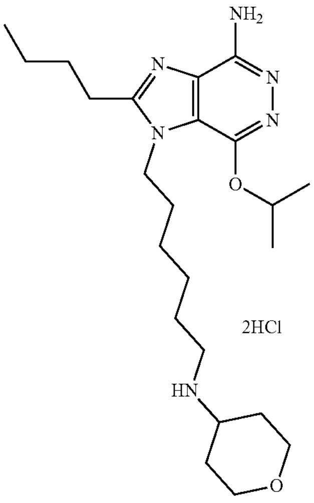

Step 1: 2-butyl-3-(6-chlorohexyl)-N,N-bis[(2,4-dimethoxyphenyl)methyl]-4-isopropoxy-imidazo[4,5-d]pyridazin-7-amine

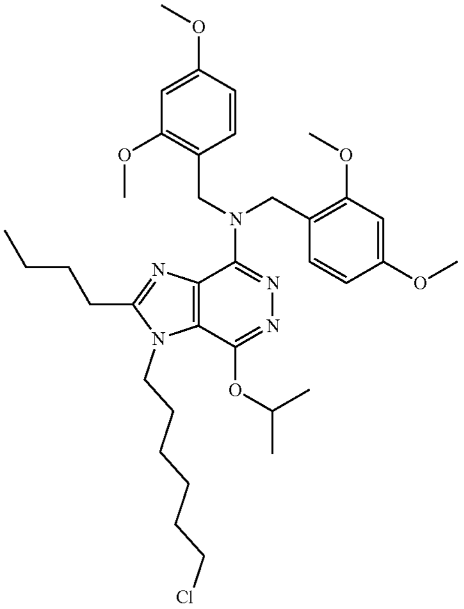

To a solution of 2-butyl-N,N-bis[(2,4-dimethoxyphenyl)methyl]-4-isopropoxy-3H-imidazo[4,5-d]pyridazin-7-amine, intermediate M (1000 mg, 1.82 mmol) in Me-THF (15 ml) was added cesium carbonate (889 mg, 2.73 mmol), and 1-bromo-6-chloro-hexane (435.6 mg, 2.18 mmol). The mixture was heated at 80° C. under microwave for 2 h. The reaction mixture was transferred to a separating funnel and washed with water. The organic layer was separated, dried over $MgSO_4$, filtered and evaporated to dryness. The crude material was purified by a silica gel column (Merck, 130 g) using as eluent a mixture Heptane/EtOAc (70/30) to give 650 mg (53% yield) of the expected product as a white solid.

$^1$H NMR (400 MHz, δ in ppm, DMSO-d6): 0.84 (t, J=7.3 Hz, 3H), 1.22-1.47 (m, 6H), 1.37 (d, J=6.4 Hz, 6H), 1.62-1.77 (m, 6H), 2.80 (t, J=7.3 Hz, 2H), 3.62 (t, J=6.6 Hz, 2H), 3.68-3.73 (m, 12H), 4.20-4.30 (m, 2H), 5.01 (s, 4H), 5.39 (spt, J=6.2 Hz, 1H), 6.38 (dd, J=8.3, 2.2 Hz, 2H), 6.52 (d, J=2.2 Hz, 2H), 6.95 (d, J=8.3 Hz, 2H)

MS method O: RT (min): 3.29; $[M+H]^+$ 668

Step 2: 2-butyl-N,N-bis[(2,4-dimethoxyphenyl)methyl]-4-isopropoxy-3-[6-(tetrahydropyran-4-ylamino)hexyl]imidazo[4,5-d]pyridazin-7-amine

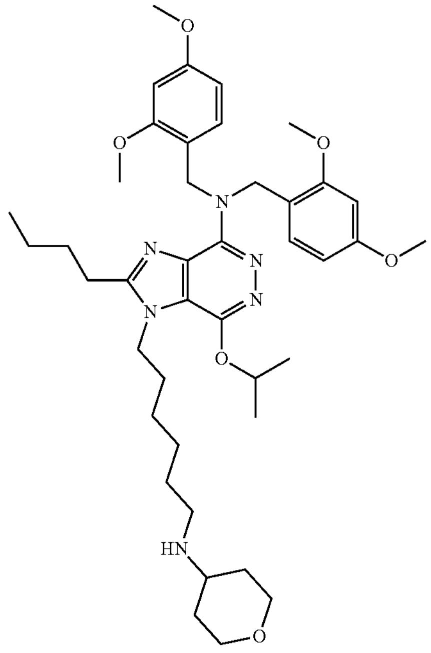

To a solution of 2-butyl-3-(4-chlorobutyl)-N,N-bis[(2,4-dimethoxyphenyl)methyl]-4-isopropoxy-imidazo[4,5-d]pyridazin-7-amine of Step 1 (220 mg, 0.329 mmol) in DMF (1 ml), was added tetrahydropyran-4-amine (499.5 mg, 4.94 mmol), tetrabutylammonium iodide (23.5 mg, 0.066 mmol), and sodium iodide (74 mg, 0.494 mmol). The mixture was heated at 90° C. under microwave for 1 h 30 min. The reaction mixture was diluted in EtOAc, transferred to a separating funnel and washed with water. The organic layer was separated, dried over $MgSO_4$, filtered and evaporated to dryness. The crude material was purified by a silica gel column (Merck, 20 g) using as eluent a mixture Heptane/EtOAc (70/30 to 50/50) to give 216 mg (89.5% yield) of the expected product.

$^1$H NMR (400 MHz, δ in ppm, DMSO-$d_6$):0.84 (t, J=7.5 Hz, 3H) 1.10-1.25 (m, 2H) 1.25-1.45 (m, 14H) 1.60-1.75 (m, 6H) 2.79 (t, J=7.3 Hz, 2H) 3.20-3.27 (m, 2H) 3.71 (m, 12H) 3.80 (m, 2H) 4.24 (br t, J=7.6 Hz, 2H) 5.00 (s, 4H) 5.38 (m, 1H) 6.38 (dd, J=8.3, 2.4 Hz, 2H) 6.52 (d, J=2.4 Hz, 2H) 6.95 (d, J=8.3 Hz, 2H)

MS method O: RT (min): 2.26; $[M+H]^+$ 733

Step 3: Example (52): Preparation of Compound 147: (2-butyl-4-isopropoxy-3-[6-(tetrahydropyran-4-ylamino)hexyl]imidazo[4,5-d]pyridazin-7-amine; dihydrochloride

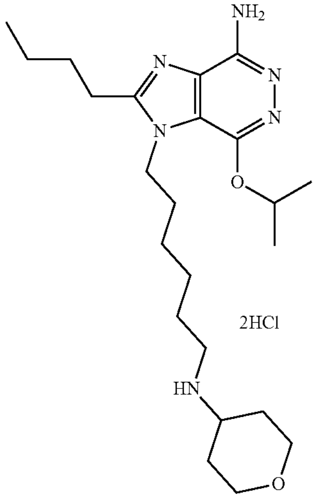

To a solution of 2-butyl-N,N-bis[(2,4-dimethoxyphenyl)methyl]-4-isopropoxy-3-[6-(tetrahydropyran-4-ylamino)hexyl]imidazo[4,5-d]pyridazin-7-amine of Step 2 (216 mg, 0.2947 mmol) in DCM (5 ml), was added 2,2,2-trifluoroacetic acid (1.8 ml, 24 mmol). The reaction mixture was stirred at rt for 18 h and evaporated to dryness under vacuum. The crude product was dissolved in MeOH and loaded into a SCX cartridge (20 g, pre-washed with 10 ml of MeOH), the cartridge was eluted with MeOH and followed by elution with MeOH—$NH_3$ (2N). The ammoniacal methanolic solution was evaporated to dryness to give 75 mg, under a form of lacquer, to which was added diethyl ether (5 ml) and HCl (2N) in diethyl ether (2 ml). A slight pink precipitate was formed which, after filtration, gave 39 mg (59% yield) of Example (52).

$^1$H NMR (400 MHz, δ in ppm, DMSO-d6: 0.94 (t, J=7 Hz, 3H), 1.28-1.51 (m, 6H), 1.42 (d, J=6 Hz, 6H), 1.57-1.70 (m, 4H), 1.70-1.84 (m, 4H), 1.94 (br d, J=10 Hz, 2H), 2.80-2.89 (m, 2H), 2.95 (t, J=8 Hz, 2H), 3.18-3.22 (m, 1H), 3.29 (br t, J=11 Hz, 2H), 3.90 (br dd, J=11, 4 Hz, 2H), 4.23-4.44 (m, 2H), 5.24 (quin, J=6 Hz, 1H), 8.55 (br s, 2H), 9.10 (br s, 2H), 13.95 (br s, 1H)

MS method O: RT (min): 1.46; $[M+H]^+$ 433

The following compounds may be made by analogy to Example 52: 150, 152, 154.

Example (53): Preparation of Compound 148: (N-[6-(7-amino-2-butyl-4-isopropoxy-imidazo[4,5-d]pyridazin-3-yl)hexyl]-N-tetrahydropyran-4-yl-acetamide

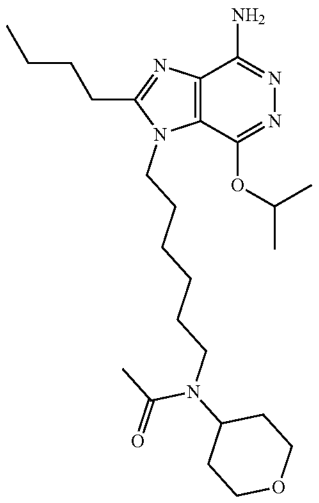

To a solution of 2-butyl-4-isopropoxy-3-[6-(tetrahydropyran-4-ylamino)hexyl]imidazo[4,5-d]pyridazin-7-amine, free base of Example (52) (37 mg, 0.086 mmol) in DCM (5 ml) was added DIPEA (7.6 μl, 0.102 mmol) and acetyl acetate (9.6 μl, 0.102 mmol). The reaction mixture was stirred at rt for 3 h, then diluted in DCM, and transferred to a separating funnel. The organic phase was washed with water, separated, dried over $MgSO_4$, filtered and evaporated to dryness. The crude materiel was dissolved in MeOH (3 ml) and treated with potassium carbonate (35.5 mg, 0.26 mmol) overnight at rt. It was then loaded into a SCX cartridge (20 g, pre-washed with 10 ml of MeOH), the cartridge was eluted with MeOH and followed by elution with MeOH—$NH_3$ (2N). The ammoniacal methanolic solution was evaporated to dryness to give 24 mg (59% yield) of Example (53) as white solid.

$^1$H NMR (400 MHz, δ in ppm, DMSO-d6: 0.93 (t, J=7 Hz, 3H), 1.19-1.85 (m, 16H), 1.36 (d, J=6 Hz, 6H), 1.91-2.10 (m, 3H), 2.85 (t, J=8 Hz, 2H), 3.02-3.19 (m, 2H), 3.30-3.42 (m, 2H), 3.75 (m, 1H), 3.87 (br d, J=12 Hz, 2H), 4.19-4.30 (m, 2H), 5.39 (dt, J=12, 6 Hz, 1H), 5.82 (s, 2H)

MS method M: RT (min): 0.98; $[M+H]^+$ 475

The following compounds may be made by analogy to Example 53: 151, 153, 155.

Example (54): Preparation of Compound 156: 2-[(7-amino-2-butyl-4-isopropoxy-imidazo[4,5-d]pyridazin-3-yl)methyl]-2-methyl-propane-1,3-diol; hydrochloride

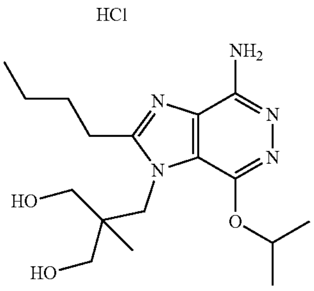 [SMILES: Cl ; CCCCc1nc2c(N)nnc(OC(C)C)c2n1CC(C)(CO)CO]

Step 1: (2,2,5-trimethyl-1,3-dioxan-5-yl)methyl methanesulfonate

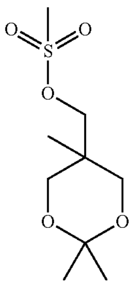

To a solution of (2,2,5-trimethyl-1,3-dioxan-5-yl)methanol (1000 mg, 6.24 mmol) in DCM (10 ml), was added at 0° C., DIPEA (1.3 ml, 6.24 mmol) and methanesulfonyl chloride (0.53 ml, 6.87 mmol). The reaction mixture was stirred at rt overnight, then diluted with DCM, and transferred to a separating funnel. The organic phase was washed with water, separated, dried over $MgSO_4$, filtered and evaporated to dryness to give 1.5 g of crude product. It was purified by a silica gel column (Merck, 70 g) using as eluent a mixture Heptane/EtOAc (50/50) to give 1.5 g (83% yield) of the expected product, as colorless oil.

$^1$H NMR (400 MHz, δ in ppm, DMSO-$d_6$):0.84 (s, 3H) 1.31 (s, 3H) 1.39 (s, 3H) 3.19 (s, 3H) 3.50-3.68 (m, 4H) 4.24 (s, 2H)

MS method N: RT (min): 1.16; $[M+H]^+$ 238

Step 2: 2-butyl-N,N-bis[(2,4-dimethoxyphenyl)methyl]-4-isopropoxy-3-[(2,2,5-trimethyl-1,3-dioxan-5-yl)methyl]imidazo[4,5-d]pyridazin-7-amine

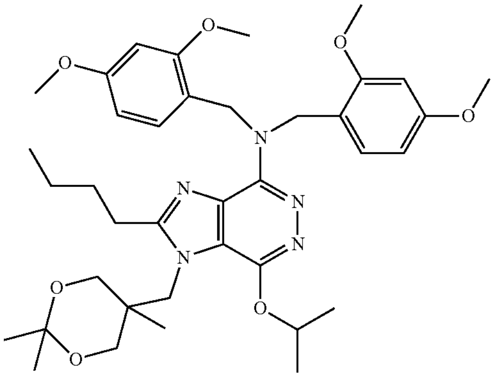

To a solution of 2-butyl-N,N-bis[(2,4-dimethoxyphenyl)methyl]-4-isopropoxy-3H-imidazo[4,5-d]pyridazin-7-amine, intermediate M (200 mg, 0.364 mmol), in Me-THF (11 ml), was added cesium carbonate (237.1 mg, 0.789 mmol) and (2,2,5-trimethyl-1,3-dioxan-5-yl)methyl methanesulfonate of Step 1 (247.1 mg, 1.04 mmol). The reaction mixture was heated under microwave at 125° C. for 4 h, it was then diluted with DCM, and transferred to a separating funnel. The organic phase was washed with water, separated, dried over $MgSO_4$, filtered and evaporated to dryness to give 0.5 g of crude product, which purified by a silica gel column (Merck, 50 g) using as eluent a mixture Heptane/EtOAc (60/40) to give 0.13 g (52% yield) of the expected product, as colorless oil.

$^1$H NMR (400 MHz, δ in ppm, DMSO-d6): 0.68 (s, 3H) 0.79-0.88 (m, 3H) 1.23-1.33 (m, 8H) 1.34-1.45 (m, 6H) 1.54-1.74 (m, 2H) 2.84-2.95 (m, 2H) 3.58 (q, J=11.8 Hz, 4H) 3.71 (s, 12H) 4.49 (s, 2H) 5.00 (s, 4H) 5.40 (m, 1H) 6.38 (dd, J=8.3, 2.3 Hz, 2H) 6.52 (d, J=2.3 Hz, 2H) 6.96 (d, J=8.3 Hz, 2H)

MS method N: RT (min): 1.75; $[M+H]^+$ 692

Step 3: Example (54): Preparation of Compound 156: 2-[(7-amino-2-butyl-4-isopropoxy-imidazo[4,5-d]pyridazin-3-yl)methyl]-2-methyl-propane-1,3-diol; hydrochloride

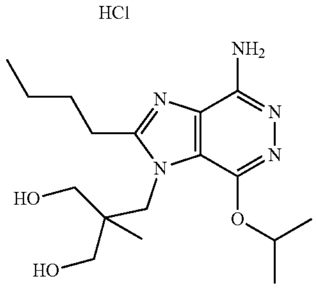 [SMILES: Cl ; CCCCc1nc2c(N)nnc(OC(C)C)c2n1CC(C)(CO)CO]

To a solution of 2-butyl-N,N-bis[(2,4-dimethoxyphenyl)methyl]-4-isopropoxy-3-[(2,2,5-trimethyl-1,3-dioxan-5-yl)methyl]imidazo[4,5-d]pyridazin-7-amine of Step 2 (110 mg, 0.091 mmol) in DCM (5 ml) was added 2,2,2-trifluoroacetic acid (1.4 ml, 18 mmol). The reaction mixture was stirred at rt for 18 h and evaporated to dryness under vacuum. The crude product was dissolved in MeOH and loaded into a SCX cartridge (20 g, pre-washed with 10 ml of MeOH), the cartridge was eluted with MeOH and followed by elution with MeOH—$NH_3$ (2N). The ammoniacal methanolic solution was evaporated to dryness, to which was added diethyl ether (5 ml) and HCl (2N) in diethyl ether (2 ml). A precipitate was formed which, after filtration, gave 27 mg (54% yield) of Example (54) as a white solid.

$^1$H NMR (400 MHz, δ in ppm, DMSO-d6: 0.66 (s, 3H), 0.93 (t, J=7 Hz, 3H), 1.35-1.50 (m, 8H), 1.78 (br s, 2H), 2.97-3.10 (m, 2H), 3.11-3.45 (m, 4H), 4.18-4.64 (m, 2H), 5.24 (quin, J=6 Hz, 1H), 8.49 (s, 2H), 13.82 (br s, 1H)

MS method N: RT (min): 0.95; $[M+H]^+$ 352

Example (55): Preparation of Compound 157: 2-[(7-amino-2-butyl-4-isopropoxy-imidazo[4,5-d]pyridazin-3-yl)methyl]propane-1,3-diol; hydrochloride

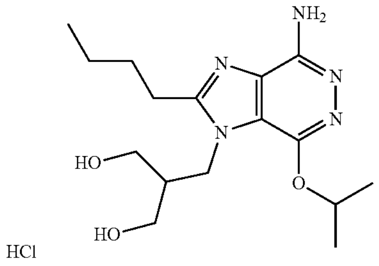 [SMILES: CCCCc1nc2c(N)nnc(OC(C)C)c2n1CC(CO)CO ; Cl]

Step 1: (((2,2-dimethyl-1,3-dioxan-5-yl)methyl methanesulfonate

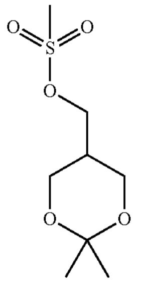

To a solution of (2,2-dimethyl-1,3-dioxan-5-yl)methanol (1000 mg, 6.84 mmol) in DCM (10 ml), was added at 0° C., DIPEA (1.4 ml, 7.52 mmol) and methanesulfonyl chloride (0.58 ml, 7.53 mmol). The reaction mixture was stirred at rt overnight, then diluted with DCM, and transferred to a separating funnel. The organic phase was washed with water, separated, dried over $MgSO_4$, filtered and evaporated to dryness to give 1.5 g of crude product. It was purified by a silica gel column (Merck, 100 g) using as eluent a mixture Heptane/EtOAc (80/20) to give 1.4 g (78% yield) of the expected product, as colourless oil.

$^1$H NMR (400 MHz, δ in ppm, DMSO-d6): 1.29-1.37 (m, 6H) 1.97 (m, 1H) 3.18 (s, 3H) 3.66 (dd, J=12.3, 5.5 Hz, 2H) 3.92-3.97 (m, 2H) 4.28 (d, J=7.3 Hz, 2H)

MS method N: RT (min): 1.1; $[M+H]^+$ 224

Step 2: 2-butyl-N,N-bis[(2,4-dimethoxyphenyl) methyl]-3-[(2,2-dimethyl-1,3-dioxan-5-yl)methyl]-4-isopropoxy-imidazo[4,5-d]pyridazin-7-amine

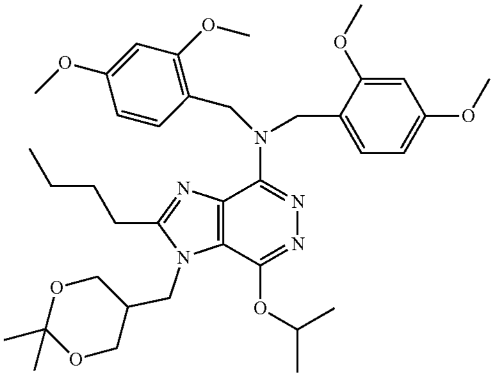

To a solution of 2-butyl-N,N-bis[(2,4-dimethoxyphenyl) methyl]-4-isopropoxy-3H-imidazo[4,5-d]pyridazin-7-amine, intermediate M (200 mg, 0.364 mmol), in Me-THF (4.5 ml), was added cesium carbonate (237.1 mg, 0.789 mmol) and (2,2,5-trimethyl-1,3-dioxan-5-yl)methyl methanesulfonate of Step 1 (106 mg, 0.473 mmol). The reaction mixture was heated under microwave at 130° C. for 1 h30, it was then diluted with EtOAc, and transferred to a separating funnel. The organic phase was washed with water, separated, dried over $MgSO_4$, filtered and evaporated to dryness to give 0.4 g of crude product, which purified by a silica gel column (Merck, 50 g) using as eluent a mixture Heptane/EtOAc (70/30) to give 0.09 g (36% yield) of the expected product, which was used directly in the next step.

Step 3: Example (55): Preparation of Compound 157: 2-[(7-amino-2-butyl-4-isopropoxy-imidazo[4,5-d]pyridazin-3-yl)methyl]propane-1,3-diol; hydrochloride

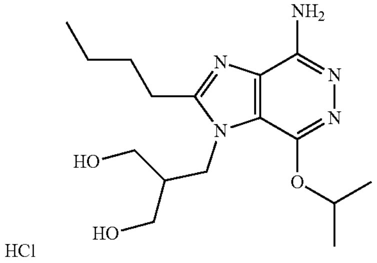 [SMILES: CCCCc1nc2c(N)nnc(OC(C)C)c2n1CC(CO)CO ; Cl]

To a solution of 2-butyl-N,N-bis[(2,4-dimethoxyphenyl) methyl]-3-[(2,2-dimethyl-1,3-dioxan-5-yl)methyl]-4-isopropoxy-imidazo[4,5-d]pyridazin-7-amine of Step 2 (90 mg, 0.133 mmol) in DCM (2 ml) was added 2,2,2-trifluoroacetic acid (900 µl, 10 mmol). The reaction mixture was stirred at rt for 18h and evaporated to dryness under vacuum. The crude product was dissolved in MeOH and loaded into a SCX cartridge (20 g, pre-washed with 10 ml of MeOH), the cartridge was eluted with MeOH and followed by elution with MeOH—$NH_3$ (2N). The ammoniacal methanolic solution was evaporated to dryness, to which was added diethyl ether (5 ml) and HCl (2N) in diethyl ether (2 ml). A precipitate was formed which, after filtration, gave 23 mg (46% yield) of Example (55) as a white solid.

$^1$H NMR (400 MHz, δ in ppm, DMSO-d6: 0.94 (t, J=7 Hz, 3H), 1.34-1.49 (m, 8H), 1.73-1.87 (m, 2H), 2.06 (m, 1H), 2.98 (br t, J=8 Hz, 2H), 3.35-3.50 (m, 4H), 4.34 (d, J=8 Hz, 2H), 4.59 (br s, 2H), 5.23 (m, 1H), 8.47 (br s, 2H), 13.80 (br s, 1H)

MS method N: RT (min): 0.90; $[M+H]^+$ 338

Example (56): Preparation of Compound 159: 1-(4-(aminomethyl)benzyl)-2-(ethoxymethyl)-7-isopropoxy-1H-imidazo[4,5-d]pyridazin-4-amine

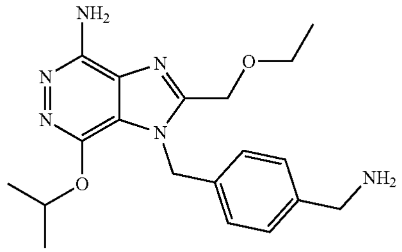

Step 1: N—[(Z)-2-amino-1,2-dicyanoethenyl]-2-ethoxyacetamide

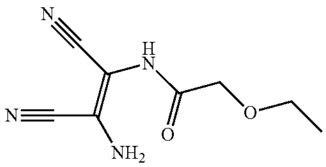

To s solution of (Z)-2,3-diaminobut-2-enenitrile (189.65 g, 1.75 mol, 1.0 eq) in EtOAc (1.0 L) was added 2-ethoxyacetyl chloride (215 g, 1.75 mol, 1.0 eq) in dropwise, the reaction solution was stirred at 25° C. for 12 hrs. TLC (Petroleum ether:EtOAc=1:1, $R_f$=0.12) showed that the reaction was completed. The suspension was filtered, and the cake washed with EtOAc (4×100.0 mL) to expected compound (242.0 g, 71.0% yield) as yellow solid.

$^1$H NMR (400 MHz, δ in ppm, DMSO-d6): 9.30 (s, 1H), 8.40 (s, 1H), 7.30 (s, 1H), 3.96 (s, 2H), 3.48 (q, J=6.0 Hz, 2H), 1.12 (t, J=6.0 Hz, 3H).

Step 2: 2-(ethoxymethyl)-1H-imidazole-4,5-dicarbonitrile

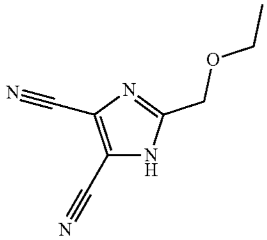

To a solution of N—[(Z)-2-amino-1,2-dicyanoethenyl]-2-ethoxyacetamide of Step 1 (64.0 g, 329.57 mmol, 1.0 eq) in NMP (800.0 mL) was added NaH (14.50 g, 362.53 mmol, 60% purity, 1.1 eq) in portion. The reaction solution was stirred at 140° C. for 24 hrs. TLC (Petroleum ether:EtOAc=0:1, Rf=0.13) showed that the reaction was completed. The reaction was cooled to rt. The reaction solution was poured into water (8.0 L) and extracted with EtOAc (2×3.0 L). The organic layer washed with water (2×3.0 L) and brine (3.0 L), dried with $Na_2SO_4$, filtered and concentrated in vacuum. The material was purified by silica gel (Petroleum ether:EtOAc=2:1 to 0:1) to give expected compound (81.0 g, 46.5% yield) as yellow solid.

$^1$H NMR (400 MHz, δ in ppm, DMSO-$d_6$): 4.56 (s, 2H), 3.53 (q, J=6.8 Hz, 2H), 1.16 (t, J=6.8 Hz, 3H).

Step 3: 2-(ethoxymethyl)-1H-imidazole-4,5-dicarboxylic acid

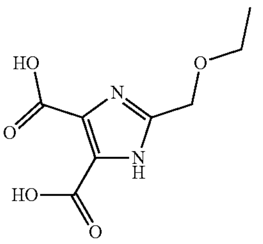

To a solution of 2-(ethoxymethyl)-1H-imidazole-4,5-dicarbonitrile of Step 2 (76.0 g, 431.39 mmol, 1.0 eq) in $H_2O$ (800.0 mL) was added NaOH (103.53 g, 2.59 mol, 6.0 eq), the reaction solution was stirred at 100° C. for 4 hrs. TLC (Petroleum ether:EtOAc=0:1, $R_f$=0.00) showed that the reaction was completed. The reaction solution was cooled to 25° C., and the pH value was adjusted to 1 with 12 N HCl, the suspension was filtered and the cake was dried in vacuum to give expected compound (70.0 g, 75.8% yield) as white solid.

$^1$H NMR (400 MHz, δ in ppm, DMSO-d6): 4.57 (s, 2H), 3.51 (q, J=6.8 Hz, 2H), 1.12 (t, J=6.8 Hz, 3H).

Step 4: dimethyl 2-(ethoxymethyl)-1H-imidazole-4,5-dicarboxylate

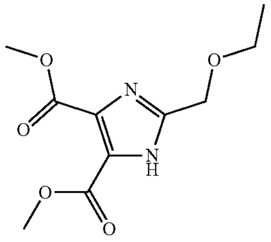 [SMILES: CCOCc1nc(C(=O)OC)c(C(=O)OC)[nH]1]

To a solution of 2-(ethoxymethyl)-1H-imidazole-4,5-dicarboxylic acid of Step 3 (72.5 g, 338.51 mmol, 1.0 eq) in MeOH (500.0 mL) was added $SOCl_2$ (201.36 g, 1.69 mol, 122.78 mL, 5.0 eq), the reaction solution was stirred at 45° C. for 12 hrs. TLC (Petroleum ether:EtOAc=0:1, $R_f$=0.16) showed the reaction was completed. The reaction solution was concentrated. The residue was diluted with water (500.0 mL) and the pH value was adjusted to 5. The solution was extracted with EtOAc (3×1 L), then washed with brine (200.0 mL), dried with $Na_2SO_4$, filtered and concentrated to give expected compound (35.0 g, 42.7% yield) as yellow solid.

$^1$H NMR (400 MHz, δ in ppm, DMSO-d6): 4.43 (s, 2H), 3.81 (s, 6H), 3.48 (q, J=6.8 Hz, 2H), 1.12 (t, J=6.8 Hz, 3H).

Step 5: 2-(ethoxymethyl)-1H-imidazole-4,5-dicarbohydrazide

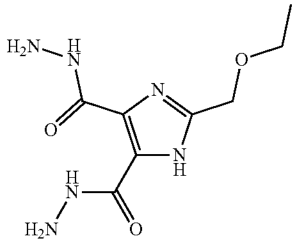 [SMILES: CCOCc1nc(C(=O)NN)c(C(=O)NN)[nH]1]

The solution of dimethyl 2-(ethoxymethyl)-1H-imidazole-4,5-dicarboxylate of Step 4 (35.0 g, 144.49 mmol, 1.0 eq) and $N_2H_4{\cdot}H_2O$ (22.14 g, 433.48 mmol, 21.50 mL, 98% purity, 3.0 eq) in MeOH (350.0 mL) was stirred at 60° C. for 1 hrs. TLC (Petroleum ether:EtOAc=3:1, $R_f$=0.33) showed the reaction was completed. The reaction solution was filtered and the cake washed with MeOH (50.0 mL) to give expected compound (25.0 g, 71.4% yield) as white solid.

$^1$H NMR (400 MHz, δ in ppm, DMSO-d6): 13.25 (s, 1H), 12.01 (s, 1H), 9.75 (s, 1H), 4.62 (s, 4H), 4.41 (s, 2H), 3.48 (q, J=6.8 Hz, 2H), 1.11 (t, J=6.8 Hz, 3H).

Step 6: 2-(ethoxymethyl)-5,6-dihydro-1H-imidazo[4,5-d]pyridazine-4,7-dione

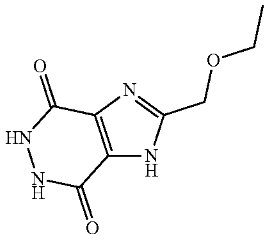

The solution of 2-(ethoxymethyl)-1H-imidazole-4,5-dicarbohydrazide of Step 5 (25.0 g, 103.21 mmol, 1.0 eq) in HCl (100.0 mL) was stirred at 100° C. for 12 hrs. The reaction solution was filtered to give the expected compound (20.0 g, 92.2% yield) as white solid.

$^1$H NMR (400 MHz, δ in ppm, DMSO-d6): 4.74 (s, 2H), 3.54 (q, J=6.8 Hz, 2H), 1.12 (t, J=6.8 Hz, 3H).

Step 7: 4,7-dichloro-2-(ethoxymethyl)-1H-imidazo[4,5-d]pyridazine

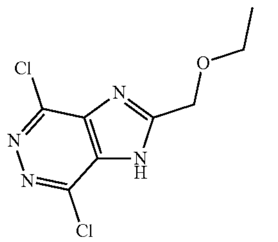

The solution of 2-(ethoxymethyl)-5,6-dihydro-1H-imidazo[4,5-d]pyridazine-4,7-dione of Step 6 (20.0 g, 95.15 mmol, 1.0 eq) in $POCl_3$ (180 mL) and N,N-dimethylaniline (20.0 mL) was stirred at 110° C. for 1 h. TLC (Petroleum ether/EtOAc=0:1, $R_f$=0.10) showed the reaction was completed. The reaction solution was concentrated in vacuo. The residue was diluted with EtOAc (500 mL) and poured into water (200 mL). The aqueous phase was extracted with ethyl acetate (4×200 ml). The combined organic phase was washed with brine (100 mL), dried with anhydrous $Na_2SO_4$, filtered and concentrated in vacuum. The residue was purified by silica gel chromatography (column height: 250 mm, diameter: 100 mm, 100-200 mesh silica gel, Petroleum ether/EtOAc=3/1 to 0/1) to afford the expected compound (7.14 g, 29.3% yield) as white solid.

$^1$H NMR (400 MHz, δ in ppm, DMSO-d6): 14.60 (s, 1H), 4.80 (s, 2H), 3.61 (q, J=6.8 Hz, 2H), 1.19 (t, J=6.8 Hz, 3H).

MS method M: RT (min): 1.559, $[M+H]^+$ 247

Step 8: 7-chloro-N,N-bis(2,4-dimethoxybenzyl)-2-(ethoxymethyl)-1H-imidazo[4,5-d]pyridazin-4-amine

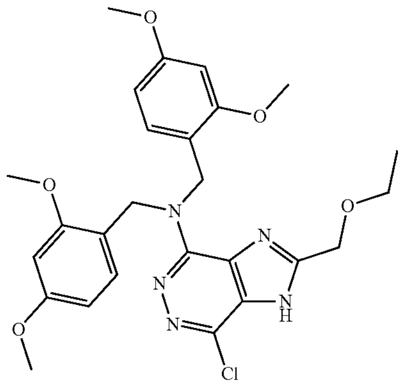 [SMILES: CCOCc1nc2c(N(Cc3ccc(OC)cc3OC)Cc3ccc(OC)cc3OC)nnc(Cl)c2[nH]1]

4,7-dichloro-2-(ethoxymethyl)-1H-imidazo[4,5-d]pyridazine of Step 7 (1.4 g, 5.67 mmol) was dissolved in n-butanol (14 ml), DIPEA (9 ml, 51.6 mmol) was added and the reaction mixture was stirred under reflux (107° C.). Bis(2,4-dimethoxybenzyl)amine (1.8 g, 5.67 mmol) was added in four equal amount every 1 h, from t 0 to t+4 h. The clear yellow solution turned brown within 1 h after heating. The mixture was maintained at reflux for 36 h, then cooled down to rt. The mixture was concentrated under reduced pressure, the residue was then taken up with DCM (200 ml), washed with deionized water (3×50 ml) and brine (50 ml), then dried using anhydrous sodium sulfate and filtered off. After concentration in vacuo of the organic phase, 4.01 g of yellow oil was obtained. Purification by flash column chromatography (8:2 DCM/Acetone) on a 200 g silica column (Merck) yielded 1.123 g of expected compound (1.123 g, 37.5%) as a white foam.

$^1$H NMR (400 MHz, δ in ppm, DMSO-$d_6$: 1.1 ppm (t, 3H, H-1), 3.5 (q, 2H, H-2), 3.8 (two s, 12H, H-3), 4.6 (s, 2H, H-4), 5.1 (s, 4H, H-5), 6.4 (dd, J=8 Hz and 2 Hz, 2H, H-6), 6.5 (d, J=2 Hz, 2H, H-7), 7.0 (d, J=8 Hz, 2H, H-8), 13.7 (s, 1H, NH)

MS (ESI, DMSO) m/z: $[M+H]^+$ 528

Step 9: N,N-bis(2,4-dimethoxybenzyl)-2-(ethoxymethyl)-7-isopropoxy-1H-imidazo[4,5-d]pyridazin-4-amine

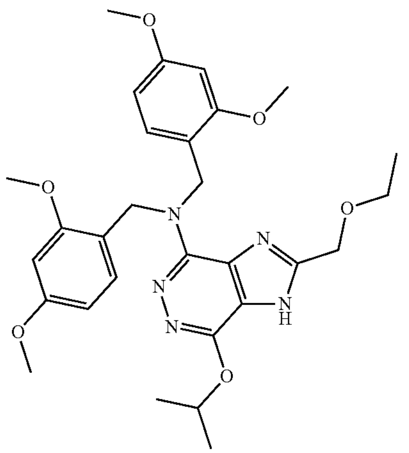 [SMILES: CCOCc1nc2c(N(Cc3ccc(OC)cc3OC)Cc3ccc(OC)cc3OC)nnc(OC(C)C)c2[nH]1]

7-chloro-N,N-bis(2,4-dimethoxybenzyl)-2-(ethoxymethyl)-1H-imidazo[4,5-d]pyridazin-4-amine of Step 8 (994 mg, 0.948 mmol) was dissolved in 1,4-Dioxane and iPrOH (5.5 ml/5.5 ml), Sodium isopropoxide (722 mg, 8.80 mmol) was added. The brown heterogeneous mixture was introduced in a 20 ml microwave vial and heated at 170° C. for 6 h, pressure inside the vial was stable at 7 bar. The suspension was filtered, concentrated under reduced pressure, taken up with EtOAc (100 ml) and washed with water (3×50 ml), brine (1×100 ml) and finally dried with $MgSO_4$. After concentration in vacuo of the organic phase 1.125 g of crude material was obtained. Purification by flash column chromatography (7:3 EtOAc/n-heptane) on a 130 g silica column (Merck) yielded 0.55 g of the expected compound (53% yield).

$^1$H NMR (400 MHz, δ in ppm, DMSO-$d_6$: 1.1 ppm (t, 3H, H-1), 1.4 (d, 6H, H-2), 3.5 (q, 2H, H-3), 3.8 (two s, 12H, H-4), 4.6 (s, 2H, H-5), 5.1 (s, 4H, H-6), 5.4 (sept, 1H, H-7), 6.4 (dd, J=8 Hz and 2 Hz, 2H, H-8), 6.5 (d, J=2 Hz, 2H, H-9), 7.0 (d, J=8 Hz, 2H, H-10), δ 13.7 (s, 1H).

MS (ESI, DMSO) m/z: $[M+H]^+$ 552

Step 10: tert-butyl (4-((7-(bis(2,4-dimethoxybenzyl) amino)-2-(ethoxymethyl)-4-isopropoxy-5H-imidazo [4,5-d]pyridazin-5-yl)methyl)benzyl)carbamate

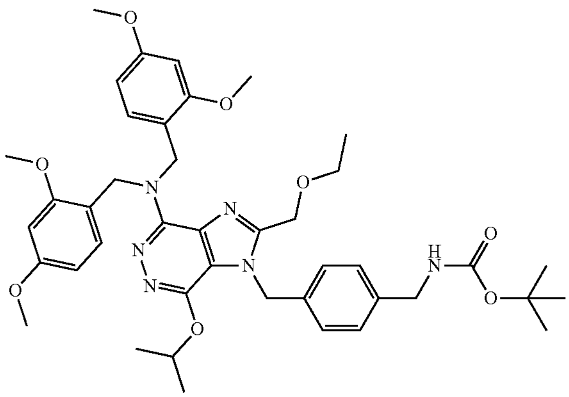 [SMILES: CCOCc1nc2c(N(Cc3ccc(OC)cc3OC)Cc3ccc(OC)cc3OC)nnc(OC(C)C)c2n1Cc1ccc(CNC(=O)OC(C)(C)C)cc1]

To a solution of N,N-bis(2,4-dimethoxybenzyl)-2-(ethoxymethyl)-7-isopropoxy-1H-imidazo[4,5-d]pyridazin-4-amine of Step 9 (130 mg, 0.235 mmol) in Me-THF (7 ml) was added cesium carbonate (315 mg, 0.957 mmol). The mixture was stirred for 1 h, then tert-butyl 4-(bromomethyl) benzylcarbamate (85 mg, 0.258 mmol) was added. The milky white homogeneous medium was stirred at rt for 24 h. The reaction mixture was filtered, concentrated under reduced pressure, taken up with Me-THF (20 ml) and washed with water (3x6 ml), brine (6 ml) and finally dried with $MgSO_4$. After concentration in vacuo of the organic phase 168 mg of crude material was obtained as a light-yellow resin. Purification by flash column chromatography (5:5 EtOAc/n-heptane) on a 15 g silica column (Merck) yielded the expected product (96 mg, 52% yield).

$^1H$ NMR (400 MHz, δ in ppm, DMSO-d6): 1.0 (t, 3H, H-1), 1.2 (d, 6H, H-2), 1.35 (s, 9H, H-3), 3.5 (q, 2H, H-4), 3.7 (two s, 12H, H-5), 4.1 (d, 2H, H-6), 4.6 (s, 2H, H-7), 5.0 (s, 4H, H-8), 5.3 (sept, 1H, H-9), 5.6 (d, 2H, H-10), 6.4 (dd, J=8 Hz and 2 Hz, 2H, H-11), 6.5 (d, J=2 Hz, 2H, H-12), 6.95 (d, J=8 Hz, 2H, H-13), 7.05 & 7.15 (d, 2H, H-14).

MS (ESI, DMSO) m/z $[M+H]^+$ 771

Step 11: Example (56): Preparation of Compound 159: 1-(4-(aminomethyl)benzyl)-2-(ethoxymethyl)-7-isopropoxy-1H-imidazo[4,5-d]pyridazin-4-amine

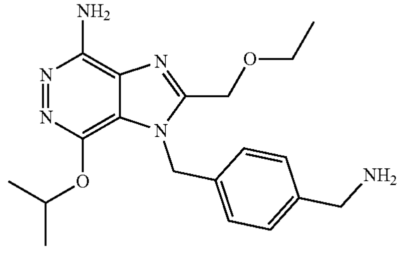

To a solution of tert-butyl (4-((7-(bis(2,4-dimethoxybenzyl)amino)-2-(ethoxymethyl)-4-isopropoxy-5H-imidazo[4,5-d]pyridazin-5-yl)methyl)benzyl)carbamate of Step 10 (96 mg, 0.125 mmol) in DCM (1 ml) was added TFA (448 μl, 4.98 mmol) were added dropwise. The mixture was stirred for 24 h at rt. The medium turned fuchsia pink within the first minute of agitation. The reaction mixture was taken up with DCM (5 ml), washed with water (2x10 ml), aqueous phases were combined, filtered and adjusted to pH 12 with NaOH 5M under stirring. The aqueous phase was firstly extracted with EtOAc 3x50 ml, then with DCM 3x50 ml and a third time with DCM/Methanol 95/05 3x50 ml. The organic layers were combined and evaporated to dryness under vacuum to give 34 mg of crude material. Purification by flash column chromatography (94/4/2 DCM/MeOH/$NH_3 \cdot H_2O$) on a 5 g silica column (Merck) yielded 27 mg (59% yield) of Example (56).

$^1H$ NMR (400 MHz, δ in ppm, DMSO-$d_6$ 1.04 (t, J=7 Hz, 3H), 1.20 (d, J=6 Hz, 6H), 1.75-2 (m, 2H), 3.48 (q, J=7 Hz, 2H), 3.66 (s, 2H), 4.68 (s, 2H), 5.31 (spt, J=6 Hz, 1H), 5.58 (s, 2H), 6.03 (s, 2H), 7.04 (d, J=8 Hz, 2H), 7.26 (d, J=8 Hz, 2H).

MS method N: RT (min): 0.47, $[M+H]^+$ 371

Example (57): Preparation of Compound 161: 3-[[4-(aminomethyl)phenyl]methyl]-4-isopropoxy-2-propylsulfanyl-imidazo[4,5-d]pyridazin-7-amine

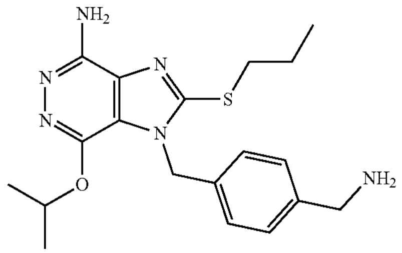

Step 1: 7-chloro-N,N-bis(2,4-dimethoxybenzyl)-1H-imidazo[4,5-d]pyridazin-4-amine

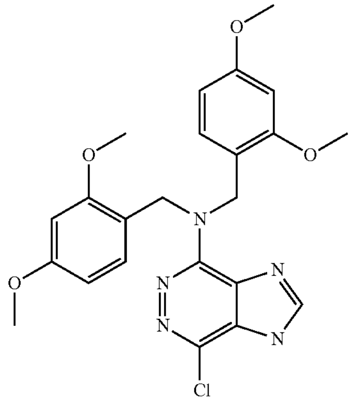

To a 25 ml round bottom flask equipped with a magnetic stir and a reflux condenser, was added 4,7-dichloro-1H-imidazo[4,5-d]pyridazine (3 g, 15.87 mmol), n-butanol (30 ml) and DIPEA (27.79 ml, 158.73 mmol), resulting a homogeneous solution. Bis(2,4-dimethoxybenzyl)amine (1.45 g, 4.48 mmol) was then added and the brown reaction mixture was heated at reflux for 1 h. 3 other portions of bis(2,4-dimethoxybenzyl)amine were added every hour (t0+2 h: 1.5 g, 4.63 mmol; t0+3 h: 1.5 g, 4.63 mmol and t0+4 h: 1.09 g, 3.37 mmol). The mixture was heated at reflux for 92 h. It was cooled to rt and evaporated under vacuum to dryness. The remaining oil was dissolved in EtOAc (400 ml), transferred to a separating funnel and washed with water (3×100 ml). The aqueous phase was extracted with 100 ml EtOAc. The combined organic layer was washed with brine, dried over $MgSO_4$, filtered and evaporated to dryness, to give 9.06 g of crude product. The crude material was purified by chromatography on a Merck cartridge (600 g of 15-40 μm silica) with $CHCl_3$/MeOH (97/3) elution, to afford 1.79 g (24%, yield) of expected compound as a yellow solid.

$^1$H NMR (400 MHz, δ in ppm, DMSO-d6): 3.72 (s, 12H) 5.07 (br s, 4H) 6.40 (dd, J=8, 3 Hz, 2H) 6.54 (d, J=3 Hz, 2H) 6.95 (d, J=8 Hz, 2H) 8.40 (s, 1H) 13.74 (br s, 1H)

MS method N: RT (min): 1.37, $[M+H]^+$ 470

Step 2: N,N-bis(2,4-dimethoxybenzyl)-7-isopropoxy-1H-imidazo[4,5-d]pyridazin-4-amine

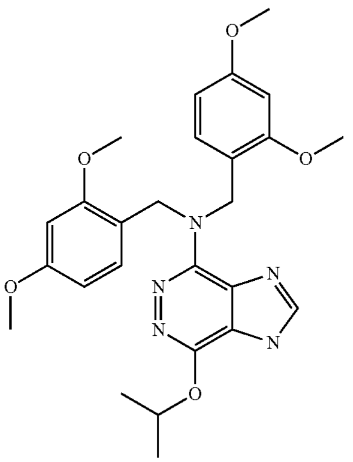

To a round bottom flask (50 ml), was added 7-chloro-N, N-bis(2,4-dimethoxybenzyl)-1H-imidazo[4,5-d]pyridazin-4-amine of Step 1 (1.44 g, 3.06 mmol), Dioxane (16 ml) and isopropanol (16 ml). The resulting solution was transferred equally into 2 microwave tube of 10-20 ml capacity, to each was added sodium isopropoxide (755 mg, 9.2 mmol). Both tubes were heated at 170° C. for 8 h. The reaction mixtures were united and diluted in EtOAc (100 ml). The organic solution was washed with water (50 ml), the aqueous phase was extracted with EtOAc (3×10 ml). The united organic layer was washed with brine, dried over $MgSO_4$, filtered and evaporated to dryness, to give 1.38 g of crude product, which was purified by chromatography on a Merck cartridge (150 g of 15-40 μm silica) with DCM/MeOH (99/1 to 98/2) elution, to afford 0.763 g (50.4% yield) of expected compound as a white foam.

$^1$H NMR (400 MHz, δ in ppm, DMSO-d6): 1.38 (d, J=6.2 Hz, 6H) 3.71 (s, 12H) 5.02 (br s, 4H) 5.41 (m, 1H) 6.40 (dd, J=8.4, 2.4 Hz, 2H) 6.53 (d, J=2.4 Hz, 2H) 6.95 (d, J=8.4 Hz, 2H) 8.21 (br s, 1H) 13.30-13.60 (br s, 1H)

MS method N: RT (min): 1.29, $[M+H]^+$ 494

Step 3: tert-butyl N-[[4-[[7-[bis[(2,4-dimethoxyphenyl)methyl]amino]-4-isopropoxy-imidazo[4,5-d]pyridazin-3-yl]methyl]phenyl]methyl]carbamate

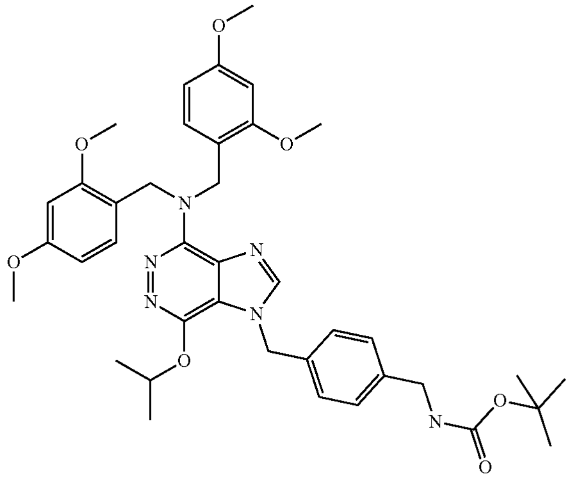

To a round-bottom flask was added N,N-bis[(2,4-dimethoxyphenyl)methyl]-4-isopropoxy-3H-imidazo[4,5-d]pyridazin-7-amine of Step 2 (450 mg, 0.91 mmol), MeTHF 6 ml), Tert-BUTYL 4-(BROMOMETHYL)BENZYLCARBAMATE (310 mg, 1.00 mmol) and $Cs_2CO_3$ (891 mg, 2.74 mmol). The resulting mixture was stirred at rt for 2 h. The reaction was then diluted with EtOAc and washed with brine. The organic layer was separated, dried over $MgSO_4$, filtered and evaporated to give a white foam. The crude material was purified by a silica gel column (80 g) using as solvent Heptane/EtOAc (60/40) to give 0.52 g (80% yield) of a white solid.

$^1$H NMR (400 MHz, δ in ppm, DMSO-$d_6$):1.28 (d, J=6.1 Hz, 6H) 1.37 (s, 9H) 3.70 (m, 12H) 4.05 (m, 2H) 4.98 (s, 4H) 5.34 (sept, J=6.2 Hz, 1H) 5.54 (s, 2H) 6.39 (dd, J=8.3, 2.4 Hz, 2H) 6.52 (d, J=2.4 Hz, 2H) 6.94 (d, J=8.3 Hz, 2H) 7.21 (m, 4H) 7.33 (m, 1H) 8.46 (s, 1H)

MS method N: RT (min): 1.57, $[M+H]^+$ 713

Step 4: tert-butyl N-[[4-[[7-[bis[(2,4-dimethoxyphenyl)methyl]amino]-4-isopropoxy-2-propylsulfanyl-imidazo[4,5-d]pyridazin-3-yl]methyl]phenyl]methyl] carbamate

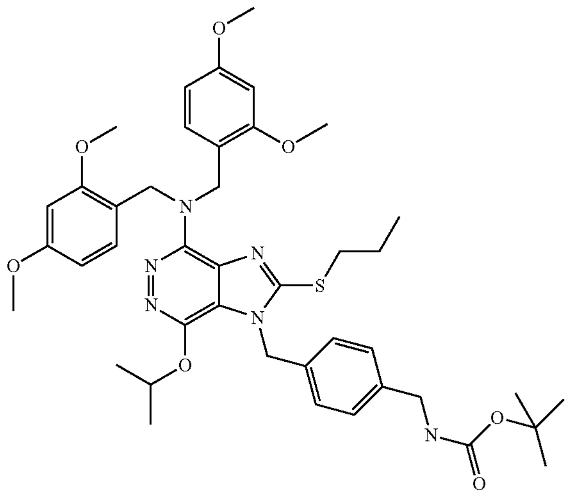 [SMILES: CCCSc1nc2c(N(Cc3ccc(OC)cc3OC)Cc3ccc(OC)cc3OC)nnc(OC(C)C)c2n1Cc1ccc(CNC(=O)OC(C)(C)C)cc1]

To a tricol Keller equipped with magnetic stir, thermometer probe, under argon, was added tert-butyl N-[[4-[[7-[bis [(2,4-dimethoxyphenyl)methyl]amino]-4-isopropoxy-imidazo[4,5-d]pyridazin-3-yl]methyl]phenyl]methyl] carbamate of Step 3 (50 mg, 0.07 mmol), and anhydrous THF (1 ml). The homogenous solution was cooled to −30° C., to which was added BuLi (50 μl, 1.6 M in heptane, 0.077 mmol) and stirred at 20 mins, followed by addition of propyl disulfide (13 μl, 0.084 mmol). The reaction mixture was allowed to reach slowly to rt and stirred for 2h. It was then cooled again to −30° C., an additional of BuLi (100 μl, 1.6 M in heptane, 0.154 mmol) was added, the reaction mixture turned to red with some slight precipitation. It was stirred for 30 mins and followed by addition of propyl disulfide (26 μl, 0.168 mmol). The reaction mixture was allowed to reach slowly to rt and stirred overnight. It was then added 20 ml of water, 30 ml of EtOAc and transferred to a separating funnel. After separation of organic phase, the aqueous phase was extracted with EtOAc (2×30 ml). The united organic phase was washed with brine, dried over $MgSO_4$, filtered and evaporated to dryness to give 55 mg of crude product. The crude material was purified by a silica gel column (5 g, Merck) using as solvent Heptane/EtOAc (70/30) to give 0.015 g (28% yield) of a white gum.

$^1H$ NMR (400 MHz, δ in ppm, DMSO-d6): 0.76 (t, J=7.3 Hz, 3H), 1.11-1.31 (m, 6H), 1.37 (s, 9H), 1.52 (sxt, J=7.3 Hz, 2H), 3.06 (t, J=7.2 Hz, 2H), 3.67-3.78 (m, 12H), 4.07 (br d, J=6.1 Hz, 2H), 4.97 (s, 4H), 5.33 (m, 1H), 5.41 (s, 2H), 6.40 (dd, J=8.5, 2.2 Hz, 2H), 6.53 (d, J=2.2 Hz, 2H), 6.98 (d, J=8.5 Hz, 2H), 7.12 (d, J=8.3 Hz, 2H), 7.19 (d, J=8.3 Hz, 2H), 7.33 (t, J=6.2 Hz, 1H)

MS method N: RT (min): 1.75, $[M+H]^+$ 787

Step 5: Example (57): Preparation of Compound 161: 3-[[4-(aminomethyl)phenyl]methyl]-4-isopropoxy-2-propylsulfanyl-imidazo[4,5-d]pyridazin-7-amine

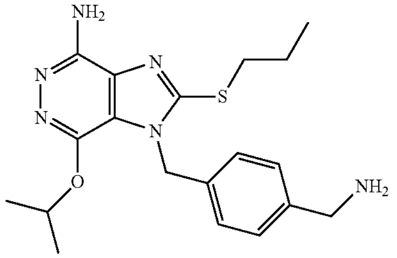 [SMILES: CCCSc1nc2c(N)nnc(OC(C)C)c2n1Cc1ccc(CN)cc1]

To a solution of tert-butyl N-[[4-[[7-[bis[(2,4-dimethoxyphenyl)methyl]amino]-4-isopropoxy-2-propylsulfanyl-imidazo[4,5-d]pyridazin-3-yl]methyl]phenyl]methyl]carbamate of Step 4 (147 mg, 0.187 mmol) in DCM (1.5 ml) was added dropwise TFA (0.50 ml, 5.55 mmol). The mixture became pink and was stirred at rt for 5 h 30 mins, then evaporated to dryness. The crude product was dissolved in MeOH with some purple precipitates which are filtered. The filtrate was loaded into a SCX cartridge (20 g, pre-washed with 10 ml of MeOH), the cartridge was eluted with MeOH (60 ml) and followed by elution with MeOH—$NH_3$ (2N). The ammoniacal methanolic solution was evaporated to dryness to give 56 mg of foam, which was purified by a silica gel column (Merck, 10 g) using as eluent a mixture DCM/$NH_3$-MeOH 7N (97/3) to give 22 mg (30.5% yield) of Example (57) as a white solid.

$^1H$ NMR (400 MHz, δ in ppm, DMSO-d6: 0.96 (t, J=7 Hz, 3H), 1.25 (d, J=6 Hz, 6H), 1.72 (sxt, J=7 Hz, 2H), 2.06-2.30 (m, 2H), 3.30-3.33 (m, 2H), 3.67 (s, 2H), 5.34 (quin, J=6 Hz, 1H), 5.43 (s, 2H), 5.91 (s, 2H), 7.11 (d, J=1 Hz, 2H), 7.29 (d, J=1 Hz, 2H)

MS method N: RT (min): 0.90, $[M+H]^+$ 387

Example (58): Preparation of Compound 162: 3-[[4-(aminomethyl)phenyl]methyl]-4-isopropoxy-2-propylsulfinyl-imidazo[4,5-d]pyridazin-7-amine

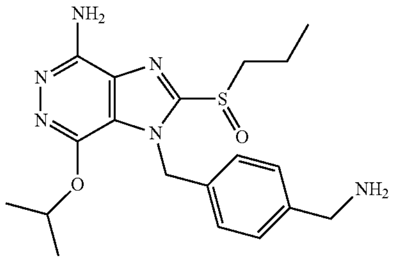 [SMILES: CCCS(=O)c1nc2c(N)nnc(OC(C)C)c2n1Cc1ccc(CN)cc1]

Step 1: tert-butyl N-[[4-[[7-[bis[(2,4-dimethoxyphenyl)methyl]amino]-4-isopropoxy-2-propylsulfinylimidazo[4,5-d]pyridazin-3-yl]methyl]phenyl]methyl]carbamate

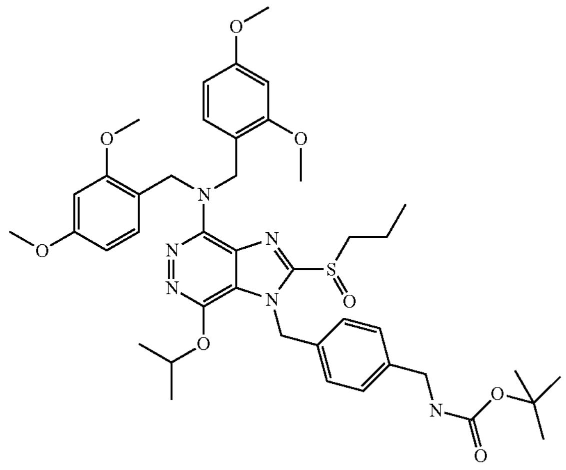 [SMILES: CCCS(=O)c1nc2c(N(Cc3ccc(OC)cc3OC)Cc3ccc(OC)cc3OC)nnc(OC(C)C)c2n1Cc1ccc(CNC(=O)OC(C)(C)C)cc1]

To a solution of tert-butyl N-[[4-[[7-[bis[(2,4-dimethoxyphenyl)methyl]amino]-4-isopropoxy-2-propylsulfanyl-imidazo[4,5-d]pyridazin-3-yl]methyl]phenyl]methyl]carbamate of Step 4 in Example (57) (255 mg, 0.324 mmol) in DCM (5 ml), was added at 0° C., mCPBA (135.5 mg, 70% dispersed oil, 0.55 mmol). The reaction mixture was allowed to reach rt and the stirring continued for 55 h. It was then diluted with DCM (30 ml) and a solution of sodium thiosulfate (1.5 M, 30 ml) was added. After 20 min stirring, the mixture was transferred to a separating funnel, after decantation and phase separation, the organic layer was washed with a $NaHCO_3$ saturated solution (30 ml) and brine (30 ml). It was then dried over $MgSO_4$, filtered and evaporated to dryness to give 243 mg of crude product. The crude material was purified by a silica gel column (30 g, Merck) using as solvent Heptane/EtOAc (60/40) to give 0.108 g (41.5% yield) of a white gum.

$^1$H NMR (400 MHz, δ in ppm, DMSO-$d_6$: 0.82 (t, J=7.4 Hz, 3H) 1.23 (dd, J=6.1, 4.6 Hz, 6H) 1.37 (s, 9H) 1.44 (m, 2H) 3.03-3.20 (m, 2H) 3.71 (s, 12H) 4.07 (br d, J=6 Hz, 2H) 4.98 (m, 4H) 5.34 (sept, J=6.1 Hz, 1H) 5.81 (s, 2H) 6.40 (dd, J=8.4, 2.4 Hz, 2H) 6.54 (d, J=2.4 Hz, 2H) 6.98 (d, J=8.4 Hz, 2H) 7.11-7.15 (m, 2H) 7.18-7.22 (m, 2H) 7.31 (m, 1H)

MS method O: RT (min): 2.92, $[M+H]^+$ 803

Step 2: Example (58): Preparation of Compound 162: 3-[[4-(aminomethyl)phenyl]methyl]-4-isopropoxy-2-propylsulfinyl-imidazo[4,5-d]pyridazin-7-amine

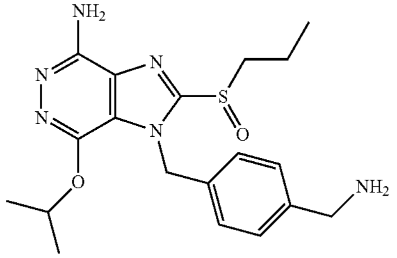 [SMILES: CCCS(=O)c1nc2c(N)nnc(OC(C)C)c2n1Cc1ccc(CN)cc1]

To a solution of tert-butyl N-[[4-[[7-[bis[(2,4-dimethoxyphenyl)methyl]amino]-4-isopropoxy-2-propylsulfinylimidazo[4,5-d]pyridazin-3-yl]methyl]phenyl]methyl]carbamate of Step 1 (100 mg, 0.125 mmol) in DCM (1.0 ml) was added dropwise TFA (0.80 ml, 8.89 mmol). The mixture became pink and was stirred at rt for 32 h, then evaporated to dryness to give 130 mg of crude product. The crude product was dissolved in MeOH with some purple precipitates, which was loaded into a SCX cartridge (10 g, pre-washed with 10 ml of MeOH), the cartridge was then washed with MeOH (60 ml) and followed by elution with MeOH—$NH_3$ (2N). The ammoniacal methanolic solution was evaporated to dryness to give 56 mg of foam, which was purified by a silica gel column (Merck, 10 g) using as eluent a mixture DCM/$NH_3$-MeOH 7N (96/4) to give 32 mg (66% yield) of Example (58) as a white powder.

$^1$H NMR (400 MHz, δ in ppm, DMSO-d6: 0.97 (t, J=7 Hz, 3H), 1.25 (dd, J=6, 2 Hz, 6H), 1.60-1.71 (m, 2H), 1.77 (br s, 2H), 3.15 (m, 1H), 3.37 (m, 1H), 3.68 (s, 2H), 5.36 (dt, J=12, 6 Hz, 1H), 5.81 (s, 2H), 6.29 (s, 2H), 7.12 (br d, J=1 Hz, 2H), 7.30 (br d, J=1 Hz, 2H)

MS method M: RT (min): 0.20, $[M+H]^+$ 403

Example (59): Preparation of Compound 163: 3-[[4-(aminomethyl)phenyl]methyl]-4-isopropoxy-N2-propyl-imidazo[4,5-d]pyridazine-2,7-diamine

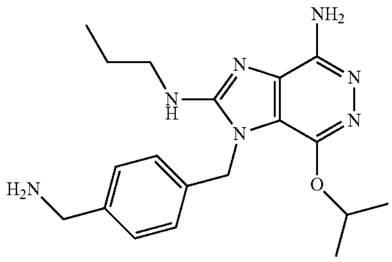 [SMILES: CCCNc1nc2c(N)nnc(OC(C)C)c2n1Cc1ccc(CN)cc1]

Step 1: tert-butyl N-[[4-[[7-[bis[(2,4-dimethoxyphenyl)methyl]amino]-2-bromo-4-isopropoxy-imidazo[4,5-d]pyridazin-3-yl]methyl]phenyl]methyl]carbamate

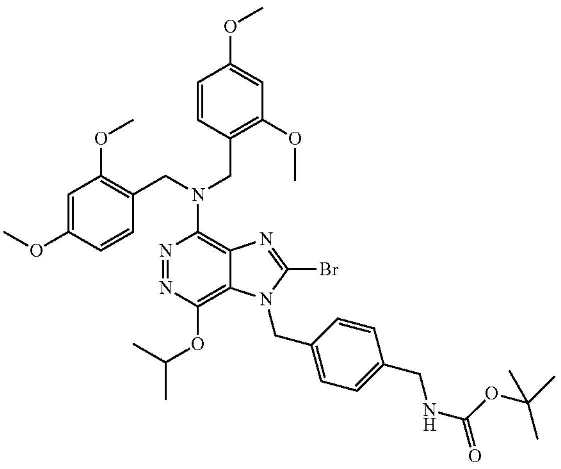 [SMILES: COc1ccc(CN(Cc2ccc(OC)cc2OC)c2nnc(OC(C)C)c3c2nc(Br)n3Cc2ccc(CNC(=O)OC(C)(C)C)cc2)c(OC)c1]

To a −30° C. solution of tert-butyl N-[[4-[[7-[bis[(2,4-dimethoxyphenyl)methyl]amino]-4-isopropoxy-imidazo[4,5-d]pyridazin-3-yl]methyl]phenyl]methyl]carbamate of Step 2 in Example (57) (103 mg, 0.144 mmol) in dry THF (2 mL), under Argon, was added a 2.5M solution of nBuLi in Hexane (0.35 ml, 0.86 mmol). The mixture was kept 30 min at the same temperature then it was added a solution of NBS (67.42 mg, 0.36 mmol) in dry THF (2 mL). Then after the addition was completed the mixture was left at rt. The reaction colour turned to yellow/orange. The reaction was stopped after 2 hours at rt. The reaction mixture was cooled at −10° C., added saturated solution of $NH_4Cl$, and diluted with Ethyl acetate. The organic solution was separated and washed with brine. Then the organic layer was separated, dried over $MgSO_4$, filtered and evaporated to give a yellow oil. The crude material was purified by a silica gel column using as eluent a mixture $CHCl_3$/Acetone (96/4) to give 24.6 mg (21% yield) of the expected product, as a yellow solid.

$^1$H NMR (400 MHz, δ in ppm, DMSO-d6: 1.24 (d, J=6.0 Hz, 6H) 1.37 (s, 9H) 3.67-3.74 (m, 12H) 4.08 (d, J=6.3 Hz, 2H) 4.94 (s, 4H) 5.33 (sept, J=6.1 Hz, 1H) 5.56 (s, 2H) 6.41 (dd, J=8.4, 2.4 Hz, 2H) 6.53 (d, J=2.4 Hz, 2H) 6.97 (d, J=8.4 Hz, 2H) 7.12 (m, J=8.3 Hz, 2H) 7.21 (m, J=8.3 Hz, 2H) 7.31 (t, J=5.8 Hz, 1H)

MS method N: RT (min): 1.67, $[M+H]^+$ 791

Step 2: tert-butyl N-[[4-[[7-[bis[(2,4-dimethoxyphenyl)methyl]amino]-4-isopropoxy-2-(propylamino)imidazo[4,5-d]pyridazin-3-yl]methyl]phenyl]methyl]carbamate

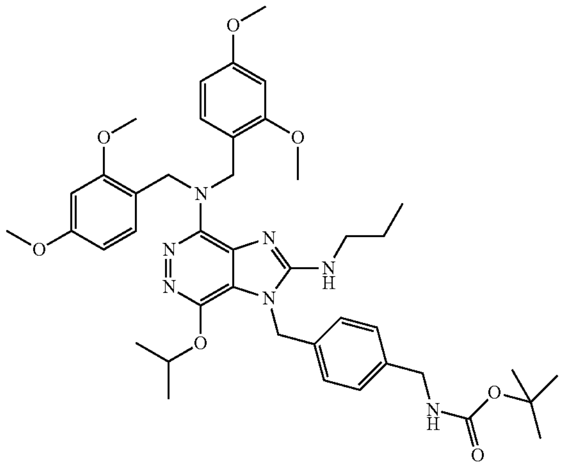 [SMILES: CCCNc1nc2c(N(Cc3ccc(OC)cc3OC)Cc3ccc(OC)cc3OC)nnc(OC(C)C)c2n1Cc1ccc(CNC(=O)OC(C)(C)C)cc1]

A mixture of tert-butyl N-[[4-[[7-[bis[(2,4-dimethoxyphenyl)methyl]amino]-2-bromo-4-isopropoxy imidazo[4,5-d]pyridazin-3-yl]methyl]phenyl]methyl]carbamate of Step 1 (85.2 mg, 0.108 mmol), n-Propylamine (1.44 ml) & DMF (0.02 ml) was heated at 100° C. in the Microwave for 2 h 30 min. The reaction mixture was diluted with Ethyl acetate, washed with $H_2O$. The organic layer was separated, dried over $MgSO_4$, filtered and evaporated to give a white transparent oil. The crude material was purified by a silica gel column using as eluent a mixture DCM/iPrOH (98/2 to 96/4) to give 67 mg the expected product $^1$H NMR (400 MHz, δ in ppm, DMSO-d6: 0.77 (t, J=7.3 Hz, 3H) 1.19 (d, J=6.1 Hz, 6H) 1.36 (s, 9H) 1.41-1.55 (m, 2H) 3.16-3.24 (m, 2H) 3.71 (s, 12H) 4.06 (d, J=5.9 Hz, 2H) 4.94 (s, 4H) 5.25 (m, 1H) 5.33 (s, 2H) 6.39 (dd, J=8.3, 2.3 Hz, 2H) 6.51 (d, J=2.3 Hz, 2H) 6.95-7.04 (m, 3H) 7.06-7.12 (m, 2H) 7.13-7.20 (m, 2H) 7.28 (t, J=5.8 Hz, 1H)

MS method N: RT (min): 1.70, $[M+H]^+$ 772

Step 3: Example (59): Preparation of Compound 163: 3-[[4-(aminomethyl)phenyl]methyl]-4-isopropoxy-N2-propyl-imidazo[4,5-d]pyridazine-2,7-diamine

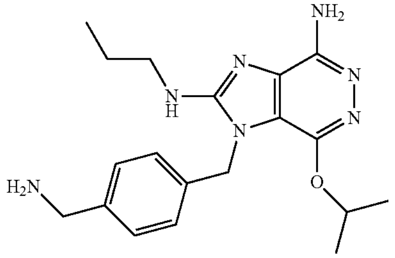 [SMILES: CCCNc1nc2c(N)nnc(OC(C)C)c2n1Cc1ccc(CN)cc1]

To a solution of tert-butyl N-[[4-[[7-[bis[(2,4-dimethoxyphenyl)methyl]amino]-4-isopropoxy-2-(propylamino)imidazo[4,5-d]pyridazin-3-yl]methyl]phenyl]methyl]carbamate (63 mg, 0.0818 mmol) in DCM (0.5 ml) was added TFA (0.19 ml, 2.11 mmol). The mixture was stirred at rt for 17 h. Then it was diluted with Ethyl acetate and evaporated (×2 times). The resulting crude material was diluted with MeOH and it was loaded to a SCX column (10 g), firstly it was eluted with MeOH then with a mixture 50% mixture MeOH/2N $NH_3$ in MeOH and finally with pure 2N $NH_3$ in MeOH. The fraction containing the product was evaporated to give 33 mg of an oil, which was crystalized by adding $Et_2O$ as a white solid. The solid was filtered and dried to give 24.1 mg (79.5% yield) of the Example (59).

$^1$H NMR (400 MHz, δ in ppm, DMSO-$d_6$ 0.87 (t, J=7 Hz, 3H), 1.21 (d, J=6 Hz, 6H), 1.60 (sxt, J=7 Hz, 2H), 3.31-3.81 (m, 6H), 5.27 (dt, J=12, 6 Hz, 1H), 5.34 (s, 2H), 5.39 (br s, 2H), 7.00 (br t, J=5 Hz, 1H), 7.10 (d, J=8 Hz, 2H), 7.27 (d, J=8 Hz, 2H)

MS method N: RT (min): 0.74 $[M+H]^+$ 370

Example (60): Preparation of Compound 164: 3-[[4-(aminomethyl)phenyl]methyl]-2-(ethylaminomethyl)-4-isopropoxy-imidazo[4,5-d]pyridazin-7-amine

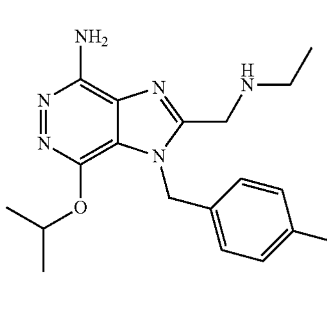

Step 1: tert-butyl N-[[4-[[7-[bis[(2,4-dimethoxyphenyl)methyl]amino]-2-formyl-4-isopropoxy-imidazo[4,5-d]pyridazin-3-yl]methyl]phenyl]methyl]carbamate

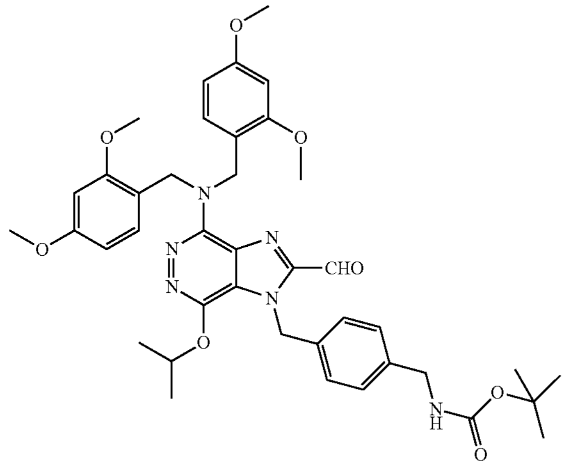 [SMILES: COc1ccc(CN(Cc2ccc(OC)cc2OC)c2nnc(OC(C)C)c3c2nc(C=O)n3Cc2ccc(CNC(=O)OC(C)(C)C)cc2)c(OC)c1]

To a ~-40° C. (about -40° C.) solution of tert-butyl N-[[4-[[7-[bis[(2,4-dimethoxyphenyl)methyl]amino]-4-isopropoxy-imidazo[4,5-d]pyridazin-3-yl]methyl]phenyl]methyl]carbamate of Step 2 in Example (57) (51 mg, 0.072 mmol) in dry THF (1.5 mL), under Argon, was added a 2.5M solution of nBuLi in Hexane (0.11 ml, 0.2862 mmol). The mixture was kept 10 min at the same temperature and then it was added a solution of DMF (0.0139 ml, 0.179 mmol) in 0.25 mL of dry THF. The mixture was left with agitation at the same temperature to get -5° C. for a period of 2 h, then it was allowed to reach rt in 30 min. A saturated aqueous solution of ammonium chloride was added to the reaction and then Ethyl acetate was added. The organic layer was separated and then it was washed with a saturated aqueous solution of NaCl. The organic layer was separated, dried over $MgSO_4$, filtered and evaporated to give a yellow oil. The crude material was purified by a silica gel column using as eluent a mixture Heptane/ETOAc (70/30 to 60/40) to give 25 mg (47% yield) of the expected product as a slightly yellow solid.

$^1$H NMR (400 MHz, δ in ppm, DMSO-d6): 1.25 (d, J=6.1 Hz, 6H) 1.37 (s, 9H) 3.71 (m, 12H) 4.07 (d, J=6.4 Hz, 2H) 5.06 (br s, 4H) 5.35 (sept, J=6.2 Hz, 1H) 5.92 (s, 2H) 6.42 (dd, J=8.4, 2.4 Hz, 2H) 6.54 (d, J=2.4 Hz, 2H) 7.00 (d, J=8.4 Hz, 2H) 7.08-7.14 (m, 2H) 7.15-7.21 (m, 2H) 7.33 (t, J=6.2 Hz, 1H) 9.97 (s, 1H)

Step 2: tert-butyl N-[[4-[[7-[bis[(2,4-dimethoxyphenyl)methyl]amino]-2-(ethyl aminomethyl)-4-isopropoxy-imidazo[4,5-d]pyridazin-3-yl]methyl]phenyl]methyl]carbamate

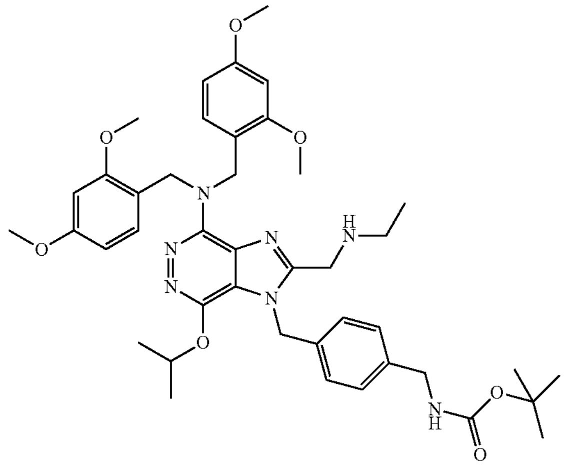 [SMILES: CCNCc1nc2c(N(Cc3ccc(OC)cc3OC)Cc3ccc(OC)cc3OC)nnc(OC(C)C)c2n1Cc1ccc(CNC(=O)OC(C)(C)C)cc1]

To a solution of tert-butyl N-[[4-[[7-[bis[(2,4-dimethoxyphenyl)methyl]amino]-2-formyl-4-isopropoxy-imidazo[4,5-d]pyridazin-3-yl]methyl]phenyl]methyl]carbamate of Step 1 (57.9 mg, 0.078 mmol) in EtOH (1.0 mL) was added a 2.0M solution of EtNH2 (0.078 mL, 0.156 mmol) in THF and then $Ti(iPrO)_4$ (0.046 mL, 0.156 mmol). The mixture was kept at rt for 10 h. Then it was added $NaBH_4$ (5.91 mg, 0.156 mmol) and the mixture was stirred at rt for 1 h 30 min. A 2M aqueous solution of ammonium hydroxide was added to the reaction and then Ethyl acetate. The white solid resulting was filtered over celite pad and the filtrate was diluted with Ethyl acetate and a saturated aqueous NaCl solution. The organic layer was separated, dried over $MgSO_4$, filtered and evaporated to give a colorless oil. The crude material was purified by a silica gel column using as eluent a mixture DCM/iPrOH (98/2 to 95/5) to give 39 mg (65% yield) of the expected product as a white solid.

$^1$H NMR (400 MHz, δ in ppm, DMSO-d6): 0.89 (t, J=7.1 Hz, 3H) 1.20 (d, J=6 Hz, 6H) 1.37 (s, 9H) 1.84-2.26 (m, 1H) 2.42-2.48 (m, 2H) 3.68-3.73 (m, 12H) 3.85 (s, 2H) 4.07 (d, J=6.0 Hz, 2H) 5.01 (s, 4H) 5.31 (m, 1H) 5.67 (s, 2H) 6.39 (dd, J=8.3, 2.5 Hz, 2H) 6.52 (d, J=2.5 Hz, 2H) 6.97 (d, J=8.5 Hz, 2H) 7.06 (m, J=8.3 Hz, 2H) 7.19 (m, J=8.3 Hz, 2H) 7.31 (t, J=6.1 Hz, 1H)

MS method N: RT (min): 1.18 $[M+H]^+$ 770

Step 3: Example (60): Preparation of Compound 164: 3-[[4-(aminomethyl)phenyl]methyl]-2-(ethylaminomethyl)-4-isopropoxy-imidazo[4,5-d]pyridazin-7-amine

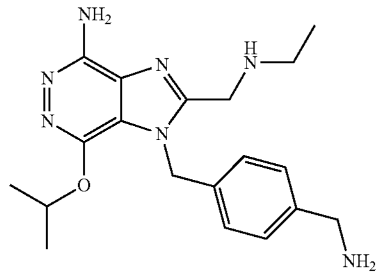 [SMILES: CCNCc1nc2c(N)nnc(OC(C)C)c2n1Cc1ccc(CN)cc1]

To a solution of tert-butyl N-[[4-[[7-[bis[(2,4-dimethoxyphenyl)methyl]amino]-2-(ethylaminomethyl)-4-isopropoxy-imidazo[4,5-d]pyridazin-3-yl]methyl]phenyl]methyl]carbamate of Step 2 (110 mg, 0.143 mmol) in DCM (1 ml) was added TFA (0.334 ml, 4.29 mmol). The mixture was stirred at rt. After 6 h 30 min, it was added 0.1 ml extra of TFA. The reaction mixture was kept in the fridge overnight. Then it was diluted with Ethyl acetate and then evaporated (×2 times). Then the resulting crude material was diluted with MeOH and it was loaded to a SCX column (25 g), firstly it was eluted with MeOH then with a mixture 50% mixture MeOH/2N $NH_3$ in MeOH and finally with pure 2N $NH_3$ in MeOH. The fraction containing the product was evaporated to give 69 mg. The crude material was purified by silica gel (Merck, 10 g) using as eluent a mixture of DCM/$NH_3$-MeOH 2N, (97/3 to 96/4) to give 56.5 mg (Q, yield) as a white solid.

$^1$H NMR (400 MHz, δ in ppm, DMSO-d6):0.96 (t, J=7 Hz, 3H), 1.22 (d, J=6 Hz, 6H), 1.76-2.25 (m, 3H), 2.52-2.61 (m, 2H), 3.66 (s, 2H), 3.90 (s, 2H), 5.32 (quin, J=6 Hz, 1H), 5.66 (s, 2H), 5.95 (s, 2H), 7.04 (d, J=8 Hz, 2H), 7.27 (d, J=8 Hz, 2H).

MS method N: RT (min): 0.12 $[M+H]^+$ 370

Pharmacological Tests:

The compounds according to the disclosure were subjected to pharmacological tests for determining their activity as TLR7 agonists or TLR7/8 agonists.

The below tests, involving measuring the in vitro activity of some compounds of the disclosure on TLR7 and TLR8, were carried out using the HEK-Blue™ cells as reporter.

The other below tests involving measuring the in vitro activity of some compounds of the disclosure on cytokines IFN-α2a, IL-6, IL29 and TNF-α were carried out using human PBMC (PBMCs).

The activity described below, with respect to TLR7, TLR8, IFN-α2a, IL-6, IL29 and TNF-α, is given by the half maximal effective concentration (EC50), which corresponds to the concentration required to obtain a 50% of the activation. The lower the EC50, the less the concentration of the compound is required to produce 50% of maximum activation and the higher the potency.

The below EC50 are generally between 1 nM to 20000 nM for example from 10 nM to 20000 nM.

In Vitro Assay for Studying the Stimulation of Human TLR7 and TLR8:

HEK-Blue™ hTLR7 Cells (#hkb-htlr7) and HEK-Blue™ hTLR8 Cells (#hkb-htlr8) from InvivoGen were used according to the manufacturer's instructions. These Reporter HEK293 cells were obtained by co-transfection of the hTLR7 or TLR8 gene and an optimized Secreted Embryonic Alkaline Phosphatase (SEAP) reporter gene which is placed under the control of the IFN-β minimal promoter fused to five NF-κB and AP-1-binding sites. Stimulation with a TLR7/8 ligand activates NF-kB and AP-1 which induce the production of SEAP. The cells are seeded in 96-well plate at 3.10E4 cells/well and incubated 18 to 24 h at 37° C., 5% CO2 before adding the compounds to evaluate. The cells are subsequently incubated with 3-fold serial dilutions of each of the compounds (0.01 to 20 μM) for 24 hours at 37° C., 5% CO2. Next, 20 μL of the supernatant is harvested and incubated with 200 μL of QUANTI-Blue™ Solution. After a 3 hours incubation at 37° C., 5% $CO_2$, SEAP activity is assessing by reading the optical density (OD) at 620 nm with an Envision microplate reader and a half maximal effective concentration (EC50) is calculated and used to rank the compounds.

The results are summarized in Table 5 below.

TABLE 5

| Compound Number | TLR7_EC50 (nM) | TLR8_EC50 (nM) |
|---|---|---|
| 1 | 103 | >20000 |
| 2 | 53 | >20000 |
| 3 | 566 | >20000 |
| 4 | 1259 | >20000 |
| 5 | 145 | >20000 |
| 6 | 295 | >20000 |
| 7 | 46 | 2100 |
| 8 | 168 | >20000 |
| 9 | 135 | >20000 |
| 10 | 120 | >20000 |
| 11 | 192 | >20000 |
| 12 | 710 | >20000 |
| 13 | 345 | >20000 |
| 14 | 219 | >20000 |
| 15 | 649 | >20000 |
| 16 | 323 | >20000 |
| 17 | 155 | >20000 |
| 18 | 355 | >20000 |
| 19 | 32 | >20000 |
| 20 | 28 | >20000 |
| 21 | 33 | 1369 |
| 22 | 30 | 2609 |
| 23 | 172 | 14631 |
| 24 | 234 | 2637 |
| 25 | 109 | >20000 |
| 26 | 144 | >20000 |
| 27 | 2097 | >20000 |
| 28 | 85 | >20000 |
| 29 | 117 | >20000 |
| 30 | 161 | >20000 |
| 31 | 326 | >20000 |
| 32 | 598 | 709 |
| 33 | 392 | 336 |
| 34 | 116 | >20000 |
| 35 | 106 | >20000 |
| 36 | 19 | 448 |
| 37 | 317 | >20000 |
| 38 | 345 | 14700 |
| 39 | 17 | 401 |
| 40 | 21 | 2290 |
| 41 | 3070 | 7190 |
| 42 | 1480 | 8780 |
| 43 | 310 | 37 |
| 44 | 1128 | 467 |
| 45 | >20000 | 9419 |
| 46 | 6139 | 4072 |
| 47 | 421 | 223 |
| 48 | 160 | >20000 |
| 49 | 353 | >20000 |
| 50 | 269 | >20000 |
| 51 | 1018 | >20000 |
| 52 | 551 | >20000 |

TABLE 5-continued

| Compound Number | TLR7_EC50 (nM) | TLR8_EC50 (nM) |
|---|---|---|
| 53 | 775 | >20000 |
| 54 | 610 | >20000 |
| 55 | 1567 | >20000 |
| 56 | 231 | >20000 |
| 57 | 344 | >20000 |
| 58 | 433 | >20000 |
| 59 | 943 | >20000 |
| 60 | 813 | >20000 |
| 61 | 1180 | >20000 |
| 62 | 771 | >20000 |
| 63 | 1180 | >20000 |
| 64 | 3095 | >20000 |
| 65 | 2213 | >20000 |
| 66 | 2875 | >20000 |
| 67 | 2060 | >20000 |
| 68 | 4769 | >20000 |
| 69 | 6760 | >20000 |
| 70 | 4003 | >20000 |
| 71 | 291 | >20000 |
| 72 | 3760 | >20000 |
| 73 | 10131 | >20000 |
| 74 | 586 | 17900 |
| 75 | 179 | >20000 |
| 76 | 1352 | >20000 |
| 77 | 390 | >20000 |
| 78 | 7745 | >20000 |
| 79 | 9710 | >20000 |
| 80 | 169 | >20000 |
| 81 | 117 | >20000 |
| 82 | 13 | 303 |
| 83 | 8 | 637 |
| 84 | 263 | 1810 |
| 85 | 606 | 3095 |
| 86 | 4400 | 6960 |
| 87 | 8517 | >20000 |
| 88 | 2980 | 13600 |
| 89 | 1204 | 7562 |
| 90 | 10600 | 12673 |
| 91 | 45% at 20000 | 10% at 20000 |
| 92 | 7965 | 15% at 20000 |
| 93 | >20000 | 17% at 20000 |
| 94 | 226 | 11% at 20000 |
| 95 | 15% at 20000 | 20.5% at 20000 |
| 96 | >20000 | 22.7% at 20000 |
| 97 | 13% at 20000 | >20000 |
| 98 | 8% at 20000 | 6% at 20000 |
| 99 | 13600 | 18% at 20000 |
| 100 | 36 | 2170 |
| 101 | 13 | 355 |
| 102 | 71 | 3830 |
| 103 | 55 | 15500 |
| 104 | 22 | 546 |
| 105 | 114 | >20000 |
| 106 | 68 | 10 595 |
| 107 | 205 | >20000 |
| 108 | 29 | 1405 |
| 109 | 50 | 243 |
| 110 | 734 | 2845 |
| 111 | 99 | >20000 |
| 112 | 248 | >20000 |
| 113 | 120 | >20000 |
| 114 | 163 | >6340 |
| 115 | 107 | >16500 |
| 116 | 34 | 1825 |
| 117 | 190 | 8880 |
| 118 | 11 | 1490 |
| 119 | 143 | 2130 |
| 120 | 133 | 14400 |
| 121 | 86 | 15900 |
| 122 | 729 | >20000 |
| 123 | 13.5% at 20000 | 10.2% at 20000 |
| 124 | 178 | 231 |
| 125 | 392 | 115 |
| 126 | 122 | 382 |
| 127 | 93 | 179 |
| 128 | 5985 | >20000 |
| 129 | 1550 | 6260 |
| 130 | 76 | 1059 |
| 131 | 607 | >20000 |
| 132 | 296 | >18500 |
| 133 | 146 | >19000 |
| 134 | 274 | >20000 |
| 135 | 136 | 252 |
| 137 | 145 | >20000 |
| 138 | 51.4 | >20000 |
| 139 | 370 | >20000 |
| 140 | 1310 | >20000 |
| 141 | 26.8% at 20000 | 19.6% at 20000 |
| 142 | 2640 | >20000 |
| 143 | 11000 | >20000 |
| 144 | >20 μM | 14.7% at 20000 |
| 145 | 2.2% at 20000 | 11.7% at 20000 |
| 146 | 191 | >20000 |
| 147 | 20.4 | 7720 |
| 148 | 34.6 | >20000 |
| 149 | 12600 | >20000 |
| 150 | 2210 | 11400 |
| 151 | 11170 | >20000 |
| 152 | 4390 | >20000 |
| 153 | 18400 | >20000 |
| 154 | 117 | 18500 |
| 155 | 596 | >20000 |
| 156 | 75 | 5 |
| 157 | 531 | 7 |
| 158 | 717 | >20000 |
| 159 | 247 | >20000 |
| 160 | 35% at 20000 | 18% at 20000 |
| 161 | 205 | 398 |
| 162 | 6700 | >20000 |
| 163 | 16.7% at 20000 | 15.4% at 20000 |
| 164 | 4.8% at 20000 | 10.8% at 20000 |
| 165 | 1570 | >20000 |

In Vitro Assay to Determine IFN-α2a, IL-6, IL29 and TNF-α Cytokine Activation:

Peripheral blood mononuclear cells were isolated by Ficoll density gradient centrifugation from peripheral blood samples obtained from healthy donors (EFS). Isolated PBMCs are washed twice with PBS and resuspended in RPMI-1640 medium supplement with 10% fetal bovine serum (FBS) at $5.10^5$ cells/well in a 96-well plate. The cells were then incubated with the compounds to test at various doses (20 μM to 4.8.10-6 μM final) for 24 h at 37° C., 5% CO2. After 24 h treatment, the plates are centrifuged and the supernatant were collected and assayed for cytokines IFN-α2a, IL-6, IL29 and TNF-α using the Meso Scale Discovery (MSD) assay platform according to the manufacturer's instructions. Briefly, 25 μL of cell culture supernatants were incubated for 1 h at Room Temperature (RT) in custom Multi-Spot 96-well plates prior coated with capture antibodies. After washing, SULFO-TAG® labeled detection antibodies were added to each of the wells and incubated for 1 h RT before adding a read buffer. The subsequent reaction resulted in the emission of light which was then quantified to approximate the concentration (pg/mL) of each cytokine.

The results are summarized in Table 6 below.

TABLE 6

| Compound Number | IFN-α2a EC50 (nM) | IL29 EC50 (nM) | IL6 EC50 (nM) | TNF-α EC50 (nM) |
|---|---|---|---|---|
| 1 | 103 | 173 | 457 | 712 |
| 2 | 3 | 6 | 99 | 573 |
| 3 | 62 | 83 | 1406 | 2816 |
| 4 | 81 | 795 | 1940 | >20000 |
| 6 | 112 | 62 | 331 | 641 |
| 9 | 16 | 15 | 149 | 380 |
| 10 | 14 | 16 | 177 | 453 |
| 14 | 18 | 20 | 106 | 708 |
| 17 | 17 | 29 | 186 | >20000 |
| 18 | 71 | 109 | 548 | 2807 |
| 20 | 0.3 | 0.3 | 83 | 2399 |
| 21 | 0.4 | 0.3 | 8 | 284 |
| 22 | 0.1 | 0.1 | 165 | 2790 |
| 23 | 3 | 3 | 204 | 5480 |
| 33 | 3 | 2 | 52 | 1281 |
| 34 | 36 | 28 | 75 | 655 |
| 35 | 21 | 15 | 40 | 343 |
| 41 | 1219 | 3042 | 1275 | 5203 |
| 43 | 22 | 15 | 3 | 21 |
| 48 | 89 | 99 | 368 | 903 |
| 49 | 75 | 388 | 1728 | 5494 |
| 71 | 63 | 57 | 571 | 1743 |
| 75 | 17 | 34 | 181 | 5119 |
| 89 | 213 | 214 | 466 | 2348 |

It is therefore apparent that the compounds of formula (I) of the present disclosure are able to stimulate TLR7 or TLR8 or dual TLR7 and TLR8. Therefore, compounds of formula (I) of the present disclosure are new TLR7 and/or TLR8 agonists compounds.

It is understood that the examples and embodiments described herein are for illustrative purposes only and that various modifications or changes in light thereof will be suggested to persons skilled in the art and are to be included within the spirit and purview of this application and scope of the appended claims.

Accordingly, in another of its aspects, the disclosure provides medicaments which comprise at least one compound of the formula (I) according to the present disclosure, or a pharmaceutically acceptable salt thereof.

The present disclosure, according to another of its aspects, also relates to the compounds of formula (I) according to the present disclosure, or a pharmaceutically acceptable salt thereof, for use as medicaments.

The present disclosure, according to another of its aspects, also relates to the compounds of formula (I) according to the present disclosure, or a pharmaceutically acceptable salt thereof, for use in therapy.

These medicaments are employed therapeutically, especially in the prevention and/or treatment of diseases or disorders linked to TLR7 and/or TLR8.

These medicaments are employed therapeutically, especially in the treatment of a disease or a disorder associated with TLR7 and/or TLR8 activity such as a cell-proliferative disease, a cancer, a chronic myelogenous, a hairy cell leukemia, a dermatological disease such as a skin lesion or a skin cancer (for example an external genital and perianal warts/condyloma acuminate, a genital herpes, an actinic keratosis, a basal cell carcinoma, a cutaneous T-cell lymphoma), an autoimmune disease, an inflammatory disease, a respiratory disease, a sepsis, an allergy (for example an allergic rhinitis or an respiratory allergy), an asthma, a graft rejection, a graft-versus-host disease, an immunodeficiency In an embodiment, is a compound of the instant disclosure, or a pharmaceutically acceptable salt thereof, for use in the prevention and/or treatment of a cancer.

In another embodiment is a compound of the instant disclosure or a pharmaceutically acceptable salt thereof, for use in a vaccine. For example, a compound of formula (I) in accordance with the disclosure can be used as a vaccine adjuvant or the vaccine can be a self-adjuvanting vaccine.

The present disclosure, according to another of its aspects, also relates to a method of treating the pathological conditions indicated above, comprising administering to a subject in need thereof a therapeutically effective amount of a compound of formula (I), or or a pharmaceutically acceptable salt thereof.

In an embodiment of this method of treatment, the subject is a human.

The present disclosure also relates to the use of a compound of the formula (I), or a pharmaceutically acceptable salt thereof according to the present disclosure, for the manufacture of a medicament useful in preventing and/or treating any of the pathological conditions indicated above, for example useful as vaccine or for treating cancer.

It is possible to treat solid or liquid cancers.

The compounds of formula (I) of the present disclosure may also be used in monotherapy or combination with radiotherapy or chemotherapy. For example, targeted chemotherapy, molecularly targeted therapy such as drugs interfering with specific targeted molecules needed for carcinogenesis and tumour growth, drugs interfering with cancer cell metabolism, immunotherapy including but not limiting to checkpoint inhibitors, cellular immunotherapy, antibody therapy and cytokine therapy, radiotherapy-based modalities, antiangiogenic therapy or adjuvant or neoadjuvant therapy.

The compound may be used alone or in combination with at least one other anticancer agent.

According to another of its aspects, the present disclosure relates to pharmaceutical compositions comprising an effective dose of at least one compound of formula (I) according to the disclosure or a pharmaceutically acceptable salt thereof, and also at least one pharmaceutically acceptable excipient.

The said excipients are selected, in accordance with the pharmaceutical form and method of administration desired, from the customary excipients, which are known to a person skilled in the art.

The unit administration forms appropriate include oral forms such as tablets, soft or hard gel capsules, powders, granules and oral solutions or suspensions, sublingual, buccal, intra-tracheal, intra-ocular and intra-nasal administration forms, forms for inhalative, topical, transdermal, subcutaneous, intra-muscular or intravenous administration, rectal administration forms and implants. For topical application it is possible to use the compounds according to the disclosure in creams, gels, ointments or lotions.

The invention claimed is:

1. A compound of formula (I) or a pharmaceutically acceptable salt thereof:

(I)

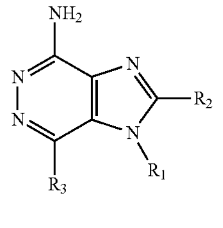

wherein:

$R_1$ represents:

a hydrogen atom, or a group selected from:

a)

a $(C_1-C_6)$alkyl- group;

a hydroxy-$(C_1-C_6)$alkyl- group;

a $NH_2$—$(C_1-C_6)$alkyl- group;

a NH—$(C_1-C_6)$alkyl-$(C_1-C_6)$alkyl- group;

a N($(C_1-C_6)$alkyl) 2-$(C_1-C_6)$alkyl- group;

a $(C_2-C_6)$alkenyl- group;

a $(C_2-C_6)$alkynyl- group;

b)

a phenyl $(C_1-C_6)$alkyl- group being unsubstituted or substituted by at least one substituent selected from:

b1)—a $(C_1-C_6)$alkoxy- group;

b2)—a hydroxyl group;

b3) a —C(O)—H group; and b4)—a $(C_1-C_6)$alkyl- group being unsubstituted or substituted by at least one substituent selected from:

b4.1)—a hydroxyl group; and b4.2)—a —$NR_4R_5$ group wherein $R_4$ and $R_5$, being independently from each other selected from:

b4.2.1)—a hydrogen atom;

b4.2.2)—a $(C_1-C_{16})$alkyl- group;

b4.2.3)—a $CH_3$—[O—$(CH_2)_2]_n$— group with n being an integer from 1 to 30, a $(C_1-C_6)$alkoxy $(C_1-C_6)$alkyl- group, or a $(C_1-C_6)$alkoxy$(C_1-C_6)$alkoxy$(C_1-C_6)$alkyl- group;

b4.2.4)—a $(C_1-C_6)$alkyl-$S(O_2)$— group;

b4.2.5)—a $(C_1-C_6)$alkyl-NH—C(O)— group;

b4.2.6)—a $(C_1-C_{16})$alkyl-C(O)— group;

b4.2.7)—a $(C_1-C_{16})$alkyl-O—C(O)— group;

b4.2.8)—a $CH_3$—[O—$(CH_2)_2]_n$—C(O)— group with n being an integer from 1 to 30;

b4.2.9)—a $(C_3-C_{10})$cycloalkyl- group being unsubstituted or substituted by at least one substituent selected from:

a hydroxyl group; and a $(C_1-C_6)$alkyl- group; or b4.2.10)—a $(C_3-C_{10})$ membered heterocycloalkyl- group comprising from one to four heteroatoms selected from oxygen, nitrogen, sulfur, —S(O)— and —$SO_2$—;

b4.2.11)—a phenyl-C(O)— group;

b4.2.12)—a $(C_1-C_6)$alkoxy-phenyl-$(C_1-C_6)$alkyl-O—C(O)— group;

b4.2.13)—a $(C_1-C_{16})$alkyl-C(O)—NH-phenyl-$(C_1-C_6)$alkyl-O—C(O)— group;

b4.2.14)—a $(C_1-C_{16})$alkyl-O—C(O)—$(C_1-C_6)$alkyl- group;

or $R_4$ and $R_5$ form together with the nitrogen atom to which they are attached a $(C_3-C_{10})$ membered heterocycloalkyl- group comprising one to four heteroatoms selected from oxygen, nitrogen and sulfur, said $(C_3-C_{10})$ membered heterocycloalkyl- group being unsubstituted or substituted by at least one substituent selected from a $(C_1-C_6)$alkyl- group, and a $CH_3$—[O—$(CH_2)_2]_n$— group with n being an integer from 1 to 30;

c)—a $(C_3-C_{10})$cycloalkyl $(C_1-C_6)$alkyl- group being unsubstituted or substituted by at least one substituent selected from-$NH_2$ and a $NH_2$—$(C_1-C_6)$alkyl- group;

d)—a $(C_3-C_{10})$membered heterocycloalkyl$(C_1-C_6)$alkyl- group comprising one to four heteroatoms selected from oxygen, nitrogen, and sulfur, said heterocycloalkyl group being unsubstituted or substituted by at least one substituent selected from a $(C_1-C_6)$alkyl- group and a $CH_3$—[O—$(CH_2)_2]_n$— group with n being an integer from 1 to 30; and e)—a $(C_5-C_{10})$ membered heteroaryl $(C_1-C_6)$alkyl- group comprising one to four heteroatoms selected from oxygen, nitrogen, and sulfur, said heteroaryl being unsubstituted or substituted by at least one substituent selected from:

a $(C_1-C_6)$alkyl- group;

a $NH_2$—$(C_1-C_6)$alkyl- group and a cyano group;

f)—a $(C_3-C_{10})$ membered heterocycloalkyl-NH—$(C_1-C_{16})$alkyl- group, said heterocycloalkyl group comprising one to four heteroatoms selected from oxygen, nitrogen, S(O), $SO_2$ and sulfur;

g)—a $(C_3-C_{10})$ membered heterocycloalkyl-N(C(O)—$(C_1-C_6)$alkyl)-$(C_1-C_{16})$alkyl- group, said heterocycloalkyl group comprising one to four heteroatoms selected from oxygen, nitrogen, S(O), $SO_2$ and sulfur;

$R_2$ represents a halogen atom, or a group selected from:

a $(C_1-C_6)$alkyl- group;

a $(C_2-C_6)$alkenyl- group;

a $(C_2-C_6)$alkynyl- group;

a $(C_1-C_6)$alkylthio- group;

a $(C_1-C_6)$alkylthio $(C_1-C_6)$alkyl- group;

a $(C_1-C_6)$alkyl-S(O)— group;

a $(C_1-C_6)$alkyl-$S(O_2)$— group;

a $(C_1-C_6)$alkyl-S(O)—$(C_1-C_6)$alkyl- group;

a $(C_1-C_6)$alkyl-$S(O_2)$—$(C_1-C_6)$alkyl- group;

a $(C_1-C_6)$alkoxy- group;

a $(C_1-C_6)$alkoxy$(C_1-C_6)$alkyl- group;

a $(C_1-C_6)$haloalkoxy$(C_1-C_6)$alkyl- group;

a $(C_3-C_5)$cycloalkyl-O—$(C_1-C_6)$alkyl- group;

a $(C_1-C_6)$alkyl-NH—$(C_1-C_6)$alkyl- group;

a $((C_1-C_6)alkyl)_2$-N—$(C_1-C_6)$alkyl- group;

a $(C_1-C_6)$alkyl-NH— group; and a $((C_1-C_6)alkyl)_2$N— group;

$R_3$ represents:

a deuterium atom;

a hydrogen atom or a group selected from:

a)

a $(C_1-C_6)$alkyl- group;

a $(C_2-C_6)$alkenyl- group;

a $(C_2-C_6)$alkynyl- group; and a $(C_1-C_6)$alkylthio- group;

b)

a —$OR_6$ group wherein $R_6$ is selected from:

a hydrogen atom;

a $(C_1-C_6)$alkyl- group;

a $CH_3$—[O—$(CH_2)_2]_n$— group with n being an integer from 1 to 30;

a $(C_2-C_6)$alkenyl- group;

a $(C_2-C_6)$alkynyl- group;

a $(C_3-C_{10})$cycloalkyl- group;

a phenyl group;

a phenyl $(C_1-C_6)$alkyl- group; and a $(C_3-C_{10})$ membered heterocycloalkyl- group comprising one to four heteroatoms selected from oxygen, nitrogen, sulfur, —S(═O)— and —$S(=O)_2$—;

c)

a —$NR_7R_8$ group wherein $R_7$ and $R_8$ being, independently from each other, selected from:

a hydrogen atom;

a $CH_3$—[O—$(CH_2)_2]_n$— with n being an integer from 1 to 30;

a $(C_1-C_6)$alkyl- group unsubstituted or substituted by a $(C_5-C_{10})$ membered heteroaryl group comprising one to four heteroatoms selected from oxygen, nitrogen and sulfur; or a phenyl group being unsubstituted or substituted by at least one substituent selected from:

a cyano group and a $NR_9R_{10}$—$(C_1-C_6)$alkyl- group wherein:

$R_9$ and $R_{10}$ being, independently from each other, selected from:

a hydrogen atom;

a $(C_1-C_6)$alkyl- group;

a $CH_3$—[O—$(CH_2)_2]_n$— with n being an integer from 1 to 30, or $R_9$ and $R_{10}$ together form with the nitrogen atom to which they are attached a $(C_3-C_{10})$ membered heterocycloalkyl- group comprising one to four heteroatoms selected from oxygen, nitrogen, and sulfur, said $(C_3-C_{10})$ membered heterocycloalkyl group being unsubstituted or substituted by at least one substituent selected from a $(C_1-C_6)$alkyl- group, and a $CH_3$—[O—$(CH_2)_2]_n$— group with n being an integer from 1 to 30;

or $R_7$ and $R_8$ form together with the nitrogen atom to which they are attached a $(C_3-C_{10})$ membered heterocycloalkyl- group comprising one to four heteroatoms selected from oxygen, nitrogen, and sulfur, said heterocycloalkyl group being unsubstituted or substituted by at least one substituent selected from:

a phenyl group and a hydroxy $(C_1-C_6)$alkyl-phenyl- group;

d)

a $(C_3-C_{10})$ membered heterocycloalkyl- group comprising one to four heteroatoms selected from oxygen, nitrogen and sulfur;

e)

a $(C_5-C_{10})$ membered heteroaryl- group comprising one to four heteroatoms selected from oxygen, nitrogen, and sulfur, said $(C_5-C_{10})$ membered heteroaryl- group being unsubstituted or substituted by at least one $(C_1-C_6)$alkyl- group;

f)

a —$(C_6-C_{10})$ membered aryl group; and g)

a $(C_3-C_{10})$cycloalkyl- group.

2. The compound of formula (I) or a pharmaceutically acceptable salt thereof according to claim 1, provided that at least one of $R_1$, and $R_3$ is other than a hydrogen atom.

3. The compound of formula (I) or a pharmaceutically acceptable salt thereof according to claim 1, wherein $R_1$ represents:

a hydrogen atom or a group selected from:

a)

a $(C_1-C_6)$alkyl- group;

a hydroxy-$(C_1-C_6)$alkyl- group or a $NH_2$—$(C_1-C_6)$alkyl- group;

b)

a phenyl $(C_1-C_6)$alkyl- group being unsubstituted or substituted by one substituent, selected from:

b1)—a $(C_1-C_6)$-alkoxy- group;

b3)—a —C(O)—H group and b4)—a $(C_1-C_6)$alkyl- group substituted by at least one substituent selected from:

b4.1)—a hydroxyl group;

b4.2)—a —$NR_4R_5$ group wherein $R_4$ and $R_5$, being independently from each other, selected from:

b4.2.1)—a hydrogen atom;

b4.2.2)—a $(C_1-C_{16})$alkyl- group;

b4.2.3)—a $CH_3$—[O—$(CH_2)_2]_n$— group with n being an integer from 1 to 30, a $(C_1C_6)$alkoxy $(C_1-C_6)$alkyl- group, or a $(C_1-C_6)$alkoxy$(C_1-C_6)$alkoxy$(C_1-C_6)$alkyl- group;

b4.2.4)—a $(C_1-C_6)$alkyl-$S(O_2)$— group;

b4.2.5)—a $(C_1-C_6)$alkyl-NH—C(O)— group;

b4.2.6)—a $(C_1-C_{16})$alkyl-C(O)— group;

b4.2.7)—a $(C_1-C_{16})$alkyl-O—C(O)— group;

b4.2.8)—a $CH_3$—[O—$(CH_2)_2]_n$—C(O)— group with n being an integer from 1 to 30;

b4.2.9)—a $(C_3-C_{10})$cycloalkyl- group being unsubstituted or substituted by at least one a $(C_1-C_6)$alkyl group or a hydroxyl group;

b4.2.10)—a $(C_3-C_{10})$ membered heterocycloalkyl- group comprising from one to four heteroatoms selected from oxygen, nitrogen and —$SO_2$—;

b4.2.11)—a phenyl-C(O)— group;

b4.2.12)—a $(C_1-C_6)$alkoxy-phenyl-$(C_1-C_6)$alkyl-O—C(O)— group;

b4.2.13)—a $(C_1-C_{16})$alkyl-C(O)—NH-phenyl-$(C_1-C_6)$alkyl-O—C(O)— group;

b4.2.14)—a $(C_1-C_{16})$alkyl-O—C(O)—$(C_1-C_6)$alkyl- group;

or $R_4$ and $R_5$ form together with the nitrogen atom to which they are attached a $(C_3C_{10})$ membered heterocycloalkyl- group comprising one to two heteroatoms selected from oxygen and nitrogen;

c)—a $(C_3-C_{10})$cycloalkyl $(C_1-C_6)$alkyl- group being unsubstituted or substituted by one substituent selected from —$NH_2$, and a $NH_2$—$(C_1-C_6)$alkyl- group;

d)—a $(C_3-C_{10})$membered heterocycloalkyl$(C_1-C_6)$alkyl-group, unsubstituted comprising one to two nitrogen heteroatoms;

e)—a $(C_5-C_{10})$membered heteroaryl $(C_1-C_6)$alkyl- group comprising one nitrogen heteroatom, said heteroaryl being unsubstituted or substituted by at least one substituent selected from:

-a $NH_2$—$(C_1-C_6)$alkyl- group and a cyano group;

f)—a $(C_3-C_{10})$membered heterocycloalkyl-NH—$(C_1-C_{16})$ alkyl- group, said heterocycloalkyl group comprising one heteroatom selected from oxygen, nitrogen, S(O), $SO_2$ and sulfur;

g)—a $(C_3-C_{10})$membered heterocycloalkyl-N(C(O)—$(C_1-C_6)$alkyl)-$(C_1-C_{16})$alkyl- group, said heterocycloalkyl group comprising one heteroatom selected from oxygen, nitrogen, S(O), $SO_2$ and sulfur.

4. The compound of formula (I) or a pharmaceutically acceptable salt thereof according to claim 1, wherein $R_2$ represents:

a $(C_1-C_6)$alkyl- group;

a $(C_1-C_6)$alkylthio- group;

a $(C_1-C_6)$alkyl-S(O)— group;

a $(C_1-C_6)$alkyl-NH—$(C_1-C_6)$alkyl- group;

a $(C_1-C_6)$alkyl-NH— group; and a $(C_1-C_6)$alkoxy$(C_1-C_6)$alkyl- group.

5. The compound of formula (I) or a pharmaceutically acceptable salt thereof according to claim 1, wherein $R_3$ represents:

a hydrogen atom or
a group selected from:
a)—a $(C_1-C_6)$alkyl- group;
a $(C_2-C_6)$alkenyl- group;
a $(C_1-C_6)$alkylthio- group;
b)
a —$OR_6$ group wherein $R_6$ is selected from:
a hydrogen atom;
a $(C_1-C_6)$alkyl- group;
a $CH_3$—[O—$(CH_2)_2]_n$— group with n being an integer from 1 to 30;
a $(C_2-C_6)$alkenyl group;
a $(C_3-C_{10})$cycloalkyl group;
a phenyl group;
a phenyl $(C_1-C_6$ alkyl)- group; and
a $(C_3-C_{10})$membered heterocycloalkyl- group comprising one heteroatom selected from oxygen, sulfur, —S(O)— and —$SO_2$—;
c)
a —$NR_7R_8$ group wherein $R_7$ and $R_8$, being independently from each other, selected from:
a hydrogen atom;
a $CH_3$—[O—$(CH_2)_2]_n$— with n being an integer from 1 to 30;
a $(C_1-C_6)$alkyl- group unsubstituted or substituted by:
a $(C_5-C_{10})$membered heteroaryl- group comprising one oxygen atom; or
a phenyl group being unsubstituted or substituted by at least one substituent selected from:
a cyano group and
a $NR_9R_{10}$-$(C_1-C_6)$alkyl- group wherein $R_9$ and $R_{10}$ being, independently from each other, selected from:
a hydrogen atom;
a —$(C_1-C_6)$alkyl group or
a $CH_3$—[O—$(CH_2)_2]_n$— with n being an integer from 1 to 30;
or $R_9$ and $R_{10}$ together form with the nitrogen atom to which they are attached a $(C_3-C_{10})$membered heterocycloalkyl- group comprising one to two heteroatoms selected from oxygen, and nitrogen,
said $(C_3-C_{10})$membered heterocycloalkyl- group being substituted by at least one $(C_1-C_6)$alkyl- group;
or $R_7$ and $R_8$ form together with the nitrogen atom to which they are attached a $(C_3C_{10})$membered heterocycloalkyl-group comprising one nitrogen heteroatom,
said heterocycloalkyl group being unsubstituted or substituted by at least one substituent selected from:
a phenyl group and
a hydroxy $(C_1-C_6)$alkyl-phenyl- group;
d)
a $(C_3-C_{10})$membered heterocycloalkyl- group comprising one heteroatom selected from oxygen and nitrogen;
e)
a $(C_5-C_{10})$membered heteroaryl- group comprising one to two heteroatoms selected from oxygen, nitrogen, and sulfur,
said $(C_5-C_{10})$membered heteroaryl- group being unsubstituted or substituted by at least one $(C_1-C_6)$alkyl- group;
f)
a $(C_6-C_{10})$membered aryl- group and
g)
a $(C_3-C_{10})$cycloalkyl- group.

6. The compound of formula (I) or a pharmaceutically acceptable salt thereof according to claim 1, said compound being selected from:

(1) 2-butyl-7-isopropoxy-1-(4-methoxybenzyl)-1H-imidazo[4,5-d]pyridazin-4-amine;
(2) 2-butyl-N7-isopropyl-1-(4-methoxybenzyl)-1H-imidazo[4,5-d]pyridazin-4,7-diamine;
(3) 2-butyl-7-(isopropylthio)-1-(4-methoxybenzyl)-1H-imidazo[4,5-d]pyridazin-4-amine;
(4) 2-butyl-1-(4-methoxybenzyl)-7-(2-methoxyethoxy)-1H-imidazo[4,5-d]pyridazin-4-amine;
(5) 2-butyl-1-(4-methoxybenzyl)-7-propoxy-1H-imidazo[4,5-d]pyridazin-4-amine;
(6) 7-(allyloxy)-2-butyl-1-(4-methoxybenzyl)-1H-imidazo[4,5-d]pyridazin-4-amine;
(7) 7-(sec-butoxy)-2-butyl-1-(4-methoxybenzyl)-1H-imidazo[4,5-d]pyridazin-4-amine;
(8) 7-butoxy-2-butyl-1-(4-methoxybenzyl)-1H-imidazo[4,5-d]pyridazin-4-amine;
(9) 2-butyl-7-(cyclopentyloxy)-1-(4-methoxybenzyl)-1H-imidazo[4,5-d]pyridazin-4-amine;
(10) 2-butyl-1-(4-methoxybenzyl)-7-(pyrrolidin-1-yl)-1H-imidazo[4,5-d]pyridazin-4-amine;
(11) 2-butyl-1-(4-methoxybenzyl)-7-(1-methyl-1H-pyrrol-3-yl)-1H-imidazo[4,5d]pyridazin-4-amine;
(12) (E)-2-butyl-1-(4-methoxybenzyl)-7-(3-methylbut-1-en-1-yl)-1H-imidazo[4,5-d]pyridazin-4-amine;
(13) 2-butyl-7-isopentyl-1-(4-methoxybenzyl)-1H-imidazo[4,5-d]pyridazin-4-amine;
(14) 2-butyl-1-(4-methoxybenzyl)-7-(1H-pyrrol-3-yl)-1H-imidazo[4,5-d]pyridazin-4-amine;
(15) 2-butyl-7-(cyclopent-1-en-1-yl)-1-(4-methoxybenzyl)-1H-imidazo[4,5-d]pyridazin-4-amine hydrochloride;
(16) 2-butyl-7-cyclopentyl-1-(4-methoxybenzyl)-1H-imidazo[4,5-d]pyridazin-4-amine;
(17) 2-butyl-1-(4-methoxybenzyl)-7-(prop-1-en-2-yl)-1H-imidazo[4,5-d]pyridazin-4-amine;
(18) 2-butyl-7-isopropyl-1-(4-methoxybenzyl)-1H-imidazo[4,5-d]pyridazin-4-amine;
(19) 4-(aminomethyl)cyclohexyl)methyl)-2-butyl-7-isopropoxy-1H-imidazo[4,5-d]pyridazin-4-amine dihydrochloride;
(20) 4-(aminomethyl)cyclohexyl)methyl)-2-butyl-7-isopropoxy-1H-imidazo[4,5-d]pyridazin-4-amine 2,2,2-trifluoroacetate;
(21) 1-(4-(aminomethyl)benzyl)-2-butyl-7-isopropoxy-1H-imidazo[4,5-d]pyridazin-4-amine;
(22) 1-(4-(aminomethyl)benzyl)-2-butyl-7-isopropoxy-1H-imidazo[4,5-d]pyridazin-4-amine 2,2,2-trifluoroacetate;
(23) 1-(((1S,3R)-3-aminocyclohexyl)methyl)-2-butyl-7-isopropoxy-1H-imidazo[4,5-d]pyridazin-4-amine (and enantiomer);
(24) 1-(4-amino-2-butyl-7-isopropoxy-1H-imidazo[4,5-d]pyridazin-1-yl)-2-methylpropan-2-ol;
(25) Trans 1-(4-aminocyclohexyl)methyl)-2-butyl-7-isopropoxy-1H-imidazo[4,5-d]pyridazin-4-amine;
(26) 1-((5-(aminomethyl)pyridin-2-yl)methyl)-2-butyl-7-isopropoxy-1H-imidazo[4,5-d]pyridazin-4-amine;
(27) 6-((4-amino-2-butyl-7-isopropoxy-1H-imidazo[4,5-d]pyridazin-1-yl)methyl) nicotinonitrile;
(28)N-(4-((4-amino-2-butyl-7-isopropoxy-1H-imidazo[4,5d]pyridazin-1-yl)methyl)benzyl)acetamide;
(29)N-(4-((4-amino-2-butyl-7-isopropoxy-1H-imidazo[4,5-d]pyridazin-1-yl)methyl)benzyl)undecanamide;
(30)N-(4-((4-amino-2-butyl-7-isopropoxy-1H-imidazo[4,5-d]pyridazin-1-yl)methyl)benzyl)pentanamide;

(31)N-(4-((4-amino-2-butyl-7-isopropoxy-1H-imidazo[4,5-d]pyridazin-1-yl)methyl)benzyl)-3-(2-methoxy-ethoxy)propanamide;

(32) 1-(((1S,3S)-3-aminocyclohexyl)methyl)-2-butyl-7-isopropoxy-1H-imidazo[4,5-]pyridazin-4-amine (and enantiomer);

(33) 1-(3-(aminomethyl)benzyl)-2-butyl-7-isopropoxy-1H-imidazo[4,5-d]pyridazin-4-amine 2,2,2-trifluoroacetate;

(34) 4-((4-amino-2-butyl-7-isopropoxy-1H-imidazo[4,5-d]pyridazin-1-yl)methyl)benzaldehyde;

(35) (4-((4-amino-2-butyl-7-isopropoxy-1H-imidazo[4,5-d]pyridazin-1-yl)methyl)phenyl)methanol;

(36) 2-butyl-1-(4-((cyclopropylamino)methyl)benzyl)-7-isopropoxy-1H-imidazo[4,5-d]pyridazin-4-amine;

(37) 3-((4-((4-amino-2-butyl-7-isopropoxy-1H-imidazo[4,5-d]pyridazin-yl)methyl)benzyl)amino)thietane 1,1-dioxide;

(38) N-(4-((4-amino-2-butyl-7-isopropoxy-1H-imidazo[4,5-d]pyridazin-1-yl)methyl)benzyl)-N-(1,1-dioxidothietan-3-yl)acetamide;

(39) 2-butyl-7-isopropoxy-1-(4-(((1-methylcyclobutyl)amino)methyl)benzyl)-1H-imidazo[4,5-d]pyridazin-4-amine;

(40) 2-butyl-7-isopropoxy-1-(4-(piperazin-1-ylmethyl)benzyl)-1H-imidazo[4,5-d]pyridazin-4-amine;

(41) 2-butyl-N7,N7,1-trimethyl-1H-imidazo[4,5-d]pyridazin-4,7-diamine;

(42) 2-butyl-1-methyl-7-(pyrrolidin-1-yl)-1H-imidazo[4,5-d]pyridazin-4-amine;

(43) 2-butyl-N7-(4-((dimethylamino)methyl)benzyl)-N7,1-dimethyl-1H-imidazo[4,5-d]pyridazin-4,7-diamine;

(44) 2-butyl-N7,1-dimethyl-N7-(4-(morpholinomethyl)benzyl)-1H-imidazo[4,5-d]pyridazine-4,7-diamine;

(45) 4-(((4-amino-2-butyl-1-methyl-1H-imidazo[4,5-d]pyridazin-7-yl)(methyl)amino)methyl)benzonitrile;

(46) N7-(4-(aminomethyl)benzyl)-2-butyl-N7,1-dimethyl-1H-imidazo[4,5-d]pyridazine-4,7-diamine;

(47) 2-butyl-N7-(4-(((2-methoxyethyl)(methyl)amino)methyl)benzyl)-N7,1-dimethyl-1H-imidazo[4,5-d]pyridazine-4,7-diamine;

(48) 2-butyl-7-ethoxy-1-(4-methoxybenzyl)-1H-imidazo[4,5-d]pyridazin-4-amine;

(49) 2-butyl-1-(4-methoxybenzyl)-N7-(2-methoxyethyl)-1H-imidazo[4,5-d]pyridazine-4,7-diamine;

(50) 2-butyl-7-methoxy-1-(4-methoxybenzyl)-1H-imidazo[4,5-d]pyridazin-4-amine;

(51) 2-butyl-7-cyclohexyl-1-(4-methoxybenzyl)-1H-imidazo[4,5-d]pyridazin-4-amine;

(52) 7-(benzyloxy)-2-butyl-1-(4-methoxybenzyl)-1H-imidazo[4,5-d]pyridazin-4-amine;

(53) 2-butyl-1-(4-methoxybenzyl)-N7-methyl-1H-imidazo[4,5-d]pyridazine-4,7-diamine;

(54) (S)-2-butyl-1-(4-methoxybenzyl)-7-((tetrahydrofuran-3-yl) oxy)-1H-imidazo[4,5-d]pyridazin-4-amine;

(55) 2-butyl-7-(furan-2-yl)-1-(4-methoxybenzyl)-1H-imidazo[4,5-d]pyridazine-4-amine;

(56) 2-butyl-1-(4-methoxybenzyl)-7-((tetrahydrofuran-3-yl) oxy)-1H-imidazo[4,5-d]pyridazin-4-amine;

(57) 2-butyl-1-(4-methoxybenzyl)-7-((tetrahydro-2H-pyran-4-yl) oxy)-1H-imidazo[4,5-d]pyridazin-4-amine;

(58) 2-butyl-1-(4-methoxybenzyl)-7-((tetrahydrothiophen-3-yl) oxy)-1H-imidazo[4,5-d]pyridazin-4-amine;

(59) 2-butyl-1-(4-methoxybenzyl)-7-(tetrahydrofuran-3-yl)-1H-imidazo[4,5-d]pyridazin-4-amine;

(60) 2-butyl-1-(4-methoxybenzyl)-7-(2-methylprop-1-en-1-yl)-1H-imidazo[4,5-d]pyridazin-4-amine;

(61) 2-butyl-7-isobutyl-1-(4-methoxybenzyl)-1H-imidazo[4,5-d]pyridazin-4-amine;

(62) 2-butyl-1-(4-methoxybenzyl)-7-(thiophen-3-yl)-1H-imidazo[4,5-d]pyridazin-4-amine;

(63) 2-butyl-1-(4-methoxybenzyl)-7-(thiophen-2-yl)-1H-imidazo[4,5-d]pyridazin-4-amine;

(64) 2-butyl-1-(4-methoxybenzyl)-7-(1H-pyrrol-2-yl)-1H-imidazo[4,5-d]pyridazin-4-amine hydrochloride;

(65) 3-((4-amino-2-butyl-1-(4-methoxybenzyl)-1H-imidazo[4,5-d]pyridazin-7-yl) oxy) tetrahydrothiophene 1-oxide isomer A;

(66) 2-butyl-7-(cyclohex-1-en-1-yl)-1-(4-methoxybenzyl)-1H-imidazo[4,5-d]pyridazin-4-amine;

(67) 2-butyl-7-(furan-3-yl)-1-(4-methoxybenzyl)-1H-imidazo[4,5-d]pyridazin-4-amine;

(68) 3-((4-amino-2-butyl-1-(4-methoxybenzyl)-1H-imidazo[4,5-d]pyridazin-7-yl) oxy) tetrahydrothiophene 1,1-dioxide;

(69) 3-((4-amino-2-butyl-1-(4-methoxybenzyl)-1H-imidazo[4,5-d]pyridazin-7-yl) oxy) tetrahydrothiophene 1-oxide isomer B;

(70) 2-butyl-1-(4-methoxybenzyl)-7-(1-methyl-1H-pyrrol-2-yl)-1H-imidazo[4,5-d]pyridazin-4-amine hydrochloride;

(71) 2-butyl-1-(4-methoxybenzyl)-N7,N7-dimethyl-1H-imidazo[4,5-d]pyridazine-4,7-diamine;

(72) 2-butyl-1-(4-methoxybenzyl)-7-phenoxy-1H-imidazo[4,5-d]pyridazin-4-amine;

(73) 2-butyl-7-(2,5-dihydrofuran-3-yl)-1-(4-methoxybenzyl)-1H-imidazo[4,5-d]pyridazin-4-amine;

(74) 2-butyl-7-isopropoxy-1-(pyridin-3-ylmethyl)-1H-imidazo[4,5-d]pyridazin-4-amine;

(75) 2-butyl-7-isopropoxy-1-(pyridin-2-ylmethyl)-1H-imidazo[4,5-d]pyridazin-4-amine;

(76) 2-butyl-7-isopropoxy-1-(pyridin-4-ylmethyl)-1H-imidazo[4,5-d]pyridazin-4-amine 2,2,2-trifluoroacetate;

(77) 1-(5-aminopentyl)-2-butyl-7-isopropoxy-1H-imidazo[4,5-d]pyridazin-4-amine;

(78) 2-butyl-7-isopropoxy-1-(2-(piperidin-4-yl) ethyl)-1H-imidazo[4,5-d]pyridazin-4-amine;

(79) 2-butyl-7-isopropoxy-1-(2-(piperazin-1-yl) ethyl)-1H-imidazo[4,5-d]pyridazin-4-amine;

(80) 1-benzyl-2-butyl-7-isopropoxy-1H-imidazo[4,5-d]pyridazin-4-amine hydrochloride;

(81) 2-butyl-1-(cyclohexylmethyl)-7-isopropoxy-1H-imidazo[4,5-d]pyridazin-4-amine hydrochloride;

(82) 2-butyl-7-isopropoxy-1-(4-(((tetrahydro-2H-pyran-4-yl)amino)methyl)benzyl)-1H-imidazo[4,5-d]pyridazin-4-amine hydrochloride;

(83) 2-butyl-7-isopropoxy-1-(4-((isopropylamino)methyl)benzyl)-1H-imidazo[4,5-d]pyridazin-4-amine dihydrochloride;

(84)N-(4-((4-amino-2-butyl-7-isopropoxy-1H-imidazo[4,5-d]pyridazin-1-yl)methyl)benzyl) heptanamide;

(85) (4-(1-(4-amino-2-butyl-1-methyl-1H-imidazo[4,5-d]pyridazin-7-yl) pyrrolidin-3-yl)phenyl)methanol hydrochloride;

(86) 2-butyl-7-isopropoxy-1-methyl-1H-imidazo[4,5-d]pyridazin-4-amine;

(87) N7-(4-(aminomethyl)benzyl)-2-butyl-1-methyl-1H-imidazo[4,5-d]pyridazine-4,7-diamine;

(88) 2-butyl-N7-isopropyl-1-methyl-1H-imidazo[4,5-d]pyridazine-4,7-diamine;

(89) 2-butyl-1-methyl-7-(3-phenylpyrrolidin-1-yl)-1H-imidazo[4,5-d]pyridazin-4-amine;

(90) N7-benzyl-2-butyl-N7,1-dimethyl-1H-imidazo[4,5-d]pyridazine-4,7-diamine;

(91) 2-butyl-1-methyl-N7-(4-((4-methylpiperazin-1-yl)methyl)benzyl)-1H-imidazo[4,5-d]pyridazine-4,7-diamine;

(92) 2-butyl-1-(4-methoxybenzyl)-7-phenyl-1H-imidazo[4,5-d]pyridazin-4-amine;

(93) 4-amino-2-butyl-1-(4-methoxybenzyl)-1H-imidazo[4,5-d]pyridazin-7-ol;

(94) 2-butyl-N7-(3-(furan-2-yl)propyl)-1-(4-methoxybenzyl)-1H-imidazo[4,5-d]pyridazine-4,7-diamine;

(95) 2-butyl-1-(4-methoxybenzyl)-1H-imidazo[4,5-d]pyridazin-4-amine;

(96) 2-butyl-1-(4-methoxybenzyl)-7-(1H-pyrazol-3-yl)-1H-imidazo[4,5-d]pyridazin-4-amine;

(97) 2-butyl-1-(4-methoxybenzyl)-7-(1-methyl-1H-pyrazol-4-yl)-1H-imidazo[4,5-d]pyridazin-4-amine;

(98) 2-butyl-N7-isopropyl-1H-imidazo[4,5-d]pyridazine-4,7-diamine;

(99) 2-butyl-7-(isopropylthio)-1H-imidazo[4,5-d]pyridazin-4-amine;

(100) (1R,3R)-3-((4-((4-amino-2-butyl-7-isopropoxy-1H-imidazo[4,5-d]pyridazin-1-yl)methyl)benzyl)amino) cyclobutan-1-ol dihydrochloride salt;

(101) 2-butyl-7-isopropoxy-1-(4-(pyrrolidin-1-ylmethyl)benzyl)-1H-imidazo[4,5-d]pyridazin-4-amine;

(102) 2-butyl-7-isopropoxy-1-(4-(morpholinomethyl)benzyl)-1H-imidazo[4,5-d]pyridazin-4-amine;

(103)N-(4-((4-amino-2-butyl-7-isopropoxy-1H-imidazo[4,5-d]pyridazin-1-yl)methyl)benzyl)propionamide;

(104) 2-butyl-7-isopropoxy-1-(4-(((2-methoxyethyl)amino)methyl)benzyl)-1H-imidazo[4,5-d]pyridazin-4-amine;

(105) 2-butyl-4-isopropoxy-3-[[4-[[2-[2-[2-[2-[2-(2-methoxyethoxy)ethoxy]ethoxy]ethoxy]ethoxy]ethylamino]methyl]phenyl]methyl]imidazo[4,5-d]pyridazin-7-amine;

(106)N-(4-((4-amino-2-butyl-7-isopropoxy-1H-imidazo[4,5-d]pyridazin-1-yl)methyl)benzyl)benzamide;

(107)N-(4-((4-amino-2-butyl-7-isopropoxy-1H-imidazo[4,5-d]pyridazin-1-yl)methyl)benzyl)-3-methoxypropanamide;

(108) 2-butyl-7-isopropoxy-1-(4-(((2-(2-methoxyethoxy)ethyl)amino)methyl)benzyl)-1H-imidazo[4,5-d]pyridazin-4-amine;

(109) 2-butyl-1-(4-((hexylamino)methyl)benzyl)-7-isopropoxy-1H-imidazo[4,5-d]pyridazin-4-amine;

(110) 2-butyl-1-(4-((decylamino)methyl)benzyl)-7-isopropoxy-1H-imidazo[4,5-d]pyridazin-4-amine;

(111) ethyl (4-((4-amino-2-butyl-7-isopropoxy-1H-imidazo[4,5-d]pyridazin-1-yl)methyl)benzyl)carbamate;

(112) 4-methoxybenzyl (4-((4-amino-2-butyl-7-isopropoxy-1H-imidazo[4,5-d]pyridazin-1-yl)methyl)benzyl)carbamate;

(113) 1-(4-((4-amino-2-butyl-7-isopropoxy-1H-imidazo[4,5-d]pyridazin-1-yl)methyl)benzyl)-3-ethylurea;

(114) 4-acetamidobenzyl (4-((4-amino-2-butyl-7-isopropoxy-1H-imidazo[4,5-d]pyridazin-1-yl)methyl)benzyl)carbamate;

(115)N-(4-((4-amino-2-butyl-7-isopropoxy-1H-imidazo[4,5-d]pyridazin-1-yl)methyl)benzyl) methanesulfonamide;

(116) 2-butyl-1-(4-((dimethylamino)methyl)benzyl)-7-isopropoxy-1H-imidazo[4,5-d]pyridazin-4-amine;

(117) tert-butyl (4-((4-amino-2-butyl-7-isopropoxy-1H-imidazo[4,5-d]pyridazin-1-yl)methyl)benzyl) glycinate;

(118) 2-butyl-7-isopropoxy-1-(4-((methylamino)methyl)benzyl)-1H-imidazo[4,5-d]pyridazin-4-amine;

(119) tert-butyl 3-((4-((4-amino-2-butyl-7-isopropoxy-1H-imidazo[4,5-d]pyridazin-1-yl)methyl)benzyl)amino)propanoate;

(120) 1-(4-(5,8,11-trioxa-2-azadodecyl)benzyl)-2-butyl-7-isopropoxy-1H-imidazo[4,5-d]pyridazin-4-amine;

(121) 2-butyl-4-isopropoxy-3-[[4-[[2-[2-[2-(2-methoxyethoxy)ethoxy]ethoxy]ethylamino]methyl]phenyl]methyl]imidazo[4,5-d]pyridazin-7-amine;

(122) 2-butyl-4-isopropoxy-3-[[4-[[2-[2-[2-[2-[2-[2-[2-(2-methoxyethoxy)ethoxy]ethoxy]ethoxy]ethoxy]ethoxy]ethoxy]ethylamino]methyl]phenyl]methyl]imidazo[4,5-d]pyridazin-7-amine di2,2,2-trifluoroacetate;

(123) 2-butyl-4-isopropoxy-3-[[4-[[2-[2-[2-[2-[2-[2-[2-[2-[2-[2-[2-(2-methoxyethoxy)ethoxy]ethoxy]ethoxy]ethoxy]ethoxy]ethoxy]ethoxy]ethoxy]ethoxy]ethoxy]ethylamino]methyl]phenyl]methyl]imidazo[4,5-d]pyridazin-7-amine di2,2,2-trifluoroacetate;

(124) 2-butyl-7-isopropoxy-1-(3-((methylamino)methyl)benzyl)-1H-imidazo[4,5-d]pyridazin-4-amine;

(125) 2-butyl-1-(3-((dimethylamino)methyl)benzyl)-7-isopropoxy-1H-imidazo[4,5-d]pyridazin-4-amine;

(126) 2-butyl-1-(3-((cyclobutylamino)methyl)benzyl)-7-isopropoxy-1H-imidazo[4,5-d]pyridazin-4-amine dihydrochloride salt;

(127) 2-butyl-1-(3-((cyclopropylamino)methyl)benzyl)-7-isopropoxy-1H-imidazo[4,5-d]pyridazin-4-amine dihydrochloride salt;

(128) 2-butyl-7-isopropoxy-1-(3-((isopropylamino)methyl)benzyl)-1H-imidazo[4,5-d]pyridazin-4-amine dihydrochloride salt;

(129) 3-((3-((4-amino-2-butyl-7-isopropoxy-1H-imidazo[4,5-d]pyridazin-1-yl)methyl)benzyl)amino)thietane 1,1-dioxide;

(130) 2-butyl-7-isopropoxy-1-(3-(((1-methylcyclobutyl)amino)methyl)benzyl)-1H-imidazo[4,5-d]pyridazin-4-amine dihydrochloride salt;

(131) 2-butyl-7-isopropoxy-1-(3-(piperazin-1-ylmethyl)benzyl)-1H-imidazo[4,5-d]pyridazin-4-amine;

(132) (E)-1-(4-(aminomethyl)benzyl)-2-butyl-7-(3-methylbut-1-en-1-yl)-1H-imidazo[4,5-d]pyridazin-4-amine;

(133) 1-(4-(aminomethyl)benzyl)-2-butyl-7-isopentyl-1H-imidazo[4,5-d]pyridazin-4-amine;

(134) 1-(4-(aminomethyl)benzyl)-2-butyl-7-(pyrrolidin-1-yl)-1H-imidazo[4,5-d]pyridazin-4-amine;

(135) 1-(4-(aminomethyl)benzyl)-2-butyl-7-(1H-pyrrol-3-yl)-1H-imidazo[4,5-d]pyridazin-4-amine 2,2,2-trifluoroacetate;

(137) 1-(((1R,4R)-4-(aminomethyl)cyclohexyl)methyl)-2-butyl-7-((E)-3-methylbut-1-en-1-yl)-1H-imidazo[4,5-d]pyridazin-4-amine (138) 1-(((1R,4R)-4-(aminomethyl)cyclohexyl)methyl)-2-butyl-7-isopentyl-1H-imidazo[4,5-d]pyridazin-4-amine;

(139) 1-(((1R,4R)-4-aminocyclohexyl)methyl)-2-butyl-7-((E)-3-methylbut-1-en-1-yl)-1H-imidazo[4,5-d]pyridazin-4-amine;

(140) 1-(((1R,4R)-4-aminocyclohexyl)methyl)-2-butyl-7-isopentyl-1H-imidazo[4,5-d]pyridazin-4-amine;

(141) 1-(((1R,4R)-4-aminocyclohexyl)methyl)-2-butyl-7-(1H-pyrrol-3-yl)-1H-imidazo[4,5-d]pyridazin-4-amine;

(142) 1-(((1R,4R)-4-(aminomethyl)cyclohexyl)methyl)-2-butyl-7-(pyrrolidin-1-yl)-1H-imidazo[4,5-d]pyridazin-4-amine;
(143) 3-[(4-aminocyclohexyl)methyl]-2-butyl-4-pyrrolidin-1-yl-imidazo[4,5-d]pyridazin-7-amine;
(144) 1-[[4-(aminomethyl)phenyl]methyl]-2-butyl-7-(2,5-dihydro-1H-pyrrol-3-yl) imidazo[4,5-d]pyridazin-4-amine;
(145) 1-[[4-(aminomethyl)phenyl]methyl]-2-butyl-7-pyrrolidin-3-yl-imidazo[4,5-d]pyridazin-4-amine;
(146) 3-(6-aminohexyl)-2-butyl-4-isopropoxy-imidazo[4,5-d]pyridazin-7-amine dihydrochloride salt;
(147) 2-butyl-4-isopropoxy-3-[6-(tetrahydropyran-4-ylamino)hexyl]imidazo[4,5-d]pyridazin-7-amine dihydrochloride salt;
(148)N-[6-(7-amino-2-butyl-4-isopropoxy-imidazo[4,5-d]pyridazin-3-yl)hexyl]-N-tetrahydropyran-4-yl-acetamide;
(149) 3-(4-aminobutyl)-2-butyl-4-isopropoxy-imidazo[4,5-d]pyridazin-7-amine dihydrochloride salt;
(150) 2-butyl-4-isopropoxy-3-[4-(tetrahydropyran-4-ylamino) butyl]imidazo[4,5-d]pyridazin-7-amine hydrochloride salt;
(151)N-[4-(7-amino-2-butyl-4-isopropoxy-imidazo[4,5-d]pyridazin-3-yl) butyl]-N-tetrahydropyran-4-yl-acetamide;
(152) 2-butyl-3-[4-[(1,1-dioxothietan-3-yl)amino] butyl]-4-isopropoxy-imidazo[4,5-d]pyridazin-7-amine;
(153) N-[4-(7-amino-2-butyl-4-isopropoxy-imidazo[4,5-d]pyridazin-3-yl) butyl]-N-(1,1-dioxothietan-3-yl)acetamide;
(154) 2-butyl-3-[6-[(1,1-dioxothietan-3-yl)amino] hexyl]-4-isopropoxy-imidazo[4,5-d]pyridazin-7-amine;
(155) N-[6-(7-amino-2-butyl-4-isopropoxy-imidazo[4,5-d]pyridazin-3-yl)hexyl]-N-(1,1-dioxothietan-3-yl)acetamide hydrochloride salt;
(156) 2-[(7-amino-2-butyl-4-isopropoxy-imidazo[4,5-d]pyridazin-3-yl)methyl]-2-methyl-propane-1,3-diol hydrochloride salt;
(157) 2-[(7-amino-2-butyl-4-isopropoxy-imidazo[4,5-d]pyridazin-3-yl)methyl]propane-1,3-diol hydrochloride salt;
(158) 1-(4-(aminomethyl)benzyl)-7-isopropoxy-2-propyl-1H-imidazo[4,5-d]pyridazin-4-amine;
(159) 1-(4-(aminomethyl)benzyl)-2-(ethoxymethyl)-7-isopropoxy-1H-imidazo[4,5-d]pyridazin-4-amine;
(160) 1-(4-(aminomethyl)benzyl)-7-isopropoxy-2-methyl-1H-imidazo[4,5-d]pyridazin-4-amine;
(161) 3-[[4-(aminomethyl)phenyl]methyl]-4-isopropoxy-2-propylsulfanyl-imidazo[4,5-d]pyridazin-7-amine;
(162) 3-[[4-(aminomethyl)phenyl]methyl]-4-isopropoxy-2-propylsulfinyl-imidazo[4,5-d]pyridazin-7-amine;
(163) 3-[[4-(aminomethyl)phenyl]methyl]-4-isopropoxy-N2-propyl-imidazo[4,5-d]pyridazine-2,7-diamine;
(164) 3-[[4-(aminomethyl)phenyl]methyl]-2-(ethylaminomethyl)-4-isopropoxy-imidazo[4,5-d]pyridazin-7-amine; and
(165) 2-butyl-7-isopropoxy-1-(piperidin-4-ylmethyl)-1H-imidazo[4,5-d]pyridazin-4-amine.

7. The Compound of formula (I) or a pharmaceutically acceptable salt thereof, according to claim 1, said compound being selected from:
(19) 4-(aminomethyl)cyclohexyl)methyl)-2-butyl-7-isopropoxy-1H-imidazo[4,5-d]pyridazin-4-amine dihydrochloride salt;
(20) 4-(aminomethyl)cyclohexyl)methyl)-2-butyl-7-isopropoxy-1H-imidazo[4,5-d]pyridazin-4-amine 2,2,2-trifluoroacetate;
(21) 1-(4-(aminomethyl)benzyl)-2-butyl-7-isopropoxy-1H-imidazo[4,5-d]pyridazin-4-amine;
(22) 1-(4-(aminomethyl)benzyl)-2-butyl-7-isopropoxy-1H-imidazo[4,5-d]pyridazin-4-amine 2,2,2-trifluoroacetate;
(23) 1-(((1S,3R)-3-aminocyclohexyl)methyl)-2-butyl-7-isopropoxy-1H-imidazo[4,5-d]pyridazin-4-amine (and enantiomer);
(24) 1-(4-amino-2-butyl-7-isopropoxy-1H-imidazo[4,5-d]pyridazin-1-yl)-2-methylpropan-2-ol;
(25) Trans 1-(4-aminocyclohexyl)methyl)-2-butyl-7-isopropoxy-1H-imidazo[4,5-d]pyridazin-4-amine;
(26) 1-((5-(aminomethyl)pyridin-2-yl)methyl)-2-butyl-7-isopropoxy-1H-imidazo[4,5-d]pyridazin-4-amine;
(28)N-(4-((4-amino-2-butyl-7-isopropoxy-1H-imidazo[4,5d]pyridazin-1-yl)methyl)benzyl)acetamide;
(33) 1-(3-(aminomethyl)benzyl)-2-butyl-7-isopropoxy-1H-imidazo[4,5-d]pyridazin-4-amine 2,2,2-trifluoroacetate;
(35) (4-((4-amino-2-butyl-7-isopropoxy-1H-imidazo[4,5-d]pyridazin-1-yl)methyl)phenyl)methanol;
(36) 2-butyl-1-(4-((cyclopropylamino)methyl)benzyl)-7-isopropoxy-1H-imidazo[4,5-d]pyridazin-4-amine;
(39) 2-butyl-7-isopropoxy-1-(4-(((1-methylcyclobutyl)amino)methyl)benzyl)-1H-imidazo[4,5-d]pyridazin-4-amine;
(40) 2-butyl-7-isopropoxy-1-(4-(piperazin-1-ylmethyl)benzyl)-1H-imidazo[4,5-d]pyridazin-4-amine;
(43) 2-butyl-N7-(4-((dimethylamino)methyl)benzyl)-N7,1-dimethyl-1H-imidazo[4,5-d]pyridazine-4,7-diamine;
(47) 2-butyl-N7-(4-(((2-methoxyethyl)(methyl)amino)methyl)benzyl)-N7,1-dimethyl-1H-imidazo[4,5-d]pyridazine-4,7-diamine;
(144) 1-[[4-(aminomethyl)phenyl]methyl]-2-butyl-7-(2,5-dihydro-1H-pyrrol-3-yl) imidazo[4,5-d]pyridazin-4-amine;
(156) 2-[(7-amino-2-butyl-4-isopropoxy-imidazo[4,5-d]pyridazin-3-yl)methyl]-2-methyl-propane-1,3-diol hydrochloride salt;
(157) 2-[(7-amino-2-butyl-4-isopropoxy-imidazo[4,5-d]pyridazin-3-yl)methyl]propane-1,3-diol hydrochloride salt;
(159) 1-(4-(aminomethyl)benzyl)-2-(ethoxymethyl)-7-isopropoxy-1H-imidazo[4,5-d]pyridazin-4-amine;
(161) 3-[[4-(aminomethyl)phenyl]methyl]-4-isopropoxy-2-propylsulfanyl-imidazo[4,5-d]pyridazin-7-amine;
(163) 3-[[4-(aminomethyl)phenyl]methyl]-4-isopropoxy-N2-propyl-imidazo[4,5-d]pyridazine-2,7-diamine; and
(164) 3-[[4-(aminomethyl)phenyl]methyl]-2-(ethylaminomethyl)-4-isopropoxy-imidazo[4,5-d]pyridazin-7-amine.

8. A process for the preparation of a compound of formula (I) or a pharmaceutically acceptable salt thereof according to claim 1, comprising at least the following steps:
(iB) providing a compound of formula (II), (II)

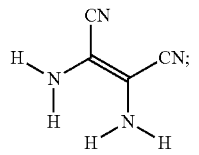

(iiB) cyclization of the compound of formula (II) provided in step (iB) by reaction with $R_2$—$C(OCH_3)_3$ or $R_2$—COCl in order to obtain a compound of formula (III), (III)

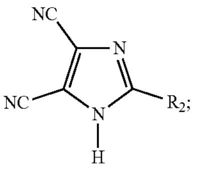

(iiiB) hydrolyzis of nitrile groups present on the compound of formula (III) obtained from step (iiB) in order to obtain a compound of formula (IV), (IV)

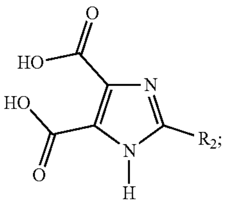

(ivB) esterification of carboxylic acid functions present on the compound of formula (IV) obtained from step (iiiB) in order to obtain a compound of formula (V), (V)

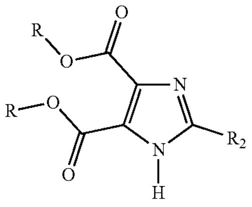

wherein R is a ($C_1$-$C_4$)alkyl- group;

(vB) optionally reacting the compound of formula (V) obtained from step (ivB) with $R_1$—X, and X represents a halogen atom, in order to obtain a compound of formula (Vb), (Vb)

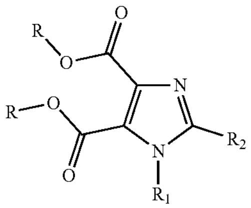

wherein R is a ($C_1$-$C_4$)alkyl group;

(viB) cyclization of the compound of formula (Vb) obtained from step (vB) or the compound of formula (V) (in which $R_1$ is a hydrogen atom) obtained from step (ivB) in order to obtain a compound of formula (VIb), (VIb)

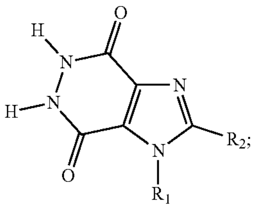

(viiB) dihalogenation of the compound of formula (VIb) obtained from step (viB) in order to obtain a compound of formula (VIIa), (VIIa)

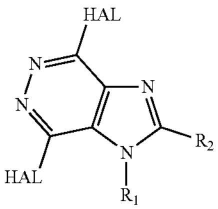

wherein HAL is a halogen atom;

(viiiB) nucleophilic aromatic substitution of the compound of formula (VIIa) obtained from step (viiB) in order to obtain a compound of formula (VIIIa), (VIIIa)

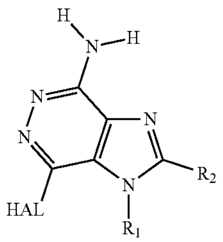

wherein HAL is a halogen atom;

(ixB) substitution and/or coupling of the compound of formula (VIIIa) obtained from step (viiiB) in order to obtain a compound of formula (Ia), (Ia)

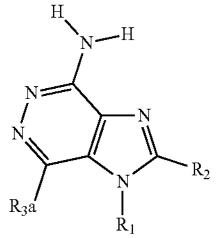

wherein $R_{3a}$ represents $R_3$ optionally further comprising a hydroxyl protecting group, an amino protecting group, a carboxylic acid protecting group, an aldehyde protecting group or a ketone protecting group;

(xB) when $R_{3a}$ is other than $R_3$ as defined in claim 1, then reacting the compound of formula (Ia) obtained from step (ixB) with any suitable reagents and in any suitable conditions in order to obtain a compound of formula (I).

9. A process for the preparation of a compound of formula (I) or a pharmaceutically acceptable salt thereof according to claim 1, comprising at least the following steps:

(i) providing a compound of formula (II), (II)

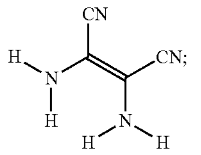

(ii) cyclization of the compound of formula (II) provided in step (i) by reaction with $R_2$—$C(OCH_3)_3$ or $R_2$—COCl wherein $R_2$ is as defined in claim 1 or is a hydrogen atom in order to obtain a compound of formula (III), (III)

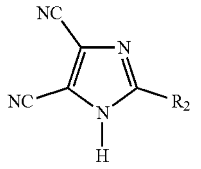

wherein $R_2$ is as defined in claim 1 or is a hydrogen atom;

(iii) hydrolysis of nitrile groups of the compound of formula (III) obtained from step (ii) in order to obtain a compound of formula (IV), (IV)

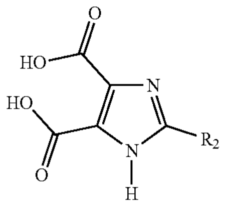

wherein $R_2$ is as defined in claim 1 or is a hydrogen atom;

(iv) esterification of carboxylic acid functions of the compound of formula (IV) obtained from step (iii) in order to obtain a compound of formula (V), (V)

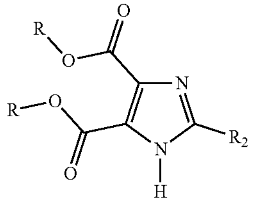

wherein R is a ($C_1$-$C_4$) alkyl group, and $R_2$ is as defined in claim 1 or is a hydrogen atom;

(v) cyclization of the compound of formula (V) obtained from step (iv) in order to obtain a compound of formula (VI), (VI)

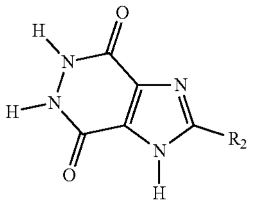

wherein $R_2$ is as defined in claim 1 or is a hydrogen atom;

(vi) dihalogenation of the compound of formula (VI) obtained from step (v) in order to obtain a compound of formula (VII), (VII)

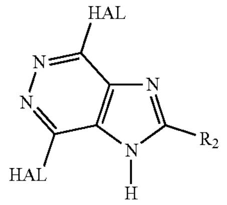

wherein $R_2$ is as defined in claim 1 or is a hydrogen atom and HAL is a halogen atom;

(vii) nucleophilic aromatic substitution of the compound of formula (VII) obtained from step (vi) with a compound of formula (AA)

(AA)

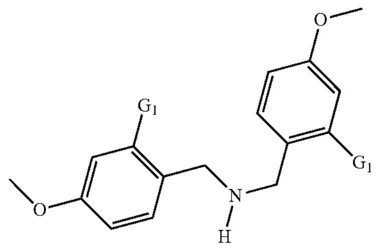

wherein the two $G_1$ represent independently a hydrogen atom or a methoxy group, for example the two $G_1$ are a methoxy group, in order to obtain a compound of formula (VIII), (VIII)

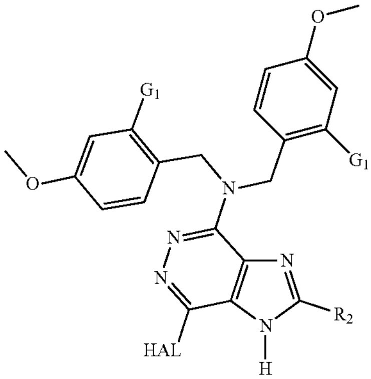

wherein $R_2$ is as defined in claim 1 or is a hydrogen atom, HAL is a halogen atom, and the two $G_1$ represent independently a hydrogen atom or a methoxy group;

(viii) substitution and/or coupling reaction of the compound of formula (VIII) obtained from step (vii) in order to obtain a compound of formula (IX), (IX)

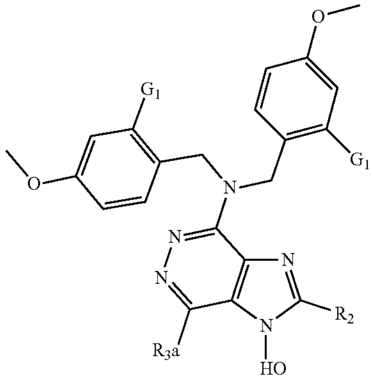

wherein $R_2$ is as defined in claim 1 or is a hydrogen atom, $R_{3a}$ represents $R_3$ as defined in claim 1 optionally further comprising a hydroxyl protecting group, an amino protecting group, a carboxylic acid protecting group, an aldehyde protecting group or a ketone protecting group, and the two $G_1$ represent independently a hydrogen atom or a methoxy group;

then either (ixAlpha) reacting the compound of formula (IX) obtained from step (viii) with $R_{1a}$—X wherein $R_{1a}$ is $R_1$ as defined in claim 1 optionally further comprising or not a hydroxyl protecting group, an amino protecting group, a carboxylic acid protecting group, an aldehyde protecting group or a ketone protecting group, and X represents a halogen atom, a tosylate or a mesylate in order to obtain a compound of formula (X), (X)

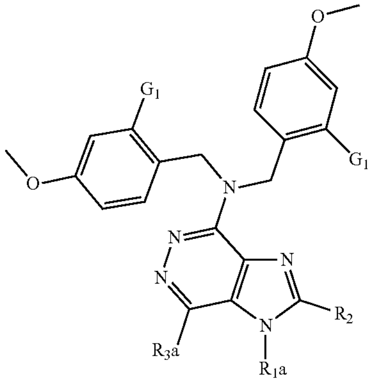

wherein $R_2$ is as defined in claim 1 or is a hydrogen atom, $R_3a$ represents $R_3$ as defined in claim 1 optionally further comprising a hydroxyl protecting group, an amino protecting group, a carboxylic acid protecting group, an aldehyde protecting group or a ketone protecting group, the two $G_1$ represent independently a hydrogen atom or a methoxy group, and $R_{1a}$ is as defined above in this step (ixAlpha);

or (ixBeta) reacting the compound of formula (IX) obtained from step (viii) with an epoxide of formula

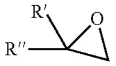

in which R' and R" are independently a hydrogen atom or a $(C_1$-$C_6)$alkyl group in order to obtain a compound of formula (X), (X)

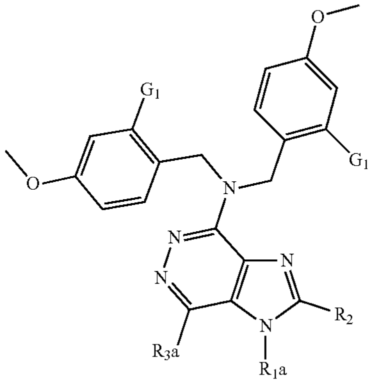

wherein $R_2$ is as defined in claim 1 or is a hydrogen atom, $R_3a$ represents $R_3$ as defined in claim 1 optionally further comprising a hydroxyl protecting group, an amino protecting group, a carboxylic acid protecting group, an aldehyde protecting group or a ketone protecting group, the two $G_1$ represent independently a hydrogen atom or a methoxy group, and $R_{1a}$ is as defined above in the step (ixAlpha);

and either (x) deprotecting the compound of formula (X) obtained from step (ixAlpha) or (ixBeta) in order to obtain a compound of formula (I); and when $R_2$ is a hydrogen atom in compound of formula (X), before deprotection, the hydrogen was transformed to $R_2$ as defined in formula (I) through chemistry modification;

or (x) deprotecting the compound of formula (X) obtained from step (ixAlpha) or (ixBeta) in order to obtain a compound of formula (XI)

(XI)

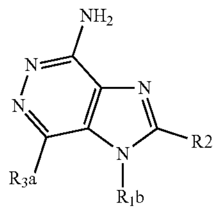

wherein $R_{3a}$ represents $R_3$ as defined in claim 1 optionally further comprising or not a hydroxyl protecting group, an amino protecting group, a carboxylic acid protecting group, an aldehyde protecting group or a ketone protecting group, $R_2$ is as defined in claim 1, and Rib is Ria as defined in claim 1 or $R_{1a}$ with a function such as an amino group, an alcohol, and an aldehyde; and then (xi) reducing, reductive aminating, nucleophilic substituting, and/or oxidating the compound of formula (XI) obtained from this step (x) in order to obtain a compound of formula (I);

or (Gamma) reducing, reductive aminating, nucleophilic substituting, and/or oxidating the compound of formula (X) obtained from step (ixAlpha) or (ixBeta) in order to obtain a compound of formula (XII)

(XII)

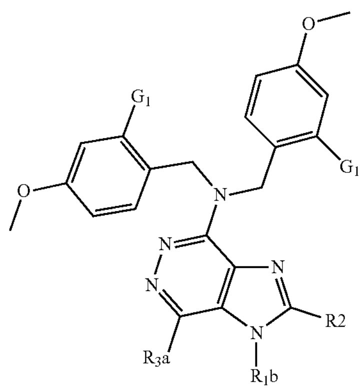

wherein $R_{3a}$ represents $R_3$ as defined in claim 1 optionally further comprising a hydroxyl protecting group, an amino protecting group, a carboxylic acid protecting group, an aldehyde protecting group or a ketone protecting group, $R_2$ is as defined in claim 1, the two $G_1$ represent independently a hydrogen atom or a methoxy group, and $R_{1b}$ is a derivative of Ria is as defined in claim 1 through reductive amination, reduction, substitution, and/or oxydation; and then (x) deprotecting the compound of formula (XII) obtained from step (Gamma) in order to obtain a compound of formula (I).

10. A process for the preparation of a compound of formula (I) or a pharmaceutically acceptable salt thereof according to claim 1, comprising at least the following steps:

(iA) providing a compound of formula (II), (II)

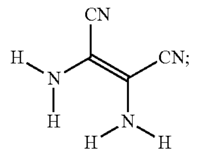

(iiA) cyclization of the compound of formula (II) provided in step (iA) by reaction with $R_2$—$C(OCH_3)_3$ or $R_2$—COCl in order to obtain a compound of formula (III), (III)

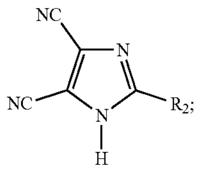

(iiiA) hydrolysis of nitrile groups of the compound of formula (III) obtained from step (iiA) in order to obtain a compound of formula (IV), (IV)

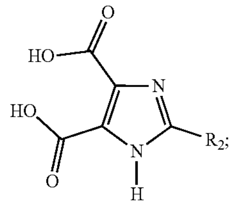

(ivA) esterification of carboxylic acid functions of the compound of formula (IV) obtained from step (iiiA) in order to obtain a compound of formula (V), (V)

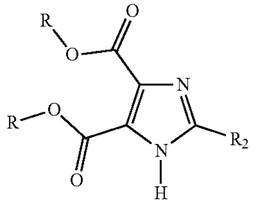

wherein R is a ($C_1$-$C_4$) alkyl group;

(vA) cyclization of the compound of formula (V) obtained from step (ivA) in order to obtain a compound of formula (VI), (VI)

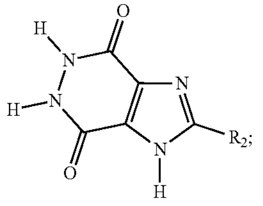

(viA) dihalogenation of the compound of formula (VI) obtained from step (vA) in order to obtain a compound of formula (VII);

(VII)

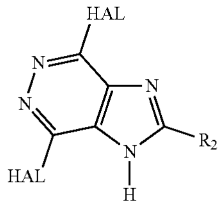

wherein HAL is a halogen atom;

(viiA) optionally reacting the compound of formula (VII) obtained from step (viA) with $R_1$—X wherein X represents a halogen atom in order to obtain a compound of formula (VIIa);

(VIIa)

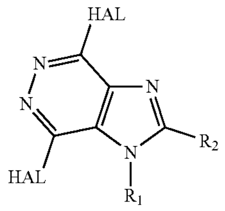

wherein HAL is a halogen atom;

(viiiA) nucleophilic aromatic substitution of the compound of formula (VIIa) obtained from step (viiA) or of the compound of formula (VII) (in which $R_1$ is a hydrogen atom) obtained from step (viA) in order to obtain a compound of formula (VIIIa), (VIIIa)

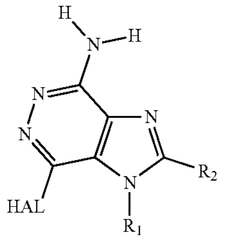

wherein HAL is a halogen atom;

(ixA) substitution and/or coupling of the compound of formula (VIIIa) obtained from step (viiiA) in order to obtain a compound of formula (Ia), (Ia)

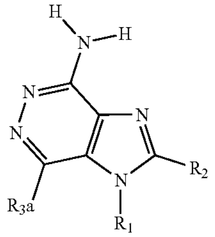

wherein $R_{3a}$ represents $R_3$ as defined in claim 1 optionally further comprising or not a hydroxyl protecting group, an amino protecting group, a carboxylic acid protecting group, an aldehyde protecting group or a ketone protecting group;

(xA) when $R_{3a}$ is other than $R_3$ as defined in claim 1, then reacting the compound of formula (Ia) obtained from step (ixA) with any suitable reagents and in any suitable conditions in order to obtain a compound of formula (I).

11. A process for the preparation of a compound of formula (I) or a pharmaceutically acceptable salt thereof according to claim 1, comprising at least the following steps:

(i) providing a compound of formula (II), (II)

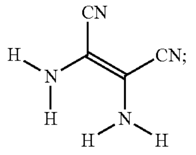

(ii) cyclization of the compound of formula (II) provided in step (i) by reaction with $R_2$—$C(OCH_3)_3$ or $R_2$—COCl in order to obtain a compound of formula (III), (III)

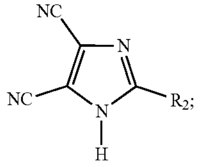

(iii) hydrolysis of nitrile groups of the compound of formula (III) obtained from step (ii) in order to obtain a compound of formula (IV), (IV)

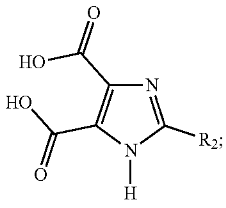

(iv) esterification of carboxylic acid functions of the compound of formula (IV) obtained from step (iii) in order to obtain a compound of formula (V), (V)

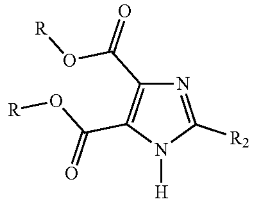

wherein R is a $(C_1-C_4)$ alkyl group;

(v) cyclization of the compound of formula (V) obtained from step (iv) in order to obtain a compound of formula (VI), (VI)

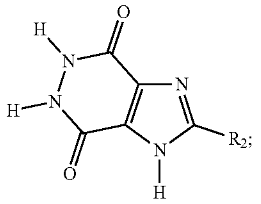

(vi) dihalogenation of the compound of formula (VI) obtained from step (v) in order to obtain a compound of formula (VII), (VII)

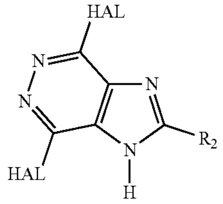

wherein HAL is a halogen atom;

then either (viialpha) reacting the compound of formula (VII) obtained from step (vi) with $R_{1a}$—X wherein $R_{1a}$ is $R_1$ as defined in claim 1 optionally further comprising a hydroxyl protecting group, an amino protecting group, a carboxylic acid protecting group, an aldehyde protecting group or a ketone protecting group, and X represents a halogen atom, a tosylate or a mesylate in order to obtain a compound of formula (VIIIaa), (VIIIaa)

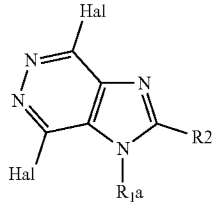

wherein HAL is a halogen atom, and $R_{1a}$ is as defined above in this step (viialpha);

or (viiBeta) reacting the compound of formula (VII) obtained from step (vi) with an epoxide of formula

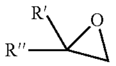

in which R' and R" are independently a hydrogen atom or a $(C_1-C_6)$alkyl group in order to obtain a compound of formula (VIIIaa), (VIIIaa)

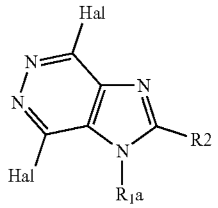

wherein HAL is a halogen atom, and $R_{1a}$ is as defined above in the step (viialpha), (viiiAA) nucleophilic aromatic substitution of the compound of formula (VIIIaa) obtained from step (viialpha) or step (viibeta) with a compound of formula (AA)

(AA)

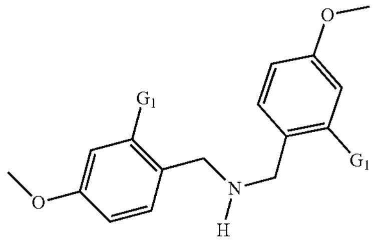

wherein the two $G_1$ represent independently a hydrogen atom or a methoxy group, in order to obtain a compound of formula (IXaa), (IXaa)

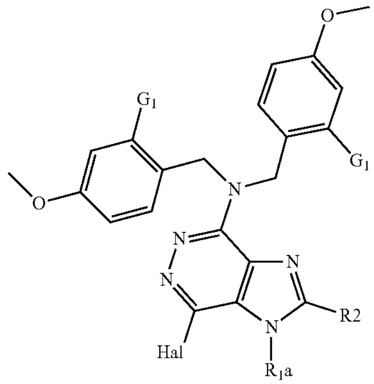

wherein HAL is a halogen atom, $R_{1a}$ is as defined above in the step (viialpha), and the two $G_1$ represent independently a hydrogen atom or a methoxy group;

(ixAA) substitution and/or coupling reaction of the compound of formula (IXaa) obtained from step (viiiAA) in order to obtain a compound of formula (X), (X)

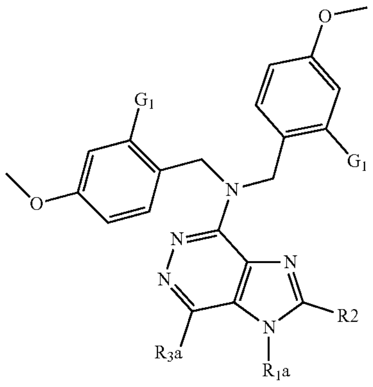

wherein $R_{1a}$ is as defined above in the step (viialpha), $R_{3a}$ represents $R_3$ as defined in claim 1 optionally further comprising a hydroxyl protecting group, an amino protecting group, a carboxylic acid protecting group, an aldehyde protecting group or a ketone protecting group and the two $G_1$ represent independently a hydrogen atom or a methoxy group;

and either (x) deprotecting the compound of formula (X) obtained from step (ixAA) in order to obtain a compound of formula (I);

or (x) deprotecting the compound of formula (X) obtained from step (ixAA) in order to obtain a compound of formula (XI)

(XI)

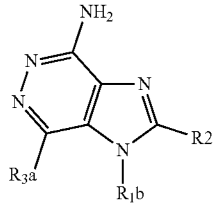

wherein $R_{3a}$ represents $R_3$ as defined in claim 1 optionally further comprising a hydroxyl protecting group, an amino protecting group, a carboxylic acid protecting group, an aldehyde protecting group or a ketone protecting group, and $R_{1b}$ is $R_1$a or $R_1$a with a function such as an amino group, an alcohol, and an aldehyde; and then (xi) reducing, reductive aminating, nucleophilic substituting, and/or oxidating the compound of formula (XI) obtained from this step (x) in order to obtain a compound of formula (I);

or (Gamma) reducing, reductive aminating, nucleophilic substituting, and/or oxidating the compound of formula (X) obtained from step (ixAA) in order to obtain a compound of formula (XII)

(XII)

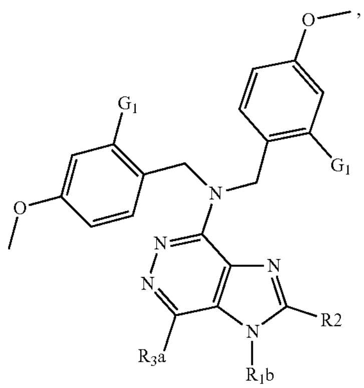

wherein $R_{3a}$ represents $R_3$ as defined in claim 1 optionally further comprising a hydroxyl protecting group, an amino protecting group, a carboxylic acid protecting group, an aldehyde protecting group or a ketone protecting group, $R_2$ is as defined in claim 1, the two $G_1$ represent independently a hydrogen atom or a methoxy group, and $R_{1b}$ is a derivative of Ria through reductive amination, reduction, substitution, and/or oxidation; and then (x) deprotecting the compound of formula (XII) obtained from step (Gamma) in order to obtain a compound of formula (I).

12. Compounds or a pharmaceutically acceptable salt thereof selected from:

(H)

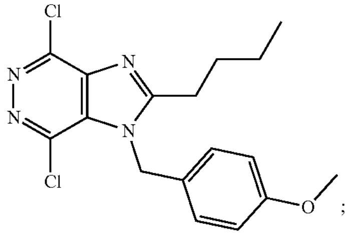

;

(IA)

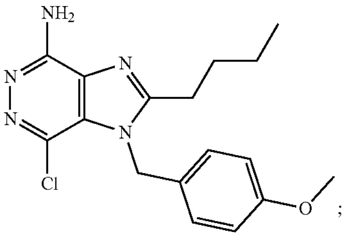

;

-continued (J)

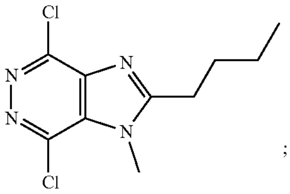

;

(K)

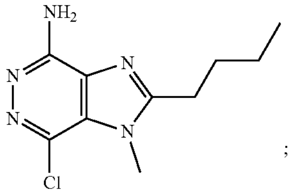

;

(L)

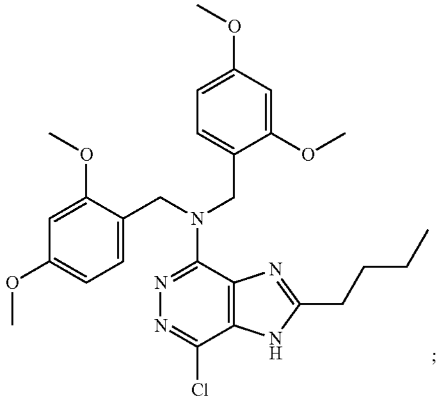

;

(M)

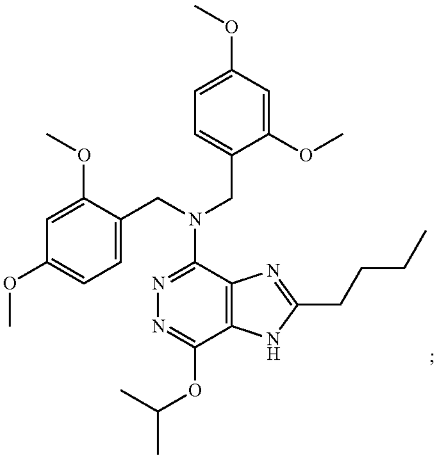

;

-continued (N)

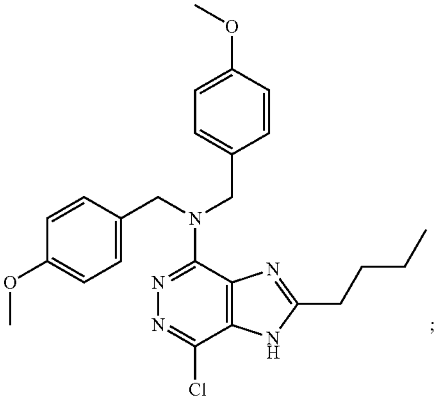

; and (R)

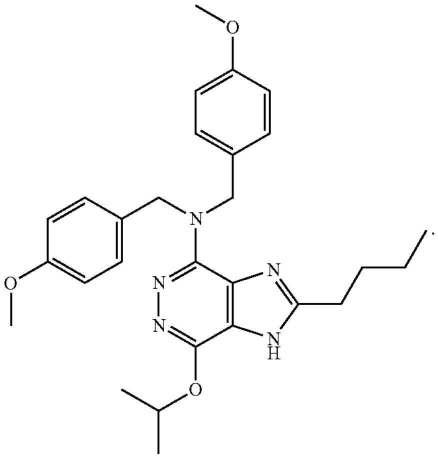

.

13. A medicament, comprising a compound of formula (I) or a pharmaceutically acceptable salt thereof according to claim 1.

14. A pharmaceutical composition, comprising a compound of formula (I) or a pharmaceutically acceptable salt thereof according to claim 1, and at least one pharmaceutically acceptable excipient.

15. A method of preventing or treating a disease or a disorder associated with TLR7 and/or TLR8 activity, said method comprising administering to a subject in need thereof a compound of formula (I) or a pharmaceutically acceptable salt thereof according to claim 1.

16. The method of claim 15, wherein the disease or disorder associated with TLR7 and/or TLR8 activity is selected from the group consisting of a cell-proliferative disease, a cancer, a chronic myelogenous, a hairy cell leukemia, a dermatological disease such as a skin lesion or a skin cancer, an autoimmune disease, an inflammatory disease, a respiratory disease, a sepsis, an allergy, an asthma, a graft rejection, a graft-versus-host disease, and an immunodeficiency.

17. The method according to claim 16, wherein the disease or disorder associated with TLR7 and/or TLR8 activity is cancer.

18. A vaccine comprising a compound of formula (I) or a pharmaceutically acceptable salt thereof according to claim 1.

* * * * *